United States Patent
Blaszczyk et al.

(10) Patent No.: US 12,053,451 B2
(45) Date of Patent: *Aug. 6, 2024

(54) ARGINASE INHIBITORS AND THEIR THERAPEUTIC APPLICATIONS

(71) Applicant: OncoArendi Therapeutics S.A., Warsaw (PL)

(72) Inventors: Roman Blaszczyk, Lodz (PL); Joanna Brzezińska, Lodz (PL); Anna Gzik, Wartkowice (PL); Adam Golebiowski, Madison, CT (US); Julita Nowicka, Wola Grzymkowa (PL); Bartlomiej Borek, Lodz (PL); Marek Dziegielewski, Lodz (PL); Karol Jedrzejczak, Lodz (PL); Krzysztof Matyszewski, Lodz (PL); Jacek Olczak, Lodz (PL)

(73) Assignee: OncoArendi Therapeutics S.A., Warsaw (PL)

( * ) Notice: Subject to any disclaimer, the term of this patent is extended or adjusted under 35 U.S.C. 154(b) by 413 days.

This patent is subject to a terminal disclaimer.

(21) Appl. No.: 17/168,291

(22) Filed: Feb. 5, 2021

(65) Prior Publication Data

US 2021/0260019 A1  Aug. 26, 2021

Related U.S. Application Data

(63) Continuation of application No. 16/540,747, filed on Aug. 14, 2019, now Pat. No. 10,912,755, which is a continuation of application No. 15/584,193, filed on May 2, 2017, now Pat. No. 10,391,077.

(60) Provisional application No. 62/444,669, filed on Jan. 10, 2017, provisional application No. 62/331,550, filed on May 4, 2016.

(30) Foreign Application Priority Data

May 4, 2016  (PL) ........................................ 417066

(51) Int. Cl.
```
C07F 5/02      (2006.01)
A61K 31/133    (2006.01)
A61K 31/23     (2006.01)
A61K 31/235    (2006.01)
A61K 31/33     (2006.01)
A61K 31/335    (2006.01)
A61K 31/343    (2006.01)
A61K 31/69     (2006.01)
A61P 11/00     (2006.01)
C07F 5/04      (2006.01)
```
(52) U.S. Cl.
CPC .......... *A61K 31/343* (2013.01); *A61K 31/133* (2013.01); *A61K 31/23* (2013.01); *A61K 31/235* (2013.01); *A61K 31/33* (2013.01); *A61K 31/335* (2013.01); *A61K 31/69* (2013.01); *A61P 11/00* (2018.01); *C07F 5/025* (2013.01); *C07F 5/04* (2013.01)

(58) Field of Classification Search
None
See application file for complete search history.

(56) References Cited

U.S. PATENT DOCUMENTS

| | | | |
|---|---|---|---|
| 9,040,703 B2 | 5/2015 | Van Zandt et al. | |
| 10,065,974 B2 | 9/2018 | Sjogren et al. | |
| 10,391,077 B2 * | 8/2019 | Blaszczyk | A61P 11/00 |
| 10,912,755 B2 * | 2/2021 | Blaszczyk | A61K 31/335 |
| 2010/0189644 A1 | 7/2010 | Christianson et al. | |
| 2012/0171116 A1 | 7/2012 | Tomezuk et al. | |
| 2014/0371175 A1 | 12/2014 | Van Zandt et al. | |
| 2016/0194340 A1 | 7/2016 | Christianson et al. | |
| 2016/0375044 A1 | 12/2016 | Gross et al. | |
| 2017/0000808 A1 | 1/2017 | Van Zandt et al. | |
| 2018/0161349 A1 | 6/2018 | Makkouk et al. | |

FOREIGN PATENT DOCUMENTS

| | | | |
|---|---|---|---|
| EP | 1604977 A1 | 6/2004 | |
| EP | 1604978 A1 | 6/2004 | |
| WO | 2013/158262 A1 | 3/2013 | |
| WO | 2013/059437 A1 | 4/2013 | |
| WO | 2016/108707 A1 | 7/2016 | |
| WO | 2016210106 A1 | 12/2016 | |
| WO | WO-2017191130 A2 * | 11/2017 | A61K 31/133 |
| WO | 2019145453 A1 | 8/2019 | |

OTHER PUBLICATIONS

Caldwell et al. "Arginase: An Old Enzyme with New Tricks". Trends Pharmacol Sci. Jun. 2015; 36(6):395-405. (Year: 2015).*
Kabalka, George W. et al., "Synthesis of 1-Amino-3-[(dihydroxyboryl)methyl]-cyclobutanecarboxylic Acid as a potential therapy agent" J.Org. Chem (2004), vol. 69, pp. 8280-8286.
Kabalka, G.W. et al., "The syntheses and in vivo biodistribution of novel boronated unnatural amino acids" Applied Radiation and Isotopes (2004) vol. 61, pp. 1111-1115.
Kabalka, George W. et al., "Synthesis of a boronated amino acid as a potential neutron therapy agent: 1-amino-3-[(dihydroxyboryl)ethyl]-cyclobutanecarboxylic acid" Tetrahedron Letters (2005) vol. 46, pp. 4915-4917.

(Continued)

*Primary Examiner* — Leslie A. Royds Draper
(74) *Attorney, Agent, or Firm* — McDonnell Boehnen Hulbert & Berghoff LLP

(57) ABSTRACT

Disclosed are small molecule therapeutic compounds that are potent inhibitors of arginase 1 and arginase 2 activity. Also disclosed are pharmaceutical compositions comprising the compounds, and methods for using the compounds for treating or preventing a disease or condition associated with arginase activity.

12 Claims, No Drawings

(56) References Cited

OTHER PUBLICATIONS

Kabalka, George W. et al., "Synthesis of a series of boronated unnatural cyclic amino acids as potential boron neutron capture therapy agents" Applied Organometallic Chemistry (2008) vol. 22(9), pp. 516-522.
Kabalka, George W. et al., "Synthesis of a novel boronated 1-aminocyclobutanecarboxylic acid as a potential boron neutron capture therapy agent" Applied Organometallic Chemistry (2003) vol. 17, pp. 398-402.
Gołębiowski, A. et al.; 2-Substituted-2-amino-6-boronohexanoic acids as arginase inhibitors; Bioorganic & Medicinal Chemistry Letters (2013) vol. 23(7), pp. 2027-2030.
Poland Search Report for PL417066 dated Feb. 22, 2017, pp. 1-2.
Communication Relating to the Results of the Partial International Search with partial search report for PCT/EP2017/060413 dated Jul. 12, 2017, pp. 1-10.
Czystowska-Kuzmicz, "Small extracellular vesicles containing arginase-1 suppress T-cell responses and promote tumor growth in ovarian carcinoma", Nature Communications, 2019, 10, 1-16.
Stanczak, PS, et al., "Development of OAT-1746: A Novel Arginase 1 and 2 Inhibitor for Cancer Immunotherapy", ESMO—Madrid, Sep. 8-12, 2017.
Grzybowksi, Marcin, et al., "Novel Dual Arginase 1/2 Inhibitor OATD-02 (OAT-1746) Improves the Efficacy of Immune Checkpoint Inhibitors", ESMO Immuno Oncology Congress—Geneva, Dec. 7-10, 2017, 1 page.
Sosnowska, Anna et al., Antitumor Activity and Mechanisms of Action of Arginase Inhibitor in Cancer Immunotherapy, ICMS—2018, 1 page.
Stanczak, PS, et al. "Development of Oat-1746: A Novel Arginase 1 and 2 Inhibitor for Cancer Immunotherapy", AACR-NCI-EORTC International Conference on Molecular Targets and Cancer Therapeutics—Philadelphia, Pennsylvania, USA, Oct. 26-30, 2017, 1 page.
Sterggerda, Susanne, et al, "Inhibition of arginase by CB-1158 blocks myeloid cell-mediated immune suppression in the tumor microenvironment", Journal for Immuno Therapy of Cancer (2017) 5:101.
Crittenden, Marka et al, "Expression of Arginase I in Myeloid Cells Limits Control of Residual Disease after Radiation Therapy of Tumors in Mice," Radiation Research 182, 182-190 (2014).
Czystowska-Kumicz, et al., "Small extracellular vesicles containing arginase-1 suppress T-cell responses and promote tumor growth in ovarian carcinoma", Nature Comm., https://doi.org/10.1038/s41467-019-10979-3.
Dufait, Ines, et al., "Ex vivo generation of myeloid-derived suppressor cells that model the tumor immunosuppressive environment in colorectal cancer", www.impactjournals.com/oncotarget/ Oncotarget, Advance Publications 2015.

Miret, Juan et al., "Suppression of Myeloid Cell Arginase Activity leads to Therapeutic Response in a NSCLC Mouse Model by Activating Anti-Tumor Immunity", Miret et al. Journal for ImmunoTherapy of Cancer (2019) 7:32 https://doi.org/10.1186/s40425-019-0504-5.
Rodriguez, Paulo C., "Arginase I Production in the Tumor Microenvironment by Mature Myeloid Cells Inhibits T-Cell Receptor Expression and Antigen-Specific T-Cell Responses", Cancer Research 64, 5839-5849, Aug. 15, 2004.
Rodriguez, Paulo C., "Regulation of T Cell Receptor CD3t Chain Expression by L-Arginine", The Journal of Biological Chemistry vol. 277, No. 24, Issue of Jun. 14, pp. 21123-21129, 2002.
Zaytouni, Tamara, et al., "Critical role for arginase 2 in obesity-associated pancreatic cancer", Nature Comm 8:242, 2017, 1-12.
ESMO—Madrid, Sep. 8-12, 2017; Stanczak, P. S. et al., "Development of OAT-1746: A Novel Arginase 1 and 2 Inhibitor for Cancer Immunotherapy", 1 page.
ESMO Immuno Oncology Congress—Geneva, Dec. 7-10, 2017; Grzybowski, M. et al., "Novel Dual Arginase 1/2 Inhibitor OATD-02 (OAT-1746) Improves the Efficacy of Immune Checkpoint Inhibitors", 1 page.
AACR-NCI-EORTC International Conference on Molecular Targets and Cancer Therapeutics—Philadelphia, Pennsylvania, USA, Oct. 26-30, 2017; "Development of OAT-1746, A novel arginase 1 and 2 inhibitor for cancer immunotherapy", 1 page.
ICMS—2018; Sosnowska, A. et al., "Antitumor activity and mechanisms of action of arginase inhibitor in cancer immunotherapy", 1 page.
AACR Annual Meeting—Washington, DC. Philadelphia, Apr. 1-5, 2017; Czystowska, M. et al., "Ovarian cancer cells release arginase-1-containing exosomes to suppress antitumor immune response", 1 page.
EFMC International Symposium on Advances in Synthetic and Medicinal Chemistry. Athens Sep. 1-5, 2019; Blaszczyk, R. et al., "Novel arginase inhibitor OATD-02 enhances anti-tumo efficacy of check point inhibitors", 1 page.
ESMO Congress Barcelona, Sep. 27-Oct. 1; Grzybowski, M. et al., "Targeting ARG2 as a novel therapeutic approach for cancer", 1 page.
ESMO Immuno Oncology Congress—Geneva, Dec. 11-14, 2019; Pilanc, P. et al., "A novel arginase inhibitor alone and in combination with an immune checkpoint inhibitor reduces tumour growth of murine experimental GL261 gliomas.", 1 page.
Czystowska-Kuzmicz et al., "Small extracellular vesicles containing arginase-1 suppress T-cell responses and promote tumor growth in ovarian carcinoma", Nature Communications, 2019, vol. 10, 1-16.
Borek et al., "Boronic acid-based arginase inhibitors in cancer immunotherapy", Bioorganic & Medicinal Chemistry, 2020, vol. 28, 115658, 14 pages.
Grzywa et al., "Potent but transient immunosuppression of T-cells is a general feature of 1 erythroid progenitor cells.", bioRxiv preprint. Jan. 19, 2021, 50 pages.

* cited by examiner

ARGINASE INHIBITORS AND THEIR THERAPEUTIC APPLICATIONS

CROSS-REFERENCE TO RELATED APPLICATIONS

This application is a continuation of U.S. application Ser. No. 16/540,747, filed Aug. 14, 2019, which is continuation of U.S. Application Ser. No. 15/584,193, filed May 2, 2017, now U.S. Pat. No. 10,391,077, which claims priority to U.S. Provisional Application No. 62/331,550, filed May 4, 2016, Poland Application No. P-417066, filed May 4, 2016, and U.S. Provisional Application No. 62/444,669, filed Jan. 10, 2017, the disclosures of each of which are hereby incorporated by reference in their entirety.

BACKGROUND OF THE INVENTION

Field of the Invention

The disclosure relates to small molecule therapeutic inhibitors of arginase 1 and arginase 2.

Description of Related Art

Two arginase isozymes (ARG-1 and ARG-2, denoted also as arginase I and II, respectively) exist in mammals, that hydrolyze arginine to ornithine and urea. Both enzymes catalyze the same biochemical reaction, but differ in cellular expression level, regulation and subcellular localization. ARG-1 is a cytosolic protein and ARG-2 is mainly localized in mitochondria (Jenkinson C P, Grody W W, Cederbaum S D. Comparative properties of arginases. *Comparative biochemistry and physiology Part B, Biochemistry & Molecular Biology.* 1996; 114(1):107-132).

The arginases are implicated in various pathological states. These include, without limitation, asthma, pulmonary hypertension, hypertension, T cell dysfunction, erectile dysfunction, atherosclerosis, renal disease, ischemia reperfusion injury, neurodegenerative diseases, wound healing, inflammatory diseases, fibrotic diseases and cancer.

Arginase expression and L-arginine depletion is known immune-suppressive pathway of the mammalian immune system (Munder M. Arginase: an emerging key player in the mammalian immune system. *Br J Pharmacol.* 2009; 158(3): 638-651). L-arginine deficiency down-regulates expression of T cell receptor (TCR) ζ chain, a key signaling element of the TCR, thereby impairing T cell function (Rodriguez P C, Zea A H, Culotta K S, Zabaleta J, Ochoa J B, Ochoa A C. Regulation of T cell receptor CD3zeta chain expression by L-arginine. *J Biol Chem.* 2002; 277(24):21123-21129). Depletion of L-arginine from the microenvironment leads to an arrest in T cell cycle progression, inhibition of IFN-γ production, and blocking of signaling through the T cell receptor.

Arginases are mainly produced by myeloid-derived suppressor cells (MDSC) that are highly enriched in the tumor-bearing state (Bronte V, Serafini P, De Santo C, Marigo I, Tosello V, Mazzoni A, Segal D M, Staib C, Lowel M, Sutter G, Colombo M P, Zanovello P: IL-4-Induced Arginase 1 Suppresses Alloreactive T Cells in Tumor-Bearing Mice *J Immunol* 2003; 170:270-278). Induction of arginase pathway is an important mechanisms involved in the evasion of anti-tumor immunity. High arginase activity has been observed in patients with various malignancies, both in blood and within tumor mass.

It was shown that T cell functions are restored and tumor growth is inhibited upon inhibition of arginase of tumor-associated MDSC or tumor-infiltrating CD11b$^+$Gr-1$^-$ mature myeloid cells in various murine tumor models (Rodriguez P C, Quiceno D G, Zabaleta J, et al. Arginase I production in the tumor microenvironment by mature myeloid cells inhibits T-cell receptor expression and antigen-specific T-cell responses. *Cancer Res.* 2004; 64(16):5839-5849). Depletion of the myeloid suppressor cells re-establishes T cell receptor- and costimulation-induced T cell activation (Zea A H, Rodriguez P C, Atkins M B, et al. Arginase-producing myeloid suppressor cells in renal cell carcinoma patients: a mechanism of tumor evasion. *Cancer Res.* 2005; 65(8): 3044-3048).

Arginase was shown to participate in the suppression of tumor-infiltrating lymphocytes in patients with prostate carcinoma (Bronte V, Kasic T, Gri G, et al. Boosting antitumor responses of T lymphocytes infiltrating human prostate cancers. *J Exp Med.* 2005; 201(8):1257-1268), non-small cell lung carcinoma (Rodriguez P C, Quiceno D G, Zabaleta J, et al. Arginase I production in the tumor microenvironment by mature myeloid cells inhibits T-cell receptor expression and antigen-specific T-cell responses. *Cancer Res.* 2004; 64(16):5839-5849) and multiple myeloma (Serafini P, Meckel K, Kelso M, et al. Phosphodiesterase-5 inhibition augments endogenous antitumor immunity by reducing myeloid-derived suppressor cell function. *J Exp Med.* 2006; 203(12):2691-2702). Not only MDSC but also dendritic cells (DCs) have been shown to suppress CD8$^+$ T cells and antitumor immune responses through ARG-1 production (Norian L A, Rodriguez P C, O'Mara L A, et al. Tumor-infiltrating regulatory dendritic cells inhibit CD8+ T cell function via L-arginine metabolism. *Cancer Res.* 2009; 69(7):3086-3094).

Given the role of arginase in various pathological states and their role in chronic inflammation and suppression of anti-tumor immunity, the present invention provides novel boron-containing compounds as inhibitors of arginase activity, as well as methodologies for using these compounds as therapeutics.

Numerous boron-containing arginase inhibitors are well-known from the literature. One of such inhibitors is 2(S)-amino-6-boronohexanoic acid, as described in WO 99/19295A1, published on Apr. 22, 1999 (incorporated by reference), and in WO 08/061612A1, published on May 29, 2008 (incorporated by reference). Besides, WO 11/133653, published on Oct. 27, 2011 (incorporated by reference), and WO 13/059437, published on Apr. 25, 2013 (incorporated by reference), describe a number of alpha-amino acid derivatives bearing a terminal B(OH)$_2$ group and a spacer, usually being a 1,3-cyclobutylene moiety. Mono- or polycyclic boron-containing amino acid compounds suitable as arginase inhibitors are described in WO 12/058065, published on May 3, 2012 (incorporated by reference). Other related patent application publications are WO 10/085797 of Jul. 29, 2010 (incorporated by reference), WO 13/158262 of Oct. 24, 2013 (incorporated by reference), and WO 12/091757 of Jun. 5, 2012 (incorporated by reference).

Significance of substitution at the alpha center of 2-amino-6-boronohecanoic acid for the inhibitory potency of arginase I and arginase II inhibitors has been discussed (Golebiowski A., et al. 2-Substituted-2-amino-6-borono-hexanoic acids as arginase inhibitors. *Bioorg. & Med. Chem. Lett.*, 2013; 23:2027-2030).

There is a need to investigate the inhibition of arginases, and to discover treatments for conditions associated with elevated expression of arginases, such as asthma and allergic responses. In particular, there is a need to explore new molecular scaffolds that effectively inhibit arginases and, therefore, can act as therapeutic agents for the treatment of these conditions.

SUMMARY OF THE INVENTION

In one aspect, the invention provides a compound represented by Formula (I):

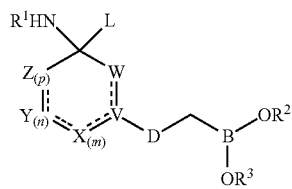

wherein:

L is —CO$_2$H, —C(O)O((C$_1$-C$_6$)alkyl), —CO$_2$CH$_2$—O-pivaloyl, —CO$_2$CH$_2$OCO$_2$-isopropyl, —C(O)NHOH, —C(O)NHCN, —C(O)NH$_2$, —C(O)NH((C$_1$-C$_6$)alkyl), —C(O)N((C$_1$-C$_6$)alkyl)$_2$, —C(O)NH(aryl), —C(O)N(aryl)((C$_1$-C$_6$)alkyl), —C(O)N(aryl)$_2$, —C(O)NH((C$_1$-C$_6$)haloalkyl), —S(O)$_2$NH$_2$, —S(O)$_2$NH((C$_1$-C$_6$)alkyl), —S(O)$_2$NH((C$_1$-C$_6$)haloalkyl), —S(O)$_2$NH(aryl), —S(O)$_2$NHC(O)((C$_1$-C$_6$)alkyl), —S(O)$_2$NHC(O)((C$_1$-C$_6$)haloalkyl), —S(O)$_2$NHC(O)(aryl), —N(H)S(O)$_2$((C$_1$-C$_6$)alkyl), —N(H)S(O)$_2$(aryl), N(H)S(O)$_2$((C$_1$-C$_6$)haloalkyl), —NHC(O)((C$_1$-C$_6$)alkyl), —NHC(O)((C$_1$-C$_6$)haloalkyl), —NHC(O)(aryl), —NHC(O)NH((C$_1$-C$_6$)alkyl), —NHC(O)NH(aryl), —C(O)N(H)S(O)$_2$((C$_1$-C$_6$)alkyl), —C(O)N(H)S(O)$_2$(aryl), —C(O)N(H)S(O)$_2$((C$_1$-C$_6$)haloalkyl), —P(O)(OH)$_2$, —CF$_3$,

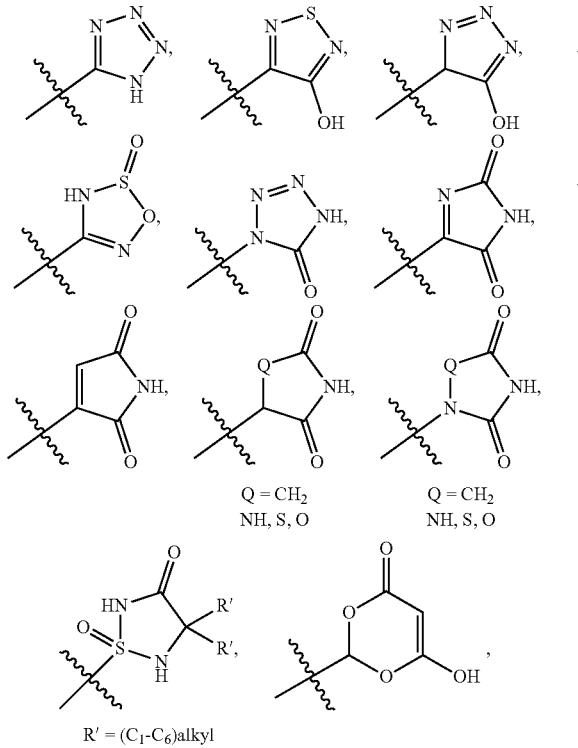

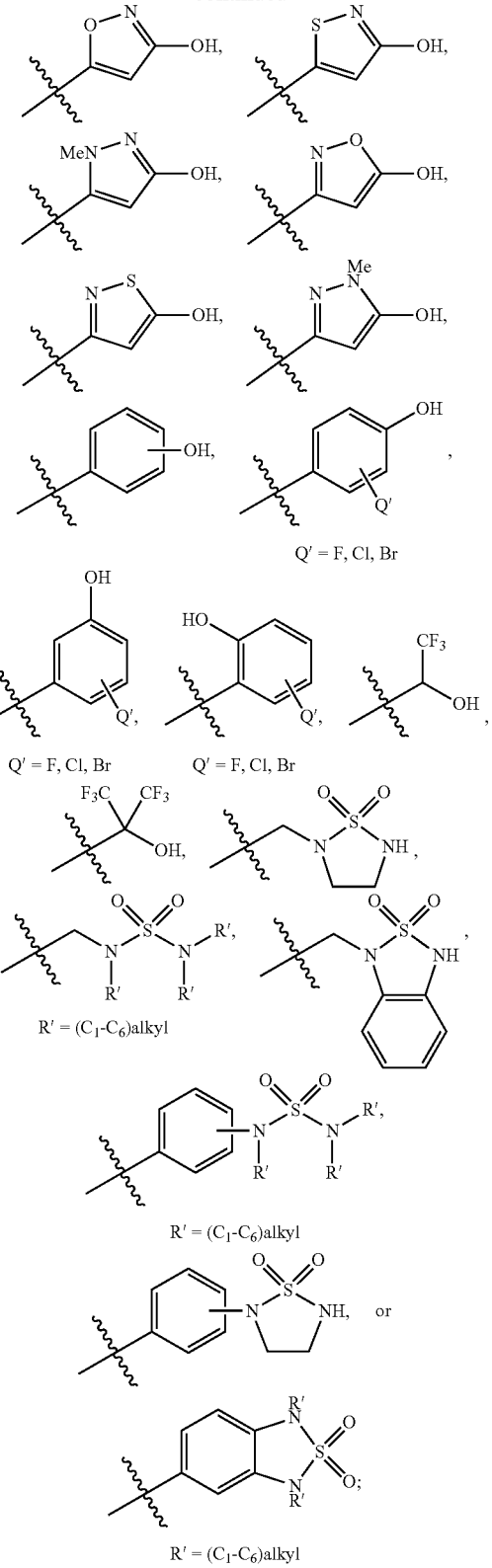

R$^1$ is selected from the group consisting of H, straight or branched (C$_1$-C$_6$) alkyl, and (C$_1$-C$_6$)-alkyl-C(O)—;

X, Y, and Z are each independently selected from the group consisting of a bond, —C(R')(R''')—, —

$C(R''')_2$—, =CR'''—, —CHF—, —CF$_2$—, —NR'''—, =N—, —O—, —C(O)—, —S—, —S(O)— and —SO$_2$—, wherein any two adjacent —CH$_2$— groups optionally represent two members of a (C$_3$-C$_{14}$)-cycloalkylenyl group or a (C$_3$-C$_{14}$)-heterocycloalkylenyl group, no more than two of X, Y, and Z simultaneously represent a bond; and no two adjacent members of X, Y, and Z are simultaneously —O—, —S—, =N—, or —NR'''—;

either X and Y or Y and Z optionally represent a fused aryl or heteroaryl ring having from 3 to 7 ring member atoms, or Z and L optionally form a fused lactone ring having 4 to 7 ring member atoms including one or two O ring atoms;

m, n, p independently are integers between 0 and 2 inclusive, wherein at least one of m, n, p is not 0;

⌊⌉ optionally represents one or more double bonds;

R$^2$ and R$^3$ are each independently selected from hydrogen, straight or branched (C$_1$-C$_6$)alkyl, or C(O)—R', or R$^2$ and R$^3$ taken together with the boron atom and oxygen atoms to which they are bound form a 4-, 5-, 6- or 7-membered ring that is fully saturated, or partially saturated, or R$^2$ and R$^3$ taken together with the boron atom and oxygen atoms to which they are bound form a diester of the boronic acid and pinanediol, or R$^2$ and R$^3$ taken together with the boron atom and oxygen atoms to which they are bound form an anhydride of the boronic acid and N-methyliminodiacetic acid;

V is selected from —C(R')(R")—, —NR'—, —C(F)(R')— or —CHF—;

W is selected from —C(R')(R''')—, —C(R''')$_2$—, —CHF—, —CF$_2$—, —NR'''—, or —C(O)—;

D is selected from the straight or branched (C$_1$-C$_5$) alkylene, straight or branched (C$_2$-C$_8$)-alkenylene, straight or branched (C$_2$-C$_8$)alkynylene, (C$_3$-C$_{14}$) arylene, or (C$_3$-C$_{14}$)cycloalkylene, wherein one or more —CH$_2$— groups in D are optionally and independently replaced with a moiety selected from —O—, —NR'—, —S—, —S(O)—, —S(O)$_2$—, —C(R')(R")—; —CHF— or —CF$_2$—, or wherein any two adjacent —CH$_2$— groups optionally represent two members of a (C$_3$-C$_{14}$)-cycloalkylenyl group; and wherein no two adjacent —CH$_2$— groups are simultaneously replaced with O, NR', S, SO, or SO$_2$;

R', R" and R''' are each independently selected from H, OH, S(O)R$^d$, S(O)$_2$R$^d$, (C$_1$-C$_8$)alkyl, (C$_3$-C$_6$)aryl, —NH$_2$, —NH(C$_1$-C$_6$)alkyl, —N[(C$_1$-C$_6$)alkyl]$_2$, —NR$^d$SO$_2$N(R$^e$)$_2$, —NR$^d$C(NR$^e$)N(R$^g$)$_2$, —C(O)NR$^d$R$^e$, —C(O)(C$_1$-C$_6$)alkyl, —C(O)(C$_3$-C$_{14}$)aryl, —C(O)O(C$_1$-C$_6$)alkyl, —C(O)O(C$_3$-C$_{14}$)aryl, (C$_3$-C$_6$)cycloalkyl, (C$_3$-C$_{14}$)heterocycloalkyl, —C(O)(C$_3$-C$_{14}$) heterocycloalkyl, (C$_3$-C$_{14}$)heteroaryl, (C$_3$-C$_{14}$)aryl-(C$_1$-C$_6$)alkylene-, —C(O) (C$_3$-C$_{14}$)aryl-(C$_1$-C$_6$) alkylene-, —C(O)(C$_3$-C$_{14}$)aryl, (C$_3$-C$_6$)cycloalkyl-(C$_1$-C$_6$)alkylene-, (C$_3$-C$_{14}$)heteroaryl-(C$_1$-C$_6$) alkylene-, (C$_3$-C$_{14}$)heterocyclyl-(C$_1$-C$_6$)alkylene-; and wherein any alkyl, alkylene, aryl, heteroaryl, cycloalkyl, or heterocycloalkyl is optionally substituted with one or more selected from the group consisting of halogen, oxo, (C$_1$-C$_3$)alkyl, —COOH, —CN, —NO$_2$, —OH, —NR$^d$R$^e$, —NR$^g$S(O)$_2$R$^h$, (C$_1$-C$_6$)alkoxy, (C$_3$-C$_{14}$)aryl, heterocyclyl having from 3 to 7 ring member atoms, (C$_1$-C$_8$)haloalkyl or (C$_3$-C$_{14}$)aryloxy;

wherein R$^d$, R$^e$, R$^g$, and R$^h$ are each independently selected from H, straight or branched (C$_1$-C$_6$)alkyl, optionally substituted (C$_3$-C$_{14}$)aryl(C$_1$-C$_6$)alkylene-, optionally substituted (C$_3$-C$_{14}$)aryl, (C$_1$-C$_6$)hydroxyalkyl, (C$_1$-C$_6$)aminoalkyl, H$_2$N(C$_1$-C$_6$)alkylene-, optionally substituted (C$_3$-C$_6$)cycloalkyl, optionally substituted (C$_3$-C$_{14}$)heterocycloalkyl, optionally substituted (C$_3$-C$_{14}$)heteroaryl, optionally substituted (C$_3$-C$_{14}$)aryl-(C$_1$-C$_6$)alkylene-, NR'R"C (O)—, or (C$_3$-C$_6$)aryl-(C$_3$-C$_{14}$)-cycloalkylene-, or R' and R''' taken together represent —(C$_1$-C$_3$)alkylene-N(Me)-(C$_1$-C$_3$)alkylene-;

or a tautomer, stereoisomer, racemate, pharmaceutically acceptable salt, ester, solvate, polymorph, active metabolite, or prodrug thereof;

with the proviso that the compound according to the Formula (I) is neither 1-amino-3-(4-boronobutyl)cyclobutane-1-carboxylic acid,
1-amino-3-(2-boronoethyl)cyclobutane-1-carboxylic acid,
1-amino-3-(boronomethyl)cyclobutane-1-carboxylic acid,
1-amino-3-(3-boronopropyl)cyclopentane-1-carboxylic acid, nor
1-amino-3-(3-boronopropyl)cyclohexane-1-carboxylic acid.

Also provided herein are pharmaceutical compositions, comprising (i) a therapeutically effective amount of at least one compound of the invention, or a stereoisomer, tautomer, pharmaceutically acceptable salt, solvate, or prodrug thereof; and (ii) a pharmaceutically acceptable carrier, including, but not limited to, bioavailability enhancers, penetration enhancers, biopolymers, PLGA-based nanoparticles, sugar-based nanoparticles, coating to avoid the deleterious effects of the stomach environment, either by protection of the compound of the invention or derivative thereof, or by release of the biologically active material beyond the stomach environment, such as in the intestine.

In another aspect, the invention provides a method for inhibiting arginase I, arginase II, or a combination thereof in a cell, comprising contacting the cell with at least one compound according to the invention, or a stereoisomer, tautomer, pharmaceutically acceptable salt, solvate, or prodrug thereof.

In another aspect, the invention provides a method for the treatment or prevention of a disease or condition associated with expression or activity of arginase I, arginase II, or a combination thereof in a subject, comprising administering to the subject a therapeutically effective amount of at least one compound according to the invention, or a stereoisomer, tautomer, pharmaceutically acceptable salt, solvate, or prodrug thereof.

In another aspect, the invention provides use of a compound according to the invention, or a stereoisomer, tautomer, pharmaceutically acceptable salt, solvate, or prodrug thereof in the manufacture of a medicament for the treatment or prevention of a disease or condition associated with expression or activity of arginase I, arginase II, or a combination thereof.

In another aspect, the invention provides a compound according to the invention, or a stereoisomer, tautomer, pharmaceutically acceptable salt, solvate, or prodrug thereof for the treatment or prevention of a disease or condition associated with expression or activity of arginase I, arginase II, or a combination thereof.

In another aspect, the invention provides use of a compound according to the invention, or a stereoisomer, tautomer, pharmaceutically acceptable salt, solvate, or prodrug thereof, for protecting an organ during transport.

DETAILED DESCRIPTION

The present invention is based on a surprising finding that some small molecule arginase inhibitors possess very high activity accompanied by superior pharmacokinetics.

Definitions

The articles "a" and "an" are used herein to refer to one or to more than one (i.e., to at least one) of the grammatical object of the article. By way of example, "an element" means one element or more than one element.

The terms used herein may be preceded and/or followed by a single dash "-", or a double dash "=", to indicate the bond order of the bond between the named substituent and its parent moiety; a single dash indicates a single bond and a double dash indicates a double bond. In the absence of a single or double dash, it is understood that a single bond is formed between the substituent and its parent moiety; further, substituents are intended to be read "from left to right," unless a dash indicates otherwise. For example, ($C_1$-$C_6$)-alkoxycarbonyloxy and —OC(O)O($C_1$-$C_6$)alkyl indicate the same functionality; similarly arylalkyl and -alkylaryl indicate the same functionality.

The term "heteroatom" is art-recognized and refers to an atom of any element other than carbon or hydrogen. Illustrative heteroatoms include boron, nitrogen, oxygen, phosphorus, sulfur and selenium.

The term "alkyl" as used herein is a term of art and refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight-chain or branched-chain alkyl has about 30 or fewer carbon atoms in its backbone (e.g., $C_1$-$C_{30}$ for straight chain, $C_3$-$C_{30}$ for branched chain), and alternatively, about 20 or fewer, 10 or fewer, or preferably 1-6 carbons.

Representative examples of alkyl include, but are not limited to, methyl, ethyl, n-propyl, isopropyl, n-butyl, sec-butyl, isobutyl, tert-butyl, n-pentyl, isopentyl, neopentyl, and n-hexyl.

The term "cycloalkyl" means mono- or bicyclic or bridged saturated or partially saturated carbocyclic rings, each having from 3 to 12 carbon atoms. Certain cycloalkyls have from 3-8, or from 3-6 carbon atoms in their ring structure. Certain cycloalkyls have from 5-12 carbon atoms in their ring structure, and may have 6-10 carbons in the ring structure.

Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems include bridged monocyclic rings and fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —($CH_2$)$_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted.

The term "heterocyclyl" as used herein refers to a radical of a non-aromatic ring system, including, but not limited to, monocyclic, bicyclic, and tricyclic rings, which can be completely saturated or which can contain one or more units of unsaturation, for the avoidance of doubt, the degree of unsaturation does not result in an aromatic ring system, and having 3 to 14, or 3 to 12 atoms including at least one heteroatom, such as nitrogen, oxygen, or sulfur. More preferred heterocycloalkyl groups have from 5-10 ring members where from 1-4 of the ring members are hetero atoms selected from the group consisting of O, N, and S, the remaining ring atoms being C. For purposes of exemplification, which should not be construed as limiting the scope of this invention, the following are examples of heterocyclic rings: aziridinyl, azirinyl, oxiranyl, thiiranyl, thiirenyl, dioxiranyl, diazirinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, azetyl, oxetanyl, oxetyl, thietanyl, thietyl, diazetidinyl, dioxetanyl, dioxetenyl, dithietanyl, dithietyl, furyl, dioxalanyl, pyrrolyl, oxazolyl, thiazolyl, imidazolyl, oxadiazolyl, thiadiazolyl, triazolyl, triazinyl, isothiazolyl, isoxazolyl, thiophenyl, pyrazolyl, tetrazolyl, pyridyl, pyridazinyl, pyrimidinyl, pyrazinyl, triazinyl, tetrazinyl, quinolinyl, isoquinolinyl, quinoxalinyl, quinazolinyl, pyridopyrazinyl, benzoxazolyl, benzothiophenyl, benzimidazolyl, benzothiazolyl, benzoxadiazolyl, benzthiadiazolyl, indolyl, benztriazolyl, naphthyridinyl, azepines, azetidinyl, morpholinyl, oxadiazolinyl, oxadiazolidinyl, oxazolinyl, oxazolidinyl, oxopiperidinyl, oxopyrrolidinyl, piperazinyl, piperidinyl, pyranyl, pyrazolinyl, pyrazolidinyl, pyrrolinyl, pyrrolidinyl, quinicludinyl, thiomorpholinyl, tetrahydropyranyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. A heterocyclyl group is optionally substituted by one or more substituents as described below.

As used herein, the term "heterocyclylene" refers to a bivalent heterocyclyl (heterocycloalkyl) group, i.e., a cyclic alkylene group, having from 3-10 members and from 1-4 hetero atoms selected from S, O, and N. An example is piperidine-2,3-dicarboxylic acid, i.e., in that compound, the piperidine ring is a heterocyclyl group.

The term "heteroatom" is art-recognized, and includes an atom of any element other than carbon or hydrogen. Illustrative heteroatoms include boron, nitrogen, oxygen, phosphorus, sulfur and selenium, and alternatively oxygen, nitrogen or sulfur.

The term "cycloalkylalkyl" as used herein refers to an alkyl group substituted with one or more cycloalkyl groups.

The term "heterocycloalkylalkyl" as used herein refers to an alkyl group substituted with one or more heterocycloalkyl (i.e., heterocyclyl) groups.

The term "alkenyl" as used herein means a straight or branched chain hydrocarbon radical containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl. The unsaturated bond(s) of the alkenyl group can be located anywhere in the moiety and can have either the (Z) or the (E) configuration about the double bond(s).

The term "alkynyl" as used herein means a straight or branched chain hydrocarbon radical containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkylene" is art-recognized, and as used herein pertains to a diradical obtained by removing two hydrogen atoms of an alkyl group, as defined above. In one embodiment an alkylene refers to a disubstituted alkane, i.e., an alkane substituted at two positions with substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. That is, in one embodiment, a "substituted alkyl" is an "alkylene".

The term "amino" is a term of art and as used herein refers to both unsubstituted and substituted amines, e.g., a moiety that may be represented by the general formulas:

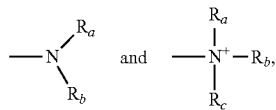

wherein $R_a$, $R_b$, and $R_c$ each independently represent a hydrogen, an alkyl, an alkenyl, —(CH$_2$)$_x$—R$_d$, or R$_a$ and R$_b$, taken together with the N atom to which they are attached complete a heterocycle having from 4 to 8 atoms in the ring structure; R$_d$ represents an aryl, a cycloalkyl, a cycloalkenyl, a heterocyclyl or a polycyclyl; and x is zero or an integer in the range of 1 to 8. In certain embodiments, only one of R$_a$ or R$_b$ may be a carbonyl, e.g., R$_a$, R$_b$, and the nitrogen together do not form an imide. In other embodiments, R$_a$ and R$_b$ (and optionally R$_c$) each independently represent a hydrogen, an alkyl, an alkenyl, or —(CH$_2$)$_x$—R$_d$.

In certain embodiments, the term "amino" refers to —NH$_2$.

The term "amido", as used herein, means —NHC(=O)—, wherein the amido group is bound to the parent molecular moiety through the nitrogen. Examples of amido include alkylamido such as CH$_3$C(=O)N(H)— and CH$_3$CH$_2$C(=O)N(H)—.

The term "acyl" is a term of art and as used herein refers to any group or radical of the form RCO— where R is any organic group, e.g., alkyl, aryl, heteroaryl, aralkyl, and heteroaralkyl. Representative acyl groups include acetyl, benzoyl, and malonyl.

The term "aminoalkyl" as used herein refers to an alkyl group substituted with one or more one amino groups. In one embodiment, the term "aminoalkyl" refers to an aminomethyl group.

The term "aminoacyl" is a term of art and as used herein refers to an acyl group substituted with one or more amino groups.

The term "aminothionyl" as used herein refers to an analog of an aminoacyl in which the O of RC(O)— has been replaced by sulfur, hence is of the form RC(S)—.

The term "phosphoryl" is a term of art and as used herein may in general be represented by the Formula:

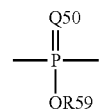

wherein Q50 represents S or O, and R59 represents hydrogen, a lower alkyl or an aryl; for example, —P(O)(OMe)- or —P(O)(OH)$_2$. When used to substitute, e.g., an alkyl, the phosphoryl group of the phosphorylalkyl may be represented by the general formulas:

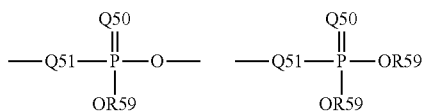

wherein Q50 and R59, each independently, are defined above, and Q51 represents O, S or N; for example, —O—P(O)(OH)OMe or —NH—P(O)(OH)$_2$. When Q50 is S, the phosphoryl moiety is a "phosphorothioate."

The term "aminophosphoryl" as used herein refers to a phosphoryl group substituted with at least one amino group, as defined herein; for example, —P(O)(OH)NMe$_2$.

The term "azide" or "azido", as used herein, means an —N$_3$ group.

The term "carbonyl" as used herein refers to —C(=O)—.

The term "thiocarbonyl" as used herein refers to —C(=S)—.

The term "alkylphosphoryl" as used herein refers to a phosphoryl group substituted with at least one alkyl group, as defined herein; for example, —P(O)(OH)Me.

The term "alkylthio" as used herein refers to alkyl-S—.

The term "carboxy", as used herein, means a —CO$_2$H group.

The term "aryl" is a term of art and as used herein refers to includes monocyclic, bicyclic and polycyclic aromatic hydrocarbon groups, for example, benzene, naphthalene, anthracene, 1,2,3,4-tetrahydronaphthalene, indene, 2,3-dihydroindene, and pyrene. The aromatic ring may be substituted at one or more ring positions with one or more substituents, such as halogen, azide, alkyl, aralkyl, alkenyl, alkynyl, cycloalkyl, cycloalkylalkyl, (cycloalkyl)alkoxyl, hydroxyl, alkoxyl, amino, nitro, sulfhydryl, imino, amido, phosphonate, phosphinate, carbonyl, carboxyl, silyl, ether, alkylthio, sulfonyl, aminosulfonyl, sulfonamido, ketone, aldehyde, ester, heterocyclyl, heterocyclylalkyl, aromatic or heteroaromatic moieties, aminoalkyl, haloalkyl, fluoroalkyl (such as trifluoromethyl), haloalkoxyl, cyano, or the like. The term "aryl" also includes polycyclic ring systems having two or more cyclic rings in which two or more carbons are common to two adjoining rings (the rings are "fused rings") wherein at least one of the rings is an aromatic hydrocarbon, e.g., the other cyclic rings may be cycloalkyls, cycloalkenyls, cycloalkynyls, aryls, heteroaryls, and/or heterocyclyls. Representative examples of the polcyclic aryl ring systems include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-6-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl, or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted. In certain embodiments, the term "aryl" refers to a phenyl group.

The term "heteroaryl" is a term of art and as used herein refers to a monocyclic, bicyclic, and polycyclic aromatic group having 3 to 14, 5 to 14, or 3 to 12 total atoms including one or more heteroatoms such as nitrogen, oxygen, or sulfur in the ring structure. More preferred heteroaryl groups have from 5-10 ring members where from 1-4 of the ring members are hetero atoms selected from the group consisting of O, N, and S. Exemplary heteroaryl groups include, for example, azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl, and the like. The "heteroaryl" may be substituted at one or more ring positions with one or more substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "heteroaryl" also includes polycyclic ring systems having two or more cyclic rings in which two or more carbons are common to two adjoining rings (the rings are "fused rings") wherein at least one of the rings is an aromatic group having one or more heteroatoms in the ring structure, e.g., the other cyclic rings may be cycloalkyls, cycloalkenyls, cycloalkynyls, aryls, heteroaryls, and/or heterocyclyls. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. Any heteroaryl or bicyclic heteroaryl can be optionally substituted as detailed below.

The term "aralkyl", "arylalkyl", or "aryl($C_1$-$C_6$)alkyl" is a term of art and as used herein refers to an alkyl group, for example a $C_1$-$C_6$ alkyl group, substituted with an aryl group, wherein the moiety is appended to the parent molecule through the alkyl group.

The term "heteroaralkyl", "heteroarylalkyl", or "heteroaryl($C_1$-$C_6$)alkyl" is a term of art and as used herein refers to an alkyl group, for example a $C_1$-$C_6$ alkyl group, substituted with a heteroaryl group, appended to the parent molecular moiety through the alkyl group.

The term "alkoxy" or "alkoxyl" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxycarbonyl" means an alkoxy group, as defined herein, appended to the parent molecular moiety through a carbonyl group, represented by —C(=O)—, as defined herein. Representative examples of alkoxycarbonyl include, but are not limited to, methoxycarbonyl, ethoxycarbonyl, and tert-butoxycarbonyl.

The term "alkylcarbonyl", as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "arylcarbonyl", as used herein, means an aryl group, as defined herein, appended to the parent molecular moiety through a carbonyl group, as defined herein. Representative examples of arylcarbonyl include, but are not limited to, benzoyl and (2-pyridinyl)carbonyl.

The term "alkylcarbonyloxy" and "arylcarbonyloxy", as used herein, means an alkylcarbonyl or arylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. Representative examples of arylcarbonyloxy include, but are not limited to phenylcarbonyloxy.

The term "alkenoxy" or "alkenoxyl" means an alkenyl group, as defined herein, appended to the parent molecular moiety through an oxygen atom. Representative examples of alkenoxyl include, but are not limited to, 2-propen-1-oxyl (i.e., $CH_2$=CH—$CH_2$—O—) and vinyloxy (i.e., $CH_2$=CH—O—).

The term "aryloxy" as used herein means an aryl group, as defined herein, appended to the parent molecular moiety through an oxygen atom.

The term "heteroaryloxy" as used herein means a heteroaryl group, as defined herein, appended to the parent molecular moiety through an oxygen atom.

The term "carbocyclyl" as used herein means a monocyclic or multicyclic (e.g., bicyclic, tricyclic, etc.) hydrocarbon radical containing from 3 to 12 carbon atoms that is completely saturated or has one or more unsaturated bonds, and for the avoidance of doubt, the degree of unsaturation does not result in an aromatic ring system (e.g., phenyl). Examples of carbocyclyl groups include 1-cyclopropyl, 1-cyclobutyl, 2-cyclopentyl, 1-cyclopentenyl, 3-cyclohexyl, 1-cyclohexenyl and 2-cyclopentenylmethyl.

The terms "cyano" and "nitrile" is a term of art and as used herein refers to —CN.

The term "nitro", as used herein, means —NO$_2$.

The term "halo" is a term of art and as used herein refers to —F, —Cl, —Br, or —I.

The term "haloalkyl" as used herein refers to an alkyl group, as defined herein, wherein some or all of the hydrogens are replaced with halogen atoms. The term "haloalkoxyl" refers to an alkoxy group, as defined herein, wherein some or all of the hydrogens are replaced with halogen atoms. An exemplary haloalkyl group is trifluoromethyl.

The term "hydroxy" is a term of art and as used herein refers to —OH.

The term "hydroxyalkyl", as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "silyl", as used herein, includes hydrocarbyl derivatives of the silyl (H$_3$Si—) group (i.e., (hydrocarbyl)$_3$Si—), wherein a hydrocarbyl groups are univalent groups formed by removing a hydrogen atom from a hydrocarbon, e.g., ethyl, phenyl. The hydrocarbyl groups can be combinations of differing groups which can be varied in order to provide a number of silyl groups, such as trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy", as used herein, means a silyl group, as defined herein, is appended to the parent molecule through an oxygen atom.

Certain compounds contained in compositions of the present invention may exist in particular geometric or stereoisomeric forms. In addition, compounds of the present invention may also be optically active. The present invention contemplates all such compounds, including cis- and trans-isomers, (R)- and (S)-enantiomers, diastereoisomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, fragmentation, decomposition, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, halogen, azide, alkyl, aralkyl, alkenyl, alkynyl, cycloalkyl, cycloalkylalkyl, (cycloalkyl)alkoxyl, hydroxyl, alkoxyl, amino, nitro, sulfhydryl, imino, amido, phosphonate, phosphinate, carbonyl, carboxyl, silyl, ether, alkylthio, sulfonyl, aminosulfonyl, sulfonamido, ketone, aldehyde, ester, heterocyclyl, heterocyclylalkyl, aromatic or heteroaromatic moieties, aminoalkyl, haloalkyl, fluoroalkyl (such as trifluoromethyl), haloalkoxyl, cyano, or other substitutents described above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group", as used herein, means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis, 2$^{nd}$ ed.*; Wiley: New York, 1991). Protected forms of the inventive compounds are included within the scope of this invention.

A "saturated" or "fully saturated" compound means that the referenced chemical structure does not contain any multiple carbon-carbon bonds. For example, a saturated cycloalkyl group as defined herein includes cyclohexyl, cyclopropyl, and the like.

A "unsaturated" or "partially saturated" compound means that the referenced chemical structure may contains on or more multiple carbon-carbon bonds, but is not aromatic. For example, a unsaturated cycloalkyl group as defined herein includes cyclohexenyl, cyclopentenyl, cyclohexadienyl, and the like.

For purposes of the invention, the chemical elements are identified in accordance with the Periodic Table of the Elements, CAS version, Handbook of Chemistry and Physics, 67th Ed., 1986-87, inside cover.

Other chemistry terms herein are used according to conventional usage in the art, as exemplified by The McGraw-Hill Dictionary of Chemical Terms (ed. Parker, S., 1985), McGraw-Hill, San Francisco, incorporated herein by reference). Unless otherwise defined, all technical and scientific terms used herein have the same meaning as commonly understood by one of ordinary skill in the art to which this invention pertains.

It will be apparent to one skilled in the art that certain compounds of this disclosure may exist in tautomeric forms, all such tautomeric forms of the compounds being within the scope of the disclosure. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure. Both the R and the S stereochemical isomers, as well as all mixtures thereof, are included within the scope of the disclosure.

The chemical structure of examples that are a mixture of diastereoisomers or a single diastereoisomer but with unknown relative configuration are drawn and named without defined stereochemical configuration.

In this document, compound structures that are depicted with particular stereochemistry and identified as being "racemic" (or "rac-") refer to an equimolar mixture of a pair of enantiomers as described at IUPAC. Compendium of Chemical Terminology, 2nd ed. (the "Gold Book"). Compiled by A. D. McNaught and A. Wilkinson. Blackwell Scientific Publications, Oxford (1997). XML on-line corrected version: http://goldbook.iupac.org (2006-) created by M. Nic, J. Jirat, B. Kosata; updates compiled by A. Jenkins. ISBN 0-9678550-9-8. https://doi.org/10.1351/goldbook.

Examples 1-22, 24-37, 40-41, 48-67 are racemic mixtures (i.e., not enantiomerically enriched). The structures (where drawn stereochemically) represent only relative configuration. Thus, racemates drawn stereochemically are named with prefix "rac-."

Examples 23, 38-39, 42-44, 46-47, 68-71 are enantiomerically enriched compounds, mostly with >99% of enantiomeric excess. The structures show absolute configuration of predominant enantiomer. Thus, the enantiomerically enriched compounds do not include the prefix "rac-" in their chemical names.

Example 25 is a mixture of two diastereoisomers. The configuration in the structure around cyclohexane ring is relative and around pinanediol moiety is an absolute configuration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, pamoic (embonic), succinic, tartaric, glycolic, salicylic, citric, methanesulfonic, benzenesulfonic, benzoic, malonic, trifluoroacetic, trichloroacetic, naphthalene-2-sulfonic, and other acids.

Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of Formula (I). As another example, the salt may comprise less than one inorganic or organic acid molecule per molecule of base, such as two molecules of compound of Formula (I) per molecule of tartaric acid.

As used herein, a protic solvent is a solvent that has a hydrogen atom bound to an oxygen (as in a hydroxyl group) or a nitrogen (as in an amine group). In general terms, any solvent that contains labile $H^+$ is called a protic solvent. The molecules of such solvents readily donate protons ($H^+$) to reagents. In contrast, an aprotic solvent is a solvent that does not have a hydrogen atom bound to an oxygen (as in a hydroxyl group) or a nitrogen (as in an amine group), and it cannot donate hydrogen.

As used herein, a polar protic solvent is a protic solvent that will dissolve many salts. In general, these solvents have high dielectric constants and high polarity. Non-limiting examples of polar protic solvents include acetic acid, ammonia, ethanol, formic acid, isopropanol, methanol, n-butanol, nitromethane, n-propanol, t-butanol, and water.

As used herein, a polar aprotic solvent is a solvent that will dissolve many salts, but lacks an acidic hydrogen; these solvents generally have intermediate to high dielectric constants and polarity. Non-limiting examples of polar aprotic solvents include acetone, acetonitrile, dichloromethane (DCM), dimethyl sulfoxide (DMSO), ethyl acetate, hexamethylphosphoric triamide (HMPT), N,N-dimethylformamide (DMF), and tetrahydrofuran (THF).

As used herein, a nonpolar aprotic solvent is a solvent that will dissolve many salts, but lacks an acidic hydrogen; these solvents generally have low dielectric constants and polarity. Non-limiting examples of nonpolar aprotic solvents include benzene, chloroform, cyclohexane, diethyl ether, hexane, pentane, and toluene.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, the mode of administration, the bioavailability of the particular compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

"Modulating" or "modulate" refers to the treating, prevention, suppression, enhancement or induction of a function, condition or disorder.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

As used herein, "subject" refers to a warm blooded animal such as a mammal, preferably a human, or a human child, which is afflicted with, or has the potential to be afflicted with one or more diseases and disorders described herein.

"$EC_{50}$" refers to a dosage, concentration or amount of a particular test compound that elicits a dose-dependent response at 50% of maximal expression of a particular response that is induced, provoked or potentiated by the particular test compound.

"$IC_{50}$" refers to an amount, concentration or dosage of a particular test compound that achieves a 50% inhibition of a maximal response in an assay that measures such response.

Compounds of the Invention

In one aspect, the invention provides a compound represented by Formula (I):

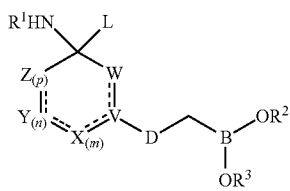

(I)

wherein:

L is —$CO_2H$, —C(O)O(($C_1$-$C_6$)alkyl), —$CO_2CH_2$—O-pivaloyl, —$CO_2CH_2OCO_2$-isopropyl, —C(O)NHOH, —C(O)NHCN, —C(O)$NH_2$, —C(O)NH(($C_1$-$C_6$)alkyl), —C(O)N(($C_1$-$C_6$)alkyl)$_2$, —C(O)NH(aryl), —C(O)N(aryl)(($C_1$-$C_6$)alkyl), —C(O)N(aryl)$_2$, —C(O)NH(($C_1$-$C_6$)haloalkyl), —S(O)$_2$$NH_2$, —S(O)$_2$NH(($C_1$-$C_6$)alkyl), —S(O)$_2$NH(($C_1$-$C_6$)haloalkyl), —S(O)$_2$NH(aryl), —S(O)$_2$NHC(O)(($C_1$-$C_6$)alkyl), —S(O)$_2$NHC(O)(($C_1$-$C_6$)haloalkyl), —S(O)$_2$NHC(O)(aryl), —N(H)S(O)$_2$(($C_1$-$C_6$)alkyl), —N(H)S(O)$_2$(aryl), N(H)S(O)$_2$(($C_1$-$C_6$)haloalkyl), —NHC(O)(($C_1$-$C_6$)alkyl), —NHC(O)(($C_1$-$C_6$)haloalkyl), —NHC(O)(aryl), —NHC(O)NH(($C_1$-$C_6$)alkyl), —NHC(O)NH(aryl), —C(O)N(H)S(O)$_2$(($C_1$-$C_6$)alkyl), —C(O)N(H)S(O)$_2$(aryl), —C(O)N(H)S(O)$_2$(($C_1$-$C_6$)haloalkyl), —P(O)(OH)$_2$, —$CF_3$,

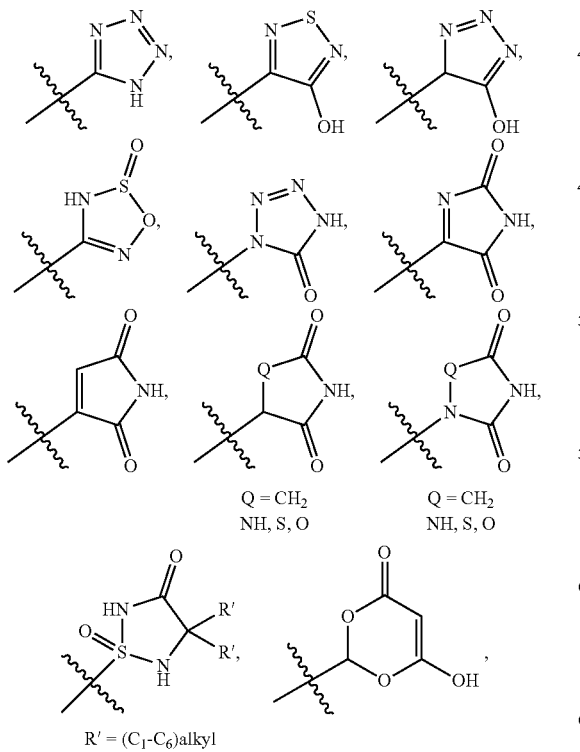

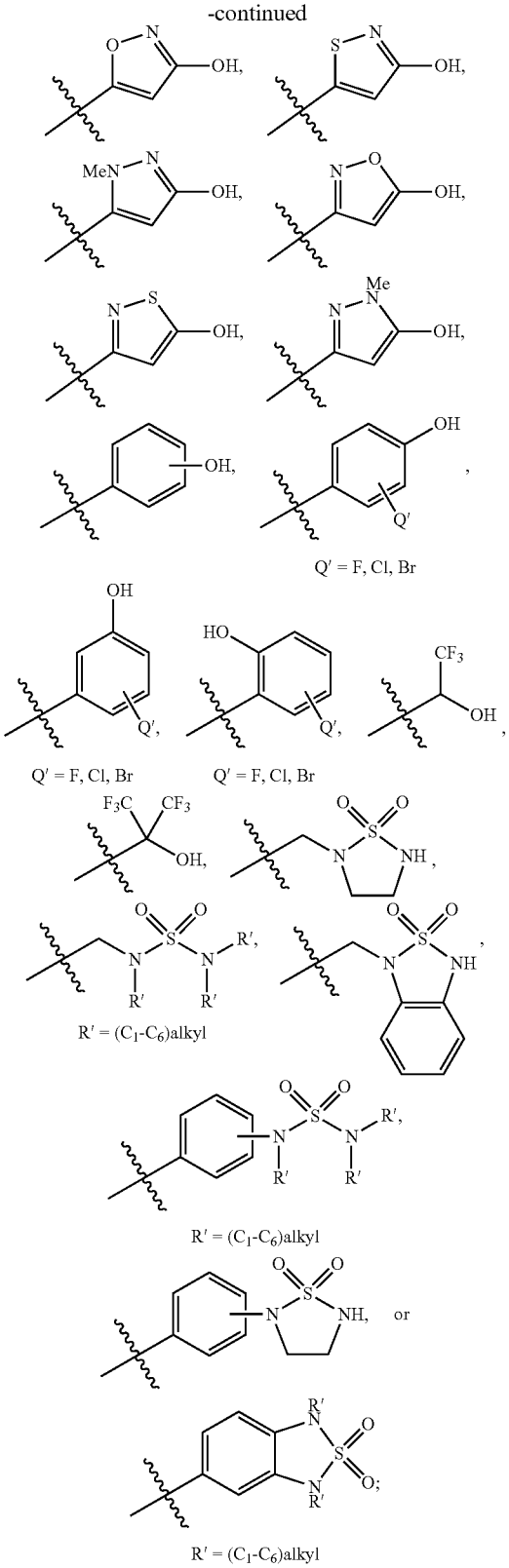

$R^1$ is selected from the group consisting of H, straight or branched ($C_1$-$C_6$) alkyl, and ($C_1$-$C_6$)-alkyl-C(O)—;

X, Y, and Z are each independently selected from the group consisting of a bond, —C(R')(R''')—, —

C(R''')$_2$—, =CR'''—, —CHF—, —CF$_2$—, —NR'''—, =N—, —O—, —C(O)—, —S—, —S(O)— and —SO$_2$—, wherein any two adjacent —CH$_2$— groups optionally represent two members of a (C$_3$-C$_{14}$)-cycloalkylenyl group or a (C$_3$-C$_{14}$)-heterocycloalkylenyl group, no more than two of X, Y, and Z simultaneously represent a bond; and no two adjacent members of X, Y, and Z are simultaneously —O—, —S—, =N—, or —NR'''—;

either X and Y or Y and Z optionally represent a fused aryl or heteroaryl ring having from 3 to 7 ring member atoms, or Z and L optionally form a fused lactone ring having 4 to 7 ring member atoms including one or two O ring atoms;

m, n, p independently are integers between 0 and 2 inclusive, wherein at least one of m, n, p is not 0;

⌊⌡ optionally represents one or more double bonds;

R$^2$ and R$^3$ are each independently selected from hydrogen, straight or branched (C$_1$-C$_6$)alkyl, or C(O)—R', or R$^2$ and R$^3$ taken together with the boron atom and oxygen atoms to which they are bound form a 4-, 5-, 6- or 7-membered ring that is fully saturated, or partially saturated, or R$^2$ and R$^3$ taken together with the boron atom and oxygen atoms to which they are bound form a diester of the boronic acid and pinanediol, or R$^2$ and R$^3$ taken together with the boron atom and oxygen atoms to which they are bound form an anhydride of the boronic acid and N-methyliminodiacetic acid;

V is selected from —C(R')(R'')—, —NR'—, or —C(F)(R')—, —CHF—;

W is selected from —C(R')(R''')—, —C(R''')$_2$—, —CHF—, —CF$_2$—, —NR'''—, or —C(O)—;

D is selected from the straight or branched (C$_1$-C$_5$) alkylene, straight or branched (C$_2$-C$_8$)-alkenylene, straight or branched (C$_2$-C$_5$)alkynylene, (C$_3$-C$_{14}$) arylene, or (C$_3$-C$_{14}$)cycloalkylene, wherein one or more —CH$_2$— groups in D are optionally and independently replaced with a moiety selected from 0, NR', S, SO, SO$_2$, or CR'R''; —CHF—, CF$_2$—, or wherein any two adjacent —CH$_2$— groups optionally represent two members of a (C$_3$-C$_{14}$)-cycloalkylenyl group; and wherein no two adjacent —CH$_2$— groups are simultaneously replaced with O, NR', S, SO, or SO$_2$;

R', R'' and R''' are each independently selected from H, OH, S(O)R$^d$, S(O)$_2$R$^d$, (C$_1$-C$_8$)alkyl, (C$_3$-C$_6$)aryl, —NH$_2$, —NH(C$_1$-C$_6$)alkyl, —N[(C$_1$-C$_6$)alkyl]$_2$, —NR$^d$SO$_2$N(R')$_2$, —NR$^d$C(NR$^e$)N(R$^g$)$_2$, —C(O)NR$^d$R$^e$, —C(O)(C$_1$-C$_6$)alkyl, —C(O)(C$_3$-C$_{14}$)aryl, —C(O)O(C$_1$-C$_6$)alkyl, —C(O)O(C$_3$-C$_{14}$)aryl, (C$_3$-C$_6$)cycloalkyl, (C$_3$-C$_{14}$)heterocycloalkyl, —C(O)(C$_3$-C$_{14}$)heterocycloalkyl, (C$_3$-C$_{14}$)heteroaryl, (C$_3$-C$_{14}$)aryl-(C$_1$-C$_6$)alkylene-, —C(O) (C$_3$-C$_{14}$)aryl-(C$_1$-C$_6$)alkylene-, —C(O)(C$_3$-C$_{14}$)aryl, (C$_3$-C$_6$)cycloalkyl-(C$_1$-C$_6$)alkylene-, (C$_3$-C$_{14}$)heteroaryl-(C$_1$-C$_6$)alkylene-, (C$_3$-C$_{14}$)heterocyclyl-(C$_1$-C$_6$)alkylene-; and wherein any alkyl, alkylene, aryl, heteroaryl, cycloalkyl, or heterocycloalkyl is optionally substituted with one or more selected from the group consisting of halogen, (C$_1$-C$_3$) alkyl, —COOH, —CN, —NO$_2$, —OH, —NR$^d$R$^e$, —NR$^g$S(O)$_2$R$^h$, (C$_1$-C$_6$)alkoxy, (C$_3$-C$_{14}$)aryl, heterocyclyl having from 3 to 7 ring member atoms, (C$_1$-C$_8$) haloalkyl or (C$_3$-C$_{14}$)aryloxy;

wherein R$^d$, R$^e$, R$^g$, and R$^h$ are each independently selected from H, straight or branched (C$_1$-C$_6$)alkyl, optionally substituted (C$_3$-C$_{14}$)aryl(C$_1$-C$_6$)alkylene-, optionally substituted (C$_3$-C$_{14}$)aryl, (C$_1$-C$_6$)hydroxyalkyl, (C$_1$-C$_6$)aminoalkyl, H$_2$N(C$_1$-C$_6$)alkylene-, optionally substituted (C$_3$-C$_6$)cycloalkyl, optionally substituted (C$_3$-C$_{14}$)heterocycloalkyl, optionally substituted (C$_3$-C$_{14}$)heteroaryl, optionally substituted (C$_3$-C$_{14}$) aryl-(C$_1$-C$_6$)alkylene-, NR'R''C(O)—, or (C$_3$-C$_6$)aryl-(C$_3$-C$_{14}$)-cycloalkylene-, or R' and R''' taken together represent —(C$_1$-C$_3$)alkyl-N(Me)-(C$_1$-C$_3$)alkyl-, or a tautomer, stereoisomer, racemate, pharmaceutically acceptable salt, ester, solvate, polymorph, active metabolite, or prodrug thereof;

with the proviso that the compound according to the Formula (I) is neither 1-amino-3-(4-boronobutyl)cyclobutane-1-carboxylic acid,
1-amino-3-(2-boronoethyl)cyclobutane-1-carboxylic acid,
1-amino-3-(boronomethyl)cyclobutane-1-carboxylic acid,
1-amino-3-(3-boronopropyl)cyclopentane-1-carboxylic acid, nor
1-amino-3-(3-boronopropyl)cyclohexane-1-carboxylic acid.

The above-defined general Formula (I) covers certain compounds of the invention, which can be described in more detail as follows.

In certain embodiments, L is CO$_2$H.
In certain embodiments, R$^1$ is H or CH$_3$.
In certain embodiments, R$^2$ is H and R$^3$ is H.
In certain embodiments, X is —CH$_2$— or C(Me)$_2$.
In certain embodiments, Y is —CH$_2$— or C(Me)$_2$.
In certain embodiments, W is —CH$_2$—.
In certain embodiments, D is —CH$_2$—.
In certain embodiments, V is =CH— or —CH(Me)-.
In certain embodiments, Z is selected from CH(OH), C(Me)OH, CH(CH$_2$NH$_2$), CH(CH$_2$NMe$_2$), CH(CH$_2$NHMe), CH(CH$_2$CH$_2$NMe$_2$), CH(CH$_2$-pyrrolidinyl), CH(CH$_2$-piperidinyl), or CH(CH$_2$CH$_2$-pyrrolidinyl).

In certain embodiments, p is 1, and n and m are 0 or 1.
In certain embodiments,
R$^1$ is H; R$^2$ is H; R$^3$ is H;
D is —CH$_2$—;
L is CO$_2$H, CO$_2$Et, CO$_2$CH$_2$—O-pivaloyl, or CO$_2$CH$_2$OCO$_2$-isopropyl;
V is C, CH, or CMe;
W is C, CH, CH$_2$, or CHMe;
X is CH, CH$_2$, CHOH, CHNH$_2$, CHCH$_2$NH$_2$, NBn, NH, CMe$_2$, CHCH$_2$NMe$_2$, CHCH$_2$-pyrrolidinyl, CHCH$_2$CH$_2$-pyrrolidinyl, CHCH$_2$-piperidinyl, or CHCH$_2$CH$_2$-piperidinyl;
Y is a bond or CH, CH$_2$, CHOH, CHNMe$_2$, CHCH$_2$NMe$_2$, CHCH$_2$CH$_2$NMe$_2$, CHCH$_2$-pyrrolidinyl, CHCH$_2$CH$_2$-pyrrolidinyl, CHNH$_2$, CMe$_2$, CHCH$_2$OH, CHCH$_2$-piperidinyl, or CHCH$_2$CH$_2$-piperidinyl;
Z is a bond or CH$_2$, CHOH, CHCH$_2$NMe$_2$, CHCH$_2$NH$_2$, CHCH$_2$-morpholinyl, CHCH$_2$NMeBn, CHCH$_2$-pyrrolidinyl, C(OH)Me, C(OH)-4-chlorobenzyl, CHCH$_2$-piperidinyl, CHCH$_2$CH$_2$-piperidinyl, C—CH$_2$-azetidinyl, CHCH$_2$-azetidinyl, CHCH$_2$CH$_2$-azetidinyl, CMeCH$_2$-azetidinyl, CHCH$_2$-azepanyl, CHCH$_2$-(4,4- dimethylpiperidinyl), CHCH$_2$-(8-azabicyclo[3.2.1]octyl), CHCH$_2$-(2,2,6,6-tetramethylpiperidinyl), C(Me)CH$_2$-pyrrolidinyl, CHCH$_2$-(7-azabicyclo[2.2.1]heptyl), CHCH$_2$-isoindolinyl, CHCH$_2$-(4,5-dichloroisoindolinyl), CHCH$_2$-tetrahydroisoquinolinyl, CHCH$_2$-(4-chlorophenyl-piperidinyl), CHCH$_2$—NHMe, CHCH$_2$—NHiPr, CHCH$_2$—NH-(4-chlorobenzyl), CHCH$_2$—N(Me)iPr, CHCH$_2$—NH—CH$_2$CF$_3$, CHCH$_2$—NMe-CH$_2$CF$_3$, CHCH$_2$—NHAc, CHCH$_2$—NHMs, CHCH$_2$—NH—SO$_2$NH$_2$, CHCH$_2$CH$_2$NH$_2$, CHCH$_2$—OH, CHCH$_2$—NH-(4-chlorophenyl), CHCHMe-pyrrolidinyl, CHNHMs, CHNHSO$_2$NH$_2$, CHCH$_2$SO$_2$NH$_2$, CHNH$_2$, CHNMe$_2$, CH-pyrrolidinyl, CHCH$_2$CH$_2$-pyrrolidinyl, or CHCH$_2$CH$_2$-piperidinyl;

m is 1 or 2; n is 0 or 1; and p is 0 or 1.

In certain embodiments,

R$^1$ is H; R$^2$ is H; R$^3$ is H;

D is —CH$_2$—;

L is CO$_2$H, CO$_2$Et, CO$_2$CH$_2$—O-pivaloyl, or CO$_2$CH$_2$OCO$_2$-isopropyl;

V is CH or CMe;

W is CH$_2$ or CHMe;

X is CH$_2$, CHOH, CHCH$_2$NH$_2$, NBn, NH, CMe$_2$, CHCH$_2$NMe$_2$, or CHCH$_2$-pyrrolidinyl;

Y is a bond or CH$_2$, CHOH, CHCH$_2$NMe$_2$, CHCH$_2$-pyrrolidinyl, CHNH$_2$, CMe$_2$, or CHCH$_2$OH;

Z is a bond or CH$_2$, CHOH, CHOMe, CHOAc, CHCH$_2$NMe$_2$, CHCH$_2$NH$_2$, CHCH$_2$-morpholinyl, CHCH$_2$NMeBn, CHCH$_2$-pyrrolidinyl, C(OH)Me, C(OH)-4-chlorobenzyl, CHCH$_2$-piperidinyl, CHCH$_2$-azetidinyl, CHCH$_2$-azepanyl, CHCH$_2$-(4,4-dimethylpiperidinyl), CHCH$_2$-(8-azabicyclo[3.2.1]octyl), CHCH$_2$-(2,2,6,6-tetramethylpiperidinyl), C(Me)CH$_2$-pyrrolidinyl, CHCH$_2$-(7-azabicyclo[2.2.1]heptyl), CHCH$_2$-isoindolinyl, CHCH$_2$-(4,5-dichloroisoindolinyl), CHCH$_2$-tetrahydroisoquinolinyl, CHCH$_2$-(4-chlorophenyl-piperidinyl), CHCH$_2$—NHMe, CHCH$_2$—NHiPr, CHCH$_2$—NH-(4-chlorobenzyl), CHCH$_2$—N(Me)iPr, CHCH$_2$—NH—CH$_2$CF$_3$, CHCH$_2$—NMe-CH$_2$CF$_3$, CHCH$_2$—NHAc, CHCH$_2$—NHMs, CHCH$_2$—NH—SO$_2$NH$_2$, CHCH$_2$CH$_2$NH$_2$, CHCH$_2$—OH, CHCH$_2$—NH-(4-chlorophenyl), CHCHMe-pyrrolidinyl, CHNHMs, CHNHSO$_2$NH$_2$, CHCH$_2$SO$_2$NH$_2$, CHNH$_2$, CHNMe$_2$, or CH-pyrrolidinyl;

m is 1; n is 0 or 1; and p is 0 or 1.

In certain embodiments,

R$^1$ is H; R$^2$ is H; R$^3$ is H;

D is —CH$_2$—;

L is CO$_2$H;

V is CH or CMe;

W is CH$_2$ or CHMe;

X is CH$_2$, CHOH, CHCH$_2$NH$_2$, NBn, or NH;

Y is CH$_2$;

Z is a bond or CH$_2$, CHOH, CHOMe, CHCH$_2$NMe$_2$, CHCH$_2$NH$_2$, CHCH$_2$-morpholinyl, CHCH$_2$NMeBn, or CHCH$_2$-pyrrolidinyl;

m is 1; n is 1; and p is 0 or 1.

In the above definitions, Ac denotes acetyl, Bn denotes benzyl, Et denotes ethyl, iPr denotes isopropyl, and Ms denotes methanesulfonyl.

In certain embodiments, the compounds of Formula (I) according to the invention have the structure of Formula (Ia):

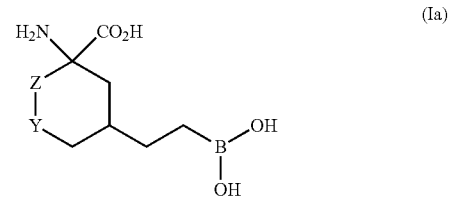

(Ia)

wherein:

Z is —C(R')(R''')—;

Y is bond, —C(R')(R''')—, —NR'''— or —O—;

R' and R''' are each independently hydrogen, —OH, (C$_1$-C$_8$)alkyl, or —NH$_2$, wherein alkyl is optionally substituted with —NR$^d$R$^e$ or heterocyclyl having from 3 to 7 ring member atoms;

wherein R$^d$ and R$^e$ are each independently hydrogen, straight or branched (C$_1$-C$_6$)alkyl, optionally substituted (C$_3$-C$_{14}$)aryl(C$_1$-C$_6$)alkylene- or optionally substituted (C$_3$-C$_{14}$)aryl;

or a tautomer, stereoisomer, racemate, pharmaceutically acceptable salt, ester, solvate, polymorph, active metabolite, or prodrug thereof;

with the proviso that the compound according to the Formula (I) is not 1-amino-3-[3-(dihydroxyboranyl)propyl]cyclopentane-1-carboxylic acid, or 1-amino-3-[3-(dihydroxyboranyl)propyl]cyclohexane-1-carboxylic acid.

In certain embodiments, the compounds of Formula (I) according to the invention have the structure of Formula (Ia) wherein Z is —C(R')(R''')—;

Y is a bond, —CH$_2$—, —NR'''— or —O—;

R' and R''' are each independently hydrogen, —OH, (C$_1$-C$_8$)alkyl, or —NH$_2$, wherein alkyl is optionally substituted with —NR$^d$R$^e$ or heterocyclyl having from 3 to 7 ring member atoms;

wherein R$^d$ and R$^e$ are each independently hydrogen, straight or branched (C$_1$-C$_6$)alkyl, optionally substituted (C$_3$-C$_{14}$)aryl(C$_1$-C$_6$)alkylene- or optionally substituted (C$_3$-C$_{14}$)aryl;

or a tautomer, stereoisomer, racemate, pharmaceutically acceptable salt, ester, solvate, polymorph, active metabolite, or prodrug thereof;

with the proviso that the compound according to the Formula (I) is not 1-amino-3-[3-(dihydroxyboranyl)propyl]cyclohexane-1-carboxylic acid.

In certain embodiments, the compounds of Formula (I) according to the invention have the structure of Formula (Ib):

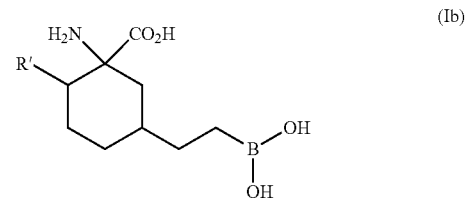

(Ib)

wherein:
R' is —OH, (C$_1$-C$_8$)alkyl, or —NH$_2$, wherein alkyl is optionally substituted with —NR$^d$R$^e$ or heterocyclyl having from 3 to 7 ring member atoms;
   wherein R$^d$ and R$^e$ are each independently hydrogen, straight or branched (C$_1$-C$_6$)alkyl, optionally substituted (C$_3$-C$_{14}$)aryl(C$_1$-C$_6$)alkylene- or optionally substituted (C$_3$-C$_{14}$)aryl;
or a tautomer, stereoisomer, racemate, pharmaceutically acceptable salt, ester, solvate, polymorph, active metabolite, or prodrug thereof.

In certain embodiments, the compounds of Formula (Ib) according to the invention have the structure of Formula (Ib-1):

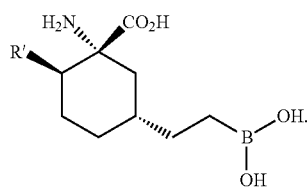

(Ib-1)

In certain embodiments, the compounds of Formula (I) according to the invention have the structure of Formula (Ib) or Formula (Ib-1) wherein R' is —OH, —CH$_2$NH$_2$, —CH$_2$NHCH$_3$, —CH$_2$NHC(CH$_3$)$_3$, —CH$_2$N(CH$_3$)$_2$, —CH$_2$N(CH$_3$)(CH$_2$CH$_3$), —CH$_2$N(CH$_2$CH$_3$)$_2$, —CH$_2$N(CH$_3$)(CH(CH$_3$)$_2$), —CH$_2$-pyrrolidinyl, —CH$_2$-piperidinyl, —CH$_2$-(7-azabicyclo[2.2.1]heptyl), —CH$_2$-morpholinyl, —CH$_2$NCH$_3$Bn, —CH$_2$-(4,4-dimethylpiperidinyl), —CH$_2$-isoindolinyl, —CH$_2$-(4-chlorophenyl-piperidinyl), —CH$_2$-tetrahydroisoquinolinyl, —CH$_2$N(CH$_3$)Ph, —CH$_2$N(CH$_3$)(4-CH$_3$OC$_6$H$_4$) or —CH$_2$N(CH$_3$)(dichlorobenzyl).

In certain embodiments, the compounds of Formula (I) according to the invention have the structure of Formula (Ib) or Formula (Ib-1) wherein
R' is (C$_1$-C$_4$)alkyl substituted with —NR$^d$R$^e$ or a heterocyclyl having from 5 to 6 ring member atoms;
   wherein R$^d$ and R$^e$ are each independently H or straight, branched (C$_1$-C$_6$)alkyl;
or a tautomer, stereoisomer, racemate, pharmaceutically acceptable salt, ester, solvate, polymorph, active metabolite, or prodrug thereof.

In certain embodiments, the compounds of Formula (I) according to the invention have the structure of Formula (Ib) or Formula (Ib-1) wherein R' is —CH$_2$NH$_2$, —CH$_2$NHCH$_3$, —CH$_2$NHC(CH$_3$)$_3$, —CH$_2$N(CH$_3$)$_2$, —CH$_2$N(CH$_3$)(CH$_2$CH$_3$), —CH$_2$N(CH$_2$CH$_3$)$_2$, —CH$_2$N(CH$_3$)(CH(CH$_3$)$_2$), —CH$_2$-pyrrolidinyl, —CH$_2$-piperidinyl, —CH$_2$-(7-azabicyclo[2.2.1]heptyl), —CH$_2$-morpholinyl, —CH$_2$NCH$_3$Bn, —CH$_2$-(4,4-dimethylpiperidinyl), —CH$_2$-isoindolinyl, —CH$_2$-(4-chlorophenyl-piperidinyl), —CH$_2$-tetrahydroisoquinolinyl, —CH$_2$N(CH$_3$)Ph, —CH$_2$N(CH$_3$)(4-CH$_3$OC$_6$H$_4$) or —CH$_2$N(CH$_3$)(dichlorobenzyl).

In certain embodiments, the compounds of Formula (I) according to the invention have the structure of Formula (Ic):

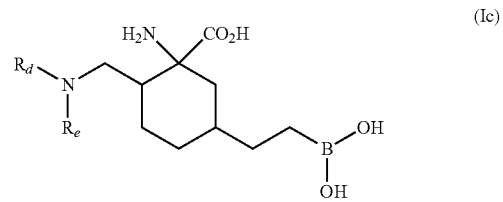

(Ic)

wherein:
R$^d$ and R$^e$ are each independently hydrogen, straight or branched (C1-C6)alkyl,
or R$^d$ and R$^e$ combine with the nitrogen atom to which they are attached to form a heterocyclyl having from 5 to 6 ring member atoms;
or a tautomer, stereoisomer, racemate, pharmaceutically acceptable salt, ester, solvate, polymorph, active metabolite, or prodrug thereof.

In certain embodiments, the compounds of Formula (Ic) according to the invention have the structure of Formula (Ic-1):

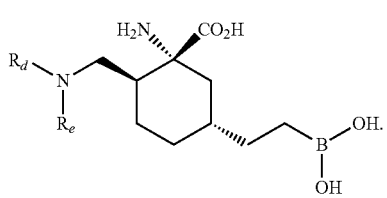

(Ic-1)

In certain embodiments, the compounds of Formula (I) according to the invention have the structure of Formula (Ic) or Formula (Ic-1) wherein
   —N(R$^d$)(R$^e$) is —NH$_2$, —NHCH$_3$, —NHC(CH$_3$)$_3$, —N(CH$_3$)$_2$, N(CH$_3$)(CH$_2$CH$_3$), N(CH$_2$CH$_3$)$_2$, N(CH$_3$)(CH(CH$_3$)$_2$), —NCH$_3$Bn, —N(CH$_3$)(4-CH$_3$OC$_6$H$_4$), —N(CH$_3$)(dichlorobenzyl) or —N(CH$_3$)Ph, or
   or R$^d$ and R$^e$ combine with the nitrogen atom to which they are attached to form azetidinyl, pyrrolidinyl, piperidinyl, (7-azabicyclo[2.2.1]heptyl), morpholinyl, (4,4-dimethylpiperidinyl), isoindolinyl, (4-chlorophenyl-piperidinyl) or tetrahydroisoquinolinyl.

In certain embodiments, the compounds of Formula (I) according to the invention have the structure of Formula (Ic) or Formula (Ic-1) wherein
   —N(R$^d$)(R$^e$) is —NH$_2$, —NHCH$_3$, —NHC(CH$_3$)$_3$, —N(CH$_3$)$_2$, N(CH$_3$)(CH$_2$CH$_3$), N(CH$_2$CH$_3$)$_2$ or N(CH$_3$)(CH(CH$_3$)$_2$), or
   or R$^d$ and R$^e$ combine with the nitrogen atom to which they are attached to form-pyrrolidinyl, piperidinyl or (7-azabicyclo[2.2.1]heptyl).

In certain embodiments, the compounds of Formula (I) according to the invention are racemates:
1-amino-3-(2-boronoethyl)cyclopentane-1-carboxylic acid;
1-amino-3-(2-boronoethyl)-2-methylcyclopentane-1-carboxylic acid;
1-amino-3-(2-boronoethyl)-3-methylcyclopentane-1-carboxylic acid;
1-amino-3-(2-boronoethyl)-4-hydroxycyclopentane-1-carboxylic acid;
1-amino-3-(aminomethyl)-4-(2-boronoethyl)cyclopentane-1-carboxylic acid;
3-amino-1-benzyl-5-(2-boronoethyl)pyrrolidine-3-carboxylic acid;

3-amino-5-(2-boronoethyl)pyrrolidine-3-carboxylic acid;

1-amino-3-(2-boronoethyl)cyclohexane-1-carboxylic acid;

1-amino-3-(2-boronoethyl)cycloheptane-1-carboxylic acid;

1-amino-5-(2-boronoethyl)-2-hydroxycyclohexane-1-carboxylic acid;

1-amino-5-(2-boronoethyl)-2-hydroxycyclohexane-1-carboxylic acid;

1-amino-5-(2-boronoethyl)-2-((dimethylamino)methyl)cyclohexane-1-carboxylic acid;

1-amino-5-(2-boronoethyl)-2-(morpholinomethyl)cyclohexane-1-carboxylic acid;

1-amino-2-((benzyl(methyl)amino)methyl)-5-(2-boronoethyl)cyclohexane-1-carboxylic acid;

1-amino-5-(2-boronoethyl)-2-(pyrrolidin-1-ylmethyl)cyclohexane-1-carboxylic acid;

1-amino-2-(aminomethyl)-5-(2-boronoethyl)cyclohexane-1-carboxylic acid;

1-amino-5-(2-boronoethyl)-2-(2-(pyrrolidin-1-yl)ethyl)cyclohexane-1-carboxylic acid;

1-amino-5-(2-boronoethyl)-2-((4,4-dimethylpiperidin-1-yl)methyl)cyclohexanecarboxylic acid;

1-amino-5-(2-boronoethyl)-2-((4-(4-chlorophenyl)piperidin-1-yl)methyl)cyclohexanecarboxylic acid;

1-amino-5-(2-boronoethyl)-2-(((3,4-dichlorobenzyl)(methyl)amino)methyl)cyclohexanecarboxylic acid;

1-amino-5-(2-boronoethyl)-2-(isoindolin-2-ylmethyl)cyclohexanecarboxylic acid;

1-amino-5-(2-boronoethyl)-2-((diethylamino)methyl)cyclohexanecarboxylic acid;

1-amino-5-(2-boronoethyl)-2-(piperidin-1-ylmethyl)cyclohexanecarboxylic acid;

1-amino-5-(2-boronoethyl)-2-((isopropyl(methyl)amino)methyl)cyclohexanecarboxylic acid;

1-amino-5-(2-boronoethyl)-2-((tert-butylamino)methyl)cyclohexanecarboxylic acid;

2-(7-azabicyclo[2.2.1]heptan-7-ylmethyl)-1-amino-5-(2-boronoethyl)cyclohexanecarboxylic acid;

1-amino-5-(2-boronoethyl)-2-((3,4-dihydroisoquinolin-2(1K)-yl)methyl)cyclohexanecarboxylic acid;

1-amino-5-(2-boronoethyl)-2-(((2,2,2-trifluoroethyl)amino)methyl)cyclohexanecarboxylic acid;

1-amino-5-(2-boronoethyl)-2-(((4-methoxyphenyl)(methyl)amino)methyl)cyclohexanecarboxylic acid;

1-amino-5-(2-boronoethyl)-2-((methylamino)methyl)cyclohexanecarboxylic acid;

1-amino-5-(2-boronoethyl)-2-((methyl(phenyl)amino)methyl)cyclohexanecarboxylic acid;

1-amino-5-(2-boronoethyl)-2-((dimethylamino)methyl)-4,4-dimethylcyclohexane-1-carboxylic acid;

1-amino-5-(2-boronoethyl)-2-(1-(dimethylamino)ethyl)cyclohexanecarboxylic acid (2-(3-amino-4-((dimethylamino)methyl)-3-(methoxycarbonyl)cyclohexyl)ethyl)boronic acid;

1-amino-2-((dimethylamino)methyl)-5-(2-(3a,5,5-trimethylhexahydro-4,6-methanobenzo[d][1,3,2]dioxaborol-2-yl)ethyl)cyclohexane-1-carboxylic acid;

1-amino-2-(pyrrolidin-1-ylmethyl)-5-(2-(3a,5,5-trimethylhexahydro-4,6-methanobenzo[d][1,3,2]dioxaborol-2-yl)ethyl)cyclohexanecarboxylic acid;

1-amino-5-(2-boronoethyl)-2-(2-(pyrrolidin-1-yl)ethyl)cyclohexanecarboxylic acid;

1-amino-5-(2-boronoethyl)-2-(2-(dimethylamino)ethyl)cyclohexanecarboxylic acid;

1,2-diamino-5-(2-boronoethyl)cyclohexanecarboxylic acid;

1-amino-5-(2-boronoethyl)-2-(hydroxymethyl)cyclohexanecarboxylic acid;

1-amino-5-(2-boronoethyl)-2-hydroxy-2-methylcyclohexanecarboxylic acid;

1-amino-5-(2-boronoethyl)-2-methylcyclohex-2-enecarboxylic acid;

1-amino-5-(2-boronoethyl)-2-(4-chlorobenzyl)-2-hydroxycyclohexanecarboxylic acid;

1-amino-5-(2-boronoethyl)-2-(4-chlorobenzyl)cyclohex-2-enecarboxylic acid;

1-amino-3-(aminomethyl)-5-(2-boronoethyl)cyclohexanecarboxylic acid;

1-amino-3-(2-boronoethyl)-5-((dimethylamino)methyl)cyclohexanecarboxylic acid;

1,3-diamino-5-(2-boronoethyl)cyclohexanecarboxylic acid;

3-amino-5-(2-boronoethyl)piperidine-3-carboxylic acid;

3-amino-5-(2-boronoethyl)-1-methylpiperidine-3-carboxylic acid;

3-amino-5-(2-boronoethyl)tetrahydro-2H-pyran-3-carboxylic acid;

1,2-diamino-4-(2-boronoethyl)cyclopentanecarboxylic acid;

1-amino-4-(2-boronoethyl)-2-hydroxycyclopentanecarboxylic acid;

1-amino-5-(2-boronoethyl)-2-(dimethylamino)cyclohexane-1-carboxylic acid;

1-amino-3-(2-boronoethyl)-5-(dimethylamino)cyclohexane-1-carboxylic acid;

1-amino-2-(aminomethyl)-4-(2-boronoethyl)cyclopentane-1-carboxylic acid;

1-amino-4-(2-boronoethyl)-2-((dimethylamino)methyl)cyclopentane-1-carboxylic acid;

2-(aminomethyl)-5-(2-boronoethyl)-1-(methylamino)cyclohexane-1-carboxylic acid;

1-amino-5-(2-boronoethyl)-2-((ethyl(methyl)amino)methyl)cyclohexane-1-carboxylic acid; or 1-amino-5-(2-boronoethyl)-2-(piperidin-1-ylmethyl)cyclohexane-1-carboxylic acid;

or a tautomer, stereoisomer, racemate, pharmaceutically acceptable salt, ester, solvate, polymorph, active metabolite, or prodrug thereof In certain embodiments, the compounds of Formula (I) according to the invention are the L-enantiomers at the amino acid moiety.

In other embodiments, the compounds of Formula (I) according to the invention are the D-enantiomers at the amino acid moiety.

Usually, the L-enantiomers (relative to L-arginine where $B(OH)_2$ is replaced by guanidine moiety, mostly with (R)-absolute configuration around the amino acid tertiary carbon) are more biologically active than the D-enantiomers (mostly with (S)-absolute configuration around the amino acid tertiary carbon).

In certain embodiments, the compounds of Formula (I) according to the invention are:

| Example No. | Compound Structure | Compound Name |
|---|---|---|
| 1 | 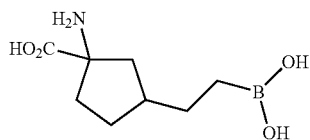 [SMILES: NC1(C(=O)O)CCC(CCB(O)O)C1] | 1-amino-3-(2-boronoethyl)cyclopentane-1-carboxylic acid |
| 2 | 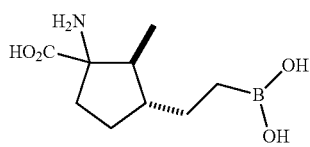 | rac-(2S,3R)-1-amino-3-(2-boronoethyl)-2-methylcyclopentane-1-carboxylic acid |
| 3 | 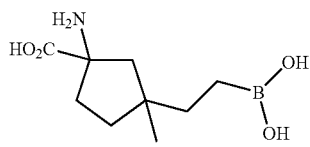 | 1-amino-3-(2-boronoethyl)-3-methylcyclopentane-1-carboxylic acid |
| 4 | 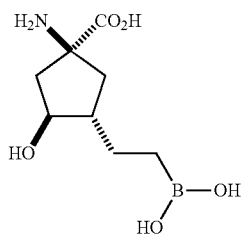 [SMILES: N[C@@]1(C(=O)O)C[C@H](CCB(O)O)[C@@H](O)C1] | rac-(1S,3S,4S)-1-amino-3-(2-boronoethyl)-4-hydroxycyclopentane-1-carboxylic acid |
| 5 | 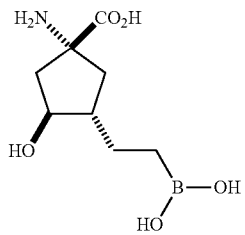 [SMILES: N[C@]1(C(=O)O)C[C@H](CCB(O)O)[C@@H](O)C1] | rac-(1R,3S,4S)-1-amino-3-(2-boronoethyl)-4-hydroxycyclopentane-1-carboxylic acid |
| 6 | 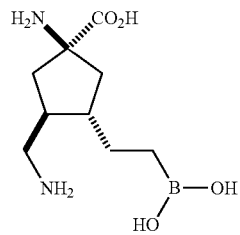 [SMILES: NC[C@H]1C[C@](N)(C(=O)O)C[C@@H]1CCB(O)O] | rac-(1S,3S,4S)-1-amino-3-(aminomethyl)-4-(2-boronoethyl)cyclopentane-1-carboxylic acid |
| 7 | 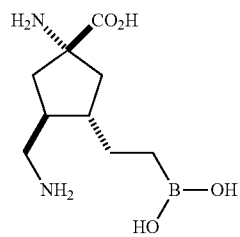 | rac-(1R,3S,4S)-1-amino-3-(aminomethyl)-4-(2-boronoethyl)cyclopentane-1-carboxylic acid |

-continued

| Example No. | Compound Structure | Compound Name |
|---|---|---|
| 8 | 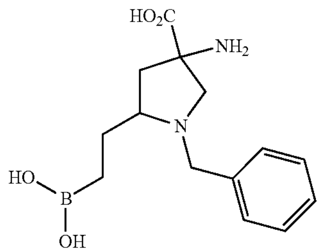 [SMILES: NC1(C(=O)O)CC(CCB(O)O)N(Cc2ccccc2)C1] | 3-amino-1-benzyl-5-(2-boronoethyl)-pyrrolidine-3-carboxylic acid |
| 9 | 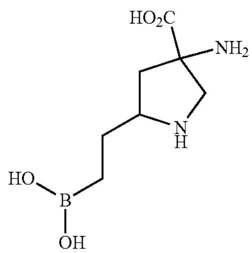 [SMILES: NC1(C(=O)O)CNC(CCB(O)O)C1] | 3-amino-5-(2-boronoethyl)pyrrolidine-3-carboxylic acid |
| 10 | 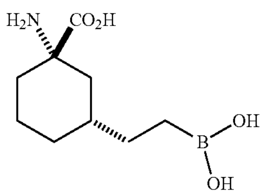 [SMILES: N[C@@]1(C(=O)O)CCC[C@@H](CCB(O)O)C1] | rac-(1S,3R)-1-amino-3-(2-boronoethyl)-cyclohexane-1-carboxylic acid |
| 11 | 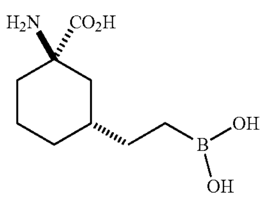 [SMILES: N[C@]1(C(=O)O)CCC[C@@H](CCB(O)O)C1] | rac-(1R,3R)-1-amino-3-(2-boronoethyl)-cyclohexane-1-carboxylic acid |
| 12 | 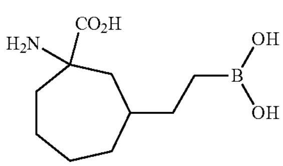 [SMILES: NC1(C(=O)O)CCCCC(CCB(O)O)C1] | 1-amino-3-(2-boronoethyl)cycloheptane-1-carboxylic acid |
| 13 | 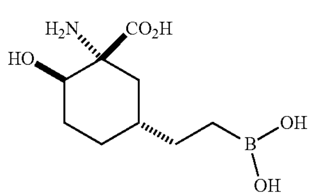 [SMILES: N[C@]1(C(=O)O)C[C@H](CCB(O)O)CC[C@H]1O] | rac-(1R,2R,5R)-1-amino-5-(2-boronoethyl)-2-hydroxycyclohexane-1-carboxylic acid |
| 14 | 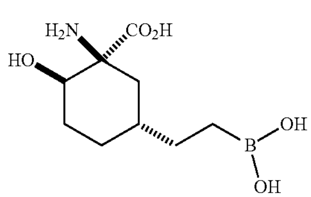 [SMILES: N[C@@]1(C(=O)O)C[C@H](CCB(O)O)CC[C@H]1O] | rac-(1S,2R,5R)-1-amino-5-(2-boronoethyl)-2-hydroxycyclohexane-1-carboxylic acid |

-continued

| Example No. | Compound Structure | Compound Name |
|---|---|---|
| 15 | 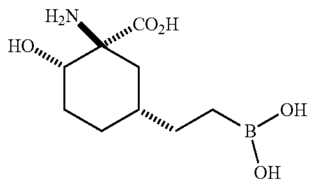 [SMILES: N[C@@]1(C(=O)O)C[C@H](CCB(O)O)CC[C@@H]1O] | rac-(1S,2S,5R)-1-amino-5-(2-boronoethyl)-2-hydroxycyclohexane-1-carboxylic acid |
| 16 | 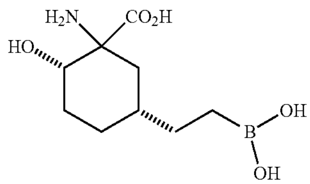 [SMILES: NC1(C(=O)O)C[C@H](CCB(O)O)CC[C@@H]1O] | rac-(2S,5R)-1-amino-5-(2-boronoethyl)-2-hydroxycyclohexane-1-carboxylic acid |
| 17 | 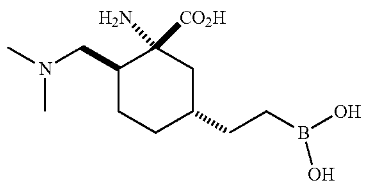 [SMILES: CN(C)C[C@@H]1CC[C@@H](CCB(O)O)C[C@]1(N)C(=O)O] | rac-(1R,2S,5R)-1-amino-5-(2-boronoethyl)-2-((dimethylamino)methyl)cyclohexane-1-carboxylic acid |
| 18 | 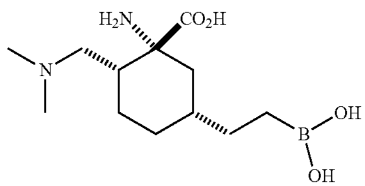 [SMILES: CN(C)C[C@H]1CC[C@@H](CCB(O)O)C[C@]1(N)C(=O)O] | rac-(1R,2R,5R)-1-amino-5-(2-boronoethyl)-2-((dimethylamino)methyl)cyclohexane-1-carboxylic acid |
| 19 | 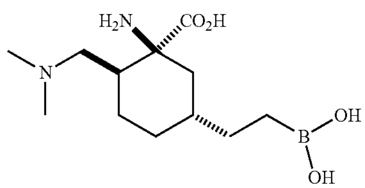 [SMILES: CN(C)C[C@@H]1CC[C@@H](CCB(O)O)C[C@@]1(N)C(=O)O] | rac-(1S,2S,5R)-1-amino-5-(2-boronoethyl)-2-((dimethylamino)methyl)cyclohexane-1-carboxylic acid |
| 20 | 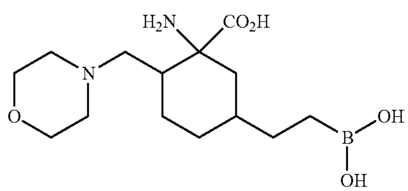 [SMILES: NC1(C(=O)O)CC(CCB(O)O)CCC1CN1CCOCC1] | 1-amino-5-(2-boronoethyl)-2-(morpholinomethyl)cyclohexane-1-carboxylic acid |
| 21 | 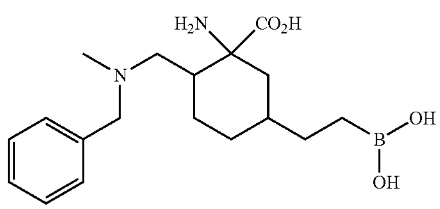 [SMILES: CN(Cc1ccccc1)CC1CCC(CCB(O)O)CC1(N)C(=O)O] | 1-amino-2-((benzyl(methyl)amino)methyl)-5-(2-boronoethyl)cyclohexane-1-carboxylic acid |
| 22 | 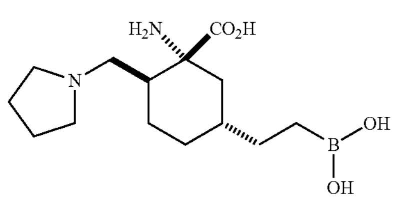 [SMILES: N[C@]1(C(=O)O)C[C@H](CCB(O)O)CC[C@H]1CN1CCCC1] | rac-(1R,2S,5R)-1-amino-5-(2-boronoethyl)-2-(pyrrolidin-1-ylmethyl)cyclohexane-1-carboxylic acid |

-continued

| Example No. | Compound Structure | Compound Name |
|---|---|---|
| 23 | 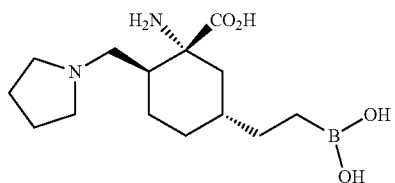 [SMILES: N[C@]1(C(=O)O)C[C@H](CCB(O)O)CC[C@H]1CN1CCCC1] | (1R,2S,5R)-1-amino-5-(2-boronoethyl)-2-(pyrrolidin-1-ylmethyl)cyclohexane-1-carboxylic acid |
| 24 | 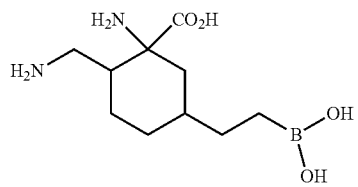 [SMILES: NCC1CCC(CCB(O)O)CC1(N)C(=O)O] | 1-amino-2-(aminomethyl)-5-(2-boronoethyl)cyclohexane-1-carboxylic acid |
| 25 | 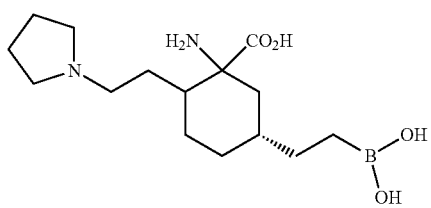 [SMILES: NC1(C(=O)O)C[C@H](CCB(O)O)CCC1CCN1CCCC1] | 1-amino-5-(2-boronoethyl)-2-(2-(pyrrolidin-1-yl)ethyl)cyclohexane-1-carboxylic acid |
| 26 | 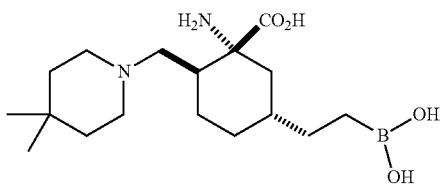 [SMILES: CC1(C)CCN(C[C@@H]2CC[C@@H](CCB(O)O)C[C@]2(N)C(=O)O)CC1] | rac-(1R,2S,5R)-1-amino-5-(2-boronoethyl)-2-((4,4-dimethylpiperidin-1-yl)methyl)cyclohexanecarboxylic acid |
| 27 | 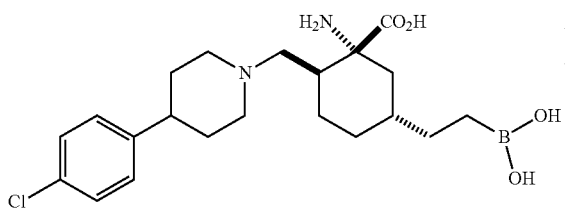 [SMILES: N[C@]1(C(=O)O)C[C@H](CCB(O)O)CC[C@H]1CN1CCC(c2ccc(Cl)cc2)CC1] | rac-(1R,2S,5R)-1-amino-5-(2-boronoethyl)-2-((4-(4-chlorophenyl)piperidin-1-yl)methyl)cyclohexanecarboxylic acid |
| 28 | 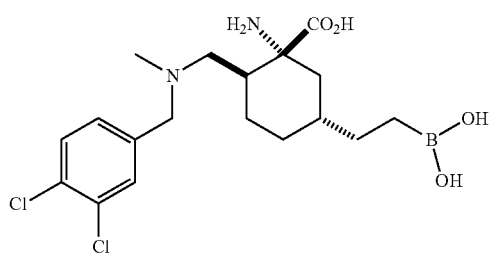 [SMILES: CN(Cc1ccc(Cl)c(Cl)c1)C[C@@H]1CC[C@@H](CCB(O)O)C[C@]1(N)C(=O)O] | rac-(1R,2S,5R)-1-amino-5-(2-boronoethyl)-2-(((3,4-dichlorobenzyl)(methyl)amino)methyl)cyclohexanecarboxylic acid |
| 29 | 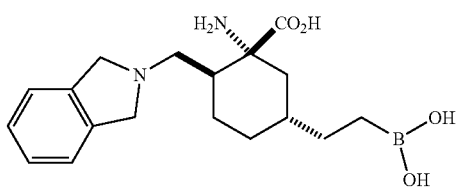 [SMILES: N[C@]1(C(=O)O)C[C@H](CCB(O)O)CC[C@H]1CN1Cc2ccccc2C1] | rac-(1R,2S,5R)-1-amino-5-(2-boronoethyl)-2-(isoindolin-2-ylmethyl)cyclohexanecarboxylic acid |

-continued

| Example No. | Compound Structure | Compound Name |
|---|---|---|
| 30 | 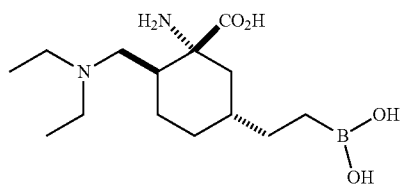 [SMILES: CCN(CC)C[C@@H]1CC[C@@H](CCB(O)O)C[C@]1(N)C(=O)O] | rac-(1R,2S,5R)-1-amino-5-(2-boronoethyl)-2-((diethylamino)methyl)cyclohexanecarboxylic acid |
| 31 | 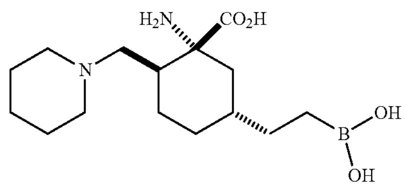 [SMILES: N[C@]1(C(=O)O)C[C@H](CCB(O)O)CC[C@H]1CN1CCCCC1] | rac-(1R,2S,5R)-1-amino-5-(2-boronoethyl)-2-(piperidin-1-ylmethyl)cyclohexanecarboxylic acid |
| 32 | 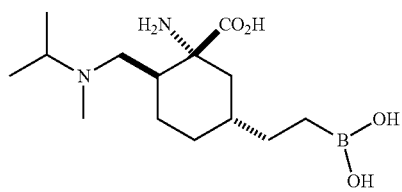 [SMILES: CC(C)N(C)C[C@@H]1CC[C@@H](CCB(O)O)C[C@]1(N)C(=O)O] | rac-(1R,2S,5R)-1-amino-5-(2-boronoethyl)-2-((isopropyl(methyl)amino)methyl)cyclohexanecarboxylic acid |
| 33 | 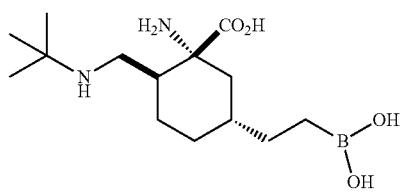 [SMILES: CC(C)(C)NC[C@@H]1CC[C@@H](CCB(O)O)C[C@]1(N)C(=O)O] | rac-(1R,2S,5R)-1-amino-5-(2-boronoethyl)-2-((tert-butylamino)methyl)cyclohexanecarboxylic acid |
| 34 | 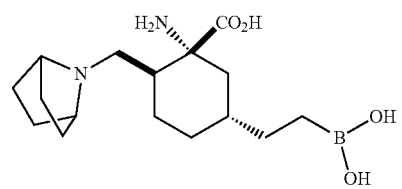 [SMILES: N[C@]1(C(=O)O)C[C@H](CCB(O)O)CC[C@H]1CN1C2CCC1CC2] | rac-(1R,2S,5R)-2-(7-azabicyclo[2.2.1]heptan-7-ylmethyl)-1-amino-5-(2-boronoethyl)cyclohexanecarboxylic acid |
| 35 | 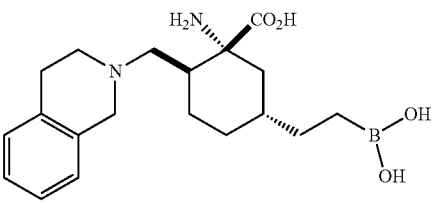 [SMILES: N[C@]1(C(=O)O)C[C@H](CCB(O)O)CC[C@H]1CN1CCc2ccccc2C1] | rac-(1R,2S,5R)-1-amino-5-(2-boronoethyl)-2-((3,4-dihydroisoquinolin-2(1H)-yl)methyl)cyclohexanecarboxylic acid |
| 36 | 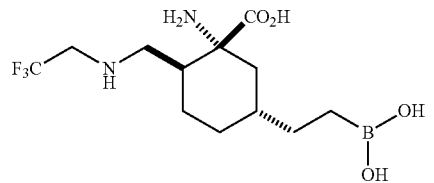 [SMILES: N[C@]1(C(=O)O)C[C@H](CCB(O)O)CC[C@H]1CNCC(F)(F)F] | rac-(1R,2S,5R)-1-amino-5-(2-boronoethyl)-2-(((2,2,2-trifluoroethyl)amino)methyl)cyclohexanecarboxylic acid |

-continued

| Example No. | Compound Structure | Compound Name |
|---|---|---|
| 37 | 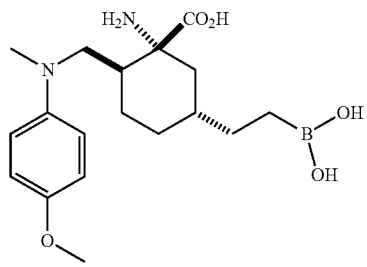 [SMILES: COc1ccc(N(C)C[C@@H]2CC[C@@H](CCB(O)O)C[C@]2(N)C(=O)O)cc1] | rac-(1R,2S,5R)-1-amino-5-(2-boronoethyl)-2-(((4-methoxyphenyl)(methyl)amino)methyl)cyclohexanecarboxylic acid |
| 38 | 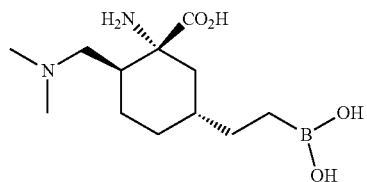 [SMILES: CN(C)C[C@@H]1CC[C@@H](CCB(O)O)C[C@]1(N)C(=O)O] | (1R,2S,5R)-1-amino-5-(2-boronoethyl)-2-((dimethylamino)methyl)cyclohexanecarboxylic acid |
| 39 | 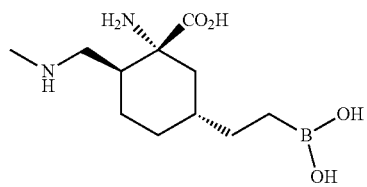 [SMILES: CNC[C@@H]1CC[C@@H](CCB(O)O)C[C@]1(N)C(=O)O] | (1R,2S,5R)-1-amino-5-(2-boronoethyl)-2-((methylamino)methyl)cyclohexanecarboxylic acid |
| 40 | 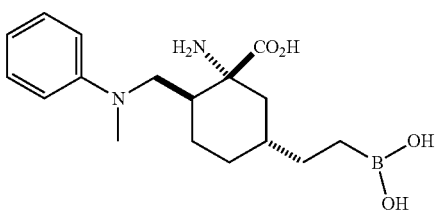 [SMILES: CN(C[C@@H]1CC[C@@H](CCB(O)O)C[C@]1(N)C(=O)O)c1ccccc1] | rac-(1R,2S,5R)-1-amino-5-(2-boronoethyl)-2-((methyl(phenyl)amino)methyl)cyclohexanecarboxylic acid |
| 41 | 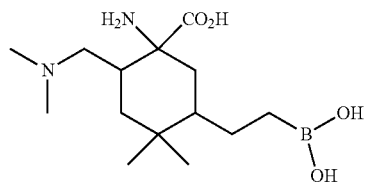 [SMILES: CN(C)CC1CC(C)(C)C(CCB(O)O)CC1(N)C(=O)O] | 1-amino-5-(2-boronoethyl)-2-((dimethylamino)methyl)-4,4-dimethylcyclohexane-1-carboxylic acid |
| 42 | 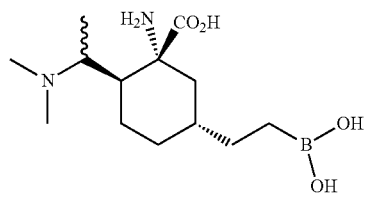 [SMILES: CC([C@@H]1CC[C@@H](CCB(O)O)C[C@]1(N)C(=O)O)N(C)C] | (1R,2S,5R)-1-amino-5-(2-boronoethyl)-2-(1-(dimethylamino)ethyl)cyclohexanecarboxylic acid |
| 43 | 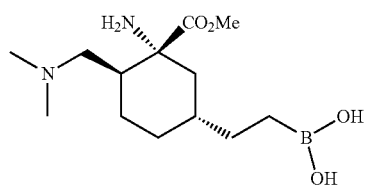 [SMILES: COC(=O)[C@@]1(N)C[C@H](CCB(O)O)CC[C@H]1CN(C)C] | (2-((1R,3R,4S)-3-amino-4-((dimethylamino)methyl)-3-(methoxycarbonyl)cyclohexyl)ethyl)boronic acid |

| Example No. | Compound Structure | Compound Name |
|---|---|---|
| 44 | 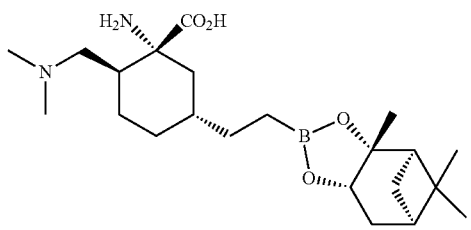 | (1R,2S,5R)-1-amino-2-((dimethylamino)methyl)-5-(2-((3aR,4R,6R,7aS)-3a,5,5-trimethylhexahydro-4,6-methanobenzo[d][1,3,2]dioxaborol-2-yl)ethyl)cyclohexane-1-carboxylic acid |
| 45 | 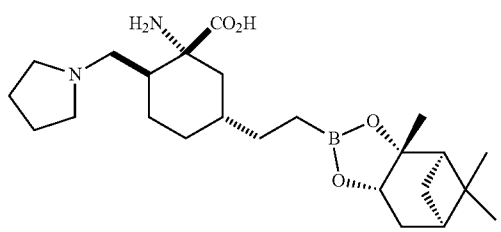 [SMILES: CC1(C)[C@H]2C[C@@H]3OB(CC[C@@H]4CC[C@@H](CN5CCCC5)[C@@](N)(C(=O)O)C4)O[C@]3(C)[C@@H]1C2] | (1R,2S,5R)-1-amino-2-(pyrrolidin-1-ylmethyl)-5-(2-((3aR,4R,6R,7aS)-3a,5,5-trimethylhexahydro-4,6-methanobenzo[d][1,3,2]dioxaborol-2-yl)ethyl)cyclohexanecarboxylic acid |
| 46 | 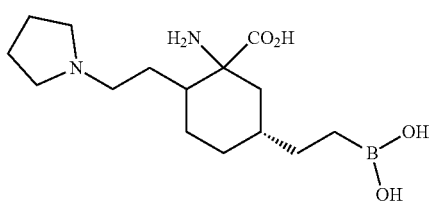 [SMILES: NC1(C(=O)O)C[C@H](CCB(O)O)CCC1CCN1CCCC1] | (5R)-1-amino-5-(2-boronoethyl)-2-(2-(pyrrolidin-1-yl)ethyl)cyclohexanecarboxylic acid |
| 47 | 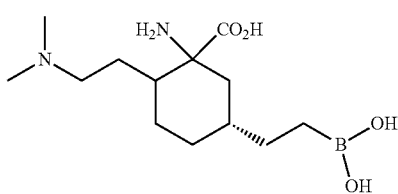 [SMILES: CN(C)CCC1CC[C@@H](CCB(O)O)CC1(N)C(=O)O] | (5R)-1-amino-5-(2-boronoethyl)-2-(2-(dimethylamino)ethyl)cyclohexanecarboxylic acid |
| 48 | 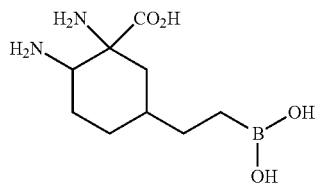 | 1,2-diamino-5-(2-boronoethyl)cyclohexanecarboxylic acid |
| 49 | 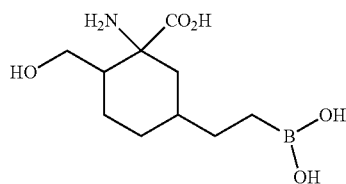 [SMILES: NC1(C(=O)O)CC(CCB(O)O)CCC1CO] | 1-amino-5-(2-boronoethyl)-2-(hydroxymethyl)cyclohexanecarboxylic acid |
| 50 | 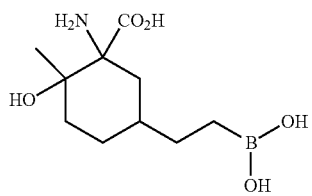 [SMILES: CC1(O)CCC(CCB(O)O)CC1(N)C(=O)O] | 1-amino-5-(2-boronoethyl)-2-hydroxy-2-methylcyclohexanecarboxylic acid |

-continued

| Example No. | Compound Structure | Compound Name |
|---|---|---|
| 51 | 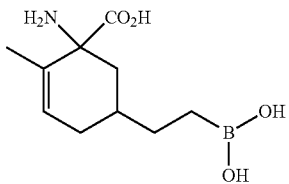 [SMILES: CC1=CCC(CCB(O)O)CC1(N)C(=O)O] | 1-amino-5-(2-boronoethyl)-2-methylcyclohex-2-enecarboxylic acid |
| 52 | 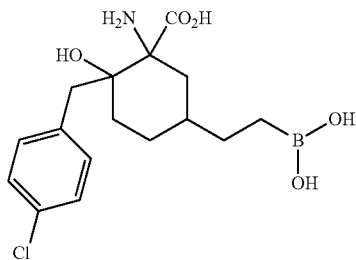 [SMILES: NC1(C(=O)O)CC(CCB(O)O)CCC1(O)Cc1ccc(Cl)cc1] | 1-amino-5-(2-boronoethyl)-2-(4-chlorobenzyl)-2-hydroxycyclohexanecarboxylic acid |
| 53 | 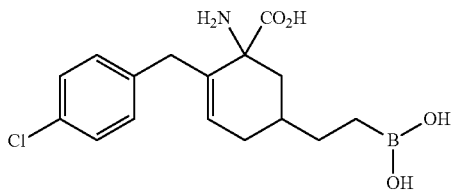 [SMILES: NC1(C(=O)O)CC(CCB(O)O)CC=C1Cc1ccc(Cl)cc1] | 1-amino-5-(2-boronoethyl)-2-(4-chlorobenzyl)cyclohex-2-enecarboxylic acid |
| 54 | 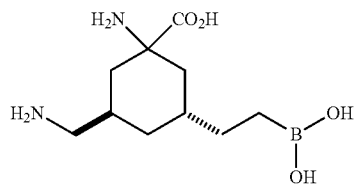 [SMILES: NC[C@@H]1C[C@@H](CCB(O)O)CC(N)(C(=O)O)C1] | rac-(3R,5R)-1-amino-3-(aminomethyl)-5-(2-boronoethyl)cyclohexanecarboxylic acid |
| 55 | 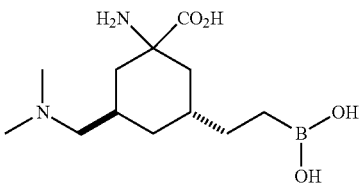 [SMILES: CN(C)C[C@@H]1C[C@@H](CCB(O)O)CC(N)(C(=O)O)C1] | rac-(3R,5R)-1-amino-3-(2-boronoethyl)-5-((dimethylamino)methyl)cyclohexanecarboxylic acid |
| 56 | 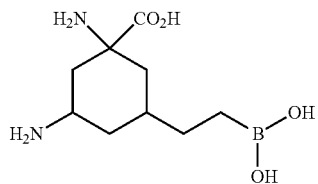 | 1,3-diamino-5-(2-boronoethyl)cyclohexanecarboxylic acid |
| 57 | 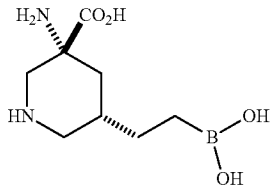 [SMILES: N[C@@]1(C(=O)O)CNC[C@@H](CCB(O)O)C1] | rac-(3R,5S)-3-amino-5-(2-boronoethyl)piperidine-3-carboxylic acid |

-continued

| Example No. | Compound Structure | Compound Name |
|---|---|---|
| 58 | 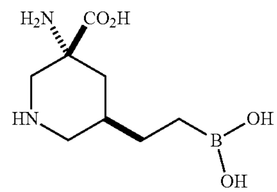 [SMILES: N[C@@]1(C(=O)O)CNC[C@H](CCB(O)O)C1] | rac-(3R,5R)-3-amino-5-(2-boronoethyl)piperidine-3-carboxylic acid |
| 59 | 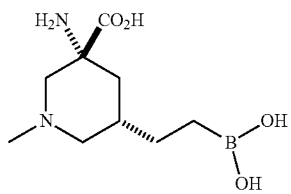 [SMILES: CN1C[C@@H](CCB(O)O)C[C@](N)(C(=O)O)C1] | rac-(3R,5S)-3-amino-5-(2-boronoethyl)-1-methylpiperidine-3-carboxylic acid |
| 60 | 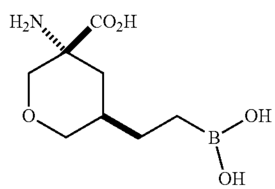 [SMILES: N[C@@]1(C(=O)O)COC[C@H](CCB(O)O)C1] | rac-(3R,5R)-3-amino-5-(2-boronoethyl)tetrahydro-2H-pyran-3-carboxylic acid |
| 61 | 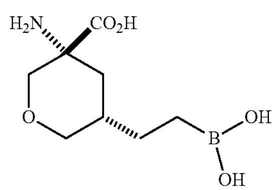 [SMILES: N[C@@]1(C(=O)O)COC[C@@H](CCB(O)O)C1] | rac-(3R,5S)-3-amino-5-(2-boronoethyl)tetrahydro-2H-pyran-3-carboxylic acid |
| 62 | 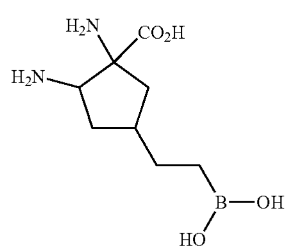 [SMILES: NC1CC(CCB(O)O)CC1(N)C(=O)O] | 1,2-diamino-4-(2-boronoethyl)cyclopentanecarboxylic acid |
| 63 | 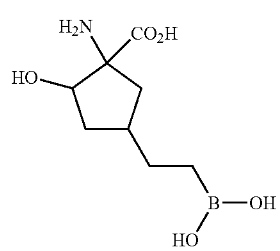 [SMILES: NC1(C(=O)O)CC(CCB(O)O)CC1O] | 1-amino-4-(2-boronoethyl)-2-hydroxycyclopentanecarboxylic acid hydrochloride |
| 64 | 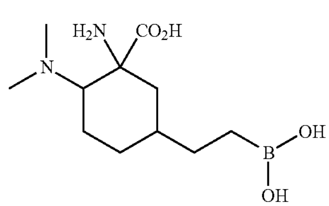 [SMILES: CN(C)C1CCC(CCB(O)O)CC1(N)C(=O)O] | rac-(1R,5R)-1-amino-5-(2-boronoethyl)-2-(dimethylamino)cyclohexane-1-carboxylic acid |

-continued

| Example No. | Compound Structure | Compound Name |
|---|---|---|
| 65 | 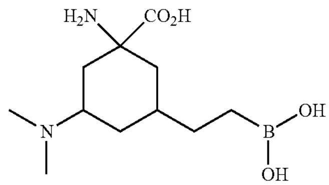 [SMILES: CN(C)C1CC(CCB(O)O)CC(N)(C(=O)O)C1] | 1-amino-3-(2-boronoethyl)-5-(dimethylamino)cyclohexane-1-carboxylic acid |
| 66 | 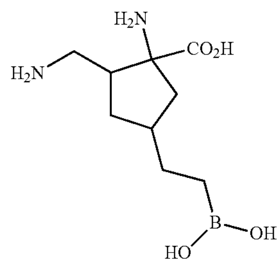 [SMILES: NCC1CC(CCB(O)O)CC1(N)C(=O)O] | 1-amino-2-(aminomethyl)-4-(2-boronoethyl)cyclopentane-1-carboxylic acid |
| 67 | 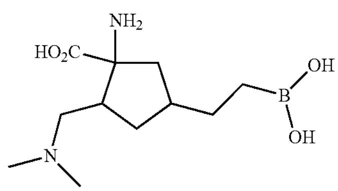 [SMILES: CN(C)CC1CC(CCB(O)O)CC1(N)C(=O)O] | 1-amino-4-(2-boronoethyl)-2-((dimethylamino)methyl)cyclopentane-1-carboxylic acid |
| 68 | 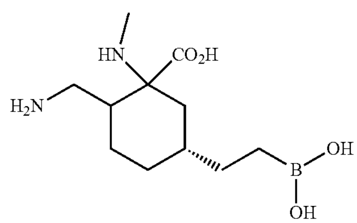 [SMILES: CNC1(C(=O)O)C[C@H](CCB(O)O)CCC1CN] | (5R)-2-(aminomethyl)-5-(2-boronoethyl)-1-(methylamino)cyclohexane-1-carboxylic acid |
| 69 | 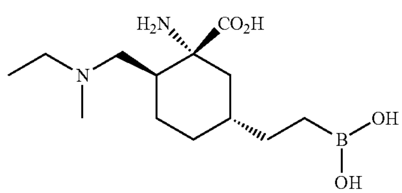 [SMILES: CCN(C)C[C@@H]1CC[C@@H](CCB(O)O)C[C@]1(N)C(=O)O] | (1R,2S,5R)-1-amino-5-(2-boronoethyl)-2-((ethyl(methyl)amino)methyl)cyclohexane-1-carboxylic acid |
| 70 | 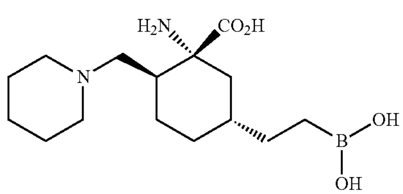 [SMILES: N[C@]1(C(=O)O)C[C@H](CCB(O)O)CC[C@H]1CN1CCCCC1] | (1R,2S,5R)-1-amino-5-(2-boronoethyl)-2-(piperidin-1-ylmethyl)cyclohexane-1-carboxylic acid |
| 71 | | (1R,2S,5R)-1-amino-5-(2-boronoethyl)-2-(pyrrolidin-1-ylmethyl)cyclohexane-1-carboxylic acid | either as a free acid or free base, or as a pharmaceutically acceptable salt thereof, or a stereoisomer, a tautomer, and/or a solvate thereof.

In certain embodiments, the compounds of Formula (I) according to the invention are:
(2S,3R)-1-amino-3-(2-boronoethyl)-2-methylcyclopentane-1-carboxylic acid;
(2R,3S)-1-amino-3-(2-boronoethyl)-2-methylcyclopentane-1-carboxylic acid;
(1S,3S,4S)-1-amino-3-(2-boronoethyl)-4-hydroxycyclopentane-1-carboxylic acid;
(1R,3R,4R)-1-amino-3-(2-boronoethyl)-4-hydroxycyclopentane-1-carboxylic acid;
(1R,3S,4S)-1-amino-3-(2-boronoethyl)-4-hydroxycyclopentane-1-carboxylic acid;
(1S,3R,4R)-1-amino-3-(2-boronoethyl)-4-hydroxycyclopentane-1-carboxylic acid;
(1S,3S,4S)-1-amino-3-(aminomethyl)-4-(2-boronoethyl)cyclopentane-1-carboxylic acid;
(1R,3R,4R)-1-amino-3-(aminomethyl)-4-(2-boronoethyl)cyclopentane-1-carboxylic acid;
(1R,3S,4S)-1-amino-3-(aminomethyl)-4-(2-boronoethyl)cyclopentane-1-carboxylic acid;
(1S,3R,4R)-1-amino-3-(aminomethyl)-4-(2-boronoethyl)cyclopentane-1-carboxylic acid;
(1S,3R)-1-amino-3-(2-boronoethyl)cyclohexane-1-carboxylic acid;
(1R,3S)-1-amino-3-(2-boronoethyl)cyclohexane-1-carboxylic acid;
(1R,3R)-1-amino-3-(2-boronoethyl)cyclohexane-1-carboxylic acid;
(1S,3S)-1-amino-3-(2-boronoethyl)cyclohexane-1-carboxylic acid;
(1R,2R,5R)-1-amino-5-(2-boronoethyl)-2-hydroxycyclohexane-1-carboxylic acid;
(1S,2S,5S)-1-amino-5-(2-boronoethyl)-2-hydroxycyclohexane-1-carboxylic acid;
(1S,2R,5R)-1-amino-5-(2-boronoethyl)-2-hydroxycyclohexane-1-carboxylic acid;
(1R,2S,5S)-1-amino-5-(2-boronoethyl)-2-hydroxycyclohexane-1-carboxylic acid;
(1S,2S,5R)-1-amino-5-(2-boronoethyl)-2-hydroxycyclohexane-1-carboxylic acid;
(1R,2R,5S)-1-amino-5-(2-boronoethyl)-2-hydroxycyclohexane-1-carboxylic acid;
(2S,5R)-1-amino-5-(2-boronoethyl)-2-hydroxycyclohexane-1-carboxylic acid;
(2R,5S)-1-amino-5-(2-boronoethyl)-2-hydroxycyclohexane-1-carboxylic acid;
(1R,2S,5R)-1-amino-5-(2-boronoethyl)-2-((dimethylamino)methyl)cyclohexane-1-carboxylic acid;
(1S,2R,5S)-1-amino-5-(2-boronoethyl)-2-((dimethylamino)methyl)cyclohexane-1-carboxylic acid;
(1R,2R,5R)-1-amino-5-(2-boronoethyl)-2-((dimethylamino)methyl)cyclohexane-1-carboxylic acid;
(1S,2S,5S)-1-amino-5-(2-boronoethyl)-2-((dimethylamino)methyl)cyclohexane-1-carboxylic acid;
(1S,2S,5R)-1-amino-5-(2-boronoethyl)-2-((dimethylamino)methyl)cyclohexane-1-carboxylic acid;
(1R,2S,5S)-1-amino-5-(2-boronoethyl)-2-((dimethylamino)methyl)cyclohexane-1-carboxylic acid;
(1R,2S,5R)-1-amino-5-(2-boronoethyl)-2-(pyrrolidin-1-ylmethyl)cyclohexane-1-carboxylic acid;
(1S,2R,5S)-1-amino-5-(2-boronoethyl)-2-(pyrrolidin-1-ylmethyl)cyclohexane-1-carboxylic acid;
(1R,2S,5R)-1-amino-5-(2-boronoethyl)-2-((4,4-dimethylpiperidin-1-yl)methyl)cyclohexanecarboxylic acid;
(1S,2R,5S)-1-amino-5-(2-boronoethyl)-2-((4,4-dimethylpiperidin-1-yl)methyl)cyclohexanecarboxylic acid;
(1R,2S,5R)-1-amino-5-(2-boronoethyl)-2-((4-(4-chlorophenyl)piperidin-1-yl)methyl)cyclohexanecarboxylic acid;
(1S,2R,5S)-1-amino-5-(2-boronoethyl)-2-((4-(4-chlorophenyl)piperidin-1-yl)methyl)cyclohexanecarboxylic acid;
(1R,2S,5R)-1-amino-5-(2-boronoethyl)-2-(((3,4-dichlorobenzyl)(methyl)amino)methyl)cyclohexanecarboxylic acid;
(1S,2R,5S)-1-amino-5-(2-boronoethyl)-2-(((3,4-dichlorobenzyl)(methyl)amino)methyl)cyclohexanecarboxylic acid;
(1R,2S,5R)-1-amino-5-(2-boronoethyl)-2-(isoindolin-2-ylmethyl)cyclohexanecarboxylic acid;
(1S,2R,5S)-1-amino-5-(2-boronoethyl)-2-(isoindolin-2-ylmethyl)cyclohexanecarboxylic acid;
(1R,2S,5R)-1-amino-5-(2-boronoethyl)-2-((diethylamino)methyl)cyclohexanecarboxylic acid;
(1S,2R,5S)-1-amino-5-(2-boronoethyl)-2-((diethylamino)methyl)cyclohexanecarboxylic acid;
(1R,2S,5R)-1-amino-5-(2-boronoethyl)-2-(piperidin-1-ylmethyl)cyclohexanecarboxylic acid;
(1S,2R,5S)-1-amino-5-(2-boronoethyl)-2-(piperidin-1-ylmethyl)cyclohexanecarboxylic acid;
(1R,2S,5R)-1-amino-5-(2-boronoethyl)-2-((isopropyl(methyl)amino)methyl)cyclohexanecarboxylic acid;
(1S,2R,5S)-1-amino-5-(2-boronoethyl)-2-((isopropyl(methyl)amino)methyl)cyclohexanecarboxylic acid;
(1R,2S,5R)-1-amino-5-(2-boronoethyl)-2-((tert-butylamino)methyl)cyclohexanecarboxylic acid;
(1S,2R,5S)-1-amino-5-(2-boronoethyl)-2-((tert-butylamino)methyl)cyclohexanecarboxylic acid;
(1R,2S,5R)-2-(7-azabicyclo[2.2.1]heptan-7-ylmethyl)-1-amino-5-(2-boronoethyl)cyclohexanecarboxylic acid;
(1S,2R,5S)-2-(7-azabicyclo[2.2.1]heptan-7-ylmethyl)-1-amino-5-(2-boronoethyl)cyclohexanecarboxylic acid;
(1R,2S,5R)-1-amino-5-(2-boronoethyl)-2-((3,4-dihydroisoquinolin-2(11)-yl)methyl)cyclohexanecarboxylic acid;
(1S,2R,5S)-1-amino-5-(2-boronoethyl)-2-((3,4-dihydroisoquinolin-2(11)-yl)methyl)cyclohexanecarboxylic acid;
(1R,2S,5R)-1-amino-5-(2-boronoethyl)-2-(((2,2,2-trifluoroethyl)amino)methyl)cyclohexanecarboxylic acid;
(1S,2R,5S)-1-amino-5-(2-boronoethyl)-2-(((2,2,2-trifluoroethyl)amino)methyl)cyclohexanecarboxylic acid;
(1R,2S,5R)-1-amino-5-(2-boronoethyl)-2-(((4-methoxyphenyl)(methyl)amino)methyl)cyclohexanecarboxylic acid;
(1S,2R,5S)-1-amino-5-(2-boronoethyl)-2-(((4-methoxyphenyl)(methyl)amino)methyl)cyclohexanecarboxylic acid;
(1R,2S,5R)-1-amino-5-(2-boronoethyl)-2-((methyl(phenyl)amino)methyl)cyclohexanecarboxylic acid;
(1S,2R,5S)-1-amino-5-(2-boronoethyl)-2-((methyl(phenyl)amino)methyl)cyclohexanecarboxylic acid;
(3R,5R)-1-amino-3-(aminomethyl)-5-(2-boronoethyl)cyclohexanecarboxylic acid;
(3S,5S)-1-amino-3-(aminomethyl)-5-(2-boronoethyl)cyclohexanecarboxylic acid;
(3R,5R)-1-amino-3-(2-boronoethyl)-5-((dimethylamino)methyl)cyclohexanecarboxylic acid;
(3S,5S)-1-amino-3-(2-boronoethyl)-5-((dimethylamino)methyl)cyclohexanecarboxylic acid;
(3R,5S)-3-amino-5-(2-boronoethyl)piperidine-3-carboxylic acid;
(3S,5R)-3-amino-5-(2-boronoethyl)piperidine-3-carboxylic acid;
(3R,5S)-3-amino-5-(2-boronoethyl)piperidine-3-carboxylic acid;

(3S,5S)-3-amino-5-(2-boronoethyl)piperidine-3-carboxylic acid;
(3R,5S)-3-amino-5-(2-boronoethyl)-1-methylpiperidine-3-carboxylic acid;
(3S,5R)-3-amino-5-(2-boronoethyl)-1-methylpiperidine-3-carboxylic acid;
(3R,5R)-3-amino-5-(2-boronoethyl)tetrahydro-2H-pyran-3-carboxylic acid;
(3S,5S)-3-amino-5-(2-boronoethyl)tetrahydro-2H-pyran-3-carboxylic acid;
(3R,5S)-3-amino-5-(2-boronoethyl)tetrahydro-2H-pyran-3-carboxylic acid;
(3S,5R)-3-amino-5-(2-boronoethyl)tetrahydro-2H-pyran-3-carboxylic acid;
(1R,5R)-1-amino-5-(2-boronoethyl)-2-(dimethylamino)cyclohexane-1-carboxylic acid; or
(1S,5S)-1-amino-5-(2-boronoethyl)-2-(dimethylamino)cyclohexane-1-carboxylic acid;
or as a pharmaceutically acceptable salt thereof, or a stereoisomer, a tautomer, and/or a solvate thereof.

In certain embodiments, the compounds of Formula (I) according to the invention can be pharmaceutically acceptable salt. For example, the representative hydrochloride salts of the compounds of Formula (I) can be:

| Example No. | Compound Structure | Compound Name |
|---|---|---|
| 1 | 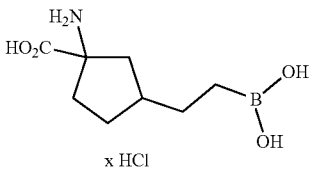 | 1-amino-3-(2-boronoethyl)cyclopentane-1-carboxylic acid hydrochloride |
| 2 | 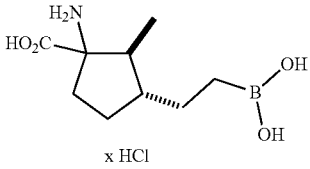 | rac-(2S,3R)-1-amino-3-(2-boronoethyl)-2-methylcyclopentane-1-carboxylic acid hydrochloride |
| 3 | 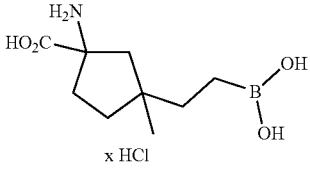 | 1-amino-3-(2-boronoethyl)-3-methylcyclopentane-1-carboxylic acid hydrochloride |
| 4 | 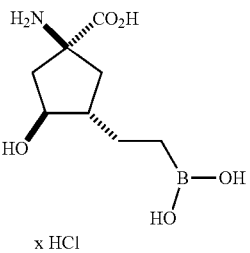 [SMILES: N[C@@]1(C(=O)O)C[C@H](CCB(O)O)[C@@H](O)C1] | rac-(1S,3S,4S)-1-amino-3-(2-boronoethyl)-4-hydroxycyclopentane-1-carboxylic acid hydrochloride |
| 5 | 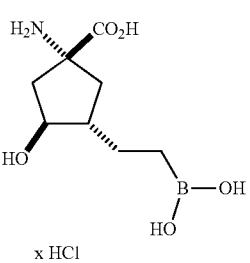 [SMILES: N[C@]1(C(=O)O)C[C@H](CCB(O)O)[C@@H](O)C1] | rac-(1R,3S,4S)-1-amino-3-(2-boronoethyl)-4-hydroxycyclopentane-1-carboxylic acid hydrochloride |

| Example No. | Compound Structure | Compound Name |
|---|---|---|
| 6 | 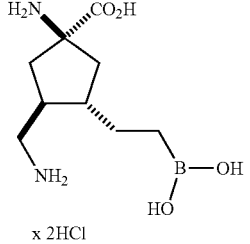 [SMILES: NC[C@H]1C[C@](N)(C(=O)O)C[C@@H]1CCB(O)O] | rac-(1S,3S,4S)-1-amino-3-(aminomethyl)-4-(2-boronoethyl)cyclopentane-1-carboxylic acid dihydrochloride |
| 7 | 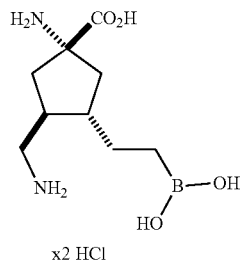 [SMILES: NC[C@H]1C[C@@](N)(C(=O)O)C[C@@H]1CCB(O)O] | rac-(1R,3S,4S)-1-amino-3-(aminomethyl)-4-(2-boronoethyl)cyclopentane-1-carboxylic acid dihydrochloride |
| 8 | 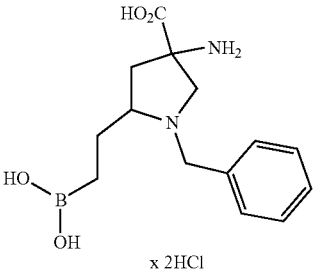 [SMILES: NC1(C(=O)O)CC(CCB(O)O)N(Cc2ccccc2)C1] | 3-amino-1-benzyl-5-(2-boronoethyl)-pyrrolidine-3-carboxylic acid dihydrochloride |
| 9 | 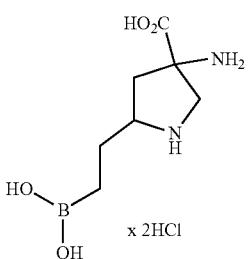 [SMILES: NC1(C(=O)O)CNC(CCB(O)O)C1] | 3-amino-5-(2-boronoethyl)pyrrolidine-3-carboxylic acid dihydrochloride |
| 10 | 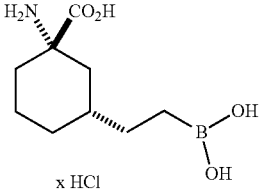 [SMILES: N[C@@]1(C(=O)O)CCC[C@@H](CCB(O)O)C1] | rac-(1S,3R)-1-amino-3-(2-boronoethyl)-cyclohexane-1-carboxylic acid hydrochloride |
| 11 | 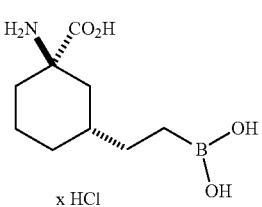 [SMILES: N[C@]1(C(=O)O)CCC[C@@H](CCB(O)O)C1] | rac-(1R,3R)-1-amino-3-(2-boronoethyl)-cyclohexane-1-carboxylic acid hydrochloride |

| Example No. | Compound Structure | Compound Name |
|---|---|---|
| 12 | 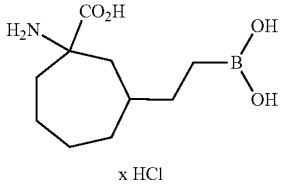 x HCl | 1-amino-3-(2-boronoethyl)cycloheptane-1-carboxylic acid hydrochloride |
| 13 | 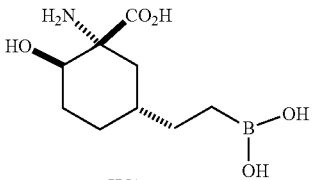 x HCl | rac-(1R,2R,5R)-1-amino-5-(2-boronoethyl)-2-hydroxycyclohexane-1-carboxylic acid hydrochloride |
| 14 | 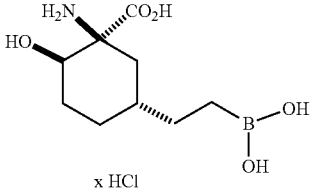 x HCl | rac-(1S,2R,5R)-1-amino-5-(2-boronoethyl)-2-hydroxycyclohexane-1-carboxylic acid hydrochloride |
| 15 | 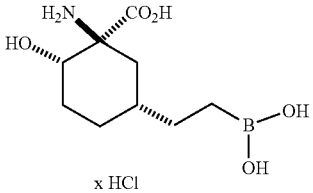 x HCl | rac-(1S,2S,5R)-1-amino-5-(2-boronoethyl)-2-hydroxycyclohexane-1-carboxylic acid hydrochloride |
| 16 | 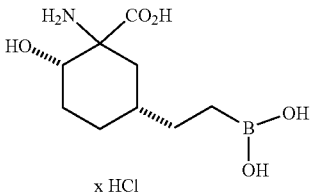 x HCl | rac-(2S,5R)-1-amino-5-(2-boronoethyl)-2-hydroxycyclohexane-1-carboxylic acid hydrochloride |
| 17 | 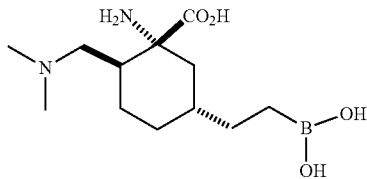 x 2HCl | rac-(1R,2S,5R)-1-amino-5-(2-boronoethyl)-2-((dimethylamino)methyl)cyclohexane-1-carboxylic acid dihydrochloride |
| 18 | 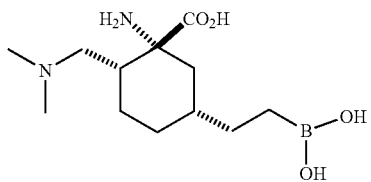 x 2HCl | rac-(1R,2R,5R)-1-amino-5-(2-boronoethyl)-2-((dimethylamino)methyl)cyclohexane-1-carboxylic acid dihydrochloride |

| Example No. | Compound Structure | Compound Name |
|---|---|---|
| 19 | 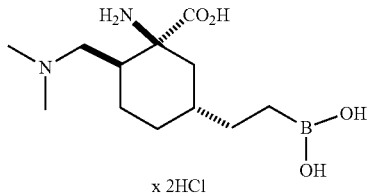 x 2HCl | rac-(1S,2S,5R)-1-amino-5-(2-boronoethyl)-2-((dimethylamino)methyl)cyclohexane-1-carboxylic acid dihydrochloride |
| 20 | 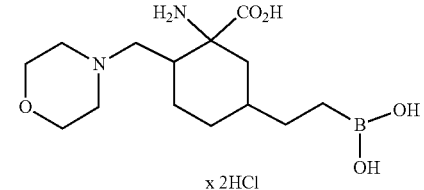 [SMILES: NC1(C(=O)O)CC(CCB(O)O)CCC1CN1CCOCC1] x 2HCl | 1-amino-5-(2-boronoethyl)-2-(morpholinomethyl)cyclohexane-1-carboxylic acid dihydrochloride |
| 21 | 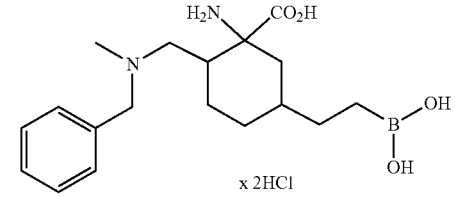 [SMILES: CN(Cc1ccccc1)CC1CCC(CCB(O)O)CC1(N)C(=O)O] x 2HCl | 1-amino-2-((benzyl(methyl)amino)methyl)-5-(2-boronoethyl)cyclohexane-1-carboxylic acid dihydrochloride |
| 22 | 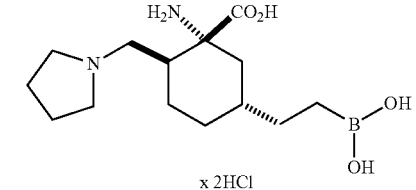 x 2HCl | rac-(1R,2S,5R)-1-amino-5-(2-boronoethyl)-2-(pyrrolidin-1-ylmethyl)cyclohexane-1-carboxylic acid dihydrochloride |
| 23 | 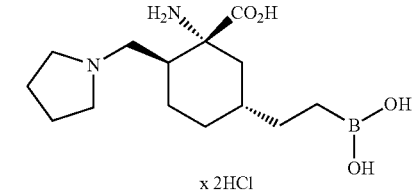 [SMILES: N[C@]1(C(=O)O)C[C@H](CCB(O)O)CC[C@H]1CN1CCCC1] x 2HCl | (1R,2S,5R)-1-amino-5-(2-boronoethyl)-2-(pyrrolidin-1-ylmethyl)cyclohexane-1-carboxylic acid dihydrochloride |
| 24 | 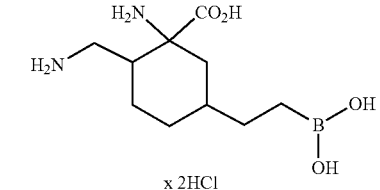 [SMILES: NCC1CCC(CCB(O)O)CC1(N)C(=O)O] x 2HCl | 1-amino-2-(aminomethyl)-5-(2-boronoethyl)cyclohexane-1-carboxylic acid dihydrochloride |
| 25 | 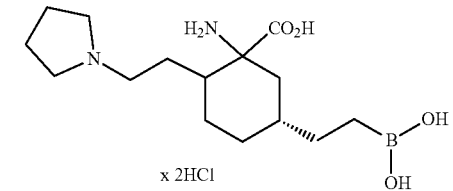 [SMILES: NC1(C(=O)O)C[C@H](CCB(O)O)CCC1CCN1CCCC1] x 2HCl | 1-amino-5-(2-boronoethyl)-2-(2-(pyrrolidin-1-yl)ethyl)cyclohexane-1-carboxylic acid dihydrochloride |

| Example No. | Compound Structure | Compound Name |
|---|---|---|
| 26 | 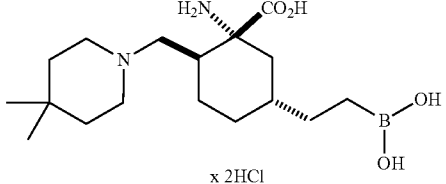 x 2HCl | rac-(1R,2S,5R)-1-amino-5-(2-boronoethyl)-2-((4,4-dimethylpiperidin-1-yl)methyl)cyclohexanecarboxylic acid dihydrochloride |
| 27 | 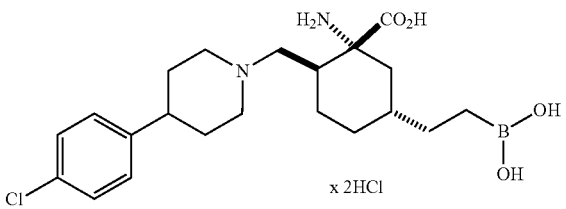 x 2HCl | rac-(1R,2S,5R)-1-amino-5-(2-boronoethyl)-2-((4-(4-chlorophenyl)piperidin-1-yl)methyl)cyclohexanecarboxylic acid dihydrochloride |
| 28 | 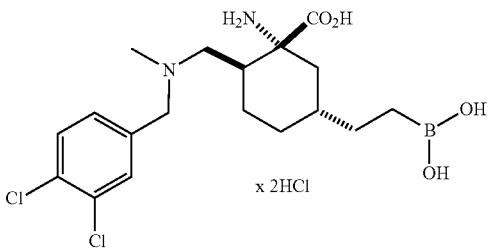 x 2HCl | rac-(1R,2S,5R)-1-amino-5-(2-boronoethyl)-2-(((3,4-dichlorobenzyl)(methyl)amino)methyl)cyclohexanecarboxylic acid dihydrochloride |
| 29 | 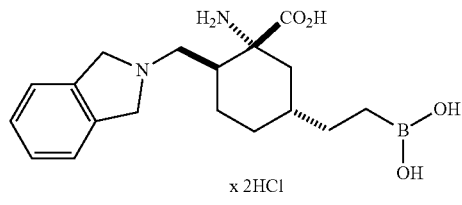 x 2HCl | rac-(1R,2S,5R)-1-amino-5-(2-boronoethyl)-2-(isoindolin-2-ylmethyl)cyclohexanecarboxylic acid dihydrochloride |
| 30 | 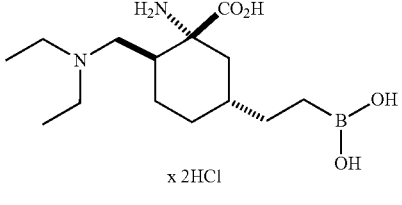 x 2HCl | rac-(1R,2S,5R)-1-amino-5-(2-boronoethyl)-2-((diethylamino)methyl)cyclohexanecarboxylic acid dihydrochloride |
| 31 | 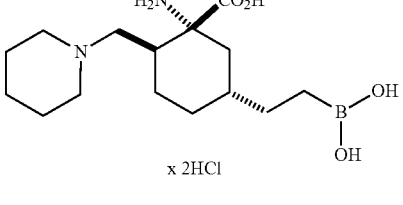 x 2HCl | rac-(1R,2S,5R)-1-amino-5-(2-boronoethyl)-2-(piperidin-1-ylmethyl)cyclohexanecarboxylic acid dihydrochloride |
| 32 | 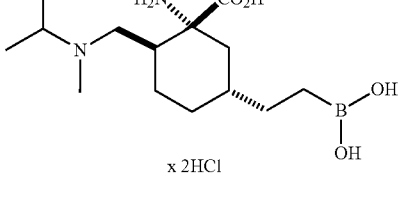 x 2HCl | rac-(1R,2S,5R)-1-amino-5-(2-boronoethyl)-2-((isopropyl(methyl)amino)methyl)cyclohexanecarboxylic acid dihydrochloride |

-continued

| Example No. | Compound Structure | Compound Name |
|---|---|---|
| 33 | 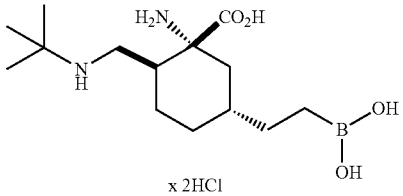 | rac-(1R,2S,5R)-1-amino-5-(2-boronoethyl)-2-((tert-butylamino)methyl)cyclohexanecarboxylic acid dihydrochloride |
| 34 | 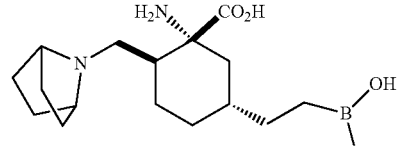 | rac-(1R,2S,5R)-2-(7-azabicyclo[2.2.1]heptan-7-ylmethyl)-1-amino-5-(2-boronoethyl)cyclohexanecarboxylic acid dihydrochloride |
| 35 | 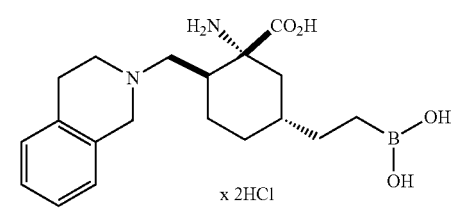 | rac-(1R,2S,5R)-1-amino-5-(2-boronoethyl)-2-((3,4-dihydroisoquinolin-2(1H)-yl)methyl)cyclohexanecarboxylic acid dihydrochloride |
| 36 | 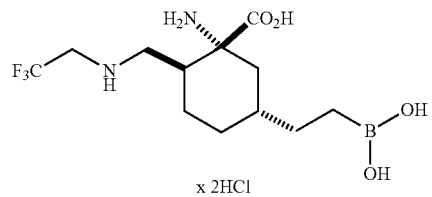 | rac-(1R,2S,5R)-1-amino-5-(2-boronoethyl)-2-((((2,2,2-trifluoroethyl)amino)methyl)cyclohexanecarboxylic acid dihydrochloride |
| 37 | 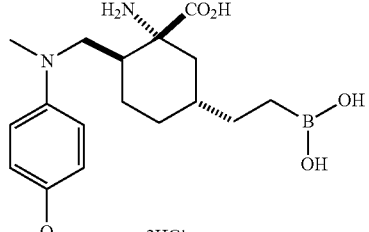 | rac-(1R,2S,5R)-1-amino-5-(2-boronoethyl)-2-((((4-methoxyphenyl)(methyl)amino)methyl)cyclohexanecarboxylic acid dihydrochloride |
| 38 | 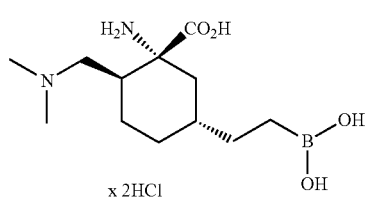 [SMILES: CN(C)C[C@@H]1CC[C@@H](CCB(O)O)C[C@]1(N)C(=O)O] | (1R,2S,5R)-1-amino-5-(2-boronoethyl)-2-((dimethylamino)methyl)cyclohexanecarboxylic acid dihydrochloride |
| 39 | 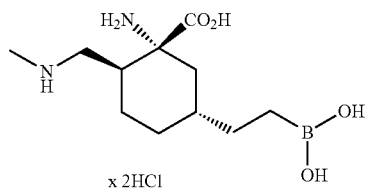 [SMILES: CNC[C@@H]1CC[C@@H](CCB(O)O)C[C@]1(N)C(=O)O] | (1R,2S,5R)-1-amino-5-(2-boronoethyl)-2-((methylamino)methyl)cyclohexanecarboxylic acid dihydrochloride |

| Example No. | Compound Structure | Compound Name |
|---|---|---|
| 40 | 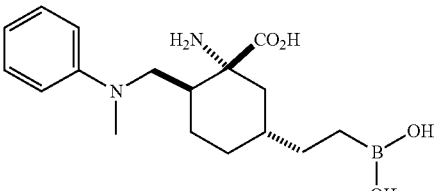 x 2HCl | rac-(1R,2S,5R)-1-amino-5-(2-boronoethyl)-2-((methyl(phenyl)amino)methyl)cyclohexanecarboxylic acid dihydrochloride |
| 41 | 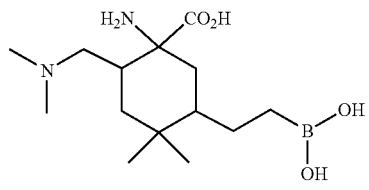 x 2HCl | 1-amino-5-(2-boronoethyl)-2-((dimethylamino)methyl)-4,4-dimethylcyclohexane-1-carboxylic acid dihydrochloride |
| 42 | 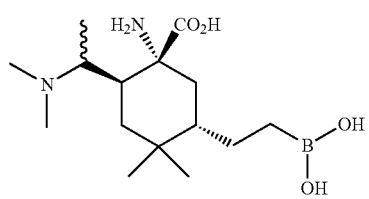 x 2HCl | (1R,2S,5R)-1-amino-5-(2-boronoethyl)-2-(1-(dimethylamino)ethyl)cyclohexanecarboxylic acid dihydrochloride |
| 43 | 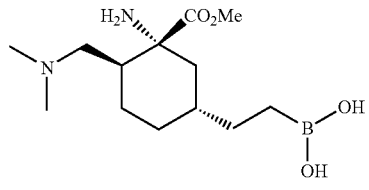 x2HCl | (2-((1R,3R,4S)-3-amino-4-((dimethylamino)methyl)-3-(methoxycarbonyl)cyclohexyl)ethyl)boronic acid dihydrochloride |
| 44 | 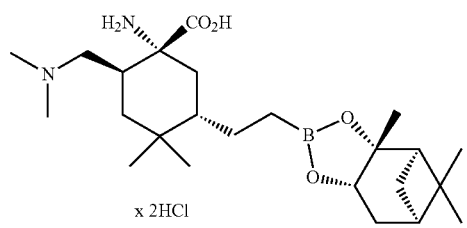 x 2HCl | (1R,2S,5R)-1-amino-2-((dimethylamino)methyl)-5-(2-((3aR,4R,6R,7aS)-3a,5,5-trimethylhexahydro-4,6-methanobenzo[d][1,3,2]dioxaborol-2-yl)ethyl)cyclohexane-1-carboxylic acid dihydrochloride |
| 45 | 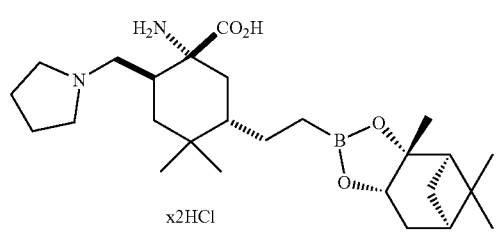 x2HCl | (1R,2S,5R)-1-amino-2-(pyrrolidin-1-ylmethyl)-5-(2-((3aR,4R,6R,7aS)-3a,5,5-trimethylhexahydro-4,6-methanobenzo[d][1,3,2]dioxaborol-2-yl)ethyl)cyclohexanecarboxylic acid dihydrochloride |
| 46 | 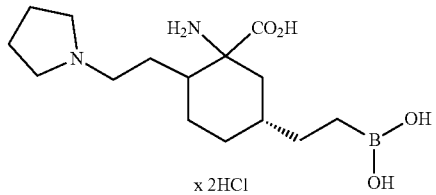 [SMILES: NC1(C(=O)O)C[C@H](CCB(O)O)CCC1CCN1CCCC1] x 2HCl | (5R)-1-amino-5-(2-boronoethyl)-2-(2-(pyrrolidin-1-yl)ethyl)cyclohexanecarboxylic acid |

-continued

| Example No. | Compound Structure | Compound Name |
|---|---|---|
| 47 | 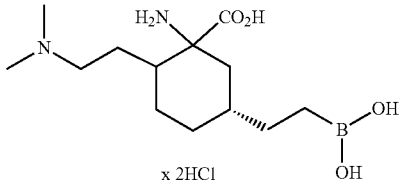 [SMILES: CN(C)CCC1CC[C@@H](CCB(O)O)CC1(N)C(=O)O] | (5R)-1-amino-5-(2-boronoethyl)-2-(2-(dimethylamino)ethyl)cyclohexanecarboxylic acid dihydrochloride |
| 48 | 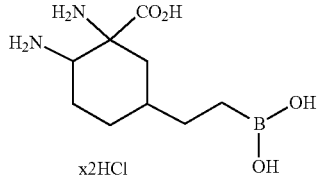 [SMILES: NC1CCC(CCB(O)O)CC1(N)C(=O)O] | 1,2-diamino-5-(2-boronoethyl)cyclohexanecarboxylic acid dihydrochloride |
| 49 | 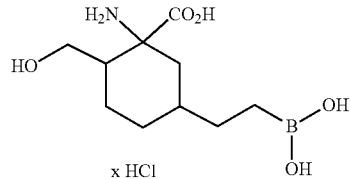 [SMILES: NC1(C(=O)O)CC(CCB(O)O)CCC1CO] | 1-amino-5-(2-boronoethyl)-2-(hydroxymethyl)cyclohexanecarboxylic acid hydrochloride |
| 50 | 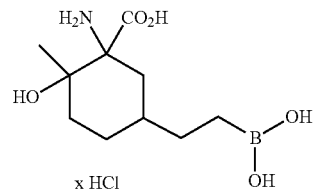 [SMILES: CC1(O)CCC(CCB(O)O)CC1(N)C(=O)O] | 1-amino-5-(2-boronoethyl)-2-hydroxy-2-methylcyclohexanecarboxylic acid hydrochloride |
| 51 | 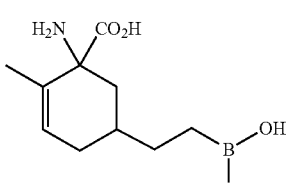 | 1-amino-5-(2-boronoethyl)-2-methylcyclohex-2-enecarboxylic acid hydrochloride |
| 52 | 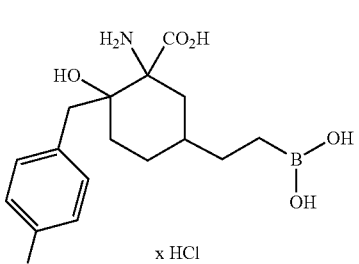 | 1-amino-5-(2-boronoethyl)-2-(4-chlorobenzyl)-2-hydroxycyclohexanecarboxylic acid hydrochloride |
| 53 | 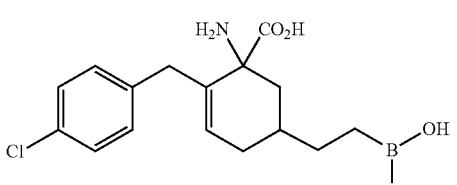 | 1-amino-5-(2-boronoethyl)-2-(4-chlorobenzyl)cyclohex-2-enecarboxylic acid hydrochloride |

-continued

| Example No. | Compound Structure | Compound Name |
|---|---|---|
| 54 | 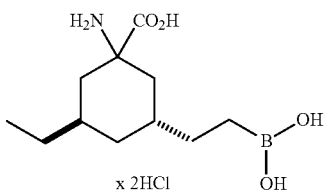 [SMILES: CC[C@@H]1C[C@@H](CCB(O)O)CC(N)(C(=O)O)C1] x 2HCl | rac-(3R,5R)-1-amino-3-(aminomethyl)-5-(2-boronoethyl)cyclohexanecarboxylic acid dihydrochloride |
| 55 | 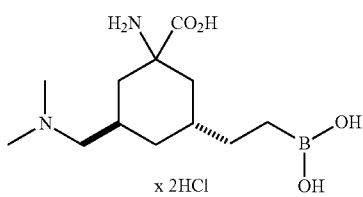 [SMILES: CN(C)C[C@@H]1C[C@@H](CCB(O)O)CC(N)(C(=O)O)C1] x 2HCl | rac-(3R,5R)-1-amino-3-(2-boronoethyl)-5-((dimethylamino)methyl)cyclohexanecarboxylic acid dihydrochloride |
| 56 | 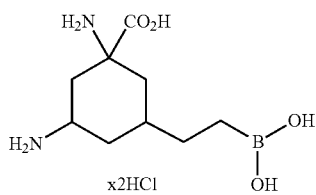 [SMILES: NC1CC(CCB(O)O)CC(N)(C(=O)O)C1] x2HCl | 1,3-diamino-5-(2-boronoethyl)cyclohexanecarboxylic acid dihydrochloride |
| 57 | 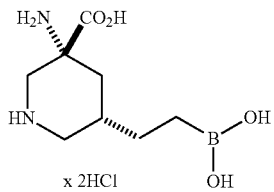 [SMILES: N[C@@]1(C(=O)O)CNC[C@@H](CCB(O)O)C1] x 2HCl | rac-(3R,5S)-3-amino-5-(2-boronoethyl)piperidine-3-carboxylic acid dihydrochloride |
| 58 | 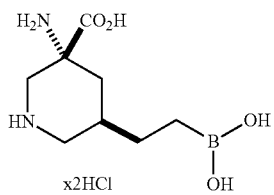 [SMILES: N[C@@]1(C(=O)O)CNC[C@H](CCB(O)O)C1] x2HCl | rac-(3R,5R)-3-amino-5-(2-boronoethyl)piperidine-3-carboxylic acid dihydrochloride |
| 59 | 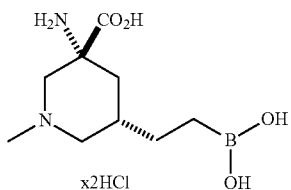 [SMILES: CN1C[C@@H](CCB(O)O)C[C@](N)(C(=O)O)C1] x2HCl | rac-(3R,5S)-3-amino-5-(2-boronoethyl)-1-methylpiperidine-3-carboxylic acid dihydrochloride |
| 60 | 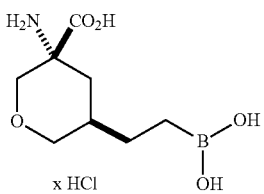 [SMILES: N[C@@]1(C(=O)O)COC[C@H](CCB(O)O)C1] x HCl | rac-(3R,5R)-3-amino-5-(2-boronoethyl)tetrahydro-2H-pyran-3-carboxylic acid hydrochloride |

| Example No. | Compound Structure | Compound Name |
|---|---|---|
| 61 | 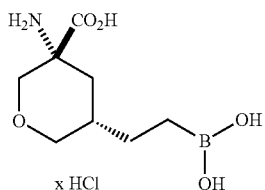 [SMILES: N[C@@]1(C(=O)O)COC[C@@H](CCB(O)O)C1] | rac-(3R,5S)-3-amino-5-(2-boronoethyl)tetrahydro-2H-pyran-3-carboxylic acid hydrochloride |
| 62 | 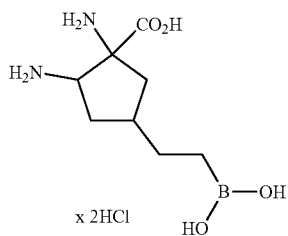 [SMILES: NC1CC(CCB(O)O)CC1(N)C(=O)O] | 1,2-diamino-4-(2-boronoethyl)cyclopentanecarboxylic acid dihydrochloride |
| 63 | 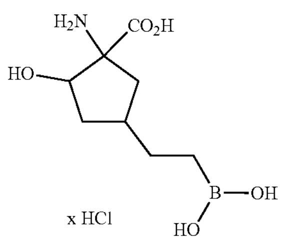 [SMILES: NC1(C(=O)O)CC(CCB(O)O)CC1O] | 1-amino-4-(2-boronoethyl)-2-hydroxycyclopentanecarboxylic acid hydrochloride |
| 64 | 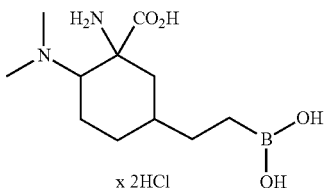 [SMILES: CN(C)C1CCC(CCB(O)O)CC1(N)C(=O)O] | rac-(1R,5R)-1-amino-5-(2-boronoethyl)-2-(dimethylamino)cyclohexane-1-carboxylic acid dihydrochloride |
| 65 | 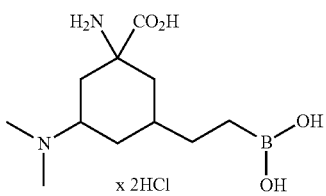 [SMILES: CN(C)C1CC(CCB(O)O)CC(N)(C(=O)O)C1] | 1-amino-3-(2-boronoethyl)-5-(dimethylamino)cyclohexane-1-carboxylic acid dihydrochloride |
| 66 | 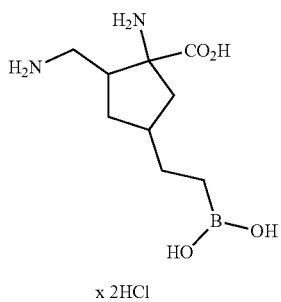 [SMILES: NCC1CC(CCB(O)O)CC1(N)C(=O)O] | 1-amino-2-(aminomethyl)-4-(2-boronoethyl)cyclopentane-1-carboxylic acid dihydrochloride |

| Example No. | Compound Structure | Compound Name |
|---|---|---|
| 67 | 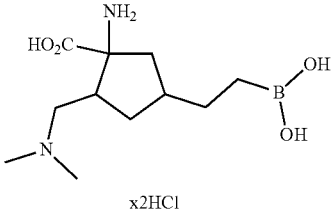 [SMILES: CN(C)CC1CC(CCB(O)O)CC1(N)C(=O)O] | 1-amino-4-(2-boronoethyl)-2-((dimethylamino)methyl)cyclopentane-1-carboxylic acid dihydrochloride dihydrochloride |
| 68 | 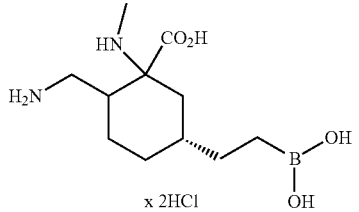 | (5R)-2-(aminomethyl)-5-(2-boronoethyl)-1-(methylamino)cyclohexane-1-carboxylic acid dihydrochloride |
| 69 | 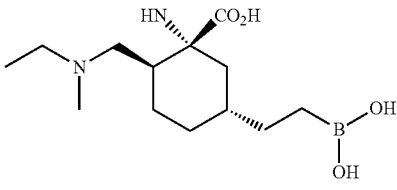 [SMILES: CCN(C)C[C@@H]1CC[C@@H](CCB(O)O)C[C@]1(N)C(=O)O] | (1R,2S,5R)-1-amino-5-(2-boronoethyl)-2-((ethyl(methyl)amino)methyl)cyclohexane-1-carboxylic acid dihydrochloride |
| 70 | 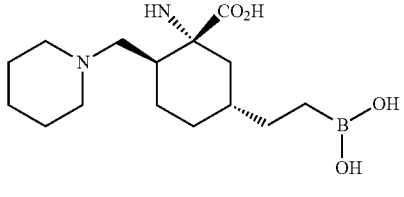 [SMILES: N[C@]1(C(=O)O)C[C@H](CCB(O)O)CC[C@H]1CN1CCCCC1] | (1R,2S,5R)-1-amino-5-(2-boronoethyl)-2-(piperidin-1-ylmethyl)cyclohexane-1-carboxylic acid dihydrochloride |
| 71 | 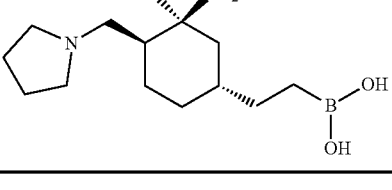 | (1R,2S,5R)-1-amino-5-(2-boronoethyl)-2-(pyrrolidin-1-ylmethyl)cyclohexane-1-carboxylic acid dihydrochloride | or a stereoisomer, a tautomer, and/or a solvate thereof.

In a particular embodiment, the compound of the invention is:

1-amino-5-(2-boronoethyl)-2-(piperidin-1-ylmethyl)cyclohexanecarboxylic acid;
1-amino-5-(2-boronoethyl)-2-((isopropyl(methyl)amino)methyl)cyclohexanecarboxylic acid;
1-amino-5-(2-boronoethyl)-2-((tert-butylamino)methyl)cyclohexanecarboxylic acid;
2-(7-azabicyclo[2.2.1]heptan-7-ylmethyl)-1-amino-5-(2-boronoethyl)cyclohexanecarboxylic acid;
1-amino-5-(2-boronoethyl)-2-((dimethylamino)methyl)cyclohexanecarboxylic acid;
1-amino-5-(2-boronoethyl)-2-((methylamino)methyl)cyclohexanecarboxylic acid;
1-amino-5-(2-boronoethyl)-2-hydroxy-2-methylcyclohexanecarboxylic acid;
1-amino-5-(2-boronoethyl)-2-(2-(dimethylamino)ethyl)cyclohexanecarboxylic acid;
1-amino-5-(2-boronoethyl)-2-(pyrrolidin-1-ylmethyl)cyclohexane-1-carboxylic acid;
1-amino-5-(2-boronoethyl)-2-((ethyl(methyl)amino)methyl)cyclohexane-1-carboxylic acid;
1-amino-2-(aminomethyl)-4-(2-boronoethyl)cyclopentane-1-carboxylic acid;
1-amino-4-(2-boronoethyl)-2-((dimethylamino)methyl)cyclopentane-1-carboxylic acid;
1-amino-5-(2-boronoethyl)-2-(2-(pyrrolidin-1-yl)ethyl)cyclohexanecarboxylic acid;
1,2-diamino-5-(2-boronoethyl)cyclohexanecarboxylic acid;
1-amino-5-(2-boronoethyl)-2-hydroxycyclohexane-1-carboxylic acid;
1-amino-3-(2-boronoethyl)-5-(dimethylamino)cyclohexane-1-carboxylic acid;
3-amino-5-(2-boronoethyl)piperidine-3-carboxylic acid;
3-amino-5-(2-boronoethyl)tetrahydro-2H-pyran-3-carboxylic acid;
1-amino-5-(2-boronoethyl)-2-((dimethylamino)methyl)cyclohexane-1-carboxylic acid; or
1-amino-5-(2-boronoethyl)-2-(piperidin-1-ylmethyl)cyclohexane-1-carboxylic acid;

or a stereoisomer, a tautomer, a pharmaceutically acceptable salt, and/or a solvate thereof.

In a particular embodiment, the invention relates to a compound selected from:
(1R,2S,5R)-1-amino-5-(2-boronoethyl)-2-(piperidin-1-ylmethyl)cyclohexanecarboxylic acid;
(1R,2S,5R)-1-amino-5-(2-boronoethyl)-2-((isopropyl(methyl)amino)methyl)cyclohexanecarboxylic acid;
(1R,2S,5R)-1-amino-5-(2-boronoethyl)-2-((tert-butylamino)methyl)cyclohexanecarboxylic acid;
(1R,2S,5R)-2-(7-azabicyclo[2.2.1]heptan-7-ylmethyl)-1-amino-5-(2-boronoethyl)cyclohexanecarboxylic acid;
(1R,2S,5R)-1-amino-5-(2-boronoethyl)-2-((dimethylamino)methyl)cyclohexanecarboxylic acid;
(1R,2S,5R)-1-amino-5-(2-boronoethyl)-2-((methylamino)methyl)cyclohexanecarboxylic acid
1-amino-5-(2-boronoethyl)-2-hydroxy-2-methylcyclohexanecarboxylic acid;
(5R)-1-amino-5-(2-boronoethyl)-2-(2-(dimethylamino)ethyl)cyclohexanecarboxylic acid;
rac-(1R,2S,5R)-1-amino-5-(2-boronoethyl)-2-(pyrrolidin-1-ylmethyl)cyclohexane-1-carboxylic acid dihydrochloride;
(1R,2S,5R)-1-amino-5-(2-boronoethyl)-2-(pyrrolidin-1-ylmethyl)cyclohexane-1-carboxylic acid;
(1R,2S,5R)-1-amino-5-(2-boronoethyl)-2-((ethyl(methyl)amino)methyl)cyclohexane-1-carboxylic acid;
1-amino-2-(aminomethyl)-4-(2-boronoethyl)cyclopentane-1-carboxylic acid;
1-amino-4-(2-boronoethyl)-2-((dimethylamino)methyl)cyclopentane-1-carboxylic acid;
(5R)-1-amino-5-(2-boronoethyl)-2-(2-(pyrrolidin-1-yl)ethyl)cyclohexanecarboxylic acid;
1,2-diamino-5-(2-boronoethyl)cyclohexanecarboxylic acid;
rac-(1R,2R,5R)-1-Amino-5-(2-boronoethyl)-2-hydroxycyclohexane-1-carboxylic acid;
rac-(1S,2R,5R)-1-Amino-5-(2-boronoethyl)-2-hydroxycyclohexane-1-carboxylic acid;
rac-(1S,2S,5R)-1-Amino-5-(2-boronoethyl)-2-hydroxycyclohexane-1-carboxylic acid;
rac-(2S,5R)-1-Amino-5-(2-boronoethyl)-2-hydroxycyclohexane-1-carboxylic acid;
1-amino-3-(2-boronoethyl)-5-(dimethylamino)cyclohexane-1-carboxylic acid;
rac-(3R,5S)-3-amino-5-(2-boronoethyl)piperidine-3-carboxylic acid;
rac-(3R,5R)-3-amino-5-(2-boronoethyl)tetrahydro-2H-pyran-3-carboxylic acid;
rac-(3R,5S)-3-amino-5-(2-boronoethyl)tetrahydro-2H-pyran-3-carboxylic acid;
rac-(1R,2S,5R)-1-amino-5-(2-boronoethyl)-2-((dimethylamino)methyl)cyclohexane-1-carboxylic acid dihydrochloride;
rac-(1R,2R,5R)-1-amino-5-(2-boronoethyl)-2-((dimethylamino)methyl)cyclohexane-1-carboxylic acid dihydrochloride;
rac-(1S,2S,5R)-1-amino-5-(2-boronoethyl)-2-((dimethylamino)methyl)cyclohexane-1-carboxylic acid dihydrochloride; or
1-amino-5-(2-boronoethyl)-2-(piperidin-1-ylmethyl)cyclohexane-1-carboxylic acid
or a pharmaceutically acceptable salt, and/or a solvate thereof.

In a particular embodiment, the invention relates to a compound selected from:
(1R,2S,5R)-1-amino-5-(2-boronoethyl)-2-(piperidin-1-ylmethyl)cyclohexanecarboxylic acid dihydrochloride;
(1R,2S,5R)-1-amino-5-(2-boronoethyl)-2-((isopropyl(methyl)amino)methyl)cyclohexanecarboxylic acid;
(1R,2S,5R)-1-amino-5-(2-boronoethyl)-2-((tert-butylamino)methyl)cyclohexanecarboxylic acid dihydrochloride;
(1R,2S,5R)-2-(7-azabicyclo[2.2.1]heptan-7-ylmethyl)-1-amino-5-(2-boronoethyl)cyclohexanecarboxylic acid dihydrochloride;
(1R,2S,5R)-1-amino-5-(2-boronoethyl)-2-((dimethylamino)methyl)cyclohexanecarboxylic acid;
(1R,2S,5R)-1-amino-5-(2-boronoethyl)-2-((methylamino)methyl)cyclohexanecarboxylic acid dihydrochloride;
1-amino-5-(2-boronoethyl)-2-hydroxy-2-methylcyclohexanecarboxylic acid hydrochloride;
(5R)-1-amino-5-(2-boronoethyl)-2-(2-(dimethylamino)ethyl)cyclohexanecarboxylic acid dihydrochloride;
rac-(1R,2S,5R)-1-amino-5-(2-boronoethyl)-2-(pyrrolidin-1-ylmethyl)cyclohexane-1-carboxylic acid dihydrochloride;
(1R,2S,5R)-1-amino-5-(2-boronoethyl)-2-(pyrrolidin-1-ylmethyl)cyclohexane-1-carboxylic acid dihydrochloride;
(1R,2S,5R)-1-amino-5-(2-boronoethyl)-2-((ethyl(methyl)amino)methyl)cyclohexane-1-carboxylic acid;
1-amino-2-(aminomethyl)-4-(2-boronoethyl)cyclopentane-1-carboxylic acid dihydrochloride;
1-amino-4-(2-boronoethyl)-2-((dimethylamino)methyl)cyclopentane-1-carboxylic acid;
(5R)-1-amino-5-(2-boronoethyl)-2-(2-(pyrrolidin-1-yl)ethyl)cyclohexanecarboxylic acid;
1,2-diamino-5-(2-boronoethyl)cyclohexanecarboxylic acid dihydrochloride;
rac-(1R,2R,5R)-1-Amino-5-(2-boronoethyl)-2-hydroxycyclohexane-1-carboxylic acid hydrochloride;
rac-(1S,2R,5R)-1-Amino-5-(2-boronoethyl)-2-hydroxycyclohexane-1-carboxylic acid hydrochloride;
rac-(1S,2S,5R)-1-Amino-5-(2-boronoethyl)-2-hydroxycyclohexane-1-carboxylic acid hydrochloride;
rac-(2S,5R)-1-Amino-5-(2-boronoethyl)-2-hydroxycyclohexane-1-carboxylic acid hydrochloride;
1-amino-3-(2-boronoethyl)-5-(dimethylamino)cyclohexane-1-carboxylic acid dihydrochloride;
rac-(3R,5S)-3-amino-5-(2-boronoethyl)piperidine-3-carboxylic acid dihydrochloride;
rac-(3R,5R)-3-amino-5-(2-boronoethyl)tetrahydro-2H-pyran-3-carboxylic acid hydrochloride;
rac-(3R,5S)-3-amino-5-(2-boronoethyl)tetrahydro-2H-pyran-3-carboxylic acid hydrochloride;
rac-(1R,2S,5R)-1-amino-5-(2-boronoethyl)-2-((dimethylamino)methyl)cyclohexane-1-carboxylic acid dihydrochloride;
rac-(1R,2R,5R)-1-amino-5-(2-boronoethyl)-2-((dimethylamino)methyl)cyclohexane-1-carboxylic acid dihydrochloride;
rac-(1S,2S,5R)-1-amino-5-(2-boronoethyl)-2-((dimethylamino)methyl)cyclohexane-1-carboxylic acid dihydrochloride; or
1-amino-5-(2-boronoethyl)-2-(piperidin-1-ylmethyl)cyclohexane-1-carboxylic acid
or a solvate thereof.

Pharmaceutical Compositions of the Invention

Also provided herein are pharmaceutical compositions, comprising (i) a therapeutically effective amount of at least one compound of the invention, or a stereoisomer, tautomer, pharmaceutically acceptable salt, solvate, or prodrug thereof; and (ii) a pharmaceutically acceptable carrier, including, but not limited to, bioavailability enhancers, penetration enhancers, biopolymers, PLGA-based nanoparticles, sugar-based nanoparticles, coating to avoid the deleterious effects of the stomach environment, either by protection of the compound of the invention or derivative thereof, or by release of the biologically active material beyond the stomach environment, such as in the intestine.

The exact nature of the carrier, or, for example excipient or diluent, will depend upon the desired use for the composition, and may be suitable or acceptable for veterinary use and/or suitable or acceptable for human use. The composition may optionally include one or more additional compounds, including one or more additional therapeutic agents.

Compounds of the invention can be combined with other therapeutic agents. The compound of the invention and other therapeutic agent may be administered simultaneously or sequentially. When the other therapeutic agents are administered simultaneously, they can be administered in the same or separate formulations, but they are administered substantially at the same time. The other therapeutic agents are administered sequentially with one another and with compound of the invention, when the administration of the other therapeutic agents and the compound of the invention is temporally separated. The separation in time between the administration of these compounds may be a matter of minutes or it may be longer.

Examples of other therapeutic agents that may be administered with the compounds of the invention include steroids, membrane stabilizers, 5LO inhibitors, leukotriene synthesis and receptor inhibitors, inhibitors of IgE isotype switching or IgE synthesis, IgG isotype switching or IgG synthesis, β-agonists, tryptase inhibitors, aspirin, COX inhibitors, methotrexate, anti-TNF drugs, rituxan, PD4 inhibitors, p38 inhibitors, PDE4 inhibitors, and antihistamines, immunotherapeutic agents, including checkpoint inhibitors such as PD-1, PD-L1 or CTLA-4 inhibitors and IDO/TDO inhibitors, immunosuppressants, agents affecting interleukins, cytokines and chemokine, kinase inhibitors, chemotherapeutic agents including alkylating antineoplastic agents, antimetabolites, anti-microtubule agents, topoisomerase inhibitors, cytotoxic antibiotics or targeted therapies such as antibodies, antibodies drug conjugates, cell-based immunotherapies, nanoparticles, anti-cancer vaccines and radiotherapy.

In some embodiments, the one or more additional chemotherapeutic agents includes aminoglutethimide, amsacrine, anastrozole, asparaginase, AZD5363, *Bacillus* Calmette-Guerin vaccine (beg), bicalutamide, bleomycin, bortezomib, buserelin, busulfan, campothecin, capecitabine, carboplatin, carfilzomib, carmustine, chlorambucil, chloroquine, cisplatin, cladribine, clodronate, cobimetinib, colchicine, cyclophosphamide, cyproterone, cytarabine, dacarbazine, dactinomycin, daunorubicin, demethoxyviridin, dexamethasone, dichloroacetate, dienestrol, diethylstilbestrol, docetaxel, doxorubicin, epirubicin, erlotinib, estradiol, estramustine, etoposide, everolimus, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, lenalidomide, letrozole, leucovorin, leuprolide, levamisole, lomustine, lonidamine, mechlorethamine, medroxyprogesterone, megestrol, melphalan, mercaptopurine, mesna, metformin, methotrexate, miltefosine, mitomycin, mitotane, mitoxantrone, MK-2206, nilutamide, nocodazole, octreotide, olaparib, oxaliplatin, paclitaxel, pamidronate, pazopanib, pentostatin, perifosine, plicamycin, pomalidomide, porfimer, procarbazine, raltitrexed, rituximab, rucaparib, selumetinib, sorafenib, streptozocin, sunitinib, suramin, talazoparib, tamoxifen, temozolomide, temsirolimus, teniposide, testosterone, thalidomide, thioguanine, thiotepa, titanocene dichloride, topotecan, trametinib, trastuzumab, tretinoin, veliparib, vinblastine, vincristine, vindesine, or vinorelbine.

In some embodiments, the one or more additional chemotherapeutic agents includes abagovomab, adecatumumab, afutuzumab, anatumomab mafenatox, apolizumab, blinatumomab, catumaxomab, durvalumab, epratuzumab, inotuzumab ozogamicin, intelumumab, ipilimumab, isatuximab, lambrolizumab, nivolumab, ocaratuzumab, olatatumab, pembrolizumab, pidilizumab, ticilimumab, samalizumab, or tremelimumab.

In some embodiments, the one or more additional immunotherapeutic agents includes epacadostat, GDC-0919, 1-methyl-D-tryptophan, BMS-986205 or PF-06840003.

In some embodiments, the one or more additional chemotherapeutic agents includes ipilimumab, nivolumab, pembrolizumab, or pidilizumab.

In other embodiments, the method further comprises administering one or more non-chemical methods of cancer treatment, such as radiation therapy, surgery, thermoablation, focused ultrasound therapy, cryotherapy, or a combination thereof.

As stated above, an "effective amount" refers to any amount that is sufficient to achieve a desired biological effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial unwanted toxicity and yet is effective to treat the particular subject. The effective amount for any particular application can vary depending on such factors as the disease or condition being treated, the particular compound of the invention being administered, the size of the subject, or the severity of the disease or condition. One of ordinary skill in the art can empirically determine the effective amount of a particular compound of the invention and/or other therapeutic agent without necessitating undue experimentation. It is preferred generally that a maximum dose be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein.

Generally, daily oral doses of active compounds will be, for human subjects, from about 0.0001 milligrams/kg per day, 0.001 milligrams/kg per day, or 0.01 milligrams/kg per day to about 100 milligrams/kg per day or 1000 milligrams/kg per day. It is expected that oral doses in the range of 0.5 to 50 milligrams/kg, in one or several administrations per day, will yield the desired results. Dosage may be adjusted appropriately to achieve desired drug levels sufficient to achieve or maintain a desired therapeutic effect, local or systemic, depending upon the mode of administration. For example, it is expected that intravenous administration would be from one order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds. The compounds may be administered once per week, several times per week (e.g., every other day), once per day or multiple times per day, depending upon, among other things, the mode of administration, the specific indication being treated and the judgment of the prescribing physician.

In one embodiment, intravenous administration of a compound of the invention may typically be from 0.1 mg/kg/day to 20 mg/kg/day.

Determination of an effective dosage of a compound for a particular use and mode of administration is well within the capabilities of those skilled in the art. Effective dosages may be estimated initially from in vitro activity and metabolism assays. For example, an initial dosage of compound for use in animals may be formulated to achieve a circulating blood or serum concentration of the metabolite active compound that is at or above an $IC_{50}$ of the particular compound as measured in as in vitro assay. Calculating dosages to achieve such circulating blood or serum concentrations taking into account the bioavailability of the particular compound via the desired route of administration is well within the capabilities of skilled artisans. Initial dosages of compound can also be estimated from in vivo data, such as animal models. For any compound described herein the therapeutically effective amount can be initially determined from animal models. A therapeutically effective dose can also be determined from human data for compounds of the invention which have been tested in humans and for compounds which are known to exhibit similar pharmacological activities, such as other related active agents. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention can be administered in pharmaceutically acceptable solutions, which may routinely contain pharmaceutically acceptable concentrations of salt, buffering agents, preservatives, compatible carriers, adjuvants, and optionally other therapeutic ingredients.

Pharmaceutical compositions comprising the compound of the invention may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the compounds into preparations which can be used pharmaceutically.

For use in therapy, an effective amount of the compound of the invention can be administered to a subject by any mode that delivers the compound of the invention to the desired surface. Administering the pharmaceutical composition of the present invention may be accomplished by any means known to the skilled artisan. Routes of administration include but are not limited to oral, buccal, nasal, rectal, vaginal, ocular, topical, intravenous, intramuscular, intraperitoneal, subcutaneous, transdermal, direct injection (for example, into an abscess), mucosal, inhalation, and insufflation.

For oral administration, the compounds (i.e., compounds of the invention, and other therapeutic agents) can be formulated readily by combining the active compound(s) with pharmaceutically acceptable carriers well known in the art. Such carriers enable the compounds of the invention to be formulated as tablets, pills, dragees, lozenges, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, binding agents, fillers, lubricants, disintegrants, and wetting agents. Suitable fillers include sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of acid hydrolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, "Soluble Polymer-Enzyme Adducts", In: Enzymes as Drugs, Hocenberg and Roberts, eds., Wiley-Interscience, New York, N.Y., pp. 367-383 (1981); Newmark et al., *J Appl Biochem* 4:185-9 (1982). Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the compound of the invention (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (e.g., powder); for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the compound of the invention (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents which can be used and can include benzalkonium chloride and benzethonium chloride. Potential non-ionic detergents that could be included in the formulation as surfactants include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound of the invention or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

The pharmaceutical compositions may, if desired, be presented in a pack or dispenser device which may contain one or more unit dosage forms containing the compound(s). The pack may, for example, comprise metal or plastic foil, such as a blister pack. The pack or dispenser device may be accompanied by instructions for administration.

For buccal administration, the compositions may take the form of tablets or lozenges formulated in conventional manner.

For topical administration, the compound may be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal oral or pulmonary administration.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

Also contemplated herein is pulmonary delivery of the compounds of the invention (or derivatives thereof). The compound of the invention (or derivative) is delivered to the lungs of a mammal while inhaling and traverses across the lung epithelial lining to the blood stream. Other reports of inhaled molecules include Adjei et al., *Pharm Res* 7:565-569 (1990); Adjei et al., *Int J Pharmaceutics* 63:135-144 (1990) (leuprolide acetate); Braquet et al., *J Cardiovasc Pharmacol* 13 (suppl. 5):143-146 (1989) (endothelin-1); Hubbard et al.,

*Annal Int Med* 3:206-212 (1989) (al-antitrypsin); Smith et al., 1989, *J Clin Invest* 84:1145-1146 (a-1-proteinase); Oswein et al., 1990, *"Aerosolization of Proteins"*, Proceedings of Symposium on Respiratory Drug Delivery II, Keystone, Colorado, March, (recombinant human growth hormone); Debs et al., 1988, *J Immunol* 140:3482-3488 (interferon-gamma and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, North Carolina; and the Spinhaler powder inhaler, manufactured by Fisons Corp., Bedford, Mass.

All such devices require the use of formulations suitable for the dispensing of compound of the invention (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified compound of the invention may also be prepared in different formulations depending on the type of chemical modification or the type of device employed.

Formulations suitable for use with a nebulizer, either jet or ultrasonic, will typically comprise compound of the invention (or derivative) dissolved in water at a concentration of about 0.1 to 25 mg of biologically active compound of the invention per mL of solution. The formulation may also include a buffer and a simple sugar (e.g., for compound of the invention stabilization and regulation of osmotic pressure). The nebulizer formulation may also contain a surfactant, to reduce or prevent surface induced aggregation of the compound of the invention caused by atomization of the solution in forming the aerosol.

Formulations for use with a metered-dose inhaler device will generally comprise a finely divided powder containing the compound of the invention (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing compound of the invention (or derivative) and may also include a bulking agent, such as lactose, sorbitol, sucrose, or mannitol in amounts which facilitate dispersal of the powder from the device, e.g., 50 to 90% by weight of the formulation. The compound of the invention (or derivative) should advantageously be prepared in particulate form with an average particle size of less than 10 micrometers (m), most preferably 0.5 to 5 m, for most effective delivery to the deep lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as sterile suspensions, solutions, or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethylcellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, buffer, dextrose solution, before use. To this end, the active compound may be dried by any art-known technique, such as lyophilization, and reconstituted prior to use.

The compounds may also be formulated in rectal or vaginal compositions such as suppositories or retention enemas, e.g., containing conventional suppository bases such as cocoa butter or other glycerides.

For transmucosal administration, penetrants appropriate to the barrier to be permeated are used in the formulation. Such penetrants are known in the art.

For ocular administration, the compound(s) may be formulated as a solution, emulsion, suspension, etc. suitable for administration to the eye. A variety of vehicles suitable for administering compounds to the eye are known in the art.

In addition to the formulations described above, for prolonged delivery, the compounds may also be formulated as a depot preparation for administration by, for example, implantation or intramuscular injection. Such long acting formulations may be formulated with suitable polymeric or hydrophobic materials (for example as an emulsion in an acceptable oil) or ion exchange resins, or as sparingly soluble derivatives, for example, as a sparingly soluble salt. Alternatively, transdermal delivery systems manufactured as an adhesive disc or patch which slowly releases the compound for percutaneous absorption may be used. To this end, permeation enhancers may be used to facilitate transdermal penetration of the compound.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R, *Science* 249:1527-33 (1990), which is incorporated herein by reference.

The compounds of the invention and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulfuric, nitric, phosphoric, maleic, acetic, salicylic, p-toluenesulfonic, tartaric, citric, methane sulfonic, formic, malonic, succinic, naphthalene-2-sulfonic, and benzenesulfonic. Also, such salts can be prepared as alkaline metal or alkaline earth salts, such as sodium, potassium or calcium salts of the carboxylic acid group.

Typically, such salts are more soluble in aqueous solutions than the corresponding free acids and bases, but salts having lower solubility than the corresponding free acids and bases may also be formed.

The compounds may alternatively be formulated in the pharmaceutical composition per se, or in the form of a hydrate, solvate, or N-oxide.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Pharmaceutical compositions of the invention contain an effective amount of a compound of the invention and optionally therapeutic agents included in a pharmaceutically acceptable carrier. The term "pharmaceutically acceptable carrier" means one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The therapeutic agent(s), including specifically but not limited to the compound of the invention, may be provided in particles. Particles as used herein means nanoparticles or microparticles (or in some instances larger particles) which can consist in whole or in part of the compound of the invention or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero-order release, first-order release, second-order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the compound of the invention in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described in Sawhney H S et al. (1993)*Macromolecules* 26:581-7, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

It will be understood by one of ordinary skill in the relevant arts that other suitable modifications and adaptations to the compositions and methods described herein are readily apparent from the description of the invention contained herein in view of information known to the ordinarily skilled artisan, and may be made without departing from the scope of the invention or any embodiment thereof.

Methods of the Invention

Another aspect of the invention is a method for treating asthma, comprising administering to a subject in need thereof a therapeutically effective amount of a compound of the invention, for example, a compound of Formula (I).

In another aspect, the invention provides a method for inhibiting arginase I, arginase II, or a combination thereof in a cell, comprising contacting the cell with at least one compound according to the invention, for example, a compound of Formula (I), or a stereoisomer, tautomer, pharmaceutically acceptable salt, solvate, or prodrug thereof.

In another aspect, the invention provides a method for the treatment or prevention of a disease or condition associated with expression or activity of arginase I, arginase II, or a combination thereof, comprising administering to a subject in need thereof a therapeutically effective amount of at least one compound according to the invention, for example, a compound of Formula (I), or a stereoisomer, tautomer, pharmaceutically acceptable salt, solvate, or prodrug thereof.

In certain embodiments, the disease or condition is selected from the group consisting of cardiovascular disorders, sexual disorders, wound healing disorders, gastrointestinal disorders, autoimmune disorders, immune disorders, infections, pulmonary disorders, hemolytic disorders, and cancers.

In certain embodiments, the disease or condition is cardiovascular disorder selected from the group consisting of systemic hypertension, pulmonary arterial hypertension (PAH), pulmonary arterial hypertension in high altitude, ischemia reperfusion (IR) injury, myocardial infarction, atherosclerosis.

In certain embodiments, the disease or condition is pulmonary arterial hypertension (PAH).

In certain embodiments, the disease or condition is myocardial infarction or atherosclerosis.

In certain embodiments, the disease or condition is a pulmonary disorder selected from the group consisting of chemically-induced lung fibrosis, idiopathic pulmonary fibrosis, cystic fibrosis, chronic obstructive pulmonary disease (COPD), and asthma.

In certain embodiments, the disease or condition is an autoimmune disorder selected from the group consisting of encephalomyelitis, multiple sclerosis, anti-phospholipid syndrome 1, autoimmune hemolytic anemia, chronic inflammatory demyelinating polyradiculoneuropathy, dermatitis herpetiformis, dermatomyositis, myasthenia gravis, pemphigus, rheumatoid arthritis, stiff-person syndrome, type 1 diabetes, ankylosing spondylitis, paroxysmal nocturnal hemoglobinuria (PNH), paroxysmal cold hemoglobinuria, severe idiopathic autoimmune hemolytic anemia, and Goodpasture's syndrome.

In certain embodiments, the disease or condition is an immune disorder selected from the group consisting of myeloid-derived suppressor cell (MDSC) mediated T-cell dysfunction, human immunodeficiency virus (HIV), autoimmune encephalomyelitis, and ABO mismatch transfusion reaction.

In certain embodiments, the disease or condition is myeloid-derived suppressor cell (MDSC) mediated T-cell dysfunction, In certain embodiments, the disease or condition is a hemolytic disorder selected from the group consisting of sickle-cell disease, thalassemias, hereditary spherocytosis, stomatocytosis, microangiopathic hemolytic anemias, pyruvate kinase deficiency, infection-induced anemia, cardiopulmonary bypass and mechanical heart valve-induced anemia, and chemical induced anemia.

In certain embodiments, the disease or condition is sickle-cell disease.

In certain embodiments, the disease or condition is a gastrointestinal disorder selected from the group consisting of gastrointestinal motility disorders, gastric cancers, inflammatory bowel disease, Crohn's disease, ulcerative colitis, and gastric ulcers.

In certain embodiments, the disease or condition is a sexual disorder selected from the group consisting of Peyronie's disease and erectile dysfunction.

In certain embodiments, the disease or condition is ischemia reperfusion (IR) injury selected from the group consisting of liver IR, kidney IR, and myocardial IR.

In certain embodiments, the disease or condition is a cancer selected from the group consisting of oesophagic, gastric, colon, ovary, breast, pancreatic, head-and-neck, bladder and lung cancers, (including squamous and non-small cell lung carcinoma), renal cell carcinoma, prostate carcinoma, multiple myeloma, neuroblastoma, glioblastoma, astrocytoma, mesothelioma and melanoma, B cells, T cells and NK cells lymphomas, acute and chronic myeloid and lymphoid leukemia.

In certain embodiments, the cancer selected from the group consisting of gastric (including but not limited to gastric or gastroesophageal junction cancer), colorectal cancer, pancreatic cancer, liver cancer, breast cancer, lung cancers (including but not limited to non-small cell lung carcinoma), renal cell carcinoma, prostate carcinoma, multiple myeloma, acute and chronic leukemias, T cell, B cell and NK cell lymphomas, brain tumors (including but not limited to neuroblastoma, glioblastoma, astrocytoma), squamous-cell carcinomas of the head and neck, and melanoma.

In certain embodiments, the disease or condition is selected from the group consisting of renal disease inflammation, psoriasis, leishmaniasis, neurodegenerative diseases, wound healing, human immunodeficiency virus (HIV), hepatitis B virus (HBV), *Helicobacter pylori* infections, fibrotic disorders, arthritis, candidiasis, periodontal disease, keloids, adenotonsilar disease, African sleeping sickness and Chagas' disease.

In certain embodiments, the disease or condition is selected from the group consisting of renal disease inflammation, psoriasis, leishmaniasis, neurodegenerative diseases, wound healing, human immunodeficiency virus (HIV) infection, hepatitis B virus (HBV) infection, hepatitis C virus (HCV) infection, *Helicobacter pylori* infections, fibrotic disorders, arthritis, candidiasis, periodontal disease, keloids, adenotonsilar disease, African sleeping sickness and Chagas' disease.

In certain embodiments, the disease or condition is a wound healing disorder selected from the group consisting of infected and uninfected wound healing.

In certain embodiments, the disease or condition is a wound healing disorder selected from the group consisting of infected and uninfected wound healing.

In certain embodiments, the subject is a mammal selected from the group consisting of human, dog, cat, horse, cow, pig, sheep, goat, ape and rodent.

In certain embodiments, the subject is a mammal selected from the group consisting of mammal selected from the group consisting of human, dog, cat, horse, cow, pig, sheep, goat, and ape.

In certain embodiments, the method of treatment further comprises administering to the patient a therapeutically effective amount of an anti-viral agent, a chemotherapeutic agent (including alkylating antineoplastic agents, antimetabolites, anti-microtubule agents), an immunosuppressant, radiation, an anti-tumor vaccine, an antiviral vaccine, cytokine therapy and/or a tyrosine kinase inhibitor, immunotherapeutic agent, including checkpoint inhibitor such as PD-1, PD-L1 or CTLA-4 inhibitor and IDO/TDO inhibitor, immunosuppressant, agent affecting interleukins, cytokine and chemokine, topoisomerase inhibitor, cytotoxic antibiotic or targeted therapie such as antibody, antibody drug conjugate, cell-based immunotherapy, nanoparticles, anticancer vaccine and radiotherapy prior to, simultaneously with, or after administration of the at least one compound according to the invention, for example, a compound of Formula (I), or a stereoisomer, tautomer, pharmaceutically acceptable salt, solvate, or prodrug thereof.

In certain embodiments, the method of treatment further comprises administering to the subject a therapeutically effective amount of an anti-viral agent, a chemotherapeutic agent including alkylating antineoplastic agents, antimetabolites, anti-microtubule agents (including but not limited to oxaliplatin, gemcitabine, dacarbazine, temozolomide, doxorubicin, 5-fluorouracil), an immunosuppressant (including but not limited to everolimus), immunomodulators (including but not limited to check-point inhibitors: anti-PD-1, anti-PD-L1, anti-CTLA-4 antibodies and IDO/TDO inhibitors), radiation, photodynamic therapy, anti-tumor vaccines, oncolytic viruses, antiviral vaccines, cytokine and chemokine therapy or a tyrosine kinase inhibitor, agents affecting interleukins, topoisomerase inhibitors, cytotoxic antibiotic, targeted therapies such as antibodies, antibodies drug conjugates, cell-based immunotherapies, nanoparticles, prior to, simultaneously with, or after administration of the at least one compound according to Formula (I), or a stereoisomer, tautomer, pharmaceutically acceptable salt, solvate, or prodrug thereof.

In certain embodiments, the method of treatment further comprises administering to the subject a therapeutically effective amount of PD-1, PD-L-1 or CTLA4 antibodies.

In some embodiments, the cancer is chronic lymphocytic leukemia, acute lymphoblastic leukemia, chronic myelogenous leukemia, acute myeloid leukemia, adrenocortical carcinoma, anal cancer, appendix cancer, atypical teratoid/rhabdoid tumor, basal cell carcinoma, bile duct cancer, bladder cancer, bone cancer, brain tumor, brain and spinal cord tumor, brain stem glioma, central nervous system atypical teratoid/rhabdoid tumor, central nervous system embryonal tumors, breast cancer, bronchial tumors, burkitt lymphoma, carcinoid tumor, carcinoma of unknown primary, central nervous system cancer, cervical cancer, childhood cancers, chordoma, chronic myeloproliferative disorders, colon cancer, craniopharyngioma, cutaneous t-cell lymphoma, ductal carcinoma in situ, embryonal tumors, endometrial cancer, ependymoblastoma, ependymoma, esophageal cancer, esthesioneuroblastoma, ewing sarcoma, extracranial germ cell tumor, extrahepatic bile duct cancer, eye cancer, fibrous histiocytoma of bone, gallbladder cancer, gastric cancer, gastrointestinal carcinoid tumor, gastrointestinal stromal tumors, germ cell tumor, extracranial germ cell tumor, extragonadal germ cell tumor, ovarian germ cell tumor, gestational trophoblastic tumor, glioma, hairy cell leukemia, head and neck cancer, heart cancer, hepatocellular cancer, histiocytosis, langerhans cell cancer, hodgkin lymphoma, hypopharyngeal cancer, intraocular melanoma, islet cell tumors, kaposi sarcoma, kidney cancer, langerhans cell histiocytosis, laryngeal cancer, lip and oral cavity cancer, lobular carcinoma in situ, lymphoma, aids-related lymphoma, macroglobulinemia, male breast cancer, medulloblastoma, medulloepithelioma, merkel cell carcinoma, malignant mesothelioma, metastatic squamous neck cancer with occult primary, midline tract carcinoma involving nut gene, mouth cancer, multiple endocrine neoplasia syndrome, plasma cell neoplasm, mycosis fungoides, myeloma, chronic myeloproliferative disorder, nasal cavity cancer, paranasal sinus cancer, nasopharyngeal cancer, non-hodgkin lymphoma, oral cancer, oral cavity cancer, lip cancer, oropharyngeal cancer, osteosarcoma, ovarian cancer, papillomatosis, paraganglioma, paranasal sinus cancer, nasal cavity cancer, parathyroid cancer, penile cancer, pharyngeal cancer, pheochromocytoma, pineal parenchymal tumors of intermediate differentiation, pineoblastoma, pituitary tumor, plasma cell neoplasm, pleuropulmonary blastoma, primary central nervous system lymphoma, rectal cancer, renal cell cancer, renal pelvis cancer, ureter cancer, transitional cell cancer, retinoblastoma, rhabdomyosarcoma, salivary gland cancer, sarcoma, sezary syndrome, skin cancer, small cell lung cancer, small intestine cancer, soft tissue sarcoma, squamous cell carcinoma, squamous neck cancer with occult primary, stomach cancer, supratentorial primitive neuroectodermal tumors, testicular cancer, throat cancer, thymoma, thymic carcinoma, thyroid cancer, transitional cell cancer of the renal pelvis and ureter, gestational trophoblastic tumor, unknown primary, unusual cancer of childhood, urethral cancer, uterine cancer, uterine sarcoma, waldenstrom macroglobulinemia, or wilms tumor.

Uses

In another aspect, the invention provides use of a compound according to the invention, for example, a compound of Formula (I), or a stereoisomer, tautomer, pharmaceutically acceptable salt, solvate, or prodrug thereof in the manufacture of a medicament for the treatment or prevention of a disease or condition associated with expression or activity of arginase I, arginase II, or a combination thereof.

In another aspect, the invention provides use of a compound according to the invention, for example, a compound of Formula (I), or a stereoisomer, tautomer, pharmaceutically acceptable salt, solvate, or prodrug thereof, for protecting an organ during transport.

Examples

The present invention is further illustrated by the following examples, which in no way should be construed as limiting the scope of the claimed invention.

Methods of Preparation and Characterization

The compounds of the present disclosure may be prepared by use of known chemical reactions and procedures. Representative methods for synthesizing compounds of the disclosure are presented below. It is understood that the nature of the substituents required for the desired target compound often determines the method of synthesis. All variable groups of these methods are as described in the generic description if they are not specifically defined below.

Those having skill in the art will recognize that the starting materials and reaction conditions may be varied, the sequence of the reactions altered, and additional steps employed to produce compounds encompassed by the present disclosure, as demonstrated by the following examples. Many general references providing commonly known chemical synthetic schemes and conditions useful for synthesizing the disclosed compounds are available (see, e.g., Smith and March, *March's Advanced Organic Chemistry: Reactions, Mechanisms, and Structure*, Fifth Edition, Wiley-Interscience, 2001; or Vogel, *A Textbook of Practical Organic Chemistry, Including Qualitative Organic Analysis*, Fourth Edition, New York: Longman, 1978).

For the more specific guidance concerning the synthetic approach to boron bearing alpha-amino acids, the reader is referred to the international patent application publications WO 11/133653 (incorporated by reference) and WO 13/059437 (incorporated by reference).

The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the disclosure.

In some cases, protection of certain reactive functionalities may be necessary to achieve some of the above transformations. In general, the need for such protecting groups as well as the conditions necessary to attach and remove such groups will be apparent to those skilled in the art of organic synthesis. An authoritative account describing the many alternatives to the trained practitioner are J. F. W. McOmie, "*Protective Groups in Organic Chemistry*," Plenum Press, London and New York 1973, in T. W. Greene and P. G. M. Wuts, "*Protective Groups in Organic Synthesis*," Third edition, Wiley, New York 1999, in "*The Peptides*"; Volume 3 (editors: E. Gross and J. Meienhofer), Academic Press, London and New York 1981, in "*Methoden der organischen Chemie*," Houben-Weyl, 4th edition, Vol. 15/1, Georg Thieme Verlag, Stuttgart 1974, in H.-D. Jakubke and H. Jescheit, "*Aminosauren, Peptide, Proteine*," Verlag Chemie, Weinheim, Deerfield Beach, and Basel 1982, and/or in Jochen Lehmann, "*Chemie der Kohlenhydrate: Monosaccharide und Derivate*," Georg Thieme Verlag, Stuttgart 1974. The protecting groups may be removed at a convenient subsequent stage using methods known from the art. The disclosures of all articles and references mentioned in this application, including patents, are incorporated herein by reference in their entirety.

Starting materials can be obtained from commercial sources or prepared by well-established literature methods known to those skilled in the art.

All solvents, substrates and reagents that were commercially available were used without further purification. TLC analysis was performed using pre-coated glass plates (0.2±0.03 mm thickness, GF-254, particle size 0.01-0.04 mm) from Fluorochem Ltd, UK. Column chromatography was performed using high-purity grade silica gel (pore size 60 Å, 220-440 mesh particle size, 35-75 μm particle size) from Fluka, Merck or Fluorochem.

Preparative HPLC were performed on LC-20AP Shimadzu with ELSD-LTII detector equipped with Hypersil GOLD 21.2/250 mm, 5 μm C18 column.

$^1$H and $^{13}$C NMR spectra were recorded on Bruker AVANCE II PLUS (Ultra Shield) NMR spectrometer at 700 MHz.

$^{19}$F NMR spectra were recorded on a 200 MHz AVANCE Bruker NMR spectrometer.

All spectra were recorded in appropriate deuterated solvents (CDCl$_3$, DMSO-d$_6$, D$_2$O, CD$_3$OD, etc.) that were commercially available.

Resonances are given in parts per million relative to tetramethylsilane. Data are reported as follows: chemical shift, multiplicity (s=singlet, d=doublet, t=triplet, m=multiplet, bs=broad singlet), coupling constants (Hz) and integration.

Specific rotations were measured on polAAr 3001 Index Instruments polarimeter at 589 nm and 24° C.

ESI-MS spectra were obtained on a Shimadzu LC-20AD LPG separation module with a SPD-M20A UV detector and LCMS-2020 mass detector equipped with Kinetex 2.1/50 mm, 2.6 μm C18 column eluted with 0.5 mL/min flow of 10-90% gradient (over 6 min) of acetonitrile in water.

Exemplary general synthetic methodologies for making compounds of Formula (I) are provided below.

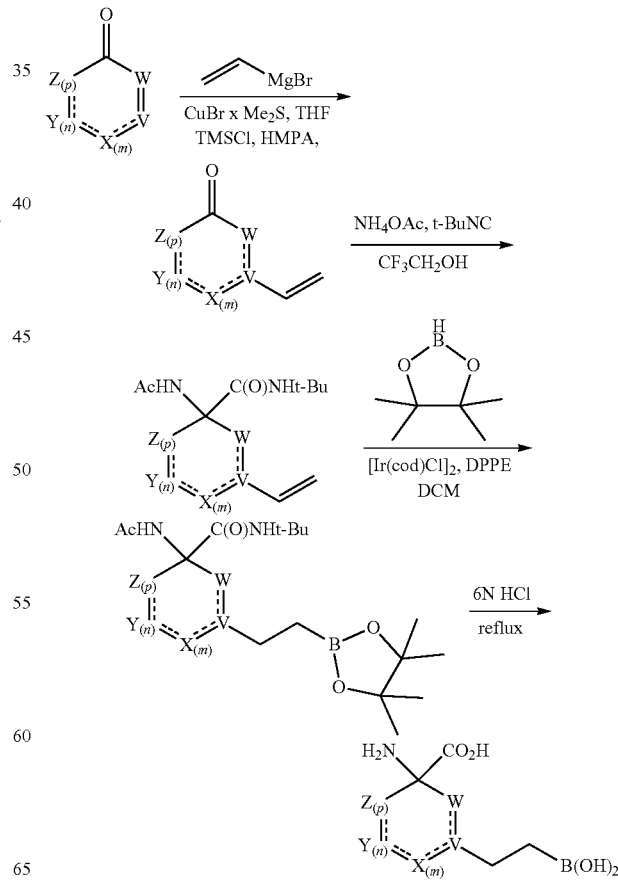

Exemplary general synthetic methodologies for making specific compounds of Formula (I) in an enantioselective fashion are provided below.
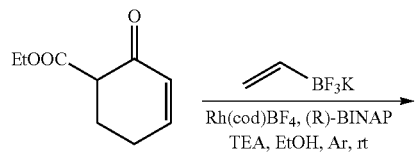
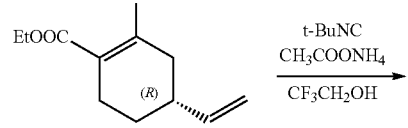
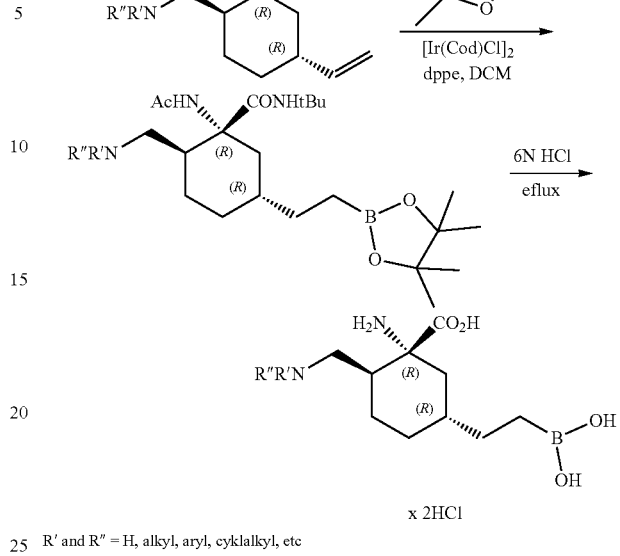
R' and R" = H, alkyl, aryl, cyklalkyl, etc
Alternative enantioselective method is provided below.
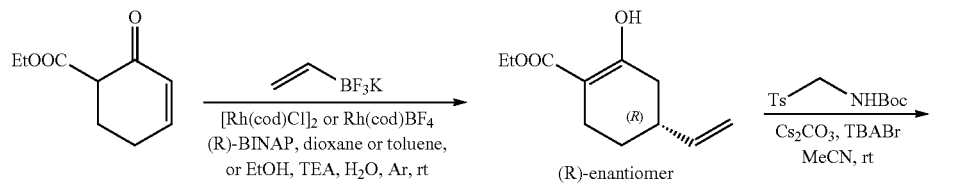
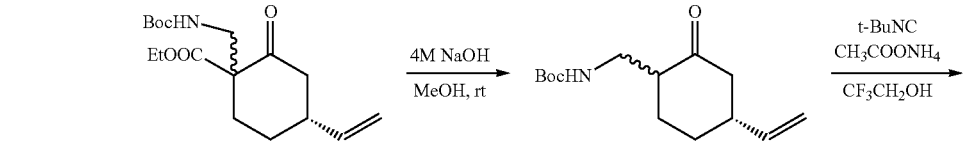
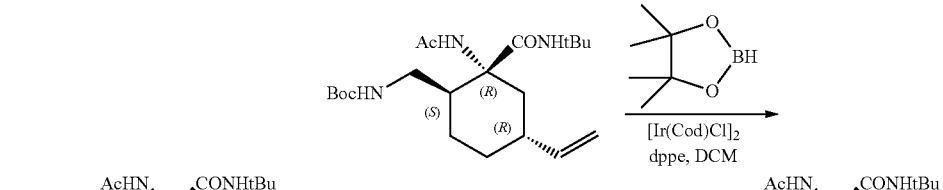
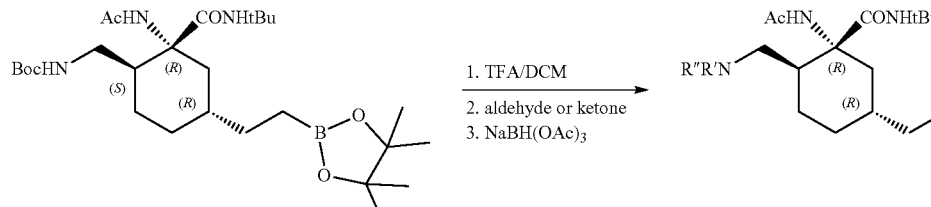
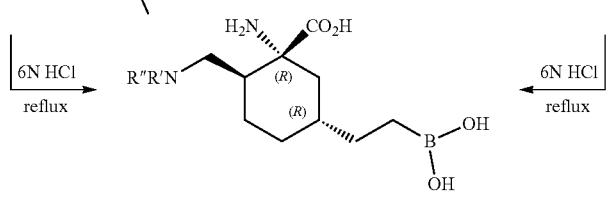
R' and/or R" = H, alkyl

Intermediates Synthesis

Intermediate 1. Ethyl rac-(1R,2R,4R)-2-acetamido-2-(tert-butylcarbamoyl)-4-vinylcyclohexane-1-carboxylate

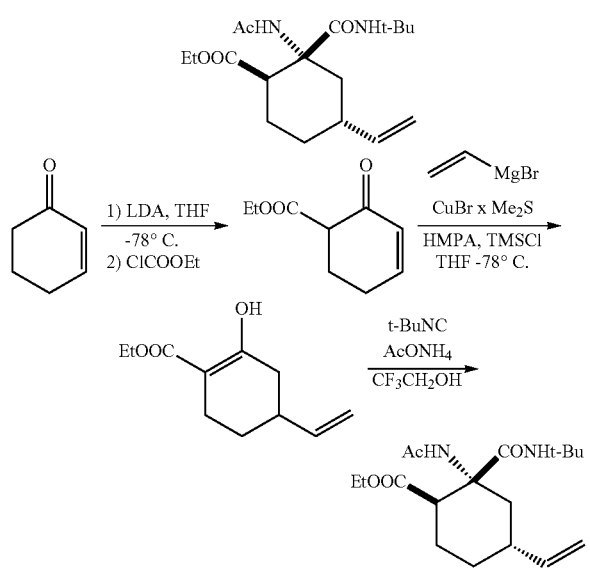

Step A. Ethyl 2-oxocyclohex-3-ene-1-carboxylate

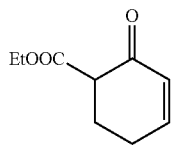 [SMILES: CCOC(=O)C1CCC=CC1=O]

To a solution of freshly distilled diisopropylamine (131.0 mL, 0.936 mol, 1.5 equiv.) in dry THF (1400 mL) a solution of n-BuLi (2.5 M in hexanes) (374.4 mL, 0.936 mol, 1.5 equiv.) was added dropwise at −20° C. under argon. The reaction mixture was stirred for 5 minutes at −20° C. Next, a solution of 2-cycloheksen-1-one (60 g, 0.624 mol, 1 equiv.) was added dropwise and the reaction mixture was stirred for 25 minutes at −20° C. After that time a solution of DMAP (3.8 g, 0,031 mol, 0.05 equiv.) in 30 mL of THF was added and next, immediately ethyl chloroformate (71 mL, 0.749 mol, 1.2 equiv.) was added dropwise at −20° C. The resulting reaction mixture was stirred for 1 h at −20° C., then allowed to warm to room temperature and stirred for 1 h at room temperature. The mixture was washed with a saturated solution of NH$_4$Cl (3×600 mL), brine (1×200 mL), dried over MgSO$_4$, filtered and concentrated in vacuo. To remove THF contamination, the solution was evaporated from hexane (2×200 mL). The crude product was purified by flash chromatography on silica gel (gradient elution, hexane/AcOEt 20:1 to 4:1) to give ethyl 2-oxocyclohex-3-enecarboxylate (71.79 g, 68%, yellow liquid). ESI+MS: m/z=169.1 (M+1)$^+$. $^1$H NMR (700 MHz, Chloroform-d) δ 7.02-6.98 (m, 1H), 6.07 (dt, J=10.1, 2.0 Hz, 1H), 4.25-4.18 (m, 2H), 3.41-3.38 (m, 1H), 2.54-2.46 (m, 1H), 2.44-2.33 (m, 2H), 2.26-2.18 (m, 1H), 1.28 (t, J=7.2, 3H).

Step B. Ethyl 2-hydroxy-4-vinylcyclohex-1-ene-1-carboxylate

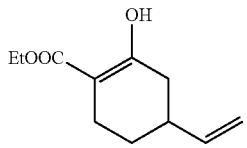

A solution of vinylmagnesium bromide (1M in THF) (119 mL, 0.119 mol, 2 equiv.) and HMPA (41.6 mL) were added dropwise to a suspension of CuBrxMe$_2$S (1.83 g, 8.92 mmol, 0.15 equiv.) in dry THF (250 mL) at −78° C. over 15 min under argon. After stirring at −78° C. for 15 min, a solution of ethyl 2-oxocyclohex-3-ene-1-carboxylate (10 g, 59.5 mmol, 1.0 equiv.) and TMSCl (37.7 mL, 0.297 mol, 5 equiv.) in dry THF (100 mL) was added dropwise (for over 30 min). The reaction mixture was stirred at −78° C. for 2 h. Then the mixture was quenched with saturated aqueous NH$_4$Cl (200 mL) and washed with AcOEt (3×150 mL). The combined organic layers were dried over MgSO$_4$ and concentrated. The crude product was purified by flash chromatography on silica gel (hexane/AcOEt 10:1) to give ethyl 2-hydroxy-4-vinylcyclohex-1-ene-1-carboxylate (4.94 g, 42%) as a pale yellow liquid. H NMR (700 MHz, chloroform-d) δ 5.91-5.70 (m, 1H), 5.16-4.90 (m, 2H), 4.22 (qd, J=7.1, 0.5 Hz, 2H), 2.45-2.30 (m, 3H), 2.24-2.12 (m, 2H), 1.89-1.74 (m, 1H), 1.45-1.18 (m, 5H).

Step C. Ethyl rac-(1R,2R,4R)-2-acetamido-2-(tert-butylcarbamoyl)-4-vinylcyclohexane-1-carboxylate

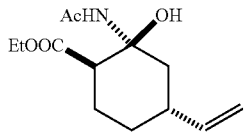 [SMILES: C=C[C@@H]1CC[C@@H](C(=O)OCC)[C@](O)(NC(C)=O)C1]

To the stirred solution of ethyl 2-hydroxy-4-vinylcyclohex-1-ene-1-carboxylate. (3.8 g, 19.3 mmol, 1 equiv.) and ammonium acetate (5.95 g, 77.2 mmol, 4 equiv.) in 2,2,2-trifluoroethanol (70 mL) tert-butyl isocyanide (4.38 mL, 38.7 mmol, 2 equiv.) was added dropwise via syringe and the resulting mixture was stirred at room temperature for 24 hours. After this time, the reaction mixture was diluted with water (25 mL) and extracted with ethyl acetate (3×50 mL). The combined organic layers were washed with brine, dried over MgSO$_4$, filtered and evaporated under reduced pressure. The residue was purified by silica gel flash chromatography (gradient elution, hexane/AcOEt 10:1 to 2:1) to give 3.66 g (56%) of the corresponding product as a white solid. ESI+MS: m/z=339.1 (M+1)$^+$, 361.1 (M+Na)$^+$. $^1$H NMR (700 MHz, chloroform-d) δ 8.10 (s, 1H), 7.57 (s, 1H), 5.72 (ddd, J=17.0, 10.4, 6.4 Hz, 1H), 5.03-4.91 (m, 2H), 4.20 (ddq, J=59.5, 10.8, 7.1 Hz, 2H), 3.29 (d, J=13.8 Hz, 1H), 2.28 (dd, J=12.4, 4.4 Hz, 1H), 2.14 (dq, J=11.6, 4.2, 3.6 Hz, 1H), 2.11-2.02 (m, 2H), 1.99 (s, 3H), 1.85-1.80 (m, 1H), 1.33-1.30 (m, 13H), 1.10 (qd, J=13.2, 4.4 Hz, 1H).

Intermediate 2. Ethyl (1R,2R,4R)-(+)-2-acetamido-2-(tert-butylcarbamoyl)-4-vinylcyclohexane-1-carboxylate

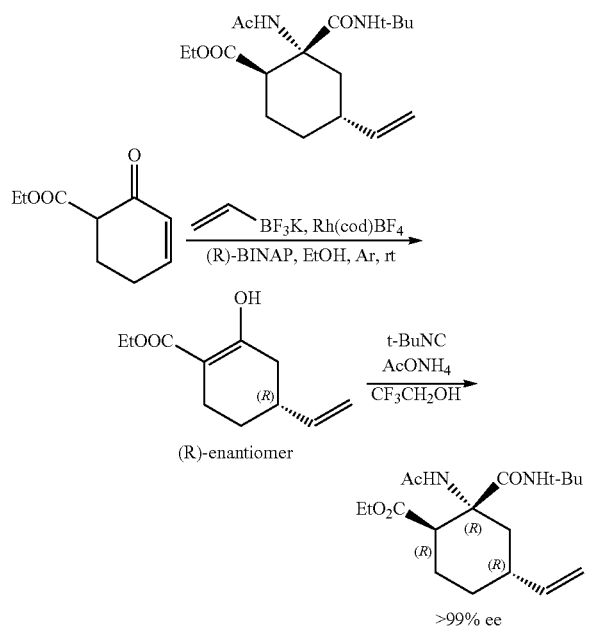

(R)-enantiomer

>99% ee

Step A. Ethyl (4R)-(+)-4-ethenyl-2-hydroxycyclohex-1-ene-1-carboxylate

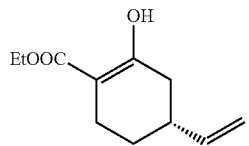

To a 6 L round-bottomed flask Rh(cod)$_2$BF$_4$ (2.74 g, 6.75 mmol, 0.033 equiv.), (R)-BINAP (4.20 g, 6.75 mmol, 0.033 equiv.) and potassium vinyl trifluoroborate (63.70 g, 475.6 mmol, 2.0 equiv.) were added. The reaction flask was flushed with argon several times and degassed EtOH (2000 mL) together with triethylamine (100.30 mL, 713.4 mmol, 3.0 equiv.) were added. After stirring the reaction mixture for 15 min at room temperature, ethyl 2-oxocyclohex-3-enecarboxylate (50 g, 297 mmol) was added. The reaction mixture was stirred for 3 days at room temperature under argon. EtOH was evaporated in vacuo and crude reaction mixture was poured to EtOAc (800 mL) and washed with 40% brine in 0.5M HCl$_{aq}$ (3×800 mL). Combined organic layers were washed with brine (1×100 mL), dried over MgSO$_4$, filtered and concentrated in vacuo. The crude product was purified by flash chromatography on silica gel (gradient elution, hexane/AcOEt 30:1 to 5:1) to give (4R)-(+)-ethyl 2-oxo-4-vinylcyclohexanecarboxylate (15.5 g, 25%, yellow liquid). ESI+MS: m/z=197.1 (M+1)$^+$. $^1$H NMR (700 MHz, Chloroform-d) δ 12.21 (s, 1H), 5.85-5.78 (m, 1H), 5.07-4.99 (m, 2H), 4.25-4.18 (m, 2H), 2.41-2.33 (m, 2H), 2.27-2.13 (m, 2H), 1.85-1.79 (m, 1H), 1.60-1.52 (m, 1H), 1.41-1.32 (m, 1H), 1.32-1.25 (m, 3H).

Step B. Ethyl (1R,2R,4R)-(+)-2-acetamido-2-(tert-butylcarbamoyl)-4-vinylcyclohexane-1-carboxylate To the stirred solution of ethyl (4R)-(+)-4-ethenyl-2-hydroxycyclohex-1-ene-1-carboxylate (8.2 g, 41.78 mmol, 1 equiv.) and ammonium acetate (12.88 g, 167.13 mmol, 4 equiv.) in 2,2,2-trifluoroethanol (164 mL) tert-butyl isocyanide (9.4 mL, 83.57 mmol, 2 equiv.) was added dropwise via syringe and the resulting mixture was stirred at room temperature for 24 hours. The solvent was removed under reduced pressure and the residue was dissolved in ethyl acetate (250 mL) and washed with water (50 mL), dried over MgSO$_4$ and concentrated under reduced pressure. The crude product was purified by silica gel flash chromatography (gradient elution, hexane/AcOEt 15:1 to 3:1) to give 7.04 g (50%) of the corresponding product as a single enantiomer (>99.5% ee) as a white solid. ESI+MS: m/z=339.1 (M+1)$^+$, 361.1 (M+Na)$^+$. [α]$_D$=+57.6 (c=1.0 in CHCl$_3$). $^1$H NMR (700 MHz, Chloroform-d) δ 8.13 (s, 1H), 7.60 (s, 1H), 5.75 (ddd, J=17.0, 10.4, 6.4 Hz, 1H), 5.06-4.93 (m, 2H), 4.23 (ddq, J=59.6, 10.8, 7.1 Hz, 2H), 3.32 (dt, J=13.9, 2.6 Hz, 1H), 2.31 (dd, J=12.4, 4.4 Hz, 1H), 2.20-2.05 (m, 2H), 2.02 (s, 3H), 1.88-1.84 (m, 1H), 1.60-1.56 (m, 1H), 1.37 (dd, J=13.9, 12.7 Hz, 1H), 1.33 (s, 9H), 1.32-1.30 (m, 3H), 1.13 (tdd, J=13.3, 12.0, 4.4 Hz, 1H). Enantiomeric excess was determined by chiral HPLC using RegisPack 250/4.6 mm, 5p column eluted with 1 mL/min flow of 10% of isopropanol in hexane.

EXAMPLES

Example 1.
1-Amino-3-(2-boronoethyl)cyclopentane-1-carboxylic acid hydrochloride

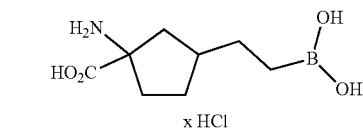

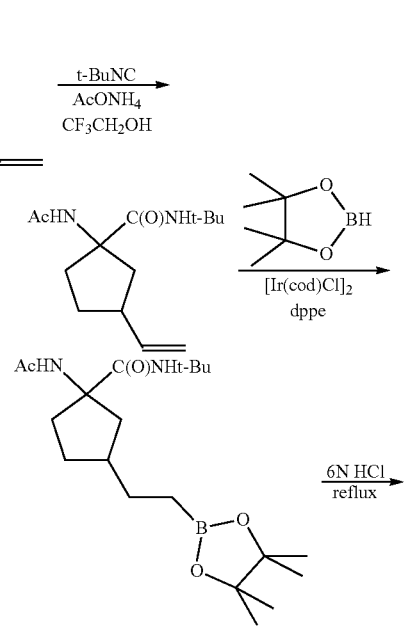

-continued

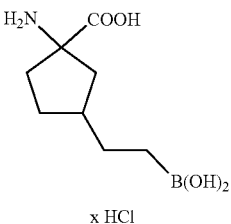

x HCl

Step A. 1-Acetamido-N-(tert-butyl)-3-vinylcyclopentane-1-carboxamide

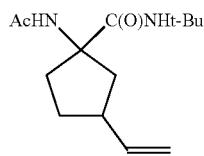

To a stirred solution of 3-vinylcyclopentan-1-one (0.60 g, 5.45 mmol) (prepared from 2-cyclopentene-1-one using literature method. *J Am. Chem. Soc.*, 103, (1981) 476-477) and ammonium acetate (1.68 g, 21.79 mmol) in 2,2,2-trifluoroethanol (1.5 mL) tert-butyl isocyanide (1.23 mL, 10.9 mmol) was added via syringe and the resulting mixture was stirred at room temperature for 24 hours. After this time, the reaction mixture was diluted with ethyl acetate (100 mL) and washed with water (2×15 mL) and brine (20 mL), dried over $MgSO_4$, filtered and evaporated under reduced pressure. The residue was triturated with diethyl ether (2 mL) and hexane (2×2 mL) to give 0.85 g (62%) of the desired product as a white solid (mixture of diastereoisomers, 1.4:1). ESI+MS: m/z=275.2 (M+Na)$^+$, ESI-MS: m/z=251.2 (M−1)$^-$. $^1$H NMR (700 MHz, CDCl$_3$) δ 7.00 (bs, 1H, single diastereoisomer), 6.88 (bs, 1H, single diastereoisomer), 5.90-5.77 (m, 2H), 5.02-5.07 (m, 1H), 4.99-4.92 (m, 1H), 2.81-2.75 (m, 1H, single diastereoisomer), 2.74-2.68 (m, 1H, single diastereoisomer), 2.65 (d, J=13.4, 1H, single diastereoisomer), 2.64 (d, J=13.4, 1H, single diastereoisomer) 2.43-2.36 (m, 1H), 2.25-2.30 (m, 1H), 2.07-1.94 (m, 5H), 1.73 (dd, J=13.4, 8.9 Hz, 1H), 1.64-1.54 (m, 1H), 1.35 (s, 9H).

Step B. 1-Acetamido-N-(tert-butyl)-3-methyl-3-(2-(4,4,5,5-tetramethyl-1,3,2-dioxaborolan-2-yl)ethyl)cyclopentane-1-carboxamide

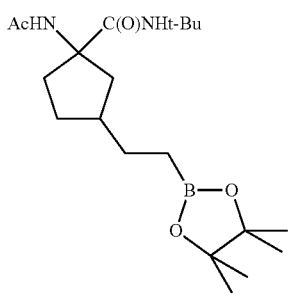

A round-bottom flask charged with bis(1,5-cyclooctadiene)diiridium (I) dichloride (64 mg, 0.095 mmol), 1,2-bis(diphenylphosphino)ethane (76 mg, 0.19 mmol) and dry $CH_2Cl_2$ (10 mL) was flushed with argon (bubbling). Subsequently, the separately prepared solution of 4,4,5,5-tetramethyl-1,3,2-dioxaborolane (0.69 mL, 4.75 mmol), 1-acetamido-N-(tert-butyl)-3-vinylcyclopentane-1-carboxamide (0.80 g, 3.17 mmol) in 5 mL of dry $CH_2Cl_2$ was added successively at room temperature. The resulting light yellow mixture was then stirred at room temperature for 24 hours. The solvent was removed under reduced pressure and the residue was subjected to flash chromatography on silica gel (using AcOEt-Hexane, 1:2 to 1:1 as the eluent) to afford 0.98 g (81%) of the desired product as a white viscous solid (mixture of diastereoisomers 1.5:1). ESI+MS: m/z=381.2 (M+H)$^+$, 403.2 (M+Na)$^+$, ESI-MS: m/z=379.3 (M−1)$^-$. $^1$H NMR (700 MHz, CDCl$_3$) δ 6.97 (bs, 1H, single diastereoisomer), 6.91 (bs, 1H, single diastereoisomer), 5.89 (bs, 1H, single diastereoisomer), 5.69 (bs, 1H, single diastereoisomer), 2.57 (dd, J=13.5, 8.2 Hz, 1H, single diastereoisomer), 2.36-2.28 (m, 1H), 2.22 (dd, J=13.7, 7.1 Hz, 1H, single diastereoisomer), 2.01 (s, 3H, single diastereoisomer), 2.00 (s, 3H, single diastereoisomer), 1.98-1.91 (m, 3H), 1.79 (dd, J=13.7, 10.5 Hz, 1H, single diastereoisomer), 1.53-1.46 (m, 2H), 1.338 (s, 9H, single diastereoisomer), 1.340 (s, 9H, single diastereoisomer), 1.261 (s, 12H, single diastereoisomer), 1.259 (s, 12H, single diastereoisomer), 0.91 (td, J=7.4, 1.1 Hz, 1H, single diastereoisomer), 0.84-0.74 (m, 2H).

Step C. 1-Amino-3-(2-boronoethyl)cyclopentane-1-carboxylic acid hydrochloride A mixture of 1-acetamido-N-(tert-butyl)-3-methyl-3-(2-(4,4,5,5-tetramethyl-1,3,2-dioxaborolan-2-yl)ethyl)cyclopentane-1-carboxamide (200 mg, 0.53 mmol) and 10 mL of 6 N HCl (aq) was heated under reflux overnight. After concentration under vacuum the residue was subjected to preparative HPLC chromatography (gradient elution 0.1-2%, acetonitrile-water). Overall yield of isolated possible stereoisomers of target product (96 mg, 77%). Diastereoisomers were partially separated as the following diastereoisomeric ratios:

trans/cis=9:1 (5 mg; white solid). ESI+MS: m/z=202.1 (M+H)$^+$, ESI-MS: m/z=200.1 (M−1)$^-$. $^1$H NMR (700 MHz, D$_2$O) (major trans-diastereoisomer) δ 2.39 (dd, J=13.9, 7.9 Hz, 1H), 2.17 (ddd, J=14.1, 12.0, 7.5 Hz, 1H), 2.10-2.05 (m, 1H), 2.02-1.96 (m, 1H), 1.91 (dd, J=14.4, 7.6 Hz, 1H), 1.45 (dd, J=15.4, 7.8 Hz, 2H), 1.33 (dt, J=14.0, 7.8 Hz, 2H), 0.76 (td, J=7.7, 3.2 Hz, 2H).

trans/cis=1:1 (58 mg; white solid). ESI+MS: m/z=202.1 (M+H)$^+$, ESI-MS: m/z=200.1 (M−1)$^-$. $^1$H NMR (700 MHz, D$_2$O) (minor cis-diastereoisomer) δ 2.37 (ddd, J=14.3, 8.9, 3.5 Hz, 1H), 2.13-2.06 (m, 2H), 2.03-1.99 (m, 1H), 1.90 (dd, J=13.6, 10.2 Hz, 1H), 1.88-1.82 (m, 1H), 1.48 (ddd, J=11.4, 6.0, 2.0 Hz, 3H), 0.79-0.74 (m, 2H).

Example 2. rac-(2S,3R)-1-Amino-3-(2-boronoethyl)-2-methylcyclopentane-1-carboxylic acid hydrochloride

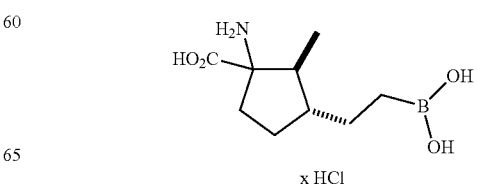

x HCl

-continued

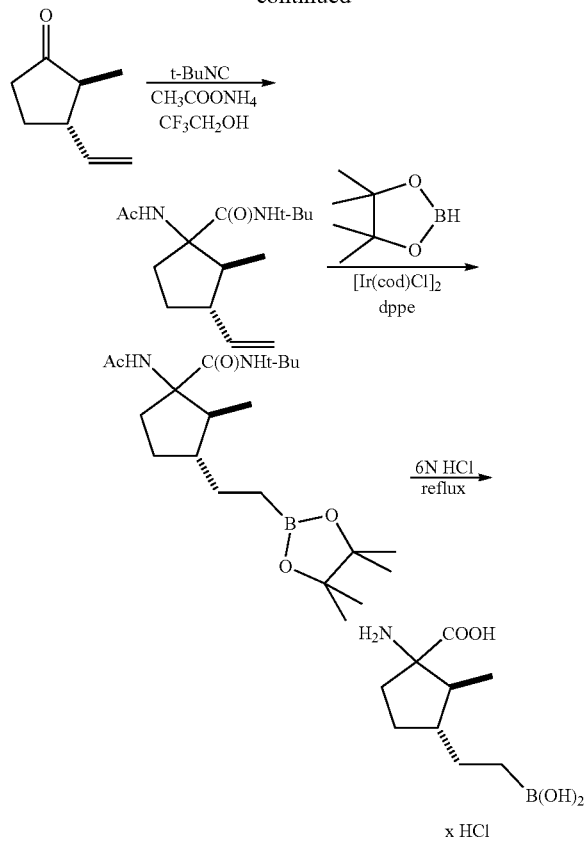

Step A. rac-(2S,3S)-1-Acetamido-N-(tert-butyl)-2-methyl-3-vinylcyclopentane-1-carboxamide

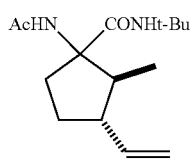

To a stirred solution of 2-methyl-3-vinylcyclopentan-1-one (1.20 g, 9.7 mmol, 1 equiv.) (dr=14:1; prepared from 2-methyl-2-cyclopenten-1-one using literature method. *J. Am. Chem. Soc.*, 103, (1981) 476-477) and ammonium acetate (2.98 g, 38.7 mmol, 4 equiv.) in 2,2,2-trifluoroethanol (3 mL) tert-butyl isocyanide (1.60 g, 2.17 mL, 19.4 mmol, 2 equiv.) was added via syringe and the resulting mixture was stirred at room temperature for 24 hours. After this time, the reaction mixture was diluted with water (50 mL) and extracted with ethyl acetate (2×50 mL). The combined organic layers were washed with brine, dried over $MgSO_4$, filtered and evaporated under reduced pressure. The residue was purified by silica gel flash chromatography (using AcOEt-Hexane, 1:10 as the eluent) to give 1-acetamido-N-(tert-butyl)-2-methyl-3-vinylcyclopentane-1-carboxamide as a mixture of two, out of four possible, diastereoisomers in 2.5:1 ratio (0.40 g, 16%, pale yellow oil). ESI+MS: m/z=289.1 (M+Na)$^+$, ESI-MS: m/z=265.2 (M−1)$^-$. $^1$H NMR (700 MHz, chloroform-d) δ 5.74-5.62 (m, 1H), 5.10-4.95 (m, 2H), 2.50 (dt, J=14.3, 9.0 Hz, 1H), 2.34-2.22 (m, 1H), 2.02 (s, 3H), 1.79-1.68 (m, 1H), [1.37, 1.35 (2s, 9H, two diastereoisomers)], 1.27 (m, 3H), [0.97, 0.96 (2d, J=6.8, J=6.6 Hz, 3H, two diastereoisomers)].

Step B. rac-(2S,3R)-1-Acetamido-N-(tert-butyl)-2-methyl-3-(2-(4,4,5,5-tetramethyl-1,3,2-dioxaborolan-2-yl)ethyl)cyclopentane-1-carboxamide

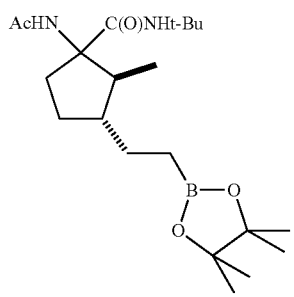

A round-bottom flask charged with bis(1,5-cyclooctadiene)diiridium (I) dichloride (15 mg, 0.022 mmol, 0.03 equiv.), 1,2-bis(diphenylphosphino)ethane (18 mg, 0.044 mmol, 0.06 equiv.) and dry $CH_2Cl_2$ (5 mL) was flushed with argon (bubbling). Subsequently, the separately prepared solution of 4,4,5,5-tetramethyl-1,3,2-dioxaborolane (0.24 g, 0.30 mL, 1.88 mmol, 2.5 equiv.), 1-acetamido-N-(tert-butyl)-2-methyl-3-vinylcyclopentane-1-carboxamide (0.20 g, 0.75 mmol, 1 equiv.) in 5 mL of dry $CH_2Cl_2$ was added successively at room temperature. The resulting light yellow mixture was then stirred at room temperature for 24 hours. The solvent was removed under reduced pressure and the residue was subjected to flash chromatography on silica gel (using AcOEt-Hexane, 1:10 as the eluent) to afford a target 1-acetamido-N-(tert-butyl)-2-methyl-3-(2-(4,4,5,5-tetramethyl-1,3,2-dioxaborolan-2-yl)ethyl)cyclopentane-1-carboxamid as a mixture of diastereoisomers, dr=2.5:1 (0.21 g, 72%, sticky pale yellow oil). ESI+MS: m/z=395.1 (M+H)$^+$, ESI-MS: m/z=393.2 (M−1)$^-$. $^1$H NMR (700 MHz, chloroform-d) δ 2.36-2.28 (m, 1H), 2.11-1.95 (m, 2H), [2.05, 2.00 (2s, 3H, two diastereoisomers)], 1.95-1.84 (m, 1H), 1.69-1.57 (m, 3H), 1.48-1.38 (m, 1H), [1.36, 1.35 (2s, 9H, two diastereoisomers)], [1.28, 1.25 (2s, 12H, two diastereoisomers)], [0.99, 0.95 (2d, J=7.30 Hz, J=7.17 Hz, 3H, two diastereoisomers)], 0.91-0.82 (m, 1H), 0.78-0.71 (m, 1H).

Step C. rac-(2S,3R)-1-Amino-3-(2-boronoethyl)-2-methylcyclopentane-1-carboxylic acid hydrochloride A mixture of 1-acetamido-N-(tert-butyl)-2-methyl-3-(2-(4,4,5,5-tetramethyl-1,3,2-dioxaborolan-2-yl)ethyl)cyclopentane-1-carboxamide (211 mg, 0.54 mmol) and 20 mL of 6 N HCl (aq) was heated under reflux for 6 hours. After concentration under vacuum the residue was subjected to preparative HPLC chromatography (gradient elution 0.1-2%, acetonitrile-water). Overall yield of isolated possible stereoisomers of a target product (47 mg, 35%). One single diastereoisomer with unknown configuration on amino acid moiety was separated. Moreover, the mixture of diastereoisomers (dr 1:1) was also isolated.

Single diastereoisomer (28 mg, 21%, white solid) ESI+MS: m/z=216.1 (M+H)$^+$, ESI-MS: m/z=196.1 (M−18−1)$^-$ $^1$H NMR (700 MHz, $D_2O$) δ 2.29 (dt, J=14.6, 8.9 Hz, 1H), 1.98-1.93 (m, 1H), 1.83-1.76 (m, 1H), 1.67-1.55 (m, 3H), 1.36-1.28 (m, 1H), 1.15-1.02 (m, 1H), 0.90 (d, J=6.3 Hz, 3H), 0.77-0.70 (m, 1H), 0.66-0.59 (m, 1H).

Mixture of diastereoisomers (dr=1:1) (19 mg, 14%, white solid). ESI+MS: m/z=215.9 (M+H)+ ESI-MS: m/z=196.0 (M−18−1)− 1H NMR (700 MHz, D2O) δ 2.32-2.26 (m, 1H), 2.03-1.89 (m, 1H), 1.80-1.73 (m, 1H), 1.65-1.48 (m, 3H), 1.41-1.28 (m, 1H), 1.17-1.09 (m, 1H), [0.90, 0.87 (2d, J=7.2 Hz, J=6.8 Hz, 3H, two diastereoisomers)], 0.76-0.70 (m, 1H), 0.66-0.60 (m, 1H).

Example 3. 1-Amino-3-(2-boronoethyl)-3-methylcyclopentane-1-carboxylic acid hydrochloride

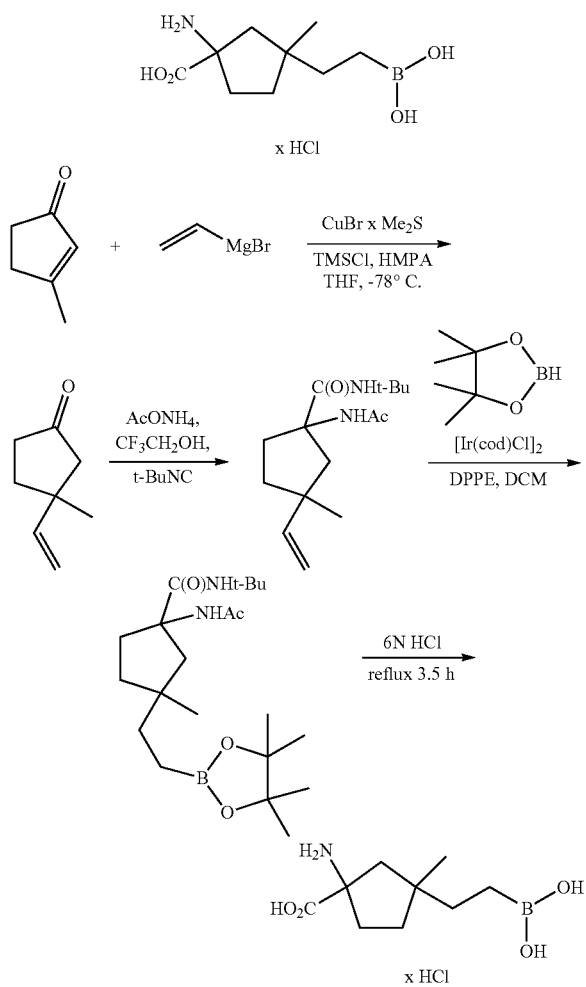

Step A. 3-Methyl-3-vinylcyclopentan-1-one

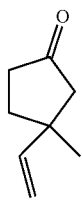

A solution of vinylmagnesium bromide (1M in THF) (32 mL, 32 mmol) and HMPA (11.13 mL, 64 mmol) were separately added dropwise to a suspension of CuBr×Me2S (802 mg, 3.9 mmol) in dry THF (100 mL) at −78° C. under argon over 10 min. After stirring at −78° C. for 15 min a solution of 3-methyl-2-cyclopenten-1-one (1.58 mL, 16 mmol) and TMSCl (10.15 mL, 80 mmol) in dry THF (35 mL) was added dropwise for over 30 min. The reaction mixture was stirred at −78° C. for 2 h. Then the mixture was slowly warmed to RT and stirred at ambient temperature overnight. Next the mixture was quenched with saturated aqueous NH4Cl (100 mL) and washed with AcOEt (3×150 mL). The combined organic layers were dried over MgSO4 and concentrated. The crude product was purified by flash chromatography on silica gel (hexane/AcOEt 25:1 to 20:1) to give 3.0 g (100%) of a desired product as a yellow liquid (contained ca. 20% of hexane). 1H NMR (700 MHz, chloroform-d) δ 5.91 (dd, J=17.4, 10.7 Hz, 1H), 5.08-4.94 (m, 2H), 2.38-2.33 (m, 1H), 2.31 (t, J=7.8 Hz, 2H), 2.10 (d, J=18.3 Hz, 1H), 2.03-1.97 (m, 1H), 1.84 (dtd, J=12.9, 7.9, 1.2 Hz, 1H), 1.22 (s, 3H).

Step B. 1-Acetamido-N-(tert-butyl)-3-methyl-3-vinylcyclopentane-1-carboxamide

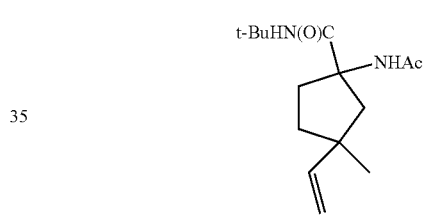

To a mixture of 3-methyl-3-vinylcyclopentan-1-one (2.9 g, 23.35 mmol), ammonium acetate (7.2 g, 93.4 mmol), 2,2,2-trifluoroethanol (5.7 mL) was added dropwise tert-butyl isocyanide (5.25 mL, 46.70 mmol). The mixture was stirred at room temperature overnight. Then the reaction mixture was quenched with water (150 mL) and washed with ethyl acetate (3×150 mL). The combined organic layers were washed with brine (2×100 mL), dried over MgSO4 and concentrated in vacuo. The residue was purified by flash chromatography on silica gel (hexane/AcOEt 90:1 to 70:1). Single diastereoisomers were separated (250 mg and 920 mg). Total yield: 1.17 g (19%).

Single diastereoisomer 1 (250 mg, yellow oil); ESI+MS: m/z=289.1 (M+Na)+, 267.2 (M+1)+, ESI-MS: m/z=265.2 (M−1)−. 1H NMR (700 MHz, chloroform-d) δ 5.94 (dd, J=17.4, 10.7 Hz, 1H), 5.03-4.94 (m, 2H), 2.50 (dt, J=13.6, 8.0 Hz, 1H), 2.28 (d, J=14.3 Hz, 1H), 2.16-2.09 (m, 1H), 1.99 (s, 3H), 1.91-1.82 (m, 1H), 1.64 (ddd, J=13.2, 7.9, 5.9 Hz, 2H), 1.34 (s, 9H), 1.17 (s, 3H).

Single diastereoisomer 2 (920 mg, white solid; ESI+MS: m/z=289.1 (M+Na)+, 267.2 (M+1)+, ESI-MS: m/z=265.2 (M−1)−. 1H NMR (700 MHz, chloroform-d) δ 5.94 (dd, J=17.5, 10.7 Hz, 1H), 5.13-4.89 (m, 2H), 2.47-2.44 (m, 1H), 2.44-2.40 (m, 1H), 2.04 (d, J=5.2 Hz, 3H), 2.02 (s, 3H), 2.01 (s, 1H), 1.89-1.84 (m, 1H), 1.79 (dt, J=12.9, 7.7 Hz, 1H), 1.34 (s, 9H), 1.21 (s, 3H).

Step C. 1-Acetamido-N-(tert-butyl)-3-methyl-3-(2-(4,4,5,5-tetramethyl-1,3,2-dioxaborolan-2-yl)ethyl)cyclopentane-1-carboxamide

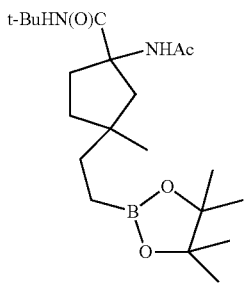

A mixture of dppe (20.5 mg, 0.052 mmol), bis(1,5-cyclooctadiene)diiridium(I) dichloride (17 mg, 0.026 mmol) was dissolved in dichloromethane (3 mL) and flushed with argon (bubbling). A solution of 1-acetamido-N-(tert-butyl)-3-methyl-3-vinylcyclopentane-1-carboxamide (230 mg, 0.86 mmol) and a pinacolborane in DCM (3 mL) (flushed with argon) was added dropwise (162 µL, 1.12 mmol). The reaction mixture was stirred at room temperature for 3 days. After this time the crude product was purified by column chromatography, on silica gel (hexane/AcOEt 5:1 to 2:1) to give the desired product (170 mg, 50%) as a yellow oil. ESI+MS: m/z=395.1 (M+1)$^+$, 335.1. ESI-MS: m/z=393.2 (M−1)$^−$. $^1$H NMR (700 MHz, chloroform-d) δ 2.45-2.39 (m, 1H), 2.15 (d, J=14.4 Hz, 1H), 2.02 (s, 3H), 1.84 (d, J=14.4 Hz, 1H), 1.66-1.57 (m, 4H), 1.55-1.49 (m, 1H), 1.49-1.45 (m, 1H), 1.39 (d, J=30.7 Hz, 1H), 1.29 (s, 9H), 1.28-1.26 (m, 12H), 0.88 (t, J=7.1 Hz, 1H), 0.77 (ddd, J=9.7, 6.8, 2.9 Hz, 2H).

The second diastereoisomer was obtained in the same way starting from 0.92 g (3.45 mmol) of 1-acetamido-N-(tert-butyl)-3-methyl-3-vinylcyclopentane-1-carboxamide. Crude product was purified by flash column chromatography on silica gel (hexane/AcOEt 2:1 to 1:1) to give 1.2 g (88%) of desired product as a yellow oil. ESI+MS: m/z=395.1 (M+1)$^+$. ESI-MS: m/z=393.2 (M−1)$^−$. $^1$H NMR (700 MHz, chloroform-d) δ 2.39 (dt, J=13.5, 7.8 Hz, 1H), 2.20 (d, J=14.4 Hz, 1H), 2.01 (s, 3H), 1.97-1.92 (m, 1H), 1.87 (d, J=14.2 Hz, 1H), 1.67-1.60 (m, 1H), 1.52-1.43 (m, 3H), 1.33 (s, 9H), 1.25 (s, 12H), 1.03 (s, 3H), 0.77-0.70 (m, 2H).

Step D. 1-Amino-3-(2-boronoethyl)-3-methylcyclopentane-1-carboxylic acid hydrochloride A mixture of 1-acetamido-N-(tert-butyl)-3-methyl-3-vinylcyclopentane-1-carboxamide (90 mg, 0.23 mmol) and 6 N HCl (aq) (1 mL) was heated under reflux 3.5 h. The reaction mixture was concentrated under reduced pressure and the residue was purified by preparative HPLC (0.1-2% MeCN in water) to give the desired product (20 mg, 25%) as a white solid. ESI+MS: m/z=216.1 (M+1)$^+$, ESI-MS: m/z=196.1 (M−18−1)$^−$. $^1$H NMR (700 MHz, deuterium oxide) δ 2.46 (dt, J=14.4, 9.2 Hz, 1H), 2.19 (d, J=15.1 Hz, 1H), 1.99 (dt, J=14.4, 5.5 Hz, 1H), 1.76-1.67 (m, 3H), 1.48 (t, J=8.5 Hz, 2H), 1.03 (s, 3H), 0.78-0.66 (m, 2H).

The second diastereoisomer was obtained in the same way starting from 200 mg (0.51 mmol) of 1-acetamido-N-(tert-butyl)-3-methyl-3-vinylcyclopentane-1-carboxamide. The crude product was purified by preparative HPLC (0.1-4% MeCN in water) to give the desired product (50 mg, 28%) as a white solid. ESI+MS: m/z=216.1 (M+1)$^+$, ESI-MS: m/z=214.1 (M−1)$^−$. $^1$H NMR (700 MHz, deuterium oxide) δ 2.37 (dt, J=14.3, 7.2 Hz, 1H), 2.29 (d, J=15.1 Hz, 1H), 2.04 (dt, J=14.3, 7.3 Hz, 1H), 1.84-1.76 (m, 1H), 1.70-1.59 (m, 2H), 1.48 (t, J=8.5 Hz, 2H), 1.04 (s, 3H), 0.76-0.65 (m, 2H).

Example 4. rac-(1S,3S,4S)-1-Amino-3-(2-boronoethyl)-4-hydroxycyclopentane-1-carboxylic acid hydrochloride

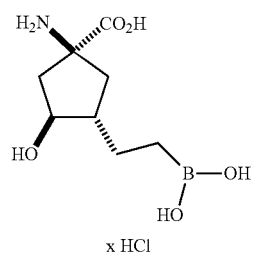

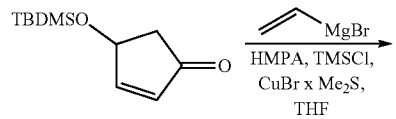

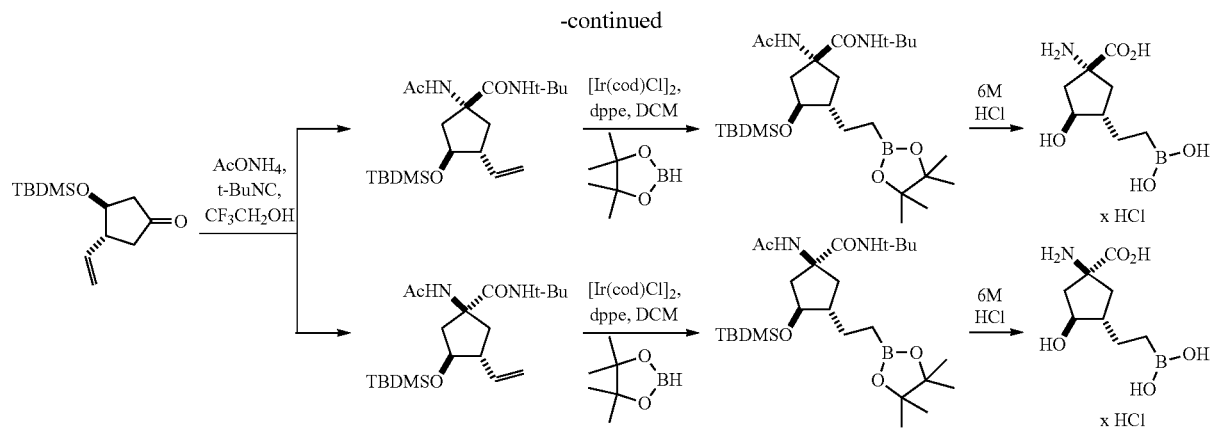

Step A. rac-(3S,4R)-3-((tert-Butyldimethylsilyl)oxy)-4-vinylcyclopentan-1-one

Step B. rac-(1R,3S,4R)- and rac-(1S,3S,4R)-1-Acetamido-N-(tert-butyl)-3-((tert-butyldimethylsilyl)oxy)-4-vinylcyclopentane-1-carboxamide

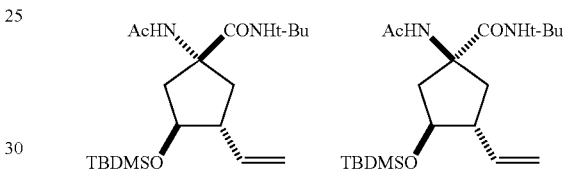

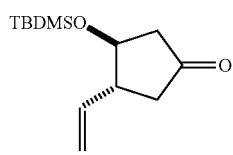 [SMILES: C=C[C@H]1CC(=O)C[C@@H]1O[Si](C)(C)C(C)(C)C]

To a suspension of CuBr×Me$_2$S (802 mg, 3.9 mmol) in tetrahydrofuran (100 mL) was added vinylmagnesium bromide (1 M in tetrahydrofuran) (32 mL, 32.0 mmol) dropwise under Ar at −78° C. Then HMPA (11.1 mL, 64.0 mmol) was added and stirred for 10 min. A solution of 4-[(tert-butyldimethylsilyl)oxy]cyclopent-2-en-1-one (3.4 g, 16.0 mmol), TMSCl (10.2 mL, 80.0 mmol) in tetrahydrofuran (35 mL) was added dropwise for 30 min. The resulting mixture was stirred at −78° C. for 30 min, then between −75° C. to −45° C. for 25 min. The mixture was quenched with NH$_4$Cl$_{(sat.)}$ and extracted with ethyl acetate three times. The organic layer was dried over magnesium sulfate, filtered and evaporated under reduced pressure. The crude product was purified by flash chromatography on silica gel (hexane/diethyl ether 20:1 to 10:1) to afford 1.4 g (36%) of the desired product as a pale yellow oil. $^1$H NMR (700 MHz, CDCl$_3$) δ 5.86-5.77 (m, 1H), 5.14-5.07 (m, 2H), 4.14 (q, J=6.1 Hz, 1H), 2.81 (p, J=7.6 Hz, 1H), 2.61-2.49 (m, 2H), 2.22-2.16 (m, 1H), 2.11 (dd, J=18.4, 8.1 Hz, 1H), 0.88 (s, 9H), 0.07 (s, 3H), 0.06 (s, 3H).

To a stirred solution of rac-(3S,4R)-3-((tert-butyldimethylsilyl)oxy)-4-vinylcyclopentan-1-one (1.3 g, 5.4 mmol) and ammonium acetate (1.66 g, 21.6 mmol) in 2,2,2-trifluoroethanol (1.5 mL) tert-butyl isocyanide (1.22 mL, 10.8 mmol) was added via syringe and the resulting mixture was stirred at room temperature for 24 hours. After this time, the reaction mixture was diluted with ethyl acetate (100 mL) and washed with water (2×15 mL) and brine (20 mL), dried over MgSO$_4$, filtered and evaporated under reduced pressure. The crude product was purified by flash chromatography on silica gel (hexane/ethyl acetate 2:1 to 1:1) to afford 60 mg (3%) of rac-(1R,3S,4R)-1-acetamido-N-(tert-butyl)-3-((tert-butyldimethylsilyl)oxy)-4-vinylcyclopentane-1-carboxamide as a white solid and 130 mg (6%) of rac-(1S,3S,4R)-1-acetamido-N-(tert-butyl)-3-((tert-butyldimethylsilyl)oxy)-4-vinylcyclopentane-1-carboxamide as a white solid.

rac-(1R,3S,4R)-isomer: ESI+MS: m/z=383.2 (M+H)$^+$, 405.1 (M+Na)$^+$, ESI-MS: m/z=381.2 (M−1)$^-$. $^1$H NMR (700 MHz, CDCl$_3$) δ 6.88 (bs, 1H), 6.20 (bs, 1H), 5.76 (ddd, J=17.1, 10.2, 8.0 Hz, 1H), 5.08-4.97 (m, 2H), 4.03 (ddd, J=7.1, 4.3, 3.1 Hz, 1H), 2.65-2.58 (m, 1H), 2.50 (dd, J=14.2, 6.7 Hz, 1H), 2.46 (ddd, J=13.9, 7.8, 2.3 Hz, 1H), 2.06 (dd, J=14.0, 10.3 Hz, 1H), 2.01 (s, 3H), 1.79 (dt, J=14.2, 2.5 Hz, 1H), 1.32 (s, 9H), 0.89 (s, 9H), 0.05 (s, 6H).

rac-(1S,3S,4R)-isomer: ESI+MS: m/z=383.2 (M+H)$^+$, 405.1 (M+Na)$^+$, ESI-MS: m/z=381.2 (M−1)$^-$. $^1$H NMR (700 MHz, CDCl$_3$) δ 6.84 (bs, 1H), 6.45 (bs, 1H), 5.84 (ddd, J=17.2, 10.2, 8.0 Hz, 1H), 5.09-5.00 (m, 2H), 4.24 (ddd, J=8.1, 5.9, 4.8 Hz, 1H), 2.87 (dd, J=14.9, 8.1 Hz, 1H), 2.62-2.54 (m, 1H), 2.28 (dd, J=13.5, 8.1 Hz, 1H), 2.09 (ddd, J=19.2, 14.2, 7.6 Hz, 2H), 1.97 (s, 3H), 1.36 (s, 9H), 0.88 (s, 9H), 0.07 (s, 3H), 0.06 (s, 3H).

Step C. rac-(1S,3S,4S)-1-Amino-N-(tert-butyl)-3-hydroxy-4-(2-(4,4,5,5-tetramethyl-1,3,2-dioxaborolan-2-yl)ethyl)cyclopentane-1-carboxamide and rac-(1R,3S,4S)-1-amino-N-(tert-butyl)-3-hydroxy-4-(2-(4,4,5,5-tetramethyl-1,3,2-dioxaborolan-2-yl)ethyl)cyclopentane-1-carboxamide

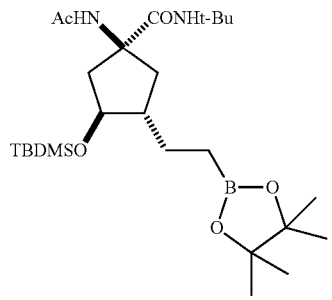

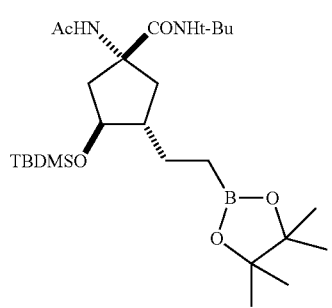

The title compounds were prepared from rac-(1S,3S,4R)- and rac-(1R,3S,4R)-1-acetamido-N-(tert-butyl)-3-((tert-butyldimethylsilyl)oxy)-4-vinylcyclopentane-1-carboxamide respectively using procedure described for the preparation of Example 1, step B.

The crude product was purified by flash chromatography on silica gel (hexane/ethyl acetate 20:1 to 1:1). Obtained:

rac-(1S,3S,4S)-isomer: 24 mg (36%). ESI+MS: m/z=511.2 (M+H)$^+$, 533.2 (M+Na)$^+$, ESI-MS: m/z=509.2 (M−1)$^-$. $^1$H NMR (700 MHz, CDCl$_3$) δ 6.88 (bs, 1H), 6.50 (bs, 1H), 4.16 (dt, J=12.0, 3.8 Hz, 1H), 2.88 (dd, J=15.0, 7.9 Hz, 1H), 2.27 (dd, J=12.2, 6.8 Hz, 1H), 2.07 (dd, J=15.0, 3.8 Hz, 1H), 1.98 (s, 3H), 1.97-1.94 (m, 1H), 1.81-1.74 (m, 1H), 1.57 (s, 9H), 1.48-1.40 (m, 1H), 1.37 (s, 9H), 1.30-1.28 (m, 1H), 1.26 (s, 12H), 0.92 (s, 9H), 0.85-0.73 (m, 2H), 0.12 (s, 3H), 0.11 (s, 3H).

Obtained:

rac-(1R,3S,4S)-isomer: 27 mg (38%). ESI+MS: m/z=511.2 (M+H)$^+$, ESI-MS: m/z=509.2 (M−1)$^-$. $^1$H NMR (700 MHz, CDCl$_3$) δ 6.90 (bs, 1H), 6.41 (bs, 1H), 4.01-3.96 (m, 1H), 2.53 (ddd, J=13.8, 7.8, 2.4 Hz, 1H), 2.38 (dd, J=14.2, 6.2 Hz, 1H), 2.00 (s, 3H), 1.81-1.76 (m, 2H), 1.71-1.64 (m, 1H), 1.58 (s, 9H), 1.39-1.36 (m, 1H), 1.35 (s, 9H), 1.29-1.27 (m, 1H), 1.26 (s, 12H), 0.79 (ddd, J=16.7, 9.7, 6.2 Hz, 2H), 0.11 (s, 3H), 0.10 (s, 3H).

Step D. rac-(1S,3S,4S)-1-Amino-3-(2-boronoethyl)-4-hydroxycyclopentane-1-carboxylic acid hydrochloride

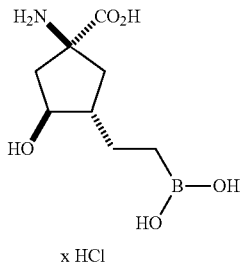 [SMILES: N[C@@]1(C(=O)O)C[C@H](CCB(O)O)[C@@H](O)C1]

The title compound was prepared from rac-(1S,3S,4S)-1-amino-N-(tert-butyl)-3-hydroxy-4-(2-(4,4,5,5-tetramethyl-1,3,2-dioxaborolan-2-yl)ethyl)cyclopentane-1-carboxamide using procedure described for the preparation of Example 1, step C. The crude product was subjected to preparative HPLC chromatography (0.1-2% MeCN) to afford 3 mg (27%) of the desired product. ESI+MS: m/z=218.0 (M+H)$^+$, 200.0 (M−18+H)$^+$, ESI-MS: m/z=198.0 (M−18−1)$^-$.

$^1$H NMR (700 MHz, D$_2$O) δ 3.95 (dd, J=17.0, 8.9 Hz, 1H), 2.49 (dd, J=14.0, 7.7 Hz, 1H), 2.29 (dd, J=14.4, 7.6 Hz, 1H), 2.23 (dd, J=14.4, 9.2 Hz, 1H), 2.04-1.95 (m, 1H), 1.77-1.59 (m, 1H), 1.45 (dd, J=14.1, 11.6 Hz, 1H), 1.42-1.32 (m, 1H), 0.88-0.72 (m, 2H).

Example 5. rac-(1R,3S,4S)-1-Amino-3-(2-boronoethyl)-4-hydroxycyclopentane-1-carboxylic acid hydrochloride

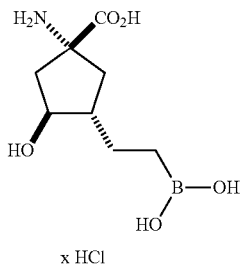

The title compound was prepared from rac-(1R,3S,4S)-1-amino-N-(tert-butyl)-3-hydroxy-4-(2-(4,4,5,5-tetramethyl-1,3,2-dioxaborolan-2-yl)ethyl)cyclopentane-1-carboxamide using procedure described for the preparation of Example 1, step C. The crude product was subjected to preparative HPLC chromatography (0.1-2% MeCN) to afford 9 mg (82%) of the desired product. ESI+MS: m/z=218.0 (M+H)$^+$, ESI-MS: m/z=216.1 (M−1)$^-$. $^1$H NMR (700 MHz, D$_2$O) δ 4.07 (q, J=6.6 Hz, 1H), 2.55 (dd, J=14.2, 6.4 Hz, 1H), 2.21 (dd, J=14.1, 7.4 Hz, 1H), 2.02-1.95 (m, 1H), 1.93 (dd, J=14.2, 9.9 Hz, 1H), 1.84 (dd, J=14.2, 6.8 Hz, 1H), 1.70-1.56 (m, 1H), 1.45-1.34 (m, 1H), 0.87-0.72 (m, 2H).

Example 6. rac-(1S,3S,4S)-1-Amino-3-(aminomethyl)-4-(2-boronoethyl)cyclopentane-1-carboxylic acid dihydrochloride
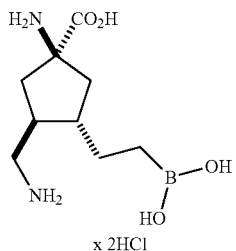
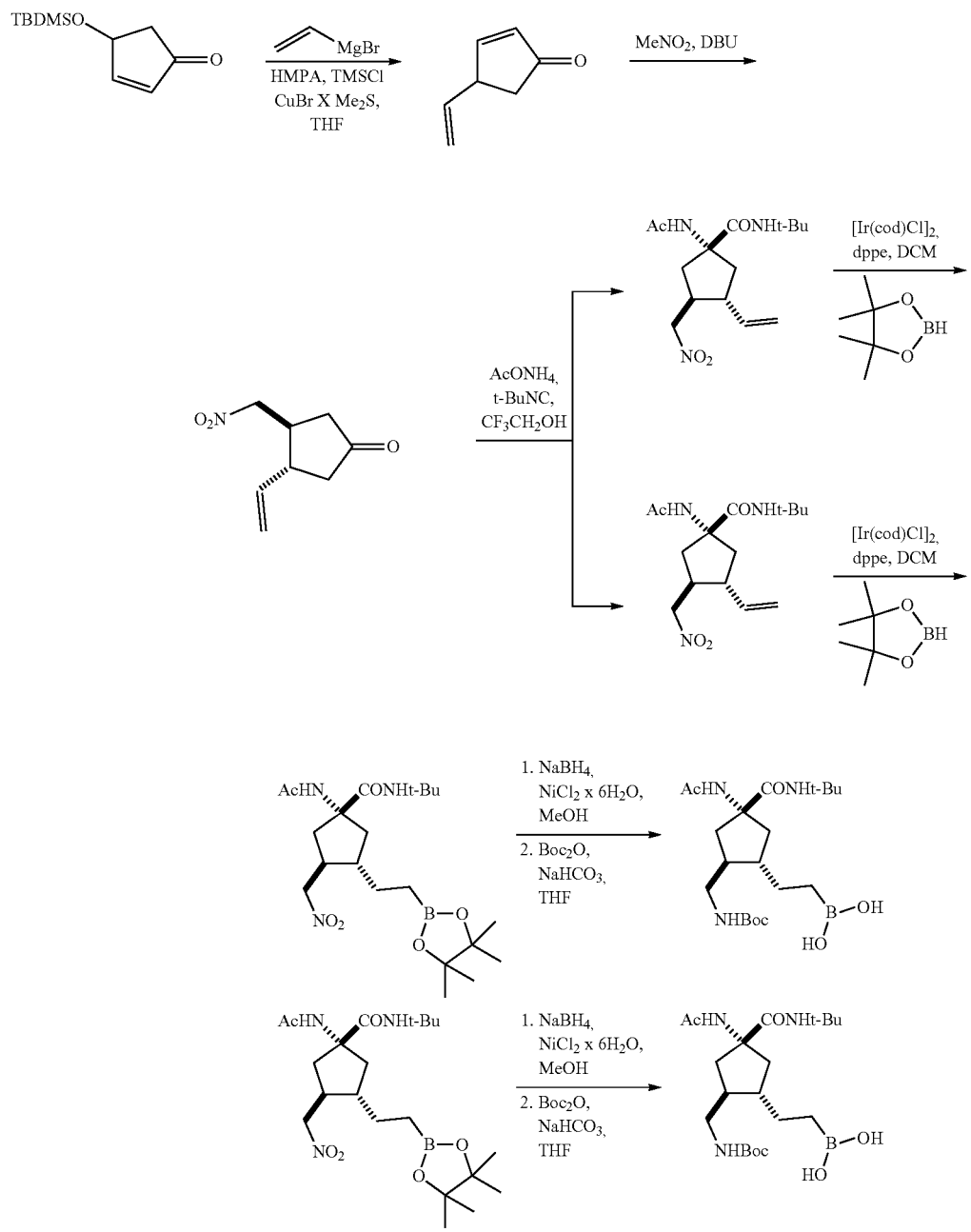

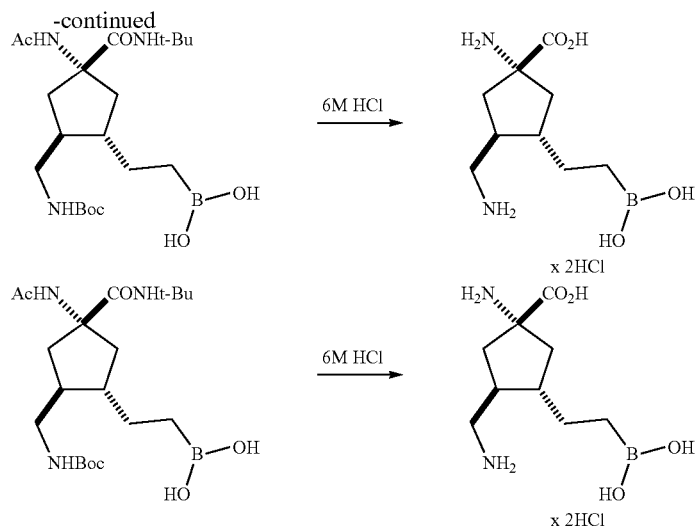

Step A. 4-Vinylcyclopent-2-en-1-one

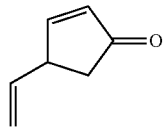

To a suspension of CuBr×Me$_2$S (2.33 g, 11.32 mmol) in tetrahydrofuran (300 mL) was added vinylmagnesium bromide (1 M in tetrahydrofuran) (94 mL, 94.34 mmol) dropwise under Ar at −78° C. Then HMPA (32.8 mL, 188.68 mmol) was added and stirred for 10 min. A solution of 4-((tert-butyldimethylsilyl)oxy)cyclopent-2-en-1-one (10 g, 47.17 mmol), TMSCl (30 mL, 235.85 mmol) in tetrahydrofuran (100 mL) was added dropwise for 15 min. The resulting mixture was stirred at −78° C. for 30 min, then between −60° C.-25° C. for 30 min. The mixture was quenched with NH$_4$Cl$_{(sat.)}$ and extracted with ethyl acetate three times. The organic layer was dried over magnesium sulfate, filtered and evaporated under reduced pressure. The crude product was purified by flash chromatography on silica gel (hexane/diethyl ether 20:1 to 2:1) to give 2.13 g (42%) of the desired product as a colorless oil. ESI+MS: m/z=131.9 (M+Na)$^+$, 108.7 (M+1)$^+$. $^1$H NMR (700 MHz, chloroform-d) δ 7.57 (dt, J=4.8, 2.4 Hz, 1H), 6.24-6.17 (m, 1H), 5.81-5.69 (m, 1H), 5.20-5.08 (m, 2H), 2.65 (dtd, J=18.8, 4.0, 2.0 Hz, 1H), 2.21-2.14 (m, 1H), 1.84 (dd, J=7.1, 3.1 Hz, 1H).

Step B. rac-(3S,4R)-3-(Nitromethyl)-4-vinylcyclopentan-1-one

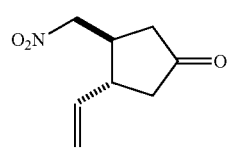

To the solution of 4-vinylcyclopent-2-en-1-one (550 mg, 5.1 mmol) in nitromethane (4.1 mL, 76.3 mmol) at 0° C. was added 7 drops of DBU. The reaction mixture was stirred at rt for 2 days. The mixture was diluted with diethyl ether and washed with 1 M HCl, water and brine. Dried over magnesium sulfate, filtered and evaporated under reduced pressure. The crude product was purified by flash chromatography on silica gel (hexane/ethyl acetate 20:1 to 5:1) to give 110 mg (13%) of the desired product as a colorless oil. $^1$H NMR (700 MHz, chloroform-d) δ 5.79-5.72 (m, 1H), 5.29-5.17 (m, 2H), 4.65 (dd, J=12.8, 4.3 Hz, 1H), 4.38 (dd, J=12.8, 9.1 Hz, 1H), 2.80-2.71 (m, 1H), 2.68 (dd, J=18.3, 7.7 Hz, 1H), 2.64-2.55 (m, 2H), 2.26-2.18 (m, 1H), 2.18-2.11 (m, 1H).

Step C. rac-(1S,3S,4R)- and rac-(1R,3S,4R)-1-Acetamido-N-(tert-butyl)-3-(nitromethyl)-4-vinylcyclopentane-1-carboxamide

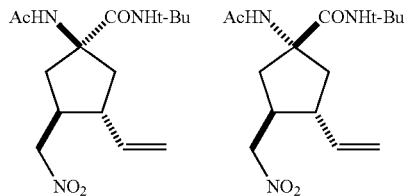

To a mixture of rac-(3S,4R)-3-(nitromethyl)-4-vinylcyclopentan-1-one (100 mg, 0.59 mmol), ammonium acetate (182 mg, 2.36 mmol), 2,2,2-trifluoroethanol (1 mL) was added dropwise tert-butyl isocyanide (132 µl, 1.18 mmol) and the mixture was stirred at room temperature overnight. The reaction mixture was diluted with water (20 mL) and extracted to ethyl acetate (3×30 mL). The organic layers was extracted with brine, dried over magnesium sulfate and concentrated in vacuo. The residue was purified by flash chromatography on silica gel (hexane/ethyl acetate 5:1 to 1:2) to give 85 mg of a mixture of diastereoisomers, [(1S,3S,4R)-isomer/(1R,3S,4R)-isomer=9:1] as a white foam, and 88 mg of a mixture of diastereoisomers, [(1S,3S,4R)-isomer/(1R,3S,4R)-isomer=1:9] as a white solid. Total yield: 94%.

Rac-(1S,3S,4R)-isomer

ESI+MS: m/z=334.1 (M+Na)⁺, 312.1 (M+1)⁺; ESI-MS: m/z=310.1 (M−1)⁻.

¹H NMR (700 MHz, chloroform-d) δ 6.88 (s, 1H), 6.04 (s, 1H), 5.68 (ddd, J=17.1, 10.1, 8.3 Hz, 1H), 5.17-5.06 (m, 2H), 4.48 (dd, J=13.0, 4.5 Hz, 1H), 4.41 (dd, J=13.0, 8.9 Hz, 1H), 2.71 (dd, J=13.5, 7.5 Hz, 1H), 2.69-2.62 (m, 1H), 2.46 (td, J=13.9, 8.7 Hz, 2H), 2.22 (dd, J=14.1, 8.6 Hz, 1H), 2.05 (s, 3H), 1.89 (dd, J=13.5, 10.9 Hz, 1H), 1.36 (d, J=2.1 Hz, 9H).

Rac-(1R,3S,4R)-isomer

ESI+MS: m/z=334.1 (M+Na)⁺, 312.1 (M+1)⁺; ESI-MS: m/z=310.1 (M−1)⁻.

¹H NMR (700 MHz, chloroform-d) δ 6.80 (s, 1H), 5.89 (s, 1H), 5.71 (ddd, J=17.1, 10.1, 8.3 Hz, 1H), 5.19-5.08 (m, 2H), 4.50 (dd, J=12.4, 4.5 Hz, 1H), 4.36 (dd, J=12.4, 7.6 Hz, 1H), 2.81 (dd, J=14.1, 8.6 Hz, 1H), 2.61-2.47 (m, 2H), 2.29 (d, J=9.5 Hz, 2H), 2.05 (s, 3H), 1.98 (dd, J=14.1, 9.2 Hz, 1H), 1.36 (s, 9H).

Step D. rac-(1S,3S,4S)-1-Acetamido-N-(tert-butyl)-3-(nitromethyl)-4-(2-(4,4,5,5-tetramethyl-1,3,2-dioxaborolan-2-yl)ethyl)cyclopentane-1-carboxamide

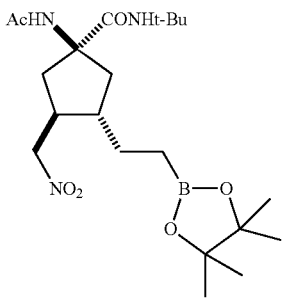

A mixture of dppe (6.2 mg, 0.016 mmol), bis(1,5-cyclooctadiene)diiridium(I) dichloride (5.2 mg, 0.008 mmol) was dissolved in degassed dichloromethane (2 mL) under Ar. Separately, a solution of rac-(1S,3S,4R)-1-acetamido-N-(tert-butyl)-3-(nitromethyl)-4-vinylcyclopentane-1-carboxamide (80 mg, 0.26 mmol, dr=9:1) was dissolved in degassed dichloromethane (2 mL) and pinacolborane (55 µl, 0.38 mmol) was added dropwise. Then this solution was added dropwise to the above-mentioned mixture of bis(1,5-cyclooctadiene)diiridium(I) dichloride and dppe in dichloromethane. The reaction mixture was stirred at rt overnight. The crude product was purified by flash chromatography on silica gel (hexane/ethyl acetate 5:1 to 1:1) to give 64 mg (56%) of the product as a colorless film (rac-(1S,3S,4S)-/rac-(1R,3S,4S)=9:1).

ESI+MS: m/z=440.0 (M+1)⁺; ESI-MS: m/z=438.1 (M−1)⁻.

¹H NMR (700 MHz, chloroform-d, rac-(1S,3S,4S)-isomer) δ 7.03 (s, 1H), 6.02 (s, 1H), 4.51 (dd, J=12.8, 4.6 Hz, 1H), 4.45 (dd, J=12.8, 9.2 Hz, 1H), 2.69 (dd, J=13.2, 7.4 Hz, 1H), 2.62-2.50 (m, 1H), 2.45 (dd, J=13.8, 8.3 Hz, 1H), 2.18 (dd, J=13.9, 8.6 Hz, 1H), 2.03 (s, 3H), 1.80-1.72 (m, 1H), 1.69 (dd, J=13.1, 9.8 Hz, 2H), 1.45-1.38 (m, 1H), 1.34 (s, 9H), 1.27 (s, 12H), 0.87-0.74 (m, 2H).

Step E. rac-(2-((1S,2S,4S)-4-Acetamido-2-(((tert-butoxycarbonyl)amino)methyl)-4-(tert-butylcarbamoyl)cyclopentyl)ethyl)boronic acid

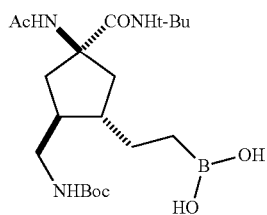

To the solution of rac-(1S,3S,4S)-1-acetamido-N-(tert-butyl)-3-(nitromethyl)-4-(2-(4,4,5,5-tetramethyl-1,3,2-dioxaborolan-2-yl)ethyl)cyclopentane-1-carboxamide (60 mg, 0.14 mmol; dr=9:1) and nickel chloride hexahydrate (32 mg, 0.14 mmol) in methanol (1 mL) was added sodium borohydride (52 mg, 1.37 mmol) portionwise at −10° C. The mixture was stirred at this temperature for 15 min. Then the reaction mixture was quenched with water (1 mL). The aqueous layer was washed with ethyl acetate (2×1 mL). The aqueous layer was diluted with tetrahydrofuran (0.5 mL) and sodium bicarbonate (12 mg, 0.14 mmol) followed by di-tert-butyl dicarbonate (61 mg, 0.28 mmol) were added. The reaction mixture was stirred at rt overnight. The mixture was diluted with water (10 mL) and extracted with ethyl acetate (3×20 mL). Dried over magnesium sulfate, filtered and concentrated under reduced pressure to give 40 mg (68%) of a desired product as a white solid (mixture of diastereoisomers 9:1, (2-((1S,2S,4S)-isomer as a major diastereoisomer). ESI+MS: m/z=450.1 (M+Na)⁺, 428.0 (M+1)⁺. ¹H NMR (700 MHz, chloroform-d) δ 5.06-5.03 (m, 1H), 4.97-4.93 (m, 1H), 3.33-3.19 (m, 1H), 2.67-2.64 (m, 1H), 2.60-2.57 (m, 1H), 2.38-2.36 (m, 1H), 2.19-2.12 (m, 1H), 2.02 (s, 3H), 1.89-1.87 (m, 1H), 1.78-1.75 (m, 1H), 1.72-1.69 (m, 1H), 1.46 (s, 9H), 1.35 (s, 9H), 0.89-0.80 (m, 2H).

Step F. rac-(1S,3S,4S)-1-Amino-3-(aminomethyl)-4-(2-boronoethyl)cyclopentane-1-carboxylic acid dihydrochloride rac-(2-((1S,2S,4S)-4-Acetamido-2-(((tert-butoxycarbonyl)amino)methyl)-4-(tert-butylcarbamoyl)cyclopentyl) ethyl)boronic acid (40 mg, 0.09 mmol; dr=9:1) was dissolved in 4 M HCl in dioxane (0.5 mL) and treated with 6 M HCl$_{(aq)}$ (2 mL). The reaction mixture was heated to reflux for 5 h. Then the mixture was concentrated under reduced pressure. The crude product was purified by preparative HPLC (0.1-1% MeCN) to give 3.7 mg (13%) of the mixture of diastereoisomers 3:1, [the major diastereoisomer is (1S,3S,4S)] as a colorless film. ESI+MS: m/z=231.0 (M+1)⁺, 213.9 (M−18)⁺. ¹H NMR (700 MHz, deuterium oxide, (1S,3S,4S)-isomer) δ 3.37-3.16 (m, 1H), 3.05-2.88 (m, 1H), 2.64-2.55 (m, 1H), 2.29 (dd, J=13.8, 7.7 Hz, 1H), 2.24-2.10 (m, 2H), 1.99-1.90 (m, 1H), 1.76-1.69 (m, 1H), 1.61 (dd, J=13.8, 11.4 Hz, 1H), 1.32-1.25 (m, 1H), 0.85-0.76 (m, 1H), 0.75-0.66 (m, 1H).

Example 7. rac-(1R,3S,4S)-1-Amino-3-(aminomethyl)-4-(2-boronoethyl)cyclopentane-1-carboxylic acid dihydrochloride

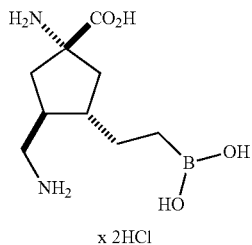 [SMILES: NC[C@H]1C[C@@](N)(C(=O)O)C[C@@H]1CCB(O)O]

Step A. rac-(1R,3S,4S)-1-Acetamido-N-(tert-butyl)-3-(nitromethyl)-4-(2-(4,4,5,5-tetramethyl-1,3,2-dioxaborolan-2-yl)ethyl)cyclopentane-1-carboxamide

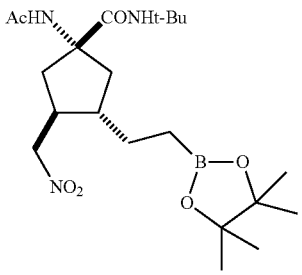

A mixture of dppe (6.4 mg, 0.016 mmol), bis(1,5-cyclooctadiene)diiridium(I) dichloride (5.4 mg, 0.008 mmol) was dissolved in degassed dichloromethane (2 mL), under Ar. Separately a solution of rac-(1R,3S,4R)-1-acetamido-N-(tert-butyl)-3-(nitromethyl)-4-vinylcyclopentane-1-carboxamide (85 mg, 0.27 mmol; dr=9:1) was dissolved in degassed dichloromethane (2 mL) and a pinacolborane (59 µl, 0.41 mmol) was added dropwise. Then the prepared solution was added dropwise to the above-mentioned mixture of bis(1,5-cyclooctadiene)diiridium(I) dichloride and dppe in dichloromethane. The reaction mixture was stirred at rt overnight. The crude product was purified by flash chromatography on silica gel (hexane/ethyl acetate 5:1 to 1:1) to give 85 mg (71%) of the desired product as a colorless oil [9:1 mixture of diastereoisomers, the major diastereoisomer is (1R,3S,4S)].

ESI+MS: m/z=440.0 (M+1)$^+$; ESI-MS: m/z=438.1 (M−1)$^−$. $^1$H NMR (700 MHz, chloroform-d) δ 6.89 (s, 1H), 5.83 (s, 1H), 4.55 (dd, J=12.1, 4.6 Hz, 1H), 4.35 (dd, J=12.2, 8.2 Hz, 1H), 2.75 (dd, J=14.2, 9.1 Hz, 1H), 2.42 (ddq, J=12.9, 8.7, 4.3 Hz, 1H), 2.32 (dd, J=13.3, 7.5 Hz, 1H), 2.06-2.03 (m, 1H), 2.02 (s, 3H), 1.99 (ddd, J=14.2, 8.2, 1.0 Hz, 1H), 1.94-1.85 (m, 1H), 1.74-1.66 (m, 1H), 1.47-1.38 (m, 1H), 1.34 (s, 9H), 1.26 (s, 12H), 0.85 (ddd, J=15.6, 9.9, 5.6 Hz, 1H), 0.76 (ddd, J=16.1, 9.9, 6.9 Hz, 1H).

Step B. rac-(2-((1S,2S,4R)-4-Acetamido-2-(((tert-butoxycarbonyl)amino)methyl)-4-(tert-butylcarbamoyl)cyclopentyl)ethyl)boronic acid

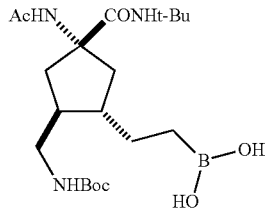

To the solution of rac-(1R,3S,4S)-1-acetamido-N-(tert-butyl)-3-(nitromethyl)-4-(2-(4,4,5,5-tetramethyl-1,3,2-dioxaborolan-2-yl)ethyl)cyclopentane-1-carboxamide (80 mg, 0.18 mmol; dr=9:1) and nickel chloride hexahydrate (43 mg, 0.18 mmol) in methanol (1 mL) was added sodium borohydride (69 mg, 1.82 mmol) portionwise at −10° C. The mixture was stirred at this temperature for 15 min. Then the reaction was quenched with water (1 mL). The aqueous layer was washed with ethyl acetate. The aqueous layer was diluted with tetrahydrofuran (0.5 mL) and sodium bicarbonate (15 mg, 0.18 mmol) followed by di-tert-butyl dicarbonate (80 mg, 0.37 mmol) were added. The reaction mixture was stirred at rt overnight. The mixture was diluted with water (20 mL) and extracted with ethyl acetate (3×30 mL), dried over magnesium sulfate, filtered and concentrated under reduced pressure to give 78 mg (100%) as a white solid (mixture of diastereoisomers 9:1; (1S,2S,4R)-isomer is a major diastereoisomer). ESI+MS: m/z=450.0 (M+Na)$^+$, 428.0 (M+1)$^+$; ESI-MS: m/z=426.2 (M−1)$^−$. $^1$H NMR (700 MHz, chloroform-d) δ 4.86-4.79 (m, 2H), 3.32-3.28 (m, 1H), 3.10-3.03 (m, 1H), 2.74-2.71 (m, 1H), 2.45-2.32 (m, 2H), 2.06 (s, 3H), 1.88-1.83 (m, 1H), 1.77-1.66 (m, 2H), 1.48 (s, 9H), 1.34 (s, 9H), 0.87-0.84 (m, 2H).

Step C. rac-(1R,3S,4S)-1-Amino-3-(aminomethyl)-4-(2-boronoethyl)cyclopentane-1-carboxylic acid dihydrochloride

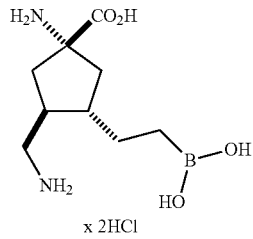

rac-(2-((1S,2S,4R)-4-acetamido-2-(((tert-butoxycarbonyl)amino)methyl)-4-(tert-butylcarbamoyl)cyclopentyl)ethyl)boronic acid (78 mg, 0.18 mmol; dr=9:1) was dissolved in 4 M HCl in dioxane (1 mL) and treated with 6 M HCl$_{(aq)}$ (2 mL). The reaction mixture was heated to reflux for 5 h. Then the mixture was concentrated under reduced pressure. The crude product was purified by preparative HPLC (0.1-2% MeCN) to give 16 mg (25%) as a colorless film (mixture of diastereoisomers 9:1, (1S,2S,4R)-isomer is a major diastereoisomer). ESI+MS: m/z=231.0 (M+1)$^+$, 213.9 (M−18)$^+$. $^1$H NMR (700 MHz, deuterium oxide) δ

3.28 (dd, J=13.0, 3.7 Hz, 1H), 2.88 (dd, J=12.9, 10.5 Hz, 1H), 2.66 (dd, J=13.8, 7.4 Hz, 1H), 2.26 (dd, J=14.6, 7.8 Hz, 1H), 2.24-2.12 (m, 1H), 2.06 (dd, J=14.6, 11.3 Hz, 1H), 1.94-1.82 (m, 1H), 1.76-1.70 (m, 1H), 1.68 (dd, J=13.8, 11.2 Hz, 1H), 1.36-1.26 (m, 1H), 0.80 (ddd, J=15.8, 10.5, 5.5 Hz, 1H), 0.75-0.63 (m, 1H).

Example 8. 3-Amino-1-benzyl-5-(2-boronoethyl)pyrrolidine-3-carboxylic acid dihydrochloride

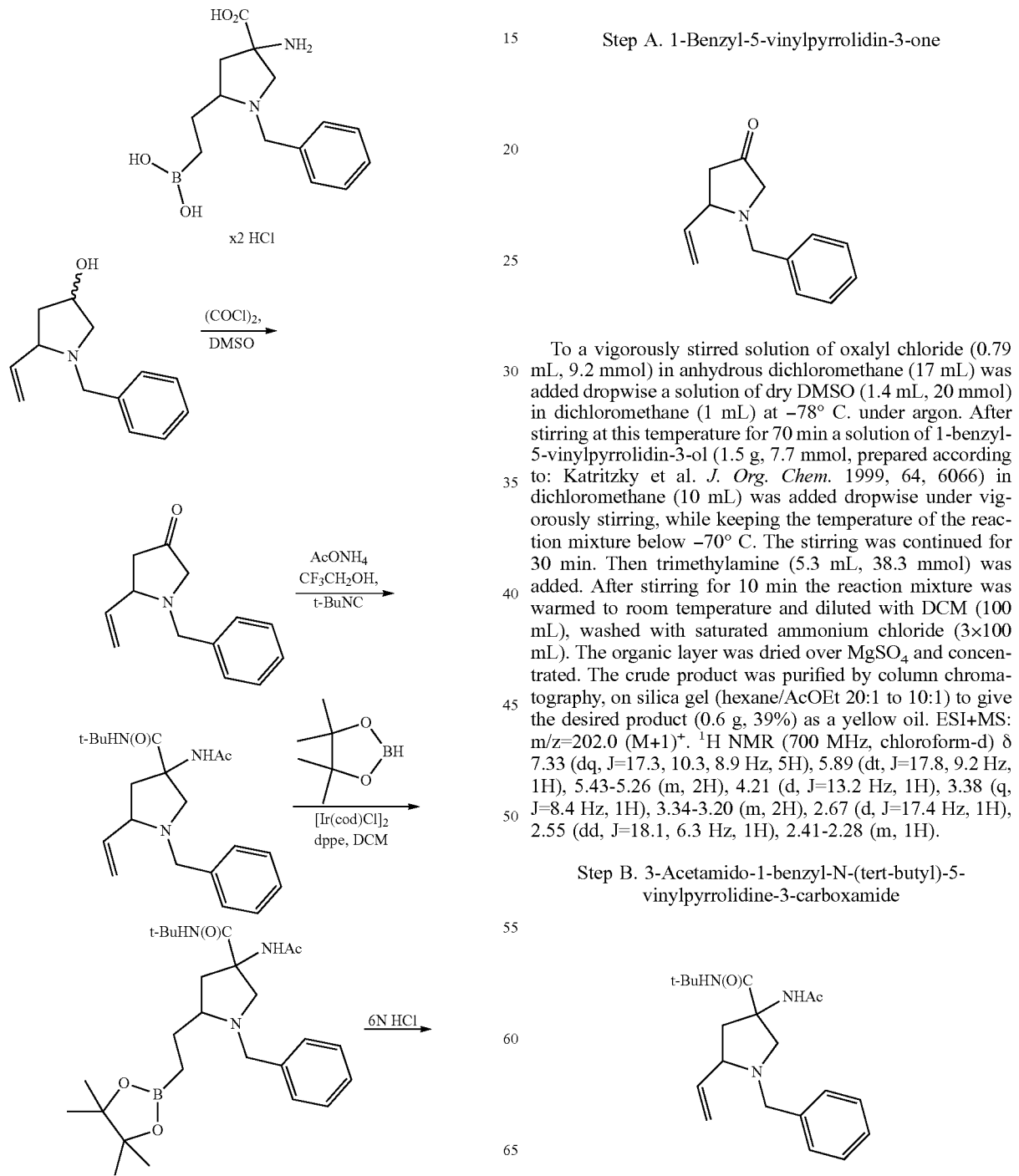

Step A. 1-Benzyl-5-vinylpyrrolidin-3-one

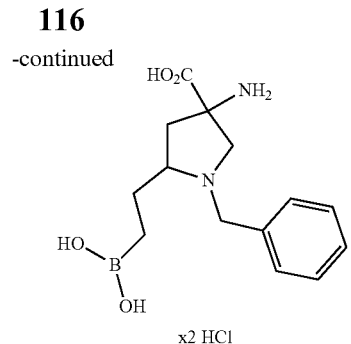

To a vigorously stirred solution of oxalyl chloride (0.79 mL, 9.2 mmol) in anhydrous dichloromethane (17 mL) was added dropwise a solution of dry DMSO (1.4 mL, 20 mmol) in dichloromethane (1 mL) at −78° C. under argon. After stirring at this temperature for 70 min a solution of 1-benzyl-5-vinylpyrrolidin-3-ol (1.5 g, 7.7 mmol, prepared according to: Katritzky et al. *J. Org. Chem.* 1999, 64, 6066) in dichloromethane (10 mL) was added dropwise under vigorously stirring, while keeping the temperature of the reaction mixture below −70° C. The stirring was continued for 30 min. Then trimethylamine (5.3 mL, 38.3 mmol) was added. After stirring for 10 min the reaction mixture was warmed to room temperature and diluted with DCM (100 mL), washed with saturated ammonium chloride (3×100 mL). The organic layer was dried over MgSO₄ and concentrated. The crude product was purified by column chromatography, on silica gel (hexane/AcOEt 20:1 to 10:1) to give the desired product (0.6 g, 39%) as a yellow oil. ESI+MS: m/z=202.0 (M+1)⁺. ¹H NMR (700 MHz, chloroform-d) δ 7.33 (dq, J=17.3, 10.3, 8.9 Hz, 5H), 5.89 (dt, J=17.8, 9.2 Hz, 1H), 5.43-5.26 (m, 2H), 4.21 (d, J=13.2 Hz, 1H), 3.38 (q, J=8.4 Hz, 1H), 3.34-3.20 (m, 2H), 2.67 (d, J=17.4 Hz, 1H), 2.55 (dd, J=18.1, 6.3 Hz, 1H), 2.41-2.28 (m, 1H).

Step B. 3-Acetamido-1-benzyl-N-(tert-butyl)-5-vinylpyrrolidine-3-carboxamide

To a mixture of 1-benzyl-5-vinylpyrrolidin-3-one (0.58 g, 2.9 mmol), ammonium acetate (0.9 g, 11.5 mmol) and 2,2,2-trifluoroethanol (0.79 mL) was added dropwise tert-butyl isocyanide (0/65 mL, 5.8 mmol) at RT, and the mixture was stirred overnight. Then the reaction mixture was quenched with water (80 mL) and extracted with ethyl acetate (3×70 ml). The combined organic layers were washed with brine (80 mL), dried over MgSO₄ and concentrated. The crude product was purified by flash chromatography, on silica gel (hexane/AcOEt 5:1 to 2:1) to give 3-acetamido-1-benzyl-N-(tert-butyl)-5-vinylpyrrolidine-3-carboxamide (0.4 g, 40%) as a yellow oil. ESI+MS: m/z=344.7 (M+1)⁺. ESI-MS: m/z=342.2 (M−1)⁻. ¹H NMR (700 MHz, chloroform-d) δ 7.35-7.30 (m, 2H), 7.28-7.25 (m, 3H), 5.81-5.65 (m, 1H), 5.43-5.21 (m, 2H), 4.17-4.12 (m, 1H), 3.61 (q, J=8.4 Hz, 1H), 3.19-3.09 (m, 2H), 2.84 (dd, J=13.6, 8.5 Hz, 1H), 2.64 (d, J=9.2 Hz, 1H), 1.98 (s, 3H), 1.88 (dd, J=13.6, 8.4 Hz, 1H), 1.30 (s, 9H).

Step C. 3-Acetamido-1-benzyl-N-(tert-butyl)-5-(2-(4,4,5,5-tetramethyl-1,3,2-dioxaborolan-2-yl)ethyl)pyrrolidine-3-carboxamide

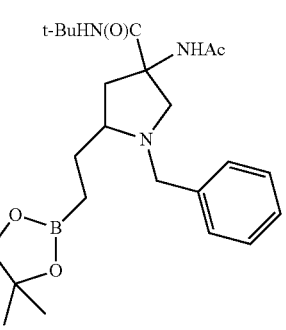

A mixture of dppe (27 mg, 0.068 mmol), bis(1,5-cyclooctadiene)diiridium(I) dichloride (23 mg, 0.034 mmol) was dissolved in dichloromethane (4 mL) and flushed with argon. Separately a solution of 3-acetamido-1-benzyl-N-(tert-butyl)-5-vinylpyrrolidine-3-carboxamide was dissolved in the same solvent (4 mL) (flushed with argon) and pinacolborane was added dropwise (215 µl, 1.48 mmol). Then the solution of 3-acetamido-1-benzyl-N-(tert-butyl)-5-vinylpyrrolidine-3-carboxamide and pinacolborane in DCM was added dropwise to the above-mentioned mixture of bis(1,5-cyclooctadiene)diiridium(I) dichloride and dppe in DCM at RT. The reaction mixture was stirred at room temperature overnight. After this time the crude product was purified by column chromatography, on silica gel (hexane/AcOEt 5:1 to 2:1) to give the desired product (260 mg, 48%) as a yellow oil. ESI+MS: m/z=472.9 (M+1)⁺, 372.0 (M-Pin-H₂O+1)⁺, ESI-MS: m/z=388.1 (M-Pin-1)⁻. ¹H NMR (700 MHz, chloroform-d) δ 7.35-7.29 (m, 3H), 7.27 (dd, J=7.4, 1.1 Hz, 2H), 4.22 (d, J=12.4 Hz, 1H), 3.16-3.10 (m, 2H), 2.73 (dd, J=13.4, 8.3 Hz, 1H), 2.58 (d, J=9.1 Hz, 1H), 1.96 (s, 3H), 1.78 (dd, J=13.4, 8.4 Hz, 1H), 1.30 (s, 9H), 1.29 (t, J=3.7 Hz, 17H).

Step D. 3-Amino-1-benzyl-5-(2-boronoethyl)pyrrolidine-3-carboxylic acid dihydrochloride A mixture of 3-acetamido-1-benzyl-N-(tert-butyl)-5-(2-(4,4,5,5-tetramethyl-1,3,2-dioxaborolan-2-yl)ethyl)pyrrolidine-3-carboxamide (140 mg, 0.3 mmol) and 6N HCl_aq (3 mL) was heated under reflux for 6 h. Then a solvent was evaporated and to residue was added 6N HCl_aq (2.5 mL) and the mixture was stirred at 90° C. overnight. Next additional amount of concentrated HCl (0.5 ml) was added and stirred at 90° C. for 2 days. The reaction mixture was concentrated under reduced pressure and the residue was purified by preparative HPLC (0.1-2% MeCN in water) to give the desired product (11 mg, 12%, single diastereoisomer) as a colorless film. ESI+MS: m/z=293.0 (M+1)⁺, 274.9 (M−H₂O+1)⁺, 247.0 (M−2×H₂O+1)⁺, ESI-MS: m/z=291.0 (M−18−1)⁻, 273.1 (M−H₂O−1)⁻. ¹H NMR (700 MHz, deuterium oxide) δ 7.49 (d, J=3.5 Hz, 5H), 4.31 (d, J=13.1 Hz, 1H), 3.93 (d, J=13.0 Hz, 1H), 3.78 (s, 1H), 3.49 (d, J=13.0 Hz, 1H), 2.77-2.64 (m, 1H), 2.48 (s, 1H), 2.20 (d, J=28.6 Hz, 1H), 1.81 (s, 1H), 0.82 (ddd, J=31.8, 10.3, 5.5 Hz, 2H).

Example 9.
3-Amino-5-(2-boronoethyl)pyrrolidine-3-carboxylic acid dihydrochloride

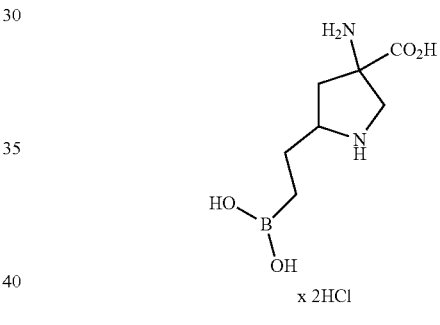

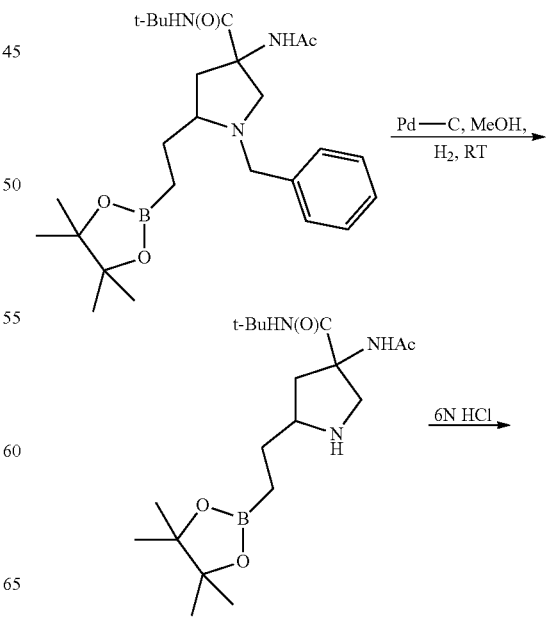

-continued

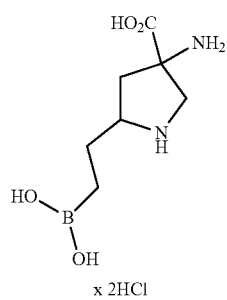

x 2HCl

Step A. 3-Acetamido-N-(tert-butyl)-5-(2-(4,4,5,5-tetramethyl-1,3,2-dioxaborolan-2-yl)ethyl)pyrrolidine-3-carboxamide

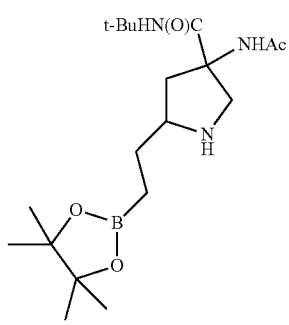

The mixture of 3-acetamido-1-benzyl-N-(tert-butyl)-5-(2-(4,4,5,5-tetramethyl-1,3,2-dioxaborolan-2-yl)ethyl)pyrrolidine-3-carboxamide (0.1 g, 0.21 mmol, Example 8, step C), palladium on activated charcoal (10 mg) and methanol (3 mL) was stirred under hydrogen atmosphere overnight. Next one drop of $HCl_{aq}$ (2M) was added and hydrogenolysis was continued for 12 days. The reaction mixture was filtered by celite and washed with MeOH. The filtrate was concentrated to give the desired product (83 mg, ca. 100%) as a yellow oil. ESI+MS: m/z=382.1 (M+1)$^+$, 282.1 (M−Pin−18+1)$^+$, ESI-MS: m/z=380.1 (M−1)$^-$, 280.0 (M−Pin−18−1)$^-$. $^1$H NMR (700 MHz, chloroform-d) δ 3.74 (d, J=11.1 Hz, 1H), 2.73 (dd, J=13.5, 7.1 Hz, 1H), 2.09 (s, 3H), 1.82 (q, J=7.2 Hz, 2H), 1.36 (s, 9H), 1.27 (s, 15H), 0.98-0.86 (m, 2H).

Step B. 3-Amino-5-(2-boronoethyl)pyrrolidine-3-carboxylic acid dihydrochloride A mixture of 3-acetamido-N-(tert-butyl)-5-(2-(4,4,5,5-tetramethyl-1,3,2-dioxaborolan-2-yl)ethyl)pyrrolidine-3-carboxamide (74 mg, 0.19 mmol) and 6N $HCl_{aq}$ (2.5 mL) was stirred at 90° C. for 2 days. Next additional amount of concentrated HCl (0.5 ml) was added and stirred at 90° C. for 1 day. The reaction mixture was concentrated under reduced pressure and the residue was purified by preparative HPLC (0.1-0.1% MeCN in water) to give the desired product (13 mg, 29%, single diastereoisomer) as a colorless film. ESI+MS: m/z=203.1 (M+1)$^+$. $^1$H NMR (700 MHz, deuterium oxide) δ 4.04 (d, J=13.4 Hz, 1H), 3.87 (d, J=7.3 Hz, 1H), 3.55 (d, J=13.4 Hz, 1H), 3.06-2.92 (m, 1H), 2.65 (d, J=23.1 Hz, 1H), 2.44-2.35 (m, 1H), 1.86 (ddd, J=31.5, 14.9, 7.7 Hz, 1H), 1.00-0.94 (m, 1H), 0.84 (t, J=8.3 Hz, 1H).

Example 10. rac-(1S,3R)-1-Amino-3-(2-borono-ethyl)cyclohexane-1-carboxylic acid hydrochloride

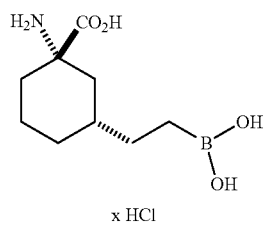

x HCl

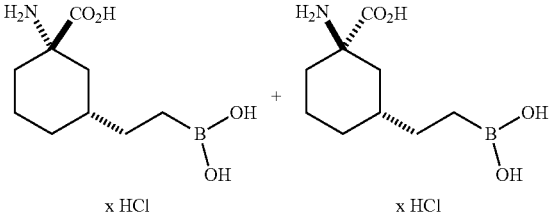

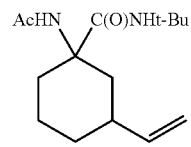

+ x HCl     x HCl

Step A. 1-Acetamido-N-(tert-butyl)-3-vinylcyclo-hexanecarboxamide

To the stirred solution of 3-vinylcyclohexanone (2.50 g, 20 mmol, 1 equiv.) (prepared from cyclohex-2-enone using literature method. Tetrahedron, 67, (2011), 4192-4195) and ammonium acetate (6.20 g, 80 mmol, 4 equiv.) in 2,2,2-trifluoroethanol (3 mL) tert-butyl isocyanide (3.32 g, 4.5 mL, 40 mmol, 2 equiv.) was added via syringe and the resulting mixture was stirred at room temperature for 24 hours. After this time, the reaction mixture was diluted with water (50 mL) and extracted with ethyl acetate (2×50 mL). The organic layer was washed with brine, dried over $MgSO_4$, filtered and evaporated under reduced pressure. The residue was purified by silica gel flash chromatography (using AcOEt-Hexane, 1:10 as the eluent) to give 1-acetamido-N-(tert-butyl)-3-vinylcyclohexanecarboxamide as a mixture of diastereoisomers dr=1:1 (2.62 g, 49%, pale yellow oil). ESI+MS: m/z=289.2 (M+Na)+, ESI-MS: m/z=265.2 (M−1)−. 1H NMR (700 MHz, chloroform-d) δ 5.74 (dddd, J=17.1, 12.7, 10.5, 6.3 Hz, 1H), 5.01 (dq, J=17.3, 1.6 Hz, 1H), 4.94 (ddt, J=10.5, 4.0, 1.4 Hz, 1H), 2.61 (m, 1H), 2.28 (m, 1H), [2.05, 1.95 (2s, 3H, two diastereoisomers)], 1.76-1.67 (m, 2H), 1.62 (td, J=13.9, 3.9 Hz, 1H), 1.55-1.48 (m, 1H), [1.33, 1.31 (2s, 9H, two diastereoisomers)], 1.18-1.11 (m, 1H), 1.09 (dq, J=12.1, 4.3 Hz, 1H).

Step B. 1-Acetamido-N-(tert-butyl)-3-(2-(4,4,5,5-tetramethyl-1,3,2-dioxaborolan-2-yl)ethyl)-cyclohexanecarboxamide

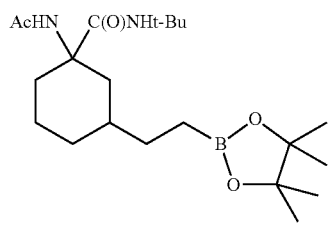

A round-bottom flask charged with bis(1,5-cyclooctadiene)diiridium (I) dichloride (144 mg, 0.21 mmol, 0.03 equiv.), 1,2-bis(diphenylphosphino)ethane (170 mg, 0.42 mmol, 0.06 equiv.) and dry CH2Cl2 (15 mL) was flushed with argon (bubbling). Subsequently, the separately prepared solution of 4,4,5,5-tetramethyl-1,3,2-dioxaborolane (1.82 g, 2.10 mL, 14.2 mmol, 2 equiv.), 1-acetamido-N-(tert-butyl)-3-vinylcyclohexanecarboxamide (1.90 g, 7.10 mmol, 1 equiv.) in 20 mL of dry CH2Cl2 was added successively at room temperature. The resulting light yellow mixture was then stirred at room temperature for 24 hours. The solvent was removed under reduced pressure and the residue was directly subjected to flash chromatography on silica gel (using AcOEt-Hexane, 1:10 as the eluent) to afford target 1-acetamido-N-(tert-butyl)-3-(2-(4,4,5,5-tetramethyl-1,3,2-dioxaborolan-2-yl)ethyl)-cyclohexane as a mixture of diastereoisomers dr=1:1 (1.68, 60%, sticky pale yellow oil). ESI+MS: m/z=395.1 (M+H)+, ESI-MS: m/z=393.1 (M−1)−. 1H NMR (700 MHz, chloroform-d) δ 2.62 (dd, J=45.4, 12.8 Hz, 2H), 2.25 (dd, J=60.2, 12.3 Hz, 2H), [2.01, 1.93 (2s, 3H, two diastereoisomers)] 1.74 (d, J=12.9 Hz, 2H), 1.67 (ddt, J=14.4, 7.7, 3.4 Hz, 2H), 1.58 (td, J=13.8, 4.0 Hz, 1H), [1.31, 1.30 (2s, 9H, two diastereoisomers)], [1.23, 1.24 (2s, 12H, two diastereoisomers)], 0.86-0.71 (m, 4H).

Step C. rac-(1S,3R)-1-Amino-3-(2-boronoethyl)cyclohexane-1-carboxylic acid hydrochloride A mixture of 1-acetamido-N-(tert-butyl)-3-(2-(4,4,5,5-tetramethyl-1,3,2-dioxaborolan-2-yl)ethyl)-cyclohexanecarboxamide (250 mg, 0.63 mmol) and 25 mL of 6N HCl was heated under reflux for 6 hours. After concentration the residue was subjected to preparative HPLC chromatography (gradient elution 0.1-2%, acetonitrile-water). Overall yield of isolated stereoisomers of target product (44 mg, 28%). Diastereoisomerically pure rac-(1S,3R)-1-Amino-3-(2-boronoethyl)cyclohexane-1-carboxylic acid hydrochloride was isolated (6.1 mg, 4%, white solid) ESI+MS: m/z=216.1 (M+H)+ ESI-MS: m/z=214.1 (M−1)− 1H NMR (700 MHz, D2O) δ 2.25-2.16 (m, 2H), 1.80-1.72 (m, 2H), 1.60 (dddd, J=22.2, 16.0, 8.4, 3.5 Hz, 2H), 1.48 (td, J=13.2, 4.5 Hz, 1H), 1.31 (m, 2H), 1.16 (t, J=12.6 Hz, 1H), 0.82 (td, J=12.7, 12.2, 3.7 Hz, 1H), 0.75 (t, J=7.7 Hz, 2H).

Example 11. rac-(1R,3R)-1-Amino-3-(2-boronoethyl)cyclohexane-1-carboxylic acid hydrochloride

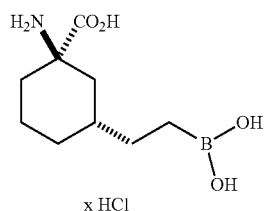 [SMILES: N[C@]1(C(=O)O)CCC[C@@H](CCB(O)O)C1]

Isolated by preparative HPLC (gradient elution 0.1-2%, acetonitrile-water) after step C from Example 10. Yield: 8.8 mg, 5.0%, white solid. ESI+MS: m/z=216.1 (M+H)+, ESI-MS: m/z=214.1 (M−1)− 1H NMR (700 MHz, D2O) δ 1.97-1.86 (m, 2H), 1.83-1.77 (m, 2H), 1.61 (dd, J=14.4, 12.8 Hz, 1H), 1.45-1.25 (m, 5H), 1.00-0.91 (m, 1H), 0.72 (t, J=8.1 Hz, 2H).

Example 12. 1-Amino-3-(2-boronoethyl)cycloheptane-1-carboxylic acid hydrochloride

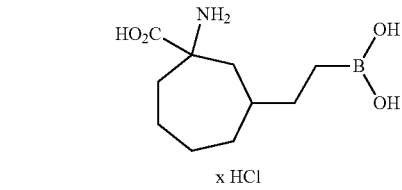

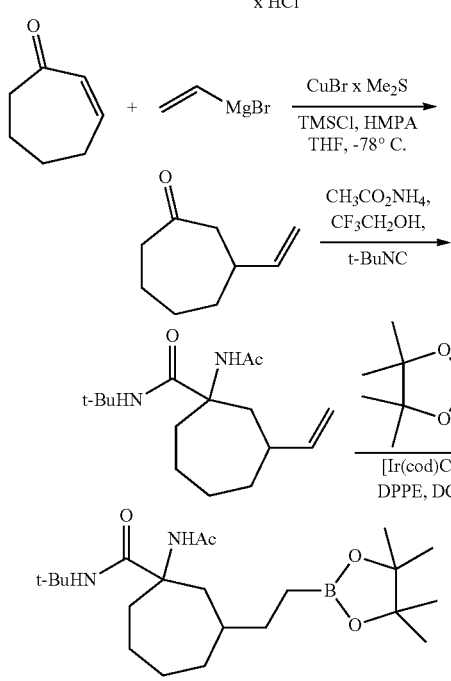

-continued

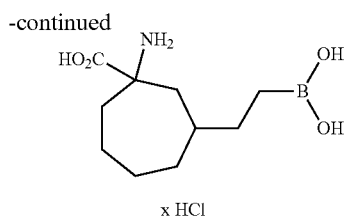

x HCl

Step A. 3-Vinylcycloheptan-1-one

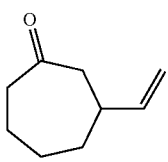

Vinylmagnesium bromide (1M in THF) (18.2 mL, 18.2 mmol) and HMPA (6.31 mL, 36.3 mmol) were separately added dropwise to a suspension of CuBr×Me₂S (281 mg, 1.36 mmol) in dry THF (70 mL) at −78° C. under argon over 10 min. After stirring at −78° C. for 15 min a solution of cyclohept-2-en-1-one (1 g, 9.1 mmol) and TMSCl (5.77 ml, 45.5 mmol) in dry THF (20 mL) was added dropwise over 30 min. The reaction mixture was stirred at −78° C. for 2 h. Then the mixture was quenched with saturated NH₄Cl (130 mL) and washed with AcOEt (3×100 ml). The organic layers were dried over MgSO₄ and concentrated. The crude product was purified by flash chromatography on silica gel (DCM) to give 3-vinylcycloheptan-1-one (1.3 g, 100%) as a yellow liquid. ¹H NMR (700 MHz, chloroform-d) δ 5.81 (ddd, J=17.2, 10.4, 6.8 Hz, 1H), 5.06-4.94 (m, 2H), 2.58-2.56 (m, 2H), 2.54-2.50 (m, 2H), 2.44-2.38 (m, 1H), 2.01-1.86 (m, 3H), 1.69-1.58 (m, 1H), 1.51-1.41 (m, 2H).

Step B. 1-Acetamido-N-(tert-butyl)-3-vinylcyclo-heptane-1-carboxamide

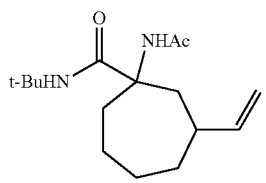

To a mixture of 3-vinylcycloheptan-1-one (1.2 g, 9.19 mmol), ammonium acetate (2.8 g, 36.8 mmol), 2,2,2-trifluoroethanol (2.5 mL) was added dropwise tert-butyl isocyanide (2.1 mL, 18.4 mmol) and the mixture was stirred at room temperature overnight. The progress of the reaction was controlled by TLC (AcOEt/hexane, 1:5). The reaction mixture was quenched with water (70 mL) and washed with ethyl acetate (3×70 mL). The combined organic layers were dried over MgSO₄ and concentrated. The crude product was purified by flash chromatography, on silica gel hexane/AcOEt (2:1 to 1:1) (mixture of diastereoisomers 3:1 and 1:2 and single diastereoisomer were isolated). ESI+MS: m/z=303.1 (M+Na)⁺, ESI-MS: m/z=279.2 (M−1)⁻. ¹H NMR (700 MHz, chloroform-d) mixture of diastereoisomers (3:1) δ 5.88-5.76 (m, 1H), 5.05-4.85 (m, 2H), 2.34-2.27 (m, 1H), 2.23-2.16 (m, 1H), 2.07 (s, 2H, CH₃ ₍₁ dia₎), 2.01 (s, 1H, CH₃ ₍₂ dia₎), 1.95 (dd, J=14.9, 10.5 Hz, 1H), 1.89 (dd, J=14.6, 6.3 Hz, 1H), 1.80 (td, J=12.6, 6.8 Hz, 2H), 1.68-1.57 (m, 3H), 1.56-1.47 (m, 1H), 1.44 (ddd, J=18.9, 10.3, 5.1 Hz, 1H), 1.35 (s, 2H, t-Bu₍₂ dia₎), 1.34 (s, 7H t-Bu₍₁ dia₎). ¹H NMR (700 MHz, chloroform-d, single diastereoisomer) δ 5.85 (ddd, J=17.4, 10.4, 7.1 Hz, 1H), 5.05-4.85 (m, 2H), 2.62 (d, J=14.3 Hz, 1H), 2.43-2.34 (m, 1H), 2.23-2.09 (m, 2H), 2.01 (s, 3H), 1.90-1.82 (m, 2H), 1.74 (dd, J=13.0, 6.8 Hz, 1H), 1.57 (dd, J=14.4, 9.1 Hz, 1H), 1.52-1.43 (m, 2H), 1.35 (s, 9H), 1.33-1.25 (m, 1H).

Step C. 1-Acetamido-N-(tert-butyl)-3-(2-(4,4,5,5-tetramethyl-1,3,2-dioxaborolan-2-yl)ethyl)cycloheptane-1-carboxamide

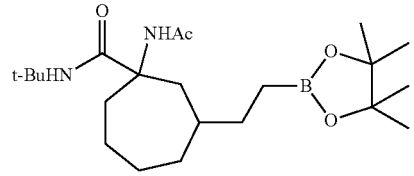

A mixture of dppe (30 mg, 0.075 mmol), bis(1,5-cyclooctadiene)diiridium(I) dichloride (25 mg, 0.037 mmol) was dissolved in dichloromethane (4.5 mL) and flushed with argon. Separately a solution of 1-acetamido-N-(tert-butyl)-3-(2-(4,4,5,5-tetramethyl-1,3,2-dioxaborolan-2-yl)ethyl)cycloheptane-1-carboxamide (dr=3:1) was dissolved in the same solvent (4.5 mL) (flushed with argon) and a pinacolborane was added dropwise (235 µl, 1.62 mmol). Then this solution was added dropwise to the above-mentioned mixture of bis(1,5-cyclooctadiene)diiridium(I) dichloride and dppe in DCM at RT. The reaction mixture was stirred at room temperature overnight. After this time the crude product was purified by flash chromatography, on silica gel (hexane/AcOEt 2:1 to 1:1) to give the desired product (0.53 g, 100%, dr=3:1) as a yellow oil. ESI+MS: m/z=431.1 (M+Na)⁺, 409.2 (M+1)⁺, ESI-MS: m/z=407.3 (M−1)⁻. ¹H NMR (700 MHz, chloroform-d) δ 2.07 (s, 1H CH₃ ₍₂ dia₎), 2.05 (s, 2H CH₃ (i dia)), 1.85-1.74 (m, 3H), 1.59 (dq, J=11.4, 5.8 Hz, 3H), 1.45-1.37 (m, 3H), 1.35 (s, 3H t-Bu₍₂ dia₎), 1.34 (s, 6H t-Bu₍₁ dia₎), 1.30 (s, 5H), 1.27 (d, J=3.0 Hz, 11H), 0.86-0.73 (m, 2H).

Step D. 1-Amino-3-(2-boronoethyl)cycloheptane-1-carboxylic acid hydrochloride

A mixture of 1-acetamido-N-(tert-butyl)-3-(2-(4,4,5,5-tetramethyl-1,3,2-dioxaborolan-2-yl)ethyl)cycloheptane-1-carboxamide (200 mg, 0.49 mmol, dr=3:1) and 6N HCl$_{aq}$ (2 mL) was heated under reflux for 4 h. The reaction mixture was concentrated under reduced pressure and the residue was purified by preparative HPLC (0.1-7% MeCN in water) to give the desired product (49 mg, 38%, dr=3:1) as a white solid. ESI+MS: m/z=230.0 (M+1)⁺, 195.0 (M−2×H₂O+1)⁺, ESI-MS: m/z=210.1 (M−18−1)⁻. ¹H NMR (700 MHz, deuterium oxide) δ 2.31-2.24 (m, 0.7H₍₁ dia₎), 2.23-2.14 (m, 0.3H₍₂ dia₎), 2.10 (dd, J=15.6, 10.7 Hz, 1H), 1.88-1.72 (m, 3H), 1.71-1.54 (m, 3H), 1.53-1.42 (m, 1H), 1.42-1.23 (m, 3H), 1.21-1.13 (m, 0.7H₍₁ dia₎), 1.13-1.04 (m, 0.3H₍₂ dia₎), 0.80-0.65 (m, 2H).

125

Example 13. rac-(1R,2R,5R)-1-Amino-5-(2-borono-ethyl)-2-hydroxycyclohexane-1-carboxylic acid hydrochloride

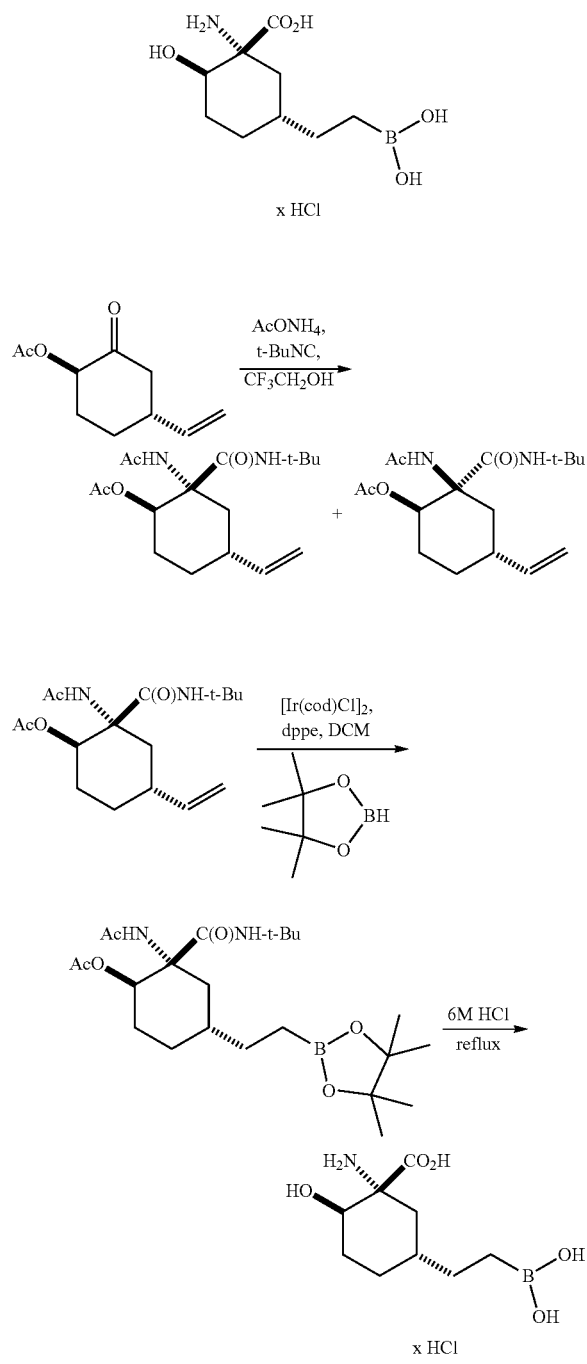

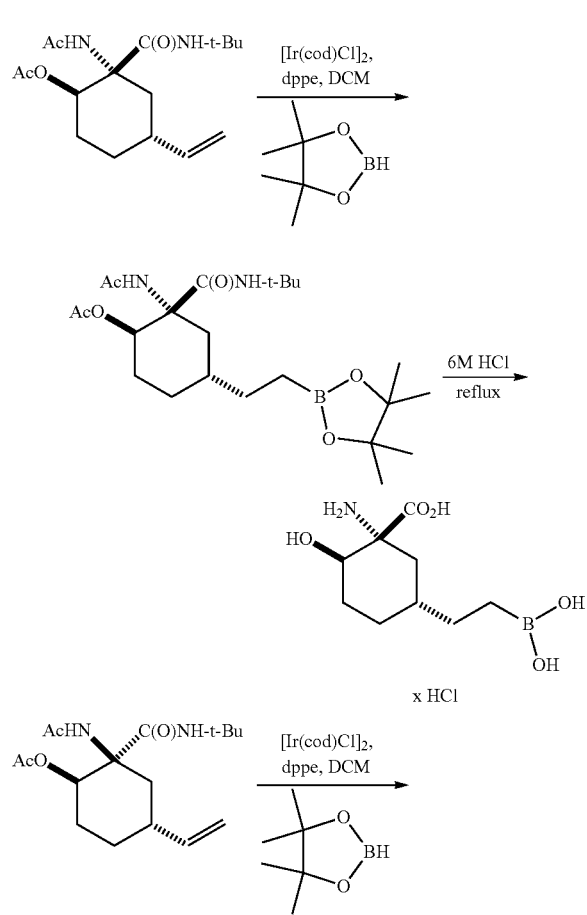

126

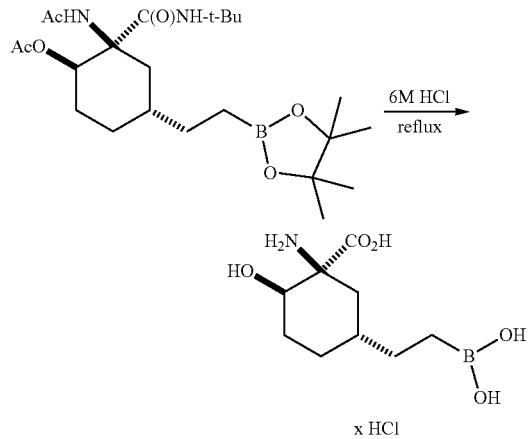

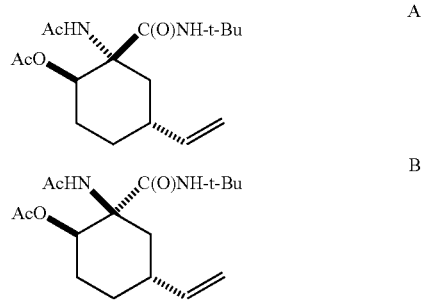

General Synthetic Route for Examples 13 and 14

Step A. rac-(1R,2R,4R)-2-Acetamido-2-(tert-butyl-carbamoyl)-4-vinylcyclohexyl acetate and rac-(1R, 2S,4R)-2-acetamido-2-(tert-butylcarbamoyl)-4-vi-nylcyclohexyl acetate Prepared from rac-(1R,4R)-4-ethenyl-2-oxocyclohexyl acetate (Diederich, F. et al., *Org. Biomol. Chem.* 2009, 7, 3947-3957), using the procedure described in Example 1, step A. The crude product was purified by flash chromatography on silica gel (hexane/ethyl acetate 4:1 to 1:1). Total yield: 430 mg (60%).

Isolated: 150 mg (mixture of diastereoisomers A:B=4:1, white solid) and 280 mg (A:B=3:7, colorless semisolid).

A (rac-(1R,2R,4R)-isomer): ESI+MS: m/z=347.1 (M+Na)+. $^1$H NMR (700 MHz, CDCl$_3$) δ 7.97 (bs, 1H), 6.44 (bs, 1H), 5.75 (ddd, J=17.0, 10.4, 6.3 Hz, 1H), 5.40 (d, J=8.5 Hz, 1H), 5.05-4.98 (m, 2H), 3.55 (ddd, J=13.2, 8.5, 4.8 Hz, 1H), 2.98 (dt, J=13.5, 2.7 Hz, 1H), 2.10-2.05 (m, 4H), 2.04 (s, 3H), 2.04-1.95 (m, 3H), 1.86-1.82 (m, 1H), 1.37 (s, 9H).

B (rac-(1R,2S,4R)-isomer): ESI+MS: m/z=347.1 (M+Na)+. $^1$H NMR (700 MHz, CDCl$_3$) δ 6.93 (bs, 1H), 5.79 (bs, 1H), 5.73 (ddd, J=17.0, 10.4, 6.3 Hz, 1H), 5.31 (dd, J=12.1, 4.8 Hz, 1H), 5.05-4.97 (m, 2H), 3.12 (dt, J=14.2, 2.9 Hz, 1H), 2.17 (s, 3H), 2.10-2.07 (m, 1H), 2.07 (s, 3H), 2.04-2.00 (m, 1H), 1.91-1.78 (m, 2H), 1.57-1.50 (m, 1H), 1.49-1.44 (m, 1H), 1.33 (s, 9H).

Step B. rac-(1R,2R,4R)-2-Acetamido-2-(tert-butyl-carbamoyl)-4-(2-(4,4,5,5-tetramethyl-1,3,2-dioxa-borolan-2-yl)ethyl)cyclohexylacetate

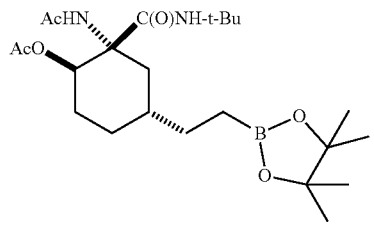

Prepared from rac-(1R,2R,4R)-2-acetamido-2-(tert-butyl-carbamoyl)-4-vinylcyclohexyl acetate (140 mg, 0.43 mmol, dr=4:1), using the procedure described in Example 1, step B. The crude product was purified by flash chromatography on silica gel (hexane/ethyl acetate 4:1 to 1:1). Yield: 85 mg (44%). ESI+MS: m/z=475.1 (M+Na)+. $^1$H NMR (700 MHz, CDCl$_3$) δ 7.89 (bs, 1H), 6.36 (bs, 1H), 5.26 (d, J=8.8 Hz, 1H), 3.48 (ddd, J=11.9, 8.9, 4.8 Hz, 1H), 2.97 (dt, J=13.6, 2.6 Hz, 1H), 2.06-2.03 (m, 4H), 2.02 (s, 3H), 1.96-1.90 (m, 2H), 1.83-1.78 (m, 2H), 1.36 (s, 9H), 1.26 (s, 12H), 0.96-0.87 (m, 2H), 0.82-0.74 (m, 2H).

Step C. rac-(1R,2R,5R)-1-Amino-5-(2-borono-ethyl)-2-hydroxycyclohexane-1-carboxylic acid hydrochloride Prepared from (1R,2R,4R)-2-acetamido-2-(tert-butylcar-bamoyl)-4-vinylcyclohexyl acetate (70 mg, 0.155 mmol), using the procedure described in Example 1, step C. The crude product was purified by preparative HPLC (0.1-2% MeCN). Yield: 18 mg (43%). ESI+MS: m/z=232.0 (M+H)+. $^1$H NMR (700 MHz, D$_2$O) δ 3.74 (dd, J=11.8, 5.3 Hz, 1H), 2.23-2.17 (m, 1H), 2.00 (ddd, J=16.6, 13.2, 4.0 Hz, 1H), 1.91-1.83 (m, 2H), 1.82-1.75 (m, 1H), 1.30-1.24 (m, 3H), 0.98 (qd, J=13.3, 3.7 Hz, 1H), 0.73 (dd, J=9.2, 6.6 Hz, 2H).

Example 14. rac-(1S,2R,5R)-1-Amino-5-(2-borono-ethyl)-2-hydroxycyclohexane-1-carboxylic acid hydrochloride

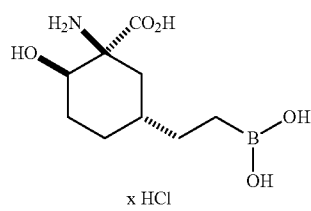 [SMILES: N[C@@]1(C(=O)O)C[C@H](CCB(O)O)CC[C@H]1O]

Step A. rac-(1R,2S,4R)-2-Acetamido-2-(tert-butyl-carbamoyl)-4-(2-(4,4,5,5-tetramethyl-1,3,2-dioxa-borolan-2-yl)ethyl)cyclohexyl acetate

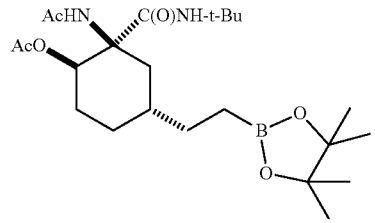

Prepared from rac-(1R,2S,4R)-2-acetamido-2-(tert-butyl-carbamoyl)-4-vinylcyclohexyl acetate (255 mg, 0.56 mmol, dr=7:3, Example 13, step A) in the same manner like in Example 13, step B. The crude product was purified by flash chromatography on silica gel (hexane/ethyl acetate 4:1 to 1:1). Yield: 212 mg (60%) dr=2:1. ESI+MS: m/z=453.1 (M+H)+, 475.1 (M+Na)+.

Major diastereoisomer (colorless oil): $^1$H NMR (700 MHz, CDCl$_3$) δ 7.02 (bs, 1H), 5.75 (bs, 1H), 5.30 (dd, J=12.1, 4.8 Hz, 1H), 3.11-3.04 (m, 1H), 2.13 (s, 3H), 2.05 (s, 3H), 2.04-2.01 (m, 1H), 1.84-1.77 (m, 2H), 1.49-1.43 (m, 1H), 1.32 (s, 9H), 1.25 (s, 12H), 1.24-1.16 (m, 2H), 1.14-1.00 (m, 1H), 0.93-0.87 (m, 2H), 0.79-0.72 (m, 1H).

Step B. rac-(1S,2R,5R)-1-Amino-5-(2-boronoethyl)-2-hydroxycyclohexane-1-carboxylic acid hydrochloride Prepared from rac-(1R,2S,4R)-2-acetamido-2-(tert-butyl-carbamoyl)-4-(2-(4,4,5,5-tetramethyl-1,3,2-dioxaborolan-2-yl)ethyl)cyclohexyl acetate (120 mg, 0.155 mmol, dr=2:1) procedure described in Example 1, step C. The crude product was purified by preparative HPLC (0.1-1% MeCN). Obtained: 35 mg (49%, single diastereoisomer). ESI+MS: m/z=232.0 (M+H)+. $^1$H NMR (700 MHz, D$_2$O) δ 4.19 (dd, J=12.2, 5.2 Hz, 1H), 2.02 (dt, J=14.9, 2.7 Hz, 1H), 2.00-1.96 (m, 1H), 1.88-1.82 (m, 1H), 1.66 (dd, J=14.7, 12.5 Hz, 1H), 1.46-1.39 (m, 1H), 1.36-1.29 (m, 3H), 1.14-1.06 (m, 1H), 0.73 (t, J=8.0 Hz, 2H).

Example 15. rac-(1S,2S,5R)-1-Amino-5-(2-borono-ethyl)-2-hydroxycyclohexane-1-carboxylic acid hydrochloride

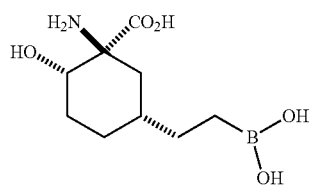

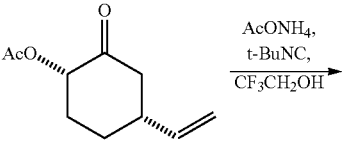

129
-continued

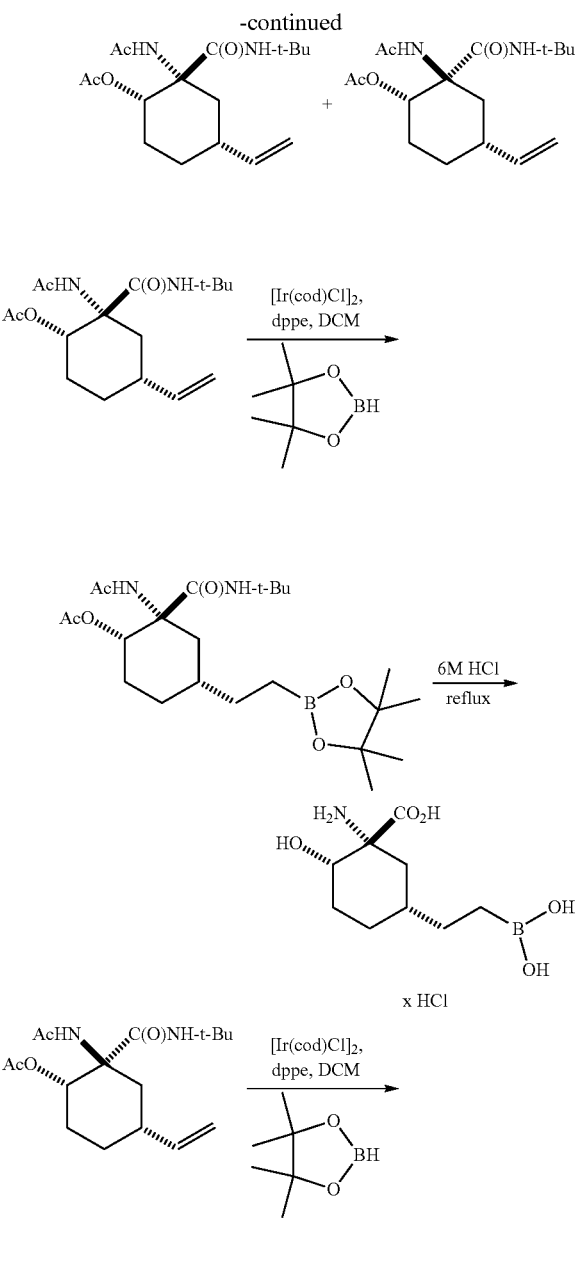

130

Step A. rac-(1S,2S,4R)-2-Acetamido-2-(tert-butyl-carbamoyl)-4-vinylcyclohexyl acetate and rac-(1S, 2R,4R)-2-acetamido-2-(tert-butylcarbamoyl)-4-vinylcyclohexyl acetate

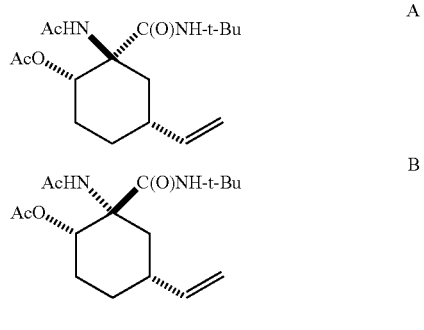

Prepared from racemic (1S,4R)-4-ethenyl-2-oxocyclohexyl acetate (Diederich, F. et al., *Org. Biomol. Chem.* 2009, 7, 3947-3957), using the procedure described in Example 1, step A. The crude product was purified by flash chromatography on silica gel (hexane/ethyl acetate 4:1 to 1:1). Yield: 516 mg (72%). Obtained: 90 mg (single diastereoisomer A, white solid), 266 mg (A:B=2:1, white solid) and 160 mg of the mixture of other diastereoisomers.

A (rac-(1S,2S,4R)-isomer): ESI+MS: m/z=347.1 (M+Na)$^+$; ESI-MS: m/z=323.2 (M−1)$^−$.

$^1$H NMR (700 MHz, CDCl$_3$) δ 7.34 (bs, 1H), 6.10 (bs, 1H), 5.82 (ddd, J=17.0, 10.4, 6.2 Hz, 1H), 5.34 (bs, 1H), 5.11 (dt, J=17.3, 1.4 Hz, 1H), 5.04 (dt, J=10.4, 1.3 Hz, 1H), 2.23-2.14 (m, 1H), 2.06 (s, 3H), 2.05 (s, 3H), 2.00-1.96 (m, 1H), 1.92 (ddd, J=14.9, 6.4, 3.6 Hz, 1H), 1.72-1.66 (m, 1H), 1.62-1.58 (m, 1H), 1.41-1.33 (m, 2H), 1.31 (s, 9H).

B (Mixture of diastereoisomers, 2:1): ESI+MS: m/z=347.1 (M+Na)$^+$; ESI-MS: m/z=323.1 (M−1)$^−$.

Step B. rac-(1S,2S,4R)-2-Acetamido-2-(tert-butylcarbamoyl)-4-(2-(4,4,5,5-tetramethyl-1,3,2-dioxaborolan-2-yl)ethyl)cyclohexyl acetate

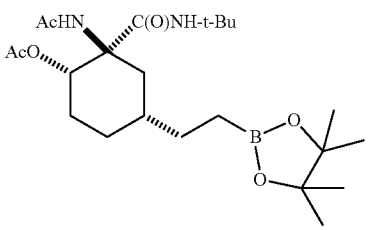

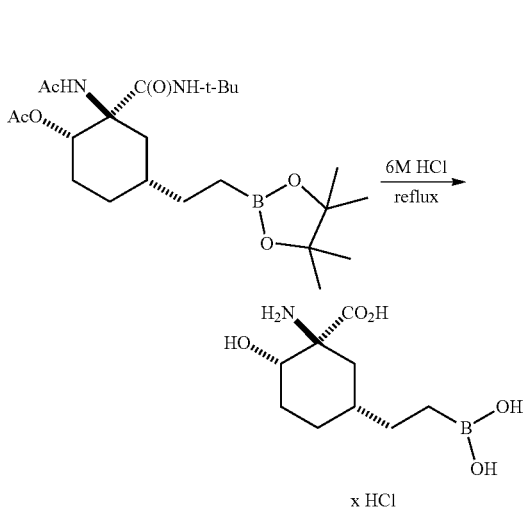

Prepared from rac-(1S,2S,4R)-2-acetamido-2-(tert-butylcarbamoyl)-4-vinylcyclohexyl acetate (80 mg, 0.25 mmol), using the procedure described in Example 1, step B. The crude product was purified by flash chromatography on silica gel (hexane/ethyl acetate 3:1 to 1:1). Yield: 89 mg (79%), white solid. ESI+MS: m/z=453.0 (M+H)$^+$, 475.0 (M+Na)$^+$; ESI-MS: m/z=451.1 (M−1)$^−$. $^1$H NMR (700 MHz, CDCl$_3$) δ 7.45 (bs, 1H), 6.11 (bs, 1H), 5.33 (bs, 1H), 2.04 (s, 3H), 2.03 (s, 3H), 1.96-1.80 (m, 4H), 1.64-1.59 (m, 1H), 1.47-1.39 (m, 3H), 1.17-1.12 (m, 1H), 0.88-0.81 (m, 2H).

Step C. rac-(1S,2S,5R)-1-Amino-5-(2-boronoethyl)-2-hydroxycyclohexane-1-carboxylic acid hydrochloride Prepared from rac-(1S,2S,4R)-2-acetamido-2-(tert-butylcarbamoyl)-4-(2-(4,4,5,5-tetramethyl-1,3,2-dioxaborolan-2-yl)ethyl)cyclohexyl acetate (26 mg, 0.155 mmol) using method described in Example 1, step C. The crude product was purified by preparative HPLC (0.1-1% MeCN). Yield: 11 mg (72%). Colorless film. ESI+MS: m/z=214.0 (M−18+H)$^+$, 232.0 (M+H)$^+$. $^1$H NMR (700 MHz, D$_2$O) δ 3.96 (s, 1H), 1.88-1.83 (m, 2H), 1.79-1.74 (m, 1H), 1.71-1.64 (m, 1H), 1.62-1.56 (m, 1H), 1.39-1.33 (m, 3H), 1.30-1.22 (m, 1H), 0.76 (t, J=8.1 Hz, 2H).

Example 16. rac-(2S,5R)-1-Amino-5-(2-boronoethyl)-2-hydroxycyclohexane-1-carboxylic acid hydrochloride

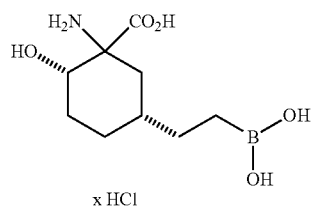 [SMILES: NC1(C(=O)O)C[C@H](CCB(O)O)CC[C@@H]1O]

x HCl

Step A. rac-(1S,4R)-2-Acetamido-2-(tert-butylcarbamoyl)-4-(2-(4,4,5,5-tetramethyl-1,3,2-dioxaborolan-2-yl)ethyl)cyclohexyl acetate

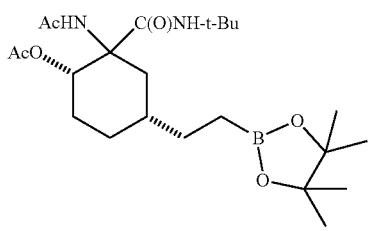

Prepared from the mixture of diastereoisomers of rac-(1S,4R)-2-acetamido-2-(tert-butylcarbamoyl)-4-vinylcyclohexyl acetate (dr=2:1) (255 mg, 0.79 mmol, Example 15, step A), using the procedure described in Example 15, step B. The crude product was purified by flash chromatography on silica gel (hexane/ethyl acetate 4:1 to 2:1). Yield: 100 mg of rac-(1S,2S,4R)-2-acetamido-2-(tert-butylcarbamoyl)-4-(2-(4,4,5,5-tetramethyl-1,3,2-dioxaborolan-2-yl)ethyl)cyclohexyl acetate and 150 mg of the mixture of rac-(1S,2R,4R)-2-acetamido-2-(tert-butylcarbamoyl)-4-(2-(4,4,5,5-tetramethyl-1,3,2-dioxaborolan-2-yl)ethyl)cyclohexyl acetate and rac-(1S,2S,4R)-2-acetamido-2-(tert-butylcarbamoyl)-4-(2-(4,4,5,5-tetramethyl-1,3,2-dioxaborolan-2-yl)ethyl)cyclohexyl acetate (1:1). Yield: 70%, white solids. rac-(1S,2R,4R)-isomer: ESI+MS: m/z=475.1 (M+Na)$^+$; ESI-MS: m/z=451.3 (M−1)$^-$.

$^1$H NMR (700 MHz, CDCl$_3$) δ 7.42 (bs, 1H), 6.01 (bs, 1H), 5.56 (bs, 1H), 2.70-2.62 (m, 1H), 2.12 (s, 3H), 1.94 (s, 3H), 1.91-1.80 (m, 3H), 1.45-1.41 (m, 3H), 1.34 (s, 9H), 1.27 (s, 12H), 1.19-1.12 (m, 2H), 0.81-0.73 (m, 2H).

Step B. rac-(2S,5R)-1-amino-5-(2-boronoethyl)-2-hydroxycyclohexane-1-carboxylic acid hydrochloride Prepared from rac-(1S,4R)-2-acetamido-2-(tert-butylcarbamoyl)-4-(2-(4,4,5,5-tetramethyl-1,3,2-dioxaborolan-2-yl)ethyl)cyclohexyl acetate (150 mg, 0.33 mmol; dr=1:1), using the procedure described in Example 15, step C. The crude product was purified by preparative HPLC (0.1-1% MeCN). Yield: 10 mg (11%, colorless film), dr=2:1; rac-(1S,2R,5R)-1-amino-5-(2-boronoethyl)-2-hydroxycyclohexane-1-carboxylic acid hydrochloride is a major diastereoisomer. ESI+MS: m/z=214.0 (M−18+H)$^+$, 232.0 (M+H)$^+$. $^1$H NMR (700 MHz, D$_2$O) δ 4.08-4.05 (m, 1H), 1.94-1.88 (m, 2H), 1.84-1.81 (m, 1H), 1.76-1.70 (m, 1H), 1.64-1.59 (m, 1H), 1.45-1.30 (m, 3H), 1.28-1.21 (m, 1H), 0.76 (t, J=8.1 Hz, 2H).

Example 17. rac-(1R,2S,5R)-1-Amino-5-(2-boronoethyl)-2-((dimethylamino)methyl)-cyclohexane-1-carboxylic acid dihydrochloride

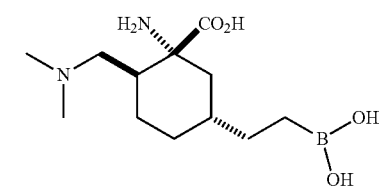

x 2HCl

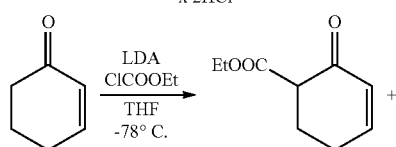

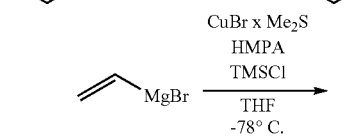

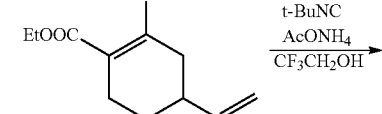

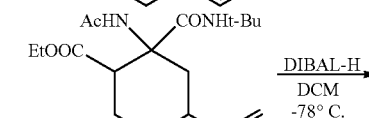

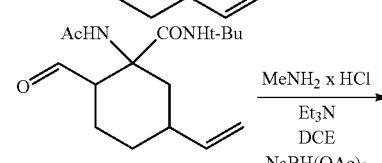

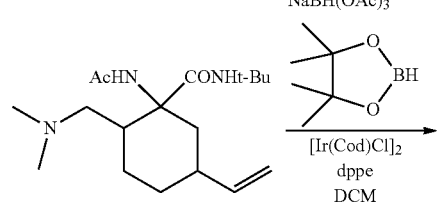

-continued

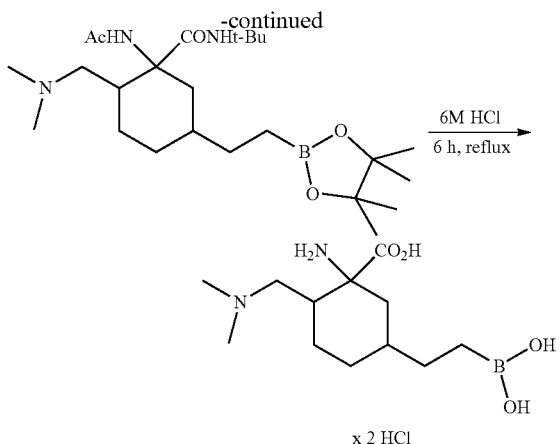

x 2 HCl

Step A. Ethyl 2-oxocyclohex-3-ene-1-carboxylate

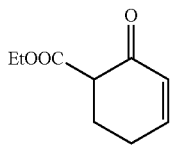 [SMILES: CCOC(=O)C1CCC=CC1=O]

To a solution of freshly distilled diisopropylamine (58.3 mL, 0.416 mol, 2 equiv.) in dry THF (375 mL) was added dropwise a solution of n-BuLi (2.5 M in hexanes) (166.4 mL, 0.416 mol, 2 equiv.) at −78° C. under argon. The reaction mixture was warmed to room temperature, stirred for 20 minutes and cooled to −78° C. Then the solution of 2-cyclohexen-1-one (20 g, 20.1 mL, 0.208 mol, 1 equiv.) in THF (78 mL) was added dropwise and the mixture was stirred for 1 h at −78° C. Ethyl chloroformate (33.8 g, 29.7 mL, 0,312 mol, 1.5 equiv.) was added dropwise and the resulting reaction mixture was stirred for 1 h at −78° C., then allowed to warm to room temperature and stirring was continued overnight. The mixture was quenched with saturated solution of NH$_4$Cl (250 mL) and the organic layer was collected. The aqueous layer was extracted with ethyl acetate (3×150 mL). The combined organic layers were washed with brine and water, dried over MgSO$_4$, filtered and concentrated in vacuo. The crude product was purified by flash chromatography on silica gel (gradient elution, hexane/AcOEt 10:1 to 5:1) to give ethyl 2-oxocyclohex-3-ene-1-carboxylate (18.5 g, 53%) as a yellow liquid. $^1$H NMR (700 MHz, chloroform-d) δ 6.96-6.90 (m, 1H), 5.98 (dt, J=10.1, 2.0 Hz, 1H), 4.20-4.07 (m, 2H), 3.35-3.29 (m, 1H), 2.46-2.39 (m, 1H), 2.36-2.26 (m, 3H), 2.19-2.11 (m, 1H), 1.27-1.14 (m, 2H).

Step B. Ethyl 2-hydroxy-4-vinylcyclohex-1-ene-1-carboxylate

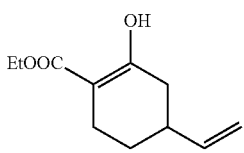

A solution of vinylmagnesium bromide (1M in THF) (119 mL, 0.119 mol, 2 equiv.) and HMPA (41.6 mL) were added dropwise to a suspension of CuBr×Me$_2$S (1.83 g, 8.92 mmol, 0.15 equiv.) in dry THF (250 mL) at −78° C. over 15 min under argon. After stirring at −78° C. for 15 min, a solution of ethyl 2-oxocyclohex-3-ene-1-carboxylate (10 g, 59.5 mmol, 1.0 equiv.) and TMSCl (37.7 mL, 0.297 mol, 5 equiv.) in dry THF (100 mL) was added dropwise (for over 30 min). The reaction mixture was stirred at −78° C. for 2 h. Then the mixture was quenched with saturated aqueous NH$_4$Cl (200 mL) and washed with AcOEt (3×150 mL). The combined organic layers were dried over MgSO$_4$ and concentrated. The crude product was purified by flash chromatography on silica gel (hexane/AcOEt 10:1) to give ethyl 2-hydroxy-4-vinylcyclohex-1-ene-1-carboxylate (4.94 g, 42%) as a pale yellow liquid. H NMR (700 MHz, chloroform-d) δ 5.91-5.70 (m, 1H), 5.16-4.90 (m, 2H), 4.22 (qd, J=7.1, 0.5 Hz, 2H), 2.45-2.30 (m, 3H), 2.24-2.12 (m, 2H), 1.89-1.74 (m, 1H), 1.45-1.18 (m, 5H).

Step C. Ethyl rac-(1R,2R,4R)-2-acetamido-2-(tert-butylcarbamoyl)-4-vinylcyclohexane-1-carboxylate and ethyl rac-(1R,2S,4R)-2-acetamido-2-(tert-butylcarbamoyl)-4-vinylcyclohexane-1-carboxylate

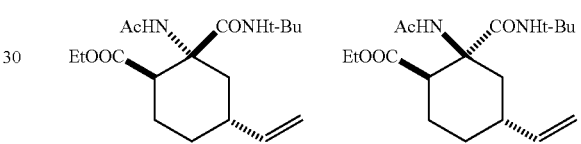

To the stirred solution of ethyl 2-hydroxy-4-vinylcyclohex-1-ene-1-carboxylate. (3.0 g, 15.29 mmol, 1 equiv.) and ammonium acetate (4.71 g, 61.15 mmol, 4 equiv.) in 2,2,2-trifluoroethanol (3 mL) tert-butyl isocyanide (3.44 mL, 30.58 mmol, 2 equiv.) was added dropwise via syringe and the resulting mixture was stirred at room temperature for 24 hours. After this time, the reaction mixture was diluted with water (25 mL) and extracted with ethyl acetate (3×50 mL). The combined organic layers were washed with brine, dried over MgSO$_4$, filtered and evaporated under reduced pressure. The residue was purified by silica gel flash chromatography (gradient elution, hexane/AcOEt 10:1 to 2:1) to give corresponding product as a separable diastereoisomers (dr=2:1) (overall yield 2.42 g, 47%). ESI+MS: m/z=339.1 (M+1)$^+$, 361.1 (M+Na)$^+$. The minor diastereoisomer (ethyl rac-(1R,2S,4R)-2-acetamido-2-(tert-butylcarbamoyl)-4-vinylcyclohexane-1-carboxylate): 0.90 g, (17%), white solid. $^1$H NMR (700 MHz, chloroform-d) δ 7.59 (s, 1H), 7.27 (s, 1H), 5.73 (ddd, J=17.0, 10.5, 6.3 Hz, 1H), 5.07-4.91 (m, 2H), 4.26-4.09 (m, 2H), 3.23 (ddd, J=13.8, 2.9, 1.7 Hz, 1H), 2.80 (dd, J=13.3, 3.6 Hz, 1H), 2.16-2.11 (m, 1H) 2.10 (s, 3H), 1.95 (dq, J=13.4, 3.6 Hz, 1H), 1.72 (qd, J=13.3, 3.9 Hz, 1H), 1.32-1.28 (m, 13H), 1.26-1.13 (m, 2H).

The major diastereoisomer (ethyl rac-(1R,2R,4R)-2-acetamido-2-(tert-butylcarbamoyl)-4-vinylcyclohexane-1-carboxylate): 1.52 g (30%); white solid. $^1$H NMR (700 MHz, chloroform-d) δ 8.10 (s, 1H), 7.57 (s, 1H), 5.72 (ddd, J=17.0, 10.4, 6.4 Hz, 1H), 5.03-4.91 (m, 2H), 4.20 (ddq, J=59.5, 10.8, 7.1 Hz, 2H), 3.29 (d, J=13.8 Hz, 1H), 2.28 (dd, J=12.4, 4.4 Hz, 1H), 2.14 (dq, J=11.6, 4.2, 3.6 Hz, 1H), 2.11-2.02 (m, 2H), 1.99 (s, 3H), 1.85-1.80 (m, 1H), 1.33-1.30 (m, 13H), 1.10 (qd, J=13.2, 4.4 Hz, 1H).

Step D. rac-(1R,2R,5R)-1-Acetamido-N-(tert-butyl)-2-formyl-5-vinylcyclohexane-1-carboxamide

To a solution of ethyl rac-(1R,2R,4R)-2-acetamido-2-(tert-butylcarbamoyl)-4-vinylcyclohexane-1-carboxylate (0.5 g, 1.48 mmol) in dry dichloromethane (15 mL) was added dropwise a solution of DIBAL-H (1M in DCM; 4.6 mL, 4.58 mmol) at −78° C. under argon. The reaction mixture was stirred at −78° C. and monitored by TLC. After 1 h the reaction mixture was quenched by methanol. White sticky precipitate was filtered through the pad of celite and washed with dichloromethane. The resulting filtrate was concentrated in vacuo to give the crude product as a colorless oil (0.43 g 99%). The crude product was used in the next step without any further purification. ESI+MS: m/z=317.1 (M+Na)+. $^1$H NMR (700 MHz, chloroform-d) δ 9.78 (s, 1H), 5.79-5.74 (m, 1H), 5.06-4.98 (m, 1H), 3.30-3.25 (m, 1H), 2.25-2.17 (m, 1H), 2.11-2.07 (m, 1H), 2.02 (s, 3H), 1.92-1.87 (m, 2H), 1.66-1.59 (m, 1H), 1.32 (s, 9H), 1.24-1.16 (m, 2H), 1.15-1.14 (m, 1H)

Step E. rac-(1R,2S,5R)-1-Acetamido-N-(tert-butyl)-2-((dimethylamino)methyl)-5-vinylcyclohexane-1-carboxamide and rac-(1R,2R,5R)-1-Acetamido-N-(tert-butyl)-2-((dimethylamino)methyl)-5-vinylcyclohexane-1-carboxamide

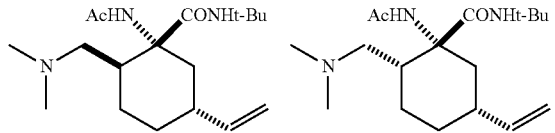

rac-(1R,2R,5R)-1-Acetamido-N-(tert-butyl)-2-formyl-5-vinylcyclohexane-1-carboxamide (0.43 g, 1.46 mmol) was dissolved in 1,2-dichloroethane (3 mL), Then, N,N-dimethylamine hydrochloride (0.14 g, 1.76 mmol) and triethylamine (0.25 mL, 1.76 mmol) were added and the reaction mixture was stirred at room temperature for 1 h. Next, sodium triacetoxyborohydride (0.62 g, 2.93 mmol) was added portionwise and the resulting reaction mixture was stirred overnight at room temperature. After this time, the mixture was quenched with 5% aqueous NaHCO$_3$ (5 ml), and washed with dichloromethane (3×30 ml). The combined organic layers were dried over MgSO$_4$, filtered and concentrated in vacuo. The residue was purified by column chromatography, on silica gel (gradient elution, CH$_2$Cl$_2$/MeOH 50:1 to 20:1) to give product as a mixture of diastereoisomers (overall yield: 146 mg, 31%). ESI+MS: m/z=324.1 (M+1)+, 346.2 (M+Na)+. The single diastereoisomers were isolated in the order of elution:

rac-(1R,2R,5R)-1-acetamido-N-(tert-butyl)-2-((dimethylamino)methyl)-5-vinylcyclohexane-1-carboxamide (36 mg, 8%, colorless oil). $^1$H NMR (700 MHz, chloroform-d) δ 5.77-5.72 (m, 1H), 5.00-4.93 (m, 2H), 3.07-3.02 (m, 1H), 2.84 (d, J=11.02 Hz, 1H), 2.54-2.50 (m, 1H), 2.30 (s, 6H), 2.12-2.08 (m, 1H), 2.01 (d, J=13.29 Hz, 2H), 1.89 (s, 3H), 1.54-1.45 (m, 2H), 1.41-1.37 (m, 1H), 1.36 (s, 9H), 1.29-1.26 (m, 1H).

rac-(1R,2S,5R)-1-acetamido-N-(tert-butyl)-2-((dimethylamino)methyl)-5-vinylcyclohexane-1-carboxamide (110 mg, 23%, colorless oil). $^1$H NMR (700 MHz, chloroform-d) δ 5.74 (ddd, J=17.1, 10.4, 6.5 Hz, 1H), 5.01-4.90 (m, 2H), 3.43-3.37 (m, 1H), 3.22 (d, J=13.3 Hz, 1H), 2.27 (s, 6H), 2.20-2.13 (m, 1H), 2.12-2.08 (m, 1H), 2.00 (d, J=13.5 Hz, 1H), 1.92 (s, 3H), 1.84-1.79 (m, 1H), 1.56-1.52 (m, 1H), 1.40-1.36 (m, 1H), 1.34 (s, 9H), 1.18 (d, J=12.9 Hz, 2H).

Step F. rac-(1R,2S,5R)-1-Acetamido-N-(tert-butyl)-2-((dimethylamino)methyl)-5-(2-(4,4,5,5-tetramethyl-1,3,2-dioxaborolan-2-yl)ethyl)cyclohexane-1-carboxamide

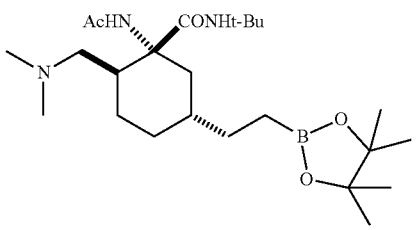

A mixture of dppe (7.7 mg, 0.019 mmol) and bis(1,5-cyclooctadiene)diiridium(I) dichloride (6.5 mg, 0.0096 mmol) in dichloromethane (2 mL) was flushed with argon. Separately rac-(1R,2S,5R)-1-acetamido-N-(tert-butyl)-2-((dimethylamino)methyl)-5-vinylcyclohexane-1-carboxamide was dissolved in dry DCM (2 mL) (flushed with argon) and a 4,4,5,5-tetramethyl-1,3,2-dioxaborolane was added dropwise (120 µl, 0.739 mmol). Next the prepared solution were added dropwise to the above-mentioned mixture of the iridium catalyst and dppe in DCM at RT. The reaction mixture was stirred at room temperature overnight. After this time, the reaction mixture was diluted with DCM (20 mL) and washed with 5% NaHCO$_3$ (20 mL). The organic layer was dried over MgSO$_4$, filtered and concentrated in vacuo. The crude product was purified by column chromatography on silica gel (CH$_2$Cl$_2$/MeOH 50:1 to MeOH) to give rac-(1R,2S,5R)-1-acetamido-N-(tert-butyl)-2-((dimethylamino)methyl)-5-(2-(4,4,5,5-tetramethyl-1,3,2-dioxaborolan-2-yl)ethyl)cyclohexane-1-carboxamide (50 mg, 34%) as a colorless oil. ESI+MS: m/z=452.1 (M+1)+, 370.1 (M-Pin)+. $^1$H NMR (700 MHz, chloroform-d) δ 3.45-3.38 (m, 1H), 3.25-3.19 (m, 1H), 2.26 (d, J=5.84 Hz, 6H), 2.04-1.91 (m, 3H), 1.89 (s, 3H), 1.82-1.77 (m, 1H), 1.58-1.54 (m, 7H), 1.33 (s, 9H), 1.25 (s, 12H), 1.02-0.92 (m, 2H).

Step G. rac-(1R,2S,5R)-1-Amino-5-(2-boronoethyl)-2-((dimethylamino)methyl)cyclohexane-1-carboxylic acid dihydrochloride A mixture of rac-(1R,2S,5R)-1-acetamido-N-(tert-butyl)-2-((dimethylamino)methyl)-5-(2-(4,4,5,5-tetramethyl-1,3,2-dioxaborolan-2-yl)ethyl)cyclohexane-1-carboxamide (50 mg, 0.11 mmol) and 6 N HCl$_{aq}$(10 mL) was heated under reflux 6 h. Next, the reaction mixture was concentrated under reduced pressure and the residue was purified by ion-exchange chromatography on DOWEX® followed by preparative HPLC (0.1-1% MeCN) to give (after acidification with 6N HCl and subsequent lyophilization) rac-(1R, 2S,5R)-1-amino-5-(2-boronoethyl)-2-((dimethylamino)-methyl)cyclohexane-1-carboxylic acid dihydrochloride (13.1 mg, 34%) as a white solid. ESI+MS: m/z=273.0 (M+1)⁺. ¹H NMR (700 MHz, deuterium oxide) δ 3.28 (dd, J=13.3, 2.6 Hz, 1H), 3.19 (dd, J=13.2, 11.0 Hz, 1H), 2.92 (s, 3H), 2.85 (s, 3H), 2.24 (d, J=11.58 Hz, 1H), 2.12 (s, 1H), 1.91-1.85 (m, 2H), 1.83-1.75 (m, 1H), 1.73-1.66 (m, 1H), 1.33-1.25 (m, 3H), 0.99-0.91 (m, 1H), 0.73 (dd, J=9.1, 7.2 Hz, 2H).

Example 18. rac-(1R,2R,5R)-1-Amino-5-(2-boronoethyl)-2-((dimethylamino)methyl)-cyclohexane-1-carboxylic acid dihydrochloride

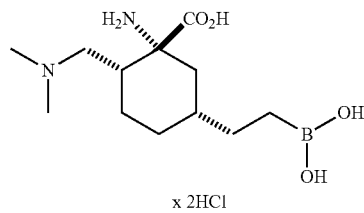 [SMILES: CN(C)C[C@H]1CC[C@@H](CCB(O)O)C[C@]1(N)C(=O)O]

x 2HCl

Step A. rac-(1R,2R,5R)-1-Acetamido-N-(tert-butyl)-2-((dimethylamino)methyl)-5-(2-(4,4,5,5-tetramethyl-1,3,2-dioxaborolan-2-yl)ethyl)cyclohexane-1-carboxamide

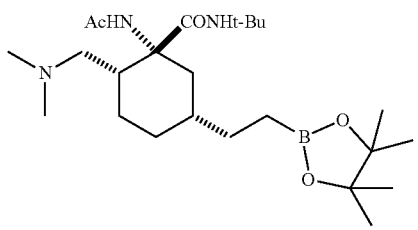

The title compound was obtained from rac-(1R,2R,5R)-1-acetamido-N-(tert-butyl)-2-((dimethylamino)methyl)-5-vinylcyclohexane-1-carboxamide (33 mg, 0.102 mmol) using the procedure described for the preparation of Example 17, step F. The crude product was purified by flash chromatography on silica gel (CH₂Cl₂/MeOH 30:1 to MeOH). Yield: 10 mg (22%); colorless oil. ESI+MS: m/z=452.1 (M+1)⁺, 474.0 (M+Na)⁺, ¹H NMR (700 MHz, chloroform-d) δ 3.07-3.03 (m, 1H), 2.84-2.78 (m, 1H), 2.55-2.50 (m, 1H), 2.29 (s, 6H), 2.15-2.06 (m, 1H), 2.01-1.96 (m, 1H), 1.91 (d, J=8.09 Hz, 3H), 1.82-1.77 (m, 1H), 1.58-1.54 (m, 7H), 1.35 (s, 9H), 1.25 (s, 12H), 0.92-0.90 (m, 2H).

Step B. rac-(1R,2R,5R)-1-Amino-5-(2-boronoethyl)-2-((dimethylamino)methyl)cyclohexane-1-carboxylic acid dihydrochloride A mixture of (1R,2R,5R)-1-acetamido-N-(tert-butyl)-2-((dimethylamino)methyl)-5-(2-(4,4,5,5-tetramethyl-1,3,2-dioxaborolan-2-yl)ethyl)cyclohexane-1-carboxamide. (10 mg, 0.022 mmol) and 6 N HCl$_{aq}$ (5 mL) was heated under reflux 6 h. The reaction mixture was concentrated under reduced pressure and the residue was purified by ion exchange chromatography on DOWEX® and next by preparative HPLC (0.1-10% MeCN in water) to give (after acidification with 6N HCl and subsequent lyophilization) 1.2 mg (16%) of a desired product as a white solid. ESI+MS: m/z=273.2 (M+1)⁺. ¹H NMR (700 MHz, deuterium oxide) δ 3.31-3.25 (m, 1H), 2.96 (dd, J=13.07, 3.13 Hz, 1H), 2.93 (s, 3H), 2.85 (s, 3H), 2.68-2.63 (m, 1H), 2.22-2.16 (m, 1H), 1.87-1.81 (m, 1H), 1.72-1.62 (m, 2H), 1.60-1.54 (m, 1H), 1.52-1.48 (m, 1H), 1.39-1.31 (m, 3H), 0.80-0.69 (m, 2H).

Example 19. rac-(1S,2S,5R)-1-amino-5-(2-boronoethyl)-2-((dimethylamino)methyl)cyclohexane-1-carboxylic acid dihydrochloride

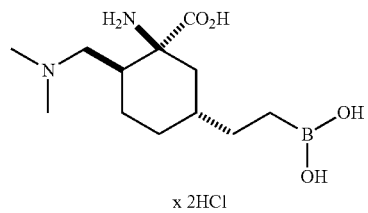 [SMILES: CN(C)C[C@@H]1CC[C@@H](CCB(O)O)C[C@@]1(N)C(=O)O]

x 2HCl

Step A. rac-(1S,2R,5R)-1-acetamido-N-(tert-butyl)-2-formyl-5-vinylcyclohexane-1-carboxamide

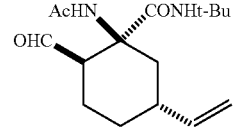

The title compound was prepared from ethyl ethyl (1R, 2S,4R)-2-acetamido-2-(tert-butylcarbamoyl)-4-vinylcyclohexane-1-carboxylate (Example 17, step C) (0.287 g, 0.85 mmol, 1 equiv.), DIBAL-H (1M in DCM, 1.78 mL, 1.78 mmol, 2.1 equiv.), solvent: DCM (8 mL) using the same procedure as described in Example 17, step D. A colorless oil (80 mg, 32%) was obtained. ESI+MS: m/z=317.2 (M+Na)⁺. ¹H NMR (700 MHz, chloroform-d) δ 10.06 (d, J=2.0 Hz, 1H), 7.56 (s, 1H), 6.96 (s, 1H), 5.72 (ddd, J=17.1, 10.4, 6.4 Hz, 1H), 5.05-4.95 (m, 2H), 3.18-3.12 (m, 1H), 3.05-2.95 (m, 1H), 2.06 (s, 3H), 1.93-1.84 (m, 2H), 1.57-1.47 (m, 1H), 1.30 (s, 9H), 1.27-1.19 (m, 2H), 1.18-1.10 (m, 1H).

Step B. rac-(1S,2S,5R)-1-acetamido-N-(tert-butyl)-2-((dimethylamino)methyl)-5-vinylcyclohexane-1-carboxamide

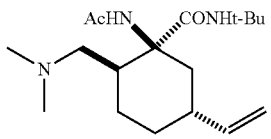

The title compound was prepared from rac-(1S,2R,5R)-1-acetamido-N-(tert-butyl)-2-formyl-5-vinylcyclohexane-1-carboxamide (80 mg, 0.27 mmol, 1 equiv.), dimethylamine hydrochloride (26.6 mg, 0.32 mmol, 1.2 equiv.), triethylamine (45 µL, 0.32 mmol, 1.2 equiv.), sodium triacetoxyborohydride (114 mg, 0.54 mmol, 2 equiv.), DCM (1.3 mL) using the same procedure as described in Example 17, step E. A single diastereoisomer was obtained as a colorless oil (60 mg, 58%). ESI+MS: m/z=324.1 (M+1)⁺, 346.2 (M+Na)⁺. ¹H NMR (700 MHz, chloroform-d) δ 7.47 (s, 1H), 7.27 (s, 1H), 5.72 (ddd, J=17.1, 10.5, 6.3 Hz, 1H), 5.04-4.81 (m, 2H), 3.03 (d, J=13.6 Hz, 1H), 2.85 (dd, J=14.6, 2.9 Hz, 1H), 2.34 (dd, J=14.6, 3.1 Hz, 1H), 2.28 (s, 6H), 2.01 (s, 3H), 1.98 (dt, J=13.1, 3.2 Hz, 1H), 1.83-1.72 (m, 2H), 1.68-1.62 (m, 1H), 1.33 (s, 9H), 1.26 (t, J=13.2 Hz, 1H), 1.22-1.07 (m, 2H).

Step C. rac-(1S,2S,5R)-1-acetamido-N-(tert-butyl)-2-((dimethylamino)methyl)-5-(2-(4,4,5,5-tetramethyl-1,3,2-dioxaborolan-2-yl)ethyl)cyclohexane-1-carboxamide

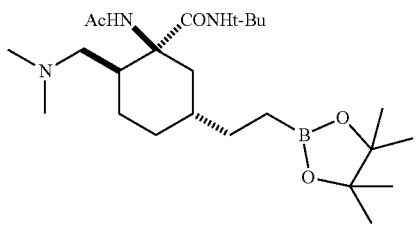

The title compound was prepared from rac-(1S,2S,5R)-1-acetamido-N-(tert-butyl)-2-((dimethylamino)methyl)-5-vinylcyclohexane-1-carboxamide (60 mg, 0.186 mmol, 1 equiv.), bis(1,5-cyclooctadiene)diiridium(I) dichloride (4 mg, 0.0055 mmol, 0.03 equiv.), dppe (5 mg, 0.011 mmol, 0.06 equiv.), 4,4,5,5-tetramethyl-1,3,2-dioxaborolane (56 µL, 0.37 mmol, 2 equiv.), DCM (1+1 mL) using the same procedure as described in Example 17, step F. A single diastereoisomer was obtained as a colorless oil (25 mg, 30%).

ESI+MS: m/z=452.1 (M+1)⁺, 370.1 (M-Pin)⁺. ¹H NMR (700 MHz, chloroform-d) δ 7.58 (s, 1H), 7.48 (s, 1H), 3.02-2-98 (m, 1H), 2.90-2.83 (m, 1H) 2.38-2.33 (m, 1H), 2.30 (s, 6H), 2.02 (s, 3H), 1.98-1.58 (m, 7H), 1.36 (s, 9H), 1.28 (s, 12H), 1.11-0.95 (m, 2H), 0.88 (m, 2H).

Step D. rac-(1S,2S,5R)-1-amino-5-(2-boronoethyl)-2-((dimethylamino)methyl)cyclohexane-1-carboxylic acid dihydrochloride The title compound was prepared from rac-(1S,2S,5R)-1-acetamido-N-(tert-butyl)-2-((dimethylamino)methyl)-5-(2-(4,4,5,5-tetramethyl-1,3,2-dioxaborolan-2-yl)ethyl)cyclohexane-1-carboxamide (25 mg, 0.055 mmol), 6 N HCl$_{aq}$ (10 mL) using the same procedure as described in Example 17, step G. A single diastereoisomer was obtained as a white solid (2.6 mg, 13%). ESI+MS: m/z=255.0 (M−18)⁺. ¹H NMR (700 MHz, deuterium oxide) δ 2.75 (dd, J=12.9, 9.3 Hz, 1H), 2.67-2.61 (m, 1H), 2.60 (s, 6H), 2.17-2.09 (m, 1H), 1.86-1.78 (m, 2H), 1.73 (d, J=13.3 Hz, 1H), 1.47-1.40 (m, 1H), 1.38-1.22 (m, 4H), 1.01-0.90 (m, 1H), 0.72 (t, J=8.1 Hz, 2H).

Example 20. 1-Amino-5-(2-boronoethyl)-2-(morpholinomethyl)cyclohexane-1-carboxylic acid dihydrochloride

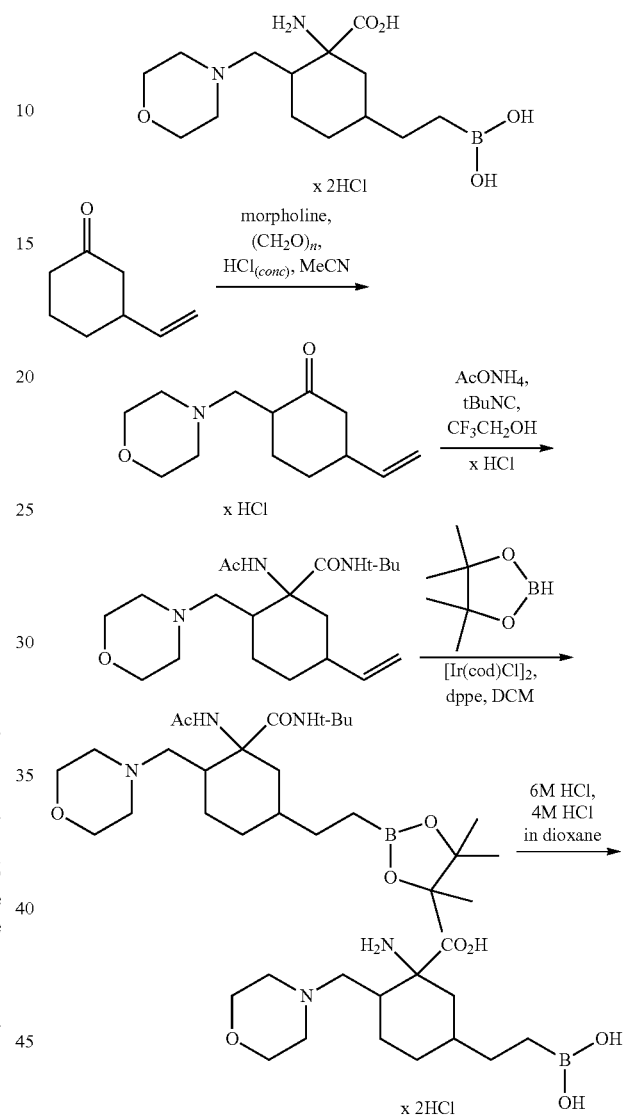

Step A. 2-(Morpholinomethyl)-5-vinylcyclohexan-1-one hydrochloride

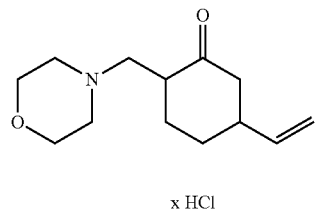 [SMILES: C=CC1CCC(CN2CCOCC2)C(=O)C1]

To the solution of 3-vinylcyclohexanone (1 g, 8.05 mmol) in acetonitrile (10 mL) was added paraformaldehyde (0.29 g, 9.68 mmol), morpholine (695 μl, 8.05 mmol) and HCl$_{(conc)}$ (0.77 mL, 9.26 mmol). The reaction mixture was stirred at 80° C. for 3 h and then at room temperature overnight. The solvent was evaporated under reduced pressure. The product was used in next step without further purification. Obtained 1.8 g as orange oil (mixture of diastereoisomers 4:1). Yield: 86%.

ESI+MS: m/z=224.1 (M+1)$^+$; ESI-MS: m/z=222.8 (M−1)$^−$.

The Major Diastereoisomer:
$^1$H NMR (700 MHz, DMSO-d$_6$) δ 5.85 (ddd, J=17.0, 10.4, 5.9 Hz, 1H), 5.08-4.96 (m, 2H), 3.96-3.84 (m, 6H), 3.57-3.49 (m, 1H), 3.44-3.31 (m, 1H), 3.18 (dq, J=11.1, 5.5 Hz, 1H), 3.11 (tt, J=14.4, 8.9 Hz, 1H), 3.05 (dt, J=9.6, 4.9 Hz, 1H), 3.04-2.95 (m, 1H), 2.87 (dt, J=13.2, 4.1 Hz, 1H), 2.43 (d, J=6.1 Hz, 1H), 2.37 (ddd, J=13.0, 6.0, 3.1 Hz, 1H), 1.86 (dd, J=11.4, 3.1 Hz, 1H), 1.65-1.55 (m, 1H), 1.43 (qd, J=13.1, 3.5 Hz, 1H).

Step B. 1-acetamido-N-(tert-butyl)-2-(morpholinomethyl)-5-vinylcyclohexane-1-carboxamide

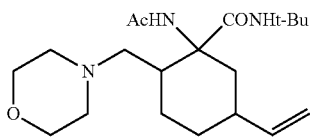

To a mixture of 2-(morpholinomethyl)-5-vinylcyclohexan-1-one hydrochloride (1.8 g, 8.07 mmol), ammonium acetate (2.4 g, 32.28 mmol), 2,2,2-trifluoroethanol (10 mL) tert-butyl isocyanide (1.81 mL, 16.1 mmol) was added dropwise and the mixture was stirred at room temperature overnight. Next, the reaction mixture was diluted with water and extracted with ethyl acetate three times. The combined organic layers were washed with 5% NaHCO$_3$. Dried over magnesium sulfate, filtered and concentrated under reduced pressure. The crude product was purified by flash chromatography on silica gel (dichloromethane/methanol 50:1 to 10:1). Yield: 1.65 g (56%); an orange solid (single diastereoisomer). ESI+MS: m/z=366.2 (M+1)$^+$; ESI-MS: m/z=364.2 (M−1)$^−$. $^1$H NMR (700 MHz, chloroform-d) δ 9.95 (s, 1H), 8.27 (s, 1H), 5.74 (ddd, J=17.1, 10.4, 6.5 Hz, 1H), 5.03-4.86 (m, 2H), 3.74 (d, J=12.6 Hz, 4H), 3.48 (dd, J=13.7, 10.1 Hz, 1H), 3.24 (dt, J=13.4, 2.3 Hz, 1H), 2.71 (s, 2H), 2.42 (s, 2H), 2.26-2.16 (m, 2H), 2.13-2.07 (m, 1H), 2.03 (s, 3H), 1.83 (dtd, J=12.6, 4.2, 2.3 Hz, 1H), 1.66-1.59 (m, 1H), 1.46-1.40 (m, 1H), 1.35 (s, 9H), 1.18 (qd, J=13.1, 5.3 Hz, 2H).

Step C. 1-Acetamido-N-(tert-butyl)-2-(morpholinomethyl)-5-(2-(4,4,5,5-tetramethyl-1,3,2-dioxaborolan-2-yl)ethyl)cyclohexane-1-carboxamide

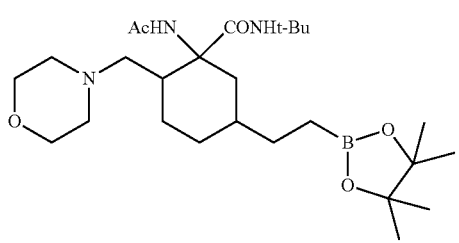

A mixture of dppe (32 mg, 0.08 mmol), bis(1,5-cyclooctadiene)diiridium(I) dichloride (27 mg, 0.04 mmol) was dissolved in degassed dichloromethane (10 mL) under argon. Separately a solution of 1-acetamido-N-(tert-butyl)-2-(morpholinomethyl)-5-vinylcyclohexane-1-carboxamide (490 mg, 1.34 mmol) in degassed dichloromethane (10 mL) was prepared and pinacolborane (291 μl, 2.01 mmol) was added dropwise. Then the thus-prepared solution was added dropwise to the above-mentioned mixture of bis(1,5-cyclooctadiene)diiridium(I) dichloride and dppe in dichloromethane. The reaction mixture was stirred at room temperature overnight. The crude product was purified by flash chromatography on silica gel (dichloromethane/acetone 40:1 to 5:1) to afford 95 mg (14%) of the desired product as a colorless oil (single diastereoisomer). ESI+MS: m/z=494.7 (M+1)$^+$. $^1$H NMR (700 MHz, chloroform-d) δ 9.94 (s, 1H), 8.29 (s, 1H), 3.77-3.66 (m, 4H), 3.47 (dd, J=13.7, 10.4 Hz, 1H), 3.22 (d, J=13.2 Hz, 1H), 2.68 (s, 2H), 2.38 (s, 2H), 2.18 (s, 3H), 2.17-2.07 (m, 2H), 1.99 (d, J=0.9 Hz, 1H), 1.82-1.77 (m, 1H), 1.63-1.56 (m, 1H), 1.39-1.35 (m, 1H), 1.32 (s, 9H), 1.31-1.25 (m, 1H), 1.24 (s, 12H), 1.23-1.21 (m, 1H), 1.01-0.92 (m, 2H), 0.82 (ddd, J=17.0, 10.9, 6.2 Hz, 1H), 0.72 (ddd, J=16.0, 11.0, 5.5 Hz, 1H).

Step D. 1-Amino-5-(2-boronoethyl)-2-(morpholinomethyl)cyclohexane-1-carboxylic acid dihydrochloride 1-Acetamido-N-(tert-butyl)-2-(morpholinomethyl)-5-(2-(4,4,5,5-tetramethyl-1,3,2-dioxaborolan-2-yl)ethyl)cyclohexane-1-carboxamide (95 mg, 0.19 mmol) was dissolved in 4 M HCl in dioxane (0.5 mL) and treated with 6 M HCl$_{(aq)}$ (2 mL). The reaction mixture was heated under reflux for 5 h. Then the mixture was concentrated under reduced pressure. The crude product was purified by preparative HPLC (0.1-10% of acetonitrile) to give 6.7 mg (9%) of a desired product as a colorless foam (single diastereoisomer). ESI+MS: m/z=315.1 (M+1)$^+$; 297.1 (M−18)$^+$. $^1$H NMR (700 MHz, deuterium oxide) δ 4.30 (s, 4H), 3.76-3.67 (m, 1H), 3.65 (s, 4H), 3.62-3.48 (m, 1H), 2.60-2.53 (m, 1H), 2.48 (t, J=11.4 Hz, 1H), 2.30-2.10 (m, 3H), 2.09-1.97 (m, 1H), 1.71-1.50 (m, 3H), 1.33-1.21 (m, 1H), 1.11-1.05 (m, 2H).

Example 21. 1-Amino-2-((benzyl(methyl)amino)methyl)-5-(2-boronoethyl)cyclohexane-1-carboxylic acid dihydrochloride

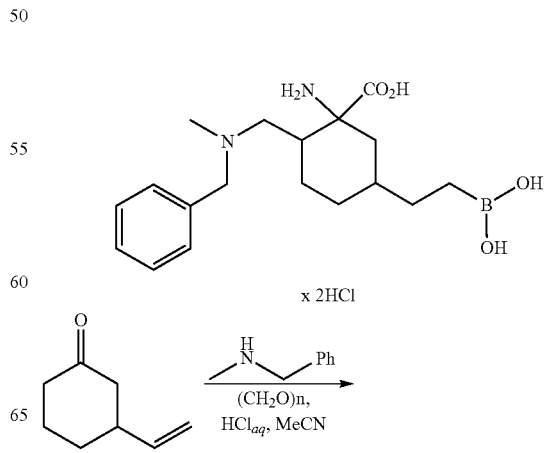

143

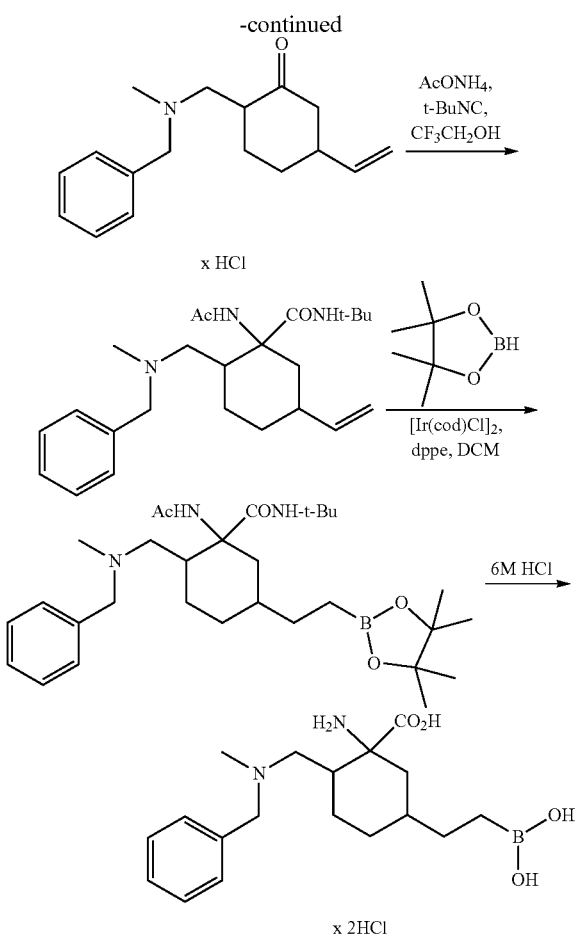

Step A. 2-((Benzyl(methyl)amino)methyl)-5-vinyl-cyclohexan-1-one hydrochloride

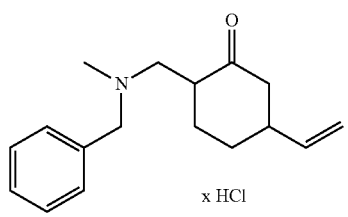 [SMILES: C=CC1CCC(CN(C)Cc2ccccc2)C(=O)C1]

The title compound was obtained in the same manner like in Example 20, step A using 3-vinylcyclohexanone (1 g; 8.05 mmol), paraformaldehyde (0.29 g; 9.68 mmol), N-benzylmethylamine (1.04 mL; 8.05 mmol), HCl$_{(conc)}$ (0.77 mL; 9.26 mmol) and MeCN (10 mL). The crude product was purified by flash chromatography on silica gel using DCM/MeOH (100:1 to 30:1). Yield: 1.5 g (63%); beige gum (dr=4:1).

The Major Diastereoisomer:
ESI+MS: m/z=258.2 (M+H)$^+$, 280.2 (M+Na)$^+$. $^1$H NMR (700 MHz, D$_2$O) δ 7.51-7.44 (m, 5H), 5.83 (ddd, J=16.7, 10.4, 6.1 Hz, 1H), 5.04-4.97 (m, 2H), 4.39-4.24 (m, 2H), 3.45 (dd, J=13.3, 9.7 Hz, 1H), 3.04-2.82 (m, 2H), 2.79 (s, 3H), 2.48-2.32 (m, 3H), 2.07-2.02 (m, 1H), 1.92-1.88 (m, 1H), 1.61-1.52 (m, 1H), 1.38 (qd, J=13.0, 3.5 Hz, 1H).

144

Step B. 1-Acetamido-2-((benzyl(methyl)amino)methyl)-N-(tert-butyl)-5-vinylcyclohexane-1-carboxamide

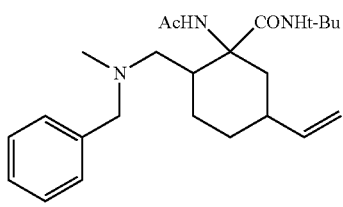

To a mixture of 2-((benzyl(methyl)amino)methyl)-5-vinylcyclohexan-1-one hydrochloride (1.39 g, 4.73 mmol), ammonium acetate (1.46 g, 18.9 mmol), 2,2,2-trifluoroethanol (4 mL) tert-butyl isocyanide (1.1 mL, 9.46 mmol) was added dropwise and the mixture was stirred at room temperature overnight. Next, the mixture was concentrated under reduced pressure and then treated with 5% aqueous NaHCO$_3$ (30 mL) and 1M NaOH (10 mL). The resulting mixture was washed with ethyl acetate (3×30 mL). The combined organic layers were washed with 5% NaHCO$_3$ (10 mL) and brine (20 mL), dried over MgSO$_4$, filtered and concentrated under reduced pressure. The crude product was purified by flash chromatography on silica gel using dichloromethane/methanol (20:1). The fractions contained desired product were combined, concentrated and purified again using DCM/acetone (20:1 to 1:1). Obtained 540 mg as orange oil. Yield: 28% (dr=2:1).

The Major Diastereoisomer:
ESI+MS: m/z=400.3 (M+H)$^+$, 422.2 (M+Na)$^+$. $^1$H NMR (700 MHz, CDCl$_3$) δ 7.35-7.30 (m, 3H), 7.30-7.25 (m, 4H), 5.76-5.71 (m, 1H), 5.01-4.96 (m, 1H), 4.94-4.89 (m, 1H), 3.64-3.58 (m, 2H), 3.39-3.30 (m, 1H), 3.27-3.19 (m, 1H), 2.23 (s, 3H), 2.13-2.02 (m, 2H), 1.87 (s, 3H), 1.84-1.79 (m, 1H), 1.64-1.52 (m, 3H), 1.45-1.40 (m, 1H), 1.31 (s, 9H).

Step C. 1-Acetamido-2-((benzyl(methyl)amino)methyl)-N-(tert-butyl)-5-(2-(4,4,5,5-tetramethyl-1,3,2-dioxaborolan-2-yl)ethyl)cyclohexane-1-carboxamide

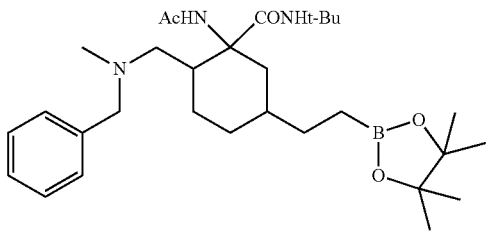

The title compound was prepared from 1-acetamido-2-((benzyl(methyl)amino)methyl)-N-(tert-butyl)-5-vinylcyclohexane-1-carboxamide hydrochloride (dr=2:1, 620 mg, 1.42 mmol), using the procedure described in the preparation of Example 20, step C. The crude product was purified by flash chromatography on silica gel (DCM/acetone 20:1 to 0:1). Yield: 320 mg (43%, dr=3:1); brown oil. The major diastereoisomer: ESI+MS: m/z=528.2 (M+H)$^+$. $^1$H NMR (700 MHz, CDCl$_3$) δ 9.94 (bs, 1H), 8.23 (bs, 1H), 7.34-7.31 (m, 2H), 7.29-7.28 (m, 1H), 7.27-7.25 (m, 2H), 5.73 (ddd, J=17.1, 10.4, 6.5 Hz, 1H), 4.99 (dt, J=17.3, 1.5 Hz, 1H), 4.94-4.90 (m, 1H), 3.64-3.59 (m, 2H), 3.39-3.34 (m, 1H), 3.26-3.22 (m, 1H), 2.23 (s, 3H), 2.20-2.16 (m, 2H), 1.87 (s, 3H), 1.84-1.80 (m, 1H), 1.65-1.60 (m, 1H), 1.44-1.40 (m, 1H), 1.36-1.33 (m, 5H), 1.31 (s, 9H), 1.26 (s, 12H), 1.19-1.15 (m, 2H).

Step D. 1-Amino-2-((benzyl(methyl)amino)methyl)-5-(2-boronoethyl)cyclohexane-1-carboxylic acid dihydrochloride

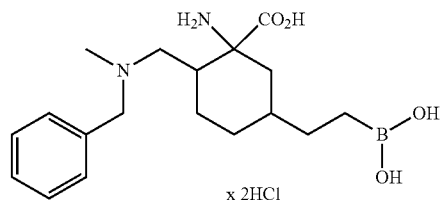 [SMILES: CN(Cc1ccccc1)CC1CCC(CCB(O)O)CC1(N)C(=O)O]

x 2HCl

The title compound was prepared from 1-acetamido-2-((benzyl(methyl)amino)methyl)-N-(tert-butyl)-5-(2-(4,4,5,5-tetramethyl-1,3,2-dioxaborolan-2-yl)ethyl)cyclohexane-1-carboxamide (125 mg, 0.33 mmol; dr=3:1), using the procedure described in the preparation of Example 20, step D. The crude product was purified by preparative HPLC (1-20% MeCN in water). Yield: 15 mg (15%; dr=3:1); white solid. The major diastereoisomer: ESI+MS: m/z=214.0 (M−18+H)⁺, 232.0 (M+H)⁺. ¹H NMR (700 MHz, D₂O) δ 7.51-7.48 (m, 3H), 7.47-7.45 (m, 2H), 4.41 (bd, J=12.4 Hz, 1H), 4.32 (bd, J=12.2 Hz, 1H), 3.24-3.18 (m, 2H), 2.88 (s, 3H), 2.27-2.18 (m, 2H), 2.04-1.88 (m, 2H), 1.80-1.60 (m, 3H), 1.32-1.22 (m, 3H), 0.72-0.67 (m, 2H).

Example 22. rac-(1R,2S,5R)-1-Amino-5-(2-boronoethyl)-2-(pyrrolidin-1-ylmethyl)-cyclohexane-1-carboxylic acid dihydrochloride

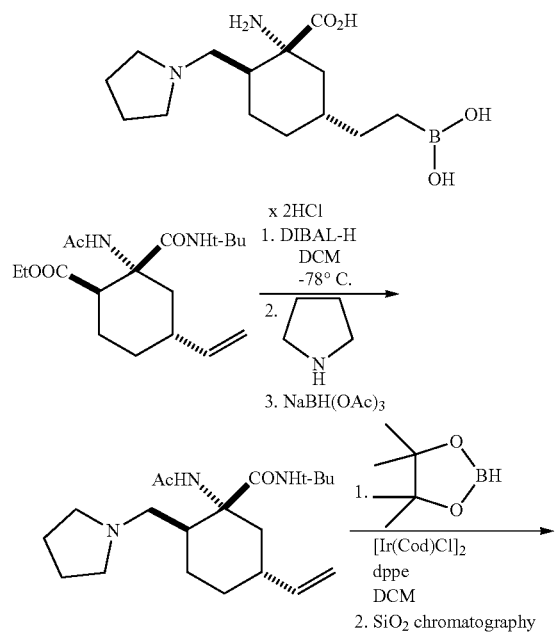

Step A. rac-(1R,2S,5R)-1-Acetamido-N-(tert-butyl)-2-(pyrrolidin-1-ylmethyl)-5-vinylcyclohexane-1-carboxamide

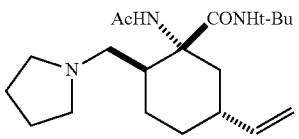

To a solution of ethyl rac-(1R,2R,4R)-2-acetamido-2-(tert-butylcarbamoyl)-4-vinylcyclohexane-1-carboxylate (Example 17, step C) (0.5 g, 1.48 mmol, 1 equiv.) in dry dichloromethane (10 mL) was added dropwise a solution of DIBAL-H (1M in DCM, 4.58 mL, 4.58 mmol, 3.1 equiv.) at −78° C. under argon. The reaction mixture was stirred at −78° C. and monitored by TLC (hexane:AcOEt 1:1). After 1 h the reaction mixture was quenched with glacial acetic acid (0.42 mL, 7.39 mmol, 5 equiv.) and was stirred at −78° C. for 10 min. Then pyrrolidine (0.24 mL, 2.95 mmol, 2 equiv.) was added dropwise and cooling bath was removed. After 15 min triacetoxyborohydride (1.25 g, 5.91 mmol, 4 equiv.) was added portionwise and the resulting mixture was allowed to warm to room temperature and was stirred for 1 h. After this time TLC test (DCM MEOH 9:1) revealed a full conversion of the in situ generated aldehyde. The mixture was diluted with dichloromethane and organic layer was washed with 5% NaHCO₃ (20 mL) and brine, dried over MgSO₄, filtered and concentrated in vacuo. The residue was purified by silica gel flash chromatography (gradient elution, DCM:MeOH 100:1 to 6:1) to give corresponding product as separable diastereoisomers (overall yield 311 mg, 60%). ESI+MS: m/z=350.2 (M+1)⁺. The desired rac-(1R,2S,5R)-1-acetamido-N-(tert-butyl)-2-(pyrrolidin-1-ylmethyl)-5-vinylcyclohexane-1-carboxamide was isolated as a colorless oil (255 mg, 49%). ¹H NMR (700 MHz, chloroform-d) δ 5.76-5.67 (m, 1H), 5.02-4.86 (m, 2H), 3.74-3.66 (m, 1H), 3.23 (d, J=13.4 Hz, 1H), 2.83-2.67 (m, 2H), 2.49-2.41 (m, 2H), 2.28-2.02 (m, 3H), 1.89 (s, 3H), 1.83-1.77 (m, 4H), 1.57-1.51 (m, 3H), 1.44-1.39 (m, 1H), 1.34 (s, 9H), 1.28-1.23 (m, 1H).

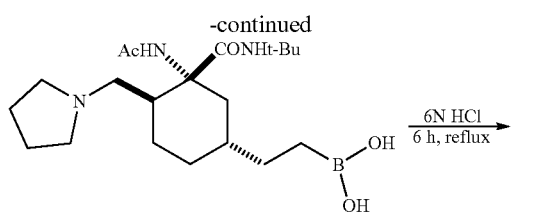

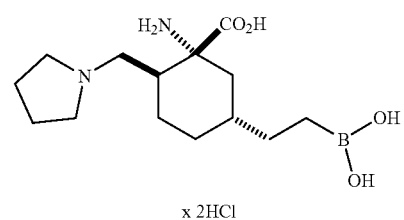

Step B. rac-(2-((1R,3R,4S)-3-acetamido-3-(tert-butylcarbamoyl)-4-(pyrrolidin-1-ylmethyl)cyclohexyl)ethyl)boronic acid

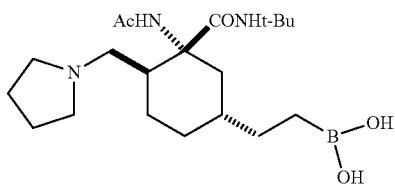

A mixture of dppe (13.67 mg, 0.0343 mmol, 0.06 equiv.) and bis(1,5-cyclooctadiene)diiridium(I) dichloride (11.53 mg, 0.0172 mmol, 0.03 equiv.) in dichloromethane (5 mL) was flushed with argon. Then the solution of rac-(1R,2S,5R)-1-acetamido-N-(tert-butyl)-2-(pyrrolidin-1-ylmethyl)-5-vinylcyclohexane-1-carboxamide (200 mg, 0.57 mmol, 1 equiv.) and 4,4,5,5-tetramethyl-1,3,2-dioxaborolane (205 μl, 1.32 mmol, 2.3 equiv.) in DCM (5 mL) was added dropwise. The reaction mixture was stirred at room temperature overnight. After this time, the reaction mixture was diluted with DCM (50 mL) and washed 5% NaHCO$_3$ (30 mL). The organic layer was dried over MgSO$_4$, filtered and concentrated in vacuo. The crude product was purified by column chromatography, on silica gel (CH$_2$Cl$_2$/MeOH 30:1 to MeOH) to give the desired product (126 mg, 56%) as a colorless oil. ESI+MS: m/z=396.25 (M+1)$^+$. $^1$H NMR (700 MHz, chloroform-d) δ 3.72-3.68 (m, 1H), 3.26-3.21 (m, 1H), 2.74-2.66 (m, 2H), 2.47-2.40 (m, 2H), 2.15-2.09 (m, 2H), 1.89 (s, 3H), 1.81-1.75 (m, 5H), 1.61-1.51 (m, 7H), 1.33 (s, 9H), 1.01-0.91 (m, 2H).

Step C. rac-(1R,2S,5R)-1-Amino-5-(2-boronoethyl)-2-(pyrrolidin-1-ylmethyl)cyclohexane-1-carboxylic acid dihydrochloride A mixture of rac-(2-((1R,3R,4S)-3-acetamido-3-(tert-butylcarbamoyl)-4-(pyrrolidin-1-ylmethyl)cyclohexyl)ethyl) boronic acid (126 mg, 0.264 mmol) and 6 N HCl$_{aq}$ (15 mL) was heated under reflux for 6 h. The reaction mixture was concentrated under reduced pressure and the residue was purified by ion exchange chromatography on DOWEX® and next by preparative HPLC (0.1-10% MeCN in water) to give (after acidification and subsequent lyophilization) (1R,2S,5R)-1-amino-5-(2-boronoethyl)-2-(pyrrolidin-1-ylmethyl)cyclohexane-1-carboxylic acid dihydrochloride (50 mg, 51%) as a white solid. ESI+MS: m/z=299.2 (M+1)$^+$. $^1$H NMR (700 MHz, deuterium oxide) δ 3.72-3.60 (m, 2H), 3.40-3.20 (m, 2H), 3.08 (dt, J=11.7, 8.1 Hz, 1H), 2.98 (dt, J=11.3, 8.4 Hz, 1H), 2.24-2.16 (m, 1H), 2.15-2.06 (m, 2H), 2.06-2.00 (m, 1H), 2.00-1.93 (m, 2H), 1.94-1.80 (m, 2H), 1.79 (dd, J=12.8, 3.3 Hz, 1H), 1.75-1.70 (m, 1H), 1.35-1.25 (m, 2H), 1.21 (t, J=12.7 Hz, 1H), 0.92 (qd, J=13.3, 12.9, 3.5 Hz, 1H), 0.76-0.69 (m, 2H).

Example 23. (1R,2S,5R)-1-Amino-5-(2-boronoethyl)-2-(pyrrolidin-1-ylmethyl)-cyclohexane-1-carboxylic acid dihydrochloride (Enantiomerically Enriched)

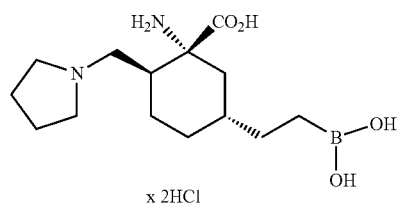 [SMILES: N[C@]1(C(=O)O)C[C@H](CCB(O)O)CC[C@H]1CN1CCCC1]

Step A. Ethyl (+)-(4R)-4-ethenyl-2-hydroxycyclohex-1-ene-1-carboxylate (Enantiomerically Enriched)

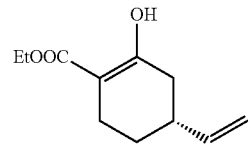

To a 100 mL round-bottomed flask were added [Rh(cod)Cl]$_2$ (178 mg, 0.36 mmol), (R)-BINAP (247 mg, 0.396 mmol), and potassium vinyl trifluoroborate (3.21 g, 0.024 mol). The flask was flushed with argon several times and degassed 1,4-dioxane (25 mL), triethylamine (5 mL, 0.036 mol), and water (12.5 mL) were added. After stirring the resulting mixture for 10 min at room temperature, ethyl 2-oxocyclohex-3-ene-1-carboxylate (Example 17, step A) (2.0 g, 0.012 mol) was added. The reaction mixture was stirred at room temperature for 96 h. The layers were separated. The aqueous layer was washed with ethyl acetate (2×40 mL). The combined organic layers were washed with 0.5 M aqueous HCl (20 mL) and brine (30 mL), dried over MgSO$_4$, filtered and concentrated under reduced pressure. The crude product was purified by silica gel chromatography using hexane/AcOEt (100:1 to 50:1) to afford 0.60 g (25%) of the desired product as a yellow oil. ESI+MS: m/z=350.2 (M+1). [α]$_D$=+32.63 (c=0.8 in CHCl$_3$). $^1$H NMR (700 MHz, chloroform-d) δ 5.91-5.70 (m, 1H), 5.16-4.90 (m, 2H), 4.22 (qd, J=7.1, 0.5 Hz, 2H), 2.45-2.30 (m, 3H), 2.24-2.12 (m, 2H), 1.89-1.74 (m, 1H), 1.45-1.18 (m, 5H).

Step B. Ethyl (1R,2R,4R)-2-acetamido-2-(tert-butylcarbamoyl)-4-vinylcyclohexane-1-carboxylate (88% ee.)

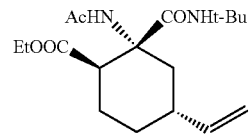

The title compound was obtained in the same manner like in Example 17, step C using enantiomerically enriched ethyl (+)-(4R)-4-ethenyl-2-hydroxycyclohex-1-ene-1-carboxylate (0.5 g; 2.55 mmol), ammonium acetate (0.79 g, 10.2 mmol), 2,2,2-trifluoroethanol (2 mL) and tert-butyl isocyanide (0.58 mL; 5.1 mmol). The crude product was purified by flash chromatography on silica gel using hexane/AcOEt (30:1 to 5:1) to give 300 mg (35%) of the desired product as a white solid. ESI+MS: m/z=339.1 (M+1)$^+$, 361.1 (M+Na)$^+$. $^1$H NMR (700 MHz, chloroform-d) δ 8.10 (s, 1H), 7.57 (s, 1H), 5.72 (ddd, J=17.0, 10.4, 6.4 Hz, 1H), 5.03-4.91 (m, 2H), 4.20 (ddq, J=59.5, 10.8, 7.1 Hz, 2H), 3.29 (d, J=13.8 Hz, 1H), 2.28 (dd, J=12.4, 4.4 Hz, 1H), 2.14 (dq, J=11.6, 4.2, 3.6 Hz, 1H), 2.11-2.02 (m, 2H), 1.99 (s, 3H), 1.85-1.80 (m, 1H), 1.33-1.30 (m, 13H), 1.10 (qd, J=13.2, 4.4 Hz, 1H).

Step C. (1R,2S,5R)-1-Acetamido-N-(tert-butyl)-2-(pyrrolidin-1-ylmethyl)-5-vinylcyclohexane-1-carboxamide (enantiomerically enriched)

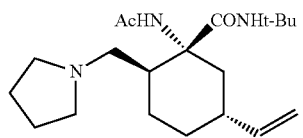

The title compound was obtained in the same manner like in Example 22, step A using ethyl (1R,2R,4R)-2-acetamido-2-(tert-butylcarbamoyl)-4-vinylcyclohexane-1-carboxylate (200 mg; 0.59 mmol), DIBAL-H (1M in DCM, 1.83 mL, 1.83 mmol), glacial acetic acid (169 μL, 2.95 mmol), pyrrolidine (98 μL, 1.18 mmol, 2 equiv.), triacetoxyborohydride (0.50 g, 2.36 mmol), DCM (3 mL). Work-up: the reaction mixture was diluted with DCM (50 mL) and washed with 1M NaOH (2×5 mL) and brine (10 mL). The crude product was purified by flash chromatography on silica gel using DCM/MeOH (100:1 to 10:1) to give 147 mg (71%) of the desired product as a colorless oil. $^1$H NMR (700 MHz, chloroform-d) δ 5.76-5.67 (m, 1H), 5.02-4.86 (m, 2H), 3.74-3.66 (m, 1H), 3.23 (d, J=13.4 Hz, 1H), 2.83-2.67 (m, 2H), 2.49-2.41 (m, 2H), 2.28-2.02 (m, 3H), 1.89 (s, 3H), 1.83-1.77 (m, 4H), 1.57-1.51 (m, 3H), 1.44-1.39 (m, 1H), 1.34 (s, 9H), 1.28-1.23 (m, 1H).

Step D. (1R,2S,5R)-1-Acetamido-N-(tert-butyl)-2-(pyrrolidin-1-ylmethyl)-5-(2-(4,4,5,5-tetramethyl-1,3,2-dioxaborolan-2-yl)ethyl)cyclohexane-1-carboxamide (Enantiomerically Enriched)

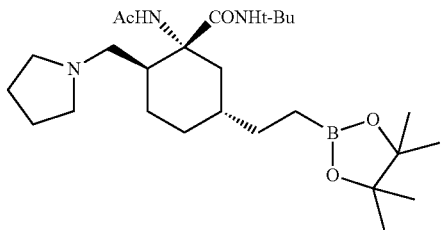

The title compound was obtained in the same manner like in Example 22, step B, using (1R,2S,5R)-1-acetamido-N-(tert-butyl)-2-(pyrrolidin-1-ylmethyl)-5-vinylcyclohexane-1-carboxamide (114 mg; 0.33 mmol), dppe (8 mg, 0.02 mmol) and bis(1,5-cyclooctadiene)diiridium(I) dichloride (6.7 mg, 0.01 mmol), a 4,4,5,5-tetramethyl-1,3,2-dioxaboro-lane (71 μl, 0.49 mmol), DCM (1.5 mL). The crude product was purified by flash chromatography on silica gel using DCM/acetone (30:1 to 1:1) to give 93 mg (59%) of the desired product as a pale yellow oil. ESI+MS: m/z=478.4 (M+1)$^+$. $^1$H NMR (700 MHz, chloroform-d) δ 3.72-3.68 (m, 1H), 3.26-3.21 (m, 1H), 2.74-2.66 (m, 2H), 2.47-2.40 (m, 2H), 2.15-2.09 (m, 2H), 1.89 (s, 3H), 1.81-1.75 (m, 5H), 1.61-1.51 (m, 7H), 1.33 (s, 9H), 1.27 (s, 12H), 1.01-0.91 (m, 2H).

Step E. (1R,2S,5R)-1-amino-5-(2-boronoethyl)-2-(pyrrolidin-1-ylmethyl)cyclohexane-1-carboxylic acid dihydrochloride (Enantiomerically Enriched)

The title compound was obtained in the same manner like in Example 22, step C, using (1R,2S,5R)-1-acetamido-N-(tert-butyl)-2-(pyrrolidin-1-ylmethyl)-5-(2-(4,4,5,5-tetramethyl-1,3,2-dioxaborolan-2-yl)ethyl)cyclohexane-1-carbox-amide (85 mg; 0.178 mmol), 6 N HCl$_{aq}$(5 mL). The crude product was purified by ion exchange chromatography on DOWEX® and next by preparative HPLC (0.1-1% MeCN in water, followed by acidification with 6M HCl and subsequent lyophilization) to give 20 mg of (1R,2S,5R)-1-amino-5-(2-boronoethyl)-2-(pyrrolidin-1-ylmethyl)cyclohexane-1-carboxylic acid dihydrochloride (27%) as a white solid. ESI+MS: m/z=299.2 (M+1)$^+$. [α]$_D$=−0.5 (c=0.238 in H$_2$O). $^1$H NMR (700 MHz, deuterium oxide) δ 3.72-3.60 (m, 2H), 3.40-3.20 (m, 2H), 3.08 (dt, J=11.7, 8.1 Hz, 1H), 2.98 (dt, J=11.3, 8.4 Hz, 1H), 2.24-2.16 (m, 1H), 2.15-2.06 (m, 2H), 2.06-2.00 (m, 1H), 2.00-1.93 (m, 2H), 1.94-1.80 (m, 2H), 1.79 (dd, J=12.8, 3.3 Hz, 1H), 1.75-1.70 (m, 1H), 1.35-1.25 (m, 2H), 1.21 (t, J=12.7 Hz, 1H), 0.92 (qd, J=13.3, 12.9, 3.5 Hz, 1H), 0.76-0.69 (m, 2H).

Example 24. 1-Amino-2-(aminomethyl)-5-(2-boronoethyl)cyclohexane-1-carboxylic acid

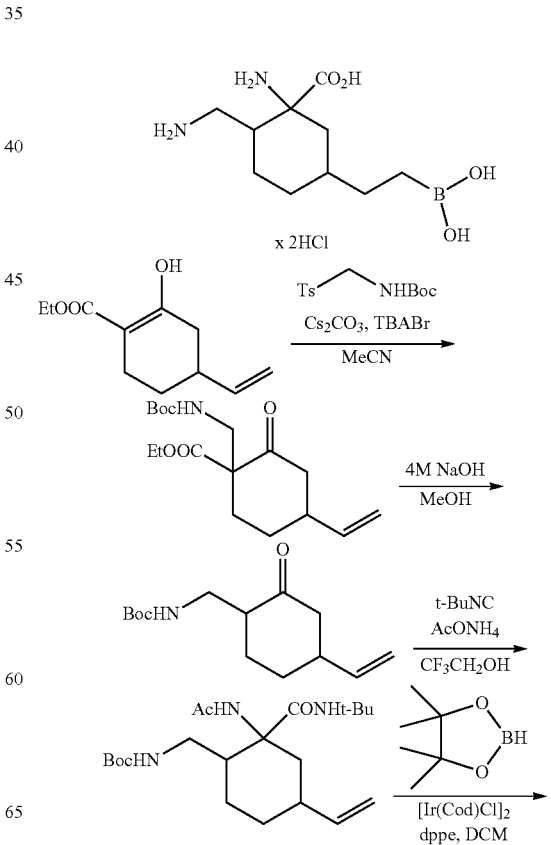

-continued

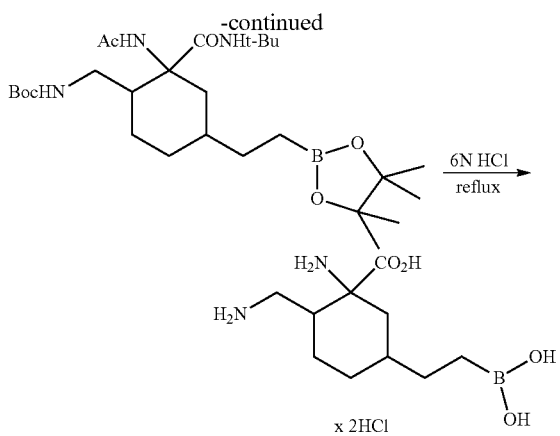

Step A. Ethyl 1-(((tert-butoxycarbonyl)amino)methyl)-2-oxo-4-vinylcyclohexane-1-carboxylate

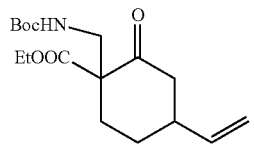 [SMILES: C=CC1CCC(CNC(=O)OC(C)(C)C)(C(=O)OCC)C(=O)C1]

To the mixture of 4-ethenyl-2-hydroxycyclohex-1-ene-1-carboxylate (1.0 g, 5.1 mmol), N-Boc-(tosylmethyl)amine (1.45 g, 0.51 mmol) and Cs$_2$CO$_3$ (5.31 g, 16.3 mmol) in acetonitrile was added TBABr (0.16 g, 0.51 mmol). The reaction mixture was stirred at room temperature overnight. After this time, the reaction was partitioned between water (25 mL) and AcOEt (30 mL). The layers were separated. The aqueous layer was washed with ethyl acetate (3×50 mL). The combined organic layers were washed with water (2×20 mL), brine (1×20 mL), dried over MgSO$_4$ and concentrated in vacuo. The desired product was obtained as a brown oil (1.65 g, 99%). ESI+MS: m/z=348.1 (M+Na)$^+$, 226.1 (M-Boc+1)$^+$. $^1$H NMR (700 MHz, chloroform-d) δ 5.80-5.72 (m, 1H), 5.11-5.01 (m, 2H), 4.23 (q, J=7.1 Hz, 2H), 3.57 (dd, J=14.0, 6.5 Hz, 1H), 3.50 (dd, J=13.9, 6.8 Hz, 1H), 2.68-2.55 (m, 1H), 2.51-2.45 (m, 1H), 1.94-1.79 (m, 2H), 1.55 (s, 1H), 1.50-1.44 (m, 1H), 1.42 (s, 9H), 1.31-1.25 (m, 4H).

Step B. tert-Butyl ((2-oxo-4-vinylcyclohexyl)methyl)carbamate

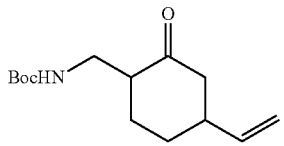 [SMILES: C=CC1CCC(CNC(=O)OC(C)(C)C)C(=O)C1]

The mixture of 1-(((tert-butoxycarbonyl)amino)methyl)-2-oxo-4-vinylcyclohexane-1-carboxylate (0.59 g, 1.90 mmol), methanol (10 mL) and 4M aqueous NaOH solution (2 mL) was stirred at room temperature overnight. After this time methanol was evaporated and the residue was washed with ethyl acetate (3×50 mL). The combined organic layers were dried over MgSO$_4$ and concentrated in vacuo. The crude product was purified by flash chromatography on silica gel (gradient elution:hexane/AcOEt 10:1 7:1) to give product as a mixture of diastereoisomers (overall yield 452 mg, 94%). ESI+MS: m/z=276.12 (M+Na)$^+$, 154.0 (M-Boc+1)$^+$. The major diastereoisomer was isolated as a colorless oil (357 mg, 74%) and was used in the next step. $^1$H NMR (700 MHz, chloroform-d) 5.80 (ddd, J=17.0, 10.4, 6.3 Hz, 1H), 5.07-5.00 (m, 2H), 3.34-3.27 (m, 1H), 2.68-2.55 (m, 1H), 3.20-3.15 (m, 1H), 2.55-2.48 (m, 1H), 2.47-2.41 (m, 1H), 2.25-2.17 (m, 1H), 2.12 (ddd, J=12.9, 5.9, 3.2 Hz, 1H), 2.00-1.94 (m, 1H), 1.63-1.57 (m, 1H), 1.45-1.43 (m, 10H).

Step C. tert-Butyl ((2-acetamido-2-(tert-butylcarbamoyl)-4-vinylcyclohexyl)methyl)carbamate

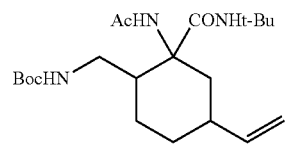

To the stirred solution of tert-butyl ((2-oxo-4-vinylcyclohexyl)methyl)carbamate (357 mg, 1.41 mmol, 1 equiv.) and ammonium acetate (434 mg, 5.64 mmol, 4 equiv.) in 2,2,2-trifluoroethanol (1 mL) tert-butyl isocyanide (317 μL, 2.82 mmol, 2 equiv.) was added dropwise via syringe and the resulting mixture was stirred at room temperature for 24 hours. After this time, the reaction mixture was diluted with water (20 mL) and extracted to ethyl acetate (3×30 mL). The organic layer was dried over MgSO$_4$, filtered and evaporated under reduced pressure. The residue was purified by silica gel flash chromatography (gradient elution, hexane/AcOEt 10:1 to 1:2) to give corresponding product as a mixture of diastereoisomers (overall yield: 555 mg, 99%). ESI+MS: m/z=418.1 (M+Na)$^+$, 296.1 (M-Boc+1)$^+$. The major diastereoisomer was isolated as a colorless oil (300 mg, 54%) and was used in the next step. $^1$H NMR (700 MHz, chloroform-d) δ 5.73 (ddd, J=17.1, 10.4, 6.5 Hz, 1H), 5.03-4.91 (m, 2H), 3.22-3.15 (m, 1H), 2.99-2.91 (m, 1H), 2.18-2.03 (m, 5H), 1.56-1.54 (m, 1H) 1.47 (s, 9H), 1.33 (s, 9H), 1.31-1.26 (m, 3H), 1.18-1.07 (m, 2H).

Step D. tert-Butyl ((2-acetamido-2-(tert-butylcarbamoyl)-4-(2-(4,4,5,5-tetramethyl-1,3,2-dioxaborolan-2-yl)ethyl)cyclohexyl)methyl)carbamate

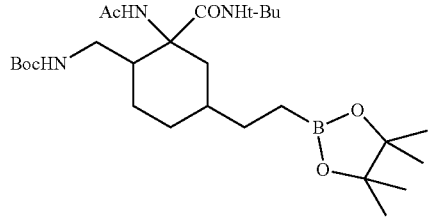

A mixture of dppe (18.1 mg, 0.045 mmol) and bis(1,5-cyclooctadiene)diiridium(I) dichloride (15.3 mg, 0.023 mmol) in dichloromethane (5 mL) was flushed with argon. Then the solution of tert-butyl ((2-acetamido-2-(tert-butylcarbamoyl)-4-vinylcyclohexyl)methyl)carbamate (300 mg, 0.758 mmol) and 4,4,5,5-tetramethyl-1,3,2-dioxaborolane (253 µl, 1.744 mmol) in DCM (5 mL) (flushed with argon) was added dropwise. The reaction mixture was stirred at room temperature overnight. After this time, the reaction mixture was concentrated in vacuo. The crude product was purified by column chromatography, on silica gel (CH$_2$Cl$_2$/MeOH 100:1) to give the desired product (390 mg, 98%) as a colorless oil. ESI+MS: m/z=546.2 (M+Na)$^+$, 424.2 (M-Boc+1)$^+$. $^1$H NMR (700 MHz, chloroform-d) δ 3.46 (dd, J=15.5, 6.5 Hz, 1H), 3.16 (d, J=13.2 Hz, 1H), 2.98-2.91 (m, 1H), 2.07 (s, 3H), 2.06-2.00 (m, 1H), 1.81-1.74 (m, 2H), 1.59-1.57 (m, 1H), 1.46 (s, 9H), 1.35-1.32 (m, 1H), 1.31 (s, 9H), 1.30-1.26 (m, 2H), 1.24 (s, 12H), 0.95 (t, J=12.9 Hz, 1H), 0.90-0.79 (m, 2H), 0.76-0.70 (m, 1H).

Step E. 1-Amino-2-(aminomethyl)-5-(2-borono-ethyl)cyclohexane-1-carboxylic acid dihydrochloride

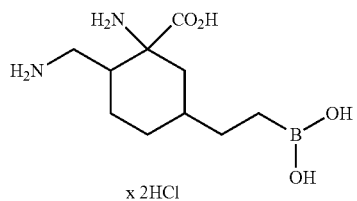 [SMILES: NCC1CCC(CCB(O)O)CC1(N)C(=O)O]

A mixture of tert-butyl ((2-acetamido-2-(tert-butylcarbamoyl)-4-(2-(4,4,5,5-tetramethyl-1,3,2-dioxaborolan-2-yl)ethyl)cyclohexyl)methyl)carbamate (100 mg, 0.19 mmol) and 6 N HCl$_{aq}$(5 mL) was heated under reflux for 6 h. The reaction mixture was concentrated under reduced pressure and the residue was purified by ion exchange chromatography on DOWEX® and next by preparative HPLC (0.1-1% MeCN in water) to give the desired product (20 mg, 33%) as a white solid. ESI+MS: m/z=245.15 (M+1)$^+$. $^1$H NMR (700 MHz, deuterium oxide) δ 3.29 (dd, J=13.1, 3.0 Hz, 1H), 2.90 (dd, J=13.1, 10.7 Hz, 1H), 2.25 (d, J=11.8 Hz, 1H), 2.03-1.99 (m, 1H), 1.94-1.87 (m, 2H), 1.75-1.63 (m, 2H), 1.34-1.25 (m, 3H), 0.97-0.88 (m, 1H), 0.76-0.70 (m, 2H).

Example 25. 1-Amino-5-(2-boronoethyl)-2-(2-(pyrrolidin-1-yl)ethyl)cyclohexane-1-carboxylic acid dihydrochloride

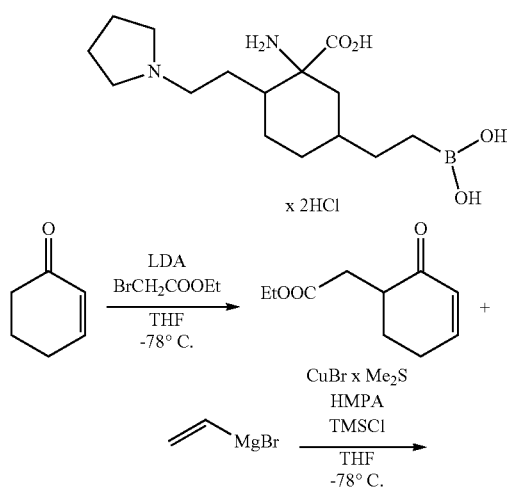

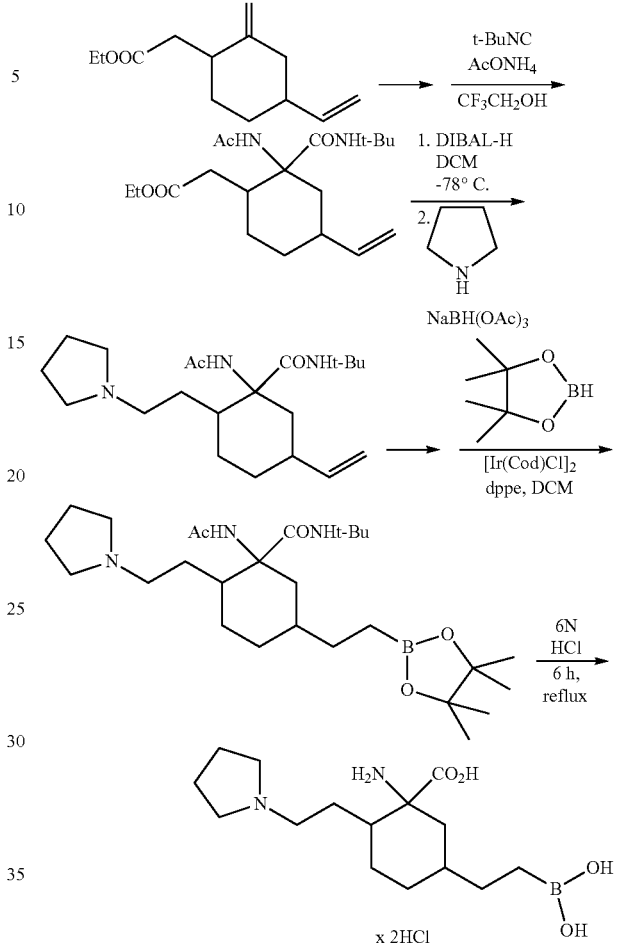

Step A. Ethyl 2-(2-oxocyclohex-3-en-1-yl)acetate

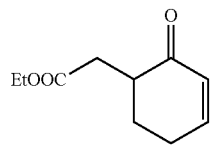 [SMILES: CCOC(=O)CC1CCC=CC1=O]

The title compound was prepared starting from 2-cyclohexen-1-one using the literature method (K. F. Podraza, R. L. Bassfield, *J. Org. Chem.*, 54, 1989, 5919-5922). To a solution of LDA 2M in THF (28.4 mL, 56.8 mmol, 1.1 equiv.) at −78° C. was added dropwise a solution of 2-cyclohexen-1-one (4.93 mL, 51.0 mmol, 1 equiv.) in THF (10 mL) under argon. The solution was stirred for 15 min, and then a solution of ethyl bromoacetate (6.81 mL, 61.2 mmol, 1.2 equiv.) in THF (10 mL) was added dropwise and the resulting reaction mixture was stirred for 2 h at −78° C. Then, the mixture was diluted with diethyl ether, and quenched with a saturated solution of NH$_4$Cl. The mixture was allowed to warm to approximately 0° C., and the aqueous layer was extracted with ether. The combined organic extracts were washed with a saturated solution of NH$_4$Cl and brine, dried over MgSO$_4$, filtered and concentrated under reduced pressure. The crude product was purified by flash chromatography on silica gel (gradient elution, hexane/AcOEt 10:1 to 5:1) to give the desired product (5.8 g, 62%) as a yellow liquid. $^1$H NMR (700 MHz, chloroform-d) δ 6.93 (dddd, J=9.7, 5.5, 2.4, 1.4 Hz, 1H), 5.99 (ddd, J=10.0, 2.9, 1.1 Hz, 1H), 4.18-4.04 (m, 2H), 2.90-2.77 (m, 2H), 2.51-2.35 (m, 2H), 2.27-2.19 (m, 1H), 2.10 (dtdd, J=13.1, 4.7, 2.5, 1.5 Hz, 1H), 1.79 (tdd, J=13.3, 11.3, 5.1 Hz, 1H), 1.23 (dt, J=8.9, 7.2 Hz, 3H).

Step B. Ethyl 2-(2-oxo-4-vinylcyclohexyl)acetate

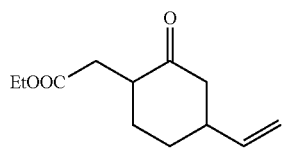

A solution of vinylmagnesium bromide (1M in THF) (33 mL, 33 mmol, 2 equiv.) and HMPA (13 mL) were added dropwise to a suspension of CuBr×Me$_2$S (0.51 g, 2.47 mmol, 0.15 equiv.) in dry THF (60 mL) at −78° C. over 15 min under argon. After stirring at −78° C. for 15 min, a solution of ethyl 2-(2-oxocyclohex-3-en-1-yl)acetate (3.0 g, 16.5 mmol, 1.0 equiv.) and TMSCl (10.5 mL, 82.5 mmol, 5 equiv.) in dry THF (30 mL) was added dropwise over 30 min. The reaction mixture was stirred at −78° C. for 2 h. Then the mixture was quenched with saturated NH$_4$Cl (100 mL) and extracted with AcOEt (3×100 mL). The organic layers were dried over MgSO$_4$, filtered and concentrated. The crude product was purified by flash chromatography on silica gel (hexane/AcOEt 10:1) to give the desired product (overall yield 2.06 g, 59%) as a mixture of diastereoisomers. The major diastereoisomer was isolated as a colorless liquid and was used in the next step. Yield: 1.45 g. $^1$H NMR (700 MHz, chloroform-d) δ 5.76 (ddd, J=17.0, 10.4, 6.3 Hz, 1H), 5.02-4.92 (m, 2H), 4.09 (qd, J=7.1, 4.4 Hz, 2H), 2.85-2.68 (m, 2H), 2.48-2.34 (m, 2H), 2.22 (td, J=12.8, 1.0 Hz, 1H), 2.17-2.08 (m, 2H), 1.91 (ddd, J=12.4, 5.9, 2.9 Hz, 1H), 1.62-1.52 (m, 1H), 1.41 (qd, J=13.1, 3.5 Hz, 1H), 1.22 (t, J=7.1 Hz, 3H).

Step C. Ethyl 2-(2-acetamido-2-(tert-butylcarbamoyl)-4-vinylcyclohexyl)acetate

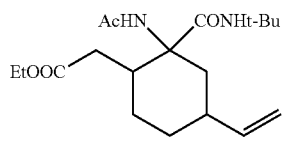

To the stirred solution of ethyl 2-(2-oxo-4-vinylcyclohexyl)acetate (1.45 g, 6.90 mmol, 1 equiv.) and ammonium acetate (2.13 g, 27.6 mmol, 4 equiv.) in 2,2,2-trifluoroethanol (3 mL) tert-butyl isocyanide (1.50 mL, 13.8 mmol, 2 equiv.) was added via syringe and the resulting mixture was stirred at room temperature for 24 hours. After this time, the reaction mixture was diluted with water (25 mL) and extracted with ethyl acetate (3×50 mL). The organic layer was washed with brine, dried over MgSO$_4$, filtered and evaporated under reduced pressure. The residue was purified by silica gel flash chromatography (gradient elution, hexane/AcOEt 8:1 to 2:1) to give corresponding product as a mixture of diastereoisomers (overall yield 1.81 g, 74%) ESI+MS: m/z=353.2 (M+1)$^+$, 375.1 (M+Na)$^+$. The major diastereoisomer was isolated as a white solid and was used in the next step. Yield: 1.60 g. $^1$H NMR (700 MHz, chloroform-d) δ 8.06 (s, 1H), 7.61 (s, 1H), 5.71 (dddd, J=17.1, 10.6, 6.4, 4.6 Hz, 1H), 5.00-4.87 (m, 2H), 4.22-4.06 (m, 2H), 3.13-2.98 (m, 2H), 2.53 (dd, J=16.8, 3.4 Hz, 1H), 2.49-2.37 (m, 1H), 2.28-2.15 (m, 1H), 2.00 (s, 3H), 1.94-1.74 (m, 2H), 1.67-1.57 (m, 1H), 1.32 (s, 9H), 1.28 (td, J=7.1, 6.1 Hz, 3H), 1.23-1.12 (m, 2H).

Step D. 1-Acetamido-N-(tert-butyl)-2-(2-(pyrrolidin-1-yl)ethyl)-5-vinylcyclohexane-1-carboxamide

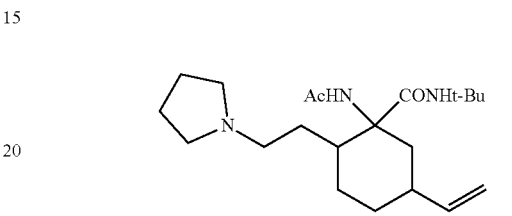

To a solution of ethyl 2-(2-acetamido-2-(tert-butylcarbamoyl)-4-vinylcyclohexyl)acetate (0.71 g, 2.0 mmol, 1 equiv.) in dry dichloromethane (15 mL), a solution of DIBAL-H (1M in DCM, 6.2 mL, 6.2 mmol, 3.1 equiv.) was added dropwise at −78° C. under argon. The reaction was stirred at −78° C. and monitored by TLC (hexane:AcOEt 1:1). After 1 h, the reaction mixture was quenched with glacial acetic acid (0.57 mL, 10.0 mmol, 5 equiv.) and was stirred at −78° C. for 10 min. Then pyrrolidine (0.33 mL, 4.0 mmol, 2 equiv.) was added dropwise and cooling bath was removed. After 15 min triacetoxyborohydride (1.70 g, 8.0 mmol, 4 equiv.) was added portionwise and the resulting mixture was allowed to warm to room temperature and was stirred for 2 h. After this time, TLC test (DCM:MEOH 9:1) revealed a full conversion of the in situ generated aldehyde. The mixture was diluted with dichloromethane and organic layer was washed with 1N NaOH and brine, dried over MgSO$_4$, filtered and concentrated in vacuo. The residue was purified by silica gel flash chromatography (gradient elution, DCM:MEOH 20:1 to 5:1) to give corresponding product as a white solid. Yield: 0.176 g, (25%). ESI+MS: m/z=364.3 (M+1)$^+$. $^1$H NMR (700 MHz, chloroform-d) δ 5.73 (ddd, J=17.1, 10.4, 6.5 Hz, 1H), 5.03-4.87 (m, 2H), 3.26-3.11 (m, 1H), 2.85-2.55 (m, 4H), 2.30-2.11 (m, 2H), 2.00-1.74 (m, 8H), 1.70-1.52 (m, 4H), 1.46-1.40 (m, 1H), 1.34 (s, 9H), 1.30-1.25 (m, 1H), 1.14-1.06 (m, 2H).

Step E. 1-Acetamido-N-(tert-butyl)-2-(2-(pyrrolidin-1-yl)ethyl)-5-(2-(4,4,5,5-tetramethyl-1,3,2-dioxaborolan-2-yl)ethyl)cyclohexane-1-carboxamide

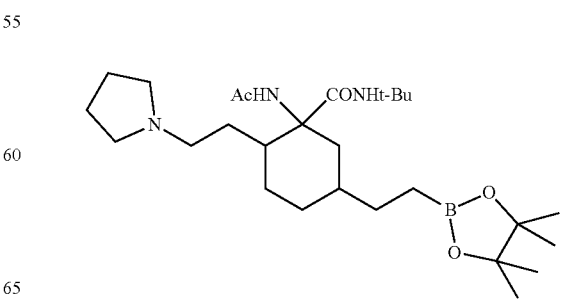

A mixture of dppe (6.2 mg, 0.0156 mmol, 0.06 equiv.) and bis(1,5-cyclooctadiene)diiridium(I) dichloride (5.2 mg, 0.0078 mmol, 0.03 equiv.) in dichloromethane (1 mL) was flushed with argon (bubbling). Next, the solution of 1-acetamido-N-(tert-butyl)-2-(2-(pyrrolidin-1-yl)ethyl)-5-vinylcyclohexane-1-carboxamide (94 mg, 0.26 mmol, 1 equiv.) and 4,4,5,5-tetramethyl-1,3,2-dioxaborolane (75 µL, 0.52 mmol, 2 equiv.) in DCM (1 mL) (flushed with argon) was added dropwise. The reaction mixture was stirred at room temperature overnight. After this time, the reaction mixture was diluted with DCM (20 mL) and washed 5% NaHCO$_3$ (20 mL). The organic layer was dried over MgSO$_4$, filtered and concentrated in vacuo. The crude product was purified by column chromatography, on silica gel (CH$_2$Cl$_2$/MeOH 20:1 to 5:1) to afford a corresponding product (62 mg, 49%) as a colorless oil. ESI+MS: m/z=492.4 (M+1)$^+$, 410.3 (M-Pin)$^+$. $^1$H NMR (700 MHz, chloroform-d) δ 3.22-3.15 (m, 1H), 2.66-2.54 (m, 4H), 2.12-2.05 (m, 2H), 1.98-1.72 (m, 10H), 1.70-1.54 (m, 6H), 1.44-1.38 (m, 1H), 1.32 (s, 9H), 1.24 (s, 12H), 1.17-1.11 (m, 1H), 0.95-0.89 (m, 2H).

Step F. 1-Amino-5-(2-boronoethyl)-2-(2-(pyrrolidin-1-yl)ethyl)cyclohexane-1-carboxylic acid dihydrochloride A mixture of 1-acetamido-N-(tert-butyl)-2-(2-(pyrrolidin-1-yl)ethyl)-5-(2-(4,4,5,5-tetramethyl-1,3,2-dioxaborolan-2-yl)ethyl)cyclohexane-1-carboxamide (62 mg, 0.126 mmol) and 6 N HCl$_{aq}$ (10 mL) was heated under reflux for 6 h. The reaction mixture was concentrated under reduced pressure and the residue was purified by ion exchange chromatography on DOWEX® and next by preparative HPLC (0.1-10% MeCN in water) to give (after acidification with 6M HCl and subsequent lyophilization) 5.2 mg (11%) of the desired product as a colorless film. ESI+MS: m/z=313.3 (M+1)$^+$, ESI-MS: m/z=311.1 (M-1)$^-$. $^1$H NMR (700 MHz, deuterium oxide) δ 3.64-3.65 (m, 2H), 3.31 (td, J=12.4, 4.7 Hz, 1H), 3.12 (td, J=12.3, 5.1 Hz, 1H), 3.05-2.96 (m, 2H), 2.19-2.13 (m, 1H), 2.11-2.04 (m, 2H), 1.98-1.89 (m, 3H), 1.87-1.76 (m, 3H), 1.67-1.57 (m, 2H), 1.54-1.46 (m, 1H), 1.32-1.24 (m, 2H), 1.22-1.15 (m, 1H), 0.90-0.81 (m, 1H) 0.75-0.68 (m, 2H).

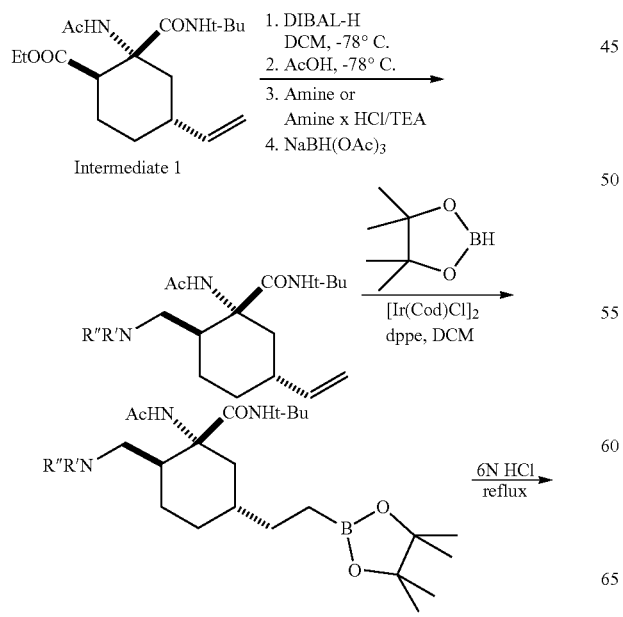

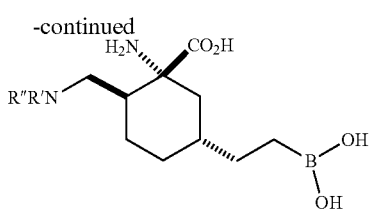

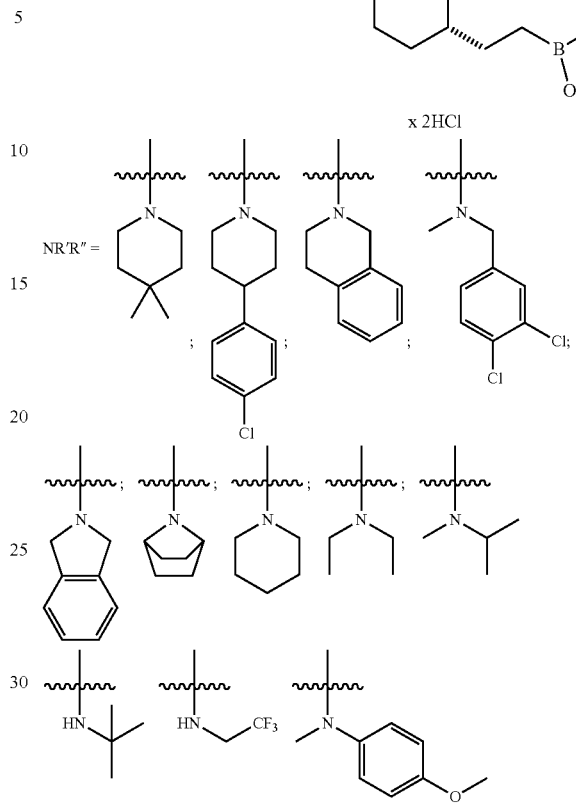

General Synthetic Route for Examples 26-37

Example 26. rac-(1R,2S,5R)-1-amino-5-(2-boronoethyl)-2-((4,4-dimethylpiperidin-1-yl)methyl)cyclohexanecarboxylic acid dihydrochloride

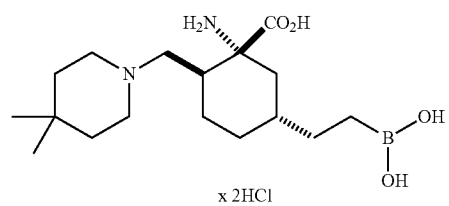 [SMILES: CC1(C)CCN(C[C@@H]2CC[C@@H](CCB(O)O)C[C@]2(N)C(=O)O)CC1]

Step A. (1R,2S,5R)-1-acetamido-N-(tert-butyl)-2-((4,4-dimethylpiperidin-1-yl)methyl)-5-vinylcyclohexanecarboxamide

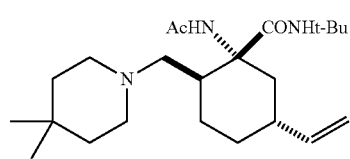

To a solution of ethyl rac-(1R,2R,4R)-2-acetamido-2-(tert-butylcarbamoyl)-4-vinylcyclohexane-1-carboxylate (Intermediate 1, 400 mg, 1.18 mmol, 1 equiv.) in dry dichloromethane (30 mL) was added dropwise a solution of DIBAL-H 1M in DCM (3.66 mL, 3.66 mmol, 3.1 equiv.) at −78° C. under argon. The reaction mixture was stirred at −78° C. and monitored by TLC (hexane:AcOEt 1:1). After 1 h the reaction mixture was quenched with glacial acetic acid (0.34 mL, 5.90 mmol, 5 equiv.) and was stirred at −78° C. for 10 min. Then, a solution of 4,4-dimethylpiperidyne hydrochloride (441 mg, 2.96 mmol, 2.5 equiv.) and TEA (0.41 mL, 2.96 mmol, 2.5 equiv.) in 10 mL of DCM was added dropwise and cooling bath was removed. After 15 min sodium triacetoxyborohydride (1.0 g, 4.72 mmol, 4 equiv.) was added portionwise and the resulting mixture was allowed to warm to room temperature and then was stirred overnight. The mixture was diluted with dichloromethane and organic layer was washed with 1N NaOH and brine, dried over MgSO$_4$, filtered and concentrated in vacuo. The residue was purified by silica gel flash chromatography (DCM:MeOH 20:1) to give corresponding product as a single diastereoisomer (310 mg, 64%, pale yellow oil). ESI+MS: m/z=392.35 (M+1)$^+$, $^1$H NMR (700 MHz, Chloroform-d) δ 10.44 (s, 1H), 8.23 (s, 1H), 5.72 (ddd, J=17.1, 10.4, 6.5 Hz, 1H), 5.04-4.83 (m, 2H), 3.40-3.35 (m, 1H), 3.25-3.20 (m, 1H), 2.38-2.05 (m, 4H), 1.96 (s, 3H), 1.61-1.45 (m, 2H), 1.42-1.33 (m, 8H), 1.32 (s, 9H), 1.19-1.12 (m, 2H), 0.93 (s, 6H).

Step B. (1R,2S,5R)-1-acetamido-N-(tert-butyl)-2-((4,4-dimethylpiperidin-1-yl)methyl)-5-(2-(4,4,5,5-tetramethyl-1,3,2-dioxaborolan-2-yl)ethyl)cyclohexanecarboxamide

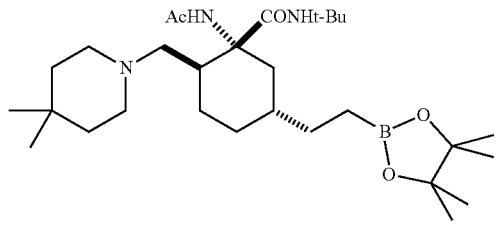

A mixture of dppe (18.3 mg, 0.046 mmol, 0.06 equiv.) and bis(1,5-cyclooctadiene)diiridium(I) dichloride (15.4 mg, 0.023 mmol, 0.03 equiv.) in dichloromethane (3 mL) was flushed with argon (bubbling). Subsequently, the separately prepared solution of 4,4,5,5-tetramethyl-1,3,2-dioxaborolane (0.22 mL, 1.53 mmol, 2 equiv.) and rac-(1R,2S,5R)-1-acetamido-N-(tert-butyl)-2-((4,4-dimethylpiperidin-1-yl)methyl)-5-vinylcyclohexanecarboxamide (300 mg, 0.76 mmol, 1 equiv.) in 3 mL of dry CH$_2$Cl$_2$ was added successively at room temperature. The resulting mixture was stirred at room temperature overnight. After that time the reaction mixture was diluted with DCM and washed with 5% NaHCO$_3$. The organic layer was dried over MgSO$_4$, filtered and concentrated in vacuo. The crude product was purified by column chromatography on silica gel (gradient elution, DCM/MeOH 30:1 to 9:1) to give corresponding product as a single diastereoisomer (230 mg, 58%, pale yellow oil). ESI+MS: m/z=520.5 (M+1)$^+$, $^1$H NMR (700 MHz, Chloroform-d) δ 10.43 (s, 1H), 8.29 (s, 1H), 3.52-3.46 (m, 1H), 3.43-3.37 (m, 1H), 3.20 (d, J=13.2 Hz, 2H), 2.44-1.98 (m, 2H), 1.95 (s, 3H), 1.41-1.30 (m, 6H), 1.31 (s, 9H), 1.28-1.23 (m, 4H), 1.23 (s, 12H), 1.21 (d, J=7.1 Hz, 2H), 0.93 (s, 6H), 0.90-0.84 (m, 2H), 0.83-0.68 (m, 2H).

Step C. rac-(1R,2S,5R)-1-amino-5-(2-boronoethyl)-2-((4,4-dimethylpiperidin-1-yl)methyl)cyclohexanecarboxylic acid dihydrochloride A mixture of rac-(1R,2S,5R)-1-acetamido-N-(tert-butyl)-2-((4,4-dimethylpiperidin-1-yl)methyl)-5-(2-(4,4,5,5-tetramethyl-1,3,2-dioxaborolan-2-yl)ethyl)cyclohexanecarboxamid (100 mg, 0.19 mmol, 1 equiv.) and 6 N HCl$_{aq}$ (15 mL) was heated under reflux for 6 h. The reaction mixture was concentrated under reduced pressure and the residue was purified by flash chromatography on DOWEX ion exchange resin (eluent 0.1N ammonia in water) to give (after acidification with 6N HCl and subsequent lyophilization) product as a single diastereoisomer (28.9 mg, 44%, white solid). ESI+MS: m/z=341.35 (M+1)$^+$, $^1$H NMR (700 MHz, Deuterium Oxide) δ 3.58-3.43 (m, 2H), 3.42-3.35 (m, 1H), 3.27-3.14 (m, 2H), 3.12-3.05 (m, 1H), 2.33-2.27 (m, 1H), 2.24-2.16 (m, 1H), 2.01-1.87 (m, 3H), 1.83-1.74 (m, 2H), 1.73-1.66 (m, 3H), 1.42-1.30 (m, 3H), 1.08 (s, 3H), 1.06 (s, 3H), 1.04-0.96 (m, 1H), 0.85-0.78 (m, 2H).

Example 27. rac-(1R,2S,5R)-1-amino-5-(2-boronoethyl)-2-((4-(4-chlorophenyl)piperidin-1-yl)methyl)cyclohexanecarboxylic acid dihydrochloride

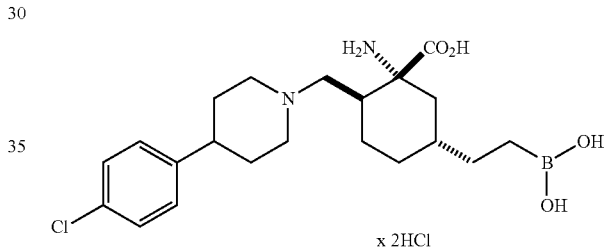

Step A. rac-(1R,2S,5R)-1-acetamido-N-(tert-butyl)-2-((4-(4-chlorophenyl)piperidin-1-yl)methyl)-5-vinylcyclohexanecarboxamide

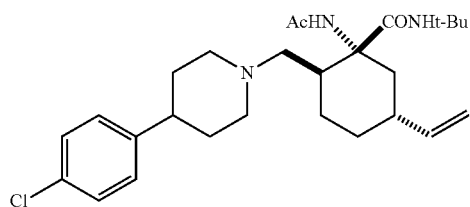

The title compound rac-(1R,2S,5R)-1-acetamido-N-(tert-butyl)-2-((4-(4-chlorophenyl)piperidin-1-yl)methyl)-5-vinylcyclohexanecarboxamide was obtained in the same manner like in Example 26, step A, using ethyl rac-(1R,2R,4R)-2-acetamido-2-(tert-butylcarbamoyl)-4-vinylcyclohexane-1-carboxylate (Intermediate 1, 300 mg, 0.887 mmol, 1 equiv.), DIBAL-H 1M in DCM (2.75 mL, 2.75 mmol, 3.1 equiv.), glacial acetic acid (0.25 mL, 4.43 mmol, 5 equiv.), 4-(4-chlorophenyl)-piperidine hydrochloride (515 mg, 2.22 mmol, 2.5 equiv.), TEA (0.31 mL, 2.22 mmol, 2.5 equiv.), sodium triacetoxyborohydride (0.75 g, 3.55 mmol, 4 equiv.)

and DCM (25 mL). The residue was purified by silica gel flash chromatography (DCM:MeOH 20:1) to give corresponding product as a single diastereoisomer (324 mg, 73%, pale yellow oil). ESI+MS: m/z=474.3 (M+1)⁺, ¹H NMR (700 MHz, Chloroform-d) δ 10.28 (s, 1H), 8.26 (s, 1H), 7.29-7.25 (m, 2H), 7.12-7.07 (m, 2H), 5.72 (ddd, J=17.1, 10.4, 6.5 Hz, 1H), 5.01-4.87 (m, 2H), 3.45 (dd, J=13.7, 10.6 Hz, 1H), 3.28-3.21 (m, 2H), 2.96 (d, J=11.8 Hz, 2H), 2.56-2.50 (m, 1H), 2.27 (td, J=11.9, 2.4 Hz, 1H), 2.22-2.11 (m, 2H), 2.01 (s, 3H), 1.97-1.90 (m, 2H), 1.69-1.61 (m, 2H), 1.62-1.57 (m, 2H), 1.41-1.32 (m, 2H), 1.33 (s, 9H), 1.28-1.07 (m, 2H).

Step B. rac-(1R,2S,5R)-1-acetamido-N-(tert-butyl)-2-((4-(4-chlorophenyl)piperidin-1-yl)methyl)-5-(2-(4,4,5,5-tetramethyl-1,3,2-dioxaborolan-2-yl)ethyl)cyclohexanecarboxamide

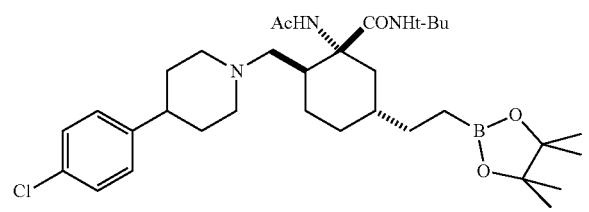

The title compound rac-(1R,2S,5R)-1-acetamido-N-(tert-butyl)-2-((4-(4-chlorophenyl)piperidin-1-yl)methyl)-5-(2-(4,4,5,5-tetramethyl-1,3,2-dioxaborolan-2-yl)ethyl)cyclohexanecarboxamide was obtained in the same manner like in Example 26, step B, using rac-(1R,2S,5R)-1-acetamido-N-(tert-butyl)-2-((4-(4-chlorophenyl)piperidin-1-yl)methyl)-5-vinylcyclohexanecarboxamide (324 mg, 0.685 mmol, 1 equiv.), dppe (16.4 mg, 0.041 mmol, 0.06 equiv.), bis(1,5-cyclooctadiene)diiridium(I) dichloride (13.8 mg, 0.02055 mmol, 0.03 equiv.), 4,4,5,5-tetramethyl-1,3,2-dioxaborolane (0.20 mL, 1.37 mmol, 2 equiv.) and DCM (8 mL). The crude product was purified by column chromatography on silica gel (gradient elution, CH₂Cl₂/MeOH 30:1 to 9:1) to give corresponding product as a single diastereoisomer (251 mg, 61%, sticky pale yellow oil). ESI+MS: m/z=602.5 (M+1)⁺, ¹H NMR (700 MHz, Chloroform-d) δ 10.26 (s, 1H), 8.23 (s, 1H), 7.30-7.25 (m, 2H), 7.12-7.08 (m, 2H), 3.51-3.41 (m, 2H), 3.30-3.18 (m, 2H), 3.01-2.91 (m, 1H), 2.57-2.48 (m, 1H), 2.31-2.21 (m, 1H), 2.15-2.06 (m, 2H), 2.01 (s, 3H), 1.98-1.85 (m, 2H), 1.69-1.57 (m, 4H), 1.54 (s, 9H), 1.41-1.32 (m, 2H), 1.32 (s, 12H), 1.28-1.07 (m, 2H), 1.02-0.89 (m, 2H), 0.88-0.73 (m, 2H).

Step C. rac-(1R,2S,5R)-1-amino-5-(2-boronoethyl)-2-((4-(4-chlorophenyl)piperidin-1-yl)methyl)cyclohexanecarboxylic acid dihydrochloride The title compound rac-(1R,2S,5R)-1-amino-5-(2-boronoethyl)-2-((4-(4-chlorophenyl)piperidin-1-yl)methyl)cyclohexanecarboxylic acid dihydrochloride was obtained in the same manner like in Example 26, step C, using (1R,2S,5R)-1-acetamido-N-(tert-butyl)-2-((4-(4-chlorophenyl)piperidin-1-yl)methyl)-5-(2-(4,4,5,5-tetramethyl-1,3,2-dioxaborolan-2-yl)ethyl)cyclohexanecarboxamide (89.0 mg, 0.15 mmol, 1 equiv.) and 6 N HCl$_{aq}$ (8 mL). The residue was purified by flash chromatography on DOWEX® ion exchange resin (eluent 0.1N ammonia in water) to give (after acidification with 6N HCl and subsequent lyophilization) product as a single diastereoisomer (15.6 mg, 25%, white solid). ESI+MS: m/z=423.3 (M+1)⁺, ¹H NMR (700 MHz, Deuterium Oxide) δ 7.48-7.43 (m, 2H), 7.37-7.32 (m, 2H), 3.86-3.80 (m, 1H), 3.77-3.71 (m, 1H), 3.42-3.38 (m, 1H), 3.31-3.23 (m, 2H), 3.16-3.08 (m, 1H), 3.03-2.95 (m, 1H), 2.34-2.28 (m, 1H), 2.27-2.15 (m, 3H), 2.10-1.90 (m, 5H), 1.85-1.75 (m, 1H), 1.43-1.31 (m, 3H), 1.08-0.98 (m, 1H), 0.85-0.80 (m, 2H).

Example 28. rac-(1R,2S,5R)-1-amino-5-(2-boronoethyl)-2-(((3,4-dichlorobenzyl)(methyl)amino)methyl)cyclohexanecarboxylic acid dihydrochloride

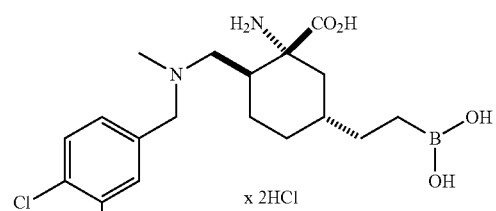

Step A. rac-(1R,2S,5R)-1-acetamido-N-(tert-butyl)-2-(((3,4-dichlorobenzyl)(methyl)amino)methyl)-5-vinylcyclohexanecarboxamide

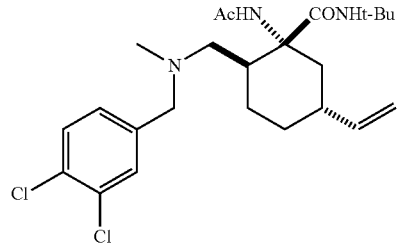

The title compound rac-(1R,2S,5R)-1-acetamido-N-(tert-butyl)-2-(((3,4-dichlorobenzyl)(methyl)amino)methyl)-5-vinylcyclohexanecarboxamide was obtained in the same manner like in Example 26, step A, using ethyl rac-(1R,2R,4R)-2-acetamido-2-(tert-butylcarbamoyl)-4-vinylcyclohexane-1-carboxylate (Intermediate 1, 500 mg, 1.48 mmol, 1 equiv.), DIBAL-H 1M in DCM (4.58 mL, 4.58 mmol, 3.1 equiv.) glacial acetic acid (0.42 mL, 7.40 mmol, 5 equiv.) (3,4-dichlorobenzyl)methyl amine (0.70 g, 3.70 mmol, 2.5 equiv), sodium triacetoxyborohydride (1.25 g, 5.92 mmol, 4 equiv.) and DCM (11 mL). The residue was purified by silica gel flash chromatography (DCM:MeOH 20:1) to give corresponding product as a single diastereoisomer (410 mg, 57%, pale yellow oil). ESI+MS: m/z=468.35 (M+1)⁺, ¹H NMR (700 MHz, Chloroform-d) δ 9.57 (s, 1H), 8.21 (s, 1H), 7.44-7.31 (m, 2H), 7.07 (dd, J=8.1, 2.0 Hz, 1H), 5.72 (ddd, J=17.1, 10.4, 6.5 Hz, 1H), 5.06-4.82 (m, 2H), 3.66-3.51 (m, 2H), 3.24 (dd, J=34.5, 13.2 Hz, 2H), 2.24 (s, 3H), 2.21-2.12 (m, 1H), 2.11-1.99 (m, 2H), 1.93 (s, 3H), 1.83-1.77 (m, 1H), 1.64-1.57 (m, 1H), 1.44-1.37 (m, 1H), 1.28 (s, 9H), 1.20-1.12 (m, 2H).

Step B. rac-(1R,2S,5R)-1-acetamido-N-(tert-butyl)-2-(((3,4-dichlorobenzyl)(methyl)amino)methyl)-5-(2-(4,4,5,5-tetramethyl-1,3,2-dioxaborolan-2-yl)ethyl)cyclohexanecarboxamide

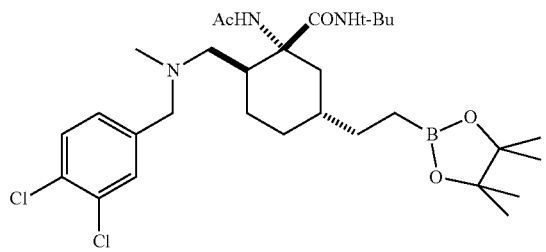

The title compound rac-(1R,2S,5R)-1-acetamido-N-(tert-butyl)-2-(((3,4-dichlorobenzyl)(methyl)amino)methyl)-5-(2-(4,4,5,5-tetramethyl-1,3,2-dioxaborolan-2-yl)ethyl)cyclohexanecarboxamide was obtained in the same manner like in Example 26, step B, using rac-(1R,2S,5R)-1-acetamido-N-(tert-butyl)-2-(((3,4-dichlorobenzyl)(methyl)amino)methyl)-5-vinylcyclohexanecarboxamide (400 mg, 0.86 mmol, 1 equiv.), dppe (20.5 mg, 0.0516 mmol, 0.06 equiv.), bis(1,5-cyclooctadiene)diiridium(I) dichloride (17.3 mg, 0.0258 mmol, 0.03 equiv.), 4,4,5,5-tetramethyl-1,3,2-dioxaborolane (0.25 mL, 1.72 mmol, 2 equiv.) and DCM (4 mL). The crude product was purified by column chromatography on silica gel (gradient elution, DCM/MeOH 40:1 to 20:1) to give corresponding product as a single diastereoisomer (430 mg, 84%, pale yellow oil). ESI+MS: m/z=596.15 (M+1)$^+$, $^1$H NMR (700 MHz, Chloroform-d) δ 9.55 (s, 1H), 8.20 (s, 1H), 7.42-7.31 (m, 2H), 7.06 (dd, J=8.1, 2.0 Hz, 1H), 3.61-3.52 (m, 2H), 3.22 (dd, J=45.3, 13.1 Hz, 2H), 2.22 (s, 3H), 2.12-2.02 (m, 2H), 1.92 (s, 3H), 1.80-1.73 (m, 1H), 1.68-1.53 (m, 3H), 1.41-1.29 (m, 4H), 1.27 (s, 9H), 1.24 (s, 12H), 1.01-0.88 (m, 2H), 0.84-0.67 (m, 2H).

Step C. rac-(1R,2S,5R)-1-amino-5-(2-boronoethyl)-2-(((3,4-dichlorobenzyl)(methyl)amino)methyl)cyclohexanecarboxylic acid hydrochloride The title compound rac-(1R,2S,5R)-1-amino-5-(2-boronoethyl)-2-(((3,4-dichlorobenzyl)(methyl)amino)methyl)cyclohexanecarboxylic acid dihydrochloride was obtained in the same manner like in Example 26, step C, using rac-(1R,2S,5R)-1-acetamido-N-(tert-butyl)-2-(((3,4-dichlorobenzyl)(methyl)amino)methyl)-5-(2-(4,4,5,5-tetramethyl-1,3,2-dioxaborolan-2-yl)ethyl)cyclohexanecarboxamide (40 mg, 0.067 mmol, 1 equiv.) and 6 N HCl$_{aq}$ (10 mL). The residue was purified by flash chromatography on DOWEX ion exchange resin (eluent 0.1N ammonia in water) and next by preparative HPLC (5-50% MeCN in water) to give (after acidification with 6N HCl and subsequent lyophilization) product as a single diastereoisomer (9.7 mg, 35%, white solid). ESI+MS: m/z=417.35 (M+1)$^+$, $^1$H NMR (700 MHz, Deuterium Oxide) δ 7.93-7.61 (m, 2H), 7.46 (dd, J=8.3, 1.9 Hz, 1H), 4.69-4.20 (m, 2H), 3.63-3.20 (m, 2H), 3.05-2.74 (m, 3H), 2.45-2.11 (m, 2H), 2.05-1.55 (m, 4H), 1.48-1.26 (m, 3H), 1.09-0.91 (m, 1H), 0.88-0.68 (m, 2H).

Example 29. rac-(1R,2S,5R)-1-amino-5-(2-boronoethyl)-2-(isoindolin-2-ylmethyl)cyclohexanecarboxylic acid dihydrochloride

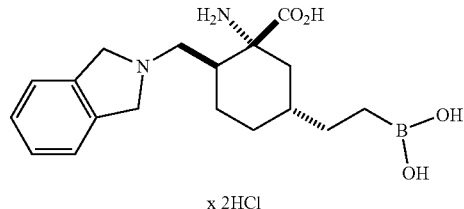

x 2HCl

Step A. rac-(1R,2S,5R)-1-acetamido-N-(tert-butyl)-2-(isoindolin-2-ylmethyl)-5-vinylcyclohexanecarboxamide

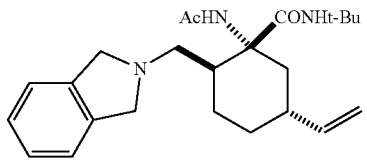

The title compound rac-(1R,2S,5R)-1-acetamido-N-(tert-butyl)-2-(isoindolin-2-ylmethyl)-5-vinylcyclohexanecarboxamide was obtained in the same manner like in Example 26, step A, using ethyl rac-(1R,2R,4R)-2-acetamido-2-(tert-butylcarbamoyl)-4-vinylcyclohexane-1-carboxylate (Intermediate 1, 300 mg, 0.887 mmol, 1 equiv.), DIBAL-H 1M in DCM (2.75 mL, 2.75 mmol, 3.1 equiv.), glacial acetic acid (0.25 mL, 4.43 mmol, 5 equiv.), Isoindoline hydrochloride (340 mg, 2.22 mmol, 2.5 equiv.), TEA (0.31 mL, 2.22 mmol, 2.5 equiv.), sodium triacetoxyborohydride (0.75 g, 3.55 mmol, 4 equiv.). The residue was purified by silica gel flash chromatography (hexane/AcOEt 10:1 to 2:1) to give corresponding product as a single diastereoisomer (180 mg, 51%, sticky, colorless solid). ESI+MS: m/z=398.3 (M+1)$^+$. $^1$H NMR (700 MHz, Chloroform-d) δ 10.27 (s, 1H), 8.23 (s, 1H), 7.21 (s, 4H), 5.74 (ddd, J=17.1, 10.4, 6.5 Hz, 1H), 5.01-4.91 (m, 2H), 4.10 (d, J=12.0 Hz, 2H), 3.90-3.84 (m, 2H), 3.23 (d, J=13.4 Hz, 1H), 2.58 (d, J=13.4 Hz, 1H), 2.28-2.19 (m, 1H), 2.12-2.05 (m, 1H), 1.88-1.80 (m, 1H), 1.67 (s, 3H), 1.62-1.54 (m, 2H), 1.50-1.46 (m, 1H), 1.34 (s, 9H), 1.25-1.18 (m, 2H).

Step B. rac-(1R,2S,5R)-1-acetamido-N-(tert-butyl)-2-(isoindolin-2-ylmethyl)-5-(2-(4,4,5,5-tetramethyl-1,3,2-dioxaborolan-2-yl)ethyl)cyclohexanecarboxamide

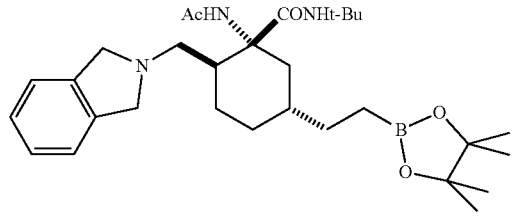

The title compound rac-(1R,2S,5R)-1-acetamido-N-(tert-butyl)-2-(isoindolin-2-ylmethyl)-5-(2-(4,4,5,5-tetramethyl-1,3,2-dioxaborolan-2-yl)ethyl)cyclohexanecarboxamide was obtained in the same manner like in Example 26, step B, using rac-(1R,2S,5R)-1-acetamido-N-(tert-butyl)-2-(isoindolin-2-ylmethyl)-5-vinylcyclohexanecarboxamide (180 mg, 0.45 mmol, 1 equiv.), dppe (11 mg, 0.027 mmol, 0.06 equiv.), bis(1,5-cyclooctadiene)diiridium(I) dichloride (9 mg, 0.013 mmol, 0.03 equiv.), 4,4,5,5-tetramethyl-1,3,2-dioxaborolane (0.13 mL, 0.90 mmol, 2 equiv.) and DCM (6 mL). The crude product was purified by column chromatography on silica gel (gradient elution, DCM/MeOH 100:1 to 20:1) to give corresponding product as a single diastereoisomer (145 mg, 60%, sticky, colorless solid). ESI+MS: m/z=526.4 (M+1)$^+$. $^1$H NMR (700 MHz, Chloroform-d) δ 10.24 (s, 1H), 8.25 (s, 1H), 7.20 (s, 4H), 4.09 (d, J=12.0 Hz, 2H), 3.88 (d, J=11.4 Hz, 2H), 3.21 (d, J=13.2 Hz, 1H), 2.56 (d, J=15.3 Hz, 1H), 2.14 (dd, J=13.8, 9.3 Hz, 1H), 1.90 (s, 1H), 1.83-1.78 (m, 1H), 1.65 (s, 3H), 1.49-1.40 (m, 2H), 1.33 (d, J=5.9 Hz, 9H), 1.29 (d, J=4.5 Hz, 1H), 1.24 (d, J=2.8 Hz, 12H), 1.04-0.93 (m, 2H), 0.89 (t, J=6.3 Hz, 1H), 0.86-0.68 (m, 3H).

Step C. rac-(1R,2S,5R)-1-amino-5-(2-boronoethyl)-2-(isoindolin-2-ylmethyl)cyclohexanecarboxylic acid dihydrochloride The title compound rac-(1R,2S,5R)-1-amino-5-(2-boronoethyl)-2-(isoindolin-2-ylmethyl)cyclohexanecarboxylic acid dihydrochloride was obtained in the same manner like in Example 26, step C, using rac-(1R,2S,5R)-1-acetamido-N-(tert-butyl)-2-(isoindolin-2-ylmethyl)-5-(2-(4,4,5,5-tetramethyl-1,3,2-dioxaborolan-2-yl)ethyl)cyclohexanecarboxamide (65 mg, 0.15 mmol, 1 equiv.), 6N HCl$_{aq}$ (20 mL). The residue was purified by flash chromatography on DOWEX® ion exchange resin (eluent 0.1N ammonia in water) to give (after acidification with 6N HCl and subsequent lyophilization) product as a single diastereoisomer (30 mg, 49%, off-white solid). ESI+MS: m/z=347.3 (M+1)$^+$. $^1$H NMR (700 MHz, Deuterium Oxide) δ 7.40-7.33 (m, 4H), 5.00-4.79 (m, 2H), 4.61-4.41 (m, 2H), 3.63 (s, 1H), 3.51 (d, J=12.9 Hz, 1H), 2.26-2.14 (m, 2H), 2.02-1.95 (m, 1H), 1.92-1.80 (m, 2H), 1.76-1.66 (m, 1H), 1.32-1.26 (m, 3H), 1.00-0.92 (m, 1H), 0.76-0.71 (m, 2H).

Example 30. rac-(1R,2S,5R)-1-amino-5-(2-boronoethyl)-2-((diethylamino)methyl)cyclohexanecarboxylic acid dihydrochloride

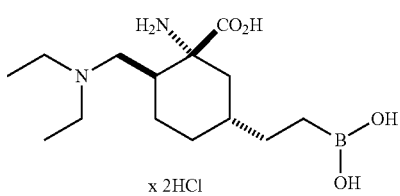

x 2HCl

Step A. rac-(1R,2S,5R)-1-acetamido-N-(tert-butyl)-2-((diethylamino)methyl)-5-vinylcyclohexanecarboxamide

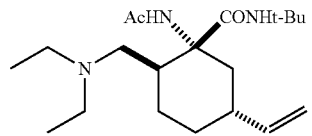

The title compound rac-(1R,2S,5R)-1-acetamido-N-(tert-butyl)-2-((diethylamino)methyl)-5-vinylcyclohexanecarboxamide was obtained in the same manner like in Example 26, step A, using ethyl rac-(1R,2R,4R)-2-acetamido-2-(tert-butylcarbamoyl)-4-vinylcyclohexane-1-carboxylate (Intermediate 1, 500 mg, 1.48 mmol, 1 equiv.), DIBAL-H 1M in DCM (4.58 mL, 4.58 mmol, 3.1 equiv.) glacial acetic acid (0.42 mL, 7.40 mmol, 5 equiv.), diethylamine (0.31 mL, 2.95 mmol, 2 equiv), sodium triacetoxyborohydride (1.25 g, 5.92 mmol, 4 equiv.). The residue was purified by silica gel flash chromatography (DCM:MeOH 20:1) to give corresponding product as a mixture of diastereoisomers, dr=3:1, (0.43 g, 82%, sticky, colorless solid). ESI+MS: m/z=352.4 (M+1)$^+$. $^1$H NMR (700 MHz, Chloroform-d) δ 10.70, 7.69 [(2s, 1H, two diastereoisomers)], 8.39, 7.45 [(2s, 1H, two diastereoisomers)], 5.72 [(dddd, J=17.1, 10.3, 6.5, 5.0 Hz, 1H, two diastereoisomers)], 5.01-4.96 [(m, 1H, two diastereoisomers)], 4.94-4.90 [(m, 1H, two diastereoisomers)], 3.76-3.52 [(m, 1H, two diastereoisomers)], 3.26-3.12 [(m, 1H, two diastereoisomers)], 2.68 (dq, J=12.8, 7.3 Hz, 2H), 2.25 (dq, J=12.8, 6.9 Hz, 2H), 2.17 (td, J=13.3, 4.4 Hz, 1H), 2.07 (dd, J=13.9, 1.9 Hz, 1H), 1.96, 1.91 [(2s, 3H, two diastereoisomers)], 1.83-1.70 (m, 1H), 1.54 (tdd, J=10.5, 4.1, 1.9 Hz, 1H), 1.38-1.35 (m, 2H), 1.34, 1.31[(2s, 9H, two diastereoisomers)], 1.23-1.12 (m, 2H), 1.05 (t, J=7.1 Hz, 6H).

Step B. rac-(1R,2S,5R)-1-acetamido-N-(tert-butyl)-2-((diethylamino)methyl)-5-(2-(4,4,5,5-tetramethyl-1,3,2-dioxaborolan-2-yl)ethyl)cyclohexanecarboxamide and rac-(2-((1R,3R,4S)-3-acetamido-3-(tert-butylcarbamoyl)-4-((diethylamino)methyl)cyclohexyl)ethyl)boronic acid

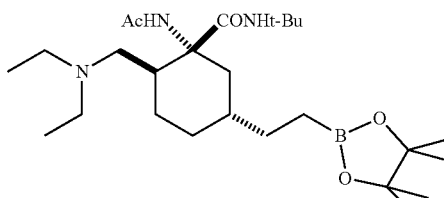

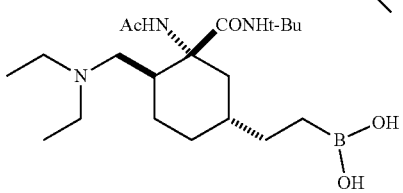

The title compounds were obtained in the same manner like in Example 26, step B, using rac-(1R,2S,5R)-1-acetamido-N-(tert-butyl)-2-((diethylamino)methyl)-5-vinylcyclohexanecarboxamide (Intermediate 1, 200 mg, 0.57 mmol, 1 equiv.), dppe (13 mg, 0.034 mmol, 0.06 equiv.), bis(1,5-cyclooctadiene)diiridium(I) dichloride (11 mg, 0.017 mmol, 0.03 equiv.), 4,4,5,5-tetramethyl-1,3,2-dioxaborolane (0.20 mL, 1.42 mmol, 2.5 equiv.) and DCM (6 mL). The crude product was purified by column chromatography on silica gel (gradient elution, DCM/MeOH 50:1 to 5:1) to give corresponding products as a single diastereoisomers (0.16 g, 82%). Product as a pinacol ester (80 mg, sticky, pale yellow solid). ESI+MS: m/z=480.6 (M+1)$^+$. Partially during purification by silica gel column chromatography pinacol ester is removed. Product as a boronic acid (80 mg, yellowish foam). ESI+MS: m/z=398.4 (M+1)$^-$ $^1$H NMR (700 MHz, Chloroform-d) δ 10.72, 10.69 [(2s, 1H, two rotamers)], 8.37, 8.35 [(2s, 1H, two rotamers)], 3.63-3.57 (m, 1H), 3.49 (d, J=3.9 Hz, 1H), 3.27-3.20 (m, 1H), 2.67 (dq, J=14.2, 7.1, 6.5 Hz, 2H), 2.29-2.21 (m, 2H), 2.14-2.03 (m, 2H), 1.91, 1.90 [(2s, 3H, two rotamers), 1.81-1.75 (m, 1H), 1.56-1.47 (m, 2H), 1.31 (s, 9H), 1.24 (d, J=17.2 Hz, 2H), 1.05 (t, J=7.1 Hz, 6H), 1.00-0.91 (m, 2H), 0.89-0.69 (m, 2H).

Step C. rac-(1R,2S,5R)-1-amino-5-(2-boronoethyl)-2-((diethylamino)methyl)cyclohexanecarboxylic acid dihydrochloride The title compound rac-(1R,2S,5R)-1-amino-5-(2-boronoethyl)-2-((diethylamino)methyl)cyclohexanecarboxylic acid dihydrochloride was obtained in the same manner like in Example 26, step C, using rac-(2-((1R,3R,4S)-3-acetamido-3-(tert-butylcarbamoyl)-4-((diethylamino)methyl)cyclohexyl)ethyl)boronic acid (80 mg, 0.20 mmol, 1 equiv.), 6 N HCl$_{aq}$(20 mL). The residue was purified by flash chromatography on DOWEX® ion exchange resin (eluent 0.1N ammonia in water) to give (after acidification with 6N HCl and subsequent lyophilization) product as a single diastereoisomer (60 mg, 80%, white solid). ESI+MS: m/z=301.4 (M+1)$^+$. $^1$H NMR (700 MHz, Deuterium Oxide) δ 3.34-3.05 (m, 6H), 2.26-2.21 (m, 1H), 2.08 (d, J=9.2 Hz, 1H), 1.92-1.85 (m, 2H), 1.79 (qd, J=14.3, 13.7, 4.1 Hz, 1H), 1.75-1.66 (m, 1H), 1.28 (ddd, J=12.2, 7.1, 3.6 Hz, 3H), 1.23 (q, J=7.4 Hz, 6H), 0.96-0.88 (m, 1H), 0.72 (dd, J=9.3, 7.0 Hz, 2H).

Example 31. rac-(1R,2S,5R)-1-amino-5-(2-boronoethyl)-2-(piperidin-1-ylmethyl)cyclohexanecarboxylic acid dihydrochloride

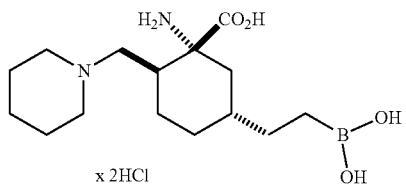

Step A. rac-(1R,2S,5R)-1-acetamido-N-(tert-butyl)-2-(piperidin-1-ylmethyl)-5-vinylcyclohexanecarboxamide

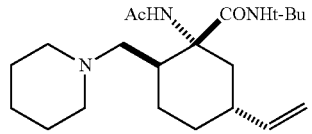

The title compound rac-(1R,2S,5R)-1-acetamido-N-(tert-butyl)-2-(piperidin-1-ylmethyl)-5-vinylcyclohexanecarboxamide was obtained in the same manner like in Example 26, step A, using ethyl rac-2-((1S,2R,4R)-2-acetamido-2-(tert-butylcarbamoyl)-4-vinylcyclohexyl)acetate (Intermediate 1, 0.3 g, 0.88 mmol, 1 equiv.), DIBAL-H 1M in DCM (2.74 mL, 2.74 mmol, 3.1 equiv.), glacial acetic acid (0.25 mL, 4.42 mmol, 5 equiv.), piperidine (0.17 mL, 1.77 mmol, 2 equiv.), sodium triacetoxyborohydride (0.75 g, 3.54 mmol, 4 equiv.), dry DCM (30 mL). The residue was purified by silica gel flash chromatography (gradient elution DCM:MeOH 100:1 to 15:1) to give corresponding product rac-(1R,2S,5R)-1-acetamido-N-(tert-butyl)-2-(piperidin-1-ylmethyl)-5-vinylcyclohexanecarboxamide as a single diastereoisomer (0.14 g, 43%, white solid). ESI+MS: m/z=364.3 (M+1)$^+$. $^1$H NMR (700 MHz, Chloroform-d) δ 10.42 (s, 1H), 8.24 (s, 1H), 5.72 (ddd, J=17.1, 10.4, 6.5 Hz, 1H), 5.03-4.85 (m, 2H), 3.33 (ddd, J=13.9, 10.7, 5.4 Hz, 1H), 3.22 (dt, J=13.2, 2.3 Hz, 1H), 2.21-2.03 (m, 3H), 1.97 (s, 3H), 1.80 (dtt, J=12.4, 4.1, 2.2 Hz, 1H), 1.64-1.40 (m, 10H), 1.38-1.34 (m, 2H), 1.32 (s, 9H), 1.14 (qd, J=13.0, 4.0 Hz, 2H).

Step B. rac-(1R,2S,5R)-1-acetamido-N-(tert-butyl)-2-(piperidin-1-ylmethyl)-5-(2-(4,4,5,5-tetramethyl-1,3,2-dioxaborolan-2-yl)ethyl)cyclohexanecarboxamide

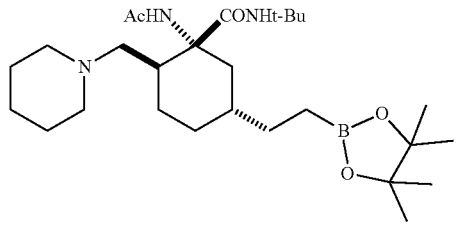

The title compound rac-(1R,2S,5R)-1-acetamido-N-(tert-butyl)-2-(piperidin-1-ylmethyl)-5-(2-(4,4,5,5-tetramethyl-1,3,2-dioxaborolan-2-yl)ethyl)cyclohexanecarboxamide was obtained in the same manner like in Example 26, step B, using rac-(1R,2S,5R)-1-acetamido-N-(tert-butyl)-2-(piperidin-1-ylmethyl)-5-vinylcyclohexanecarboxamide (0.14 g, 0.38 mmol, 1 equiv.), dppe (0.009 g, 0.02 mmol, 0.06 equiv.), bis(1,5-cyclooctadiene)diiridium(I) dichloride (0.008 g, 0.01. mmol, 0.03 equiv.), 4,4,5,5-tetramethyl-1,3,2-dioxaborolane (0.073 mL, 0.50 mmol, 1.3 equiv). The crude product was purified by column chromatography on silica gel (gradient elution, DCM/MeOH 100:1 to 10:1) to give corresponding product (1R,2S,5R)-1-acetamido-N-(tert-butyl)-2-(piperidin-1-ylmethyl)-5-(2-(4,4,5,5-tetramethyl-1,3,2-dioxaborolan-2-yl)ethyl)cyclohexanecarboxamide as a single diastereoisomer (0.11 g, 58%, yellow solid). ESI+MS: m/z=492.5 (M+1)$^+$, 410.4 (M−Pin+1)$^+$. $^1$H NMR (700 MHz, Chloroform-d) δ 10.41 (s, 1H), 8.31 (s, 1H), 3.40-3.29 (m, 1H), 3.25-3.18 (m, 1H), 2.73-2.41 (m, 2H), 2.39-2.13 (m, 2H), 2.13-2.02 (m, 2H), 1.96 (s, 3H), 1.82-1.74 (m, 1H), 1.61-1.51 (m, 7H), 1.51-1.38 (m, 2H), 1.34-1.32 (m, 3H), 1.31 (br s, 6H), 1.31-1.28 (m, 1H), 1.27 (s, 1H), 1.27-1.25 (m, 1H), 1.24 (s, 1H), 1.23 (s, 9H), 0.99-0.90 (m, 2H), 0.90-0.85 (m, 1H), 0.84-0.76 (m, 1H), 0.72 (ddd, J=16.2, 11.2, 5.2 Hz, 1H).

Step C. rac-(1R,2S,5R)-1-amino-5-(2-boronoethyl)-2-(piperidin-1-ylmethyl)cyclohexanecarboxylic acid dihydrochloride The title compound rac-(1R,2S,5R)-1-amino-5-(2-boronoethyl)-2-(piperidin-1-ylmethyl)cyclohexanecarboxylic acid dihydrochloride was obtained in the same manner like in Example 26, step C, using compound rac-(1R,2S,5R)-1-acetamido-N-(tert-butyl)-2-(piperidin-1-ylmethyl)-5-(2-(4,4,5,5-tetramethyl-1,3,2-dioxaborolan-2-yl)ethyl)cyclohexanecarboxamide (0.11 g, 0.22 mmol, 1 equiv.), 6N HCl$_{aq}$(3 mL). The residue was purified by flash chromatography on DOWEX® ion exchange resin (eluent 0.1N ammonia in water) and next by preparative HPLC (0.1-1% MeCN in water) to give (after acidification with 6N HCl and subsequent lyophilization) product (1R,2S,5R)-1-amino-5-(2-boronoethyl)-2-(piperidin-1-ylmethyl)cyclohexanecarboxylic acid dihydrochloride (0.033 g, 43%, white solid). ESI+MS: m/z=313.1 (M+1)$^+$. ESI-MS: m/z=311.0 (M−1)$^-$. $^1$H NMR (700 MHz, Deuterium Oxide) δ 3.54 (d, J=12.5 Hz, 1H), 3.46 (d, J=12.2 Hz, 1H), 3.27 (dd, J=13.6, 2.3 Hz, 1H), 3.08 (dd, J=13.6, 10.6 Hz, 1H), 2.97 (td, J=12.3, 3.2 Hz, 1H), 2.83 (td, J=12.3, 3.1 Hz, 1H), 2.23 (ddd, J=13.1, 3.2, 1.8 Hz, 1H), 2.19-2.09 (m, 1H), 1.95-1.83 (m, 4H), 1.80 (td, J=13.0, 3.6 Hz, 1H), 1.77-1.71 (m, 2H), 1.71-1.62 (m, 2H), 1.53-1.36 (m, 1H), 1.35-1.21 (m, 3H), 0.92 (qd, J=13.1, 3.9 Hz, 1H), 0.72 (dd, J=9.0, 7.3 Hz, 2H).

Example 32. rac-(1R,2S,5R)-1-amino-5-(2-boronoethyl)-2-((isopropyl(methyl)amino)methyl)cyclohexanecarboxylic acid

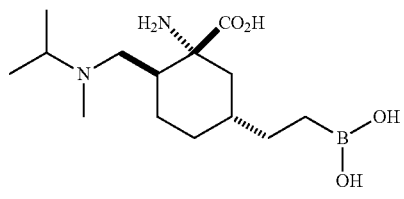

Step A. rac-(1R,2S,5R)-1-Acetamido-N-(tert-butyl)-2-((isopropyl(methyl)amino)methyl)-5-vinylcyclohexanecarboxamide

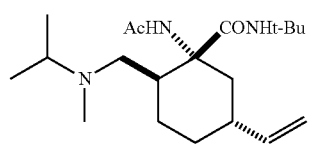

The title compound was prepared from ethyl rac-(1R,2R,4R)-2-acetamido-2-(tert-butylcarbamoyl)-4-vinylcyclohexane-1-carboxylate (Intermediate 1, 500 mg, 1.48 mmol), using the procedure described in Example 26, step A. The crude product was purified by flash chromatography on silica gel (DCM/MeOH 40:1 to 15:1) to give the desired product as a colorless oil (123 mg, 24%). ESI+MS: m/z=352.5 (M+1)$^+$. $^1$H NMR (700 MHz, CDCl$_3$) δ 10.71 (s, 1H), 8.34 (s, 1H), 5.75 (ddd, J=17.1, 10.4, 6.5 Hz, 1H), 4.96 (ddt, J=42.3, 10.4, 1.5 Hz, 2H), 3.64-3.56 (m, 1H), 3.24 (dt, J=13.6, 2.5 Hz, 1H), 2.84 (h, J=6.6 Hz, 1H), 2.25 (s, 3H), 2.22-2.15 (m, 1H), 2.10-2.04 (m, 2H), 1.92 (s, 3H), 1.86-1.79 (m, 1H), 1.55-1.50 (s, 1H), 1.40-1.35 (m, 1H), 1.34 (s, 9H), 1.22-1.14 (m, 2H), 1.02 (dd, J=26.3, 6.6 Hz, 6H).

Step B. rac-(2-((1R,3R,4S)-3-Acetamido-3-(tert-butylcarbamoyl)-4-((isopropyl(methyl)amino)methyl)cyclohexyl)ethyl)boronic acid

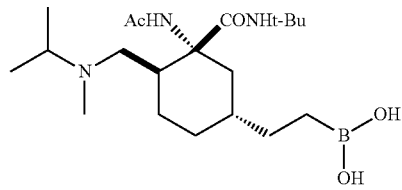

The title compound was prepared from rac-(1R,2S,5R)-1-acetamido-N-(tert-butyl)-2-((isopropyl(methyl)amino)methyl)-5-vinylcyclohexanecarboxamide (120 mg, 0.34 mmol), using the procedure described in Example 26, step B. The crude product was purified by flash chromatography on silica gel (DCM/MeOH 40:1 to 0:1) to give the desired product (80 mg, 59%) as a colorless oil. ESI+MS: m/z=398.55 (M+1)$^+$, 396.3 (M−1)$^-$. $^1$H NMR (700 MHz, chloroform-d) δ 10.67 (s, 1H), 8.32 (s, 1H), 3.27-3.18 (m, 1H), 2.27 (s, 3H), 2.16-2.06 (m, 2H), 1.94 (s, 3H), 1.83-1.75 (m, 1H), 1.44-1.34 (m, 2H), 1.33 (s, 9H), 1.30-1.22 (m, 4H), 1.11-0.92 (m, 8H), 0.91-0.72 (m, 3H).

Step C. rac-(1R,2S,5R)-1-Amino-5-(2-boronoethyl)-2-((isopropyl(methyl)amino)methyl)cyclohexanecarboxylic acid The title compound was prepared from rac-(2-((1R,3R,4S)-3-acetamido-3-(tert-butylcarbamoyl)-4-((isopropyl(methyl)amino)methyl)cyclohexyl)ethyl)boronic acid (80 mg, 0.20 mmol), using the procedure described in Example 26, step C. The crude product was purified by ion exchange chromatography on DOWEX® to the desired product (36 mg, 60%) as a white solid. ESI+MS: m/z=301.3 (M+1)$^+$. $^1$H NMR (700 MHz, deuterium oxide) δ 3.39-3.30 (m, 1H), 3.21-3.13 (m, 1H), 2.86-2.79 (m, 1H), 2.54 (s, 3H), 2.00-1.96 (m, 1H), 1.79-1.74 (m, 2H), 1.72-1.64 (m, 1H), 1.52-1.47 (m, 1H), 1.46-1.39 (m, 1H), 1.27-1.17 (m, 2H), 1.14 (dd, J=6.7, 3.6 Hz, 6H), 0.97 (t, J=12.6 Hz, 1H), 0.92-0.83 (m, 1H), 0.69 (t, J=8.1 Hz, 2H).

Example 33. rac-(1R,2S,5R)-1-amino-5-(2-borono-ethyl)-2-((tert-butylamino)methyl)cyclohexanecarboxylic acid dihydrochloride

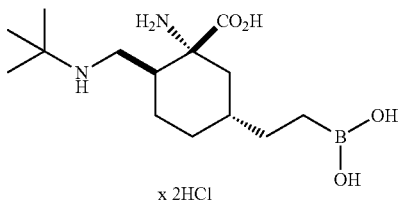 [SMILES: CC(C)(C)NC[C@@H]1CC[C@@H](CCB(O)O)C[C@]1(N)C(=O)O]

Step A. rac-(1R,2S,5R)-1-Acetamido-N-(tert-butyl)-2-((tert-butylamino)methyl)-5-vinylcyclohexanecarboxamide

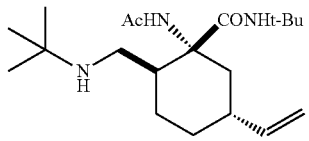

The title compound was prepared from rac-(1R,2R,4R)-2-acetamido-2-(tert-butylcarbamoyl)-4-vinylcyclohexane-1-carboxylate (Intermediate 1, 150 mg, 0.44 mmol), using the procedure described in the preparation of Example 26, step A. The crude product was purified by flash chromatography on silica gel (DCM/MeOH 20:1 to 0:1)) to afford 30 mg (19%) of the desired product as a colorless oil. ESI+MS: m/z=352.3 (M+1)$^+$. $^1$H NMR (700 MHz, chloroform-d) δ 10.85 (s, 1H), 8.35 (s, 1H), 5.79-5.63 (m, 1H), 5.08-4.86 (m, 2H), 3.48-3.39 (m, 1H), 3.31-3.19 (m, 1H), 2.75-2.56 (s, 1H), 2.30-2.18 (m, 2H), 2.16-2.03 (m, 1H), 1.97 (s, 3H), 1.90-1.76 (m, 1H), 1.45-1.40 (m, 2H), 1.35 (s, 9H), 1.22-1.16 (m, 1H), 1.12 (s, 9H).

Step B. rac-(1R,2S,5R)-1-Acetamido-N-(tert-butyl)-2-((tert-butylamino)methyl)-5-(2-(4,4,5,5-tetramethyl-1,3,2-dioxaborolan-2-yl)ethyl)cyclohexanecarboxamide

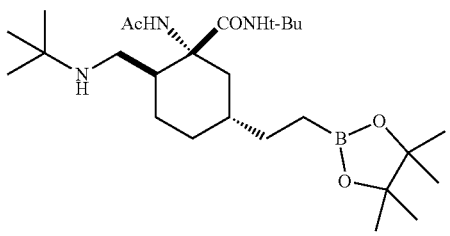

The title compound was prepared from rac-(1R,2S,5R)-1-acetamido-N-(tert-butyl)-2-((tert-butylamino)methyl)-5-vinylcyclohexanecarboxamide (30 mg, 0.085 mmol), using the procedure described in the preparation of Example 26, step B. The crude product was purified by flash chromatography on silica gel (DCM/MeOH 30:1 to 0:1)) to afford 20 mg (49%) of the desired product as a colorless oil. ESI+MS: m/z=480.45 (M+1)$^+$. $^1$H NMR (700 MHz, chloroform-d) δ 10.19 (s, 1H), 8.68 (s, 1H), 6.26 (s, 1H), 3.04-2.95 (m, 1H), 2.95-2.87 (m, 1H), 2.70-2.58 (m, 1H), 2.56-2.48 (m, 1H), 2.09 (s, 3H), 1.89-1.80 (m, 1H), 1.70-1.63 (m, 1H), 1.44 (s, 9H), 1.38 (s, 9H), 1.34-1.28 (m, 2H), 1.24 (s, 12H), 1.20-1.14 (m, 1H), 1.13-0.97 (m, 2H), 0.91 (t, J=7.4 Hz, 1H), 0.85-0.70 (m, 2H).

Step C. rac-(1R,2S,5R)-1-Amino-5-(2-boronoethyl)-2-((tert-butylamino)methyl)cyclohexanecarboxylic acid dihydrochloride The title compound was prepared from rac-(1R,2S,5R)-1-acetamido-N-(tert-butyl)-2-((tert-butylamino)methyl)-5-(2-(4,4,5,5-tetramethyl-1,3,2-dioxaborolan-2-yl)ethyl)cyclohexanecarboxamide (17.5 mg, 0.036 mmol), using the procedure described in the preparation of Example 26, step C. The crude product was purified by ion exchange chromatography with DOWEX® and next by preparative HPLC (0.1-1% MeCN in water) to give (after acidification with 6M HCl and subsequent lyophilization) the desired product (2.2 mg, 16%) as a white solid. ESI+MS: m/z=301.3 (M+1)$^+$, 323.3 (M+Na)$^+$. $^1$H NMR (700 MHz, deuterium oxide) δ 3.29 (dd, J=13.0, 3.0 Hz, 1H), 2.86 (dd, J=12.9, 10.2 Hz, 1H), 2.23-2.17 (m, 1H), 1.98-192 (m, 1H), 1.88-1.82 (m, 2H), 1.80-1.71 (m, 1H), 1.70-1.62 (m, 1H), 1.30 (s, 9H), 1.29-1.21 (m, 3H), 0.94-0.83 (m, 1H), 0.74-0.67 (m, 2H).

Example 34. rac-(1R,2S,5R)-2-(7-azabicyclo[2.2.1]heptan-7-ylmethyl)-1-amino-5-(2-boronoethyl)cyclohexanecarboxylic acid dihydrochloride

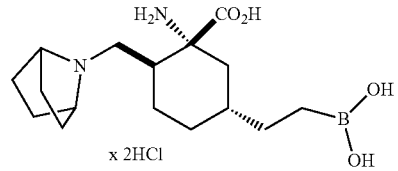 [SMILES: N[C@]1(C(=O)O)C[C@H](CCB(O)O)CC[C@H]1CN1C2CCC1CC2]

Step A. rac-(1R,2S,5R)-2-(7-Azabicyclo[2.2.1]heptan-7-ylmethyl)-1-acetamido-N-(tert-butyl)-5-vinylcyclohexanecarboxamide

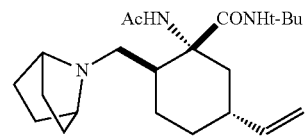

The title compound was prepared from rac-(1R,2R,4R)-2-acetamido-2-(tert-butylcarbamoyl)-4-vinylcyclohexane-1-carboxylate (Intermediate 1, 300 mg, 0.89 mmol), using the procedure described in the preparation of Example 26, step A. The crude product was purified by flash chromatography on silica gel (DCM/MeOH 20:1 to 2:1)) to afford 85 mg (26%) of the desired product as a colorless oil. ESI+MS: m/z=376.3 (M+1)$^+$. $^1$H NMR (700 MHz, chloroform-d) δ 8.97 (s, 1H), 8.48 (s, 1H), 5.70 (ddd, J=17.1, 10.4, 6.5 Hz, 1H), 5.02-4.90 (m, 2H), 4.04-4.01 (m, 1H), 3.93-3.90 (m, 1H), 3.51-3.36 (m, 2H), 3.20-3.08 (m, 2H), 2.57-2.40 (m, 2H), 2.24 (s, 3H), 2.22-2.17 (m, 1H), 2.16-2.08 (m, 2H), 2.05-1.99 (d, J=16.6 Hz, 1H), 1.83-1.69 (m, 5H), 1.65-1.60 (m, 1H), 1.32 (s, 9H), 1.29-1.25 (m, 1H), 1.24-1.15 (m, 1H).

Step B. rac-(1R,2S,5R)-2-(7-Azabicyclo[2.2.1]heptan-7-ylmethyl)-1-acetamido-N-(tert-butyl)-5-(2-(4,4,5,5-tetramethyl-1,3,2-dioxaborolan-2-yl)ethyl)cyclohexanecarboxamide

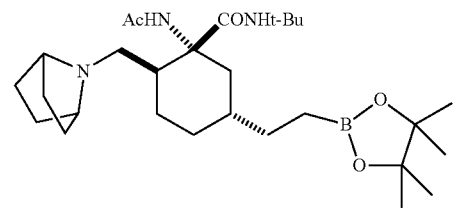

The title compound was prepared from rac-(1R,2S,5R)-2-(7-azabicyclo[2.2.1]heptan-7-ylmethyl)-1-acetamido-N-(tert-butyl)-5-vinylcyclohexanecarboxamide (85 mg, 0.23 mmol), using the procedure described in the preparation of Example 26, step B. The crude product was purified by flash chromatography on silica gel (DCM/MeOH 30:1 to 0:1) to afford 40 mg (35%) of the desired product as a colorless oil. ESI+MS: m/z=504.4 (M+1)$^+$. $^1$H NMR (700 MHz, chloroform-d) δ 9.00 (s, 1H), 8.45 (s, 1H), 4.08-4.02 (m, 1H), 3.95-3.90 (m, 1H), 3.56-3.50 (m, 1H), 3.47-3.41 (m, 1H), 3.21-3.12 (m, 2H), 2.60-2.52 (m, 1H), 2.51-2.44 (m, 1H), 2.26 (s, 3H), 2.23-2.06 (m, 4H), 1.82-1.71 (m, 5H), 1.67-1.61 (m, 1H), 1.34 (s, 9H), 1.27 (s, 12H), 1.24-1.20 (m, 1H), 1.14-1.07 (m, 1H), 1.04-0.97 (m, 1H), 0.95-0.88 (m, 1H), 0.86-0.79 (m, 1H), 0.77-0.70 (m, 1H).

Step C. rac-(1R,2S,5R)-2-(7-Azabicyclo[2.2.1]heptan-7-ylmethyl)-1-amino-5-(2-boronoethyl)cyclohexanecarboxylic acid dihydrochloride The title compound was prepared from rac-(1R,2S,5R)-2-(7-azabicyclo[2.2.1]heptan-7-ylmethyl)-1-acetamido-N-(tert-butyl)-5-(2-(4,4,5,5-tetramethyl-1,3,2-dioxaborolan-2-yl)ethyl)cyclohexanecarboxamide (40 mg, 0.079 mmol), using the procedure described in the preparation of Example 26, step C. The crude product was purified by ion exchange chromatography on DOWEX® and next by preparative HPLC (0.1-1% MeCN in water) to give (after acidification with 6M HCl and subsequent lyophilization) the desired product (22 mg, 70%) as a white solid. ESI+MS: m/z=325.25 (M+1)$^+$. $^1$H NMR (700 MHz, deuterium oxide) δ 4.12 (t, J=4.2 Hz, 1H), 4.08 (t, J=4.6 Hz, 1H), 3.21 (dd, J=13.8, 3.0 Hz, 1H), 3.03 (dd, J=13.8, 10.1 Hz, 1H), 2.22-2.18 (m, 1H), 2.12-2.06 (m, 1H), 2.05-1.91 (m, 5H), 1.91-1.85 (m, 1H), 1.85-1.72 (m, 5H), 1.71-1.63 (m, 1H), 1.31-1.19 (m, 3H), 0.92 (qd, J=12.8, 3.8 Hz, 1H), 0.72 (dd, J=9.0, 7.3 Hz, 2H).

Example 35. rac-(1R,2S,5R)-1-amino-5-(2-boronoethyl)-2-((3,4-dihydroisoquinolin-2(1H)-yl)methyl)cyclohexanecarboxylic acid dihydrochloride

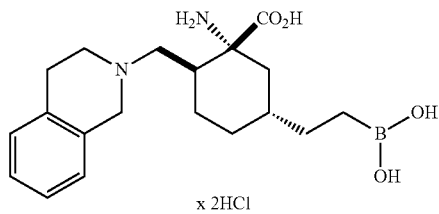 [SMILES: N[C@]1(C(=O)O)C[C@H](CCB(O)O)CC[C@H]1CN1CCc2ccccc2C1]

x 2HCl

Step A. rac-(1R,2S,5R)-1-Acetamido-N-(tert-butyl)-2-((3,4-dihydroisoquinolin-2(1H)-yl)methyl)-5-vinylcyclohexanecarboxamide

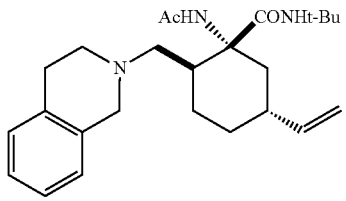

The title compound was prepared from rac-(1R,2R,4R)-2-acetamido-2-(tert-butylcarbamoyl)-4-vinylcyclohexane-1-carboxylate (Intermediate 1, 300 mg, 0.89 mmol), using the procedure described in the preparation of Example 101, step A. The crude product was purified by flash chromatography on silica gel (DCM/MeOH 100:1 to 90:1)) to afford 88 mg (24%) of the desired product as a colorless oil. ESI+MS: m/z=412.45 (M+1)$^+$, 434.5 (M+Na)$^+$. $^1$H NMR (700 MHz, chloroform-d) δ 10.29 (s, 1H), 8.23 (s, 1H), 7.17-7.09 (m, 3H), 7.06-7.01 (m, 1H), 5.73 (ddd, J=17.1, 10.4, 6.5 Hz, 1H), 5.06-4.87 (m, 2H), 3.83-3.73 (m, 1H), 3.67-3.52 (m, 2H), 3.24-3.18 (m, 1H), 3.03-2.95 (m, 1H), 2.92 (t, J=5.9 Hz, 2H), 2.70-2.60 (m, 1H), 2.36-2.29 (m, 1H), 2.25-2.16 (m, 1H), 2.14-2.05 (m, 1H), 1.87-1.80 (m, 1H), 1.75-1.64 (m, 1H), 1.60 (s, 3H), 1.46-1.40 (m, 1H), 1.34 (s, 9H), 1.26-1.15 (m, 2H).

Step B. rac-(1R,2S,5R)-1-Acetamido-N-(tert-butyl)-2-((3,4-dihydroisoquinolin-2(1H)-yl)methyl)-5-(2-(4,4,5,5-tetramethyl-1,3,2-dioxaborolan-2-yl)ethyl)cyclohexanecarboxamide

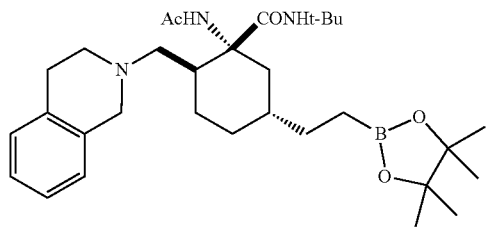

The title compound was prepared from rac-(1R,2S,5R)-1-acetamido-N-(tert-butyl)-2-((3,4-dihydroisoquinolin-2

(1H)-yl)methyl)-5-vinylcyclohexanecarboxamide (85 mg, 0.206 mmol), using the procedure described in the preparation of Example 26, step B. The crude product was purified by flash chromatography on silica gel (DCM/MeOH 100:1 to 0:1)) to afford 78 mg (70%) of the desired product as a colorless oil. ESI+MS: m/z=540.7 (M+1)$^+$, 562.65 (M+Na)$^+$. $^1$H NMR (700 MHz, chloroform-d) δ 10.26 (s, 1H), 8.27 (s, 1H), 7.16-7.12 (m, 2H), 7.11-7.08 (m, 1H), 7.05-7.03 (m, 1H), 3.80-3.72 (m, 1H), 3.68-3.59 (m, 1H), 3.62-3.53 (m, 1H), 3.51-3.47 (m, 1H), 3.23-3.18 (m, 1H), 3.03-2.94 (m, 1H), 2.91 (t, J=5.9 Hz, 2H), 2.69-2.57 (m, 1H), 2.33-2.28 (m, 1H), 2.17-2.10 (m, 1H), 1.83-1.78 (m, 1H), 1.71-1.64 (m, 1H), 1.59 (s, 3H), 1.42-1.37 (m, 1H), 1.32 (s, 9H), 1.31-1.28 (m, 1H), 1.24 (s, 12H), 1.03-0.94 (m, 2H), 0.91-0.78 (m, 2H), 0.77-0.69 (m, 1H).

Step C. rac-(1R,2S,5R)-1-Amino-5-(2-boronoethyl)-2-((3,4-dihydroisoquinolin-2(1H)-yl)methyl)cyclohexanecarboxylic acid dihydrochloride The title compound was prepared from (1R,2S,5R)-1-acetamido-N-(tert-butyl)-2-((3,4-dihydroisoquinolin-2(1H)-yl)methyl)-5-(2-(4,4,5,5-tetramethyl-1,3,2-dioxaborolan-2-yl)ethyl)cyclohexanecarboxamide (78 mg, 0.145 mmol), using the procedure described in the preparation of Example 26, step C. The crude product was purified by ion exchange chromatography on DOWEX® and next by preparative HPLC (0.1-10% MeCN in water) to give (after acidification with 6M HCl) the desired product (3.1 mg, 5%) as a white solid. ESI+MS: =361.4 (M+1)$^+$. $^1$H NMR (700 MHz, deuterium oxide) δ 7.46-7.14 (m, 4H), 4.63-4.54 (m, 1H), 4.43-4.24 (m, 1H), 3.89-3.74 (m, 1H), 3.52-3.44 (m, 1H), 3.44-3.05 (m, 4H), 2.29-2.20 (m, 2H), 1.93-1.83 (m, 3H), 1.79-1.68 (m, 1H), 1.34-1.22 (m, 3H), 1.02-0.91 (m, 1H), 0.77-0.70 (m, 2H).

Example 36. rac-(1R,2S,5R)-1-amino-5-(2-boronoethyl)-2-(((2,2,2-trifluoroethyl)amino)methyl)cyclohexanecarboxylic acid dihydrochloride

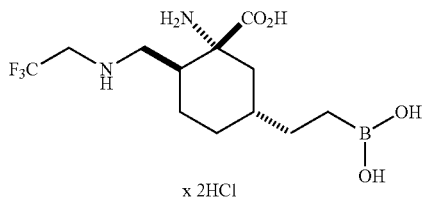 [SMILES: N[C@]1(C(=O)O)C[C@H](CCB(O)O)CC[C@H]1CNCC(F)(F)F]

Step A. rac-(1R,2S,5R)-1-acetamido-N-(tert-butyl)-2-(((2,2,2-trifluoroethyl)amino)methyl)-5-vinylcyclohexanecarboxamide

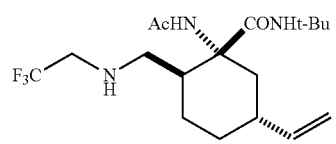

The title compound rac-(1R,2S,5R)-1-acetamido-N-(tert-butyl)-2-(((2,2,2-trifluoroethyl)amino)methyl)-5-vinylcyclohexanecarboxamide was obtained in the same manner like in Example 26, step A, using rac-(1R,2R,4R)-2-acetamido-2-(tert-butylcarbamoyl)-4-vinylcyclohexane-1-carboxylate (Intermediate 1, 400 mg, 1.18 mmol, 1 equiv.), DIBAL-H 1M in DCM (3.66 mL, 3.66 mmol, 3.1 equiv.), glacial acetic acid (337 μL, 5.9 mmol, 5 equiv.), 2,2,2-trifluoroethylamine hydrochloride (480 mg, 3.54 mmol, 3 equiv.), sodium triacetoxyborohydride (1.0 g, 4.72 mmol, 4 equiv.). The residue was purified by flash chromatography on silica gel (hexane/AcOEt 2:1 to 1:1) to give corresponding product as a single diastereoisomer (50 mg, 11%, white solid). ESI+MS: m/z=378.2 (M+1)$^+$; ESI-MS: m/z=376.1 (M−1)$^-$. $^1$H NMR (700 MHz, Chloroform-d) δ 9.21 (s, 1H), 8.26 (s, 1H), 5.71 (ddd, J=17.1, 10.4, 6.5 Hz, 1H), 4.99-4.91 (m, 2H), 3.57 (t, J=10.8 Hz, 1H), 3.25-3.20 (m, 3H), 3.18-3.07 (m, 1H), 2.79 (d, J=12.9 Hz, 1H), 2.16 (qd, J=13.3, 4.3 Hz, 1H), 2.10-2.02 (m, 1H), 1.93 (s, 3H), 1.85-1.76 (m, 1H), 1.51-1.46 (m, 1H), 1.45-1.39 (m, 1H), 1.32 (s, 8H), 1.20-1.10 (m, 2H).

Step B. rac-(1R,2S,5R)-1-acetamido-N-(tert-butyl)-5-(2-(4,4,5,5-tetramethyl-1,3,2-dioxaborolan-2-yl)ethyl)-2-(((2,2,2-trifluoroethyl)amino)methyl)cyclohexanecarboxamide

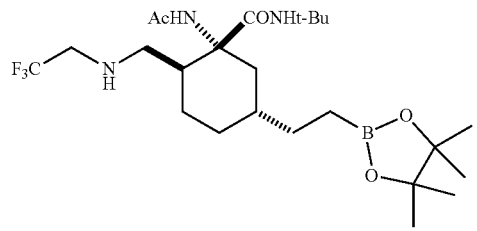

The title compound rac-(1R,2S,5R)-1-acetamido-N-(tert-butyl)-5-(2-(4,4,5,5-tetramethyl-1,3,2-dioxaborolan-2-yl)ethyl)-2-(((2,2,2-trifluoroethyl)amino)methyl)cyclohexanecarboxamide was obtained in the same manner like in Example 26, step B, using rac-(1R,2S,5R)-1-acetamido-N-(tert-butyl)-2-(((2,2,2-trifluoroethyl)amino)methyl)-5-vinylcyclohexanecarboxamide (40 mg, 0.11 mmol, 1 equiv.), dppe (2.5 mg, 0.006 mmol, 0.06 equiv.), bis(1,5-cyclooctadiene)diiridium(I) dichloride (2.1 mg, 0.003 mmol, 0.03 equiv.), 4,4,5,5-tetramethyl-1,3,2-dioxaborolane (23 μL, 0.16 mmol, 1.5 equiv.) and DCM (2 mL). The crude product was purified by column chromatography on silica gel (hexane/AcOEt 10:1 to 1:2) to give corresponding product as a single diastereoisomer (40 mg, 56%, white solid). ESI+MS: m/z=506.4 (M+1)$^+$. $^1$H NMR (700 MHz, Chloroform-d) δ 9.18 (s, 1H), 8.28 (s, 1H), 3.61-3.55 (m, 1H), 3.29-3.17 (m, 2H), 3.17-3.08 (m, 1H), 2.76 (d, J=12.8 Hz, 1H), 2.08 (qd, J=13.1, 4.3 Hz, 1H), 1.92 (s, 3H), 1.81-1.72 (m, 1H), 1.66-1.57 (m, 1H), 1.49-1.38 (m, 2H), 1.36-1.31 (m, 1H), 1.31 (s, 9H), 1.23 (s, 12H), 1.03-0.86 (m, 3H), 0.80 (ddd, J=17.1, 11.0, 6.1 Hz, 1H), 0.72 (ddd, J=16.0, 11.0, 5.5 Hz, 1H).

Step C. rac-(1R,2S,5R)-1-amino-5-(2-boronoethyl)-2-(((2,2,2-trifluoroethyl)amino)methyl)cyclohexanecarboxylic acid dihydrochloride The title compound rac-(1R,2S,5R)-1-amino-5-(2-boronoethyl)-2-(((2,2,2-trifluoroethyl)amino)methyl)cyclohexanecarboxylic acid dihydrochloride was obtained in the same manner like in Example 26, step C, using (1R,2S,5R)-

1-acetamido-N-(tert-butyl)-5-(2-(4,4,5,5-tetramethyl-1,3,2-dioxaborolan-2-yl)ethyl)-2-(((2,2,2-trifluoroethyl)amino)methyl)cyclohexanecarboxamide (30 mg, 0.06 mmol, 1 equiv.) and 6N HCl$_{aq}$ (2 mL). The residue was purified by preparative HPLC (0.1-5% MeCN in water) to give (after acidification with 6N HCl and subsequent lyophilization) corresponding product as a single diastereoisomer (0.8 mg, 3%, white solid). ESI+MS: m/z=309.2 (M–18)$^+$. $^1$H NMR (700 MHz, Deuterium Oxide) δ 4.30-4.22 (m, 1H), 4.15-4.03 (m, 1H), 3.98 (dd, J=11.0, 5.8 Hz, 1H), 3.38 (d, J=11.0 Hz, 1H), 2.61-2.55 (m, 1H), 2.39-2.32 (m, 1H), 2.19-2.13 (m, 1H), 1.82-1.75 (m, 1H), 1.47-1.36 (m, 3H), 1.34-1.27 (m, 1H), 1.17-1.08 (m, 1H), 1.07-0.99 (m, 1H), 0.86-0.80 (m, 2H).

Example 37. rac-(1R,2S,5R)-1-amino-5-(2-boronoethyl)-2-(((4-methoxyphenyl)(methyl)amino)methyl)cyclohexanecarboxylic acid dihydrochloride

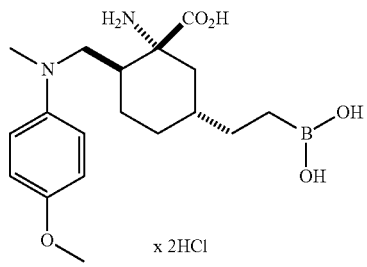 [SMILES: COc1ccc(N(C)C[C@@H]2CC[C@@H](CCB(O)O)C[C@]2(N)C(=O)O)cc1]

Step A. rac-(1R,2S,5R)-1-acetamido-N-(tert-butyl)-2-(((4-methoxyphenyl)(methyl)amino)methyl)-5-vinylcyclohexane-1-carboxamide

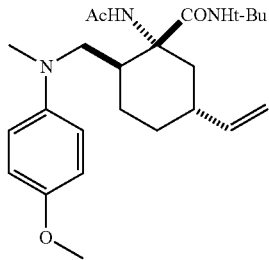

To a solution of ethyl rac-(1R,2R,4R)-2-acetamido-2-(tert-butylcarbamoyl)-4-vinylcyclohexanecarboxylate (Intermediate 1, 317 mg, 0.94 mmol, 1 equiv.) in dry dichloromethane (20 mL) a solution of DIBAL-H 1M in DCM (2.80 mL, 2.80 mmol, 2.98 equiv.) was added dropwise at –78° C. under argon. The reaction was stirred at –78° C. and monitored by TLC (hexane:AcOEt 1:5). After 1 h the reaction mixture was quenched with glacial acetic acid (268 μL, 4.70 mmol, 5 equiv.) and was stirred at –78° C. for 10 min. Then, p-methoxy-N-methylaniline (258 mg, 1.88 mmol, 2 equiv.) was added dropwise and cooling bath was removed. After 15 min sodium triacetoxyborohydride (798 mg, 3.76 mmol, 4 equiv.) was added portionwise and the resulting mixture was allowed to warm to room temperature and then was stirred overnight. The mixture was diluted with dichloromethane and organic layer was washed with 1N NaOH (10 mL) and brine, dried over MgSO$_4$, filtered and concentrated in vacuo. The residue was purified by silica gel flash chromatography (gradient elution, DCM:MeOH, 1:0 to 3:1) to give corresponding product rac-(1R,2S,5R)-1-acetamido-N-(tert-butyl)-2-(((4-methoxyphenyl)(methyl)amino)methyl)-5-vinylcyclohexanecarboxamide (yield: 212 mg, 54%, colorless oil). ESI+ MS: m/z=416.50 (M+1)$^+$. $^1$H NMR (700 MHz, Chloroform-d) δ 8.99 (s, 1H), 8.31 (s, 1H), 6.90-6.86 (m, 2H), 6.85-6.82 (m, 2H), 5.72 (ddd, 1H, J=17.1, 10.4, 6.5 Hz), 4.98 (dt, 1H, J=17.3, 1.5 Hz), 4.92 (dt, 1H, J=10.4, 1.7 Hz), 4.14-4.07 (m, 2H), 3.77 (s, 3H), 3.20 (dt, 1H, J=13.4, 2.4 Hz), 2.89 (dd, 1H, J=14.7, 2.35 Hz), 2.80 (s, 3H), 2.18 (qd, 1H, J=13.2, 4.4 Hz), 2.14-2.08 (m, 1H), 1.86-1.81 (m, 1H), 1.79-1.73 (m, 4H), 1.53-1.47 (m, 1H), 1.36 (s, 9H), 1.18 (qd, 1H, J=12.9, 4.4 Hz).

Step B. rac-(1R,2S,5R)-1-acetamido-N-(tert-butyl)-2-(((4-methoxyphenyl)(methyl)amino)methyl)-5-(2-(4,4,5,5-tetramethyl-1,3,2-dioxaborolan-2-yl)ethyl)cyclohexane-1-carboxamide

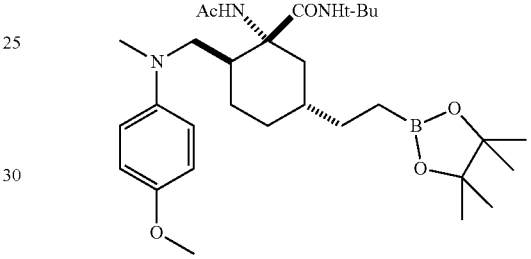

A mixture of dppe (12.2 mg, 0.031 mmol, 0.06 equiv.) and bis(1,5-cyclooctadiene)diiridium(I) dichloride (10.3 mg, 0.015 mmol, 0.03 equiv.) in dichloromethane (5 mL) was flushed with argon (bubbling). Subsequently, the separately prepared solution of the 4,4,5,5-tetramethyl-1,3,2-dioxaborolane (0.11 μL, 0.76 mmol, 1.5 equiv.) and rac-(1R,2S,5R)-1-acetamido-N-(tert-butyl)-2-(((4-methoxyphenyl)(methyl)amino)methyl)-5-vinylcyclohexanecarboxamide (212 mg, 0.51 mmol, 1 equiv.) in of dry CH$_2$Cl$_2$ (5 mL) was added successively at room temperature. The resulting mixture was stirred at room temperature overnight. Product was concentrated in vacuo and purified by flash chromatography on silica gel (gradient elution, hexane/AcOEt 1:0 to 3:1) to give rac-(1R,2S,5R)-1-acetamido-N-(tert-butyl)-2-(((4-methoxyphenyl)(methyl)amino)methyl)-5-(2-(4,4,5,5-tetramethyl-1,3,2-dioxaborolan-2-yl)ethyl)cyclohexanecarboxamide (41 mg, 15%, colorless oil). ESI+MS: m/z=543.95 (M+1)$^+$. $^1$H NMR (700 MHz, Chloroform-d) δ 8.94 (s, 1H), 8.34 (s, 1H), 6.88-6.85 (m, 2H), 6.85-6.81 (m, 2H), 4.15-4.10 (m, 2H), 3.77 (s, 3H), 3.49 (d, 1H, J=5.2 Hz), 3.20-3.16 (m, 1H), 2.86 (dd, 1H, J=14.9, 2.1 Hz), 2.79 (s, 3H), 2.10 (qd, 1H, J=13.3, 4.1 Hz), 1.84-1.79 (m, 1H), 1.78-1.72 (m, 4H), 1.48-1.43 (m, 1H), 1.35 (s, 9H), 1.34-1.25 (m, 3H), 1.23 (s, 12H), 0.85-0.78 (m, 2H).

Step C. rac-(1R,2S,5R)-1-amino-5-(2-boronoethyl)-2-(((4-methoxyphenyl)(methyl)amino)methyl)cyclohexanecarboxylic acid dihydrochloride A mixture of (1R,2S,5R)-1-acetamido-N-(tert-butyl)-2-(((4-methoxyphenyl)(methyl)amino)methyl)-5-(2-(4,4,5,5-tetramethyl-1,3,2-dioxaborolan-2-yl)ethyl)cyclohexanecarboxamide (41 mg, 0.075 mmol, 1 equiv.) and 6 N HCl$_{aq}$ (15 mL) was heated under reflux for 6 h. The reaction mixture was concentrated under reduced pressure and the residue was purified by preparative HPLC (gradient elution, 5-50%, MeCN in H₂O) acidified with 6N HCl and freeze dried to give rac-(1R,2S,5R)-1-amino-5-(2-boronoethyl)-2-(((4-methoxyphenyl)(methyl)amino)methyl)cyclohexanecarboxylic acid dihydrochloride (4.7 mg, 17%, white solid). ESI+ MS: m/z=365.25 (M+1)⁺. ¹H NMR (700 MHz, Chloroform-d) δ 7.60-7.56 (m, 2H), 7.25-7.21 (m, 2H), 3.95-3.88 (m, 4H), 3.61 (dd, 1H, J=10.8, 13.1), 3.34 (s, 3H), 2.27-2.21 (m, 1H), 1.96-1.81 (m, 3H), 1.78-1.71 (m, 1H), 1.71-1.63 (m, 1H), 1.35-1.26 (m, 2H), 1.22-1.18 (m, 1H), 1.18-1.12 (m, 1H), 0.81-0.74 (m, 2H).

Example 38. (1R,2S,5R)-1-amino-5-(2-boronoethyl)-2-((dimethylamino)methyl)cyclohexanecarboxylic acid

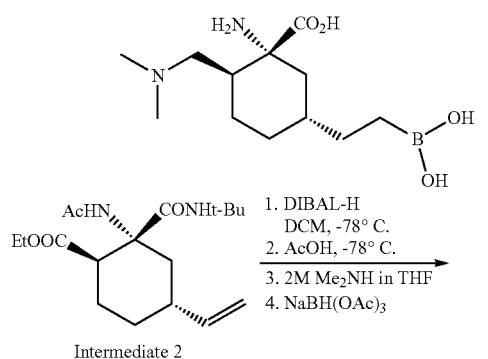

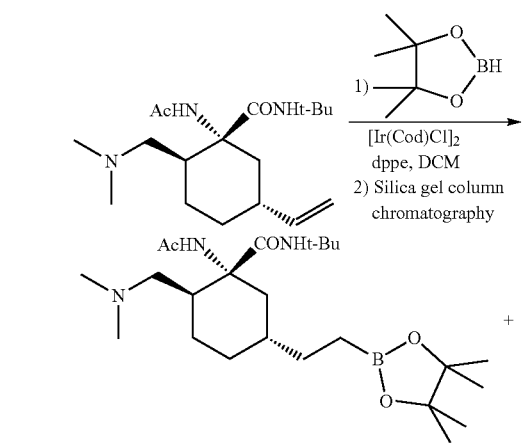

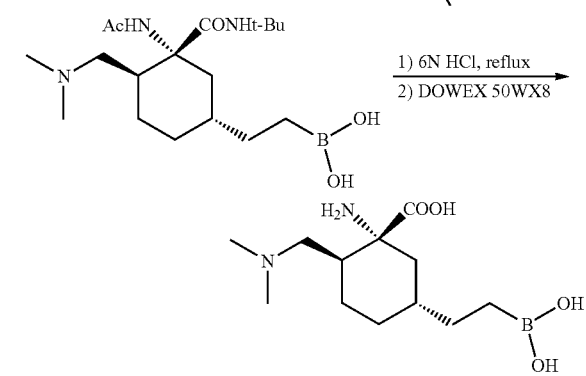

Step A. (1R,2S,5R)-(+)-1-acetamido-N-(tert-butyl)-2-((dimethylamino)methyl)-5-vinylcyclohexanecarboxamide

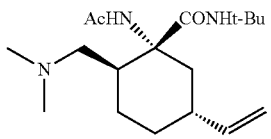

The title compound (1R,2S,5R)-1-acetamido-N-(tert-butyl)-2-((dimethylamino)methyl)-5-vinylcyclohexanecarboxamide was obtained in the same manner like in Example 26, step A, using ethyl (1R,2R,4R)-2-acetamido-2-(tert-butylcarbamoyl)-4-vinylcyclohexane-1-carboxylate (Intermediate 2, 2.5 g, 7.39 mmol, 1 equiv.), DIBAL-H 1M in DCM (22.9 mL, 22.9 mmol, 3.1 equiv.), glacial acetic acid (2.1 mL, 36.93 mmol, 5 equiv.), 2M solution of dimethylamine in THF (7.40 mL, 14.77 mmol, 2 equiv.), sodium triacetoxyborohydride (6.26 g, 29.55 mmol, 4 equiv.). The crude product was purified by silica gel flash chromatography (DCM/MeOH, 50:1 to 10:1) to give corresponding product as a single diastereoisomer (1.69 g, 70%, white solid). ESI+MS: m/z=324.2 (M+1)⁺. [α]$_D$=+114.95 (c=0.455 in CHCl₃). ¹H NMR (700 MHz, Chloroform-d) δ 10.22 (s, 1H), 8.22 (s, 1H), 5.72 (ddd, J=17.1, 10.4, 6.5 Hz, 1H), 4.97 (dt, J=17.3, 1.5 Hz, 1H), 4.93-4.88 (m, 1H), 3.40 (dd, J=13.4, 10.6 Hz, 1H), 3.21 (d, J=13.3 Hz, 1H), 2.25 (s, 6H), 2.19-2.06 (m, 2H), 1.99 (d, J=13.5 Hz, 1H), 1.90 (s, 3H), 1.82-1.78 (m, 1H), 1.56-1.50 (m, 1H), 1.39-1.35 (m, 1H), 1.33 (s, 9H), 1.21-1.11 (m, 2H).

Step B. (1R,2S,5R)-1-acetamido-N-(tert-butyl)-2-((dimethylamino)methyl)-5-(2-(4,4,5,5-tetramethyl-1,3,2-dioxaborolan-2-yl)ethyl)cyclohexanecarboxamide and (2-((1R,3R,4S)-3-acetamido-3-(tert-butylcarbamoyl)-4-((dimethylamino)methyl)cyclohexyl)ethyl)boronic acid

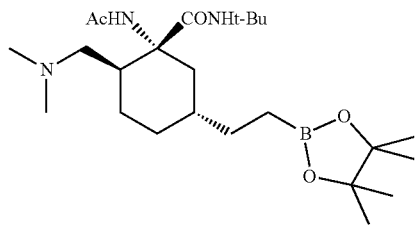

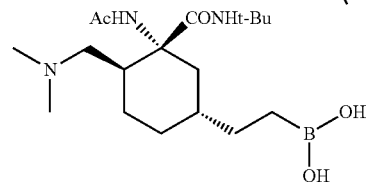

The title compounds (1R,2S,5R)-1-acetamido-N-(tert-butyl)-2-((dimethylamino)methyl)-5-(2-(4,4,5,5-tetramethyl-1,3,2-dioxaborolan-2-yl)ethyl)cyclohexanecarboxamide and (2-((1R,3R,4S)-(+)-3-acetamido-3-(tert-butylcarbamoyl)-4-((dimethylamino)methyl)cyclohexyl)ethyl)boronic acid were obtained in the same manner like in Example 26, step B, using (1R,2S,5R)-1-acetamido-N-(tert-butyl)-2-((dimethylamino)methyl)-5-vinylcyclohexanecarboxamide (1.59 g, 4.91 mmol, 1 equiv.), dppe (0.12 g, 0.29 mmol, 0.06 equiv.), bis(1,5-cyclooctadiene)diiridium(I) dichloride (0.10 g, 0.15 mmol, 0.03 equiv.), 4,4,5,5-tetramethyl-1,3,2-dioxaborolane (1.78 mL, 12.29 mmol, 2.5 equiv.) and DCM (60 mL). The crude product was purified by column chromatography on silica gel (gradient elution, DCM/MeOH 40:1 to 5:1) to give corresponding products as a single diastereoisomers (1.49 g, 68%).

(1R,2S,5R)-1-acetamido-N-(tert-butyl)-2-((dimethylamino)methyl)-5-(2-(4,4,5,5-tetramethyl-1,3,2-dioxaborolan-2-yl)ethyl)cyclohexanecarboxamide: 0.86 g, sticky, pale yellow solid. ESI+MS: m/z=452.4 (M+1)$^+$. $^1$H NMR (700 MHz, Chloroform-d) δ 10.21 (s, 1H), 8.26 (s, 1H), 3.45-3.38 (m, 1H), 3.19 (d, J=13.3 Hz, 1H), 2.24 (s, 6H), 2.15-2.03 (m, 1H), 2.00-1.94 (m, 1H), 1.89 (s, 3H), 1.86-1.74 (m, 1H), 1.56-1.44 (m, 2H), 1.31 (s, 12H), 1.30-1.24 (m, 2H), 1.23 (s, 9H), 1.22-1.20 (m, 1H), 1.01-0.90 (m, 2H), 0.76 (ddd, J=47.1, 10.9, 5.4 Hz, 2H). During the purification on silica gel column chromatography pinacolboronate ester was partially deprotected to give a free boronic acid (2-((1R,3R,4S)-3-acetamido-3-(tert-butylcarbamoyl)-4-((dimethylamino)methyl)cyclohexyl)ethyl)boronic acid: 0.63 g, yellowish foam. [α]$_D$=+48.15 (c=0.34 in CHCl$_3$). ESI+MS: m/z=370.2 (M+1)$^+$. $^1$H NMR (700 MHz, Chloroform-d) δ 10.24 (s, 1H), 8.16 (s, 1H), 4.57-4.54 (m, 1H), 3.46-3.36 (m, 1H), 3.23-3.14 (m, 1H), 2.47-2.30 (m, 1H), 2.24 (s, 6H), 2.15-2.03 (m, 2H), 1.98 (dt, J=15.6, 6.6 Hz, 1H), 1.90 (s, 3H), 1.81-1.74 (m, 1H), 1.67-1.60 (m, 2H), 1.33 (d, J=7.8 Hz, 1H), 1.31 (s, 9H), 1.29-1.25 (m, 2H), 0.99 (dd, J=14.1, 9.4 Hz, 2H), 0.89-0.70 (m, 1H).

Step C. (1R,2S,5R)-1-amino-5-(2-boronoethyl)-2-((dimethylamino)methyl)cyclohexanecarboxylic acid The title compound (1R,2S,5R)-1-amino-5-(2-boronoethyl)-2-((dimethylamino)methyl)cyclohexanecarboxylic acid was obtained in the same manner like in Example 26, step C, using (2-((1R,3R,4S)-3-acetamido-3-(tert-butylcarbamoyl)-4-((dimethylamino)methyl)cyclohexyl)ethyl)boronic acid (0.63 g, 1.70 mmol, 1 equiv.), 6 N HCl$_{aq}$ (40 mL). The crude product was purified by flash chromatography on DOWEX® 50WX8 ion exchange resin (eluent 0.1 N ammonia in water) to give a desired product as a white solid (0.43 g, 73%). ESI+MS: m/z=273.3 (M+1)$^+$. [α]$_D$=−44.8 (c=0.125 in H$_2$O). $^1$H NMR (700 MHz, Deuterium Oxide) δ 2.87 (dd, J=13.1, 9.5 Hz, 1H), 2.63 (dd, J=13.2, 4.7 Hz, 1H), 2.46 (s, 6H), 2.00 (ddd, J=13.0, 3.5, 1.9 Hz, 1H), 1.81-1.72 (m, 2H), 1.59 (dddt, J=16.5, 12.8, 10.4, 3.4 Hz, 2H), 1.54-1.48 (m, 1H), 1.22 (ddt, J=11.5, 6.9, 2.9 Hz, 2H), 1.01 (t, J=12.6 Hz, 1H), 0.88 (qd, J=12.9, 4.2 Hz, 1H), 0.72-0.67 (m, 2H).

(1R,2S,5R)-1-amino-5-(2-boronoethyl)-2-((dimethylamino)methyl)cyclohexanecarboxylic acid dihydrochloride Treatment of (1R,2S,5R)-1-amino-5-(2-boronoethyl)-2-((dimethylamino)methyl)cyclohexanecarboxylic acid with 6N HCl$_{aq}$ and subsequent lyophilization afforded dihydrochloride salt as a white solid in quantitative yield. ESI+MS: m/z=273.3 (M+1)$^+$. [α]$_D$=+6.98 (c=0.345 in H$_2$O). $^1$H NMR (700 MHz, Deuterium Oxide) δ 3.27 (dd, J=13.3, 2.6 Hz, 1H), 3.23-3.16 (m, 1H), 2.90 (s, 3H), 2.84 (s, 3H), 2.25 (d, J=14.9 Hz, 1H), 2.13 (s, 1H), 1.87 (d, J=12.8 Hz, 2H), 1.82-1.75 (m, 1H), 1.71-1.62 (m, 1H), 1.33-1.25 (m, 3H), 0.98-0.90 (m, 1H), 0.72 (dd, J=9.1, 7.3 Hz, 2H).

Example 39. (1R,2S,5R)-1-amino-5-(2-boronoethyl)-2-((methylamino)methyl)cyclohexanecarboxylic acid dihydrochloride

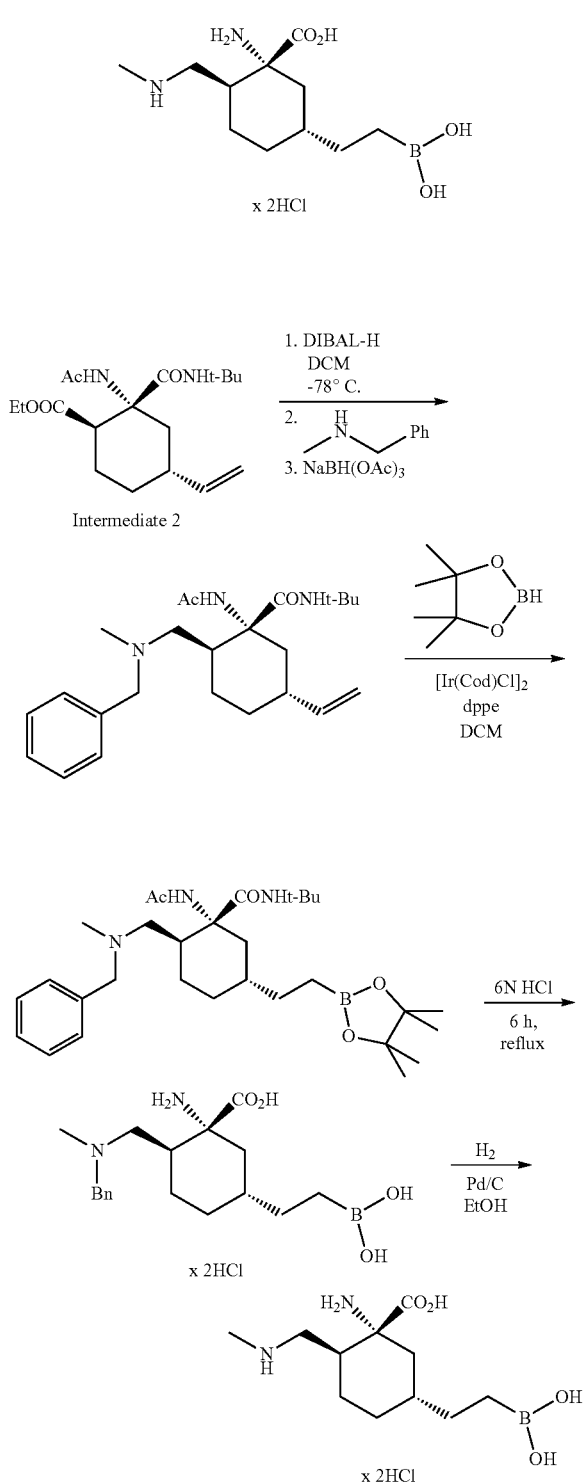

Step A. (1R,2S,5R)-1-acetamido-2-((benzyl(methyl)amino)methyl)-N-(tert-butyl)-5-vinylcyclohexanecarboxamide

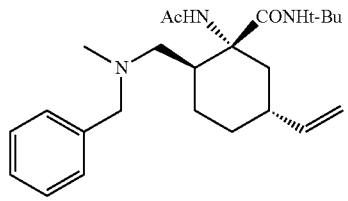

The title compound (1R,2S,5R)-1-acetamido-2-((benzyl(methyl)amino)methyl)-N-(tert-butyl)-5-vinylcyclohexanecarboxamide was obtained in the same manner like in Example 26, step A, using ethyl (1R,2R,4R)-2-acetamido-2-(tert-butylcarbamoyl)-4-vinylcyclohexane-1-carboxylate (Intermediate 2, 400 mg, 1.18 mmol, 1 equiv.), DIBAL-H 1M in DCM (3.66 mL, 3.66 mmol, 3.1 equiv.), glacial acetic acid (0.34 mL, 5.90 mmol, 5 equiv.), N-benzylmethylamine (0.38 mL, 2.95 mmol, 2.5 equiv.), sodium triacetoxyborohydride (1.0 g, 4.72 mmol, 4 equiv.) and DCM (30 mL). The residue was purified by silica gel flash chromatography (DCM:MeOH 20:1) to give corresponding product as a single diastereoisomer (418 mg, 84%, yellow oil). ESI+MS: m/z=400.3 (M+1)+ 1H NMR (700 MHz, Chloroform-d) δ 9.92 (s, 1H), 8.22 (s, 1H), 7.37-7.18 (m, 5H), 5.72 (ddd, J=17.1, 10.4, 6.5 Hz, 1H), 5.04-4.85 (m, 2H), 3.59 (dd, J=13.5, 9.8 Hz, 2H), 3.29 (dd, J=88.2, 13.0 Hz, 2H), 2.21 (s, 3H), 2.19-2.13 (m, 2H), 2.12-2.03 (m, 1H), 1.85 (s, 3H), 1.82-1.76 (m, 1H), 1.64-1.57 (m, 1H), 1.43-1.38 (m, 1H), 1.29 (s, 9H), 1.19-1.11 (m, 2H).

Step B. (1R,2S,5R)-1-acetamido-2-((benzyl(methyl)amino)methyl)-N-(tert-butyl)-5-(2-(4,4,5,5-tetramethyl-1,3,2-dioxaborolan-2-yl)ethyl)cyclohexanecarboxamide

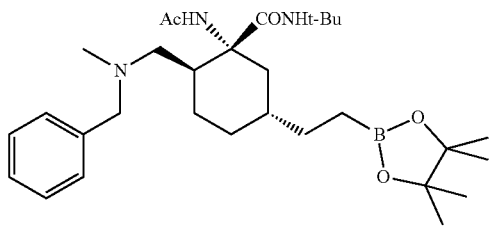

The title compound (1R,2S,5R)-1-acetamido-2-((benzyl(methyl)amino)methyl)-N-(tert-butyl)-5-(2-(4,4,5,5-tetramethyl-1,3,2-dioxaborolan-2-yl)ethyl)cyclohexanecarboxamide was obtained in the same manner like in Example 26, step B, using compound (1R,2S,5R)-1-acetamido-2-((benzyl(methyl)amino)methyl)-N-(tert-butyl)-5-vinylcyclohexanecarboxamide (405 mg, 1.01 mmol, 1 equiv.), dppe (24.1 mg, 0.0606 mmol, 0.06 equiv.), bis(1,5-cyclooctadiene)diiridium(I) dichloride (20.4 mg, 0.0303 mmol, 0.03 equiv.), 4,4,5,5-tetramethyl-1,3,2-dioxaborolane (0.3 mL, 2.02 mmol, 2 equiv.) and DCM (6 mL). The crude product was purified by column chromatography on silica gel (gradient elution, DCM/MeOH 40:1 to 20:1) to give corresponding product as a single diastereoisomer (387 mg, 72%, yellow oil). ESI+MS: m/z=528.45 (M+1)+, 1H NMR (700 MHz, Chloroform-d) δ 9.94 (s, 1H), 8.19 (s, 1H), 7.37-7.18 (m, 5H), 3.64-3.56 (m, 2H), 3.37-3.18 (m, 2H), 2.20 (s, 3H), 2.17-2.05 (m, 2H), 1.84 (s, 3H), 1.71-1.66 (m, 4H), 1.41-1.29 (m, 2H), 1.28 (s, 9H), 1.23 (s, 12H), 1.03-0.90 (m, 2H), 0.85-0.68 (m, 2H).

Step C. (1R,2S,5R)-1-amino-2-((benzyl(methyl)amino)methyl)-5-(2-boronoethyl)cyclohexanecarboxylic acid dihydrochloride

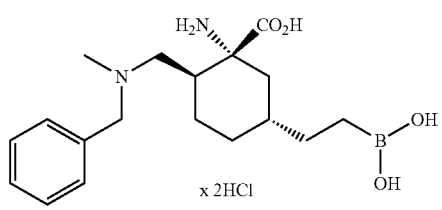 [SMILES: CN(Cc1ccccc1)C[C@@H]1CC[C@@H](CCB(O)O)C[C@]1(N)C(=O)O]

The title compound (1R,2S,5R)-1-amino-2-((benzyl(methyl)amino)methyl)-5-(2-boronoethyl)cyclohexanecarboxylic acid dihydrochloride was obtained in the same manner like in Example 26, step C, using (1R,2S,5R)-1-acetamido-2-((benzyl(methyl)amino)methyl)-N-(tert-butyl)-5-(2-(4,4,5,5-tetramethyl-1,3,2-dioxaborolan-2-yl)ethyl)cyclohexanecarboxamide (145 mg, 0.275 mmol, 1 equiv.) and 6 N HCl$_{aq}$ (10 mL). The residue was purified by preparative HPLC (5-30% MeCN in water) to give (after acidification with 6N HCl and subsequent lyophilization) product as a single diastereoisomer (51.2 mg, 53%, white solid). ESI+MS: m/z=349.25 (M+1)+. 1H NMR (700 MHz, Deuterium Oxide) δ 7.74-7.26 (m, 5H), 4.35 (dd, J=76.1, 13.0 Hz, 2H), 3.33-3.11 (m, 2H), 2.87 (s, 3H), 2.37-2.16 (m, 1H), 2.10-1.83 (m, 2H), 1.82-1.37 (m, 3H), 1.36-1.15 (m, 3H), 1.00-0.81 (m, 1H), 0.76-0.63 (m, 2H).

Step D. (1R,2S,5R)-1-amino-5-(2-boronoethyl)-2-((methylamino)methyl)cyclohexanecarboxylic acid dihydrochloride (1R,2S,5R)-1-amino-2-((benzyl(methyl)amino)methyl)-5-(2-boronoethyl)cyclohexanecarboxylic acid dihydrochloride (45 mg, 0.13 mmol, 1 equiv.) was dissolved in 2 mL of absolute EtOH and flushed with argon. Next, 8 mg of Pd/C wet 10% was added and the resulting mixture was stirred under hydrogen atmosphere (balloon) for 3 h. Then, a mixture was filtered through the pad of Celite (washed several times with EtOH$_{abs}$) and solvent was evaporated. The residue was dissolved in water and lyophilized to give product as a single diastereoisomer (21.7 mg, 65%, white solid). ESI+MS: m/z=259.15 (M+1)+. [α]$_D$=−39.8 (c=0.125 in H$_2$O). 1H NMR (700 MHz, Deuterium Oxide) δ 3.48 (m, 1H), 3.31-3.25 (m, 1H), 2.94 (s, 3H), 2.53-2.43 (m, 1H), 2.33-2.25 (s, 1H), 2.17-2.08 (m, 3H), 2.05-1.95 (m, 1H), 1.94-1.85 (m, 1H), 1.56-1.48 (m, 3H), 1.21-1.13 (m, 1H), 1.00-0.92 (m, 2H).

Example 40. rac-(1R,2S,5R)-1-amino-5-(2-borono-ethyl)-2-((methyl(phenyl)amino)methyl)cyclohexan-ecarboxylic acid dihydrochloride

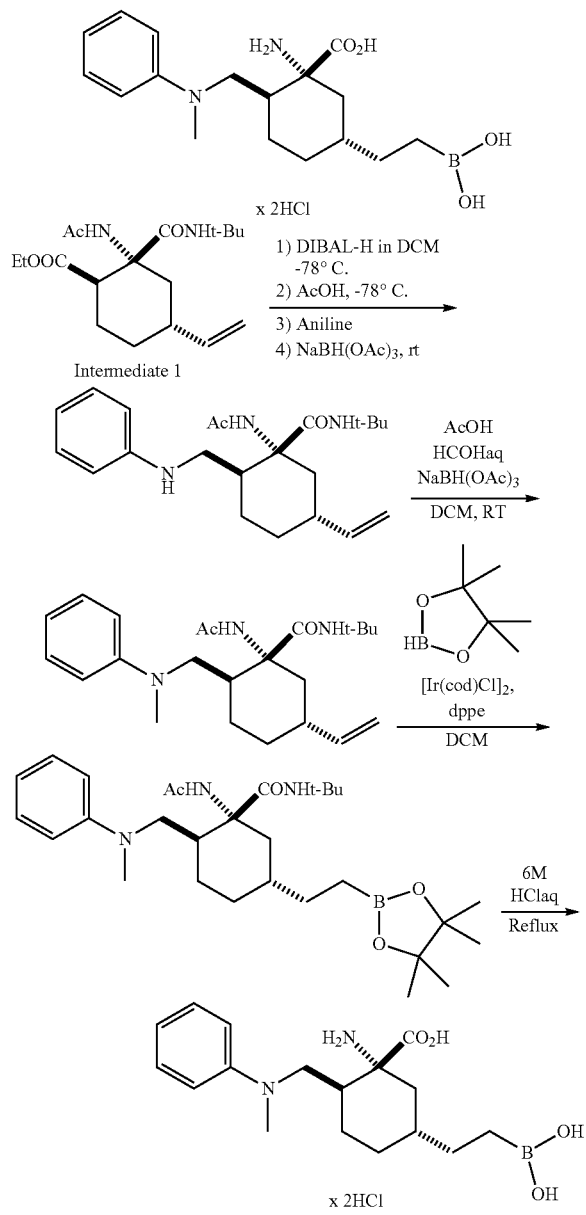

Step A. rac-(1R,2S,5R)-1-acetamido-N-(tert-butyl)-2-((phenylamino)methyl)-5-vinylcyclohexane-1-carboxamide To a solution of ethyl rac-(1R,2R,4R)-2-acetamido-2-(tert-butylcarbamoyl)-4-vinylcyclohexanecarboxylate (Intermediate 1, 100 mg, 0.30 mmol, 1 equiv.) in dry dichloromethane (10 mL), DIBAL-H 1M in DCM (0.92 mL, 0.92 mmol, 3.1 equiv.) was added dropwise at −78° C. under argon. Next, aniline (54 μL, 0.60 mmol, 2 equiv.) and acetic acid glacial (85 μL, 1.48 mmol, 5 equiv.) were added. Reaction was stirred for 30 min at room temperature and sodium triacetoxyborohydride (254 mg, 1.2 mmol, 4 equiv.) was added. The reaction mixture was diluted with DCM (10 mL), washed with 1M NaOH (2×10 mL), brine, dried over MgSO$_4$, filtered and concentrated in vacuo. Product was purified by flash chromatography on silica gel (gradient elution, DCM/MeOH 1:0 to 50:1) to give (1R,2S,5R)-1-acetamido-N-(tert-butyl)-2-((phenylamino)methyl)-5-vinyl-cyclohexanecarboxamide as a single diastereoisomer (yield 137 mg, 100%, white solid). ESI+MS: m/z=385.50 (M+1)$^+$. $^1$H NMR (700 MHz, Chloroform-d) δ 8.13-8.06 (m, 1H), 7.98 (s, 1H), 7.24-7.20 (m, 2H), 6.82 (t, 1H, J=7.3 Hz), 6.71 (d, 2H, J=7.8 Hz), 5.73 (ddd, 1H, J=10.6, 6.4, 3.9 Hz), 4.99 (dt, 1H, J=17.3, 1.5 Hz), 4.94 (dt, 1H, J=10.4, 1.4 Hz), 4.01-3.88 (m, 1H), 3.15-3.06 (m, 2H), 2.19-2.09 (m, 2H), 1.89-1.83 (m, 1H), 1.83-1.76 (m, 4H), 1.73-1.67 (m, 1H), 1.36 (s, 9H), 1.33-1.18 (m, 3H).

Step B. rac-(1R,2S,5R)-1-acetamido-N-(tert-butyl)-2-((methyl(phenyl)amino)methyl)-5-vinylcyclo-hexane-1-carboxamide To a solution of rac-(1R,2S,5R)-1-acetamido-N-(tert-butyl)-2-((phenylamino)methyl)-5-vinylcyclohexanecarboxamide (222 mg, 0.60 mmol, 1 equiv.) in dry dichloromethane (10 mL), formaline (231 μL, 3.00 mmol, 5 equiv.) and glacial acetic acid (34 μL, 0.60 mmol, 1 equiv.) were added. The reaction mixture was stirred for 30 min at room temperature and sodium triacetoxyborohydride (381 mg, 1.80 mmol, 3 equiv.) was added and stirred for 3 days. Next the reaction mixture was quenched with 5% NaHCO$_3$ (10 mL) and layers were separated. Aqueous layer was washed with dichloromethane (3×10 mL) and combined organic layer was washed with brine, dried over MgSO$_4$, filtered and concentrated in vacuo to give corresponding product as a single diastereoisomer (yield 264 mg, 23%, white solid). ESI+MS: m/z=385.50 (M+1)$^+$. $^1$H NMR (700 MHz, Chloroform-d) δ 8.30 (s, 1H), 8.29 (s, 1H), 7.28-7.24 (m, 2H), 6.89-6.83 (m, 3H), 5.73 (ddd, 1H, J=7.3, 17.1, 6.5 Hz), 4.99 (dt, 1H, J=17.3, 1.5 Hz), 4.93 (dt, 1H, J=10.4, 1.4 Hz), 4.22 (dd, 1H, J=15.1, 10.2 Hz), 3.17 (dt, 1H, J=13.3, 2.3 Hz), 3.04 (dd, 1H, J=15.1, 3.0 Hz), 2.89 (s, 3H), 2.18 (dq, 1H, J=13.3, 4.3 Hz), 2.16-2.08 (m, 1H), 1.90-1.83 (m, 2H), 1.69 (s, 3H), 1.58-1.52 (m, 2H), 1.38 (s, 9H), 1.30-1.17 (m, 2H).

Step C. rac-(1R,2S,5R)-1-acetamido-N-(tert-butyl)-2-((methyl(phenyl)amino)methyl)-5-(2-(4,4,5,5-tetramethyl-1,3,2-dioxaborolan-2-yl)ethyl)cyclohexane-1-carboxamide

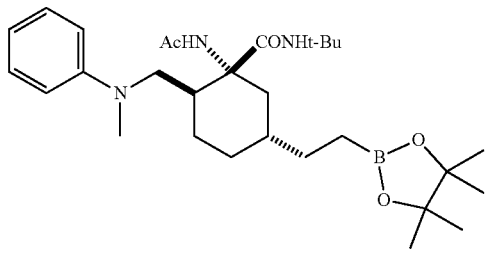

A mixture of dppe (13.1 mg, 0.033 mmol, 0.06 equiv.) and bis(1,5-cyclooctadiene)diiridium(I) dichloride (11.1 mg, 0.016 mmol, 0.03 equiv.) in dichloromethane (5 mL) was flushed with argon (bubbling). Subsequently, the separately prepared solution of the 4,4,5,5-tetramethyl-1,3,2-dioxaborolane (0.12 µL, 0.83 mmol, 1.5 equiv.) and (1R,2S,5R)-1-acetamido-N-(tert-butyl)-2-((methyl(phenyl)amino)methyl)-5-vinylcyclohexanecarboxamide (211 mg, 0.55 mmol, 1 equiv.) in dry $CH_2Cl_2$ (5 mL) was added successively at room temperature. The resulting mixture was stirred at room temperature overnight. After concentration the crude product was purified by flash chromatography on silica gel (gradient elution, hexane/AcOEt 1:0 to 4:1) to give rac-(1R,2S,5R)-1-acetamido-N-(tert-butyl)-2-((methyl(phenyl)amino)methyl)-5-(2-(4,4,5,5-tetramethyl-1,3,2-dioxaborolan-2-yl)ethyl)cyclohexanecarboxamide (161 mg, 57%, yellow liquid). ESI+MS: m/z=514.70 (M+1)$^+$. $^1$H NMR (700 MHz, Chloroform-d) δ 8.29 (s, 1H), 7.24 (s, 1H), 7.27-7.23 (m, 2H), 6.88-6.81 (m, 3H), 4.23 (dd, 1H, J=15.1, 10.8 Hz), 3.14 (d, 1H, J=13.4 Hz), 3.01 (dd, 1H, J=15.1, 3.1 Hz), 2.88 (s, 3H), 2.08 (dq, 1H, J=8.6, 4.5 Hz), 1.92-1.80 (m, 2H), 1.66 (s, 3H), 1.55-1.49 (m, 1H), 1.36 (s, 9H), 1.35-1.28 (m, 3H), 1.23 (s, 12H), 1.05 (dd, 1H, J=12.1, 13.3 Hz), 0.98 (dq, 1H, J=13.1, 4.6 Hz), 0.85-0.78 (m, 1H), 0.76-0.70 (m, 1H).

Step D. rac-(1R,2S,5R)-1-amino-5-(2-boronoethyl)-2-((methyl(phenyl)amino)methyl)cyclohexanecarboxylic acid dihydrochloride A mixture of rac-(1R,2S,5R)-1-acetamido-N-(tert-butyl)-2-((methyl(phenyl)amino)methyl)-5-(2-(4,4,5,5-tetramethyl-1,3,2-dioxaborolan-2-yl)ethyl)cyclohexanecarboxamide (160 mg, 0.19 mmol, 1 equiv.) and 6 N $HCl_{aq}$ (15 mL) was heated under reflux for 6 h. The reaction mixture was concentrated under reduced pressure and the residue was purified by flash chromatography on DOWEX® ion exchange resin (eluent 0.1N ammonia in water) to give (after acidification with 6N HCl and subsequent lyophilization) a desired product as a single diastereoisomer (22.9 mg, 18%, white solid). ESI+MS: m/z=335.50 (M+1)$^+$. $^1$H NMR (700 MHz, Chloroform-d) δ 7.27-7.68 (m, 2H), 7.68-7.64 (m, 1H), 7.63-7.60 (m, 2H), 3.97 (dd, 1H, J=13.6, 2.5 Hz), 3.65 (dd, 1H, J=10.6, 13.4 Hz), 2.36 (s, 3H), 2.26-2.21 (m, 1H), 1.96-1.82 (m, 3H), 1.79-1.72 (m, 1H), 1.72-1.66 (m, 1H), 1.34-1.26 (m, 2H), 1.14 (t, 1H, J=12.6 Hz), 0.82-0.72 (m, 3H).

Example 41. 1-amino-5-(2-boronoethyl)-2-((dimethylamino)methyl)-4,4-dimethylcyclohexane-1-carboxylic acid dihydrochloride

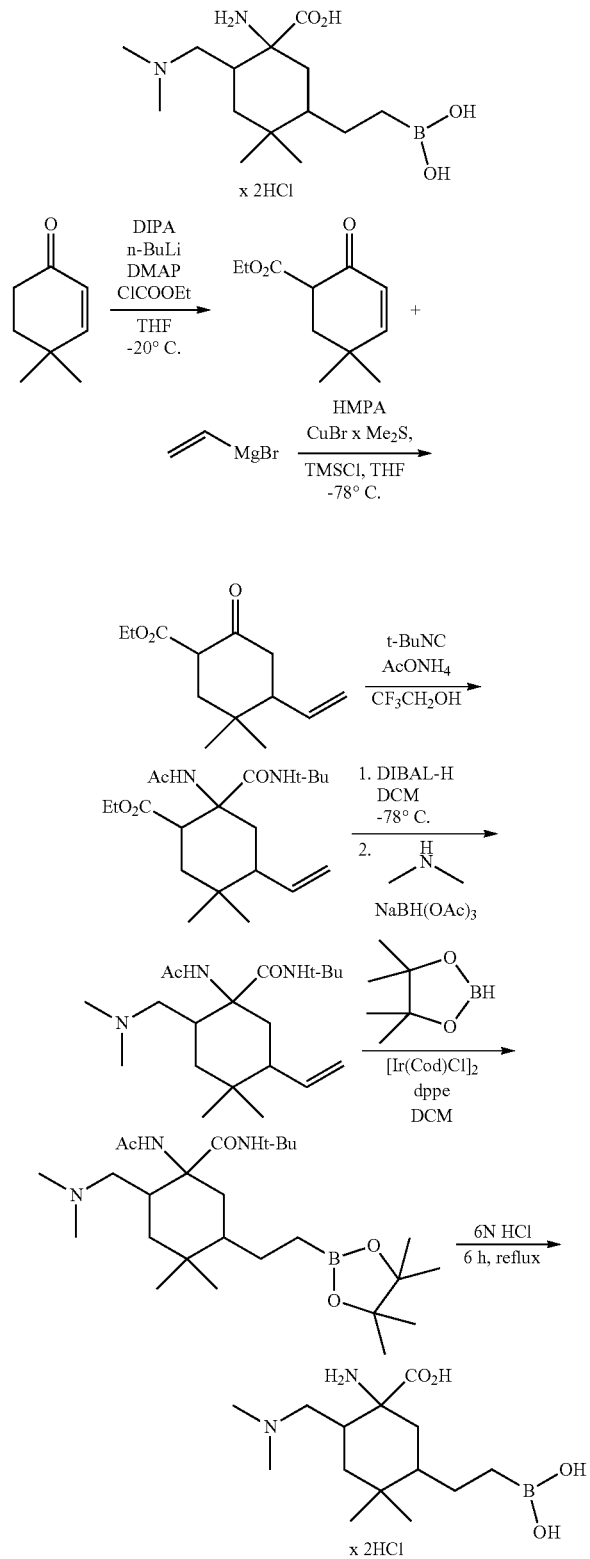

Step A. Ethyl 5,5-dimethyl-2-oxocyclohex-3-enecarboxylate

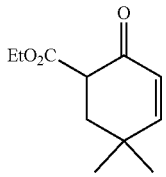

The title compound ethyl 5,5-dimethyl-2-oxocyclohex-3-enecarboxylate was obtained in the same manner like in the step A from the synthesis of the intermediate 1 using 4,4-dimethylcyclohexenone (2.6 mL, 20.13 mmol, 1 equiv.), ethyl chloroformate (2.3 mL, 24.15 mmol, 1.2 equiv.), n-BuLi (2.5 M in hexane) (12.1 mL, 30.19 mmol, 1.5 equiv.), diisopropylamine (4.2 mL, 30.19 mmol, 1.5 eqiuv.), 4-dimethylaminopyridine (0.12 g, 1 mmol, 0.05 equiv.), dry THF (45 mL). The crude product was purified by column chromatography on silica gel (gradient elution, hexane/AcOEt 200:1 to 10:1) to give corresponding product ethyl 5,5-dimethyl-2-oxocyclohex-3-enecarboxylate (1.28 g, 32%, yellow oil). ESI+MS: m/z=197.1 (M+1)$^+$. $^1$H NMR (700 MHz, Chloroform-d) δ 6.10-6.03 (m, 1H), 5.86 (d, J=9.8 Hz, 1H), 4.25 (q, J=7.1 Hz, 2H), 1.35-1.31 (m, 3H), 1.29 (t, J=7.11, 3H), 1.23 (s, 3H), 1.22 (s, 3H).

Step B. Ethyl 5,5-dimethyl-2-oxo-4-vinylcyclohexanecarboxylate

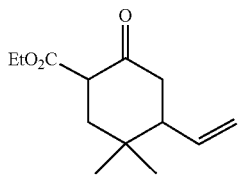 [SMILES: C=CC1CC(=O)C(C(=O)OCC)CC1(C)C]

The title compound ethyl 5,5-dimethyl-2-oxo-4-vinylcyclohexanecarboxylate as a mixture diastereoisomers was obtained in the same manner like in the step B from the synthesis of The intermediate 1, using ethyl 5,5-dimethyl-2-oxocyclohex-3-enecarboxylate (1.0 g, 5.30 mmol, 1 equiv.), Vinylmagnesium bromide (1 M in THF) (18.5 mL, 18.50 mmol, 3.5 equiv.), HMPA (3.7 mL, 21.20 mmol), CuBr×Me$_2$S (0.16 g, 0.80 mmol, 0.15 equiv.), and TMSCl (3.4 mL, 26.5 mmol, 5 equiv.), dry THF (23 mL+11 mL). The crude product was purified by flash chromatography on silica gel (gradient elution, hexane/AcOEt 200:1 to 20:1) to give corresponding product ethyl 5,5-dimethyl-2-oxo-4-vinylcyclohexanecarboxylate as a mixture diastereoisomers dr=3:2 (0.1 g, 8%, yellow oil). ESI+MS: m/z=225.1 (M+1)$^+$. $^1$H NMR (700 MHz, Chloroform-d) δ 5.76 (ddd, J=17.0, 10.4, 8.4 Hz, 1H), 5.23-4.92 (m, 2H), 4.24 (dtq, J=10.8, 7.4, 3.8 Hz, 2H), 2.39, 2.36 [(2 d, J=5.7 Hz, 1H, two diastereoisomers)], 2.26-2.22 (m, 1H), 2.17-2.10 (m, 2H), 2.07-2.04 (m, 1H), 1.33 (t, J=7.1 Hz, 3H), 1.30 (dd, J=16.9, 7.1 Hz, 1H), 0.99 (s, 3H), 0.87 (s, 3H).

Step C. Ethyl 2-acetamido-2-(tert-butylcarbamoyl)-5,5-dimethyl-4-vinylcyclohexanecarboxylate

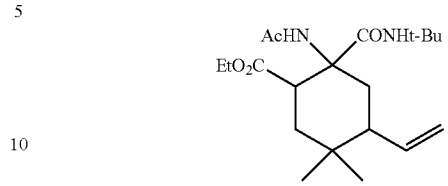

The title compound ethyl 2-acetamido-2-(tert-butylcarbamoyl)-5,5-dimethyl-4-vinylcyclohexanecarboxylate was obtained in the same manner like in the step C from the synthesis of The intermediate 1 using a ethyl 5,5-dimethyl-2-oxo-4-vinylcyclohexanecarboxylate (dr=3:2) (0.1 g, 0.45 mmol, 1 equiv.), ammonium acetate (0.14 g, 1.78 mmol, 4 equiv.), tert-butylisocyanide (0.1 mL, 0.89 mmol, 2 equiv.) and 2,2,2-trifluoroethanol (1.6 mL) as a solvent. The residue was purified by silica gel flash chromatography (gradient elution, hexane/AcOEt 50:1 to 1:1) to give corresponding product ethyl 2-acetamido-2-(tert-butylcarbamoyl)-5,5-dimethyl-4-vinylcyclohexanecarboxylat as a mixture of two diastereoisomers (dr=1:1) (0.66 g, 40%, white solid). ESI+MS: m/z=367.3 (M+1)$^+$. $^1$H NMR (700 MHz, Chloroform-d) δ 8.11 (s, 1H), 7.49 (s, 1H), 5.78-5.59 (m, 1H), 5.12-4.90 (m, 2H), 4.24, 4.16 [(2dq, J=10.8, 7.1 Hz; J=10.9, 7.1 Hz, 2H, two diastereoisomers)], 3.00 (dd, J=14.4, 3.0 Hz, 1H), 2.54 (dd, J=13.0, 4.2 Hz, 1H), 2.01 (s, 3H), 1.99-1.94 (m, 1H), 1.90-1.84 (m, 1H), 1.83-1.71 (m, 1H), 1.50 (s, 3H), 1.31 (s, 9H), 1.19-1.08 (m, 1H), 0.93 (s, 3H), 0.85 (s, 3H).

Step D. 1-acetamido-N-(tert-butyl)-2-((dimethylamino)methyl)-4,4-dimethyl-5-vinylcyclohexanecarboxamide

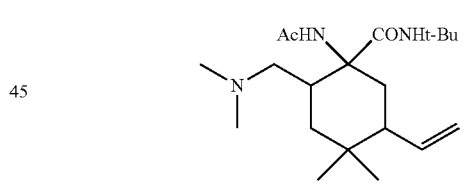

The title compounds 1-acetamido-N-(tert-butyl)-2-((dimethylamino)methyl)-4,4-dimethyl-5-vinylcyclohexanecarboxamide was obtained in the same manner like in Example 26, step A, using ethyl 2-acetamido-2-(tert-butylcarbamoyl)-5,5-dimethyl-4-vinylcyclohexanecarboxylate (dr=1:1), (0.6 g, 0.17 mmol, 1 equiv.), DIBAL-H 1M in DCM (0.5 mL, 0.52 mmol, 3.1 equiv.), glacial acetic acid (0.05 mL, 0.83 mmol, 5 equiv.), dimethyl amine (2N in THF) (0.17 mL, 0.33 mmol, 2 equiv.), sodium triacetoxyborohydride (0.14 g, 0.07 mmol, 4 equiv.), dry DCM (5 mL). The residue was purified by silica gel flash chromatography (gradient elution DCM:MeOH 100:1 to 10:1) to give the corresponding products 1-acetamido-N-(tert-butyl)-2-((dimethylamino)methyl)-4,4-dimethyl-5-vinylcyclohexanecarboxamide as a mixture of diastereoisomers (dr=1:1) (34 mg, 58%, colorless oil). ESI+MS: m/z=352.2 (M+1)$^+$. $^1$H NMR (700 MHz, Chloroform-d) δ 10.14 (s, 1H), 8.12 (s, 1H), 5.68 (ddd, J=17.1, 10.4, 8.5 Hz, 1H), 5.03-4.93 (m, 2H), 3.49-3.35 (m, 1H), 2.97-2.92 [(m, 1H, two diastereoisomers)], 2.28 (s, 3H), 2.21-2.19 (m, 1H), 2.14-2.06 (m, 1H), 1.99-1.95 (m, 1H), 1.92 (s, 3H), 1.88-1.78 (m, 1H), 1.62-1.59 (m, 1H), 1.53 (s, 3H), 1.34 (s, 9H), 1.02, 1.00 [(2 d, J=3.9 Hz, J=4.0 Hz, 1H two diastereoisomers)], 0.91 (s, 3H), 0.89 (s, 3H).

Step E. 1-acetamido-N-(tert-butyl)-2-((dimethylamino)methyl)-4,4-dimethyl-5-(2-(4,4,5,5-tetramethyl-1,3,2-dioxaborolan-2-yl)ethyl)cyclohexanecarboxamide

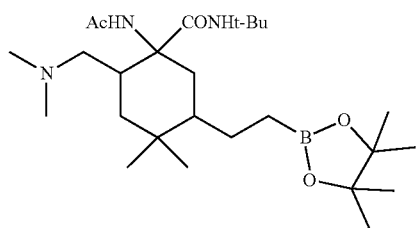

The title compound was obtained in the same manner like in Example 26, step B, using 1-acetamido-N-(tert-butyl)-2-((dimethylamino)methyl)-4,4-dimethyl-5-vinylcyclohexanecarboxamide (dr=1:1), (0.034 g, 0.1 mmol, 1 equiv.), dppe (2.5 mg, 0.006 mmol, 0.06 equiv.), bis(1,5-cyclooctadiene)diiridium(I) dichloride (2 mg, 0.003. mmol, 0.03 equiv.), 4,4,5,5-tetramethyl-1,3,2-dioxaborolane (0.018 mL, 0.013 mmol, 1.3 eq). The crude product used to next step without any further purification (134 mg of crude mixture, ca. 11%, yellow oil). ESI+MS: m/z=480.4 (M+1)$^+$.

Step F. 1-amino-5-(2-boronoethyl)-2-((dimethylamino)methyl)-4,4-dimethylcyclohexane-1-carboxylic acid dihydrochloride The title compound was obtained in the same manner like in Example 26, step C, using 1-acetamido-N-(tert-butyl)-2-((dimethylamino)methyl)-4,4-dimethyl-5-(2-(4,4,5,5-tetramethyl-1,3,2-dioxaborolan-2-yl)ethyl)cyclohexanecarboxamide (crude, 134 mg, 0.28 mmol, 1 equiv.), 6 N HCl$_{aq}$(1.5 mL). The residue was purified by preparative HPLC (0.1-1% MeCN in water) and next by flash chromatography on DOWEX® ion exchange resin (eluent 0.1N ammonia in water) to give (after acidification with 6N HCl and subsequent lyophilization) 1-amino-5-(2-boronoethyl)-2-((dimethylamino)methyl)-4,4-dimethylcyclohexane-1-carboxylic acid dihydrochloride as a mixture of two diastereoisomers (dr=1:1) (2.5 mg, 2%, white solid). ESI+MS: m/z=301.2 (M+1)$^+$. ESI-MS: m/z=299.1 (M−1)$^−$. $^1$H NMR (700 MHz, Deuterium Oxide) δ 3.27 (d, J=15.5 Hz, 1H), 3.18 (t, J=12.7 Hz, 1H), 2.90 (s, 3H), 2.82 (s, 3H), 2.39-2.21 (m, 1H), 2.20-2.19 (m, 1H), 2.17-2.10 (m, 1H), 1.82-1.73 (m, 1H), 1.71-1.62 (m, 1H), 1.48 (td, J=10.1, 9.0, 5.6 Hz, 3H), 1.28-1.17 (m, 1H), 0.95 (s, 3H), 0.81 (s, 3H), 0.63-0.53 (m, 1H).

Example 42. (1R,2S,5R)-1-amino-5-(2-boronoethyl)-2-(1-(dimethylamino)ethyl)cyclohexanecarboxylic acid dihydrochloride

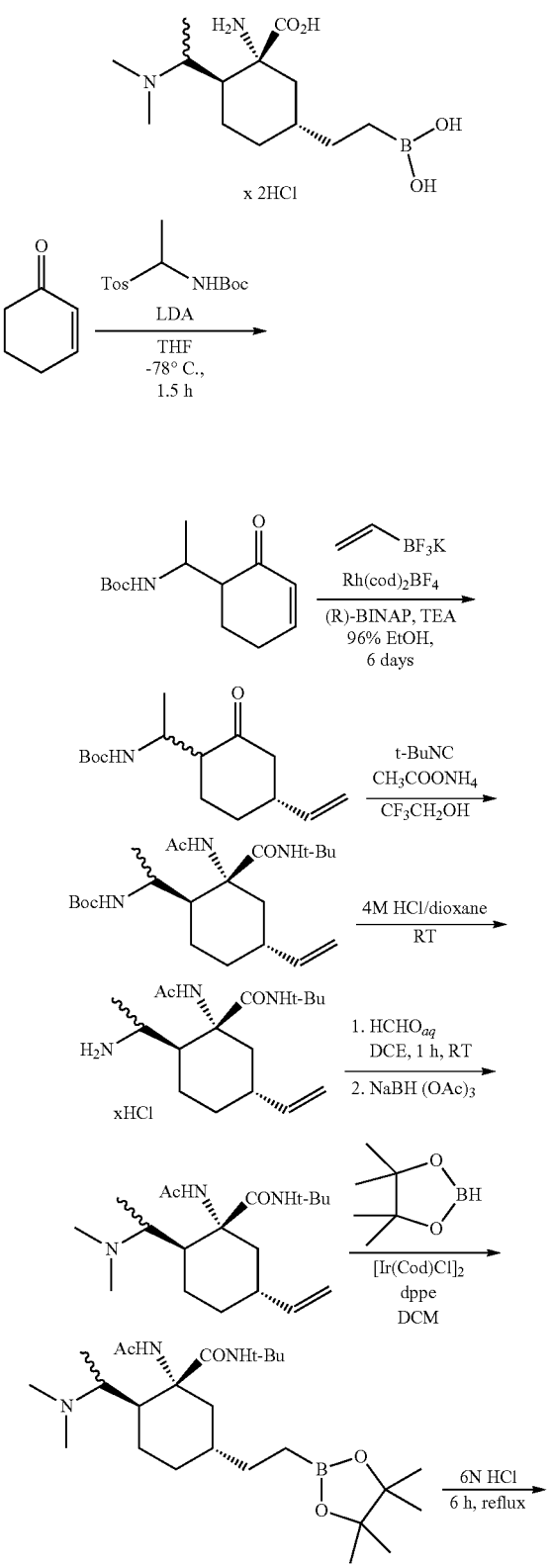

-continued

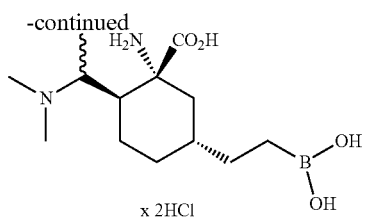

x 2HCl

Step A. tert-Butyl (1-(2-oxocyclohex-3-en-1-yl)ethyl)carbamate

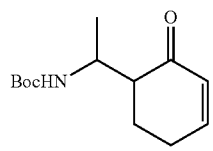 [SMILES: CC(NC(=O)OC(C)(C)C)C1CCC=CC1=O]

To a solution of diisopropylamine (11.76 mL, 83.22 mmol) in dry THF (91 mL) was added dropwise a solution of n-BuLi in THF (2.5M, 33.3 mL, 83.22 mmol) at −78° C. under argon. The reaction mixture was warmed to room temperature, stirred for 15 min and cooled to −78° C. A 2-cycloheksen-1-one (4 g, 41.61 mmol) was added dropwise and the mixture was stirred for 1 h at this temperature. Next a solution of tert-butyl-(1-tosylethyl)carbamate (12.46 g, 41.61 mmol) in THF (53 mL) was added dropwise and the reaction was stirred for 1.5 h at −78° C. Then, the mixture was quenched with saturated NH$_4$Cl (150 mL) and the organic layer was collected. The aqueous layer was extracted with ethyl acetate (3×100 mL). The combined organic extracts were dried over MgSO$_4$, filtered and concentrated in vacuo. The crude product was purified by flash chromatography on silica gel using hexane/AcOEt (20:1-2:1) to give product (3.2 g, 32%) as colorless oil. ESI+MS: m/z=240.15 (M+1)$^+$, 140.15 (M-Boc+1)$^+$. $^1$H NMR (700 MHz, chloroform-d) δ 7.00-6.95 (m, 1H), 6.01-5.96 (m, 1H), 5.70-5.65 (m, 1H), 3.86-3.79 (m, 1H), 2.59-2.49 (m, 1H), 2.49-2.38 (m, 2H), 2.02-1.9 (m, 1H), 1.88 (tdd, J=13.1, 10.6, 5.1 Hz, 1H), 1.45 (s, 9H), 1.16 (d, J=6.9 Hz, 3H).

Step B. tert-Butyl (1-((4R)-2-oxo-4-vinylcyclohexyl)ethyl)carbamate

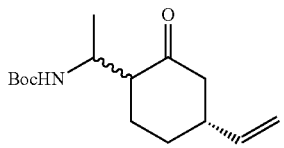 [SMILES: C=C[C@@H]1CCC(C(C)NC(=O)OC(C)(C)C)C(=O)C1]

To a 250 mL round-bottomed flask were added Rh(cod)BF$_4$ (178 mg, 0.437 mmol), (R)-BINAP (272 mg, 0.437 mmol), and potassium vinyl trifluoroborate (3.55 g, 26.49 mmol). The flask was flushed with argon several times and degassed 96% EtOH (105 mL) and trimethylamine (5.54 mL, 39.74 mmol) were added. After stirring the resulting mixture for 10 min at room temperature, tert-butyl (1-(2-oxocyclohex-3-en-1-yl)ethyl)carbamate (3.17 g, 13.25 mmol) was added and the reaction mixture was stirred at room temperature for 6 days. The EtOH was evaporated. The residue was diluted with ethyl acetate (100 mL) and washed with 0.5 M aqueous HCl (30 mL) and brine (30 mL), dried over MgSO$_4$, filtered and concentrated under reduced pressure. The crude product was purified by silica gel chromatography using hexane/AcOEt (15:1 to 5:1) to afford product as a mixture of diastereoisomers (overall yield: 430 mg, 12%). ESI+MS: m/z=290.15 (M+Na)$^+$, 168.15 (M−Boc+1)$^+$, 212.15 (M−56+1)$^+$. The first diastereoisomer was isolated as a colorless oil (320 mg, 9%). [α]$_D$=+6.6 (c=0.250 in CHCl$_3$). $^1$H NMR (700 MHz, chloroform-d) δ 5.79 (ddd, J=16.9, 10.4, 6.2 Hz, 1H), 5.27 (s, 1H), 5.07-4.98 (m, 2H), 3.87-3.73 (m, 1H), 2.58-2.51 (m, 1H), 2.50-2.40 (m, 2H), 2.25-2.14 (m, 1H), 2.12-2.05 (m, 1H), 2.02-1.97 (m, 1H), 1.60-1.56 (m, 2H), 1.45 (s, 9H), 1.25 (d, J=6.9 Hz, 3H). The second diastereoisomer was isolated as a colorless oil (110 mg, 3%). $^1$H NMR (700 MHz, chloroform-d) δ 5.87-5.73 (m, 1H), 5.23 (s, 1H), 5.09-4.97 (m, 2H), 3.88-3.72 (m, 1H), 2.56-2.35 (m, 3H), 2.31-2.14 (m, 1H), 2.14-1.95 (m, 1H), 1.95-1.76 (m, 2H), 1.73-1.63 (m, 1H), 1.44 (s, 9H), 1.22 (d, J=6.9 Hz, 3H).

Step C. tert-Butyl (1-((1S,2R,4R)-2-acetamido-2-(tert-butylcarbamoyl)-4-vinylcyclohexyl)ethyl)carbamate

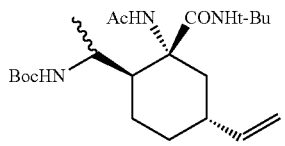

To the stirred solution of tert-butyl (1-((4R)-2-oxo-4-vinylcyclohexyl)ethyl)carbamate (550 mg, 2.45 mmol) and ammonium acetate (0.76 g, 9.87 mmol) in 2,2,2-trifluoroethanol (10 mL) tert-butyl isocyanide (0.55 mL, 4.94 mmol) was added dropwise via syringe and the resulting mixture was stirred at room temperature for 24 hours. After this time, 2,2,2-trifluoroethanol was evaporated and the residue was diluted with ethyl acetate (40 mL) and washed with water (20 mL). The aqueous layer was extracted with ethyl acetate (3×30 mL). The combined organic layers were dried over MgSO$_4$, filtered and evaporated under reduced pressure. The crude product was purified by flash chromatography on silica gel using hexane/AcOEt (30:1 to 1:1) to give a mixture of diastereoisomers (overall yield: 495 mg, 49%). ESI+MS: m/z=410.25 (M+1)$^+$, 354.25 (M−56+1)$^+$, 310.2 (M-Boc+1)$^+$. The first diastereoisomer was isolated as a colorless oil (190 mg, 19%) and was used in the next step. $^1$H NMR (700 MHz, chloroform-d) δ 7.87 (s, 1H), 6.33 (s, 1H), 5.72 (ddd, J=17.1, 10.5, 6.4 Hz, 1H), 5.02-4.92 (m, 2H), 4.77 (d, J=10.5 Hz, 1H), 3.44-3.38 (m, 1H), 2.53-2.37 (m, 1H), 2.09 (s, 3H), 1.94-1.84 (m, 2H), 1.84-1.75 (m, 2H), 1.45 (s, 9H), 1.36 (s, 9H), 1.30 (d, J=6.5 Hz, 3H), 1.22 (d, J=6.8 Hz, 1H), 1.19-1.12 (m, 2H).

Step D. (1R,2S,5R)-1-Acetamido-2-(1-aminoethyl)-N-(tert-butyl)-5-vinylcyclohexanecarboxamide hydrochloride

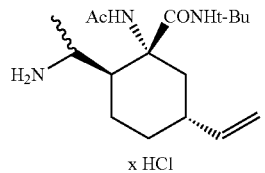

x HCl

To the tert-butyl (1-((1S,2R,4R)-2-acetamido-2-(tert-butylcarbamoyl)-4-vinylcyclohexyl)ethyl)carbamate (190 mg, 0.464 mmol) was added 4M HCl in dioxane (2 mL) and the solution was stirred at room temperature until substrate was consumed (TLC monitoring). Then it was concentrated in vacuo and obtained 160 mg (99%) of crude product as a colorless oil and was used in the next step. ESI+MS: m/z=310.15 (M+1)$^+$. $^1$H NMR (700 MHz, chloroform-d) δ 8.56 (s, 2H), 7.41 (s, 1H), 6.81 (s, 1H), 5.74 (ddd, J=16.6, 10.8, 5.8 Hz, 1H), 5.17-4.93 (m, 2H), 3.43-3.27 (m, 1H), 2.80-2.42 (m, 2H), 2.31 (s, 3H), 2.03-1.73 (m, 4H), 1.54-1.49 (m, 2H), 1.41 (s, 9H), 1.34-1.12 (m, 3H).

Step E. (1R,2S,5R)-1-Acetamido-N-(tert-butyl)-2-(1-(dimethylamino)ethyl)-5-vinylcyclohexanecarboxamide

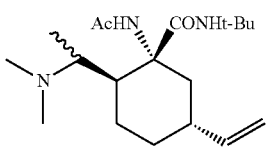

(1R,2S,5R)-1-acetamido-2-(1-aminoethyl)-N-(tert-butyl)-5-vinylcyclohexanecarboxamide hydrochloride (160 mg, 0.46 mmol), formaline (36%, 0.14 mL, 1.85 mmol) were dissolved in 1,2-dichloroethane (1.5 mL). The mixture was stirred at room temperature for 1 h. To the reaction mixture was added sodium triacetoxyborohydride (0.39 g, 6.2 mmol) and was stirred at room temperature overnight. The reaction mixture was next diluted with DCM (50 mL) and washed with 5% NaHCO$_3$ (30 mL). The organic layer was dried over MgSO$_4$, filtered and concentrated in vacuo. The crude product was purified by flash chromatography on silica gel (DCM/MeOH 50:1 to 5:1)) to afford 74 mg (38%) of the desired product as a colorless oil. ESI+MS: m/z=338.05 (M+1)$^+$. $^1$H NMR (700 MHz, chloroform-d) δ 7.85 (s, 1H), 7.25 (s, 1H), 5.76 (ddd, J=17.1, 10.4, 6.4 Hz, 1H), 5.07-4.88 (m, 2H), 2.75-2.66 (m, 1H), 2.26 (s, 6H), 2.17-2.10 (m, 1H), 2.05 (s, 3H), 1.85-1.65 (m, 3H), 1.62-1.44 (m, 2H), 1.35 (s, 9H), 1.29-1.21 (m, 1H), 1.01 (d, J=7.1 Hz, 3H).

Step F. (2-((1R,3R,4S)-3-Acetamido-3-(tert-butylcarbamoyl)-4-((1-(dimethylamino)ethyl)cyclohexyl)ethyl)boronic acid

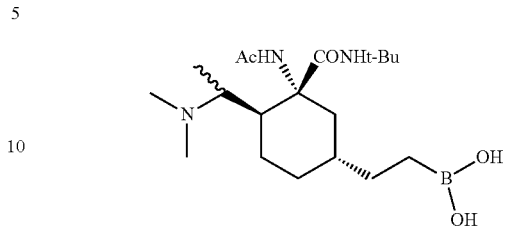

A mixture of dppe (4.9 mg, 0.012 mmol) and bis(1,5-cyclooctadiene)diiridium(I) dichloride (4.1 mg, 0.0061 mmol) in dry dichloromethane (2 mL) was flushed with argon. Then the solution of (1R,2S,5R)-1-acetamido-N-(tert-butyl)-2-(1-(dimethylamino)ethyl)-5-vinylcyclohexanecarboxamide (69 mg, 0.204 mmol) and 4,4,5,5-tetramethyl-1,3,2-dioxaborolane (136 μl, 0.94 mmol) in DCM (2 mL) (flushed with argon) was added dropwise. The reaction mixture was stirred at room temperature overnight. After this time, the reaction mixture was diluted with DCM (20 mL) washed with 5% NaHCO$_3$ (2×20 mL). The organic layer was dried over MgSO$_4$ and concentrated in vacuo. The crude product was purified by column chromatography, on silica gel (CH$_2$Cl$_2$/MeOH 20:1 to MeOH) to give the product (35 mg, 45%) as a colorless oil. ESI+MS: 384.2 (M+1)$^+$. $^1$H NMR (700 MHz, chloroform-d) δ 3.71-3.55 (m, 1H), 2.87-2.78 (m, 1H), 2.76-2.60 (m, 1H), 2.22 (s, 6H), 2.07-2.01 (m, 5H), 1.86-1.72 (m, 2H), 1.34 (s, 9H), 1.24-2.12 (m, 3H), 0.98-0.91 (m, 3H), 0.88 (t, J=7.2 Hz, 3H).

Step G. (1R,2S,5R)-1-Amino-5-(2-boronoethyl)-2-(1-(dimethylamino)ethyl)cyclohexanecarboxylic acid dihydrochloride A mixture of (2-((1R,3R,4S)-3-acetamido-3-(tert-butylcarbamoyl)-4-(1-(dimethylamino)ethyl)cyclohexyl)ethyl) boronic acid (30 mg, 0.078 mmol and 6 N HCl$_{aq}$ (5 mL) was heated under reflux for 6 h. The reaction mixture was concentrated under reduced pressure and the residue was purified by ion exchange chromatography on DOWEX® and next by preparative HPLC (0.1-1% MeCN in water) to give (after acidification with 6M HCl and subsequent lyophilization) the desired product (11 mg, 38%) as a white solid. ESI+MS: 287.1 (M+1)$^+$. $^1$H NMR (700 MHz, deuterium oxide) a 3.31 (q, J=6.9 Hz, 1H), 2.78 (d, J=14.3 Hz, 6H), 2.55 (dd, J=13.6, 3.4 Hz, 1H), 2.04 (d, J=14.4 Hz, 1H), 1.94-1.84 (m, 2H), 1.74-1.67 (m, 1H), 1.59-1.49 (m, 1H), 1.36-1.26 (m, 3H), 1.25 (d, J=7.0 Hz, 3H), 1.16-1.08 (m, 1H), 0.74-0.65 (m, 2H).

Example 43. (2-((1R,3R,4S)-3-amino-4-((dimethylamino)methyl)-3-(methoxycarbonyl)cyclohexyl)ethyl)boronic acid dihydrochloride

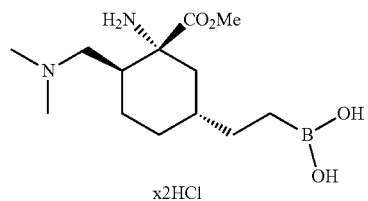

x2HCl

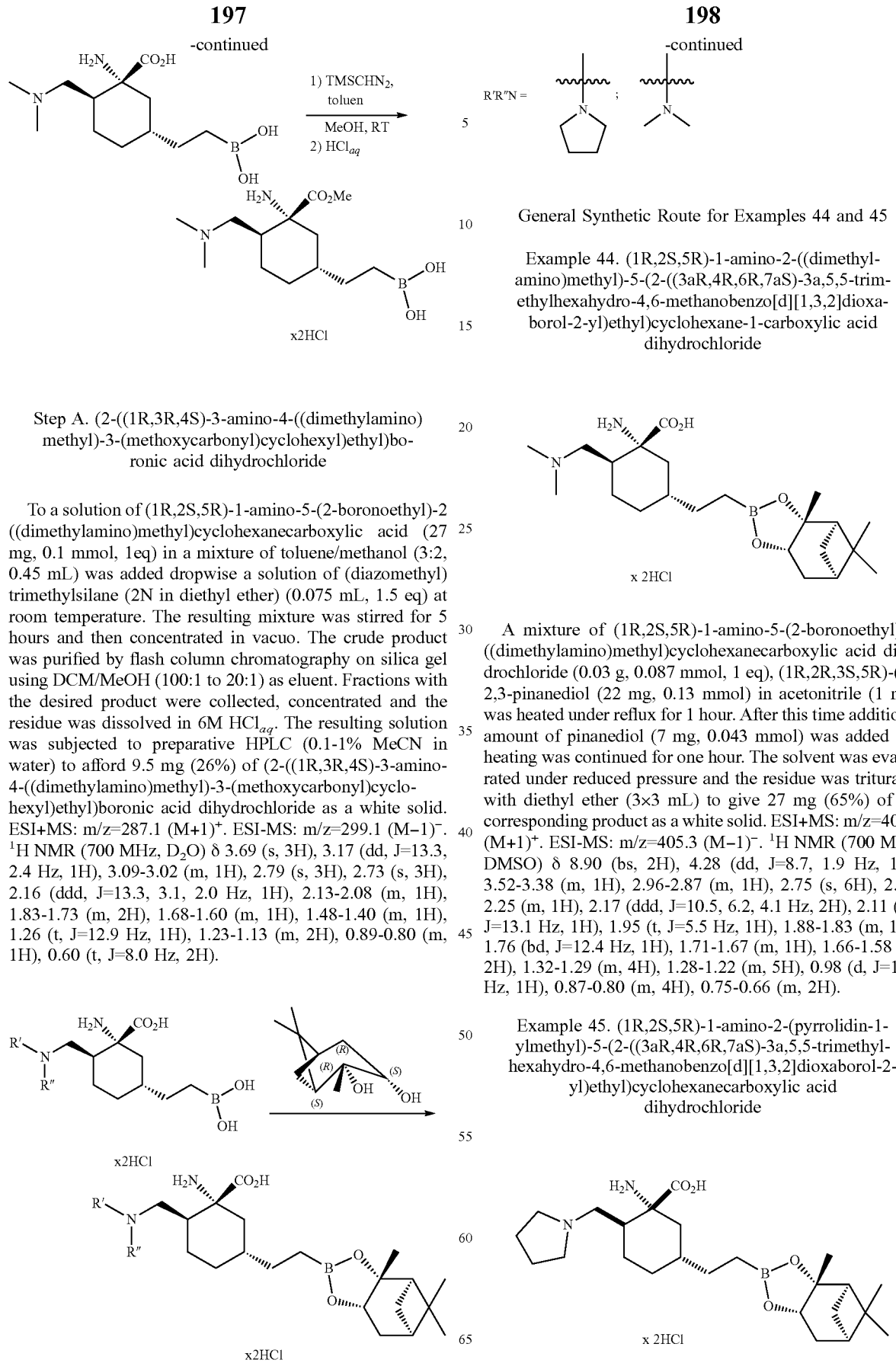

Step A. (2-((1R,3R,4S)-3-amino-4-((dimethylamino)methyl)-3-(methoxycarbonyl)cyclohexyl)ethyl)boronic acid dihydrochloride To a solution of (1R,2S,5R)-1-amino-5-(2-boronoethyl)-2-((dimethylamino)methyl)cyclohexanecarboxylic acid (27 mg, 0.1 mmol, 1eq) in a mixture of toluene/methanol (3:2, 0.45 mL) was added dropwise a solution of (diazomethyl)trimethylsilane (2N in diethyl ether) (0.075 mL, 1.5 eq) at room temperature. The resulting mixture was stirred for 5 hours and then concentrated in vacuo. The crude product was purified by flash column chromatography on silica gel using DCM/MeOH (100:1 to 20:1) as eluent. Fractions with the desired product were collected, concentrated and the residue was dissolved in 6M $HCl_{aq}$. The resulting solution was subjected to preparative HPLC (0.1-1% MeCN in water) to afford 9.5 mg (26%) of (2-((1R,3R,4S)-3-amino-4-((dimethylamino)methyl)-3-(methoxycarbonyl)cyclohexyl)ethyl)boronic acid dihydrochloride as a white solid. ESI+MS: m/z=287.1 $(M+1)^+$. ESI-MS: m/z=299.1 $(M-1)^-$. $^1$H NMR (700 MHz, $D_2O$) δ 3.69 (s, 3H), 3.17 (dd, J=13.3, 2.4 Hz, 1H), 3.09-3.02 (m, 1H), 2.79 (s, 3H), 2.73 (s, 3H), 2.16 (ddd, J=13.3, 3.1, 2.0 Hz, 1H), 2.13-2.08 (m, 1H), 1.83-1.73 (m, 2H), 1.68-1.60 (m, 1H), 1.48-1.40 (m, 1H), 1.26 (t, J=12.9 Hz, 1H), 1.23-1.13 (m, 2H), 0.89-0.80 (m, 1H), 0.60 (t, J=8.0 Hz, 2H).

General Synthetic Route for Examples 44 and 45

Example 44. (1R,2S,5R)-1-amino-2-((dimethylamino)methyl)-5-(2-((3aR,4R,6R,7aS)-3a,5,5-trimethylhexahydro-4,6-methanobenzo[d][1,3,2]dioxaborol-2-yl)ethyl)cyclohexane-1-carboxylic acid dihydrochloride A mixture of (1R,2S,5R)-1-amino-5-(2-boronoethyl)-2-((dimethylamino)methyl)cyclohexanecarboxylic acid dihydrochloride (0.03 g, 0.087 mmol, 1 eq), (1R,2R,3S,5R)-(−)-2,3-pinanediol (22 mg, 0.13 mmol) in acetonitrile (1 mL) was heated under reflux for 1 hour. After this time additional amount of pinanediol (7 mg, 0.043 mmol) was added and heating was continued for one hour. The solvent was evaporated under reduced pressure and the residue was triturated with diethyl ether (3×3 mL) to give 27 mg (65%) of the corresponding product as a white solid. ESI+MS: m/z=407.4 $(M+1)^+$. ESI-MS: m/z=405.3 $(M−1)^-$. $^1$H NMR (700 MHz, DMSO) δ 8.90 (bs, 2H), 4.28 (dd, J=8.7, 1.9 Hz, 1H), 3.52-3.38 (m, 1H), 2.96-2.87 (m, 1H), 2.75 (s, 6H), 2.31-2.25 (m, 1H), 2.17 (ddd, J=10.5, 6.2, 4.1 Hz, 2H), 2.11 (bd, J=13.1 Hz, 1H), 1.95 (t, J=5.5 Hz, 1H), 1.88-1.83 (m, 1H), 1.76 (bd, J=12.4 Hz, 1H), 1.71-1.67 (m, 1H), 1.66-1.58 (m, 2H), 1.32-1.29 (m, 4H), 1.28-1.22 (m, 5H), 0.98 (d, J=10.7 Hz, 1H), 0.87-0.80 (m, 4H), 0.75-0.66 (m, 2H).

Example 45. (1R,2S,5R)-1-amino-2-(pyrrolidin-1-ylmethyl)-5-(2-((3aR,4R,6R,7aS)-3a,5,5-trimethylhexahydro-4,6-methanobenzo[d][1,3,2]dioxaborol-2-yl)ethyl)cyclohexanecarboxylic acid dihydrochloride A mixture of rac-(1R,2S,5R)-1-amino-5-(2-boronoethyl)-2-(pyrrolidin-1-ylmethyl)cyclohexanecarboxylic acid dihydrochloride (0.03 g, 0.08 mmol, 1 equiv.), (1R,2R,3S,5R)-(−)-2,3-pinanediol (0.02 g, 0.12 mmol, 1.5 equiv.) in acetonitrile (3 mL) was sonicated for 30 min. at 35° C. After this time the solvent was evaporated under reduced pressure. The residue was titurated with diethyl ether (3×3 mL). The white solid was filtered and sonicated with acetone (1 mL) for 1 min at 35° C. The product was separated (0.04 g, 98%) as a white solid. ESI+MS: m/z=433.5 (M+1)$^+$. ESI-MS: m/z=431.3 (M−1)$^−$. $^1$H NMR (700 MHz, Deuterium Oxide) δ 4.36 (d, J=7.2 Hz, 1H), 3.66 (dp, J=11.3, 4.1 Hz, 2H), 3.37-3.20 (m, 2H), 3.07 (dt, J=11.4, 8.1 Hz, 1H), 2.96 (dt, J=11.4, 8.4 Hz, 1H), 2.43-2.27 (m, 1H), 2.23-2.16 (m, 2H), 2.15-2.01 (m, 3H), 2.01-1.83 (m, 6H), 1.81-1.72 (m, 2H), 1.72-1.65 (m, 1H), 1.33 (d, J=1.3 Hz, 2H), 1.28 (dd, J=37.2, 6.5 Hz, 2H), 1.24-1.17 (m, 5H), 0.94 (dd, J=11.0, 4.2 Hz, 2H), 0.81 (t, J=7.9 Hz, 2H), 0.77 (s, 3H).

Example 46. (5R)-1-amino-5-(2-boronoethyl)-2-(2-(pyrrolidin-1-yl)ethyl)cyclohexanecarboxylic acid dihydrochloride

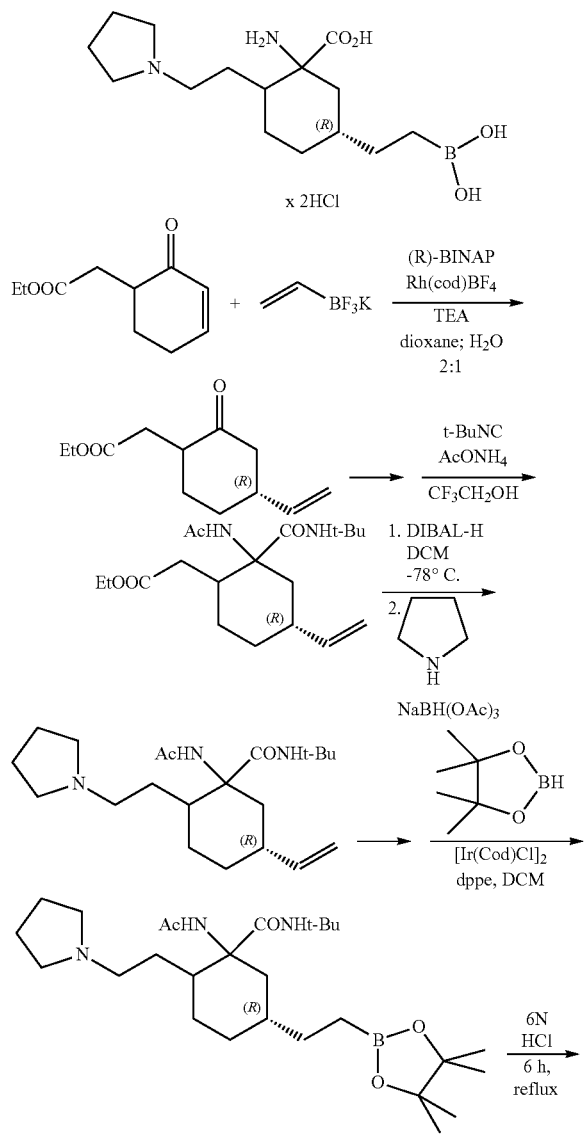

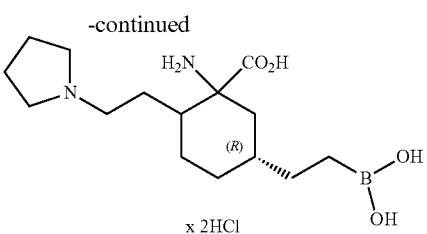

Step A. Ethyl 2-((1R,4R)-2-oxo-4-vinylcyclohexyl)acetate and Ethyl 2-((1S,4R)-2-oxo-4-vinylcyclohexyl)acetate

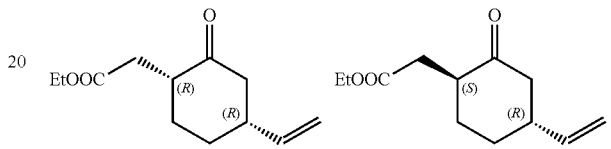

The three-neck round bottom flask was charged with [Rh(cod)$_2$]BF$_4$ (0.78 g, 1.92 mmol, 0.03 eqiuv.), (R)-BINAP (1.31 g, 2.11 mmol, 0.033 eqiuv.) and potassium vinyl trifluoroborate salt (17.1 g, 0.128 mol, 2.0 eqiuv.). The reaction flask was flushed with argon several times and degassed mixture of dioxane:H$_2$O (150:75 mL) together with triethylamine (26.7 mL, 0.192 mol, 3.0 eqiuv.) were added. After stirring the reaction mixture for 10 min at room temperature ethyl 2-(2-oxocyclohex-3-en-1-yl)acetate (11.7 g, 0.064 mol, 1 equiv.) was added. The reaction mixture was stirred for 4 days at room temperature under argon. Solvents were evaporated in vacuo and crude reaction mixture was partitioned between water and EtOAc. The aqueous layer was washed with AcOEt. The combined organic layers were washed with 0.5M HCl$_{aq}$ and brine, dried over MgSO$_4$, filtered and concentrated in vacuo. The crude product was purified by flash chromatography on silica gel (hexane/AcOEt, 30:1) to give product as a mixture of diastereoisomers, dr=1:1, (1.6 g, 12%, yellow liquid). [α]$_D$=−3.12 (c=1.0 in CHCl$_3$). $^1$H NMR (700 MHz, Chloroform-d) δ 5.85-5.62 [(m, 1H) two diastereoisomers], 5.14-4.91 [(m, 2H, two diastereoisomers)], 4.12-4.07 [(m, 2H, two diastereoisomers)], 2.85-2.78 (m, 1H), 2.76-2.68 (m, 1H), 2.51-2.37 (m, 2H), 2.27-2.17 (m, 1H), 2.16-2.09 (m, 2H), 1.95-1.89 (m, 1H), 1.64-1.55 (m, 1H), 1.42 (qd, J=13.1, 3.5 Hz, 1H), 1.24-1.21 [(m, 3H, two diasteroisomers)].

Step B. Ethyl 2-(4R)-2-acetamido-2-(tert-butylcarbamoyl)-4-vinylcyclohexyl)acetate

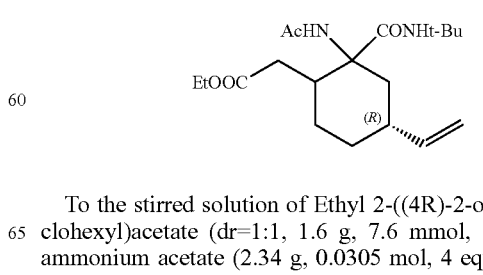

To the stirred solution of Ethyl 2-((4R)-2-oxo-4-vinylcyclohexyl)acetate (dr=1:1, 1.6 g, 7.6 mmol, 1 equiv.) and ammonium acetate (2.34 g, 0.0305 mol, 4 equiv.) in 2,2,2-trifluoroethanol (4 mL) tert-butylisocyanide (1.71 mL, 0.0152 mol, 2 equiv.) was added via syringe and the resulting mixture was stirred at room temperature for 24 hours. After that time the solvent was evaporated and the crude material was partitioned between ethyl acetate (50 mL) and water (20 mL). The aqueous layer was separated and extracted with ethyl acetate (3×20 mL). The organic layers were combined and washed with brine (10 mL), dried over MgSO$_4$, filtered and evaporated under reduced pressure. The residue was purified by silica gel flash chromatography (gradient elution, hexane/AcOEt 10:1 to 2:1) to give corresponding product as a mixture of diastereoisomers, dr=1:1 (0.7 g, 25%, white solid). [α]$_D$=−2.92 (c 1.0 in CHCl$_3$). ESI+MS: m/z=first diastereoisomer 353.35 (M+1)$^+$, 375.35 (M+Na)$^+$, second diastereoisomer 353.4 (M+1)$^+$, 375.40 (M+Na)$^+$, $^1$H NMR (700 MHz, Chloroform-d) δ 8.07, 7.87 [2s, 1H, two diastereoisomers)], 7.60, 7.46 [(s, 1H, two diastereoisomers)], 5.76-5.62 [(m, 1H two diastereoisomers)] 5.05-4.84 [(m, 2H two diastereoisomers)], 4.23-4.06 (m, 2H), 3.14-2.96 (m, 2H), 2.67, 2.53 [(dd, J=16.8, 6.9 Hz, dd, J=16.8, 3.3 Hz, 1H, two diastereoisomers), 2.43 (dd, J=17.9, 3.5 Hz, 1H), 2.29-2.13 (m, 1H), 2.10, 2.00 [(2s, 3H, two diastereoisomers)], 1.93-1.85 (m, 1H), 1.81-1.73 (m, 1H), 1.67-1.57 (m, 1H), 1.33, 1.32 [(2s, 9H, two diastereoisomers)], 1.29-1.25 (m, 3H), 1.24-1.10 (m, 2H).

Step C. (5R)-1-acetamido-N-(tert-butyl)-2-(2-(pyrrolidin-1-yl)ethyl)-5-vinylcyclohexanecarboxamide

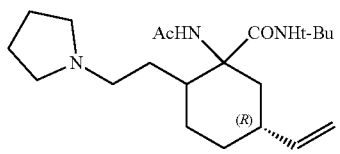

The title compound (5R)-1-acetamido-N-(tert-butyl)-2-(2-(pyrrolidin-1-yl)ethyl)-5-vinylcyclohexanecarboxamide was obtained in the same manner like in Example 26, step A, using Ethyl 2-(4R)-2-acetamido-2-(tert-butylcarbamoyl)-4-vinylcyclohexyl)acetate (700 mg, 2.0 mmol, 1 equiv.), DIBAL-H 1M in DCM (6.2 mL, 6.2 mmol, 3.1 equiv.), glacial acetic acid (0.57 mL, 10 mmol, 5 equiv.), pyrrolidine (0.33 mL, 4.0 mmol, 2.0 equiv.), sodium triacetoxyborohydride (1.7 g, 8.0 mmol, 4 equiv.) and DCM (12 mL). The residue was purified by silica gel flash chromatography (DCM:MeOH 20:1) to give corresponding product as a mixture of diastereoisomers, dr=1:3 (180 mg, 25%, pale yellow oil). [α]$_D$=+32.59 (c=1.0 in CHCl$_3$). ESI+MS: m/z=first diastereoisomer 364.4 (M+1)$^+$, second diastereoisomer 364.45 (M+1)$^+$, $^1$H NMR (700 MHz, Chloroform-d) δ 5.92-5.54 [(m, 1H, two diastereoisomers)], 5.13-4.76 [(m, 2H, two diastereoisomers)], 3.18, 3.07 [(d, J=12.8 Hz, d, J=14.0 Hz, 1H, two diastereoisomers)], 2.86-2.53 (m, 4H), 2.28-2.19 (m, 2H), 2.15-1.83 (m, 8H), 1.70-1.53 (m, 4H), 1.51-1.40 (m, 1H), 1.33, 1.32 [(2s, 9H, two diastereoisomers)], 1.29-1.20 (m, 1H), 1.16-1.03 (m, 2H).

Step D. (5R)-1-acetamido-N-(tert-butyl)-2-(2-(pyrrolidin-1-yl)ethyl)-5-(2-(4,4,5,5-tetramethyl-1,3,2-dioxaborolan-2-yl)ethyl)cyclohexanecarboxamide

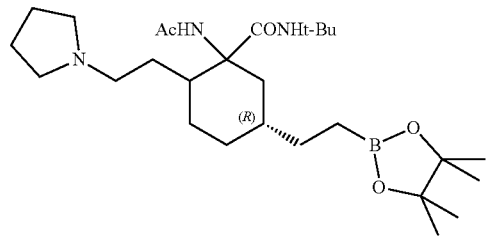

The title compound (5R)-1-acetamido-N-(tert-butyl)-2-(2-(pyrrolidin-1-yl)ethyl)-5-(2-(4,4,5,5-tetramethyl-1,3,2-dioxaborolan-2-yl)ethyl)cyclohexanecarboxamide was obtained in the same manner like in Example 26, step B, using (5R)-1-acetamido-N-(tert-butyl)-2-(2-(pyrrolidin-1-yl)ethyl)-5-vinylcyclohexanecarboxamide (178 mg, 0.49 mmol, 1 equiv.), dppe (11.7 mg, 0.0294 mmol, 0.06 equiv.), bis(1,5-cyclooctadiene)diiridium(I) dichloride (9.8 mg, 0.0147 mmol, 0.03 equiv.), 4,4,5,5-tetramethyl-1,3,2-dioxaborolane (0.14 mL, 0.98 mmol, 2 equiv.) and DCM (4 mL). The crude product was purified by column chromatography on silica gel (gradient elution, DCM/MeOH 20:1 to 9:1) to give corresponding product as a mixture of diastereoisomers, dr=1:3 (50 mg, 21%, pale yellow oil). [α]$_D$=+4.23 (c=1.0 in CHCl$_3$). ESI+MS: m/z=first diastereoisomer 492.6 (M+1)$^+$, second diastereoisomer 492.55 (M+1)$^+$, $^1$H NMR (700 MHz, Chloroform-d) δ 3.08 (d, J=13.5 Hz, 1H), 2.99-2.82 (m, 4H), 2.33-2.21 (m, 2H), 2.14-1.92 (m, 10H), 1.81-1.63 (m, 3H), 1.61-1.48 (m, 3H), 1.41-1.35 (m, 1H), 1.30, 1.29 [(2s, 9H, two diastereoisomers)], 1.22, 1.21 [(2s, 12H, two diastereoisomers)], 0.90-0.82 (m, 1H), 0.80-0.64 (m, 2H).

Step E. (5R)-1-amino-5-(2-boronoethyl)-2-(2-(pyrrolidin-1-yl)ethyl)cyclohexanecarboxylic acid dihydrochloride The title compound (5R)-1-amino-5-(2-boronoethyl)-2-(2-(pyrrolidin-1-yl)ethyl)cyclohexanecarboxylic acid dihydrochloride was obtained in the same manner like in Example 26, step C, using (5R)-1-acetamido-N-(tert-butyl)-2-(2-(pyrrolidin-1-yl)ethyl)-5-(2-(4,4,5,5-tetramethyl-1,3,2-dioxaborolan-2-yl)ethyl)cyclohexanecarboxamide (50 mg, 0.1 mmol, 1 equiv.) and 6 N HCl$_{aq}$(10 mL). The residue was purified by flash chromatography on DOWEX® ion exchange resin (eluent 0.1N ammonia in water) and next by preparative HPLC (0.1-10% MeCN in water) to give (after acidification with 6N HCl and subsequent lyophilization) product as a separable diastereoisomers (7.4 mg, 23%, white solids).

First diastereoisomer (1.2 mg), ESI+MS: m/z=313.40 (M+1)$^+$. [α]$_D$=−42.2 (c=0.125 in H$_2$O). $^1$H NMR (700 MHz, Deuterium Oxide) δ 3.72-3.60 (m, 2H), 3.37-3.22 (m, 2H), 3.14-3.02 (m, 2H), 2.21-2.07 (m, 3H), 2.06-1.90 (m, 5H), 1.74-1.63 (m, 2H), 1.61-1.52 (m, 1H), 1.45-1.34 (m, 3H), 1.33-1.22 (m, 1H), 1.16-1.04 (m, 1H), 0.86-0.76 (m, 2H). Second diastereoisomer (6.2 mg), ESI+MS: m/z=313.35 (M+1)$^+$, $^1$H NMR (700 MHz, Deuterium Oxide) δ 3.73-3.65 (m, 2H), 3.41 (td, J=12.3, 4.7 Hz, 1H), 3.23 (td, J=12.2, 4.9 Hz, 1H), 3.16-3.06 (m, 2H), 2.29 (ddd, J=13.2, 3.3, 1.8 Hz, 1H), 2.22-2.12 (m, 2H), 2.10-1.98 (m, 3H), 1.96-1.81 (m, 3H), 1.79-1.66 (m, 2H), 1.65-1.56 (m, 1H), 1.42-1.28 (m, 3H), 1.02-0.90 (m, 1H), 0.86-0.75 (m, 2H).

Example 47. (5R)-1-amino-5-(2-boronoethyl)-2-(2-(dimethylamino)ethyl)cyclohexanecarboxylic acid dihydrochloride

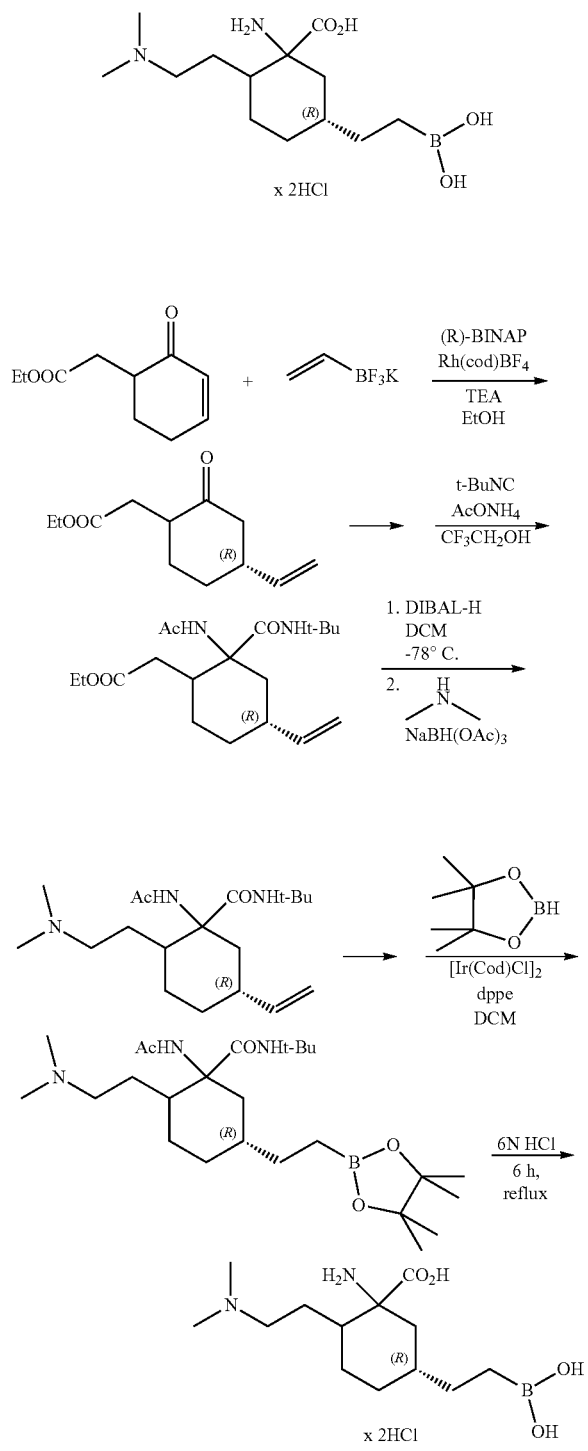

Step A. Ethyl 2-((1R,4R)-2-oxo-4-vinylcyclohexyl)acetate and Ethyl 2-((1S,4R)-2-oxo-4-vinylcyclohexyl)acetate

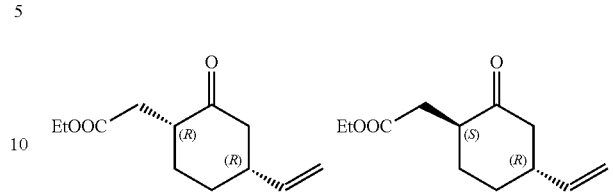

The title compound ethyl 2-((1R,4R)-2-oxo-4-vinylcyclohexyl)acetate and Ethyl 2-((1S,4R)-2-oxo-4-vinylcyclohexyl)acetate was obtained in the same manner like in Example 46, step A, using Ethyl 2-(2-oxocyclohex-3-en-1-yl)acetate (7.05 g, 0.0387 mol, 1 equiv.), [Rh(cod)$_2$]BF$_4$ (0.47 g, 1.16 mmol, 0.03 eqiuv.), (R)-BINAP (0.79 g, 1.28 mmol, 0.033 eqiuv.) and potassium vinyl trifluoroborate salt (10.4 g, 0.0774 mol, 2.0 eqiuv.), triethylamine (16.3 mL, 0.116 mol, 3.0 eqiuv.) and EtOH$_{abs}$. (312 mL) as a solvent. The crude product was purified by flash chromatography on silica gel (Hex:AcOEt, 30:1) to give the desired product as a mixture of diastereoisomers, dr=1:1, (1.6 g, 19%, yellow liquid). [α]$_D$=+38.9 (c=0.250 in CHCl$_3$). $^1$H NMR (700 MHz, Chloroform-d) δ 5.79-5.67 (in, 1H, two diastereoisomers)], 5.07-4.92 (m, 2H, two diastereoisomers)], 4.13-4.05 (in, 2H, two diastereoisomers)], 2.85-2.76 (m, 1H), 2.75-2.67 (m, 1H), 2.52-2.36 (m, 2H), 2.27-2.16 (m, 1H), 2.15-2.08 (m, 2H), 1.95-1.87 (m, 1H), 1.64-1.54 (m, 1H), 1.46-1.34 (m, 1H), 1.24-1.17 (in, 3H, two diastereoisomers)].

Step B. Ethyl 2-(4R)-2-acetamido-2-(tert-butylcarbamoyl)-4-vinylcyclohexyl)acetate

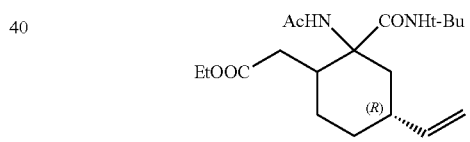

The title compound ethyl 2-(4R)-2-acetamido-2-(tert-butylcarbamoyl)-4-vinylcyclohexyl)acetate was obtained in the same manner like in Example 46, step B, using ethyl 2-((1R,4R)-2-oxo-4-vinylcyclohexyl)acetate and ethyl 2-((1S,4R)-2-oxo-4-vinylcyclohexyl)acetate (1.6 g, 7.6 mmol, 1 equiv.), ammonium acetate (2.34 g, 0.0305 mol, 4 equiv.), tert-butylisocyanide (1.71 mL, 0.0152 mol, 2 equiv.) and 2,2,2-trifluoroethanol (5 mL) as a solvent. The residue was purified by silica gel flash chromatography (gradient elution, hexane/AcOEt 10:1 to 7:1) to give corresponding product as a mixture of diastereoisomers, dr=1:1 (1.5 g, 52%, white solid). ESI+MS: m/z=first diastereoisomer 353.45 (M+1)$^+$, second diastereoisomer 353.45 (M+1)$^+$. [α]$_D$=+31.9 (c=0.250 in CHCl$_3$). $^1$H NMR (700 MHz, Chloroform-d) δ 8.05, 7.87 [(2s, 1H, two diastereoisomers)], 7.60, 7.46 [(2s, 1H, two diastereoisomers)], 5.75-5.60 [(m, 1H, two diastereoisomers)], 5.03-4.83 [(m, 2H, two diastereoisomers)], 4.27-4.03 (m, 2H), 3.17-2.90 (m, 2H), 2.66, 2.52 [(dd, J=16.8, 6.9 Hz; dd, J=16.8, 3.4 Hz, 1H, two diastereoisomers)], 2.45-2.39 (m, 1H), 2.25-2.13 (m, 1H), 2.09, 2.00 [(2s, 3H, two diastereoisomers)], 1.94-1.85 (m, 1H), 1.81-1.72 (m, 1H), 1.66-1.56 (m, 1H), 1.32, 1.31 [(2s, 9H, two diastereoisomers)], 1.29-1.24 (m, 3H), 1.23-1.12 (m, 2H).

Step C. (5R)-1-acetamido-N-(tert-butyl)-2-(2-(dimethylamino)ethyl)-5-vinylcyclohexanecarboxamide

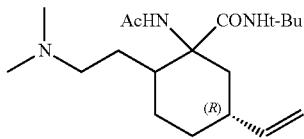

The title compound (5R)-1-acetamido-N-(tert-butyl)-2-(2-(dimethylamino)ethyl)-5-vinylcyclohexanecarboxamide was obtained in the same manner like in Example 26, step A, using ethyl 2-(4R)-2-acetamido-2-(tert-butylcarbamoyl)-4-vinylcyclohexyl)acetate (1.5 g, 4.26 mmol, 1 equiv.), DIBAL-H 1M in DCM (13.2 mL, 0.0132 mol, 3.1 equiv.), glacial acetic acid (1.2 mL, 0.0213 mol, 5 equiv.), dimethyl amine 2N in THF (5.32 mL, 0.0106 mmol, 2.5 equiv.), sodium triacetoxyborohydride (3.6 g, 0.017 mmol, 4 equiv.) and DCM (15 mL). The crude product was purified by silica gel flash chromatography (gradient elution DCM:MeOH 10:1 to 5:1) to give corresponding product as a mixture of diastereoisomers, dr=1:4 (480 mg, 34%, pale yellow oil). ESI+MS: m/z=first diastereoisomer 338.45 (M+1)+, second diastereoisomer 338.45 (M+1)+. [α]$_D$=+53.2 (c=0.250 in CHCl$_3$). $^1$H NMR (700 MHz, Chloroform-d) δ 5.80-5.65 [(m, 1H, two diastereoisomers)], 5.10-4.83 [(m, 2H, two diastereoisomers)], 3.22, 3.11 (dt, J=13.4, 2.5 Hz; dt, J=13.5, 3.1 Hz, 1H, two diastereoisomers)], 2.42-2.34 (m, 1H), 2.30, 2.27 (2s, 6H, two diastereoisomers)], 2.23 (td, J=13.1, 4.2 Hz, 1H), 2.17-2.02 (m, 2H), 2.00, 1.94 (2s, 3H, two diastereoisomers)], 1.84-1.73 (m, 1H), 1.68-1.56 (m, 2H), 1.55-1.47 (m, 1H), 1.33, 1.32 [(2s, 9H, two diastereoisomers)], 1.31-1.15 (m, 1H), 1.15-1.03 (m, 2H).

Step D. (5R)-1-acetamido-N-(tert-butyl)-2-(2-(dimethylamino)ethyl)-5-(2-(4,4,5,5-tetramethyl-1,3,2-dioxaborolan-2-yl)ethyl)cyclohexanecarboxamide

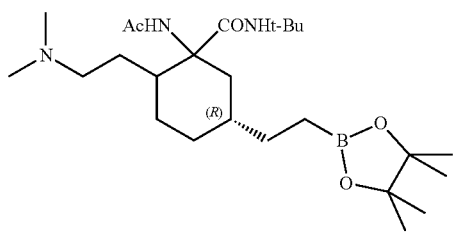

The title compound (5R)-1-acetamido-N-(tert-butyl)-2-(2-(dimethylamino)ethyl)-5-(2-(4,4,5,5-tetramethyl-1,3,2-dioxaborolan-2-yl)ethyl)cyclohexanecarboxamide was obtained in the same manner like in Example 26, step B, using (5R)-1-acetamido-N-(tert-butyl)-2-(2-(dimethylamino)ethyl)-5-vinylcyclohexanecarboxamide (470 mg, 1.39 mmol, 1 equiv.), dppe (33.0 mg, 0.0834 mmol, 0.06 equiv.), bis(1,5-cyclooctadiene)diiridium(I) dichloride (28 mg, 0.0417 mmol, 0.03 equiv.), 4,4,5,5-tetramethyl-1,3,2-dioxaborolane (0.4 mL, 2.78 mmol, 2 equiv.) and DCM (6 mL). The crude product was purified by column chromatography on silica gel (gradient elution, DCM/MeOH 20:1 to 9:1) to give corresponding product as a mixture of diastereoisomers, dr=1:3 (340 mg, 52%, pale yellow oil). ESI+MS: m/z=first diastereoisomer 466.65 (M+1)+, second diastereoisomer 466.6 (M+1)+. [α]$_D$=+51.8 (c 0.250 in CHCl$_3$). $^1$H NMR (700 MHz, Chloroform-d) δ 3.16, 3.00 (d, J=13.3 Hz; d, J=8.5 Hz, 1H, two diastereoisomers)], 2.50-2.40 (m, 2H), 2.36, 2.33 (2s, 6H two diastereoisomers)], 2.28-2.17 (m, 2H), 2.14-2.02 (m, 2H), 1.98, 1.96 (2s, 3H, two diastereoisomers)], 1.82-1.70 (m, 1H), 1.67-1.53 (m, 1H), 1.30, 1.29 (2s, 9H two diastereoisomers)], 1.22, 1.21 (2s, 12H two diastereoisomers)], 1.17-1.07 (m, 1H), 0.96-0.81 (m, 4H), 0.81-0.66 (m, 2H).

Step E. (5R)-1-amino-5-(2-boronoethyl)-2-(2-(dimethylamino)ethyl)cyclohexanecarboxylic acid dihydrochloride The title compounds (5R)-1-amino-5-(2-boronoethyl)-2-(2-(dimethylamino)ethyl)cyclohexanecarboxylic acid dihydrochloride was obtained in the same manner like in Example 26, step C, using (5R)-1-acetamido-N-(tert-butyl)-2-(2-(dimethylamino)ethyl)-5-(2-(4,4,5,5-tetramethyl-1,3,2-dioxaborolan-2-yl)ethyl)cyclohexanecarboxamide (330 mg, 0.65 mmol, 1 equiv.) and 6 N HCl$_{aq}$ (10 mL). The residue was purified by flash chromatography on DOWEX ion exchange resin (eluent 0.1N ammonia in water) and next by preparative HPLC (0.1-1% MeCN in water) to give (after acidification with 6N HCl and subsequent lyophilization) product as diastereoisomers (19.1 mg, white solid). One single diastereoisomer was separated (16.2 mg, 8%, white solid). ESI+MS: m/z=isolated single diastereoisomer 287.35 (M+1)+, $^1$H NMR (700 MHz, Deuterium Oxide) δ 3.35 (td, J=12.4, 4.8 Hz, 1H), 3.18 (td, J=12.3, 4.9 Hz, 1H), 2.92 (s, 3H), 2.91 (s, 3H), 2.31 (ddd, J=13.2, 3.4, 1.8 Hz, 1H), 2.07 (tdd, J=12.5, 4.9, 2.2 Hz, 1H), 1.94-1.86 (m, 2H), 1.86-1.74 (m, 2H), 1.71 (qd, J=12.8, 3.3 Hz, 1H), 1.66-1.57 (m, 1H), 1.40-1.34 (m, 3H), 0.96 (qd, J=12.9, 3.6 Hz, 1H), 0.84-0.78 (m, 2H).

Example 48.
1,2-diamino-5-(2-boronoethyl)cyclohexanecarboxylic acid dihydrochloride

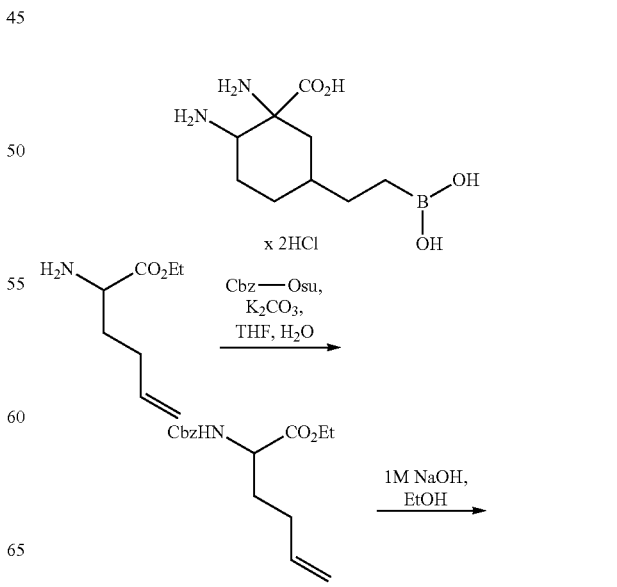

-continued

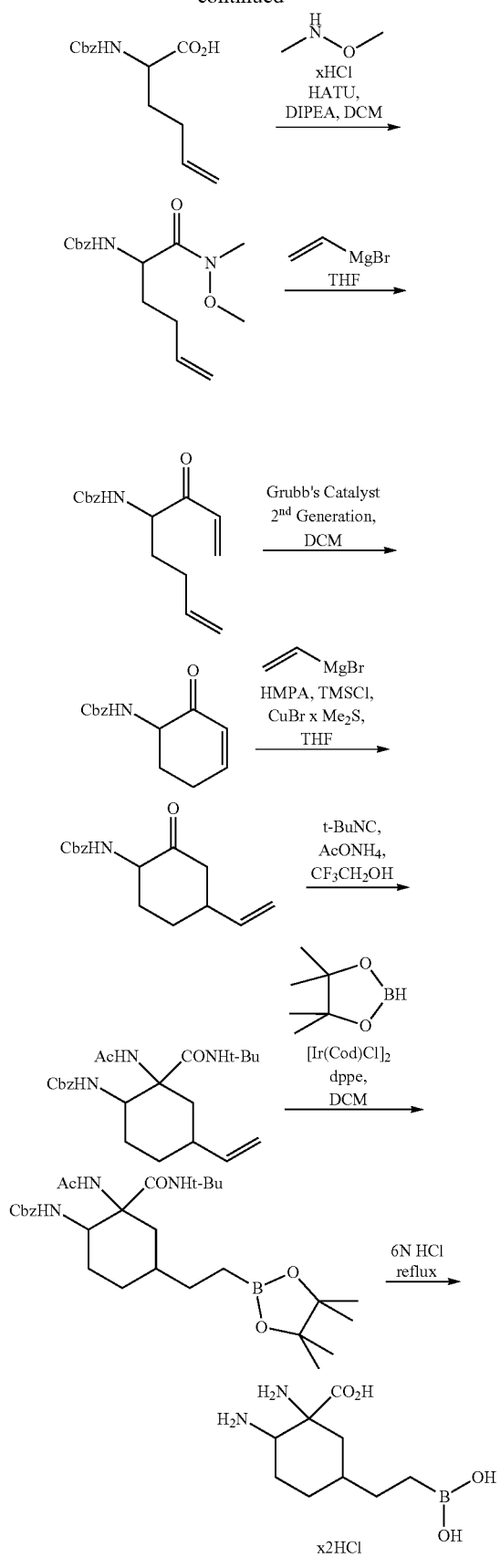

Step A. Ethyl 2-(((benzyloxy)carbonyl)amino)hex-5-enoate

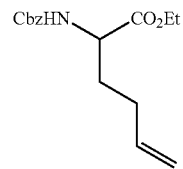

To a solution of ethyl 2-aminohex-5-enoate (4 g, 25 mmol, 1 equiv., prepared from N-(diphenylmethylene)glycine ethyl ester using literature method, WO 2014/009509) in THF-H$_2$O (35 mL-35 mL) was added potassium carbonate (6.9 g, 50 mmol, 2 equiv.). The mixture was cooled to 0° C. and N-(Benzyloxycarbonyloxy)succinimide (6.35 g, 25 mmol, 1 equiv.) was added. The reaction mixture was stirred at room temperature overnight. Aqueous layer was separated and washed with ethyl acetate. The organic layers were combined, dried over MgSO$_4$, filtered and concentrated in vacuo. The crude product was purified by flash chromatography on silica gel (petroleum ether/AcOEt, 20:1 to 8:1) to give corresponding product (7.15 g, 96%, colorless oil). ESI+MS: m/z=314.3 (M+Na)$^+$. $^1$H NMR (700 MHz, Chloroform-d) δ 7.43-7.31 (m, 5H), 5.81 (td, J=16.8, 6.6 Hz, 1H), 5.32 (d, J=7.6 Hz, 1H), 5.13 (s, 2H), 5.04 (dd, J=31.1, 13.6 Hz, 2H), 4.40 (q, J=7.6 Hz, 1H), 4.22 (q, J=7.0 Hz, 2H), 2.13 (qt, J=14.6, 6.9 Hz, 2H), 1.97 (dq, J=14.2, 6.2 Hz, 1H), 1.78 (dq, J=14.0, 8.2 Hz, 1H), 1.32-1.28 (m, 3H).

Step B. 2-(((benzyloxy)carbonyl)amino)hex-5-enoic acid

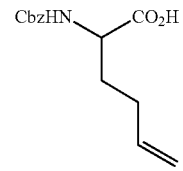 [SMILES: C=CCCC(NC(=O)OCc1ccccc1)C(=O)O]

To a solution of ethyl 2-(((benzyloxy)carbonyl)amino) hex-5-enoate (7.15 g, 24 mmol, 1 equiv.) in ethanol (50 mL) was added 1N NaOH$_{aq}$ (50 mL) and the mixture was stirred at room temperature for 3 h. The solvent was evaporated in vacuo. The aqueous layer was acidified to pH=2 using 2N HCl$_{aq}$ and extracted with ethyl acetate three times. The combined organic layers was dried over MgSO$_4$, filtered and concentrated in vacuo to give the corresponding product (5.9 g, 91%, white solid). ESI+MS: m/z=286.25 (M+Na)$^+$; ESI-MS: m/z=262.1 (M-1)$^-$. $^1$H NMR (700 MHz, Chloroform-d) δ 7.40-7.30 (m, 5H), 5.79 (dt, J=16.7, 8.3 Hz, 1H), 5.27 (d, J=8.2 Hz, 1H), 5.19-5.09 (m, 2H), 5.04 (dd, J=32.4, 13.6 Hz, 2H), 4.44 (q, J=7.7 Hz, 1H), 2.16 (q, J=7.2 Hz, 2H), 2.01 (dq, J=13.2, 7.7 Hz, 1H), 1.80 (dq, J=14.7, 7.7 Hz, 1H).

Step C. Benzyl (1-(methoxy(methyl)amino)-1-oxo-hex-5-en-2-yl)carbamate

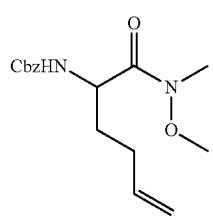 [SMILES: C=CCCC(NC(=O)OCc1ccccc1)C(=O)N(C)OC]

To a solution of 2-(((benzyloxy)carbonyl)amino)hex-5-enoic acid (5.9 g, 22 mmol, 1 equiv.) in dichloromethane (50 mL) was added N,N-diisopropylethylamine (8.19 mL, 47 mmol, 2.1 equiv.), N,O-dimethylhydroxylamine hydrochloride (2.3 g, 24 mmol, 1.05 equiv.) and HATU (8.95 g, 24 mmol, 1.05 equiv.). The reaction mixture was stirred at room temperature overnight. The mixture was diluted with ethyl acetate and washed with 1N NaOH$_{aq}$, 1N HCl$_{aq}$ and brine, dried over MgSO$_4$, filtered and concentrated in vacuo. The crude product was purified by flash chromatography on silica gel (hexane/AcOEt, 10:1 to 4:1) to give corresponding product (6.7 g, 98%, white solid). ESI+MS: m/z=307.35 (M+1)$^+$. $^1$H NMR (700 MHz, Chloroform-d) δ 7.40-7.28 (m, 5H), 5.79 (td, J=16.9, 6.6 Hz, 1H), 5.45 (d, J=8.6 Hz, 1H), 5.17-5.02 (m, 3H), 4.99 (d, J=10.2 Hz, 1H), 4.76 (s, 1H), 3.77 (s, 3H), 3.21 (s, 3H), 2.19-2.08 (m, 2H), 1.88-1.77 (m, 1H), 1.71-1.63 (m, 1H).

Step D. Benzyl (3-oxoocta-1,7-dien-4-yl)carbamate

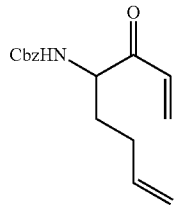 [SMILES: C=CCCC(NC(=O)OCc1ccccc1)C(=O)C=C]

To a solution of benzyl (1-(methoxy(methyl)amino)-1-oxohex-5-en-2-yl)carbamate (6.6 g, 22 mmol, 1 equiv.) in dry THF (30 mL) under Ar at −78° C. was added vinylmagnesium bromide 1M in THF (75 mL, 75 mmol, 3.5 equiv.). The reaction mixture was slowly warmed to room temperature and was stirred for 1.5 h. The reaction mixture was quenched with 2N HCl$_{aq}$ and extracted with ethyl acetate. The organic layer was washed with brine, dried over MgSO$_4$, filtered and concentrated in vacuo. The crude product was purified by flash chromatography on silica gel (hexane/AcOEt, 30:1 to 8:1) to give corresponding product (670 mg, 9%, colorless oil). ESI+MS: m/z=296.3 (M+Na)$^+$. $^1$H NMR (700 MHz, Chloroform-d) δ 7.40-7.29 (m, 5H), 6.48 (dd, J=17.5, 10.4 Hz, 1H), 6.40 (d, J=17.4 Hz, 1H), 5.91 (d, J=10.4 Hz, 1H), 5.83-5.74 (m, 1H), 5.57 (d, J=7.1 Hz, 1H), 5.11 (s, 2H), 5.02 (dd, J=27.7, 13.6 Hz, 2H), 4.77-4.70 (m, 1H), 2.17-2.08 (m, 1H), 2.07-1.92 (m, 2H), 1.70-1.61 (m, 1H).

Step E. Benzyl (2-oxocyclohex-3-en-1-yl)carbamate

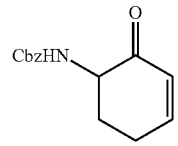

To a solution of benzyl (3-oxoocta-1,7-dien-4-yl)carbamate (670 mg, 2.45 mmol, 1 equiv.) in dry dichloromethane (120 mL) under Ar was added Grubbs Catalyst, 2$^{nd}$ Generation (104 mg, 0.12 mmol, 0.05 equiv.). The reaction mixture was stirred at room temperature overnight. The solvent was evaporated in vacuo. The crude product was purified by flash chromatography on silica gel (hexane/AcOEt, 15:1 to 3:1) to give corresponding product (520 mg, 86%, white solid). ESI+MS: m/z=246.4 (M+1)$^+$. $^1$H NMR (700 MHz, Chloroform-d) δ 7.39-7.30 (m, 5H), 7.01-6.96 (m, 1H), 6.08 (dd, J=10.0, 2.4 Hz, 1H), 5.77 (s, 1H), 5.12 (s, 2H), 4.35-4.24 (m, 1H), 2.64 (dd, J=49.9, 11.6 Hz, 2H), 2.48 (dt, J=19.5, 4.7 Hz, 1H), 1.80 (qd, J=12.5, 5.0 Hz, 1H).

Step F. Benzyl (2-oxo-4-vinylcyclohexyl)carbamate

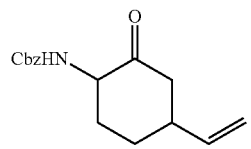 [SMILES: C=CC1CCC(NC(=O)OCc2ccccc2)C(=O)C1]

The title compound benzyl (2-oxo-4-vinylcyclohexyl)carbamate was obtained in the same manner like in the step B from the synthesis of the intermediate 1, using benzyl (2-oxocyclohex-3-en-1-yl)carbamate (500 mg, 2.04 mmol, 1 equiv.), vinylmagnesium bromide 1M in THF (5.1 mL, 5.1 mmol, 2.5 equiv.), HMPA (1.4 mL, 8.16 mmol, 4 equiv.), copper(I) bromide dimethyl sulfide complex (63 mg, 0.31 mmol, 0.15 equiv.), trimethylsilyl chloride (1.3 mL, 10.2 mmol, 5 equiv.) and THF (13 mL). The crude product was purified by silica gel flash chromatography (hexane/AcOEt, 15:1 to 4:1) to give corresponding product as a mixture of diastereoisomers, dr=1:1, (170 mg, 30%, colorless oil). ESI+MS: m/z=274.1 (M+1)$^+$. $^1$H NMR (700 MHz, Chloroform-d) δ 7.40-7.29 (m, 5H), 5.81-5.76 (m, 1H), 5.75-5.71 (m, 1H), 5.17-4.97 (m, 4H), 4.31-4.15 (m, 1H), 3.02-2.63 [(m, 1H, two diastereoisomers)], 2.57 (ddd, J=13.0, 4.0, 2.4 Hz, 1H), 2.49-2.41 (m, 1H), 2.31-2.07[(m, 1H, two diastereoisomers)], 1.97-1.84 [(m, 1H, two diastereoisomers)], 1.74-1.57 [(m, 1H, two diastereoisomers)], 1.46-1.41 (m, 1H).

Step G. Benzyl (2-acetamido-2-(tert-butylcarbamoyl)-4-vinylcyclohexyl)carbamate

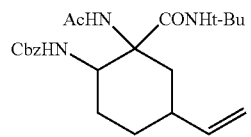

The title compound benzyl (2-acetamido-2-(tert-butylcarbamoyl)-4-vinylcyclohexyl)carbamate was obtained in the same manner like in step C from the synthesis of the intermediate 1, using benzyl (2-oxo-4-vinylcyclohexyl)carbamate (170 mg, 0.62 mmol, 1 equiv.), ammonium acetate (192 mg, 2.50 mmol, 4 equiv.), tert-butylisocyanide (140 µL, 1.24 mmol, 2 equiv.) and 2,2,2-trifluoroethanol (3 mL) as a solvent. The residue was purified by flash chromatography on silica gel (hexane/AcOEt 15:1 to 2:1) to give corresponding product as a mixture of separable diastereoisomers. Total yield: 47%.

First diastereoisomer (A): (80 mg, colorless oil); ESI+MS: m/z=416.2 (M+1)+. 1H NMR (700 MHz, Chloroform-d) δ 8.39 (s, 1H), 7.39-7.29 (m, 5H), 6.98 (s, 1H), 6.08 (d, J=9.8 Hz, 1H), 5.71 (ddd, J=17.1, 10.4, 6.5 Hz, 1H), 5.17-5.03 (m, 2H), 5.01-4.91 (m, 2H), 3.93-3.49 (m, 1H), 3.24-2.73 (m, 1H), 2.30-2.19 (m, 1H), 2.06-1.99 (m, 1H), 1.93 (s, 3H), 1.87-1.77 (m, 2H), 1.32 (s, 9H), 1.25-1.15 (m, 2H).

Second diastereoisomer (B): (40 mg, white solid); ESI+MS: m/z=416.2 (M+1)+. 1H NMR (700 MHz, Chloroform-d) δ 7.76 (s, 1H), 7.56 (s, 1H), 7.38-7.30 (m, 5H), 6.15 (d, J=7.0 Hz, 1H), 5.74-5.67 (m, 1H), 5.12-5.05 (m, 2H), 5.02-4.92 (m, 2H), 3.65 (ddd, J=12.8, 7.1, 3.8 Hz, 1H), 2.81 (dt, J=14.0, 2.7 Hz, 1H), 2.45 (qd, J=14.7, 13.9, 5.0 Hz, 1H), 2.11-2.05 (m, 1H), 2.05 (s, 3H), 1.91-1.78 (m, 2H), 1.29 (s, 9H), 1.28-1.20 (m, 2H).

Step H. Benzyl (2-acetamido-2-(tert-butylcarbamoyl)-4-(2-(4,4,5,5-tetramethyl-1,3,2-dioxaborolan-2-yl)ethyl)cyclohexyl)carbamate

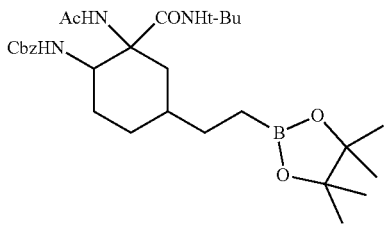

The title compound benzyl (2-acetamido-2-(tert-butylcarbamoyl)-4-(2-(4,4,5,5-tetramethyl-1,3,2-dioxaborolan-2-yl)ethyl)cyclohexyl)carbamate was obtained in the same manner like in Example 26, step B, using benzyl (2-acetamido-2-(tert-butylcarbamoyl)-4-vinylcyclohexyl)carbamate (diastereoisomer A, 70 mg, 0.17 mmol, 1 equiv.), dppe (4.1 mg, 0.010 mmol, 0.06 equiv.), bis(1,5-cyclooctadiene)diiridium(I) dichloride (3.4 mg, 0.005 mmol, 0.03 equiv.), 4,4,5,5-tetramethyl-1,3,2-dioxaborolane (32 µL, 0.25 mmol, 1.5 equiv.) and DCM (3 mL). The crude product was purified by column chromatography on silica gel (hexane/AcOEt 15:1 to 2:1) to give corresponding product as a single diastereoisomer A (70 mg, 76%, colorless oil). ESI+MS: m/z=544.4 (M+1)+. 1H NMR (700 MHz, Chloroform-d) δ 8.40 (s, 1H), 7.38-7.28 (m, 5H), 6.91 (s, 1H), 6.12 (d, J=9.6 Hz, 1H), 5.18-5.00 (m, 2H), 3.83-3.51 (m, 1H), 3.20-2.70 (m, 1H), 2.23-2.12 (m, 1H), 1.91 (s, 3H), 1.83-1.73 (m, 2H), 1.37-1.30 (m, 2H), 1.30 (s, 9H), 1.23 (s, 12H), 1.07-0.94 (m, 2H), 0.82-0.76 (m, 1H), 0.75-0.67 (m, 2H).

The second diastereoisomer was obtained in the same way starting from: benzyl (2-acetamido-2-(tert-butylcarbamoyl)-4-vinylcyclohexyl)carbamate (diastereoisomer B, 40 mg, 0.096 mmol, 1 equiv.), dppe (2.3 mg, 0.006 mmol, 0.06 equiv.), bis(1,5-cyclooctadiene)diiridium(I) dichloride (2.0 mg, 0.003 mmol, 0.03 equiv.), 4,4,5,5-tetramethyl-1,3,2-dioxaborolane (21 µL, 0.14 mmol, 1.5 equiv.) and DCM (2 mL). The crude product was purified by column chromatography on silica gel (hexane/AcOEt 15:1 to 2:1) to give corresponding product as a single diastereoisomer (35 mg, 67%, colorless oil). ESI+MS: m/z=544.4 (M+1)+. 1H NMR (700 MHz, Chloroform-d) δ 7.48 (s, 1H), 7.46 (s, 1H), 7.38-7.28 (m, 5H), 6.30 (d, J=7.1 Hz, 1H), 5.08 (s, 2H), 3.70-3.61 (m, 1H), 2.69 (d, J=14.0 Hz, 1H), 2.29 (qd, J=13.3, 3.8 Hz, 1H), 2.02 (s, 3H), 1.88-1.75 (m, 3H), 1.38-1.32 (m, 2H), 1.28 (s, 9H), 1.23 (s, 12H), 1.18-1.10 (m, 1H), 1.04-0.92 (m, 1H), 0.80-0.68 (m, 2H).

Step I.
1,2-diamino-5-(2-boronoethyl)cyclohexanecarboxylic acid dihydrochloride The title compound 1,2-diamino-5-(2-boronoethyl)cyclohexanecarboxylic acid dihydrochloride was obtained in the same manner like in Example 26, step C, using benzyl (2-acetamido-2-(tert-butylcarbamoyl)-4-(2-(4,4,5,5-tetramethyl-1,3,2-dioxaborolan-2-yl)ethyl)cyclohexyl)carbamate (diastereoisomer A, 70 mg, 0.13 mmol, 1 equiv.) and 6N HCl$_{aq}$ (4 mL). The residue was purified by flash chromatography on DOWEX® ion exchange resin (eluent 0.1N ammonia in water) and then by preparative HPLC (0.1-1% MeCN in water) to give (after acidification with 6N HCl and subsequent lyophilization) corresponding product as a single diastereoisomer A (6.7 mg, 17%, white solid). ESI+MS: m/z=231.1 (M+1)+. 1H NMR (700 MHz, Deuterium Oxide) δ 3.58 (dd, J=12.1, 5.1 Hz, 1H), 2.44 (dt, J=13.1, 2.7 Hz, 1H), 2.21-2.06 (m, 2H), 2.01-1.93 (m, 1H), 1.64-1.52 (m, 1H), 1.44-1.35 (m, 3H), 1.12 (qd, J=13.3, 4.2 Hz, 1H), 0.85-0.80 (m, 2H).

The second diastereoisomer was obtained in the same way starting from: benzyl (2-acetamido-2-(tert-butylcarbamoyl)-4-(2-(4,4,5,5-tetramethyl-1,3,2-dioxaborolan-2-yl)ethyl)cyclohexyl)carbamate (diastereoisomer B, 35 mg, 0.06 mmol, 1 equiv.) and 6N HCl$_{aq}$ (3 mL). The residue was purified by flash chromatography on DOWEX® ion exchange resin (eluent 0.1N ammonia in water) and then by preparative HPLC (0.1-1% MeCN in water) to give (after acidification with 6N HCl and subsequent lyophilization) corresponding product as a single diastereoisomer (6.5 mg, 33%, white solid). ESI+MS: m/z=231.2 (M+1)+. 1H NMR (700 MHz, Deuterium Oxide) δ 3.92 (dd, J=13.3, 4.4 Hz, 1H), 2.24-2.12 (m, 2H), 2.08-1.99 (m, 1H), 1.85-1.75 (m, 1H), 1.75-1.69 (m, 1H), 1.58-1.49 (m, 1H), 1.42 (tt, J=13.1, 6.3 Hz, 2H), 1.31-1.20 (m, 1H), 0.82 (t, J=8.3 Hz, 2H).

Example 49. 1-amino-5-(2-boronoethyl)-2-(hydroxymethyl)cyclohexanecarboxylic acid hydrochloride

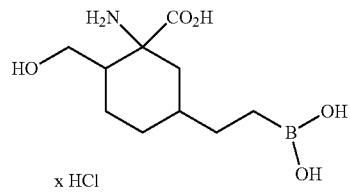

-continued

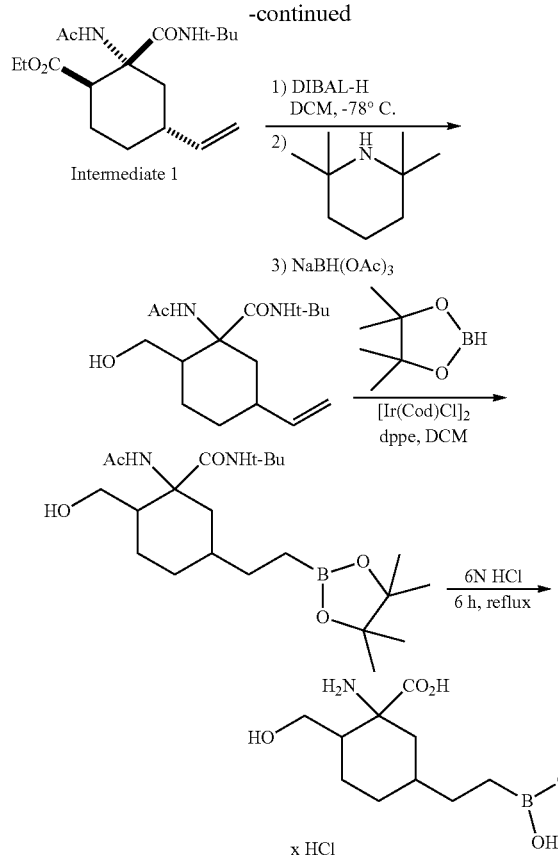

Step A. 1-acetamido-N-(tert-butyl)-2-(hydroxymethyl)-5-vinylcyclohexane-1-carboxamide

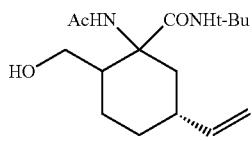

The title compound 1-acetamido-N-(tert-butyl)-2-(hydroxymethyl)-5-vinylcyclohexane-1-carboxamide was obtained in the same manner like in Example 26, step A, using ethyl rac-2-((1S,2R,4R)-2-acetamido-2-(tert-butylcarbamoyl)-4-vinylcyclohexyl)acetate (0.3 g, 0.88 mmol, 1 equiv.), DIBAL-H 1M in DCM (2.74 mL, 2.74 mmol, 3.1 equiv.), glacial acetic acid (0.25 mL, 4.42 mmol, 5 equiv.), 2,2,6,6-tetramethylpiperidine (0.30 mL, 1.77 mmol, 2 equiv.), sodium triacetoxyborohydride (0.75 g, 3.54 mmol, 4 equiv.), dry DCM (30 mL). The residue was purified by silica gel flash chromatography (gradient elution hexane:AcOEt 10:1 to 1:10) to give corresponding product 1-acetamido-N-(tert-butyl)-2-(hydroxymethyl)-5-vinylcyclohexane-1-carboxamide as a mixture diastereoisomers 1:1 (0.21 g, 80%, white solid). ESI+MS: m/z=297.2 (M+1)$^+$, ESI-MS: m/z=295.0 (M−1)$^−$. $^1$H NMR (700 MHz, Chloroform-d) δ 7.70 (s, 1H), 7.41 (s, 1H), 5.78-5.69 (m, 1H), 4.99 (dt, J=17.3, 1.5 Hz, 1H), 4.93 (dt, J=10.4, 1.4 Hz, 1H), 4.24-4.14 (m, 1H), 3.76-3.68 (m, 1H), 3.24-3.10 (m, 1H), 2.23-2.16 (m, 1H), 1.97 (s, 3H), 1.94-1.78 (m, 2H), 1.75-1.65 (m, 1H), 1.34 (s, 9H), 1.28-1.11 (m, 3H).

Step B. 1-acetamido-N-(tert-butyl)-2-(hydroxymethyl)-5-(2-(4,4,5,5-tetramethyl-1,3,2-dioxaborolan-2-yl)ethyl)cyclohexanecarboxamide

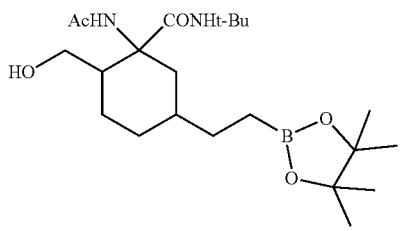

The title compound 1-acetamido-N-(tert-butyl)-2-(hydroxymethyl)-5-(2-(4,4,5,5-tetramethyl-1,3,2-dioxaborolan-2-yl)ethyl)cyclohexanecarboxamide was obtained in the same manner like in Example 26, step B, using 1-acetamido-N-(tert-butyl)-2-(piperidin-1-ylmethyl)-5-vinylcyclohexanecarboxamide (0.20 g, 0.68 mmol, 1 equiv.), dppe (0.016 g, 0.04 mmol, 0.06 equiv.), bis(1,5-cyclooctadiene)diiridium (I) dichloride (0.014 g, 0.02 mmol, 0.03 equiv.), 4,4,5,5-tetramethyl-1,3,2-dioxaborolane (0.13 mL, 0.88 mmol, 1.3 eq). The crude product was purified by column chromatography on silica gel (gradient elution, hexane/AcOEt 10:1 to 1:110) to give corresponding product 1-acetamido-N-(tert-butyl)-2-(hydroxymethyl)-5-(2-(4,4,5,5-tetramethyl-1,3,2-dioxaborolan-2-yl)ethyl)cyclohexanecarboxamide as a mixture diastereoisomers 1:1 (0.17 g, 59%, white solid). ESI+MS: m/z=425.4 (M+1)$^+$, ESI-MS: m/z=423.2 (M−1)$^−$. $^1$H NMR (700 MHz, Chloroform-d) δ 7.67 (s, 1H), 7.34 (s, 1H), 4.34-4.03 (m, 1H), 3.76-3.58 (m, 1H), 3.17-2.94 (m, 1H), 1.95 (s, 3H), 1.87-1.73 (m, 2H), 1.73-1.65 (m, 1H), 1.53 (s, 9H), 1.51-1.48 (m, 2H), 1.33 (br s, 5H), 1.28-1.24 (m, 2H), 1.23 (br s, 7H), 1.10-1.05 (m, 1H), 1.00-0.92 (m, 1H), 0.86-0.76 (m, 1H), 0.76-0.68 (m, 1H).

Step C. 1-amino-5-(2-boronoethyl)-2-(hydroxymethyl)cyclohexanecarboxylic acid hydrochloride The title compound 1-amino-5-(2-boronoethyl)-2-(hydroxymethyl)cyclohexanecarboxylic acid hydrochloride was obtained in the same manner like in Example 26, step C, using compound 1-acetamido-N-(tert-butyl)-2-(hydroxymethyl)-5-(2-(4,4,5,5-tetramethyl-1,3,2-dioxaborolan-2-yl)ethyl)cyclohexanecarboxamide as a mixture of diastereoisomers (0.10 g, 0.23 mmol, 1 equiv.), 6 N HCl$_{aq}$ (3 mL). The residue was purified by preparative HPLC (0.1-5% MeCN in water) to give (after acidification with 6N HCl and subsequent lyophilization) product 1-amino-5-(2-boronoethyl)-2-(hydroxymethyl)cyclohexanecarboxylic acid hydrochloride as a mixture of diastereoisomers (0.058 g, 89%, white solid).

First mixture of diastereoisomers dr=17:3 (5.9 mg, white solid) ESI+MS: m/z=228.2 (M−H$_2$O+1)$^+$, ESI-MS: m/z=244.0 (M−1)$^−$. $^1$H NMR (700 MHz, Deuterium Oxide) δ 4.61, 3.62[(2dd, J=9.9, 5.3 Hz, J=11.3, 4.9 Hz, 1H, two diastereoisomers)], 4.18, 3.55 [(2dd, J=9.98, 1.46 Hz, 1H, two diastereoisomers)], 2.69-2.62 (m, 1H), 2.30 (ddd, J=13.3, 3.4, 1.2 Hz, 1H), 2.09 (ddt, J=14.8, 6.5, 4.3 Hz, 1H), 1.73-1.56[(in, 1H, two diastereoisomers)], 1.39 (dd, J=13.4, 12.3 Hz, 1H), 1.37-1.31 (m, 2H), 1.31-1.26 [(m, 1H, two diastereoisomers)], 1.22-1.07 [(m, 1H, two diastereoisomers)], 0.97-0.85 [(m, 1H, two diastereoisomers)], 0.76-0.69 (m, 2H).

Second mixture of diastereoisomers dr=13:7 (11.8 mg, white solid)) ESI+MS: m/z=246.2 (M+1)$^+$, 228.2 (M−H$_2$O+1)$^+$, ESI-MS: m/z=244.0 (M−1)$^−$. $^1$H NMR (700 MHz, Deuterium Oxide) δ 4.61, 3.64 [(2dd, J=10.0, 5.3 Hz, J=11.4, 4.9 Hz 1H, two diastereoisomers)], 4.18, 3.54 [(2dd, J=10.0, 1.5 Hz, 1H, two diastereoisomers)], 2.69-2.61 (m, 1H), 2.32-2.27 (m, 1H), 2.14-2.06 (m, 1H), 1.84-1.68 (m, 1H), 1.36-1.31 (m, 1H), 1.37-1.31 (m, 2H), 1.30-1.16 [(m, 1H, two diastereoisomers)], 1.15-1.08 (m, 1H), 0.99-0.84 (m, 1H), 0.73 (td, J=9.2, 6.2 Hz, 2H).

Third mixture of diastereoisomers dr=3:2 (6.7 mg, white solid) ESI-MS: m/z=244.0 (M−1)$^−$. $^1$H NMR (700 MHz, Deuterium Oxide) 4.61 (dd, J=9.9, 5.3 Hz, 1H), 4.18 (dd, J=9.9, 1.4 Hz, 1H), 2.67-2.60 [(m, 1H, two diastereoisomers)], 2.32-2.17 (m, 1H), 2.15-2.05 (m, 1H), 1.90-1.77 (m, 1H), 1.75-1.55 (m, 1H), 1.43-1.24 (m, 3H), 1.24-1.08 (m, 1H), 0.99-0.84 [(m, 1H, two diastereoisomers)], 0.77-0.69 (m, 2H).

Example 50. 1-amino-5-(2-boronoethyl)-2-hydroxy-2-methylcyclohexanecarboxylic acid hydrochloride

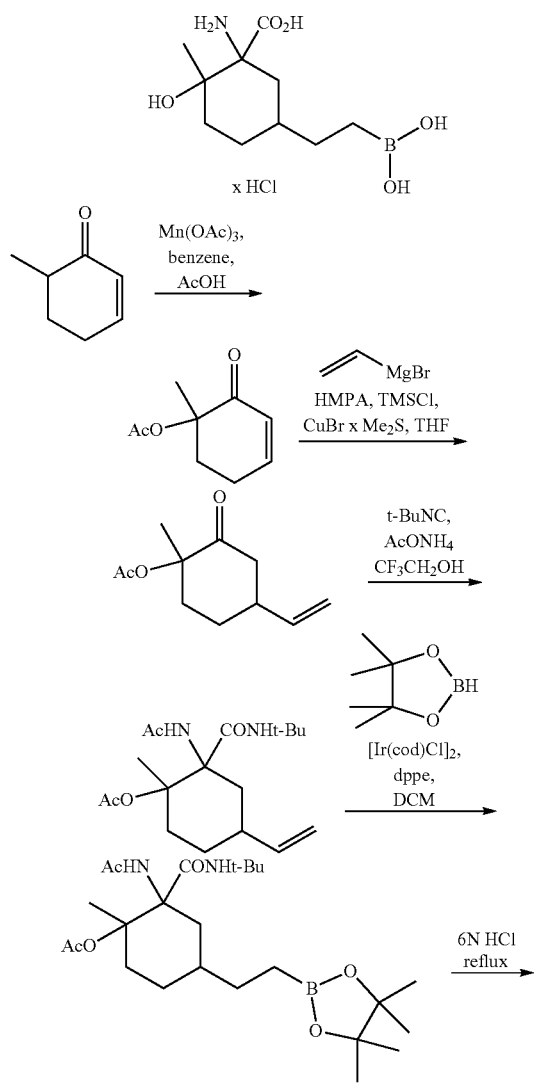

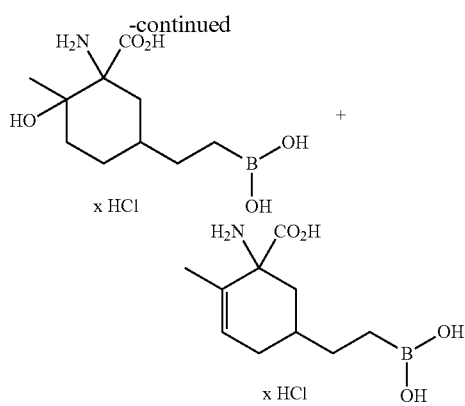

Step A. 1-methyl-2-oxocyclohex-3-en-1-yl acetate

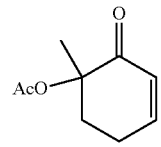

A mixture of 6-methyl-2-cyclohexenone (1.58 g, 14 mmol, 1 equiv., prepared from 2-cyclohexenone using literature method, *J Nat. Prod.*, 2004, 67, 1939), benzene (135 mL), acetic acid (15 mL) and manganese(III) acetate dihydrate (5 g, 21 mmol, 1.5 equiv.) was heated under reflux for 6 h. The mixture was filtered through a Celite. The filtrate was diluted with diethyl ether and washed with brine. The organic layers was dried over MgSO$_4$, filtered and concentrated in vacuo. The crude product was purified by flash chromatography on silica gel (hexane/AcOEt, 30:1 to 5:1) to give corresponding product (500 mg, 21%, colorless oil). $^1$H NMR (700 MHz, Chloroform-d) δ 6.88 (dddd, J=9.6, 5.4, 2.6, 1.2 Hz, 1H), 6.03 (ddd, J=10.1, 2.7, 1.2 Hz, 1H), 2.91-2.82 (m, 1H), 2.54-2.47 (m, 1H), 2.43 (dddt, J=19.3, 10.9, 5.4, 2.7 Hz, 1H), 2.06 (s, 3H), 1.93 (dddd, J=12.8, 5.4, 2.7, 1.2 Hz, 1H), 1.44 (s, 3H).

Step B. 1-methyl-2-oxo-4-vinylcyclohexyl acetate

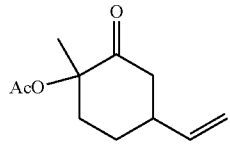

The title compound 1-methyl-2-oxo-4-vinylcyclohexyl acetate was obtained in the same manner like in the step B from the synthesis of the intermediate 1, using 1-methyl-2-oxocyclohex-3-en-1-yl acetate (500 mg, 2.97 mmol, 1 equiv.), vinylmagnesium bromide 1M in THF (7.4 mL, 7.44 mmol, 2.5 equiv.), HMPA (2.06 mL, 11.9 mmol, 4 equiv.), copper(I) bromide dimethyl sulfide complex (92 mg, 0.44 mmol, 0.15 equiv.), trimethylsilyl chloride (1.87 mL, 14.85 mmol, 5 equiv.) and THF (20 mL). The residue was purified by silica gel flash chromatography (hexane/AcOEt, 30:1 to 5:1) to give corresponding product as a single diastereoisomer (310 mg, 53%, colorless oil). ¹H NMR (700 MHz, Chloroform-d) δ 5.76 (ddd, J=17.0, 10.5, 6.3 Hz, 1H), 5.09-4.97 (m, 2H), 2.73 (tt, J=10.0, 5.0 Hz, 1H), 2.66 (ddd, J=15.2, 4.7, 2.1 Hz, 1H), 2.42 (ddd, J=13.3, 11.3, 4.3 Hz, 1H), 2.27 (dd, J=15.2, 10.5 Hz, 1H), 2.08 (s, 3H), 2.05-1.96 (m, 1H), 1.91 (ddd, J=13.4, 5.5, 3.9 Hz, 1H), 1.58-1.54 (m, 1H), 1.46 (s, 3H).

Step C. 2-acetamido-2-(tert-butylcarbamoyl)-1-methyl-4-vinylcyclohexyl acetate

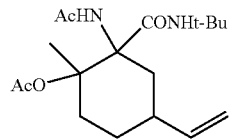

The title compound 2-acetamido-2-(tert-butylcarbamoyl)-1-methyl-4-vinylcyclohexyl acetate was obtained in the same manner like in the step C from the synthesis of the intermediate 1, using 1-methyl-2-oxo-4-vinylcyclohexyl acetate (310 mg, 1.58 mmol, 1 equiv.), ammonium acetate (487 mg, 6.32, mol, 4 equiv.), tert-butylisocyanide (355 µL, 3.16 mmol, 2 equiv.) and 2,2,2-trifluoroethanol (4 mL) as a solvent. The residue was purified by flash chromatography on silica gel (hexane/AcOEt 10:1 to 1:2) to give corresponding product as a single diastereoisomer (300 mg, 56%, white solid). ESI+MS: m/z=339.2 (M+1)⁺; ESI-MS: m/z=338.1 (M−1)⁻. ¹H NMR (700 MHz, Chloroform-d) δ 7.66 (s, 1H), 6.27 (s, 1H), 5.68 (ddd, J=17.0, 10.4, 6.3 Hz, 1H), 5.08-4.82 (m, 2H), 3.27 (d, J=11.2 Hz, 1H), 3.04-2.95 (m, 1H), 2.53-2.42 (m, 1H), 2.07 (s, 3H), 2.02 (s, 3H), 1.90 (dt, J=13.2, 3.7 Hz, 1H), 1.80-1.73 (m, 1H), 1.68 (s, 3H), 1.31 (s, 9H), 1.30-1.24 (m, 1H), 1.24-1.15 (m, 1H).

Step D. 2-acetamido-2-(tert-butylcarbamoyl)-1-methyl-4-(2-(4,4,5,5-tetramethyl-1,3,2-dioxaborolan-2-yl)ethyl)cyclohexyl acetate

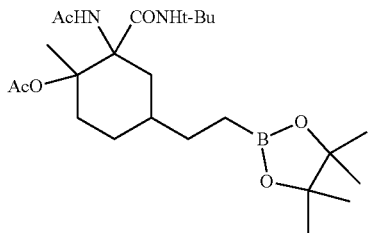

The title compound 2-acetamido-2-(tert-butylcarbamoyl)-1-methyl-4-(2-(4,4,5,5-tetramethyl-1,3,2-dioxaborolan-2-yl)ethyl)cyclohexyl acetate was obtained in the same manner like in the Example 26, step B, using 2-acetamido-2-(tert-butylcarbamoyl)-1-methyl-4-vinylcyclohexyl acetate (200 mg, 0.59 mmol, 1 equiv.), dppe (14 mg, 0.035 mmol, 0.06 equiv.), bis(1,5-cyclooctadiene)diiridium(I) dichloride (12 mg, 0.018 mmol, 0.03 equiv.), 4,4,5,5-tetramethyl-1,3,2-dioxaborolane (130 µL, 0.89 mmol, 1.5 equiv.) and DCM (10 mL). The crude product was purified by column chromatography on silica gel (hexane/AcOEt 5:1 to 1:2) to give corresponding product as a single diastereoisomer (220 mg, 80%, white solid). ESI+MS: m/z=467.4 (M+1)⁺. ¹H NMR (700 MHz, Chloroform-d) δ 7.75 (s, 1H), 6.55 (s, 1H), 3.22 (d, J=12.0 Hz, 1H), 2.53-2.43 (m, 1H), 2.05 (s, 3H), 2.01 (s, 3H), 2.01-1.97 (m, 1H), 1.90-1.85 (m, 1H), 1.81-1.74 (m, 1H), 1.63 (s, 3H), 1.42-1.36 (m, 1H), 1.30 (s, 9H), 1.22 (s, 12H), 1.21-1.17 (m, 1H), 1.08-0.98 (m, 2H), 0.80-0.72 (m, 2H).

Step E. 1-amino-5-(2-boronoethyl)-2-hydroxy-2-methylcyclohexanecarboxylic acid hydrochloride The title compound 1-amino-5-(2-boronoethyl)-2-hydroxy-2-methylcyclohexanecarboxylic acid hydrochloride was obtained in the same manner like in the Example 26, step C, using 2-acetamido-2-(tert-butylcarbamoyl)-1-methyl-4-(2-(4,4,5,5-tetramethyl-1,3,2-dioxaborolan-2-yl)ethyl)cyclohexyl acetate (200 mg, 0.43 mmol, 1 equiv.) and 6N HCl$_{aq}$ (4 mL). The residue was purified by preparative HPLC (0.1-5% MeCN in water) to give (after acidification with 6N HCl and subsequent lyophilization) corresponding product as a single diastereoisomer (25 mg, 20%, white solid) and by-product (1-amino-5-(2-boronoethyl)-2-methylcyclohex-2-enecarboxylic acid hydrochloride, Ex. 51) as a single diastereoisomer (1.7 mg, 2%, white solid).

1-amino-5-(2-boronoethyl)-2-hydroxy-2-methylcyclohexanecarboxylic acid hydrochloride ESI+MS: m/z=246.2 (M+1)⁺. ¹H NMR (700 MHz, Deuterium Oxide) δ 2.41-2.32 (m, 1H), 2.20-2.14 (m, 1H), 1.87-1.80 (m, 1H), 1.78-1.67 (m, 2H), 1.43-1.36 (m, 3H), 1.35 (s, 3H), 1.15 (qd, J=14.0, 4.4 Hz, 1H), 0.87-0.73 (m, 2H).

Example 51. 1-amino-5-(2-boronoethyl)-2-methylcyclohex-2-enecarboxylic acid hydrochloride

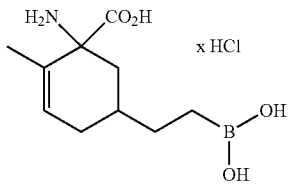 [SMILES: CC1=CCC(CCB(O)O)CC1(N)C(=O)O]

Obtained in step E from the example 50 (1.7 mg, 2%, white solid). ESI+MS: m/z=228.2 (M+1)⁺; ESI-MS: m/z=226.0 (M−1)⁻. ¹H NMR (700 MHz, Deuterium Oxide) δ 5.98 (d, J=5.6 Hz, 1H), 2.33-2.24 (m, 2H), 2.00-1.91 (m, 1H), 1.77-1.74 (m, 1H), 1.73 (s, 3H), 1.51 (t, J=12.9 Hz, 1H), 1.45-1.37 (m, 2H), 0.87-0.78 (m, 2H).

Example 52. 1-amino-5-(2-boronoethyl)-2-(4-chlorobenzyl)-2-hydroxycyclohexanecarboxylic acid hydrochloride

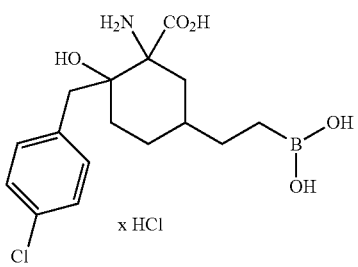

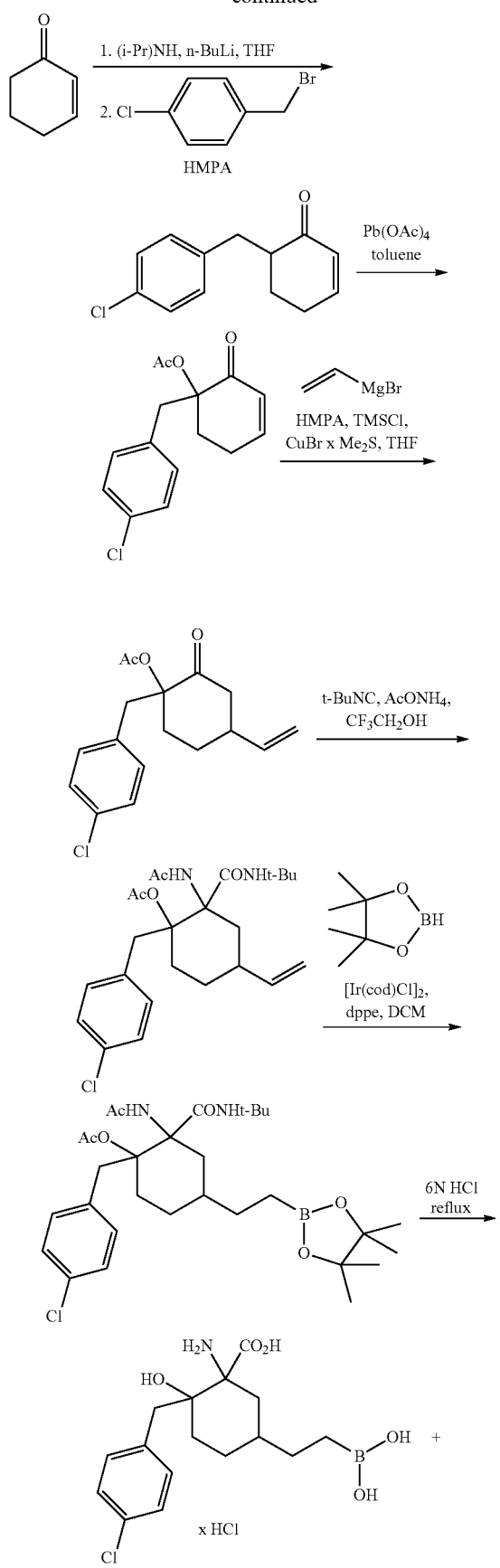

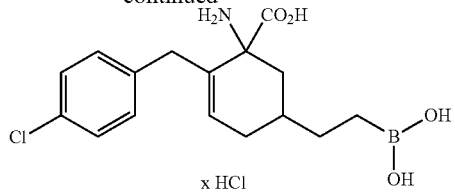

Step A. 6-(4-chlorobenzyl)cyclohex-2-enone

To a solution of diisopropylamine (10.9 mL, 0.078 mol, 1.5 equiv.) in THF (45 mL) at 0° C. was added n-BuLi 2.5M in hexanes (29 mL, 0.072 mol, 1.4 equiv.). After stirring for 30 min the solution was cooled to −78° C. and 2-cyclohexenone (5 g, 0.052 mol, 1 equiv.) in THF (45 mL) was added dropwise. The solution was stirred for 30 min followed by dropwise addition of 4-chlorobenzyl bromide (21 g, 0.104 mol, 2 equiv.). After stirring for 30 min at −78° C., HMPA (30 mL) was added. The resulting mixture was stirred at −78° C. for 3 h. Diethyl ether was added to the reaction mixture at 0° C. and the organic layer was washed with $NH_4Cl_{sat}$ and brine. Dried over $MgSO_4$, filtered and concentrated in vacuo. The crude product was purified by flash chromatography on silica gel (hexane/AcOEt, 40:1 to 10:1) to give corresponding product (6.6 g, 58%, colorless oil). ESI+MS: m/z=221.2 (M+1)+. $^1$H NMR (700 MHz, Chloroform-d) δ 7.26-7.21 (m, 2H), 7.10 (d, J=8.3 Hz, 2H), 6.93 (dt, J=8.9, 3.9 Hz, 1H), 6.02 (dt, J=10.0, 1.7 Hz, 1H), 3.27 (dd, J=11.5, 6.8 Hz, 1H), 2.55-2.48 (m, 2H), 2.36 (dq, J=19.2, 4.0 Hz, 1H), 2.29 (dddd, J=19.3, 10.2, 5.2, 2.8 Hz, 1H), 1.95 (dq, J=12.9, 4.2 Hz, 1H), 1.67-1.58 (m, 1H).

Step B. 1-(4-chlorobenzyl)-2-oxo-4-vinylcyclohexyl acetate

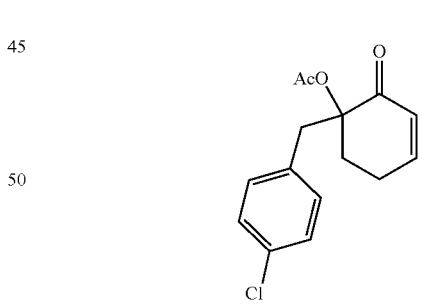

The suspension of 6-(4-chlorobenzyl)cyclohex-2-enone (3 g, 0.014 mol, 1 equiv.), lead(IV) acetate (10.6 g, 0.024 mol, 1.75 equiv.) in toluene (16 mL) was refluxed for 28 h. The solvent was evaporated in vacuo. The crude product was purified by flash chromatography on silica gel (hexane/AcOEt, 20:1 to 5:1) to give corresponding product (880 mg, 23%, white solid). $^1$H NMR (700 MHz, Chloroform-d) δ 7.29 (d, J=8.5 Hz, 2H), 7.21 (d, J=8.5 Hz, 2H), 6.95-6.90 (m, 1H), 6.11 (dt, J=10.1, 1.9 Hz, 1H), 3.04 (d, J=14.4 Hz, 1H), 2.92 (d, J=14.4 Hz, 1H), 2.76 (dt, J=12.5, 8.2 Hz, 1H), 2.50-2.46 (m, 2H), 2.07 (s, 3H), 1.85-1.80 (m, 1H).

Step C. 1-(4-chlorobenzyl)-2-oxo-4-vinylcyclohexyl acetate

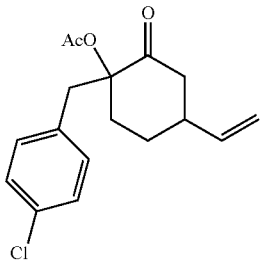 [SMILES: C=CC1CCC(Cc2ccc(Cl)cc2)(OC(C)=O)C(=O)C1]

The title compound 1-(4-chlorobenzyl)-2-oxo-4-vinylcyclohexyl acetate was obtained in the same manner like in the step B from the synthesis of the intermediate 1, using 1-(4-chlorobenzyl)-2-oxo-4-vinylcyclohexyl acetate (860 mg, 3.08 mmol, 1 equiv.), vinylmagnesium bromide 1M in THF (7.7 mL, 7.7 mmol, 2.5 equiv.), HMPA (2.15 mL, 12.3 mmol, 4 equiv.), copper(I) bromide dimethyl sulfide complex (95 mg, 0.46 mmol, 0.15 equiv.), trimethylsilyl chloride (1.94 mL, 15.4 mmol, 5 equiv.) and THF (22 mL). The residue was purified by flash chromatography on silica gel (hexane/AcOEt, 15:1 to 10:1) to give corresponding product as a mixture of diastereoisomers, dr=85:15, (680 mg, 72%, colorless oil). $^1$H NMR (700 MHz, Chloroform-d) δ 7.30-7.24 [(m, 2H, two diastereoisomers)], 7.14-7.11 [(m, 2H, two diastereoisomers)], 5.85-5.78 [(m, 1H, two diastereoisomers)], 5.13-4.97 [(m, 2H, two diastereoisomers)], 3.15-3.06 [(m, 1H, two diastereoisomers)], 2.99-2.94 [(m, 1H, two diastereoisomers)], 2.83-2.75 (m, 1H), 2.74-2.54 [(m, 1H, two diastereoisomers)], 2.34-2.16 [(m, 2H, two diastereoisomers)], 2.08, 2.04 [(2s, 3H, two diastereoisomers)], 2.01-1.90 (m, 1H), 1.86-1.64 [(m, 1H, two diastereoisomers)], 1.61-1.54 (m, 1H).

Step D. 2-acetamido-2-(tert-butylcarbamoyl)-1-(4-chlorobenzyl)-4-vinylcyclohexyl acetate

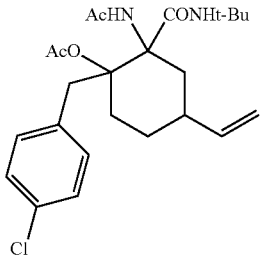

The title compound 2-acetamido-2-(tert-butylcarbamoyl)-1-(4-chlorobenzyl)-4-vinylcyclohexyl acetate was obtained in the same manner like in the step C from the synthesis of the intermediate 1, using 1-(4-chlorobenzyl)-2-oxo-4-vinylcyclohexyl acetate (670 mg, 2.18 mmol, 1 equiv.), ammonium acetate (672 mg, 8.76 mmol, 4 equiv.), tert-butylisocyanide (490 μL, 4.37 mmol, 2 equiv.) and 2,2,2-trifluoroethanol (2 mL) as a solvent. The residue was purified by flash chromatography on silica gel (hexane/AcOEt 10:1 to 1:6) to give corresponding product as a mixture of separable diastereoisomers. Total yield: 11%.

First diastereoisomer (A): (85 mg, white foam); ESI+MS: m/z=471.3 (M+Na)$^+$. $^1$H NMR (700 MHz, Chloroform-d) δ 8.40 (s, 1H), 7.31-7.27 (m, 2H), 7.10 (d, J=8.3 Hz, 2H), 6.20 (s, 1H), 5.74 (ddd, J=17.0, 10.4, 6.3 Hz, 1H), 5.12-4.87 (m, 2H), 3.80 (d, J=13.5 Hz, 1H), 3.52-3.40 (m, 1H), 3.16-3.02 (m, 2H), 2.36-2.25 (m, 1H), 2.04 (s, 3H), 2.03 (s, 3H), 1.81-1.75 (m, 1H), 1.71 (dt, J=13.9, 3.5 Hz, 1H), 1.48-1.33 (m, 2H), 1.31 (s, 9H).

Second diastereoisomer (B): (20 mg, white solid); $^1$H NMR (700 MHz, Chloroform-d) δ 7.28-7.25 (m, 2H), 7.21 (d, J=8.4 Hz, 2H), 6.97 (s, 1H), 5.91 (s, 1H), 5.79 (ddd, J=17.2, 10.5, 5.8 Hz, 1H), 5.09-4.97 (m, 2H), 2.88 (d, J=14.1 Hz, 1H), 2.82 (d, J=14.3 Hz, 1H), 2.72 (dt, J=13.3, 2.6 Hz, 1H), 2.12-2.06 (m, 1H), 2.05 (s, 3H), 1.81-1.73 (m, 1H), 1.73-1.66 (m, 1H), 1.63 (dt, J=14.1, 3.2 Hz, 1H), 1.54 (s, 3H), 1.46-1.38 (m, 1H), 1.33 (s, 9H), 1.32-1.27 (m, 1H).

Step E. 2-acetamido-2-(tert-butylcarbamoyl)-1-(4-chlorobenzyl)-4-(2-(4,4,5,5-tetramethyl-1,3,2-dioxaborolan-2-yl)ethyl)cyclohexyl acetate

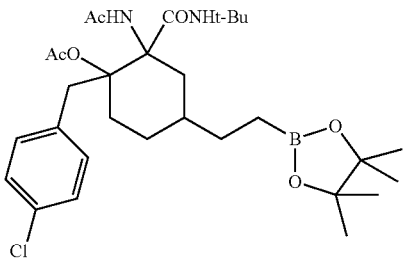

The title compound 2-acetamido-2-(tert-butylcarbamoyl)-1-(4-chlorobenzyl)-4-(2-(4,4,5,5-tetramethyl-1,3,2-dioxaborolan-2-yl)ethyl)cyclohexyl acetate was obtained in the same manner like in the Example 26, step B, using 2-acetamido-2-(tert-butylcarbamoyl)-1-(4-chlorobenzyl)-4-vinylcyclohexyl acetate (diastereoisomer A, 85 mg, 0.19 mmol, 1 equiv.), dppe (4.5 mg, 0.011 mmol, 0.06 equiv.), bis(1,5-cyclooctadiene)diiridium(I) dichloride (3.8 mg, 0.0057 mmol, 0.03 equiv.), 4,4,5,5-tetramethyl-1,3,2-dioxaborolane (41 μL, 0.89 mmol, 1.5 equiv.) and DCM (3 mL). The crude product was purified by column chromatography on silica gel (hexane/AcOEt 10:1 to 2:1) to give corresponding product as a single diastereoisomer A (70 mg, 64%, white foam). ESI+MS: m/z=599.6 (M+Na)$^+$. $^1$H NMR (700 MHz, Chloroform-d) δ 8.48 (s, 1H), 7.27 (d, J=8.4 Hz, 2H), 7.07 (d, J=8.4 Hz, 2H), 6.42 (s, 1H), 3.77 (d, J=14.8 Hz, 1H), 3.42 (d, J=14.8 Hz, 1H), 3.02 (d, J=14.8 Hz, 1H), 2.27 (td, J=14.3, 2.6 Hz, 1H), 2.14-2.06 (m, 1H), 2.03 (s, 3H), 2.02 (s, 3H), 1.82-1.76 (m, 1H), 1.67 (dt, J=13.9, 3.3 Hz, 1H), 1.51-1.43 (m, 1H), 1.30 (s, 9H), 1.24 (s, 12H), 1.22-1.10 (m, 3H), 0.80 (ddd, J=9.3, 6.6, 1.6 Hz, 2H).

The second diastereoisomer was obtained in the same way starting from: 2-acetamido-2-(tert-butylcarbamoyl)-1-(4-chlorobenzyl)-4-vinylcyclohexyl acetate (diastereoisomer B, 20 mg, 0.045 mmol, 1 equiv.), dppe (1 mg, 0.0027 mmol, 0.06 equiv.), bis(1,5-cyclooctadiene)diiridium(I) dichloride (0.9 mg, 0.0014 mmol, 0.03 equiv.), 4,4,5,5-tetramethyl-1,3,2-dioxaborolane (10 μL, 0.067 mmol, 1.5 equiv.) and DCM (2 mL). The crude product was purified by column chromatography on silica gel (hexane/AcOEt 8:1 to 2:1) to give corresponding product as a single diastereoisomer B (25 mg, 100%, white solid). $^1$H NMR (700 MHz, Chloroform-d) δ 8.44 (s, 1H), 7.25 (d, J=8.4 Hz, 2H), 7.19 (d, J=8.4

Hz, 2H), 6.92 (s, 1H), 2.85 (d, J=14.0 Hz, 1H), 2.79 (d, J=14.2 Hz, 1H), 2.66 (d, J=12.3 Hz, 1H), 2.03 (s, 3H), 1.75-1.64 (m, 2H), 1.58 (s, 3H), 1.58-1.53 (m, 1H), 1.50-1.43 (m, 1H), 1.40-1.33 (m, 2H), 1.31 (s, 9H), 1.24 (s, 12H), 1.24-1.20 (m, 1H), 1.10-1.02 (m, 1H), 0.78 (dt, J=9.6, 6.2 Hz, 2H).

Step F. 1-amino-5-(2-boronoethyl)-2-(4-chlorobenzyl)-2-hydroxycyclohexanecarboxylic acid hydrochloride The title compound 1-amino-5-(2-boronoethyl)-2-(4-chlorobenzyl)-2-hydroxycyclohexanecarboxylic acid hydrochloride was obtained in the same manner like in the Example 26, step C, using 2-acetamido-2-(tert-butylcarbamoyl)-1-(4-chlorobenzyl)-4-(2-(4,4,5,5-tetramethyl-1,3,2-dioxaborolan-2-yl)ethyl)cyclohexyl acetate (diastereoisomer A, 70 mg, 0.12 mmol, 1 equiv.) and 6N HCl$_{aq}$ (3 mL). The residue was purified by preparative HPLC (5-50% MeCN in water) to give (after acidification with 6N HCl and subsequent lyophilization) corresponding product as a single diastereoisomer A (6.1 mg, 13%, white solid) and by-product (1-amino-5-(2-boronoethyl)-2-(4-chlorobenzyl)cyclohex-2-enecarboxylic acid hydrochloride, Example 53) as a single diastereoisomer (6.3 mg, 13%, white solid). ESI+ MS: m/z=356.3 (M+1)$^+$. $^1$H NMR (700 MHz, Deuterium Oxide) δ 7.45-7.40 (m, 2H), 7.38-7.34 (m, 2H), 3.11 (d, J=13.4 Hz, 1H), 2.77 (d, J=13.3 Hz, 1H), 2.28 (dd, J=13.8, 2.3 Hz, 1H), 2.11-1.97 (m, 2H), 1.80-1.73 (m, 1H), 1.61-1.55 (m, 1H), 1.51-1.40 (m, 3H), 1.29-1.19 (m, 1H), 0.84 (td, J=7.7, 2.9 Hz, 2H).

The second diastereoisomer was obtained in the same way starting from: 2-acetamido-2-(tert-butylcarbamoyl)-1-(4-chlorobenzyl)-4-(2-(4,4,5,5-tetramethyl-1,3,2-dioxaborolan-2-yl)ethyl)cyclohexyl acetate (diastereoisomer B, 25 mg, 0.43 mmol, 1 equiv.) and 6N HCl$_{aq}$ (3 mL). The residue was purified by preparative HPLC (5-50% MeCN in water) to give (after acidification with 6N HCl and subsequent lyophilization) corresponding product as a single diastereoisomer B (25 mg, 70%, white solid). ESI+MS: m/z=356.4 (M+1)$^+$. $^1$H NMR (700 MHz, Deuterium Oxide) δ 7.43 (d, J=8.5 Hz, 2H), 7.37 (d, J=8.5 Hz, 2H), 3.11 (d, J=13.4 Hz, 1H), 2.77 (d, J=13.3 Hz, 1H), 2.32-2.26 (m, 1H), 2.10-1.98 (m, 2H), 1.80-1.74 (m, 1H), 1.62-1.55 (m, 1H), 1.49 (dt, J=13.7, 3.3 Hz, 1H), 1.45 (q, J=8.0 Hz, 2H), 1.25 (qd, J=13.8, 3.6 Hz, 1H), 0.85 (td, J=7.7, 3.1 Hz, 2H).

Example 53. 1-amino-5-(2-boronoethyl)-2-(4-chlorobenzyl)cyclohex-2-enecarboxylic acid hydrochloride

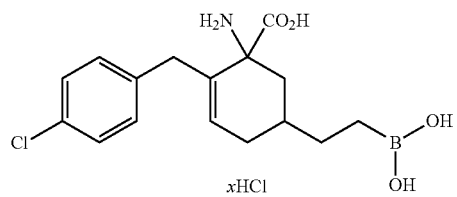 [SMILES: NC1(C(=O)O)CC(CCB(O)O)CC=C1Cc1ccc(Cl)cc1]

Obtained in step F from the Example 52 (6.3 mg, 13%, white solid). ESI+MS: m/z=338.2 (M+1)$^+$. $^1$H NMR (700 MHz, Deuterium Oxide) δ 7.44-7.37 (m, 2H), 7.25 (d, J=8.5 Hz, 2H), 5.75 (d, J=4.3 Hz, 1H), 3.40 (d, J=15.9 Hz, 1H), 3.27 (d, J=16.0 Hz, 1H), 2.33 (dt, J=13.1, 2.6 Hz, 1H), 2.30-2.23 (m, 1H), 2.01-1.88 (m, 1H), 1.82-1.70 (m, 1H), 1.57 (t, J=13.0 Hz, 1H), 1.47-1.38 (m, 2H), 0.87-0.75 (m, 2H).

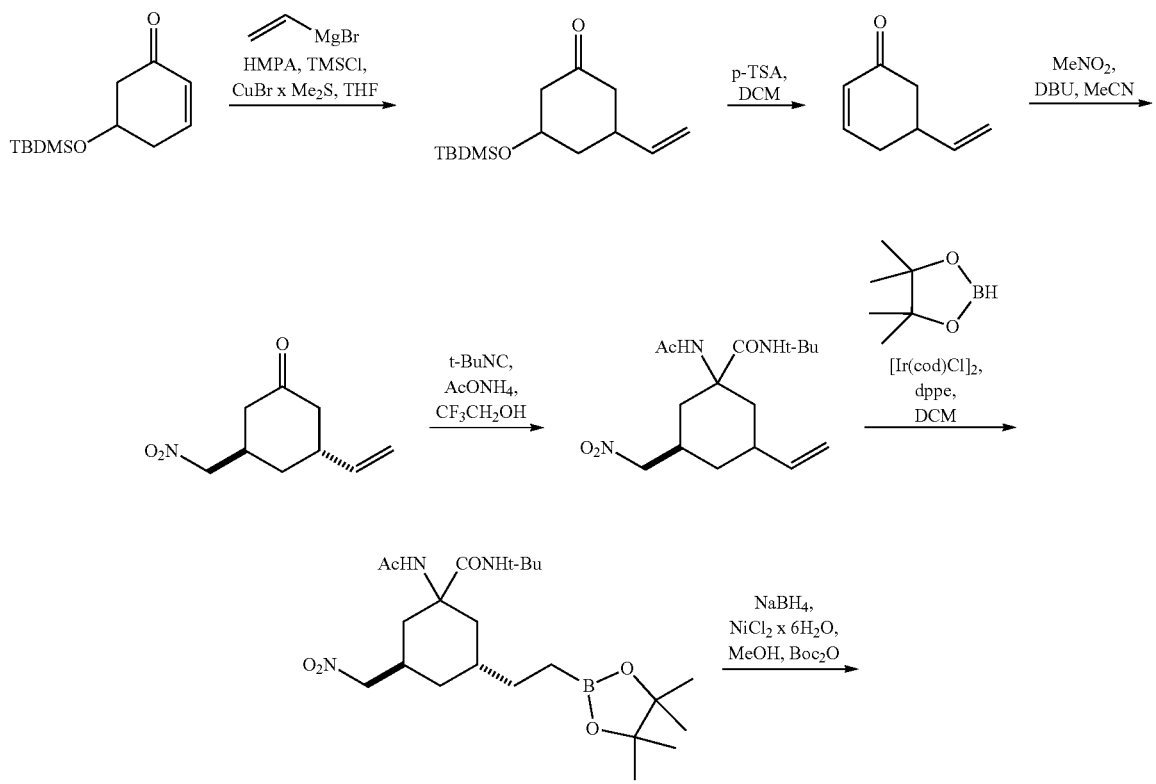

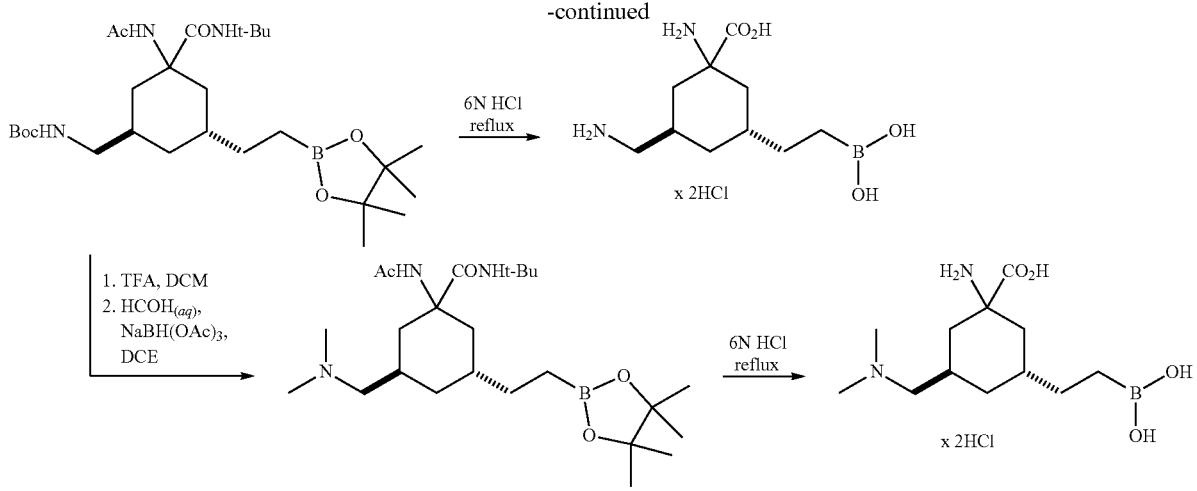

General Synthetic Route for Examples 54 and 55

Example 54. rac-(3R,5R)-1-amino-3-(aminomethyl)-5-(2-boronoethyl)cyclohexanecarboxylic acid dihydrochloride

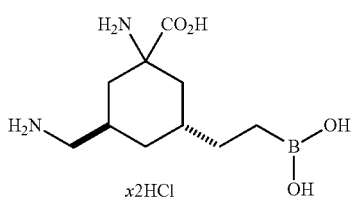 [SMILES: NC[C@@H]1C[C@@H](CCB(O)O)CC(N)(C(=O)O)C1]

Step A. 3-((tert-butyldimethylsilyl)oxy)-5-vinylcyclohexanone

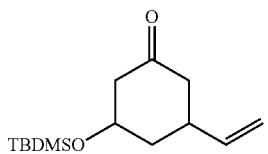 [SMILES: C=CC1CC(=O)CC(O[Si](C)(C)C(C)(C)C)C1]

The title compound 3-((tert-butyldimethylsilyl)oxy)-5-vinylcyclohexanone was obtained in the same manner like in the step B from the synthesis of the intermediate 1, using 5-((tert-butyldimethylsilyl)oxy)cyclohex-2-enone (1.77 g, 7.8 mmol, 1 equiv., prepared from 1,3,5-cyclohexanetriol using literature method, *J Org. Chem.*, 2001, 66, 8277), vinylmagnesium bromide 1M in THF (27.3 mL, 27.3 mmol, 3.5 equiv.), HMPA (5.4 mL, 31.2 mmol, 4 equiv.), copper(I) bromide dimethyl sulfide complex (242 mg, 1.17 mmol, 0.15 equiv.), trimethylsilyl chloride (4.9 mL, 39.0 mmol, 5 equiv.) and THF (50 mL). The residue was purified by flash chromatography on silica gel (hexane/AcOEt, 100:1 to 10:1) to give corresponding product as a mixture of diastereoisomers, dr=9:1, (1.5 mg, 76%, pale yellow oil). ESI+MS: m/z=255.1 (M+1)$^+$. $^1$H NMR (700 MHz, Chloroform-d) δ 5.81 (ddd, J=17.0, 10.4, 6.4 Hz, 1H), 5.10-5.00 [(m, 2H, two diastereoisomers)], 4.43-3.88 [(m, 1H, two diastereoisomers)], 2.98-2.78 [(m, 1H, two diastereoisomers)], 2.64-2.29 [(m, 3H, two diastereoisomers)], 2.17-2.10 [(m, 1H, two diastereoisomers)], 1.98-1.90 (m, 1H), 1.68-1.52 [(m, 1H, two diastereoisomers)], 0.88, 0.82 [(2s, 9H, two diastereoisomers)], 0.07, 0.05 [(2d, J=7.7 Hz, J=4.8 Hz, 6H, two diastereoisomers)].

Step B. 5-vinylcyclohex-2-enone

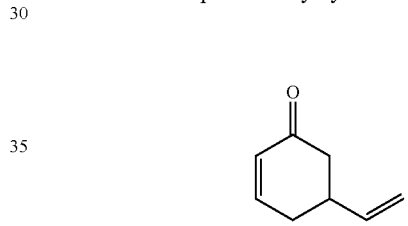

To a solution of 3-((tert-butyldimethylsilyl)oxy)-5-vinylcyclohexanone (1.5 g, 5.9 mmol, 1 equiv.) in dichloromethane was added p-toluenesulfonic acid monohydrate (0.33 g, 1.7 mmol, 0.3 equiv.). The reaction mixture was stirred at room temperature overnight. The reaction was quenched with NaHCO$_{3(sat)}$ and extracted with dichloromethane three times. The organic layer was dried over MgSO$_4$, filtered and concentrated in vacuo. The crude product was purified by flash chromatography on silica gel (DCM) to give corresponding product (700 mg, 97%, pale yellow oil). ESI+MS: m/z=123.0 (M+1)$^+$. $^1$H NMR (700 MHz, Chloroform-d) δ 6.97 (ddd, J=10.1, 5.5, 2.8 Hz, 1H), 6.05 (ddt, J=10.1, 2.6, 1.2 Hz, 1H), 5.83 (ddd, J=17.0, 10.4, 6.4 Hz, 1H), 5.13-4.95 (m, 2H), 2.86-2.73 (m, 1H), 2.57 (dd, J=16.3, 4.1 Hz, 1H), 2.52-2.46 (m, 1H), 2.31 (dd, J=16.3, 12.2 Hz, 1H), 2.24 (ddt, J=18.6, 9.9, 2.7 Hz, 1H).

Step C. rac-(3R,5R)-3-(nitromethyl)-5-vinylcyclohexanone

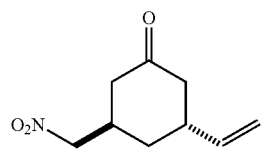

To a solution of 5-vinylcyclohex-2-enone (266 mg, 2.18 mmol, 1 equiv.) in acetonitrile (7 mL) nitromethane (0.6 mL, 10.9 mmol, 5 equiv.) and 1,8-diazabicyclo[5.4.0]undec-7-ene (0.49 mL, 3.27 mmol, 1.5 equiv.) were added. The reaction mixture was stirred at room temperature for 1.5 h. The solvent was evaporated in vacuo. The residue was purified by silica gel flash chromatography (hexane/DCM, 5:1 to 1:9) to give corresponding product as a single diastereoisomer (85 mg, 21%, colorless oil). ¹H NMR (700 MHz, Chloroform-d) δ 5.77 (ddd, J=17.3, 10.6, 5.4 Hz, 1H), 5.16-5.01 (m, 2H), 4.47-4.27 (m, 2H), 2.97-2.82 (m, 2H), 2.58-2.43 (m, 3H), 2.18 (dd, J=14.4, 9.9 Hz, 1H), 1.92 (dt, J=13.3, 4.6 Hz, 1H), 1.81 (ddd, J=13.8, 9.5, 4.4 Hz, 1H).

Step D. rac-(3R,5R)-1-acetamido-N-(tert-butyl)-3-(nitromethyl)-5-vinylcyclohexanecarboxamide

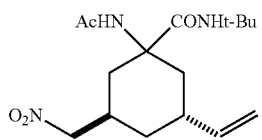

The title compound rac-(3R,5R)-1-acetamido-N-(tert-butyl)-3-(nitromethyl)-5-vinylcyclohexanecarboxamide was obtained in the same manner like in the step C from the synthesis of the intermediate 1, using (3R,5R)-3-(nitromethyl)-5-vinylcyclohexanone (70 mg, 0.38 mmol, 1 equiv.), ammonium acetate (120 mg, 1.52 mmol, 4 equiv.), tert-butylisocyanide (86 μL, 0.76 mmol, 2 equiv.) and 2,2,2-trifluoroethanol (4 mL) as a solvent. The residue was purified by flash chromatography on silica gel (DCM/methanol 100:1 to 70:1) to give corresponding product as a mixture of separable diastereoisomers. One single diastereoisomer was separated. Moreover, the mixture of diastereoisomers (dr=85:15) was also isolated. Total yield: 80%.

Mixture of diastereoisomers (85:15): (20 mg, white solid); ESI+MS: m/z=326.2 (M+1)⁺. Major diastereoisomer ¹H NMR (700 MHz, Chloroform-d) δ 6.83 (s, 1H), 5.98 (ddd, J=17.6, 10.8, 4.8 Hz, 1H), 5.71 (s, 1H), 5.25-5.14 (m, 2H), 4.35 (dd, J=12.6, 5.5 Hz, 1H), 4.25 (dd, J=12.6, 9.0 Hz, 1H), 2.79-2.68 (m, 1H), 2.64-2.51 (m, 1H), 2.30 (d, J=14.7 Hz, 1H), 2.10 (d, J=4.7 Hz, 2H), 1.97 (s, 3H), 1.97-1.93 (m, 1H), 1.81-1.73 (m, 1H), 1.43-1.36 (m, 1H), 1.31 (s, 9H).

Single diastereoisomer (80 mg, white solid); ESI+MS: m/z=326.2 (M+1)⁺. ¹H NMR (700 MHz, Chloroform-d) δ 7.02 (s, 1H), 5.87 (s, 1H), 5.76 (ddd, J=17.1, 10.4, 6.4 Hz, 1H), 5.11-4.98 (m, 2H), 4.56 (dd, J=11.5, 8.2 Hz, 1H), 4.49 (dd, J=11.5, 7.9 Hz, 1H), 2.93-2.85 (m, 1H), 2.43-2.26 (m, 2H), 2.15 (dd, J=15.2, 5.7 Hz, 1H), 2.06 (s, 3H), 2.05-2.04 (m, 1H), 1.92-1.83 (m, 1H), 1.67-1.61 (m, 1H), 1.62-1.55 (m, 1H), 1.31 (s, 9H).

Step E. rac-(3R,5R)-1-acetamido-N-(tert-butyl)-3-(nitromethyl)-5-(2-(4,4,5,5-tetramethyl-1,3,2-dioxaborolan-2-yl)ethyl)cyclohexanecarboxamide

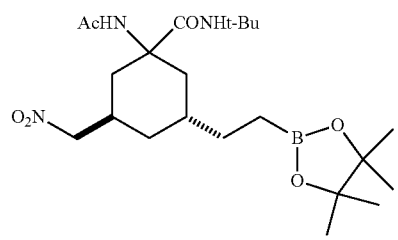

The title compound rac-(3R,5R)-1-acetamido-N-(tert-butyl)-3-(nitromethyl)-5-(2-(4,4,5,5-tetramethyl-1,3,2-dioxaborolan-2-yl)ethyl)cyclohexanecarboxamide was obtained in the same manner like in the Example 26, step B, using rac-(3R,5R)-1-acetamido-N-(tert-butyl)-3-(nitromethyl)-5-vinylcyclohexanecarboxamide (mixture of diastereoisomers 85:15, 20 mg, 0.06 mmol, 1 equiv.), dppe (1.4 mg, 0.0036 mmol, 0.06 equiv.), bis(1,5-cyclooctadiene) diiridium(I) dichloride (1.2 mg, 0.0018 mmol, 0.03 equiv.), 4,4,5,5-tetramethyl-1,3,2-dioxaborolane (13 μL, 0.09 mmol, 1.5 equiv.) and DCM (1 mL). The crude product was purified by column chromatography on silica gel (hexane/AcOEt 8:1 to 1:2) to give corresponding product as a mixture of diastereoisomers, dr=85:15 (27 mg, 97%, colorless oil). ESI+MS: m/z=454.3 (M+1)⁺; ESI-MS: m/z=452.3 (M−1)⁻. ¹H NMR (700 MHz, Chloroform-d) δ 7.19, 7.00 [(2s, 1H, two diastereoisomers)], 6.00, 5.85 [(2s, 1H, two diastereoisomers)], 4.52-4.24 [(m, 2H, two diastereoisomers)], 2.83-2.50 [(m, 1H, two diastereoisomers)], 2.32-2.24 (m, 1H), 2.16-2.10 (m, 1H), 2.04, 2.03 [(2s, 3H, two diastereoisomers)], 1.93 (dd, J=13.9, 9.4 Hz, 1H), 1.82-1.74 (m, 2H), 1.66-1.58 (m, 1H), 1.53-1.49 (m, 1H), 1.48-1.41 (m, 2H), 1.32, 1.31 [(2s, 9H, two diastereoisomers)], 1.25, 1.24 [(2s, 12H, two diastereoisomers)], 0.93-0.84 (m, 1H), 0.83-0.73 (m, 1H).

The second diastereoisomer was obtained in the same way starting from: rac-(3R,5R)-1-acetamido-N-(tert-butyl)-3-(nitromethyl)-5-vinylcyclohexanecarboxamide (single diasteroisomer, 80 mg, 0.24 mmol, 1 equiv.), dppe (5.7 mg, 0.014 mmol, 0.06 equiv.), bis(1,5-cyclooctadiene)diiridium (I) dichloride (4.8 mg, 0.007 mmol, 0.03 equiv.), 4,4,5,5-tetramethyl-1,3,2-dioxaborolane (55 μL, 0.37 mmol, 1.5 equiv.) and DCM (8 mL). The crude product was purified by column chromatography on silica gel (hexane/AcOEt 8:1 to 1:4) to give corresponding product as a single diastereoisomer (100 mg, 90%, white solid). ESI+MS: m/z=454.3 (M+1)⁺. ¹H NMR (700 MHz, Chloroform-d) δ 7.02 (s, 1H), 5.86 (s, 1H), 4.96-4.24 (m, 2H), 2.87-2.79 (m, 1H), 2.38-2.30 (m, 1H), 2.19-2.11 (m, 2H), 2.06 (s, 3H), 1.67-1.58 (m, 2H), 1.47-1.35 (m, 3H), 1.33 (s, 9H), 1.29-1.26 (m, 1H), 1.26 (s, 12H), 0.80 (t, J=8.0 Hz, 2H).

Step F. tert-butyl rac-(((1R,5R)-3-acetamido-3-(tert-butylcarbamoyl)-5-(2-(4,4,5,5-tetramethyl-1,3,2-dioxaborolan-2-yl)ethyl)cyclohexyl)methyl)carbamate

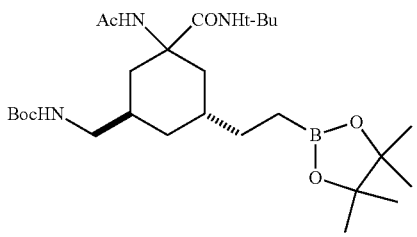

A solution of rac-(3R,5R)-1-acetamido-N-(tert-butyl)-3-(nitromethyl)-5-(2-(4,4,5,5-tetramethyl-1,3,2-dioxaborolan-2-yl)ethyl)cyclohexanecarboxamide (mixture of diastereoisomers 85:15, 20 mg, 0.044 mmol, 1 equiv.) in methanol (1 mL) was cooled to −20° C. and added di-tert-butyl dicarbonate (20 mg, 0.088 mmol, 2 equiv.), nickel(II) chloride hexahydrate (10 mg, 0.044 mmol, 1 equiv.) and sodium borohydride (17 mg, 0.44 mmol, 10 equiv.) in portions. The mixture was allowed to warm to room temperature and stirred for 3 h. The solvent was evaporated in vacuo. The residue was dissolved in ethyl acetate and washed with $H_2O$, $NH_4Cl_{sat}$ and brine. The organic layer was dried over $MgSO_4$, filtered and concentrated in vacuo to give corresponding product as a mixture of diastereoisomers, dr=85:15, (20 mg, 87%, white solid). ESI+MS: m/z=524.0 (M+1)$^+$. $^1$H NMR (700 MHz, Chloroform-d) δ 7.12, 7.07 [(2s, 1H, two diastereoisomers)], 5.82 (s, 1H), 4.91-4.72 [(m, 1H, two diastereoisomers)], 3.12-3.04 (m, 1H), 3.10-2.79 [(m, 1H, two diastereoisomers)], 2.24-2.13 (m, 1H), 2.05-1.99 (m, 1H), 1.98, 1.96 [(2s, 3H, two diastereoisomers)], 1.91-1.78 (m, 3H), 1.80-1.74 (m, 1H), 1.73-1.63 (m, 1H), 1.60-1.55 (m, 1H), 1.46, 1.44 [(2s, 9H, two diastereoisomers)], 1.36-1.33 (m, 1H), 1.31, 1.30 [(2s, 9H, two diastereoisomers)], 1.28-1.24 (m, 1H), 1.24, 1.23 [(2s, 12H, two diastereoisomers)], 0.90-0.80 (m, 1H), 0.80-0.74 (m, 1H).

The second diastereoisomer was obtained in the same way starting from: rac-(3R,5R)-1-acetamido-N-(tert-butyl)-3-(nitromethyl)-5-(2-(4,4,5,5-tetramethyl-1,3,2-dioxaborolan-2-yl)ethyl)cyclohexanecarboxamide (single diastereoisomer, 100 mg, 0.22 mmol, 1 equiv.), di-tert-butyl dicarbonate (95 mg, 0.44 mmol, 2 equiv.), nickel(II) chloride hexahydrate (52 mg, 0.22 mmol, 1 equiv.) and sodium borohydride (83 mg, 2.2 mmol, 10 equiv.) and methanol (5 mL). The crude product was purified by column chromatography on silica gel (hexane/AcOEt 5:1 to 1:9) to give corresponding product as a single diastereoisomer (78 mg, 68%, white solid). ESI+MS: m/z=524.0 (M+1)$^+$. $^1$H NMR (700 MHz, Chloroform-d) δ 8.03 (s, 1H), 7.07 (s, 1H), 4.85-4.67 (m, 1H), 3.76-3.51 (m, 1H), 2.97-2.66 (m, 2H), 2.06 (s, 3H), 1.97-1.85 (m, 3H), 1.77-1.70 (m, 1H), 1.46 (s, 9H), 1.42-1.31 (m, 2H), 1.30 (s, 9H), 1.23 (s, 12H), 1.21-1.13 (m, 2H), 0.78-0.71 (m, 2H).

Step G. rac-(3R,5R)-1-amino-3-(aminomethyl)-5-(2-boronoethyl)cyclohexanecarboxylic acid dihydrochloride The title compound rac-(3R,5R)-1-amino-3-(aminomethyl)-5-(2-boronoethyl)cyclohexanecarboxylic acid dihydrochloride was obtained in the same manner like in the Example 26, step C, using racemic tert-butyl (((1R,5R)-3-acetamido-3-(tert-butylcarbamoyl)-5-(2-(4,4,5,5-tetramethyl-1,3,2-dioxaborolan-2-yl)ethyl)cyclohexyl)methyl)carbamate (mixture of diastereoisomers 85:15, 20 mg, 0.038 mmol, 1 equiv.) and 6N HCl$_{aq}$ (3 mL). The residue was purified by flash chromatography on DOWEX® ion exchange resin (eluent 0.1N ammonia in water) and then by preparative HPLC (0.1-1% MeCN in water) to give (after acidification with 6N HCl and subsequent lyophilization) corresponding product as a mixture of diastereoisomers, dr=85:15 (4.7 mg, 31%, white solid). ESI+MS: m/z=245.1 (M+1)$^+$. $^1$H NMR (700 MHz, Deuterium Oxide) δ 3.12-2.97 [(m, 2H, two diastereoisomers)], 2.47-2.29 [(m, 3H, two diastereoisomers)], 1.93, 1.86 [(2dd, J=14.4, 5.3 Hz, J=14.0, 4.9 Hz, 1H, two diastereoisomers)], 1.84-1.73 (m, 1H), 1.72 (dt, J=14.1, 4.4 Hz, 1H), 1.53-1.36 (m, 4H), 0.87-0.80 [(m, 2H, two diastereoisomers)].

The second diastereoisomer was obtained in the same way starting from: racemic tert-butyl (((1R,5R)-3-acetamido-3-(tert-butylcarbamoyl)-5-(2-(4,4,5,5-tetramethyl-1,3,2-dioxaborolan-2-yl)ethyl)cyclohexyl)methyl)carbamate (single diasteroisomer, 20 mg, 0.038 mmol, 1 equiv.) and 6N HCl$_{aq}$ (3 mL). The residue was purified by flash chromatography on DOWEX® ion exchange resin (eluent 0.1N ammonia in water) and then by preparative HPLC (0.1-1% MeCN in water) to give (after acidification with 6N HCl and subsequent lyophilization) corresponding product as a single diastereoisomer (4.9 mg, 41%, white solid). ESI+MS: m/z=245.1 (M+1)$^+$. $^1$H NMR (700 MHz, Deuterium Oxide) δ 3.08-2.93 (m, 2H), 2.52-2.27 (m, 3H), 1.97-1.90 (m, 1H), 1.87 (dd, J=14.0, 5.0 Hz, 1H), 1.76 (d, J=13.4 Hz, 1H), 1.51-1.30 (m, 4H), 0.81 (td, J=8.1, 4.5 Hz, 2H).

Example 55. rac-(3R,5R)-1-amino-3-(2-boronoethyl)-5-((dimethylamino)methyl)cyclohexanecarboxylic acid dihydrochloride

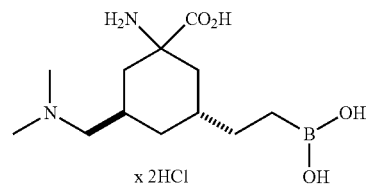 [SMILES: CN(C)C[C@@H]1C[C@@H](CCB(O)O)CC(N)(C(=O)O)C1]

Step H. rac-(3R,5R)-1-acetamido-N-(tert-butyl)-3-((dimethylamino)methyl)-5-(2-(4,4,5,5-tetramethyl-1,3,2-dioxaborolan-2-yl)ethyl)cyclohexanecarboxamide

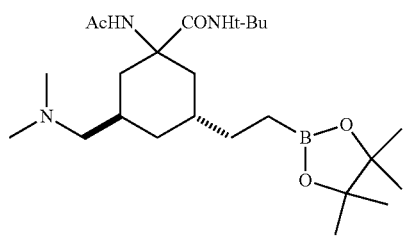

To a solution of racemic tert-butyl (((1R,5R)-3-acetamido-3-(tert-butylcarbamoyl)-5-(2-(4,4,5,5-tetramethyl-1, 3,2-dioxaborolan-2-yl)ethyl)cyclohexyl)methyl)carbamate (46 mg, 0.088 mmol, 1 equiv.)(second diastereoisomer) in dichloromethane (3 mL) was added trifluoroacetic acid (1 mL). The reaction mixture was stirred at room temperature for 1.5 h. The solvents was evaporated in vacuo. The residue was dissolved in 1,2-dichloroethane (1 mL) and added formaldehyde$_{aq}$(25 μL, 0.34 mmol, 4 equiv.) and stirred at room temperature for 1 h. Then was added sodium triacetoxyborohydride (72 mg, 0.34 mmol, 4 equiv.). The resulting mixture was stirred at room temperature overnight. The mixture was diluted with dichloromethane and washed with 5% NaHCO$_3$. The aqueous layer was extracted with dichloromethane three times. The combined organic layers were dried over MgSO$_4$, filtered and concentrated in vacuo to give corresponding product as a single diastereoisomer (30 mg, 76%, white solid). ESI+MS: m/z=452.4 (M+1)$^+$. $^1$H NMR (700 MHz, Chloroform-d) δ 7.88 (s, 1H), 7.56 (s, 1H), 3.01-2.76 (m, 1H), 2.52 (t, J=13.3 Hz, 1H), 2.22 (s, 6H), 2.18-2.14 (m, 1H), 1.99-1.97 (m, 2H), 1.96 (s, 3H), 1.84-1.78 (m, 1H), 1.43-1.37 (m, 2H), 1.31 (s, 9H), 1.29-1.24 (m, 2H), 1.23 (s, 12H), 1.16-1.10 (m, 2H), 0.76 (dt, J=9.5, 6.3 Hz, 2H).

Step I. rac-(3R,5R)-1-amino-3-(2-boronoethyl)-5-((dimethylamino)methyl)cyclohexanecarboxylic acid dihydrochloride The title rac-(3R,5R)-1-amino-3-(2-boronoethyl)-5-((dimethylamino)methyl)cyclohexanecarboxylic acid hydrochloride was obtained in the same manner like in the Example 26, step C, using rac-(3R,5R)-1-acetamido-N-(tert-butyl)-3-((dimethylamino)methyl)-5-(2-(4,4,5,5-tetramethyl-1,3,2-dioxaborolan-2-yl)ethyl)cyclohexanecarboxamide (30 mg, 0.07 mmol, 1 equiv.) and 6N HCl$_{aq}$ (3 mL). The residue was purified by flash chromatography on DOWEX® ion exchange resin (eluent 0.1N ammonia in water) and then by preparative HPLC (0.1-1% MeCN in water) to give (after acidification with 6N HCl and subsequent lyophilization) corresponding product as a single diastereoisomer (1.2 mg, 5%, white solid). ESI+MS: m/z=273.2 (M+1)$^+$. $^1$H NMR (700 MHz, Deuterium Oxide) δ 3.15 (d, J=7.5 Hz, 2H), 2.96 (d, J=12.9 Hz, 6H), 2.65-2.51 (m, 1H), 2.38-2.31 (m, 2H), 1.97-1.87 (m, 1H), 1.84 (dd, J=14.1, 5.0 Hz, 1H), 1.74-1.68 (m, 1H), 1.53-1.30 (m, 4H), 0.88-0.70 (m, 2H).

Example 56.
1,3-diamino-5-(2-boronoethyl)cyclohexanecarboxylic acid dihydrochloride

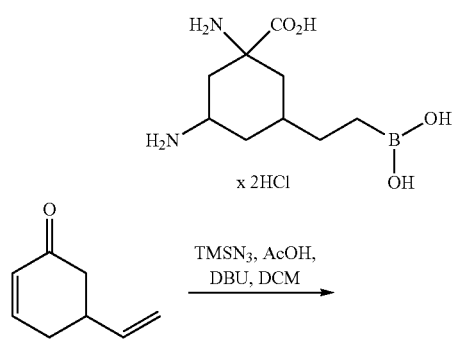

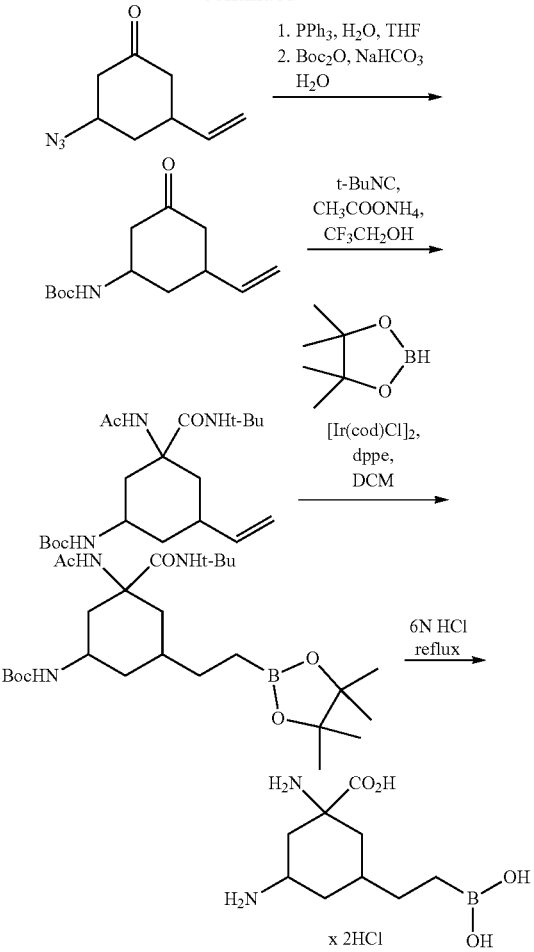

Step A. 3-azido-5-vinylcyclohexanone

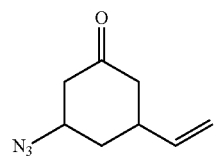

To a solution of trimethylsilyl azide (3.87 mL, 29.5 mmol, 5 equiv.) in dichloromethane (25 mL) was added acetic acid (1.68 mL, 29.5 mmol, 5 equiv.) and stirred at room temperature for 20 min. Then was added 5-vinylcyclohex-2-enone (0.72 g, 5.9 mmol, 1 equiv.) in dichloromethane (5 mL) followed by addition of 1,8-diazabicyclo[5.4.0]undec-7-ene (176 μL, 1.18 mmol, 0.2 equiv.). The reaction mixture was stirred at room temperature for 3 h. The mixture was diluted with dichloromethane and washed with H$_2$O, 5% NaHCO$_3$. The combined organic layers were dried over MgSO$_4$, filtered and concentrated in vacuo to give corresponding product as a mixture of diastereoisomers, dr=85:15, (0.9 g, 93%, orange oil). $^1$H NMR (700 MHz, Chloroform-d) δ 5.85-5.75 [(m, 1H, two diastereoisomers)], 5.13-5.03 (m, 2H), 4.22-3.63 [(m, 1H, two diastereoisomers)], 2.89-2.72 [(m, 1H, two diastereoisomers)], 2.59-2.54 (m, 1H), 2.53-2.38 [(m, 2H, two diastereoisomers)], 2.36-2.24 [(m, 1H, two diastereoisomers)], 2.16 (t, J=13.5 Hz, 1H), 2.10-2.02 (m, 1H), 1.85-1.55 [(m, 1H, two diastereoisomers)].

Step B. tert-butyl (3-oxo-5-vinylcyclohexyl)carbamate

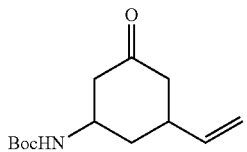 [SMILES: C=CC1CC(=O)CC(NC(=O)OC(C)(C)C)C1]

To a solution of 3-azido-5-vinylcyclohexanone (0.9 g, 5.45 mmol, 1 equiv.) in tetrahydrofuran (10 mL) were added triphenylphosphine (2.85 g, 10.9 mmol, 2 equiv.) and H$_2$O (0.49 mL, 27.2 mmol, 5 equiv.). The reaction mixture was stirred at room temperature for 3 h. Then to the mixture were added sodium bicarbonate (0.91 g, 10.9 mmol, 2 equiv.), di-tert-butyl dicarbonate (1.42 g, 6.54 mmol, 1.2 equiv.) and H$_2$O (10 mL). The resulting mixture was stirred at room temperature for 2 days. The mixture was diluted with ethyl acetate and washed with H$_2$O and brine. The organic layer was dried over MgSO$_4$, filtered and concentrated in vacuo. The crude product was purified by flash chromatography on silica gel (hexane/AcOEt, 50:1 to 3:1) to give corresponding product as a mixture of diastereoisomers, dr=85:15, (200 mg, 15%, white solid). ESI+MS: m/z=184.0 (M−tBu)$^+$. $^1$H NMR (700 MHz, Chloroform-d) δ 5.82-5.75 [(m, 1H, two diastereoisomers)], 5.17-5.00 (m, 2H), 4.42, 4.21 [(2br s, 1H, two diastereoisomers)], 2.75-2.71 (m, 1H), 2.61 (dd, J=14.3, 5.1 Hz, 1H), 2.49-2.38 (m, 2H), 2.37-2.26 [(m, 2H, two diastereisomers)], 2.20-2.02 [(m, 1H, two diastereoisomers)], 1.85-1.82 (m, 1H), 1.45, 1.43 [(2s, 9H, two diastereoisomers)].

Step C. tert-butyl (3-acetamido-3-(tert-butylcarbamoyl)-5-vinylcyclohexyl)carbamate

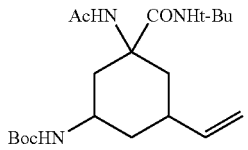

The title compound tert-butyl (3-acetamido-3-(tert-butylcarbamoyl)-5-vinylcyclohexyl)carbamate was obtained in the same manner like in the step C from the synthesis of the intermediate 1, using tert-butyl (3-oxo-5-vinylcyclohexyl)carbamate (200 mg, 0.84 mmol, 1 equiv.), ammonium acetate (258 mg, 3.36 mmol, 4 equiv.), tert-butylisocyanide (187 μL, 1.67 mmol, 2 equiv.) and 2,2,2-trifluoroethanol (8 mL) as a solvent. The residue was purified by flash chromatography on silica gel (hexane/AcOEt 12:1 to 2:1) to give corresponding product as a mixture of diastereoisomers. Total yield: 78%. Diastereoisomers were partially separated as the following diastereoisomeric ratios:

Mixture of diastereoisomers (dr=9:1): (140 mg, white solid); ESI+MS: m/z=382.2 (M+1)$^+$. $^1$H NMR (700 MHz, Chloroform-d) δ 6.96, 6.76 [(2s, 1H, two diastereoisomers)], 5.93, 5.86 [(2s, 1H, two diastereoisomers)], 5.74 (ddd, J=17.0, 10.4, 6.2 Hz, 1H), 5.07-5.00 [(m, 2H, two diastereoisomers)], 4.61, 4.45 [(2d, J=6.0 Hz, J=9.4 Hz, 1H, two diastereoisomers)], 4.01-3.63 [(m, 1H, two diastereoisomers)], 2.62, 2.55 [(2d, J=12.2 Hz, J=13.2 Hz, 1H, two diastereoisomers)], 2.40 (d, J=14.1 Hz, 1H), 2.28-2.17 [(m, 1H, two diastereoisomers)], 2.05, 2.03 [(2s, 3H, two diastereoisomers)], 1.82 (dd, J=15.0, 4.1 Hz, 2H), 1.69-1.49 [(m, 1H, two diastereoisomers)], 1.46, 1.44 [(2s, 9H, two diastereoisomers)], 1.31 (s, 9H).

Mixture of diastereoisomers (1:1), (110 mg, white solid); ESI+MS: m/z=382.2 (M+1)$^+$. $^1$H NMR (700 MHz, Chloroform-d) δ 7.14, 5.65 [(2s, 1H, two diastereoisomers)], 5.86-5.69 [(m, 1H, two diastereoisomers)], 5.47 (s, 2H), 5.17-4.95 [(m, 2H, two diastereoisomers)], 3.97-3.74 [(m, 1H, two diastereoisomers)], 2.95-2.63 [(m, 1H, two diastereoisomers)], 2.36-2.24 [(m, 2H, two diastereoisomers)], 2.04, 1.96[(2s, 3H, two diastereoisomers)], 2.03-1.85 (m, 1H, two diastereoisomers)], 1.74-1.65 [(m, 2H, two diastereoisomers)], 1.43 (s, 9H), 1.35, 1.33 [(s, 9H, two diastereoisomers)], 1.14-0.96 [(m, 1H, two diastereoisomers)].

Step D. tert-butyl (3-acetamido-3-(tert-butylcarbamoyl)-5-(2-(4,4,5,5-tetramethyl-1,3,2-dioxaborolan-2-yl)ethyl)cyclohexyl)carbamate

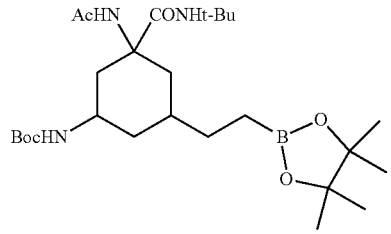

The title compound tert-butyl (3-acetamido-3-(tert-butylcarbamoyl)-5-(2-(4,4,5,5-tetramethyl-1,3,2-dioxaborolan-2-yl)ethyl)cyclohexyl)carbamate was obtained in the same manner like in Example 26, step B, using tert-butyl (3-acetamido-3-(tert-butylcarbamoyl)-5-vinylcyclohexyl)carbamate (dr=9:1, 140 mg, 0.37 mmol, 1 equiv.), dppe (8.8 mg, 0.022 mmol, 0.06 equiv.), bis(1,5-cyclooctadiene) diiridium(I) dichloride (7.4 mg, 0.011 mmol, 0.03 equiv.), 4,4,5,5-tetramethyl-1,3,2-dioxaborolane (80 μL, 0.55 mmol, 1.5 equiv.) and DCM (12 mL). The crude product was purified by column chromatography on silica gel (hexane/AcOEt 5:1 to 1:1) to give corresponding product as a mixture of diastereoisomers 9:1 (100 mg, 53%, white solid). ESI+MS: m/z=510.4 (M+1)$^+$; ESI-MS: m/z=508.4 (M−1)$^−$. $^1$H NMR (700 MHz, Chloroform-d) δ 6.81 (s, 1H), 5.87 (s, 1H), 4.62 (s, 1H), 4.03-3.88 (m, 1H), 2.55 (d, J=15.1 Hz, 1H), 2.35 (d, J=13.7 Hz, 1H), 2.00 (s, 3H), 1.86-1.75 (m, 2H), 1.56-1.50 (m, 1H), 1.46 (s, 9H), 1.46-1.40 (m, 3H), 1.38-1.32 (m, 1H), 1.30 (s, 9H), 1.25 (s, 12H), 0.81 (t, J=7.6 Hz, 2H).

The second mixture of diastereoisomers was obtained in the same way starting from: tert-butyl (3-acetamido-3-(tert-butylcarbamoyl)-5-vinylcyclohexyl)carbamate (dr=1:1, 100 mg, 0.26 mmol, 1 equiv.), dppe (6.2 mg, 0.015 mmol, 0.06 equiv.), bis(1,5-cyclooctadiene)diiridium(I) dichloride (5.2 mg, 0.0078 mmol, 0.03 equiv.), 4,4,5,5-tetramethyl-1,3,2-dioxaborolane (57 μL, 0.39 mmol, 1.5 equiv.) and DCM (8 mL). The crude product was purified by column chromatography on silica gel (hexane/AcOEt 4:1 to 1:1) to give corresponding product as a mixture of diastereoisomers, dr=1:1, (116 mg, 87%, white solid). ESI+MS: m/z=510.4 (M+1)+; ESI-MS: m/z=508.4 (M−1)−. ¹H NMR (700 MHz, Chloroform-d) δ 6.02, 5.51 [(2s, 1H, two diastereisomers)], 5.44, 5.42 [(2s, 1H, two diastereoisomers)], 3.95, 3.69 [(2s, 1H, two diastereoisomers)], 2.62-2.47 [(m, 2H, two diastereoisomers)], 2.02-1.78 [(m, 1H, two diastereoisomers)], 1.97, 1.93 [(2s, 3H, two diastereoisomers)], 1.70-1.60 [(m, 1H, two diastereoisomers)], 1.43, 1.42 [(2s, 9H, two diastereoisomers)], 1.42-1.35 (m, 2H), 1.34, 1.33 [(2s, 9H, two diastereoisomers)], 1.33-1.28 (m, 2H), 1.28-1.23 (m, 1H), 1.24, 1.23 [(2s, 12H, two diastereoisomers)], 1.22-1.15 (m, 1H), 0.83-0.74 (m, 2H).

Step E.
1,3-diamino-5-(2-boronoethyl)cyclohexanecarboxylic acid dihydrochloride

The title compound 1,3-diamino-5-(2-boronoethyl)cyclohexanecarboxylic acid dihydrochloride was obtained in the same manner like in Example 26, step C, using tert-butyl (3-acetamido-3-(tert-butylcarbamoyl)-5-(2-(4,4,5,5-tetramethyl-1,3,2-dioxaborolan-2-yl)ethyl)cyclohexyl)carbamate (dr=9:1, 20 mg, 0.04 mmol, 1 equiv.) and 6N HCl$_{aq}$ (2 mL). The residue was purified by flash chromatography on DOWEX® ion exchange resin (eluent 0.1N ammonia in water) and then by preparative HPLC (0.1-1% MeCN in water) to give (after acidification with 6N HCl and subsequent lyophilization) corresponding product as a single diastereoisomer (3.1 mg, 26%, white solid). ESI+MS: m/z=231.0 (M+1)+; ESI-MS: m/z=229.1 (M−1)−. ¹H NMR (700 MHz, Deuterium Oxide) δ 4.01-3.91 (m, 1H), 2.65-2.60 (m, 1H), 2.34 (dd, J=13.9, 4.0 Hz, 1H), 2.08-2.00 (m, 2H), 1.82 (dd, J=14.0, 5.1 Hz, 1H), 1.74-1.63 (m, 2H), 1.48 (dt, J=16.1, 7.8 Hz, 2H), 0.85-0.69 (m, 2H).

The second mixture of diastereoisomers was obtained in the same way starting from: tert-butyl (3-acetamido-3-(tert-butylcarbamoyl)-5-(2-(4,4,5,5-tetramethyl-1,3,2-dioxaborolan-2-yl)ethyl)cyclohexyl)carbamate (dr=1:1, 20 mg, 0.04 mmol, 1 equiv.) and 6N HCl$_{aq}$ (2 mL). The residue was purified by flash chromatography on DOWEX® ion exchange resin (eluent 0.1N ammonia in water) and then by preparative HPLC (0.1-1% MeCN in water) to give (after acidification with 6N HCl and subsequent lyophilization) corresponding product as a mixture of diastereoisomers, dr=3:2, (1.6 mg, 13%, white solid). ESI+MS: m/z=231.0 (M+1)+. ¹H NMR (700 MHz, Deuterium Oxide) δ 3.93-3.89 (m, 1H), 2.64-2.40 [(m, 1H, two diastereoisomers)], 2.36-2.24 [(m, 1H, two diastereoisomers)], 2.22-2.16 [(m, 1H, two diastereoisomers)], 2.11-1.99 [(m, 1H, two diastereoisomers)], 1.86-1.74 (m, 1H), 1.71-1.41 [(m, 3H, two diastereoisomers)], 1.39-1.06 [(m, 1H, two diastereoisomers)], 0.84 (q, J=6.9 Hz, 2H).

Example 57. rac-(3R,5S)-3-amino-5-(2-boronoethyl)piperidine-3-carboxylic acid dihydrochloride

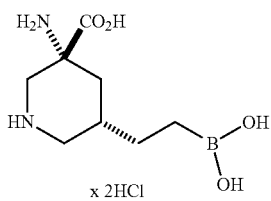

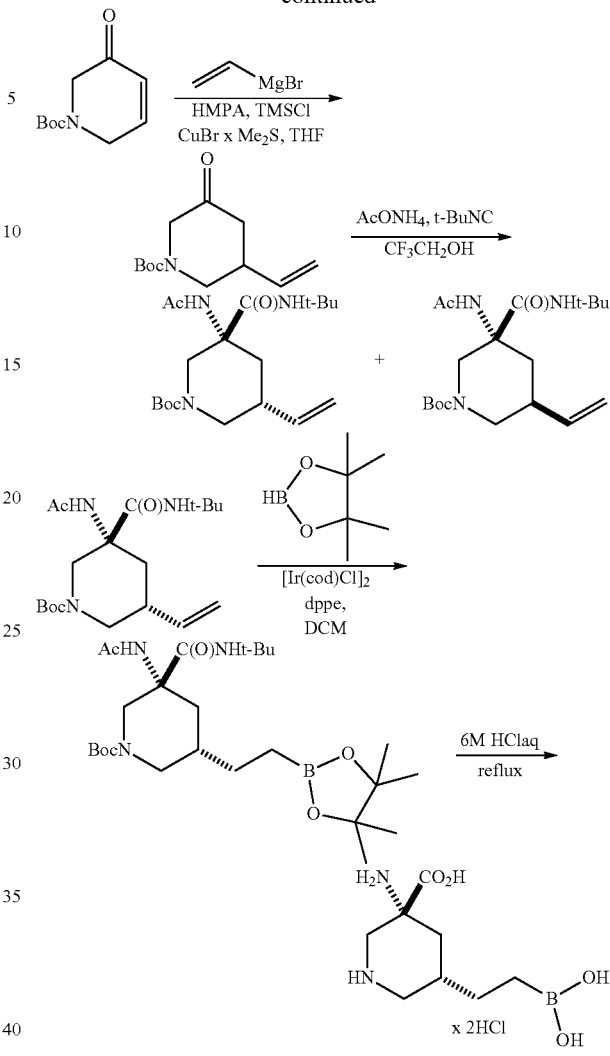

Step A. tert-butyl 3-oxo-5-vinylpiperidine-1-carboxylate

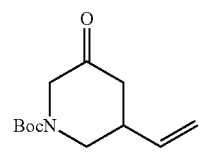 [SMILES: C=CC1CC(=O)CN(C(=O)OC(C)(C)C)C1]

A solution of vinylmagnesium bromide (1M in THF) (14.7 mL, 14.7 mmol) and HMPA (2.92 mL, 16.8 mmol) were separately added dropwise to a suspension of CuBr× Me₂S (129 mg, 0.63 mmol) in dry THF (20 mL) at −78° C. under argon for over 10 min. After stirring at −78° C. for 15 min a solution of tert-butyl 5-oxo-5,6-dihydropyridine-1 (2H)-carboxylate (obtained according to procedure described in WO 2012/025155) (0.83 g, 4.2 mmol) and TMSCl (2.67 mL, 21 mmol) in dry THF (10 mL) was added dropwise for over 30 min. The reaction mixture was stirred at −78° C. for 2 h. Then the mixture was slowly warmed to room temperature and stirred at ambient temperature overnight. Next the mixture was quenched with saturated aqueous NH₄Cl (70 mL) and washed with AcOEt (3×100 mL). The crude product (1.95 g) contained HMPA was used in the next step without any further purification. ¹H NMR (700 MHz, Chloroform-d) δ 5.78 (ddd, J=17.0, 10.5, 6.2 Hz, 1H), 5.20-5.08 (m, 2H), 4.10 (d, J=18.2 Hz, 1H), 4.02-3.77 (m, 2H), 3.31-3.12 (m, 1H), 2.75 (td, J=9.4, 4.5 Hz, 1H), 2.62 (dd, J=16.5, 4.9 Hz, 1H), 2.38 (dd, J=16.4, 10.0 Hz, 1H), 1.47 (s, 9H).

Step B. Racemic tert-butyl (3R,5R)- and (3R,5S)-3-acetamido-3-(tert-butylcarbamoyl)-5-vinylpiperidine-1-carboxylate

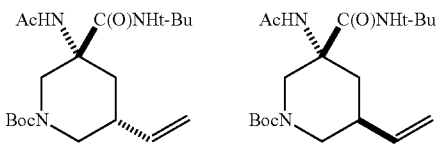

The title compounds were prepared from tert-butyl 3-oxo-5-vinylpiperidine-1-carboxylate (1.9 g, crude) using procedure described for the preparation of The intermediate 1, step C using ammonium acetate (2.6 g, 33.7 mmol), t-butyl isocyanide (1.91 mL, 16.87 mmol) and trifluoroethanol (30 mL). Purified by flash column chromatography on silica gel using hexane/AcOEt (20:1 to 1:1) as eluents. Total yield (after two steps): 1.08 g (70%).

rac-(3R,5R)-tert-butyl 3-acetamido-3-(tert-butylcarbamoyl)-5-vinylpiperidine-1-carboxylate; 0.85 g, white solid; ESI+MS: m/z=368.2 (M+1)⁺. ¹H NMR (700 MHz, Chloroform-d) δ 7.03 (bs, 1H), 5.98 (s, 1H), 5.75 (ddd, J=17.0, 10.6, 6.0 Hz, 1H), 5.16 (dt, J=17.5, 1.4 Hz, 1H), 5.10 (dt, J=10.6, 1.3 Hz, 1H), 4.40 (d, J=14.2 Hz, 1H), 3.80 (dd, J=13.46, 3.39 Hz 1H), 3.50 (d, J=14.2 Hz, 1H), 3.04 (dd, J=13.1, 8.7 Hz, 1H), 2.38 (s, 1H), 2.29 (d, J=12.9 Hz, 1H), 1.95 (s, 3H), 1.50 (s, 9H), 1.35 (s, 9H).

rac-(3R,5S)-tert-butyl 3-acetamido-3-(tert-butylcarbamoyl)-5-vinylpiperidine-1-carboxylate; 0.23 g; white solid; ESI+MS: m/z=368.2 (M+1)⁺. ¹H NMR (700 MHz, Chloroform-d) δ 7.25 (s, 1H), 6.66 (bs, 1H), 5.67 (ddd, J=17.2, 10.6, 6.5 Hz, 1H), 5.15-5.04 (m, 2H), 4.30-3.98 (m, 2H), 3.11 (m, 1H), 2.99 (m, 1H), 2.59 (m, 1H), 2.21 (m, 1H), 2.02 (s, 3H), 1.66 (m, 1H), 1.51 (s, 9H), 1.34 (s, 9H).

Step C. tert-butyl rac-(3R,5S)-3-acetamido-3-(tert-butylcarbamoyl)-5-(2-(4,4,5,5-tetramethyl-1,3,2-dioxaborolan-2-yl)ethyl)piperidine-1-carboxylate

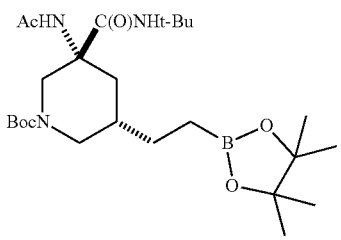

The title compounds were prepared from rac-(3R,5R)-tert-butyl 3-acetamido-3-(tert-butylcarbamoyl)-5-vinylpiperidine-1-carboxylate (0.2 g, 0.54 mmol) using procedure described in Example 26, step B. The crude product was purified by flash chromatography on silica gel (hexane/ethyl acetate 30:1 to 2:1). Obtained: 90 mg (white solid) as a mixture of the desired product and product without pinacol. ESI+MS: m/z=496.4 (M+1)⁺.

Step D. rac-(3R,5S)-3-amino-5-(2-boronoethyl)piperidine-3-carboxylic acid dihydrochloride The title compounds were prepared from tert-butyl (3R, 5S)-3-acetamido-3-(tert-butylcarbamoyl)-5-(2-(4,4,5,5-tetramethyl-1,3,2-dioxaborolan-2-yl)ethyl)piperidine-1-carboxylate (70 mg, 0.14 mmol, mixture from step C) using procedure described in Example 26, step C. The crude product was purified on Dowex® 8WX50 and then (after acidified with 6M HCl aq) by preparative HPLC (0.1-1% MeCN in H₂O). Obtained: 7 mg (17%) as a white solid. ESI+MS: m/z=217.1 (M+1)⁺. ¹H NMR (700 MHz, Deuterium Oxide) δ 3.70 (d, J=12.4 Hz, 1H), 3.45 (d, J=8.8 Hz, 1H), 3.03 (d, J=12.4 Hz, 1H), 2.62 (t, J=12.5 Hz, 1H), 2.29 (d, J=13.0 Hz, 1H), 2.00-1.90 (m, 1H), 1.47 (t, J=12.8 Hz, 1H), 1.43-1.31 (m, 2H), 0.79-0.65 (m, 2H).

Example 58. rac-(3R,5R)-3-amino-5-(2-boronoethyl)piperidine-3-carboxylic acid

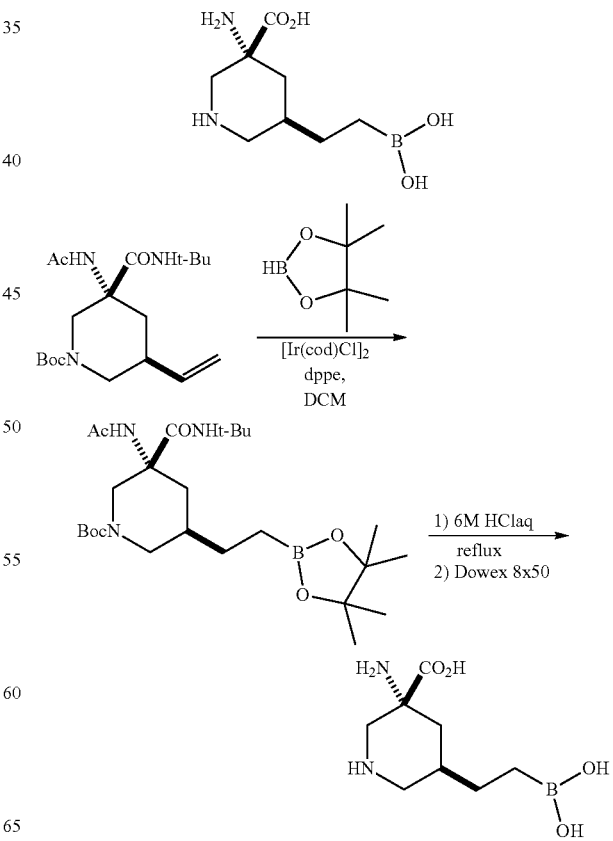

239

Step A. Racemic tert-butyl (3R,5R)-3-acetamido-3-(tert-butylcarbamoyl)-5-(2-(4,4,5,5-tetramethyl-1,3,2-dioxaborolan-2-yl)ethyl)piperidine-1-carboxylate

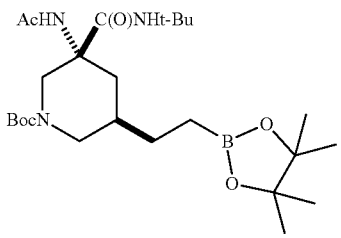

The title compounds were prepared from racemic tert-butyl (3R,5S)-3-acetamido-3-(tert-butylcarbamoyl)-5-vinylpiperidine-1-carboxylate (see Example 57, step B, 130 mg, 0.35 mmol) using procedure described for the preparation of Example 26, step B. The crude product was purified by flash chromatography on silica gel (DCM/acetone 50:1 to 2:1). Obtained: 120 mg (70%) as a white solid. ESI+MS: m/z=496.4 (M+1)$^+$. $^1$H NMR (700 MHz, Chloroform-d) δ 7.36 (bs, 1H), 6.65 (bs, 1H) 4.31-3.98 (m, 2H), 3.19-2.87 (m, 2H), 2.44-2.30 (m, 1H), 1.98 (s, 3H), 1.50 (s, 9H), 1.42-1.38 (m, 2H), 1.33 (s, 9H), 1.27-1.26 (m, 2H), 1.26 (d, J=1.2 Hz, 12H), 0.82-0.76 (m, 2H).

Step B. rac-(3R,5R)-3-amino-5-(2-boronoethyl)piperidine-3-carboxylic acid

The title compounds were prepared from racemic (3R,5R)-tert-butyl 3-acetamido-3-(tert-butylcarbamoyl)-5-(2-(4,4,5,5-tetramethyl-1,3,2-dioxaborolan-2-yl)ethyl)piperidine-1-carboxylate (100 mg, 0.2 mmol) using procedure described for the preparation of Example 26. The crude product was purified by preparative HPLC (0.1-1% MeCN in H$_2$O) and by Dowex® 8WX50. Obtained: 34 mg (78%) as a white solid. ESI+MS: m/z=217.1 (M+1)$^+$. ESI-MS: m/z=215.1 (M−1)$^−$. $^1$H NMR (700 MHz, Deuterium Oxide) δ 3.29 (d, J=10.4 Hz, 1H), 3.15-3.05 (m, 2H), 2.50 (t, J=12.2 Hz, 1H), 1.90-1.81 (m, 2H), 1.54-1.46 (m, 1H), 1.39-1.23 (m, 2H), 0.78-0.66 (m, 2H).

Example 59. rac-(3R,5S)-3-amino-5-(2-boronoethyl)-1-methylpiperidine-3-carboxylic acid

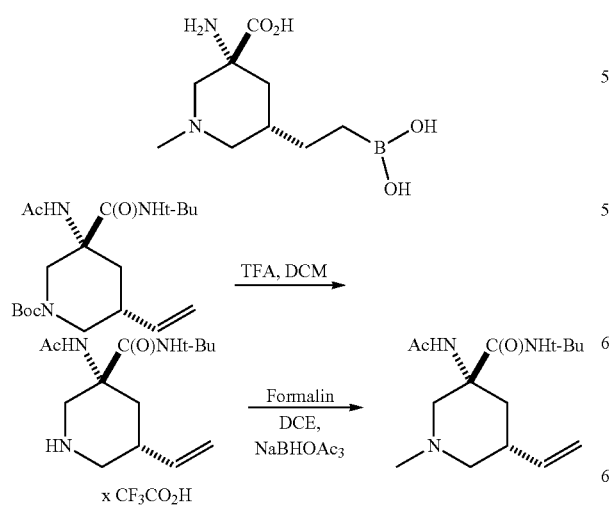

240

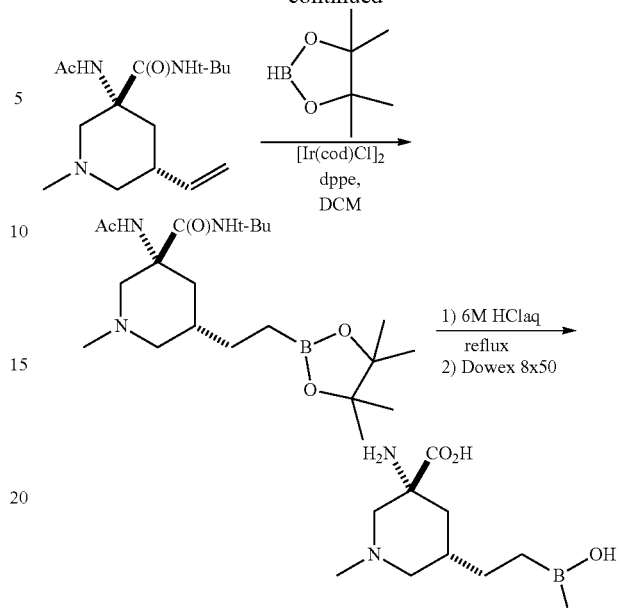

Step A. rac-(3R,5R)-3-acetamido-N-(tert-butyl)-5-vinylpiperidine-3-carboxamide trifluoroacetate

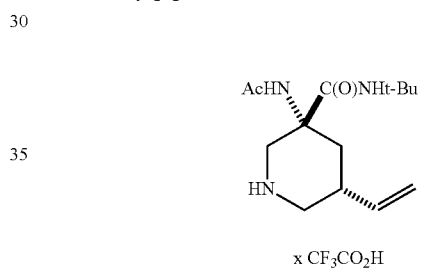

To the solution of tert-butyl rac-(3R,5R)-3-acetamido-3-(tert-butylcarbamoyl)-5-vinylpiperidine-1-carboxylate (see Example 57, step B, 0.5 g, 1.36 mmol) in DCM (3 mL) was added trifluoroacetic acid (3 mL). The mixture was stirred for one hour and then concentrated under reduced pressure to give crude product (1 g) as an orange liquid. The crude product was used in the next step without any further purification. ESI+MS: m/z=268.2 (M+1)$^+$. $^1$H NMR (700 MHz, Chloroform-d) δ 9.02 (bd, J=11.2 Hz, 1H), 8.30-8.25 (m, 1H), 7.82 (s, 1H), 6.76 (s, 1H), 5.63 (ddd, J=17.2, 10.5, 6.8 Hz, 1H), 5.26 (d, J=10.4 Hz, 1H), 5.19 (dd, J=17.2, 1.2 Hz, 1H), 4.31 (d, J=12.4 Hz, 1H), 3.48-3.43 (m, 1H), 2.96-2.84 (m, 2H), 2.64-2.57 (m, 1H), 2.30-2.24 (m, 1H), 2.09 (s, 3H), 1.84 (t, J=13.1 Hz, 1H), 1.35 (s, 9H).

Step B. rac-(3R,5R)-3-acetamido-N-(tert-butyl)-1-methyl-5-vinylpiperidine-3-carboxamide

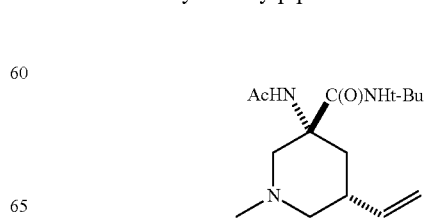

To the solution of rac-(3R,5R)-3-acetamido-N-(tert-butyl)-5-vinylpiperidine-3-carboxamide trifluoroacetate (1 g, crude) in DCE (1.5 mL) was added formalin (0.5 mL). The mixture was stirred for 30 min. followed by NaBH(OAc)₃ (1.3 g, 6.13 mmol) was added portion-wise. After stirring overnight the reaction mixture was diluted with DCM (70 mL), subsequent washed with NaOH (aq) (1 M, 2×10 mL), brine (10 mL), dried over MgSO₄ and concentrated to give 0.27 g (70%, after two steps) of the desired product as a white solid. ESI+MS: m/z=282.2 (M+1)⁺. ¹H NMR (700 MHz, Chloroform-d) δ 9.47 (bs, 1H), 6.66 (s, 1H), 5.67 (ddd, J=17.2, 10.4, 6.7 Hz, 1H), 5.07-5.01 (m, 2H), 3.07 (d, J=11.5 Hz, 1H), 2.92 (d, J=11.5, 1H), 2.83 (dd, J=10.7, 3.9 Hz, 1H), 2.55-2.50 (m, 1H), 2.33 (s, 3H), 2.14-2.05 (m, 1H), 1.98 (d, J=1.2 Hz, 3H), 1.95 (t, J=11.3 Hz, 1H), 1.77 (ddd, J=13.0, 4.1, 1.9 Hz, 1H), 1.37 (s, 9H).

Step C. rac-(3R,5S)-3-acetamido-N-(tert-butyl)-1-methyl-5-(2-(4,4,5,5-tetramethyl-1,3,2-dioxaborolan-2-yl)ethyl)piperidine-3-carboxamide

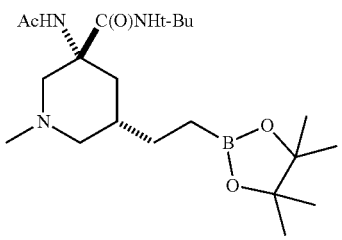

The title compound was prepared from rac-(3R,5R)-3-acetamido-N-(tert-butyl)-1-methyl-5-vinylpiperidine-3-carboxamide (0.26 g, 0.92 mmol) using procedure described for the preparation of Example 26, step B. The crude product was purified by flash chromatography on silica gel (DCM/acetone 50:1 to 0:1). Obtained: 0.28 g (74%) of the desired product (colorless oil) and 0.06 g of the product without pinacol (white viscous solid). ESI+MS: m/z=410.3 (M+1)⁺. ¹H NMR (700 MHz, Chloroform-d) δ 9.51 (s, 1H), 6.62 (s, 1H), 2.98 (d, J=11.4 Hz, 1H), 2.92 (dt, J=11.4, 1.6 Hz, 1H), 2.86-2.80 (m, 1H), 2.29 (s, 3H), 1.96 (s, 3H), 1.85-1.70 (m, 4H), 1.34 (s, 9H), 1.37-1.30 (m, 2H), 1.24 (s, 12H), 0.82-0.69 (m, 2H).

Step D. rac-(3R,5S)-3-amino-5-(2-boronoethyl)-1-methylpiperidine-3-carboxylic acid The title compounds were prepared from rac-(3R,5S)-3-acetamido-N-(tert-butyl)-1-methyl-5-(2-(4,4,5,5-tetramethyl-1,3,2-dioxaborolan-2-yl)ethyl)piperidine-3-carboxamide (100 mg, 0.24 mmol) using procedure described for the preparation of Example 26, step C. The crude product was purified by preparative HPLC (0.1-1% MeCN in H₂O) and then by Dowex 8×50. Obtained: 17 mg (30%) as a white solid. ESI+MS: m/z=231.1 (M+1)⁺. ¹H NMR (700 MHz, Deuterium Oxide) δ 3.43 (d, J=11.9 Hz, 1H), 3.40-3.33 (m, 1H), 2.83 (s, 3H), 2.67 (d, J=12.0 Hz, 1H), 2.53-2.49 (m, 1H), 2.06 (dd, J=11.4, 1.7 Hz, 1H), 1.76-1.68 (m, 1H), 1.38-1.26 (m, 2H), 1.10 (t, J=12.9 Hz, 1H), 0.75-0.65 (m, 2H).

Example 60. rac-(3R,5R)-3-amino-5-(2-boronoethyl)tetrahydro-2H-pyran-3-carboxylic acid hydrochloride

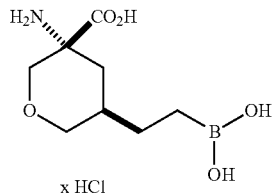 [SMILES: N[C@@]1(C(=O)O)COC[C@H](CCB(O)O)C1]

Step A. 5-vinyldihydro-2H-pyran-3(4H)-one

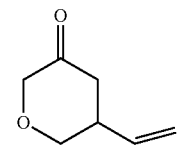

The title compound 5-vinyldihydro-2H-pyran-3(4H)-one was obtained in the same manner like in the step B from the synthesis of the intermediate 1, using vinylmagnesium bromide (1 M in THF) (10.2 mL, 10.2 mmol), HMPA (3.6 mL, 20.51 mmol), CuBr×Me₂S (0.16 g, 0.76 mmol), 2H-Pyran-3(6H)-one (CAS Number: 98166-23-5) (0.5 g, 5.1 mmol), TMSCl (3.2 mL, 25.5 mmol) and dry THF (20 mL+8.5 mL). The crude product was purified by flash chromatography on silica gel (gradient elution, hexane/Et₂O 100:1 to 20:1) to give corresponding product as a solution in hexane/Et₂O mixture. The fractions from silica gel flash chromatography were partially concentrated and used in the next step, because the desired product is volatile. ¹H NMR (700 MHz, Chloroform-d) δ 5.77-5.76 (m, 2H), 5.23-5.10 (m, 1H), 4.16-4.07 (m, 1H), 4.02 (ddd, J=10.9, 4.9, 0.8 Hz, 1H), 3.95 (d, J=15.9 Hz, 1H), 3.56 (dd, J=11.5, 8.9 Hz, 1H), 2.92-2.89 (m, 1H), 2.75-2.67 (m, 1H), 2.42 (dd, J=16.1, 10.2 Hz, 1H).

Step B. rac-(3R,5S)-3-acetamido-N-(tert-butyl)-5-vinyltetrahydro-2H-pyran-3-carboxamide and rac-(3R,5R)-3-acetamido-N-(tert-butyl)-5-vinyltetrahydro-2H-pyran-3-carboxamide

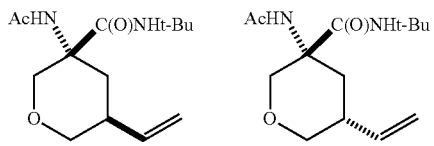

The title compounds were obtained in the same manner like in the step C from the synthesis of the intermediate 1, using a solution of 5-vinyldihydro-2H-pyran-3(4H)-one in hexane/Et₂O mixture, ammonium acetate (4.84 mmol.), tert-butylisocyanide (0.27 mL, 2.42 mmol) and 2,2,2-trifluoroethanol (5 mL) as a solvent. The crude product was purified by silica gel flash chromatography (gradient elution, hexane/AcOEt 10:1 to 1:1) to give corresponding product as a separable diastereoisomers (64 mg, 5% over two steps, white solid).

rac-(3R,5S)-3-acetamido-N-(tert-butyl)-5-vinyltetrahydro-2H-pyran-3-carboxamide (14 mg, white solid); ESI+ MS: m/z=269.1 (M+1)⁺. ¹H NMR (700 MHz, Chloroform-c) δ 7.08 (s, 1H), 5.86 (s, 1H), 5.61 (ddd, J=17.3, 10.5, 6.8 Hz, 1H), 5.14-5.06 (m, 2H), 3.93-3.88 (m, 2H), 3.61 (d, J=12.2 Hz, 1H), 3.15 (t, J=11.3 Hz, 1H), 2.76-2.72 (m, 1H), 2.39 (dd, J=11.2, 5.3 Hz, 1H), 2.10 (s, 3H), 1.78 (dd, J=13.6, 12.5 Hz, 1H), 1.34 (s, 9H).

rac-(3R,5R)-3-acetamido-N-(tert-butyl)-5-vinyltetrahydro-2H-pyran-3-carboxamide (50 mg, white solid); ESI+ MS: m/z=269.3 (M+1)⁺¹H NMR (700 MHz, Chloroform-c) δ 7.37 (s, 1H), 6.40 (s, 1H), 5.62 (ddd, J=17.3, 10.5, 6.8 Hz, 1H), 5.14-5.08 (m, 2H), 4.24 (d, J=11.8 Hz, 1H), 4.13-4.08 (m, 1H), 3.95 (dd, J=11.2, 3.0 Hz, 1H), 3.31 (t, J=11.2 Hz, 1H), 2.65-2.52 (m, 1H), 2.33-2.26 (m, 1H), 1.99 (s, 3H), 1.98-1.95 (m, 1H), 1.40 (s, 9H).

Step C. rac-(3R,5R)-3-acetamido-N-(tert-butyl)-5-(2-(4,4,5,5-tetramethyl-1,3,2-dioxaborolan-2-yl)ethyl)tetrahydro-2H-pyran-3-carboxamide and rac-(3R,5S)-3-acetamido-N-(tert-butyl)-5-(2-(4,4,5,5-tetramethyl-1,3,2-dioxaborolan-2-yl)ethyl)tetrahydro-2H-pyran-3-carboxamide

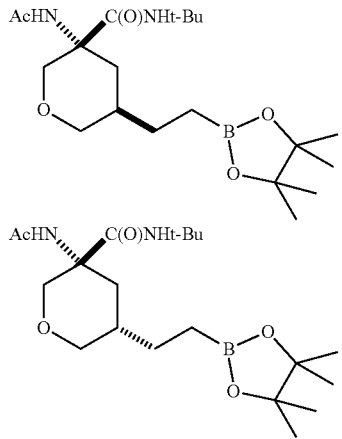

The title compound rac-(3R,5R)-3-acetamido-N-(tert-butyl)-5-(2-(4,4,5,5-tetramethyl-1,3,2-dioxaborolan-2-yl)ethyl)tetrahydro-2H-pyran-3-carboxamide was obtained in the same manner like in Example 26, step B, using rac-(3R,5S)-3-acetamido-N-(tert-butyl)-5-vinyltetrahydro-2H-pyran-3-carboxamide (14 mg, 0.052 mmol, 1 equiv.), dppe (1 mg, 0.0031 mmol, 0.06 equiv.), bis(1,5-cyclooctadiene)diiridium(I) dichloride (1 mg, 0.0015 mmol, 0.03 equiv.), 4,4,5,5-tetramethyl-1,3,2-dioxaborolane (19 µl, 0.13 mmol, 2.5 equiv.) and DCM (2 mL). The crude product was purified by column chromatography on silica gel (gradient elution, DCM/MeOH 100:1 to 50:1) to give corresponding product as a single diastereoisomer (15 mg, 75%, pale yellow, sticky solid). ESI+MS: m/z=397.2 (M+1)⁺. ¹H NMR (700 MHz, Chloroform-d) δ 7.15 (s, 1H), 5.79 (s, 1H), 3.93 (ddd, J=26.9, 11.6, 2.8 Hz, 2H), 3.58 (d, J=12.1 Hz, 1H), 3.00 (t, J=11.3 Hz, 1H), 2.69 (d, J=14.2 Hz, 1H), 2.07 (s, 3H), 1.52-1.45 (m, 1H), 1.33 (s, 9H), 1.31-1.27 (m, 3H), 1.25 (s, 12H), 0.82-0.71 (m, 2H).

The title compound rac-(3R,5S)-3-acetamido-N-(tert-butyl)-5-(2-(4,4,5,5-tetramethyl-1,3,2-dioxaborolan-2-yl)ethyl)tetrahydro-2H-pyran-3-carboxamide was obtained in the same manner like in Example 26, step B, using rac-(3R,5R)-3-acetamido-N-(tert-butyl)-5-vinyltetrahydro-2H-pyran-3-carboxamide (50 mg, 0.19 mmol, 1 equiv.), dppe (4 mg, 0.011 mmol, 0.06 equiv.), bis(1,5-cyclooctadiene)diiridium(I) dichloride (4 mg, 0.0055 mmol, 0.03 equiv.), 4,4,5,5-tetramethyl-1,3,2-dioxaborolane (68 µl, 0.46 mmol, 2.5 equiv.) and DCM (2ML). The crude product was purified by column chromatography on silica gel (gradient elution, DCM/MeOH 40:1 to 10:1) to give corresponding product as a single diastereoisomer (50 mg, 67%, pale yellow, sticky solid). ESI+MS: m/z=397.2 (M+1)⁺. ¹H NMR (700 MHz, Chloroform-d) δ 7.38 (s, 1H), 6.41 (s, 1H), 4.21 (dd, J=16.2, 11.7 Hz, 1H), 4.12-4.06 (m, 1H), 4.02-3.94 (m, 1H), 3.12 (t, J=12.0 Hz, 1H), 2.06-1.98 (m, 1H), 1.97 (s, 3H), 1.88-1.74 (m, 1H), 1.54 (d, J=1.7 Hz, 1H), 1.38 (s, 9H), 1.37-1.33 (m, 1H), 1.25 (s, 12H), 1.23-1.15 (m, 1H), 0.82-0.68 (m, 2H).

Step D. rac-(3R,5R)-3-amino-5-(2-boronoethyl)tetrahydro-2H-pyran-3-carboxylic acid hydrochloride The title compound rac-(3R,5R)-3-amino-5-(2-boronoethyl)tetrahydro-2H-pyran-3-carboxylic acid hydrochloride was obtained in the same manner like in Example 26, step C, using rac-(3R,5R)-3-acetamido-N-(tert-butyl)-5-(2-(4,4,5,5-tetramethyl-1,3,2-dioxaborolan-2-yl)ethyl)tetrahydro-2H-pyran-3-carboxamide (15 mg, 0.037 mmol, 1 equiv.), 6 N HCl$_{aq}$ (10 mL). The residue was purified by flash chromatography on DOWEX® ion exchange resin (eluent 0.1N ammonia in water) to give (after acidification with 6N HCl and subsequent lyophilization) product as a single diastereoisomer (4.5 mg, 56%, white solid). ESI+MS: m/z=218.1 (M+1)⁺. ¹H NMR (700 MHz, Deuterium Oxide) δ 4.01-3.97 (m, 1H), 3.82 (dd, J=12.5, 2.5 Hz, 1H), 3.66 (d, J=12.5 Hz, 1H), 3.11 (t, J=11.2 Hz, 1H), 2.06-2.02 (m, 1H), 1.74 (q, J=15.2, 14.0 Hz, 2H), 1.33-1.25 (m, 1H), 1.25-1.17 (m, 1H), 0.73 (ddd, J=16.3, 10.4, 6.2 Hz, 1H), 0.68 (ddd, J=15.7, 10.4, 6.3 Hz, 1H).

Example 61. rac-(3R,5S)-3-amino-5-(2-boronoethyl)tetrahydro-2H-pyran-3-carboxylic acid hydrochloride

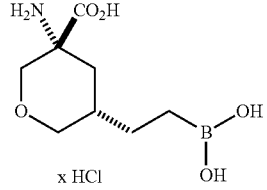 [SMILES: N[C@@]1(C(=O)O)COC[C@@H](CCB(O)O)C1]

The title compound rac-(3R,5S)-3-amino-5-(2-boronoethyl)tetrahydro-2H-pyran-3-carboxylic acid hydrochloride was obtained in the same manner like in Example 26, step C, using rac-(3R,5S)-3-acetamido-N-(tert-butyl)-5-(2-(4,4,5,5-tetramethyl-1,3,2-dioxaborolan-2-yl)ethyl)tetrahydro-2H-pyran-3-carboxamide (40 mg, 0.10 mmol, 1 equiv.), 6 N HCl$_{aq}$ (10 mL). The residue was purified by flash chromatography on DOWEX® ion exchange resin (eluent 0.1N ammonia in water) and next by preparative HPLC (0.1-1% MeCN in water) to give (after acidification with 6N HCl and subsequent lyophilization) product as a single diastereoisomer (10 mg, 45%, white solid). ESI+MS: m/z=218.1 (M+1)⁺. ¹H NMR (700 MHz, Deuterium Oxide) δ 4.21 (dd, J=11.6, 2.2 Hz, 1H), 3.94 (dd, J=11.4, 3.2 Hz, 1H), 3.45 (d, J=11.6 Hz, 1H), 3.09 (t, J=11.1 Hz, 1H), 2.42 (d, J=17.3 Hz, 1H), 1.96-1.90 (m, 1H), 1.41 (dd, J=13.2, 11.6 Hz, 1H), 1.32 (ddt, J=13.7, 9.8, 6.8 Hz, 1H), 1.22 (ddt, J=13.5, 10.1, 6.7 Hz, 1H), 0.78-0.67 (m, 2H).

Example 62. 1,2-diamino-4-(2-boronoethyl)cyclopentanecarboxylic acid dihydrochloride

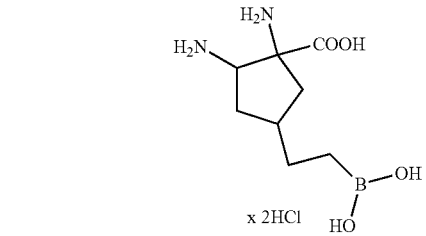

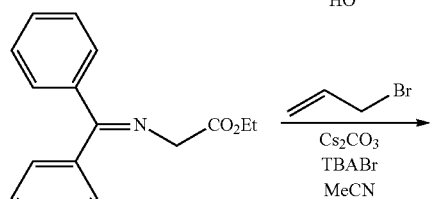

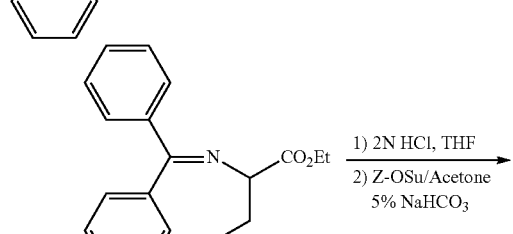

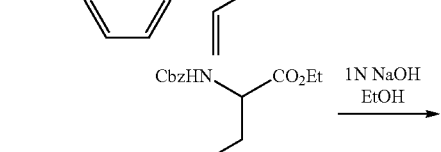

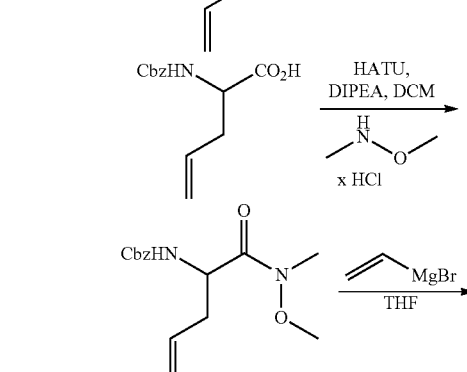

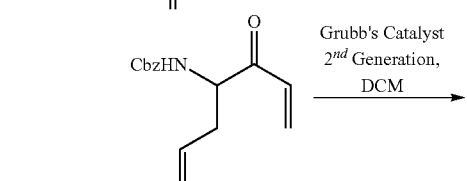

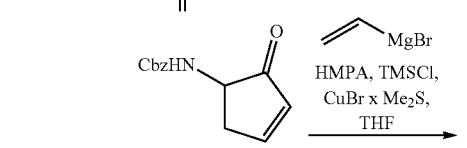

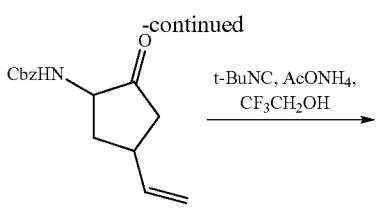

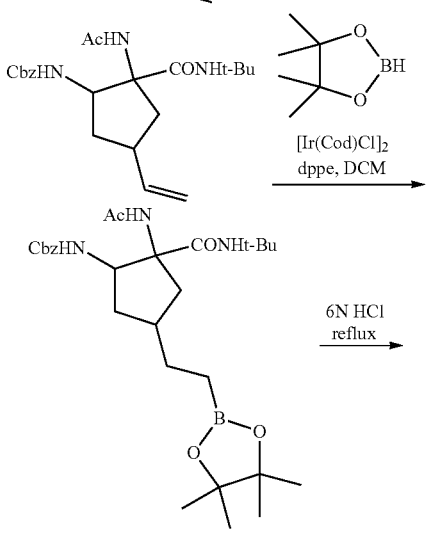

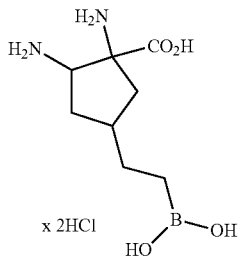

Step A. ethyl 2-((diphenylmethylene)amino)pent-4-enoate

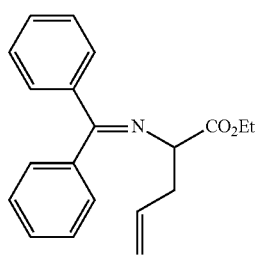 [SMILES: C=CCC(N=C(c1ccccc1)c1ccccc1)C(=O)OCC]

To the mixture of ethyl n-(diphenylmethylene) glycinate (20 g, 74.82 mmol), allyl bromide (7.1 mL, 82.30 mmol) and $Cs_2CO_3$ (53.6 g, 164.6 mmol) in acetonitrile (500 mL) was added TBABr (2.4 g, 7.48 mmol). The reaction mixture was stirred at room temperature overnight. After this time, the reaction mixture was partitioned between water (250 mL) and AcOEt (300 mL). The layers were separated. The aqueous layer was washed with ethyl acetate (3×150 mL). The combined organic layers were washed with water (2×200 mL), brine (200 mL), dried over $MgSO_4$ and concentrated in vacuo. The desired product was obtained as an orange oil (23.5 g). The crude product was used in next reaction step without further purification. ESI+MS: m/z=308.0 (M+1)⁺. ¹H NMR (700 MHz, Chloroform-d) δ 7.68-7.64 (m, 2H), 7.48-7.44 (m, 3H), 7.43-7.39 (m, 1H), 7.37-7.33 (m, 2H), 7.20 (dd, J=7.4, 1.7 Hz, 2H), 5.71 (ddt, J=17.1, 10.2, 7.1 Hz, 1H), 5.09 (dd, J=17.1, 1.5 Hz, 1H), 5.04 (d, J=10.2 Hz, 1H), 4.26-4.13 (m, 3H), 2.72 (dt, J=12.2, 6.0 Hz, 1H), 2.65 (dt, J=14.2, 7.6 Hz, 1H), 1.28 (t, J=7.1 Hz, 3H).

Step B. ethyl 2-(((benzyloxy)carbonyl)amino)pent-4-enoate

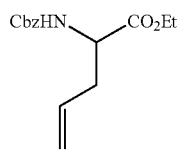

To the solution of ethyl 2-((diphenylmethylene)amino)pent-4-enoate (22.9 g, 74.49 mmol) in THF (50 mL), 2N HCl$_{aq}$ (50 mL) was added. The reaction mixture was stirred at room temperature for 3 h. Next the reaction mixture was washed with Et$_2$O (6×50 mL). The aqueous residue was alkalized with 5% NaHCO$_3$ to pH=8. Next to the reaction mixture acetone (100 mL) was added followed by Z-OSu (18.6 g, 249.22 mmol) addition. The resulting mixture was stirred at room temperature overnight. The acetone was evaporated. The aqueous layer was acidified with 1N HCl$_{aq}$ and washed with DCM (2×100 mL). The combined organic layers were dried over MgSO$_4$, filtered and concentrated in vacuo. The desired product was obtained as an orange oil (20.04 g). The crude product was used in next reaction step without further purification. ESI+MS: m/z=277.9 (M+1)⁺. ¹H NMR (700 MHz, Chloroform-d) δ 7.38 (d, J=4.7 Hz, 4H), 7.36-7.31 (m, 1H), 5.71 (td, J=17.0, 7.3 Hz, 1H), 5.34 (d, J=4.9 Hz, 1H), 5.20-5.10 (m, 4H), 4.46 (d, J=7.3 Hz, 1H), 4.28-4.14 (m, 2H), 2.66-2.46 (m, 2H), 1.30 (t, J=7.1 Hz, 3H).

Step C. 2-(((benzyloxy)carbonyl)amino)pent-4-enoic acid

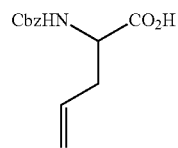 [SMILES: C=CCC(NC(=O)OCc1ccccc1)C(=O)O]

The mixture of ethyl 2-(((benzyloxy)carbonyl)amino)pent-4-enoate, ethanol (72 mL) and 4M NaOH$_{aq}$ (20 mL) was stirred at room temperature for 4 h. After this time ethanol was evaporated under reduced pressure and the aqueous layer was acidified with 1N HCl and washed with AcOEt (2×100 mL). The organic layer was dried over MgSO$_4$, filtered and concentrated in vacuo. The desired product was obtained as a yellowish oil (17.3 g). The crude product was used in next reaction step without further purification. ESI+MS: m/z=248.05 (M−1)⁻. ¹H NMR (700 MHz, Chloroform-d) δ 7.38 (d, J=5.1 Hz, 4H), 7.36-7.31 (m, 1H), 5.74 (dq, J=17.0, 7.2 Hz, 1H), 5.31 (p, J=9.2 Hz, 1H), 5.22-5.11 (m, 4H), 4.51 (q, J=6.5, 6.0 Hz, 1H), 2.62 (ddt, J=50.4, 15.2, 6.8 Hz, 2H).

Step D. benzyl (1-(methoxy(methyl)amino)-1-oxopent-4-en-2-yl)carbamate

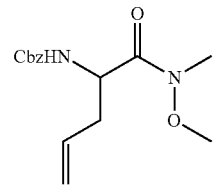 [SMILES: C=CCC(NC(=O)OCc1ccccc1)C(=O)N(C)OC]

To the solution of 2-(((benzyloxy)carbonyl)amino)pent-4-enoic acid (17.2 g, 68.99 mmol, crude) in DCM (170 mL) N,O-dimethylhydroxylamine hydrochloride (7.07 g, 72.44 mmol) and DIPEA (24.8 mL, 144.87 mmol) were added. Next to the reaction mixture HATU (27.54 g, 72.44 mmol) was added and it was stirred at room temperature overnight. After this time, the mixture was diluted with DCM and washed with 1N HCl (2×100 mL), 1N NaOH (2×100 mL), brine (1×100 mL), dried over MgSO$_4$ and concentrated in vacuo. The desired product was crystallized from AcOEt/hexane to give pure product (14.69 g, 67%-over 5 steps, white solid). ESI+MS: m/z=293.0 (M+1)⁺. ¹H NMR (700 MHz, Chloroform-d) δ 7.37 (d, J=5.4 Hz, 4H), 7.35-7.31 (m, 1H), 5.77 (td, J=17.2, 7.2 Hz, 1H), 5.47 (d, J=10.4 Hz, 1H), 5.15-5.09 (m, 4H), 4.84 (s, 1H), 3.81 (s, 3H), 3.23 (s, 3H), 2.54 (dt, J=12.9, 6.1 Hz, 1H), 2.42 (dt, J=14.1, 7.1 Hz, 1H).

Step E. benzyl (3-oxohepta-1,6-dien-4-yl)carbamate

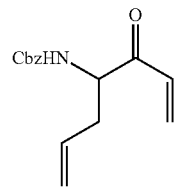 [SMILES: C=CCC(NC(=O)OCc1ccccc1)C(=O)C=C]

To a solution of benzyl (1-(methoxy(methyl)amino)-1-oxopent-4-en-2-yl)carbamate (5 g, 17.11 mmol) in dry THF (100 mL) was added dropwise a solution of vinyl magnesium bromide 1M in THF (60 mL, 59.87 mmol) at −78° C. under argon. The reaction mixture was stirred from −78° C. to 0° C. for 3 h. The mixture was once again cooled to −78° C. and poured onto cold solution of 2N HCl. The aqueous layer was extracted with AcOEt (2×100 mL). Organic layer was washed with brine, dried over MgSO$_4$, filtered and concentrated in vacuo. The residue was purified by silica gel flash chromatography (gradient elution, hexane/AcOEt 10:1 to 3:1) to give corresponding product (3.14 g, 71%, white solid). ESI+MS: m/z=282.0 (M+Na)⁺. ¹H NMR (700 MHz, Chloroform-d) δ 7.40-7.36 (m, 4H), 7.34 (td, J=8.4, 3.7 Hz, 1H), 6.52 (dd, J=17.5, 10.5 Hz, 1H), 6.42 (d, J=17.3 Hz, 1H), 5.93 (d, J=10.6 Hz, 1H), 5.66 (td, J=17.2, 7.2 Hz, 1H), 5.58 (d, J=8.2 Hz, 1H), 5.16-5.08 (m, 4H), 4.80-4.71 (m, 1H), 2.71-2.66 (m, 1H), 2.45 (dt, J=13.8, 6.6 Hz, 1H).

Step F. benzyl (2-oxocyclopent-3-en-1-yl)carbamate

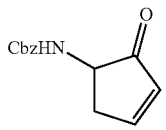

To the solution of benzyl (3-oxohepta-1,6-dien-4-yl)carbamate (4.1 g, 15.81 mmol) in DCM (850 mL) under argon Grubbs Catalyst, 2$^{nd}$ Generation (0.67 g, 0.79 mmol) was added. The reaction mixture was stirred at room temperature overnight. After that time the solvent was evaporated and the residue was purified by silica gel flash chromatography (gradient elution, hexane/AcOEt 10:1 to 3:1) to give corresponding product (3.03 g, 84%, off-white solid). ESI+MS: m/z=254.0 (M+Na)$^{+}$. $^1$H NMR (700 MHz, Chloroform-d) δ 7.71 (s, 1H), 7.38 (d, J=5.6 Hz, 4H), 7.34 (dd, J=9.7, 4.6 Hz, 1H), 6.28 (d, J=5.0 Hz, 1H), 5.28 (s, 1H), 5.18-5.12 (m, 2H), 4.10 (s, 1H), 3.25 (d, J=20.7 Hz, 1H), 2.68 (d, J=17.8 Hz, 1H).

Step G. benzyl (2-oxo-4-vinylcyclopentyl)carbamate

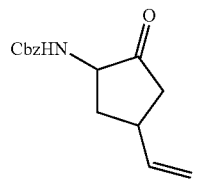 [SMILES: C=CC1CC(=O)C(NC(=O)OCc2ccccc2)C1]

The title compound benzyl (2-oxo-4-vinylcyclopentyl)carbamate was obtained in the same manner like in Example 57, step A, using benzyl (2-oxocyclopent-3-en-1-yl)carbamate (3 g, 12.97 mmol), Vinylmagnesium bromide (1 M in THF) (45.41 mL, 45.41 mmol), HMPA (9 mL, 51.90 mmol), CuBr×Me$_2$S (0.4 g, 1.95 mmol) and TMSCl (8.2 mL, 64.86 mmol), dry THF (62 mL+31 mL). The crude product was purified by flash chromatography on silica gel (gradient elution, hexane/AcOEt 100:1 to 5:1) to give corresponding product as a mixture of diastereoisomers, dr=1:1, (2.72 g, 81%, white solid). ESI+MS: m/z=260.0 (M+1)$^{+}$. $^1$H NMR (700 MHz, Chloroform-d) δ 7.41-7.36 (m, 4H), 7.36-7.31 (m, 1H), 6.01-5.78 (m, 1H), 5.26-5.06 (m, 5H), 4.11-4.02 (m, 1H), 3.09-2.70 (m, 1H), 2.66-2.39 (m, 2H), 2.11-1.95 (m, 1H), 1.59-1.53 (m, 1H).

Step H. benzyl (2-acetamido-2-(tert-butylcarbamoyl)-4-vinylcyclopentyl)carbamate

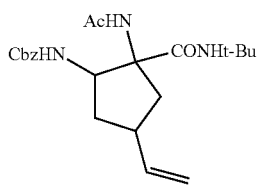

The title compound benzyl (2-acetamido-2-(tert-butylcarbamoyl)-4-vinylcyclopentyl)carbamate was obtained in the same manner like in the step C from the synthesis of the intermediate 1, using benzyl (2-oxo-4-vinylcyclopentyl)carbamate (2.65 g, 10.03 mmol, 1 equiv.), ammonium acetate (3.15 g, 40.93 mol, 4 equiv.), tert-butylisocyanide (2.3 mL, 20.07 mol, 2 equiv.) and 2,2,2-trifluoroethanol (36 mL) as a solvent. The residue was purified by silica gel flash chromatography (gradient elution, hexane/AcOEt 100:1 to 1:1) to give corresponding product as a mixture of partially separable diastereoisomers (2.36 g, 57%, white solids). The first diastereoisomer: (0.34 g, white solid); ESI+MS: m/z=402.1 (M+1)$^{+}$. $^1$H NMR (700 MHz, Chloroform-d) δ 7.48 (s, 1H), 7.37 (s, 4H), 7.36-7.31 (m, 2H), 5.87 (d, J=9.2 Hz, 1H), 5.79 (ddd, J=17.2, 10.2, 7.2 Hz, 1H), 5.19-5.10 (m, 2H), 5.00 (d, J=17.1 Hz, 1H), 4.98-4.93 (m, 1H), 4.15 (d, J=10.1 Hz, 1H), 3.03 (dd, J=13.6, 7.7 Hz, 1H), 2.84 (s, 1H), 2.14-2.05 (m, 1H), 2.03 (s, 3H), 1.94-1.87 (m, 1H), 1.73-1.67 (m, 1H), 1.31 (s, 9H).

Mixture of the second and the third diastereoisomers: dr=1:1, (1.61 g, white solid); ESI+MS: m/z=402.1 (M+1)$^{+}$. $^1$H NMR (700 MHz, Chloroform-d) δ 7.40-7.36 (m, 4H), 7.34 (dd, J=7.4, 3.7 Hz, 1H), 7.16, 6.96 [(2s, 1H, two diastereoisomers)], 6.91-6.66 (m, 1H), 5.88-5.76 (m, 1H), 5.54-5.13 (m, 2H), 5.12-4.92 (m, 3H), 4.37-4.00 (m, 1H), 2.76-2.42 (m, 2H), 2.36-2.17 (m, 2H), 2.05, 1.90 [(2s, 3H, two diastereoisomers)], 1.96-1.85 (m, 1H), 1.37, 1.28 [(2s, 9H, two diastereoisomers)].

The fourth diastereoisomer: (0.43 g, white solid); ESI+MS: m/z=402.1 (M+1)$^{+}$. $^1$H NMR (700 MHz, Chloroform-d) δ 7.50-7.41 (m, 1H), 7.40-7.33 (m, 5H), 7.19-7.07 (m, 1H), 5.84 (ddd, J=17.1, 10.3, 6.7 Hz, 1H), 5.39-5.34 (m, 1H), 5.14 (d, J=12.2 Hz, 1H), 5.12-5.06 (m, 2H), 5.03 (d, J=10.3 Hz, 1H), 4.28 (d, J=8.0 Hz, 1H), 2.90-2.83 (m, 1H), 2.68 (dd, J=14.0, 8.7 Hz, 1H), 2.49-2.42 (m, 1H), 2.08-2.02 (m, 1H), 1.98 (s, 4H), 1.34 (s, 9H).

Step I. benzyl (2-acetamido-2-(tert-butylcarbamoyl)-4-(2-(4,4,5,5-tetramethyl-1,3,2-dioxaborolan-2-yl)ethyl)cyclopentyl)carbamate

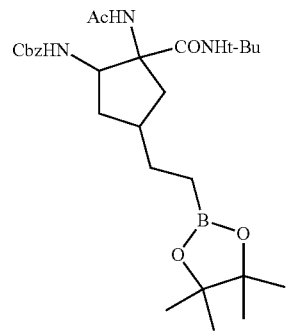

The first diastereoisomer of the title compound benzyl (2-acetamido-2-(tert-butylcarbamoyl)-4-(2-(4,4,5,5-tetramethyl-1,3,2-dioxaborolan-2-yl)ethyl)cyclopentyl)carbamate was obtained in the same manner like in Example 26, step B, using (2-acetamido-2-(tert-butylcarbamoyl)-4-vinylcyclopentyl)carbamate (0.34 g, 0.85 mmol, 1 equiv.), dppe (20 mg, 0.05 mmol, 0.06 equiv.), bis(1,5-cyclooctadiene) diiridium(I) dichloride (17 mg, 0.025 mmol, 0.03 equiv.), 4,4,5,5-tetramethyl-1,3,2-dioxaborolane (0.31 mL, 2.12 mmol 2.5 equiv.) and DCM (10 mL). The crude product was purified by column chromatography on silica gel (gradient elution, DCM/MeOH 100:1 to 50:1) to give corresponding as a single diastereoisomer (0.37 g, 82%, white solid). ESI+MS: m/z=530.4 (M+1)$^+$. $^1$H NMR (700 MHz, Chloroform-d) δ 7.59 (s, 1H), 7.40-7.31 (m, 6H), 5.92 (d, J=9.2 Hz, 1H), 5.20-5.09 (m, 2H), 4.14-4.02 (m, 1H), 2.98 (dd, J=13.4, 7.4 Hz, 1H), 2.13-2.06 (m, 1H), 2.00 (s, 4H), 1.75-1.70 (m, 1H), 1.50-1.40 (m, 3H), 1.30 (s, 9H), 1.25 (s, 12H), 0.76 (t, J=8.1 Hz, 2H).

The second and the third diastereoisomer of the title compound benzyl (2-acetamido-2-(tert-butylcarbamoyl)-4-(2-(4,4,5,5-tetramethyl-1,3,2-dioxaborolan-2-yl)ethyl)cyclopentyl)carbamate were obtained in the same manner like in Example 26, step B, using (2-acetamido-2-(tert-butylcarbamoyl)-4-vinylcyclopentyl)carbamate (0.59 g, 1.47 mmol, 1 equiv.), dppe (35 mg, 0.088 mmol, 0.06 equiv.), bis(1,5-cyclooctadiene)diiridium(I) dichloride (30 mg, 0.044 mmol, 0.03 equiv.), 4,4,5,5-tetramethyl-1,3,2-dioxaborolane (0.53 mL, 3.68 mmol, 2.5 equiv.) and DCM (28 mL). The crude product was purified by column chromatography on silica gel (gradient elution, hexane/AcOEt 10:1 to 1:1) to give corresponding product as a mixture of separable diastereoisomers (0.44 g, 56%, white, sticky solid).

Second diastereoisomer: (0.10 g, white solid); ESI+MS: m/z=530.3 (M+1)$^+$. $^1$H NMR (700 MHz, Chloroform-d) δ 7.40-7.33 (m, 6H), 7.15 (s, 1H), 6.84 (s, 1H), 5.58 (d, J=6.9 Hz, 1H), 5.16 (d, J=12.2 Hz, 1H), 5.11-5.08 (m, 1H), 4.18-4.10 (m, 1H), 4.02-3.94 (m, 1H), 2.45-2.39 (m, 1H), 2.27-2.21 (m, 1H), 2.03 (s, 3H), 2.01-1.96 (m, 1H), 1.68-1.60 (m, 1H), 1.51 (d, J=2.7 Hz, 1H), 1.28 (s, 9H), 1.24 (s, 12H), 0.78-0.74 (m, 2H).

The third diastereoisomer: (40 mg, white solid); ESI+MS: m/z=530.3 (M+1)$^+$. $^1$H NMR (700 MHz, Chloroform-d) δ 7.39-7.31 (m, 6H), 7.17-7.06 (m, 1H), 6.87-6.71 (m, 1H), 5.14 (d, J=12.3 Hz, 1H), 5.10-5.05 (m, 1H), 4.29 (q, J=10.4, 9.2 Hz, 1H), 2.40-2.34 (m, 1H), 2.33-2.27 (m, 1H), 2.02-1.96 (m, 1H), 1.90 (s, 3H), 1.87-1.80 (m, 1H), 1.72 (dt, J=12.6, 9.9 Hz, 1H), 1.52-1.47 (m, 2H), 1.36 (s, 9H), 1.25 (s, 12H), 0.79 (t, J=8.1 Hz, 2H).

The fourth diastereoisomer of the title compound benzyl (2-acetamido-2-(tert-butylcarbamoyl)-4-(2-(4,4,5,5-tetramethyl-1,3,2-dioxaborolan-2-yl)ethyl)cyclopentyl)carbamate was obtained in the same manner like in Example 26, step B, using (2-acetamido-2-(tert-butylcarbamoyl)-4-vinylcyclopentyl)carbamate (0.43 g, 10.72 mmol, 1 equiv.), dppe (26 mg, 0.064 mmol, 0.06 equiv.), bis(1,5-cyclooctadiene)diiridium(I) dichloride (22 mg, 0.032 mmol, 0.03 equiv.), 4,4,5,5-tetramethyl-1,3,2-dioxaborolane (0.39 mL, 26.81 mmol, 2.5 equiv.) and DCM (21 mL). The crude product was purified by column chromatography on silica gel (gradient elution, hexane/AcOEt 50:1 to 1:1) to give corresponding product as a single diastereoisomer (0.43 mg, 76%, off-white, sticky solid). ESI+MS: m/z=530.3 (M+1)$^+$. $^1$H NMR (700 MHz, Chloroform-d) δ 7.44-7.36 (m, 6H), 7.36-7.32 (m, 1H), 5.54-5.41 (m, 1H), 5.14 (d, J=12.3 Hz, 1H), 5.09 (d, J=12.3 Hz, 1H), 4.19 (q, J=7.4 Hz, 1H), 2.55 (dd, J=13.8, 8.3 Hz, 1H), 2.31 (dt, J=13.9, 6.9 Hz, 1H), 2.15-2.03 (m, 1H), 1.97 (s, 3H), 1.79-1.69 (m, 2H), 1.49-1.45 (m, 2H), 1.33 (s, 9H), 1.25 (s, 12H), 0.78-0.72 (m, 2H).

Step J. 1,2-diamino-4-(2-boronoethyl)cyclopentanecarboxylic acid dihydrochloride The first diastereoisomer of the title compound 1,2-diamino-4-(2-boronoethyl)cyclopentanecarboxylic acid dihydrochloride was obtained in the same manner like in Example 26, step C, using benzyl (2-acetamido-2-(tert-butylcarbamoyl)-4-(2-(4,4,5,5-tetramethyl-1,3,2-dioxaborolan-2-yl)ethyl)cyclopentyl)carbamate (60 mg, 0.11 mmol, 1 equiv.), 6 N HCl$_{aq}$(15 mL). The residue was purified by flash chromatography on DOWEX® ion exchange resin (eluent 0.1N ammonia in water) and next by preparative HPLC (0.1-1% MeCN in water) to give (after acidification with 6N HCl and subsequent lyophilization) product as a single diastereoisomer (15.4 mg, 47%, white solid). ESI+MS: m/z=217.1 (M+1)$^+$. $^1$H NMR (700 MHz, Deuterium Oxide) δ 3.92 (dd, J=9.2, 5.5 Hz, 1H), 2.54 (dd, J=13.7, 6.6 Hz, 1H), 2.34 (dt, J=15.9, 8.3 Hz, 1H), 2.15-2.09 (m, 1H), 1.99 (dt, J=14.2, 9.0 Hz, 1H), 1.65 (dd, J=13.7, 10.5 Hz, 1H), 1.47-1.41 (m, 2H), 0.74-0.69 (m, 2H).

The second diastereoisomer of the title compound 1,2-diamino-4-(2-boronoethyl)cyclopentanecarboxylic acid dihydrochloride was obtained in the same manner like in Example 26, step C, using benzyl (2-acetamido-2-(tert-butylcarbamoyl)-4-(2-(4,4,5,5-tetramethyl-1,3,2-dioxaborolan-2-yl)ethyl)cyclopentyl)carbamate (54 mg, 0.10 mmol, 1 equiv.), 6 N HCl$_{aq}$(15 mL). The residue was purified by flash chromatography on DOWEX® ion exchange resin (eluent 0.1N ammonia in water) and next by preparative HPLC (0.1-1% MeCN in water) to give (after acidification with 6N HCl and subsequent lyophilization) product as a single diastereoisomer (10.55 mg, 36%, white solid). ESI+MS: m/z=217.1 (M+1)$^+$. $^1$H NMR (700 MHz, Deuterium Oxide) δ 3.77 (dd, J=10.9, 7.1 Hz, 1H), 2.42 (dt, J=12.8, 6.3 Hz, 1H), 2.23 (dd, J=13.3, 6.3 Hz, 1H), 2.11 (dt, J=11.6, 6.2 Hz, 1H), 2.05 (dd, J=14.0, 11.3 Hz, 1H), 1.68-1.60 (m, 1H), 1.47 (dq, J=14.1, 7.1, 6.2 Hz, 2H), 0.73 (t, J=8.1 Hz, 2H).

The third diastereoisomer of the title compound 1,2-diamino-4-(2-boronoethyl)cyclopentanecarboxylic acid dihydrochloride was obtained in the same manner like in Example 26, step C, using benzyl (2-acetamido-2-(tert-butylcarbamoyl)-4-(2-(4,4,5,5-tetramethyl-1,3,2-dioxaborolan-2-yl)ethyl)cyclopentyl)carbamate (30 mg, 0.056 mmol, 1 equiv.), 6 N HCl$_{aq}$(10 mL). The residue was purified by flash chromatography on DOWEX® ion exchange resin (eluent 0.1N ammonia in water) and next by preparative HPLC (0.1-1% MeCN in water) to give (after acidification with 6N HCl and subsequent lyophilization) product as a single diastereoisomer (6.6 mg, 41%, white solid). ESI+MS: m/z=217.1 (M+1)$^+$. $^1$H NMR (700 MHz, Deuterium Oxide) δ 4.11 (dd, J=12.7, 6.4 Hz, 1H), 2.57 (dd, J=14.9, 9.1 Hz, 1H), 2.41 (dt, J=12.4, 6.3 Hz, 1H), 2.14-2.05 (m, 1H), 1.64 (dd, J=14.9, 9.5 Hz, 1H), 1.54 (q, J=12.4 Hz, 1H), 1.51-1.43 (m, 2H), 0.74 (t, J=8.2 Hz, 2H).

The fourth diastereoisomer of the title compound 1,2-diamino-4-(2-boronoethyl)cyclopentanecarboxylic acid dihydrochloride was obtained in the same manner like in Example 26, step C, using benzyl (2-acetamido-2-(tert-butylcarbamoyl)-4-(2-(4,4,5,5-tetramethyl-1,3,2-dioxaborolan-2-yl)ethyl)cyclopentyl)carbamate (60 mg, 0.11 mmol, 1 equiv.), 6 N HCl$_{aq}$ (15 mL). The residue was purified by flash chromatography on DOWEX® ion exchange resin (eluent 0.1N ammonia in water) and next by preparative HPLC (0.1-1% MeCN in water) to give (after acidification with 6N HCl and subsequent lyophilization) product as a single diastereoisomer (9.2 mg, 28%, white solid). ESI+MS: m/z=217.1 (M+1)$^+$. $^1$H NMR (700 MHz, Deuterium Oxide) δ 4.26-4.16 (m, 1H), 2.33-2.20 (m, 2H), 2.12-2.01 (m, 2H), 2.02-1.95 (m, 1H), 1.55-1.41 (m, 2H), 0.71 (t, J=8.1 Hz, 2H).

Example 63. 1-amino-4-(2-boronoethyl)-2-hydroxy-cyclopentanecarboxylic acid hydrochloride

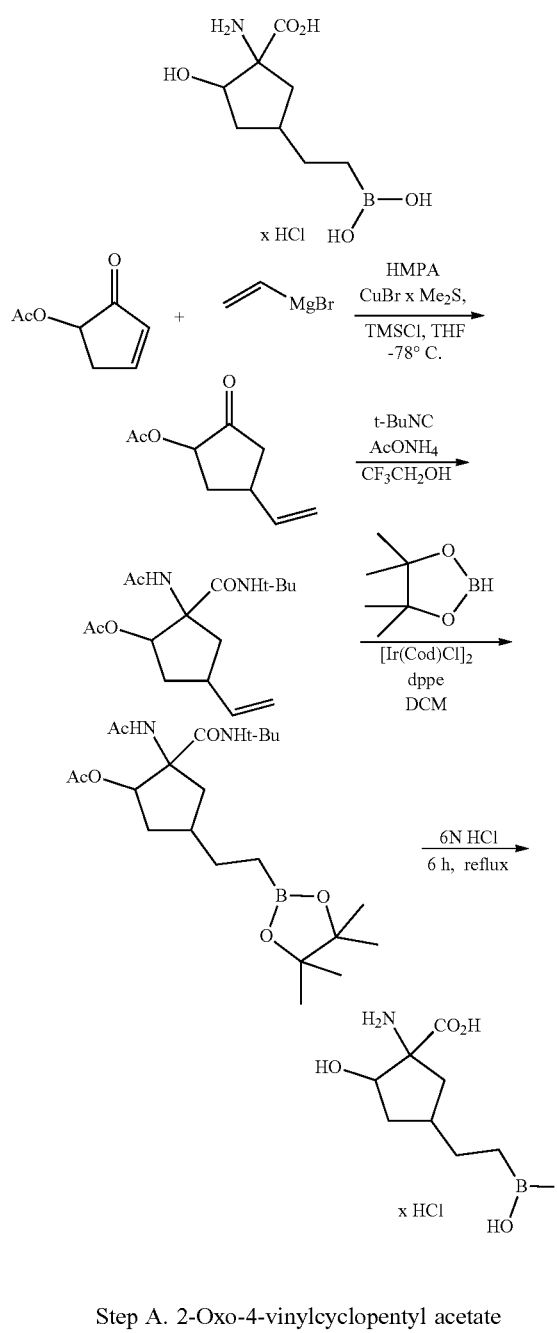

Step A. 2-Oxo-4-vinylcyclopentyl acetate

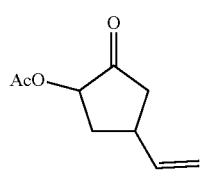

The title compound 2-oxo-4-vinylcyclopentyl acetate was obtained in the same manner like in the step B from the synthesis of the intermediate 1, using 2-oxocyclopent-3-en-1-yl acetate (2.5 g, 17.80 mmol, 1 equiv.), vinylmagnesium bromide (1 M in THF) (35.6 mL, 35.56 mmol, 2 equiv.), HMPA (12.4 mL, 71.36 mmol, 4 equiv.), CuBr×Me$_2$S (0.55 g, 2.67 mmol, 0.15 equiv.), and TMSCl (11.3 mL, 89.0 mmol, 5 equiv.), dry THF (140 mL+40 mL). The crude product was purified by flash chromatography on silica gel (gradient elution, hexane/AcOEt 200:1 to 20:1) to give corresponding product 2-oxo-4-vinylcyclopentyl acetate as a mixture of diastereoisomers dr=9:1 (2.1 g 67%, yellow oil). $^1$H NMR (700 MHz, Chloroform-d) δ 5.90, 5.82 [(2ddd, J=17.0, 10.4, 6.3 Hz, J=17.1, 10.2, 6.8 Hz, 1H, two diastereoisomers)], 5.16-5.03 (m, 2H), 3.14-2.98 (m, 1H), 2.55 (dd, J=18.7, 8.4 Hz, 1H), 2.35-2.23 (m, 2H), 2.18-2.12 (m, 1H), 2.11 (s, 3H), 1.35-1.22 (m, 1H).

Step B. 2-acetamido-2-(tert-butylcarbamoyl)-4-vinylcyclopentyl acetate

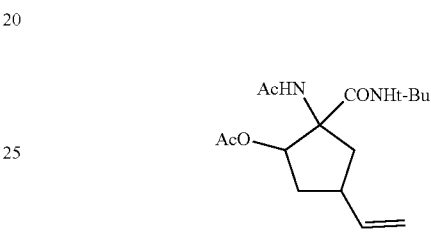

The title compound 2-acetamido-2-(tert-butylcarbamoyl)-4-vinylcyclopentyl acetate as a mixture of diastereoisomers was obtained in the same manner like in the step C from the synthesis of the intermediate 1, using a 2-oxo-4-vinylcyclopentyl acetate (1.9 g, 11.30 mmol, 1 equiv.), ammonium acetate (3.48 g, 45.20 mmol, 4 equiv.), tert-butylisocyanide (2.5 mL, 22.60 mmol, 2 equiv.) and 2,2,2-trifluoroethanol (3.1 mL) as a solvent. The residue was purified by silica gel flash chromatography (gradient elution, hexane/AcOEt 20:1 to 1:2) to give product 2-acetamido-2-(tert-butylcarbamoyl)-4-vinylcyclopentyl acetate as a mixture of four diastereoisomers (1.65 g, 47%, yellow solid).

First Diastereoisomer:
Single diastereoisomer (0.92 g, yellow solid)ESI+MS: m/z=311.3 (M+1)$^+$, 333.3 (M+Na)$^+$. $^1$H NMR (700 MHz, Chloroform-d) δ 6.64 (br s, 1H), 6.37 (br s, 1H), 5.88-5.76 (m, 1H), 5.08-4.91 (m, 1H), 3.16 (dd, J=14.3, 9.1 Hz, 1H), 3.10-3.03 (m, 1H), 2.22 (ddd, J=13.7, 9.1, 6.6 Hz, 1H), 2.08 (s, 2H), 2.00 (s, 2H), 1.95 (ddd, J=13.4, 7.0, 5.9 Hz, 1H), 1.68 (dd, J=14.3, 6.7 Hz, 1H), 1.55 (s, 8H), 1.53-1.50 (m, 1H).

Second Diastereoisomer:
Single diastereoisomer (0.37 g, yellow solid) ESI+MS: m/z=311.3 (M+1)$^+$, 333.3 (M+Na)$^+$. $^1$H NMR (700 MHz, Chloroform-c) δ 6.64 (s, 1H), 6.37 (s, 1H), 5.81 (ddd, J=17.1, 10.3, 6.9 Hz, 1H), 5.10-4.90 (m, 2H), 3.16 (dd, J=14.3, 9.1 Hz, 1H), 3.07 (dt, J=15.8, 7.9 Hz, 1H), 2.22 (ddd, J=13.7, 9.1, 6.6 Hz, 1H), 2.08 (s, 3H), 2.00 (s, 3H), 1.95 (ddd, J=13.4, 7.0, 5.9 Hz, 1H), 1.68 (dd, J=14.3, 6.7 Hz, 1H), 1.55 (s, 9H), 1.52-1.51 (m, 1H).

The First and the Third Diastereoisomer:
Mixture of diastereoisomers, dr=4:3, (0.24 g, yellow solid)ESI+MS: m/z=311.3 (M+1)$^+$, 333.4 (M+Na)$^+$. $^1$H NMR (700 MHz, Chloroform-c) δ 6.64, 6.61 [(2s, 1H, two diastereoisomers)], 6.37, 6.18 [(2s, 1H, two diastereoisomers)], 5.87, 5.81 [(2ddd, J=17.2, 10.2, 7.4 Hz, J=17.2, 10.3, 6.9 Hz, 1H, two diastereoisomers)], 5.08-4.95 [(m, 2H, two diastereoisomers)], 3.16, 2.64 [(2dd, J=14.3, 9.2 Hz, J=14.5, 10.2 Hz, 1H, two diastereoisomers)], 3.12-2.68 [(m, 1H, two diastereoisomers)], 2.27-2.18 (m, 1H), 2.08, 2.07 [(2s, 3H, two diastereoisomers)] 2.02, 2.00 [(s, 3H, two diastereoisomers)], 1.97-1.86 (m, 1H), 1.68 (dd, J=14.3, 6.7 Hz, 1H), 1.52-1.49 (m, 1H), 1.32 (s, 8H).

The First, the Second, the Third, the Fourth Diastereoisomers:

Mixture of $1^{st}$, $2^{nd}$, $3^{rd}$ and $4^{th}$ diastereoisomers 1:1:4:4 (0.12 g, yellow solid). ESI+MS: m/z=311.3 (M+1)$^+$, 333.3 (M+Na)$^+$. $^1$H NMR (700 MHz, Chloroform-c) δ 7.16, 7.11, 6.64, 6.61 [(4s, 1H, four diastereoisomers)], 6.18 (s, 1H), 5.81 (dddd, J=89.1, 17.2, 10.2, 7.1 Hz, 1H), 5.16-4.82 (m, 2H), 2.79-2.57 (m, 2H), 2.49-2.41 (m, 1H), 2.23-2.18 (m, 1H), 2.11, 2.10, 2.08, 2.07 [(4s, 3H, four diastereoisomers)], 2.05, 2.04, 2.02, 2.00 [(4s, 3H, four diastereoisomers)], 1.52-1.51 (m, 2H), 1.32 (s, 9H).

Step C. 2-acetamido-2-(tert-butylcarbamoyl)-4-(2-(4,4,5,5-tetramethyl-1,3,2-dioxaborolan-2-yl)ethyl) cyclopentyl acetate

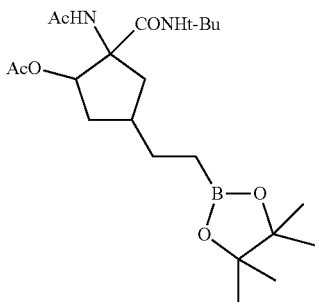

The title compound 2-acetamido-2-(tert-butylcarbamoyl)-4-(2-(4,4,5,5-tetramethyl-1,3,2-dioxaborolan-2-yl)ethyl)cyclopentyl acetate as a 1' single diastereoisomer was obtained in the same manner like in Example 26, step B, using 2-acetamido-2-(tert-butylcarbamoyl)-4-vinylcyclopentyl acetate (0.92 g, 2.96 mmol, 1 equiv.), dppe (0.071 g, 0.18 mmol, 0.06 equiv.), bis(1,5-cyclooctadiene)diiridium(I) dichloride (0.06 g, 0.089 mmol, 0.03 equiv.), 4,4,5,5-tetramethyl-1,3,2-dioxaborolane (0.56 mL, 3.85 mmol 1.3 equiv.). The crude product was purified by column chromatography on silica gel (gradient elution, hexane/AcOEt 20:1 to 1:2) to give corresponding product 2-acetamido-2-(tert-butylcarbamoyl)-4-(2-(4,4,5,5-tetramethyl-1,3,2-dioxaborolan-2-yl) ethyl)cyclopentyl acetate as a single diastereoisomer (1.26 g, 97%, pale yellow solid). ESI+MS: m/z=439.5 (M+1)$^+$, 461.4 (M+Na)$^+$. $^1$H NMR (700 MHz, Chloroform-d) δ 6.75 (br s, 1H), 6.44 (br s, 1H), 3.04 (dd, J=14.4, 9.2 Hz, 1H), 2.29 (hept, J=7.8 Hz, 1H), 2.13 (ddd, J=13.7, 9.2, 6.5 Hz, 1H), 2.06 (s, 3H), 1.99 (s, 3H), 1.76 (dd, J=13.9, 6.6 Hz, 1H), 1.50-1.42 (m, 3H), 1.31 (s, 8H), 1.26-1.25 (m, 1H), 1.24 (s, 11H), 1.24-1.22 (m, 1H), 0.81-0.70 (m, 2H).

The title compound 2-acetamido-2-(tert-butylcarbamoyl)-4-(2-(4,4,5,5-tetramethyl-1,3,2-dioxaborolan-2-yl)ethyl)cyclopentyl acetate was obtained in the same manner like in Example 26, step B, using 2-acetamido-2-(tert-butylcarbamoyl)-4-vinylcyclopentyl acetate ($2^{nd}$ single diastereoisomer) (0.36 g, 1.71 mmol, 1 equiv.), dppe (0.041 g, 0.10 mmol, 0.06 equiv.), bis(1,5-cyclooctadiene)diiridium(I) dichloride (0.034 g, 0.051 mmol, 0.03 equiv.), 4,4,5,5-tetramethyl-1,3,2-dioxaborolane (0.32 mL, 2.22 mmol 1.3 equiv.). The crude product was purified by column chromatography on silica gel (gradient elution, hexane/AcOEt 20:1 to 1:5) to give corresponding product 2-acetamido-2-(tert-butylcarbamoyl)-4-(2-(4,4,5,5-tetramethyl-1,3,2-dioxaborolan-2-yl) ethyl)cyclopentyl acetate as a mixture of diastereoisomers dr=4:1 (0.48 g, 64%, pale yellow solid). ESI+MS: m/z=439.5 (M+1)$^+$, 461.4 (M+Na)$^+$. 1H NMR (700 MHz, Chloroform-c) δ 7.17 (s, 1H), 6.18, 6.09 [(2s, 1H, two diastereoisomers)], 5.57-5.47 (m, 1H), 2.73, 2.58 [(2dd, J=13.7, 8.0 Hz, J=13.5, 8.0 Hz, 1H, two diastereoisomers)], 2.08 (s, 3H), 2.06, 2.02 [(2s, 3H, two diastereoisomers)], 1.96-1.86 (m, 1H), 1.79-1.72 (m, 2H), 1.50-1.41 (m, 2H), 1.31, 1.30 [(2s, 9H, two diastereoisomers)], 1.24 (d, J=1.8 Hz, 1H), 1.23 (d, J=1.7 Hz, 3H), 1.23 (br s, 9H), 0.73 (dt, J=13.5, 8.1 Hz, 2H).

The title compound 2-acetamido-2-(tert-butylcarbamoyl)-4-(2-(4,4,5,5-tetramethyl-1,3,2-dioxaborolan-2-yl)ethyl)cyclopentyl acetate was obtained in the same manner like in Example 26, step B, using 2-acetamido-2-(tert-butylcarbamoyl)-4-vinylcyclopentyl acetate as a mixture diastereoisomers ($1^{st}$ and $3^{rd}$ diastereoisomers dr=4:3) (0.24 g, 0.77 mmol, 1 equiv.), dppe (0.018 g, 0.046 mmol, 0.06 equiv.), bis(1,5-cyclooctadiene)diiridium(I) dichloride (0.016 g, 0.023 mmol, 0.03 equiv.), 4,4,5,5-tetramethyl-1,3,2-dioxaborolane (0.15 mL, 1.00 mmol 1.3 equiv.). The crude product was purified by column chromatography on silica gel (gradient elution, hexane/AcOEt 20:1 to 1:2) to give corresponding product 2-acetamido-2-(tert-butylcarbamoyl)-4-(2-(4,4,5,5-tetramethyl-1,3,2-dioxaborolan-2-yl) ethyl)cyclopentyl acetate as a mixture of three diastereoisomers dr=5:4:1 (0.27 g, 80%, pale yellow solid). ESI+MS: m/z=439.4 (M+1)$^+$, 461.4 (M+Na)$^+$. $^1$H NMR (700 MHz, Chloroform-d) δ 6.76, 6.75, 6.50, [(3s, 1H, three diastereoisomers)], 6.44, 6.30, 6.28 [(3s, 1H, three diastereoisomers)], 3.09, 3.04, 2.40 [(3dd, J=14.2, 8.84, J=14.4, 9.2 Hz, J=14.4, 10.1 Hz, 1H, three diastereoisomers)], 2.32-2.23 (m, 1H), 2.20-2.08 (m, 2H), 2.05, 2.04, 2.02 [(3s, 3H, three diastereoisomers)], 2.01, 2.00, 1.99 [(3s, 3H, three diastereoisomers)], 1.75-1.30 (m, 1H), 1.68-1.60 (m, 1H), 1.54-1.51 (m, 1H), 1.49-1.44 (m, 2H), 1.32, 1.31, 1.30 [(3s, 9H, three diastereoisomers), 1.24 (br s, 8H), 1.23 (br s, 2H), 0.91-0.73 (m, 3H).

The title compound 2-acetamido-2-(tert-butylcarbamoyl)-4-(2-(4,4,5,5-tetramethyl-1,3,2-dioxaborolan-2-yl)ethyl)cyclopentyl acetate was obtained in the same manner like in Example 26, step B, using 2-acetamido-2-(tert-butylcarbamoyl)-4-vinylcyclopentyl acetate ($1^{st}$, $2^{nd}$, $3^{rd}$ and $4^{th}$ diastereoisomers 1:1:4:4) (0.12 g, 0.39 mmol, 1 equiv.), dppe (0.009 g, 0.023 mmol, 0.06 equiv.), bis(1,5-cyclooctadiene) diiridium(I) dichloride (0.008 g, 0.012 mmol, 0.03 equiv.), 4,4,5,5-tetramethyl-1,3,2-dioxaborolane (0.07 mL, 0.50 mmol 1.3 equiv.). The crude product was purified by column chromatography on silica gel (gradient elution, hexane/AcOEt 20:1 to 1:2) to give corresponding product 2-acetamido-2-(tert-butylcarbamoyl)-4-(2-(4,4,5,5-tetramethyl-1,3,2-dioxaborolan-2-yl)ethyl)cyclopentyl acetate as a mixture of four diastereoisomers dr=10:8:1:1 (0.14 g, 82%, colourless film). ESI+MS: m/z=439.5 (M+1)$^+$, 461.4 (M+Na)$^+$. 1H NMR (700 MHz, Chloroform-d) δ 7.17, 6.75, 6.56, 6.49 [(4s, 1H, four diastereoisomers)], 6.44, 6.29, 6.18 6.09 [(4s, 1H, four diastereoisomers)], 2.58 (dd, J=13.5, 7.9 Hz, 1H), 2.45-2.35 (m, 1H), 2.18-2.09 (m, 1H), 2.08, 2.06, 2.05, 2.05 [(s, 3H four diastereoisomers)], 2.02, 2.01, 2.00, 1.99 [(4s, 3H four diastereoisomers)], 1.98-1.92 (m, 1H), 1.88 (dd, J=13.5, 9.0 Hz, 1H), 1.68-1.60 (m, 1H), 1.56 (q, J=8.0 Hz, 1H), 1.51-1.49 (m, 2H), 1.49-1.42 (m, 2H), 1.37-1.33 (m, 1H), 1.31 (dd, J=3.6, 2.1 Hz, 6H), 1.27, 1.24, 1.24, 1.23 [(4s, 9H, four diastereoisomers)], 1.26-1.25 (m, 1H), 0.9-0.74 (m, 3H).

Step D. 1-amino-4-(2-boronoethyl)-2-hydroxycyclopentanecarboxylic acid hydrochloride The title compound 1-amino-4-(2-boronoethyl)-2-hydroxycyclopentanecarboxylic acid hydrochloride was obtained in the same manner like in Example 26, step C, using compound 2-acetamido-2-(tert-butylcarbamoyl)-4-(2-(4,4,5,5-tetramethyl-1,3,2-dioxaborolan-2-yl)ethyl)cyclopentyl acetate as a $1^{st}$ single diastereoisomer (1.24 g, 2.83 mmol, 1 equiv.), 6 N $HCl_{aq}$ (10 mL). The residue was purified by preparative HPLC (0.1-1% MeCN in water) and next by flash chromatography on DOWEX® ion exchange resin (eluent 0.1N ammonia in water) to give (after acidification with 6N HCl and subsequent lyophilization) product 1-amino-4-(2-boronoethyl)-2-hydroxycyclopentanecarboxylic acid hydrochloride as a mixture of diastereoisomers dr=9:1 (0.50 g, 70%, white solid). ESI+MS: m/z=218.2 (M+1)$^+$. ESI-MS: m/z=216.0 (M-1)$^-$, 198.0 (M-H$_2$O-1). $^1$H NMR (700 MHz, Deuterium Oxide) δ 4.43-4.3 [(m, 1H, two diastereoisomers)], 2.57 (dd, J=14.0, 8.0 Hz, 1H), 2.34 (p, J=8.5 Hz, 1H), 2.03 (dt, J=14.7, 7.7 Hz, 1H), 1.90-1.71 (m, 1H), 1.51-1.37 (m, 3H), 0.72 (td, J=7.5, 1.6 Hz, 2H).

The title compound 1-amino-4-(2-boronoethyl)-2-hydroxycyclopentanecarboxylic acid hydrochloride was obtained in the same manner like in Example 26, step C, using compound 2-acetamido-2-(tert-butylcarbamoyl)-4-(2-(4,4,5,5-tetramethyl-1,3,2-dioxaborolan-2-yl)ethyl)cyclopentyl acetate as a mixture of diastereoisomers 4:1 (0.47 g, 1.07 mmol, 1 equiv.), 6 N $HCl_{aq}$ (8 mL). The residue was purified by flash chromatography on DOWEX® ion exchange resin (eluent 0.1N ammonia in water) and next by preparative HPLC (0.1-1% MeCN in water) to give (after acidification with 6N HCl and subsequent lyophilization) product 1-amino-4-(2-boronoethyl)-2-hydroxycyclopentanecarboxylic acid hydrochloride as a mixture diastereoisomers dr=4:1 (0.14 g, 50%, white solid). ESI+MS: m/z=218.3 (M+1)$^+$. ESI-MS: m/z=216.0 (M-1)$^-$, 198.0 (M-H$_2$O-1). $^1$H NMR (700 MHz, Deuterium Oxide) δ 4.51, 4.45[(t, J=6.8 Hz, dd, J=10.6, 6.5 Hz, 1H, two diastereoisomers)], 2.46, 2.11 [(2dd, J=14.6, 8.0 Hz, J=14.5, 7.5 Hz, 1H, two diastereoisomers)], 2.26, 2.16 [(2dt, J=13.0, 6.5 Hz, J=15.9, 8.1 Hz, 1H), 1.88 (dd, J=14.5, 9.2 Hz, 1H), 1.83 (td, J=7.7, 3.7 Hz, 2H), 1.54-1.27 [(m, 2H, two diastereoisomers)], 0.72 (td, J=8.7, 8.0, 4.2 Hz, 2H).

The title compound 1-amino-4-(2-boronoethyl)-2-hydroxycyclopentanecarboxylic acid hydrochloride was obtained in the same manner like in Example 26, step C, using compound 2-acetamido-2-(tert-butylcarbamoyl)-4-(2-(4,4,5,5-tetramethyl-1,3,2-dioxaborolan-2-yl)ethyl)cyclopentyl acetate as a mixture of three diastereoisomers 5:4:1 (0.27 g, 0.62 mmol, 1 equiv.), 6 N $HCl_{aq}$(5 mL). The residue was purified by flash chromatography on DOWEX® ion exchange resin (eluent 0.1N ammonia in water) and next by preparative HPLC (0.1-1% MeCN in water) to give (after acidification with 6N HCl and subsequent lyophilization) product 1-amino-4-(2-boronoethyl)-2-hydroxycyclopentanecarboxylic acid hydrochloride as a mixture diastereoisomers dr=5:4:1 (0.11 g, 74%, white solid). ESI+MS: m/z=218.3 (M+1)$^+$. ESI-MS: m/z=216.0 (M-1)$^-$, 198.0 (M-H$_2$O-1)$^-$. $^1$H NMR (700 MHz, Deuterium Oxide) δ 4.52-4.27 [(m, 1H, three diastereoisomers)], 2.61-2.24[(m, 1H, three diastereoisomers)], 2.23-2.11 (m, 1H), 2.06-1.94 (m, 1H), 1.88-1.57 [(m, 1H, three diastereoisomers)], 1.54-1.27 (m, 3H), 0.72 (t, J=8.1 Hz, 2H).

The title compound 1-amino-4-(2-boronoethyl)-2-hydroxycyclopentanecarboxylic acid hydrochloride was obtained in the same manner like in Example 26, step C, using compound 2-acetamido-2-(tert-butylcarbamoyl)-4-(2-(4,4,5,5-tetramethyl-1,3,2-dioxaborolan-2-yl)ethyl)cyclopentyl acetate as a mixture of four diastereoisomers 4:4:1:1 (0.14 g, 0.32 mmol, 1 equiv.), 6 N $HCl_{aq}$(5 mL). The residue was purified by flash chromatography on DOWEX® ion exchange resin (eluent 0.1N ammonia in water) to give (after acidification with 6N HCl and subsequent lyophilization) product 1-amino-4-(2-boronoethyl)-2-hydroxycyclopentanecarboxylic acid hydrochloride as a mixture diastereoisomers dr=10:8:1:1 (0.09 g, 100%, white solid). ESI+MS: m/z=218.2 (M+1)$^+$. ESI-MS: m/z=216.0 (M-1)$^-$, 198.0 (M-H$_2$O-1). $^1$H NMR (700 MHz, Deuterium Oxide) δ 4.63-4.16 [(m, 1H, four diastereoisomers)], 2.63-2.25 [(m, 1H, four diastereoisomers)], 2.27-2.11 (m, 1H), 2.09-1.60 (m, 2H), 1.53-1.29 (m, 3H), 0.90-0.63 (m, 2H).

Example 64. rac-(1R,5R)-1-amino-5-(2-boronoethyl)-2-(dimethylamino)cyclohexane-1-carboxylic acid dihydrochloride

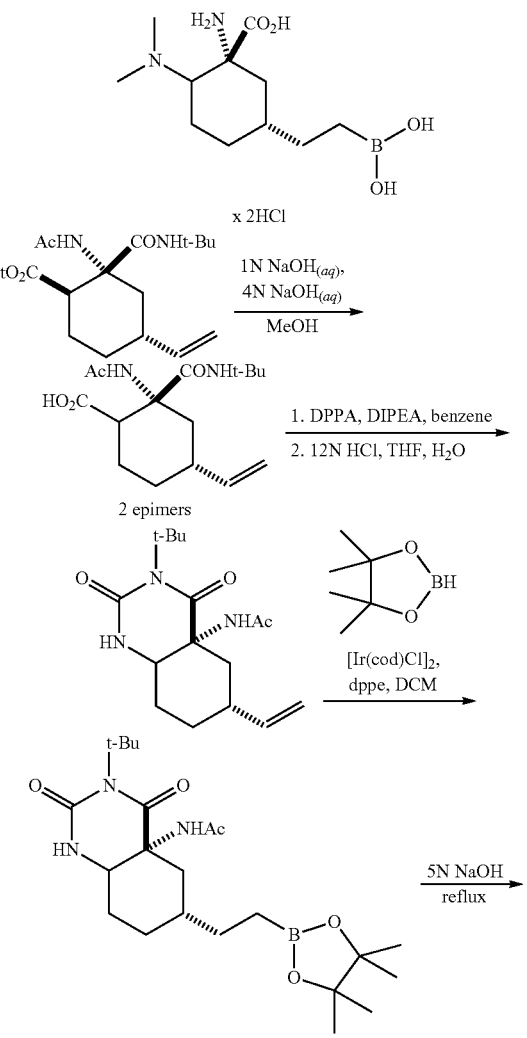

-continued

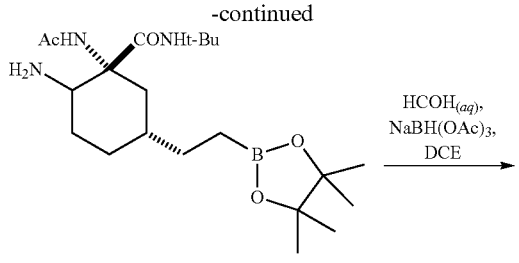

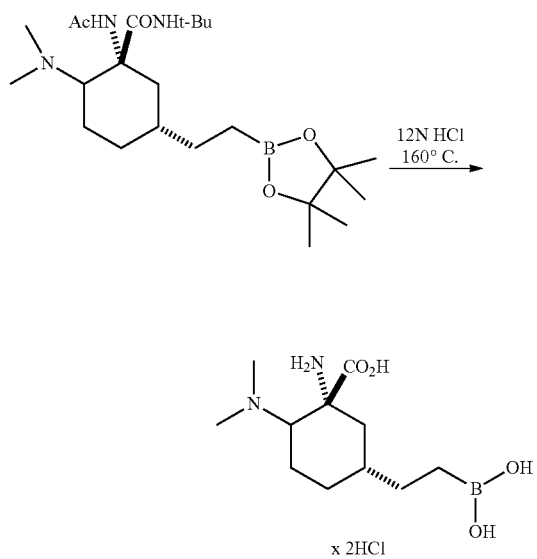

Step A. rac-(2R,4R)-2-acetamido-2-(tert-butylcarbamoyl)-4-vinylcyclohexane-1-carboxylic acid

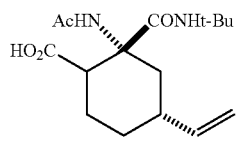

To a solution of rac-(1R,2R,4R)-2-acetamido-2-(tert-butylcarbamoyl)-4-vinylcyclohexane-1-carboxylate (Intermediate 1, 2 g, 5.91 mmol, 1 equiv.) in methanol (20 mL) was added 1N NaOH (2 mL) and 4N NaOH (2 mL). The reaction mixture was stirred at room temperature overnight. The solvent was evaporated in vacuo. The residue was dissolved in H₂O and washed with diethyl ether. Then the aqueous layer was acidified by 6N HCl to pH=2. The solid was filtered off and dried in vacuo to give corresponding product as a mixture of epimers, dr=7:3 (1.64 g, 90%, white solid). ESI+MS: m/z=311.0 (M+1)⁺; ESI-MS: m/z=309.0 (M−1)⁻. ¹H NMR (700 MHz, Chloroform-d) δ 8.32, 7.81 [(2s, 1H, two epimers)], 7.02, 6.19 [(2s, 1H, two epimers)], 5.78-5.66 (m, 1H), 5.07-4.94 (m, 2H), 3.29-2.83 (m, 1H, two epimers), 2.81-2.39 (m, 1H, two epimers), 2.32-2.12 (m, 2H), 2.07, 2.03 [(2s, 3H, two epimers)], 1.96-1.85 (m, 2H), 1.36, 1.35 [(2s, 9H, two epimers)], 1.33-1.13 (m, 2H).

Step B. rac-N-((4aR,6R)-3-(tert-butyl)-2,4-dioxo-6-vinyloctahydroquinazolin-4a(2H)-yl)acetamide

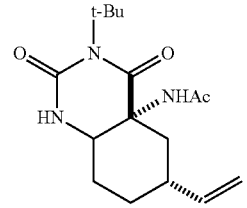

To a solution of rac-(2R,4R)-2-acetamido-2-(tert-butylcarbamoyl)-4-vinylcyclohexane-1-carboxylic acid (1.26 g, 4.06 mmol, 1 equiv.) in benzene (50 mL) was added N,N-diisopropylethylamine (2.1 mL, 12.18 mmol, 3 equiv.) and diphenylphosphoryl azide (1.75 mL, 8.12 mmol, 2 equiv.). The mixture was refluxed for 6.5 h. The reaction was quenched with 2N HCl. The organic layer was washed with brine, dried over MgSO₄, filtered and concentrated in vacuo. The residue was dissolved in tetrahydrofuran-H₂O (15 mL: 15 mL) and stirred at room temperature for 2 h. Then was added 12N HCl (5 mL) and was stirred for 3 h. The solvent was evaporated in vacuo. The aqueous layers was extracted with DCM twice. The organic layer was washed with 1M NaOH, brine, dried over MgSO₄, filtered and concentrated in vacuo. The crude product was purified by flash chromatography on silica gel (hexane/AcOEt, 3:1) to give corresponding product as a single diastereoisomer (760 mg, 61%, white solid). ESI+MS: m/z=308.2 (M+1)⁺; ESI-MS: m/z=306.2 (M−1)⁻. ¹H NMR (700 MHz, Chloroform-d) δ 7.16 (s, 1H), 5.75 (ddd, J=17.1, 10.4, 6.5 Hz, 1H), 5.15 (s, 1H), 5.08-4.97 (m, 2H), 3.46 (dt, J=13.0, 4.0 Hz, 1H), 2.97-2.83 (m, 2H), 2.52 (s, 3H), 2.36-2.27 (m, 1H), 1.97 (dtt, J=13.4, 4.0, 1.8 Hz, 1H), 1.85 (dtd, J=12.3, 4.5, 2.3 Hz, 1H), 1.33 (s, 9H), 1.32-1.26 (m, 1H).

Step C. rac-N-((4aR,6R)-3-(tert-butyl)-2,4-dioxo-6-(2-(4,4,5,5-tetramethyl-1,3,2-dioxaborolan-2-yl)ethyl)octahydroquinazolin-4a(2H)-yl)acetamide

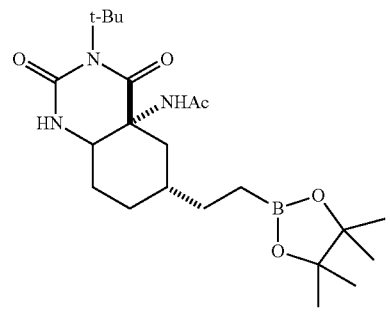

The title compound was obtained in the same manner like in Example 26, step B, using rac-N-((4aR,6R)-3-(tert-butyl)-2,4-dioxo-6-vinyloctahydroquinazolin-4a(2H)-yl)acetamide (760 mg, 2.47 mmol, 1 equiv.), dppe (59 mg, 0.148 mmol, 0.06 equiv.), bis(1,5-cyclooctadiene)diiridium(I) dichloride (50 mg, 0.074 mmol, 0.03 equiv.), 4,4,5,5-tetramethyl-1,3,2-dioxaborolane (466 µL, 0.25 mmol, 1.3 equiv.) and DCM (20 mL). The crude product was purified by column chromatography on silica gel (DCM/MeOH 100:1 to 50:1) to give corresponding product (590 mg, 55%, white solid). ESI+MS: m/z=436.3 (M+1)$^+$; ESI-MS: m/z=434.2 (M−1)$^−$. $^1$H NMR (700 MHz, Chloroform-d) δ 7.16 (s, 1H), 4.99 (s, 1H), 3.43 (dd, J=13.0, 4.1 Hz, 1H), 2.90 (d, J=3.4 Hz, 1H), 2.87-2.79 (m, 1H), 2.51 (s, 3H), 1.98-1.92 (m, 1H), 1.82-1.77 (m, 1H), 1.54-1.52 (m, 1H), 1.44-1.38 (m, 2H), 1.31 (s, 9H), 1.26 (d, J=1.3 Hz, 12H), 1.11 (qd, J=12.7, 4.9 Hz, 1H), 0.85-0.73 (m, 2H)

Step D. rac-(1R,5R)-1-acetamido-2-amino-N-(tert-butyl)-5-(2-(4,4,5,5-tetramethyl-1,3,2-dioxaborolan-2-yl)ethyl)cyclohexane-1-carboxamide A mixture of rac-N-((4aR,6R)-3-(tert-butyl)-2,4-dioxo-6-(2-(4,4,5,5-tetramethyl-1,3,2-dioxaborolan-2-yl)ethyl)octahydroquinazolin-4a(2H)-yl)acetamide (270 mg, 0.62 mmol, 1 equiv.) and 5N NaOH (2 mL) was heated under reflux for 3.5 h. Then was added 6N HCl to pH=9 and extracted with DCM three times. The organic layer was dried over MgSO$_4$, filtered and concentrated in vacuo to give corresponding product as a mixture of epimers, dr=9:1 (150 mg, 59%, colorless oil). ESI+MS: m/z=410.2 (M+1)$^+$. $^1$H NMR (700 MHz, Chloroform-d) δ 7.25 (s, 1H), 6.07 (d, J=9.9 Hz, 1H), 3.79 (ddd, J=12.2, 9.8, 5.3 Hz, 1H), 3.74 (q, J=7.0 Hz, 2H), 3.70-3.62 (m, 1H), 2.24-2.17 (m, 1H), 2.00, 1.98 [(2s, 3H, two epimers)], 1.87-1.75 (m, 1H), 1.53-1.48 (m, 1H), 1.34, 1.33 [(2s, 9H, two epimers)], 1.26, 1.25 [(2s, 12H, two epimers)], 1.17 (t, J=7.4 Hz, 1H), 1.06-0.89 (m, 2H), 0.86-0.69 (m, 2H).

Step E. rac-(1R,5R)-1-acetamido-N-(tert-butyl)-2-(dimethylamino)-5-(2-(4,4,5,5-tetramethyl-1,3,2-dioxaborolan-2-yl)ethyl)cyclohexane-1-carboxamide To a solution of rac-(1R,5R)-1-acetamido-2-amino-N-(tert-butyl)-5-(2-(4,4,5,5-tetramethyl-1,3,2-dioxaborolan-2-yl)ethyl)cyclohexane-1-carboxamide (96 mg, 0.23 mmol, 1 equiv.) in 1,2-dichloroethane (1.5 mL) was added formaldehyde (0.5 mL, 6.65 mmol, 30 equiv.). The mixture was stirred at room temperature for 30 min. Then was added sodium triacetoxyborohydride (0.5 g, 10 equiv.) and was stirred overnight. The mixture was diluted with dichloromethane and washed with 5% NaHCO$_3$. The aqueous layer was extracted with dichloromethane three times. The combined organic layers were dried over MgSO$_4$, filtered and concentrated in vacuo. The crude product was purified by column chromatography on silica gel (DCM/MeOH 50:1 to 20:1) to give corresponding product as a mixture of epimers, dr=9:1 (35 mg, 34%, colorless oil). ESI+MS: m/z=438.4 (M+1)$^+$. $^1$H NMR (700 MHz, Chloroform-d) δ 6.71 (d, J=9.9 Hz, 1H), 6.56 (s, 1H), 4.18-4.11 (m, 1H), 2.35 (s, 6H), 1.93, 1.91 [(2s, 3H, two epimers)], 1.78-1.69 (m, 1H), 1.65-1.61 (m, 1H), 1.38 (s, 9H), 1.36-1.32 (m, 2H), 1.30-1.28 (m, 3H), 1.26, 1.25 [(2s, 12H, two epimers)], 0.94-0.86 (m, 2H), 0.81-0.69 (m, 2H).

Step F. rac-(1R,5R)-1-amino-5-(2-boronoethyl)-2-(dimethylamino)cyclohexane-1-carboxylic acid A mixture of rac-(1R,5R)-1-acetamido-N-(tert-butyl)-2-(dimethylamino)-5-(2-(4,4,5,5-tetramethyl-1,3,2-dioxaborolan-2-yl)ethyl)cyclohexane-1-carboxamide (35 mg, 0.08 mmol, 1 equiv.) and 6 N HCl$_{aq}$(2 mL) was heated at 160° C. for 29 h. The residue was purified by flash chromatography on DOWEX® ion exchange resin (eluent 0.1N ammonia in water) and then by preparative HPLC (0.1-1% MeCN in water) to give (after acidification with 6N HCl and subsequent lyophilization) corresponding product as a separable diastereoisomers. Total yield: 9%.

First Epimer:

Single epimer (1.6 mg, colorless film); ESI+MS: m/z=258.0 (M+1)$^+$. $^1$H NMR (700 MHz, Deuterium Oxide) δ 3.83 (dd, J=12.3, 3.7 Hz, 1H), 2.92 (s, 6H), 2.32 (ddd, J=14.4, 4.1, 1.9 Hz, 1H), 2.14 (dq, J=13.6, 3.6, 3.2 Hz, 1H), 2.00-1.94 (m, 1H), 1.76 (ddq, J=12.5, 8.2, 4.1 Hz, 1H), 1.64 (td, J=13.0, 3.4 Hz, 1H), 1.56 (dd, J=14.4, 12.6 Hz, 1H), 1.50 (ddt, J=13.5, 10.8, 5.6 Hz, 1H), 1.36-1.27 (m, 1H), 1.12-1.02 (m, 1H), 0.82 (ddd, J=16.2, 10.4, 6.0 Hz, 1H), 0.72 (ddd, J=15.8, 10.3, 6.1 Hz, 1H).

Second Epimer:

Single epimer (0.7 mg, colorless film); ESI+MS: m/z=258.0 (M+1)$^+$. $^1$H NMR (700 MHz, Deuterium Oxide) δ 3.75 (dd, J=12.4, 3.7 Hz, 1H), 2.78 (s, 6H), 2.25 (ddd, J=14.4, 4.0, 2.0 Hz, 1H), 2.15-2.07 (m, 1H), 2.00-1.90 (m, 1H), 1.73 (ddq, J=12.4, 8.1, 4.0 Hz, 1H), 1.63 (qd, J=13.3, 3.5 Hz, 1H), 1.54-1.43 (m, 2H), 1.31 (dddd, J=13.8, 10.1, 8.0, 6.1 Hz, 1H), 1.06 (qd, J=13.3, 3.7 Hz, 1H), 0.80 (ddd, J=16.2, 10.5, 6.2 Hz, 1H), 0.72 (ddd, J=15.7, 10.3, 6.2 Hz, 1H).

Example 65. 1-amino-3-(2-boronoethyl)-5-(dimethylamino)cyclohexane-1-carboxylic acid dihydrochloride

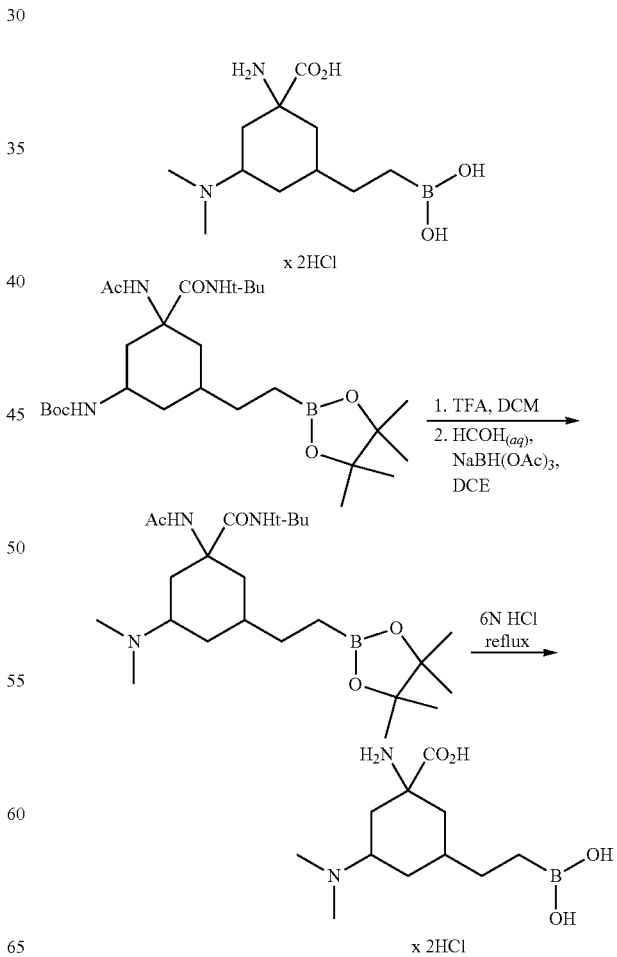

Step A. 1-acetamido-N-(tert-butyl)-3-(dimethylamino)-5-(2-(4,4,5,5-tetramethyl-1,3,2-dioxaborolan-2-yl)ethyl)cyclohexane-1-carboxamide

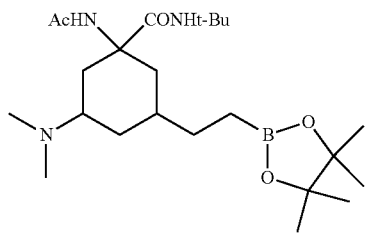

To a solution of tert-butyl (3-acetamido-3-(tert-butylcarbamoyl)-5-(2-(4,4,5,5-tetramethyl-1,3,2-dioxaborolan-2-yl)ethyl)cyclohexyl)carbamate (Ex. 56, Step D; 80 mg, 0.157 mmol, 1 equiv.) in dichloromethane (6 mL) was added trifluoroacetic acid (2 mL). The reaction mixture was stirred at room temperature for 1.5 h. The solvents was evaporated in vacuo. The residue was dissolved in 1,2-dichloroethane (1 mL) and added formaldehyde$_{aq}$(50 µL, 0.627 mmol, 4 equiv.) and stirred at room temperature for 1 h. Then was added sodium triacetoxyborohydride (132 mg, 0.627 mmol, 4 equiv.). The resulting mixture was stirred at room temperature overnight. The mixture was diluted with dichloromethane and washed with 5% NaHCO$_3$. The aqueous layer was extracted with dichloromethane three times. The combined organic layers were dried over MgSO$_4$, filtered and concentrated in vacuo. The residue was dissolved in methanol-dioxane (2 mL-70 µL) and added formaldehyde$_{aq}$ (70 µL, 0.942 mmol, 6 equiv.) and sodium cyanoborohydride (10 mg, 0.330 mmol, 2.1 equiv.). The mixture was stirred at room temperature overnight. The mixture was concentrated in vacuo. The residue was dissolved in chloroform (150 µL) and added triethylsilane (150 µL, 0.942 mmol, 6 equiv.) and trifluoroacetic acid (150 µL). The resulting mixture was stirred at 60° C. for 7 h. The solvent was evaporated in vacuo and purified by column chromatography on silica gel (DCM/MeOH 60:1 to 1:1) to give corresponding product as a mixture of diastereoisomers, dr=9:1 (60 mg, 70%, white foam). ESI+MS: m/z=438.4 (M+1)$^+$. $^1$H NMR (700 MHz, Chloroform-d) δ 8.97-8.90 [(2s, 1H, two diastereoisomers)], 6.03, 5.98 [(2s, 1H, two diastereoisomers)]), 3.32-3.23 (m, 1H), 2.92 (d, J=15.7 Hz, 1H), 2.89-2.82 (m, 6H), 2.80-2.56 (m, 2H), 2.20-2.14 (m, 1H), 2.12-2.10 (m, 1H), 2.02, 2.01 [(2s, 3H, two diastereoisomers)], 2.01-1.99 (m, 1H), 1.64-1.51 (m, 1H), 1.49-1.36 (m, 2H), 1.32, 1.31 [(2s, 9H, two diastereoisomers)], 1.25, 1.24 [(2s, 12H, two diastereoisomers)], 0.84-0.74 (m, 2H).

The second mixture of diastereoisomers was obtained was obtained in the same manner like in Example 56, step H, using tert-butyl (3-acetamido-3-(tert-butylcarbamoyl)-5-(2-(4,4,5,5-tetramethyl-1,3,2-dioxaborolan-2-yl)ethyl)cyclohexyl)carbamate (80 mg, 0.157 mmol, 1 equiv.), trifluoroacetic acid (2 mL), dichloromethane (6 mL), formaldehyde$_{aq}$(50 µL, 0.627 mmol, 4 equiv.), 1,2-dichloroethane (2 mL), sodium triacetoxyborohydride (130 mg, 0.627 mmol, 4 equiv.). The crude product was purified by column chromatography on silica gel (DCM/MeOH 50:1 to 1:1) to give corresponding product (40 mg, 58%, white solid). ESI+MS: m/z=438.2 (M+1)$^+$.

Step B. 1-amino-3-(2-boronoethyl)-5-(dimethylamino)cyclohexane-1-carboxylic acid dihydrochloride The title compound was obtained in the same manner like in Example 26, step C, using 1-acetamido-N-(tert-butyl)-3-(dimethylamino)-5-(2-(4,4,5,5-tetramethyl-1,3,2-dioxaborolan-2-yl)ethyl)cyclohexane-1-carboxamide (60 mg, 0.137 mmol, 1 equiv.) and 6N HCl$_{aq}$ (4 mL). The residue was purified by flash chromatography on DOWEX® ion exchange resin (eluent 0.1N ammonia in water) and then by preparative HPLC (0.1-1% MeCN in water) to give (after acidification with 6N HCl and subsequent lyophilization) corresponding product as a mixture of diastereoisomers, dr=4:1 (5.5 mg, 12%, colorless film). ESI+MS: m/z=259.0 (M+1)$^+$; ESI-MS: m/z=257.0 (M−1)$^-$. $^1$H NMR (700 MHz, Deuterium Oxide) δ 3.92-3.41 (m, 1H, two diastereoisomers), 2.83 (d, J=8.1 Hz, 6H), 2.57-2.17 (in, 2H, two diastereoisomers), 2.05-1.90 (m, 2H, two diastereoisomers), 1.80-1.57 (in, 3H, two diastereoisomers), 1.46-1.33 (m, 2H, two diastereoisomers), 0.77-0.66 (m, 2H).

The second mixture of diastereoisomers was obtained in the same way starting from: 1-acetamido-N-(tert-butyl)-3-(dimethylamino)-5-(2-(4,4,5,5-tetramethyl-1,3,2-dioxaborolan-2-yl)ethyl)cyclohexane-1-carboxamide (20 mg, 0.04 mmol, 1 equiv.) and 6N HCl$_{aq}$ (2 mL). The residue was purified by flash chromatography on DOWEX® ion exchange resin (eluent 0.1N ammonia in water) and then by preparative HPLC (0.1-1% MeCN in water) to give (after acidification with 6N HCl and subsequent lyophilization) corresponding product as a mixture of diastereoisomers, dr=9:1, (1.5 mg, 5%, colorless film). ESI+MS: m/z=259.0 (M+1)$^+$. $^1$H NMR (700 MHz, Deuterium Oxide) δ 3.62-3.43 (m, 1H), 2.85 (s, 3H), 2.84-2.81 (m, 1H), 2.80 (s, 3H), 2.66-2.59 (m, 1H), 2.28 (dt, J=16.0, 2.5 Hz, 1H), 2.23-2.15 (m, 1H), 1.97-1.90 (m, 1H), 1.76-1.55 (m, 1H), 1.38-1.30 (m, 3H), 0.77-0.70 (m, 2H).

Example 66. 1-amino-2-(aminomethyl)-4-(2-boronoethyl)cyclopentane-1-carboxylic acid dihydrochloride

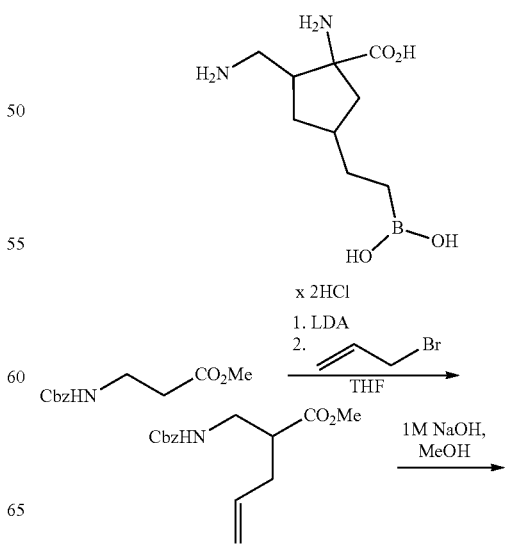

265
-continued

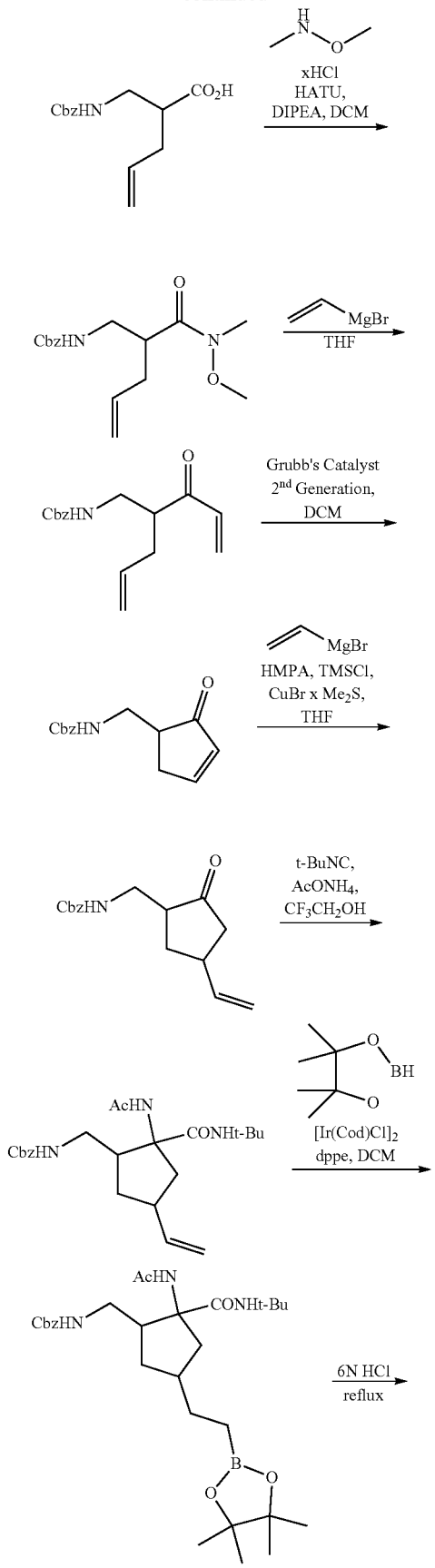

266
-continued

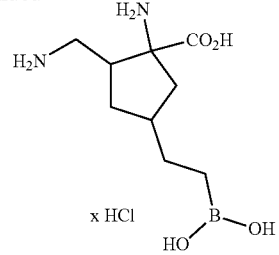

Step A. methyl 2-((((benzyloxy)carbonyl)amino)methyl)pent-4-enoate

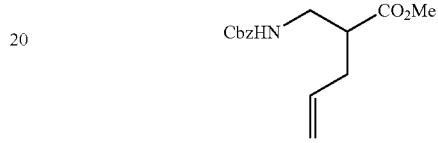

To a solution of methyl 3-([(benzyloxy)carbonyl]amino)propanoate (8 g, 33.71 mmol, 1 equiv.) in tetrahydrofuran (100 mL) under argon at −78° C. lithium diisopropylamide (2.0 M solution in THF/heptane/ethylbenzene) (37 mL, 74.17 mmol, 2.1 equiv.) was added dropwise. The reaction mixture was stirred for 30 min and a solution of allyl bromide (3.2 mL, 37.08 mmol, 1.1 equiv.) in tetrahydrofuran (40 mL) was added dropwise at −78° C. The resulting mixture was stirred at room temperature overnight. The reaction was quenched with saturated aqueous NH$_4$Cl and extracted with AcOEt. The combined organic layers were washed with brine, dried over MgSO$_4$ and concentrated. The crude product was purified by flash chromatography on silica gel (hexane/AcOEt 20:1 to 8:1) to give corresponding product (8.79 g, 94%, yellow oil). ESI+MS: m/z=300.0 (M+23)$^+$. $^1$H NMR (700 MHz, Chloroform-d) δ 7.44-7.30 (m, 5H), 5.77 (ddt, J=17.1, 10.0, 7.0 Hz, 1H), 5.10 (dtt, J=17.0, 11.4, 6.7 Hz, 4H), 4.72 (d, J=6.0 Hz, 1H), 3.70 (s, 3H), 3.49-3.44 (m, 1H), 3.35 (ddd, J=14.1, 8.5, 5.8 Hz, 1H), 2.75 (dq, J=8.7, 2.7 Hz, 1H), 2.42 (dt, J=14.1, 6.9 Hz, 1H), 2.31 (dt, J=14.3, 7.1 Hz, 1H).

Step B. 2-((((benzyloxy)carbonyl)amino)methyl)pent-4-enoic acid

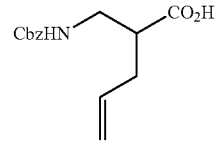 [SMILES: C=CCC(CNC(=O)OCc1ccccc1)C(=O)O]

The title compound was obtained in the same manner like in Example 48, step B, using methyl 2-((((benzyloxy)carbonyl)amino)methyl)pent-4-enoate (8.79 g, 31.7 mmol, 1 equiv.), 1M NaOH (30 mL) and MeOH (90 mL). Obtained corresponding product (8 g, 96%, white solid). The product was used to next step without further purification. ESI+MS: m/z=264.0 (M+1)$^+$. $^1$H NMR (700 MHz, Chloroform-d) δ 7.41-7.30 (m, 5H), 5.80 (ddd, J=17.1, 10.0, 7.2 Hz, 1H), 5.25-5.04 (m, 5H), 3.51 (ddd, J=14.0, 6.9, 4.4 Hz, 1H), 3.35 (ddd, J=14.2, 8.3, 5.8 Hz, 1H), 2.85-2.70 (m, 1H), 2.53-2.40 (m, 1H), 2.40-2.30 (m, 1H).

Step C. benzyl (2-(methoxy(methyl)carbamoyl)pent-4-en-1-yl)carbamate

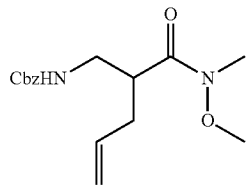 [SMILES: C=CCC(CNC(=O)OCc1ccccc1)C(=O)N(C)OC]

The title compound was obtained in the same manner like in Example 48, step C, using 2-((((benzyloxy)carbonyl)amino)methyl)pent-4-enoic acid (8.0 g, 30.38 mmol, 1 equiv) N,N-diisopropylethylamine (11 mL, 63.81 mmol, 2.1 equiv.), N,O-dimethylhydroxylamine hydrochloride (3.2 g, 31.90 mmol, 1.05 equiv.) HATU (12.2 g, 31.90 mmol, 1.05 equiv.) and dichloromethane (90 mL). The residue was purified by flash chromatography on silica gel (hexane/AcOEt 15:1 to 1:1) to give corresponding product (7.42 g, 80%, yellow oil). ESI+MS: m/z=307.0 (M+1)$^+$. $^1$H NMR (700 MHz, Chloroform-d) δ 7.42-7.29 (m, 5H), 5.77 (ddt, J=17.2, 10.4, 6.8 Hz, 1H), 5.32 (br s, 1H), 5.15-4.99 (m, 4H), 3.59 (d, J=8.5 Hz, 3H), 3.46-3.38 (m, 1H), 3.38-3.27 (m, 1H), 3.24 (br s, 1H), 3.16 (dd, J=6.6, 3.6 Hz, 3H), 2.35 (ddt, J=13.9, 6.9, 3.9 Hz, 1H), 2.23 (dt, J=14.2, 6.8 Hz, 1H).

Step D. benzyl (2-allyl-3-oxopent-4-en-1-yl)carbamate

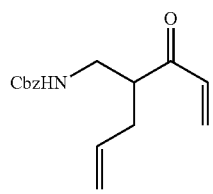 [SMILES: C=CCC(CNC(=O)OCc1ccccc1)C(=O)C=C]

The title compound was obtained in the same manner like in Example 48, step D, using benzyl (2-(methoxy(methyl)carbamoyl)pent-4-en-1-yl)carbamate (6.56 g, 21.44 mmol, 1 equiv), vinylmagnesium bromide (1M in THF) (100 mL, 100.7 mmol, 4.7 equiv.) and THF (130 mL). The residue was purified by flash chromatography on silica gel (hexane/AcOEt 10:1 to 4:1) to give corresponding product (2.1 g, 36%, yellow oil). ESI+MS: m/z=274.0 (M+1)$^+$. $^1$H NMR (700 MHz, Chloroform-d) δ 7.41-7.31 (m, 5H), 6.49-6.20 (m, 1H), 5.88-5.69 (m, 1H), 5.13-5.05 (m, 7H), 4.18 (dddd, J=13.2, 6.4, 4.9, 2.0 Hz, 1H), 2.51 (d, J=31.3 Hz, 1H), 2.40 (dt, J=13.9, 6.9 Hz, 1H), 2.24 (dd, J=14.4, 7.3 Hz, 1H), 2.13-2.05 (m, 1H).

Step E. benzyl ((2-oxocyclopent-3-en-1-yl)methyl)carbamate

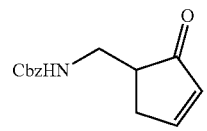 [SMILES: O=C(NCC1CC=CC1=O)OCc1ccccc1]

The title compound was obtained in the same manner like in Example 48, step E, using benzyl (2-allyl-3-oxopent-4-en-1-yl)carbamate (2.1 g, 7.68 mmol, 1 equiv), Grubbs Catalyst, 2$^{nd}$ Generation (0.32 g, 0.38 mmol, 0.05 equiv.) and dichloromethane (413 mL). The residue was purified by flash chromatography on silica gel (hexane/AcOEt 10:1 to 3:1) to give corresponding product (0.32 g, 17%, yellow oil). ESI+MS: m/z=245.0 (M+1)$^+$. $^1$H NMR (700 MHz, Chloroform-d) δ 7.79-7.71 (m, 1H), 7.40-7.32 (m, 5H), 6.20 (dt, J=5.8, 2.1 Hz, 1H), 5.35 (br s, 1H), 5.12 (s, 2H), 3.63 (dt, J=12.0, 5.7 Hz, 1H), 3.37 (dt, J=13.0, 6.4 Hz, 1H), 2.94-2.85 (m, 1H), 2.57-2.51 (m, 2H).

Step F. benzyl ((2-oxocyclopent-3-en-1-yl)methyl)carbamate

The title compound was obtained in the same manner like in the step B from the synthesis of the intermediate 1, using benzyl ((2-oxocyclopent-3-en-1-yl)methyl)carbamate (320 mg, 1.30 mmol, 1 equiv.), vinylmagnesium bromide 1M in THF (4.6 mL, 4.57 mmol, 3.5 equiv.), HMPA (0.91 mL, 5.22 mmol, 4 equiv.), copper(I) bromide dimethyl sulfide complex (40 mg, 0.20 mmol, 0.15 equiv.), trimethylsilyl chloride (0.83 mL, 6.52 mmol, 5 equiv.) and THF (10 mL). The residue was purified by silica gel flash chromatography (hexane/AcOEt, 10:1 to 8:1) to give corresponding product as a mixture of diastereoisomers, dr=4:1, (307 mg, 86%, colorless oil). ESI+MS: m/z=274.0 (M+1)$^+$. $^1$H NMR (700 MHz, Chloroform-d) δ 7.41-7.31 (m, 5H), 5.94-5.78 (m, 1H), 5.34, 5.29 [(2s, 1H, two diastereoisomers)], 5.13-5.05 (m, 4H), 3.51 (dq, J=13.7, 7.9, 6.7 Hz, 1H), 3.30 (ddt, J=26.3, 13.4, 6.3 Hz, 1H), 3.02-2.74 (m, 1H, two diastereoisomers), 2.60-2.24 (m, 3H), 2.12-1.91 (m, 2H).

Step F. benzyl ((2-acetamido-2-(tert-butylcarbamoyl)-4-vinylcyclopentyl)methyl)carbamate

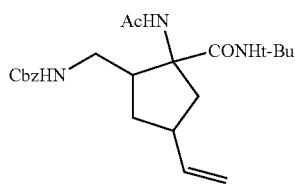

The title compound was obtained in the same manner like in step C from the synthesis of the intermediate 1, using benzyl ((2-oxocyclopent-3-en-1-yl)methyl)carbamate (300 mg, 1.10 mmol, 1 equiv.), ammonium acetate (338 mg, 4.39 mmol, 4 equiv.), tert-butylisocyanide (250 µL, 2.20 mmol, 2 equiv.) and 2,2,2-trifluoroethanol (4.5 mL) as a solvent. The residue was purified by flash chromatography on silica gel (hexane/AcOEt 10:1 to 1:1) to give corresponding product as a mixture of diastereoisomers. Total yield: 80%. Diastereoisomers were partially separated as the following diastereoisomeric ratios:

Single diastereoisomer (66 mg, colorless oil); ESI+MS: m/z=416.2 (M+1)$^+$; ESI-MS: m/z=414.2 (M−1)$^-$. $^1$H NMR (700 MHz, Chloroform-d) δ 7.39-7.30 (m, 5H), 7.07 (br s, 1H), 6.63 (br s, 1H), 5.75 (ddd, J=17.2, 10.2, 7.1 Hz, 1H), 5.35 (br s, 1H), 5.14-5.08 (m, 2H), 5.03-4.90 (m, 2H), 3.40-3.29 (m, 2H), 2.96-2.88 (m, 1H), 2.74-2.64 (m, 1H), 2.39 (d, J=8.6 Hz, 2H), 2.04-2.00 (m, 1H), 1.99 (s, 3H), 1.46-1.38 (m, 1H), 1.30 (s, 9H).

Mixture of diastereoisomers (dr=3:1) (219 mg, colorless oil); ESI+MS: m/z=416.2 (M+1)$^+$; ESI-MS: m/z=414.2 (M−1)$^-$. $^1$H NMR (700 MHz, Chloroform-d) δ 7.39-7.31 (m, 5H), 7.14-6.92 (m, 1H, two diastereoisomers), 6.63, 6.45 [(2s, 1H, two diastereoisomers)], 5.85-5.71 (m, 1H), 5.49, 5.34 [(2s, 1H, two diastereoisomers)], 5.20-5.07 (m, 2H), 5.05-4.87 (m, 2H), 3.50-3.17 (m, 2H), 3.06-2.85 (m, 1H), 2.80-2.65 (m, 1H, two diastereoisomers), 2.40-2.29 (m, 1H, two diastereoisomers), 2.03, 1.99 (2s, 3H, two diastereoisomers), 2.02-2.02 (m, 1H), 1.86-1.68 (m, 2H), 1.30, 1.29 [(2s, 9H, two diastereoisomers).

Mixture of diastereoisomers (dr=9:1) (83 mg, colorless oil); ESI+MS: m/z=416.2 (M+1)$^+$; ESI-MS: m/z=414.2 (M−1)$^-$. $^1$H NMR (700 MHz, Chloroform-d) δ 7.40-7.31 (m, 5H), 6.43 (s, 1H), 6.38 (s, 1H), 5.90-5.75 (m, 1H, two diastereoisomers), 5.50-5.40 [(2s, 1H, two diastereoisomers)], 5.19-4.91 (m, 4H), 3.37-3.20 (m, 2H), 2.86-2.72 (m, 1H), 2.53-2.50 (m, 1H), 2.39-2.28 (m, 2H), 2.09 (dt, J=13.7, 7.2 Hz, 1H), 2.03, 2.00 [(2s, 3H, two diastereoisomers)], 1.53-1.42 (m, 1H), 1.34, 1.29 [(2s, 9H, two diastereoisomers)].

Step G. benzyl ((2-acetamido-2-(tert-butylcarbamoyl)-4-(2-(4,4,5,5-tetramethyl-1,3,2-dioxaborolan-2-yl)ethyl)cyclopentyl)methyl)carbamate

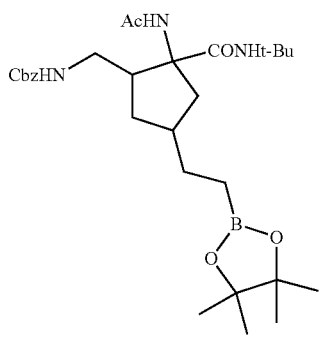

The title compound was obtained in the same manner like in Example 26, step B, using benzyl ((2-acetamido-2-(tert-butylcarbamoyl)-4-vinylcyclopentyl)methyl)carbamate (66 mg, 0.159 mmol, 1 equiv.), dppe (4 mg, 0.0095 mmol, 0.06 equiv.), bis(1,5-cyclooctadiene)diiridium(I) dichloride (3.2 mg, 0.0048 mmol, 0.03 equiv.), 4,4,5,5-tetramethyl-1,3,2-dioxaborolane (37 µL, 0.09 mmol, 1.5 equiv.) and DCM (3 mL). The crude product was purified by column chromatography on silica gel (DCM/MeOH 30:1 to 9:1) to give corresponding product as a single diastereoisomer (106 mg, 100%, colorless oil). ESI+MS: m/z=544.4 (M+1)$^+$. $^1$H NMR (700 MHz, Chloroform-d) δ 7.41-7.27 (m, 5H), 7.07 (br s, 1H), 6.50 (br s, 1H), 5.12-4.97 (m, 2H), 3.40-3.13 (m, 2H), 2.88-2.77 (m, 1H), 2.27 (dd, J=14.4, 9.0 Hz, 1H), 2.21-2.14 (m, 1H), 1.97 (s, 3H), 1.95-1.84 (m, 3H), 1.50-1.32 (m, 2H), 1.27 (s, 9H), 1.23 (s, 12H), 1.18-1.03 (m, 1H), 0.78-0.63 (m, 2H).

The second mixture of diastereoisomers was obtained in the same way starting from: benzyl ((2-acetamido-2-(tert-butylcarbamoyl)-4-vinylcyclopentyl)methyl)carbamate (dr=3:1) (222 mg, 0.53 mmol, 1 equiv.), dppe (13 mg, 0.032 mmol, 0.06 equiv.), bis(1,5-cyclooctadiene)diiridium(I) dichloride (11 mg, 0.016 mmol, 0.03 equiv.), 4,4,5,5-tetramethyl-1,3,2-dioxaborolane (125 µL, 0.80 mmol, 1.5 equiv.) and DCM (5 mL). The crude product was purified by column chromatography on silica gel (hexane/AcOEt 10:1 to 2:1) to give corresponding product as a mixture of diastereoisomers, dr=3:2, (200 mg, 69%, white foam). ESI+MS: m/z=544.1 (M+1)$^+$. $^1$H NMR (700 MHz, Chloroform-d) δ 7.41-7.29 (m, 5H), 7.11-6.91 (m, 1H), 6.52, 6.20 [(2s, 1H, two diastereoisomers)], 5.68-5.29 (m, 1H), 5.18-5.05 (m, 2H), 3.50-3.30 (m, 1H), 3.30-3.18 (m, 1H), 3.02-2.88 (m, 1H), 2.89-2.80 (m, 1H), 2.33-2.09 (m, 1H), 2.01, 1.99 [(2s, 3H, two diastereoisomers)], 1.97-1.76 (m, 1H), 1.66-1.39 (m, 4H), 1.30, 1.29 [(2s, 9H, two diastereoisomers)], 1.25, 1.24 [(2s, 12H, two diastereoisomers)], 0.80-0.70 (m, 2H).

The third mixture of diastereoisomers was obtained in the same way starting from: benzyl ((2-acetamido-2-(tert-butylcarbamoyl)-4-vinylcyclopentyl)methyl)carbamate (dr=9:1) (70 mg, 0.19 mmol, 1 equiv.), dppe (5 mg, 0.0115 mmol, 0.06 equiv.), bis(1,5-cyclooctadiene)diiridium(I) dichloride (4 mg, 0.0057 mmol, 0.03 equiv.), 4,4,5,5-tetramethyl-1,3,2-dioxaborolane (45 µL, 0.29 mmol, 1.5 equiv.) and DCM (3 mL). The crude product was purified by column chromatography on silica gel (DCM/MeOH 100:1 to 50:1) to give corresponding product as a mixture of diastereoisomers, dr=9:1, (66 mg, 64%, colorless oil). ESI+MS: m/z=544.2 (M+1)$^+$. $^1$H NMR (700 MHz, Chloroform-d) δ 7.40-7.30 (m, 5H), 6.56 (s, 1H), 6.33, 6.19 [(2s, 1H, two diastereoisomers)], 5.64, 5.43 [(2s, 1H, two diastereoisomers)], 5.19-4.98 (m, 2H), 3.39-3.28 (m, 1H), 3.27-3.13 (m, 1H), 3.03-2.31 (m, 1H, two diastereoisomers), 2.23-2.17 (m, 1H), 2.14-2.02 (m, 1H), 2.01, 1.99 [(2s, 3H, two diastereoisomers)], 1.54-1.42 (m, 2H), 1.34, 1.33 [(2s, 9H, two diastereoisomers)], 1.30-1.26 (m, 3H), 1.25, 1.24 [(2s, 12H, two diastereoisomers)], 0.83-0.68 (m, 2H).

Step H. 1-amino-2-(aminomethyl)-4-(2-boronoethyl)cyclopentane-1-carboxylic acid dihydrochloride The title compound was obtained in the same manner like in Example 26, step C, using benzyl ((2-acetamido-2-(tert-butylcarbamoyl)-4-(2-(4,4,5,5-tetramethyl-1,3,2-dioxaborolan-2-yl)ethyl)cyclopentyl)methyl)carbamate (18 mg, 0.033 mmol, 1 equiv.) and 6N HCl$_{aq}$ (5 mL). The residue was purified by preparative HPLC (0.1-1% MeCN in water) and then by flash chromatography on DOWEX® ion exchange resin (eluent 0.1N ammonia in water) to give (after acidification with 2N HCl and subsequent lyophilization) corresponding product as a single diastereoisomer. (2.1 mg, 21%, white foam). ESI+MS: m/z=231.0 (M+1)$^+$. $^1$H NMR (700 MHz, Deuterium Oxide) δ 3.16 (dd, J=12.7, 4.4 Hz, 1H), 2.92 (dd, J=12.7, 11.0 Hz, 1H), 2.76-2.70 (m, 1H), 2.64 (ddt, J=14.0, 9.1, 2.8 Hz, 1H), 2.26 (dt, J=12.4, 6.2 Hz, 1H), 2.14-2.06 (m, 1H), 1.54-1.42 (m, 3H), 1.23 (td, J=12.7, 11.4 Hz, 1H), 0.77-0.71 (m, 2H).

The second mixture of diastereoisomers was obtained in the same way starting from: benzyl ((2-acetamido-2-(tert-butylcarbamoyl)-4-(2-(4,4,5,5-tetramethyl-1,3,2-dioxaborolan-2-yl)ethyl)cyclopentyl)methyl)carbamate (50 mg, 0.092 mmol, 1 equiv.) and 6N HCl$_{aq}$ (10 mL). The residue was purified by preparative HPLC (0.1-1% MeCN in water) and then by flash chromatography on DOWEX® ion exchange resin (eluent 0.1N ammonia in water) to give (after acidification with 2N HCl and subsequent lyophilization) corresponding product as a mixture of diastereoisomers, dr=1:1, (10.2 mg, 37%, white foam). ESI+MS: m/z=231.0 (M+1)$^+$. $^1$H NMR (700 MHz, Deuterium Oxide) δ 3.21-3.05 (m, 1H, two diastereoisomers), 2.96-2.87 (m, 1H), 2.87-2.69 (m, 1H, two diastereoisomers), 2.67-1.97 (in, 1H, two diastereoisomers), 2.29-1.87 (m, 1H, two diastereoisomers), 2.20-2.15 (m, 1H), 2.12-1.75 (m, 1H, two diastereoisomers), 1.57-1.16 (m, 3H), 0.77-0.69 (m, 2H).

The third mixture of diastereoisomers was obtained in the same way starting from: benzyl ((2-acetamido-2-(tert-butylcarbamoyl)-4-(2-(4,4,5,5-tetramethyl-1,3,2-dioxaborolan-2-yl)ethyl)cyclopentyl)methyl)carbamate, dr=9:1 (33 mg, 0.061 mmol, 1 equiv.) and 6N HCl$_{aq}$ (5 mL). The residue was purified by preparative HPLC (0.1-1% MeCN in water) and then by flash chromatography on DOWEX® ion exchange resin (eluent 0.1N ammonia in water) to give (after acidification with 2N HCl and subsequent lyophilization) corresponding product as a single diastereoisomer (1.5 mg, 8%, white solid). ESI+MS: m/z=231.05 (M+1)$^+$. $^1$H NMR (700 MHz, Deuterium Oxide) δ 3.18 (dd, J=12.7, 3.6 Hz, 1H), 2.89 (t, J=12.0 Hz, 1H), 2.46-2.40 (m, 1H), 2.23-2.14 (m, 1H), 2.14-2.01 (m, 3H), 1.45-1.37 (m, 2H), 1.33-1.21 (m, 1H), 0.71-0.61 (m, 2H).

Example 67. 1-amino-4-(2-boronoethyl)-2-((dimethylamino)methyl)cyclopentane-1-carboxylic acid

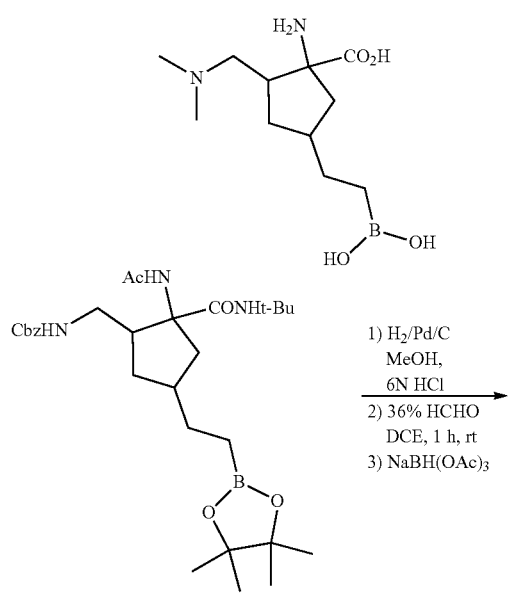

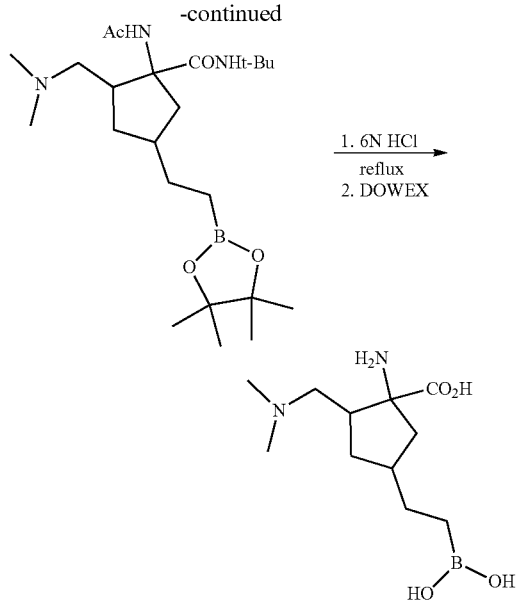

Step A. 1-acetamido-N-(tert-butyl)-2-((dimethylamino)methyl)-4-(2-(4,4,5,5-tetramethyl-1,3,2-dioxaborolan-2-yl)ethyl)cyclopentane-1-carboxamide

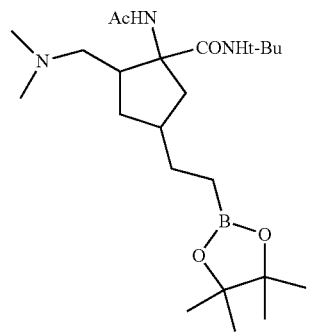

To benzyl ((2-acetamido-2-(tert-butylcarbamoyl)-4-(2-(4,4,5,5-tetramethyl-1,3,2-dioxaborolan-2-yl)ethyl)cyclopentyl)methyl)carbamate, dr=9:1, (33 mg, 0.061 mmol, 1 equiv.) in MeOH (2 mL) was added 3 drops of 6N HCl and the reaction mixture was degassed, then 25 mg Pd/C (wet 10%) was added. The mixture was degassed, charged with H$_2$, and stirred overnight. The mixture was filtered through a pad of Celite, washed with methanol (2×10 mL), the filtrate was concentrated in vacuo to give product as colorless oil (27 mg, 99.8%). ESI+MS: m/z=410.0 (M+1)$^+$. The crude product (27 mg, 0.061 mmol, 1 equiv.) was dissolved in 1,2-dichloroethane (1 mL) and added formaline (18 µL, 0.24 mmol, 4 equiv.). The mixture was stirred at room temperature for 1 h. Then sodium triacetoxyborohydride (52 mg, 0.24 mmol, 4 equiv.) was added to the reaction mixture and stirred at room temperature overnight. The mixture was diluted DCM (10 mL) and quenched by adding 1M NaOH (5 mL). The product was extracted with dichloromethane (2×10 mL). The combined organic phases were dried over MgSO$_4$, filtered, concentrated in vacuo and obtained 15 mg (57%) the crude product as colorless oil. It was used for the next step. ESI+MS: m/z=438.05 (M+1)$^+$.

Step B. 1-amino-4-(2-boronoethyl)-2-((dimethyl-amino)methyl)cyclopentane-1-carboxylic acid The title compound was obtained in the same manner like in Example 1, step C, using 1-acetamido-N-(tert-butyl)-2-((dimethylamino)methyl)-4-(2-(4,4,5,5-tetramethyl-1,3,2-dioxaborolan-2-yl)ethyl)cyclopentane-1-carboxamide (15 mg, 0.19 mmol, 1 equiv.) and 6 N HClaq (5 mL). The residue was purified by preparative HPLC (0.1-1% MeCN in water) and next flash chromatography on DOWEX® 50WX8 ion exchange resin (eluent 0.1 N ammonia in water) to give a desired product as a white solid (1.2 mg, 14%). ESI+MS: m/z=259.0 (M+1)$^+$.

Example 68. (5R)-2-(aminomethyl)-5-(2-borono-ethyl)-1-(methylamino)cyclohexane-1-carboxylic acid dihydrochloride

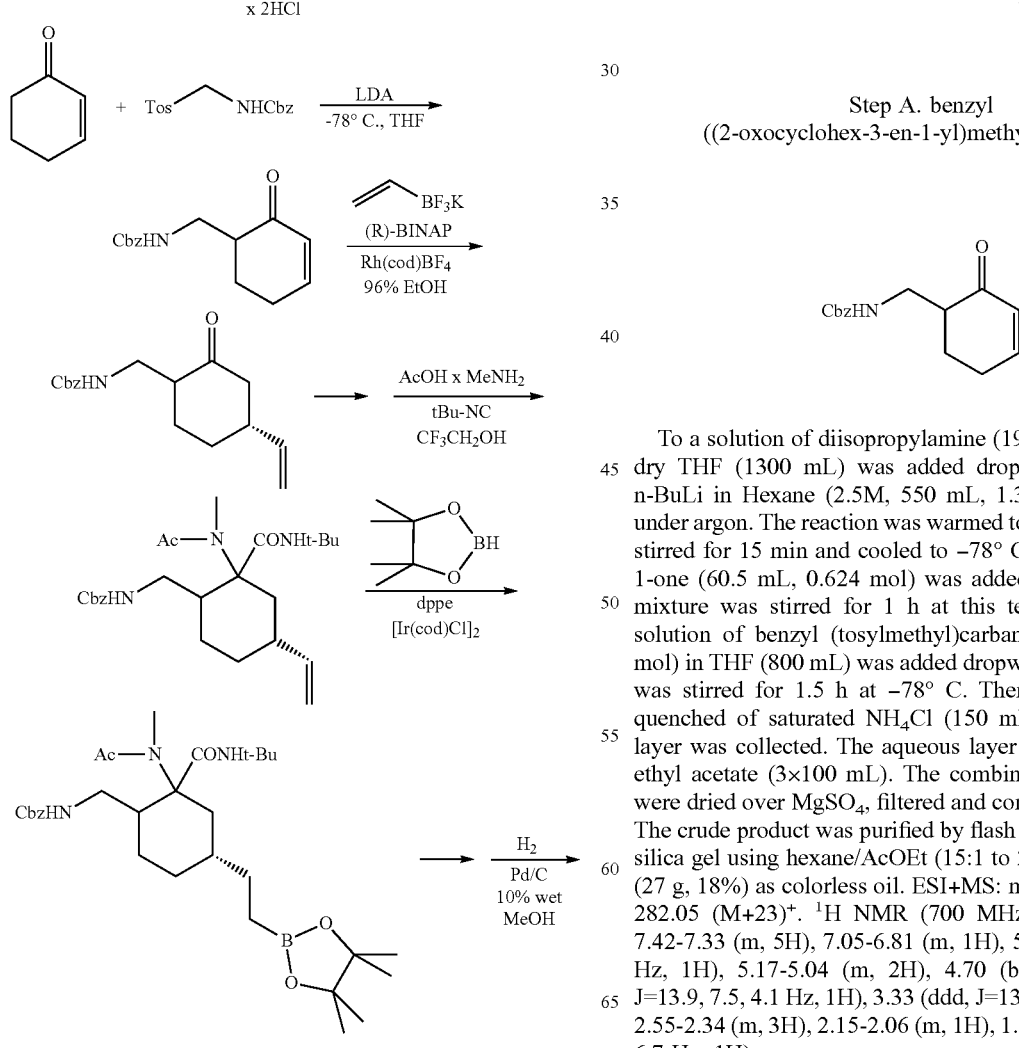

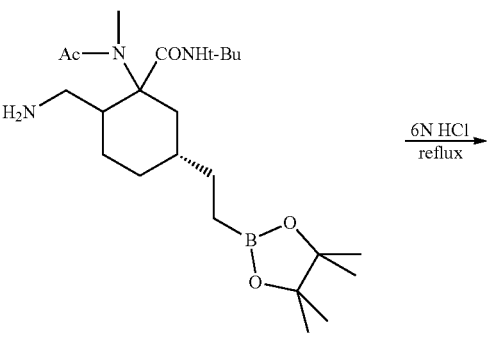

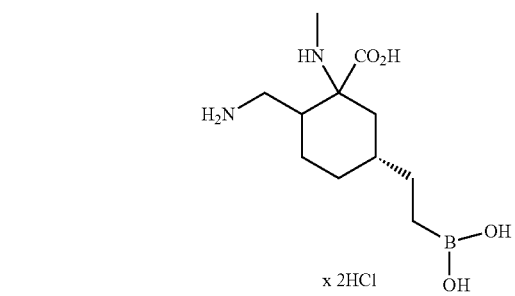

Step A. benzyl ((2-oxocyclohex-3-en-1-yl)methyl)carbamate

To a solution of diisopropylamine (192 mL, 1.37 mol) in dry THF (1300 mL) was added dropwise a solution of n-BuLi in Hexane (2.5M, 550 mL, 1.37 mol) at −78° C. under argon. The reaction was warmed to room temperature, stirred for 15 min and cooled to −78° C. A 2-cycloheksen-1-one (60.5 mL, 0.624 mol) was added dropwise and the mixture was stirred for 1 h at this temperature. Next a solution of benzyl (tosylmethyl)carbamate (219 g, 0.686 mol) in THF (800 mL) was added dropwise and the reaction was stirred for 1.5 h at −78° C. Then, the mixture was quenched of saturated NH$_4$Cl (150 mL) and the organic layer was collected. The aqueous layer was extracted with ethyl acetate (3×100 mL). The combined organic extracts were dried over MgSO$_4$, filtered and concentrated in vacuo. The crude product was purified by flash chromatography on silica gel using hexane/AcOEt (15:1 to 2:1) to give product (27 g, 18%) as colorless oil. ESI+MS: m/z=260.05 (M+1)$^+$, 282.05 (M+23)$^+$. $^1$H NMR (700 MHz, Chloroform-d) δ 7.42-7.33 (m, 5H), 7.05-6.81 (m, 1H), 5.99 (dt, J=10.0, 2.0 Hz, 1H), 5.17-5.04 (m, 2H), 4.70 (bs, 1H), 3.50 (ddd, J=13.9, 7.5, 4.1 Hz, 1H), 3.33 (ddd, J=13.3, 7.2, 5.4 Hz, 1H), 2.55-2.34 (m, 3H), 2.15-2.06 (m, 1H), 1.80 (tdd, J=13.4, 9.6, 6.7 Hz, 1H).

Step B. benzyl (((4R)-2-oxo-4-vinylcyclohexyl)methyl)carbamate

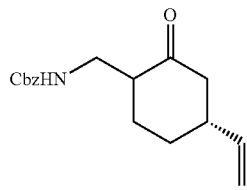 [SMILES: C=C[C@@H]1CCC(CNC(=O)OCc2ccccc2)C(=O)C1]

To a 50 mL round-bottomed flask were added Rh(cod)BF$_4$ (52 mg, 0.127 mmol), (R)-BINAP (79 mg, 0.127 mmol), and potassium vinyl trifluoroborate (1.03 g, 7.713 mmol). The flask was flushed with argon several times and degassed 96% EtOH (23 mL) and trimethylamine (55 µL, 0.386 mmol) were added. After stirring the resulting mixture for 10 min at room temperature, benzyl ((2-oxocyclohex-3-en-1-yl)methyl)carbamate (1.00 g, 3.86 mmol) was added and the reaction mixture was stirred for 2 h under reflux. The EtOH was evaporated. The residue was diluted ethyl acetate (50 mL) and washed with 1 M aqueous HCl (30 mL) and brine (30 mL), dried over MgSO$_4$, filtered and concentrated under reduced pressure. The crude product was purified by silica gel chromatography using hexane/AcOEt (13:1 to 5:1) to afford product as a white solid (overall yield: 460 mg, 44%). $[\alpha]_D$=+10.8 (c 0.250 in CHCl$_3$). ESI+MS: m/z=288.10 (M+1)$^+$, 310.10 (M+23)$^+$ $^1$H NMR (700 MHz, Chloroform-d) δ 7.38-7.28 (m, 5H), 5.78 (ddd, J=16.9, 10.4, 6.2 Hz, 1H), 5.39-5.29 (m, 1H), 5.05-4.98 (m, 2H), 3.37 (ddd, J=13.9, 7.6, 3.7 Hz, 1H), 3.24 (ddd, J=13.6, 7.7, 5.3 Hz, 1H), 2.45 (dd, J=4.0, 2.1 Hz, 1H), 2.44-2.37 (m, 1H), 2.22-2.16 (m, 1H), 2.15-2.09 (m, 1H), 2.00-1.92 (m, 1H), 1.60-1.55 (m, 3H), 1.43 (qd, J=13.2, 3.6 Hz, 1H).

Step C. benzyl (((4R)-2-(tert-butylcarbamoyl)-2-(N-methylacetamido)-4-vinylcyclohexyl)methyl)carbamate

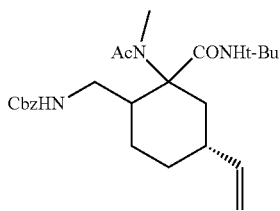

To the stirred solution of benzyl (((4R)-2-oxo-4-vinylcyclohexyl)methyl)carbamate (560 mg, 1.95 mmol) and methylammonium acetate (0.75 g, 7.80 mmol) in 2,2,2-trifluoroethanol (3 mL) tert-butyl isocyanide (0.66 mL, 5.85 mmol) was added dropwise via syringe and the resulting mixture was stirred at room temperature for 24 hours. After this time, 2,2,2-trifluoroethanol was evaporated and the residue was diluted ethyl acetate (10 mL) and washed with water (20 mL). The water was extracted with ethyl acetate (3×10 mL) and the organic layer was dried over MgSO$_4$, filtered and evaporated under reduced pressure. The crude product was purified by flash chromatography on silica gel using hexane/AcOEt (20:1 to 1:1) to give product as a white solid (95 mg, 11%). ESI+MS: m/z=444.30 (M+1)$^+$, 466.30 (M+23)$^+$. $^1$H NMR (700 MHz, Chloroform-d) δ 7.39-7.32 (m, 4H), 7.32-7.28 (m, 1H), 5.77 (ddd, J=17.0, 10.4, 6.4 Hz, 1H), 5.13-5.06 (m, 2H), 5.03 (d, J=17.2 Hz, 1H), 4.95 (dt, J=10.4, 1.4 Hz, 1H), 4.84 (br s, 1H), 3.56-3.29 (m, 2H), 3.01 (dt, J=13.9, 3.8 Hz, 1H), 2.88 (s, 3H), 2.40-2.27 (m, 1H), 2.16 (s, 3H), 1.99-1.88 (m, 1H), 1.78-1.67 (m, 1H), 1.58-1.54 (m, 1H), 1.50-1.36 (m, 2H), 1.31 (s, 9H), 1.27-1.23 (m, 2H).

Step D. benzyl (((4R)-2-(tert-butylcarbamoyl)-2-(N-methylacetamido)-4-(2-(4,4,5,5-tetramethyl-1,3,2-dioxaborolan-2-yl)ethyl)cyclohexyl)methyl)carbamate

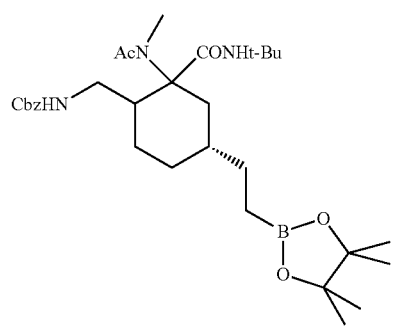

A mixture of dppe (4.8 mg, 0.012 mmol) and bis(1,5-cyclooctadiene)diiridium(I) dichloride (4.0 mg, 0.006 mmol) in dry dichloromethane (2 mL) was flushed with argon. Then the solution of benzyl (((4R)-2-(tert-butylcarbamoyl)-2-(N-methylacetamido)-4-vinylcyclohexyl)methyl)carbamate (90 mg, 0.204 mmol) and 4,4,5,5-tetramethyl-1,3,2-dioxaborolane (37 µl, 0.26 mmol) in DCM (2 mL) (flushed with argon) was added dropwise. The reaction mixture was stirred at room temperature overnight. After this time, the reaction was diluted DCM (10 mL) washed 5% NaHCO$_3$ (2×20 mL). The organic layer was dried over MgSO$_4$ and concentrated in vacuo. The crude product was used to the next step without further purification.

Step E. (5R)-2-(aminomethyl)-N-(tert-butyl)-1-(N-methylacetamido)-5-(2-(4,4,5,5-tetramethyl-1,3,2-dioxaborolan-2-yl)ethyl)cyclohexane-1-carboxamide

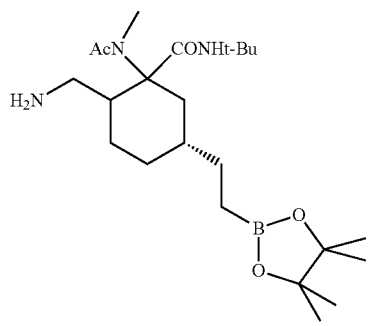

Benzyl (((4R)-2-(tert-butylcarbamoyl)-2-(N-methylacetamido)-4-(2-(4,4,5,5-tetramethyl-1,3,2-dioxaborolan-2-yl)ethyl)cyclohexyl)methyl)carbamate (115 mg, 0.20 mmol, 1 equiv.) was dissolved in 6 mL of MeOH and flushed with argon. Next, 10 mg of Pd/C wet 10% and 3 drops of 6N HCl were added and the resulting mixture was stirred under hydrogen atmosphere (balloon) for 3 h. Then, a mixture was filtered through the pad of Celite (washed several times with MeOH$_{abs}$) and solvent was evaporated. The residue was taken to the last step without further purification.

Step F. (5R)-2-(aminomethyl)-5-(2-boronoethyl)-1-(methylamino)cyclohexane-1-carboxylic acid dihydrochloride (5R)-2-(aminomethyl)-N-(tert-butyl)-1-(N-methylacetamido)-5-(2-(4,4,5,5-tetramethyl-1,3,2-dioxaborolan-2-yl)ethyl)cyclohexane-1-carboxamide (38 mg, 0.083 mmol) and 6 N HClaq (8 mL) was heated under reflux for 6 h. The reaction mixture was concentrated under reduced pressure and the residue was purified by ion exchange chromatography on DOWEX® and next by preparative HPLC (0.1-1% MeCN in water) to give (after acidification with 6M HCl) the desired product as a single diastereoisomers (6.2 mg, overall yield 22%).

The first diastereoisomer: 4.1 mg, white solid. ESI+MS: m/z=259.10 (M+1)$^+$, $^1$H NMR (700 MHz, Deuterium Oxide) δ 3.26 (dd, J=13.4, 10.3 Hz, 1H), 3.02 (dd, J=13.4, 3.9 Hz, 1H), 2.65 (s, 3H), 2.40-2.30 (m, 1H), 2.09-2.01 (m, 1H), 1.97-1.81 (m, 2H), 1.81-1.75 (m, 1H), 1.60 (dd, J=15.8, 13.1 Hz, 1H), 1.47 (tdd, J=9.5, 7.9, 4.3 Hz, 2H), 1.34 (dddq, J=16.7, 10.2, 7.1, 3.8, 3.3 Hz, 1H), 1.24-1.10 (m, 1H), 0.91-0.79 (m, 2H).

The second diastereoisomer: 2.1 mg, white solid. ESI+MS: m/z=259.05 (M+1)$^+$, $^1$H NMR (700 MHz, Deuterium Oxide) δ 3.29 (dd, J=13.4, 10.6 Hz, 1H), 3.03-2.99 (m, 1H), 2.68 (s, 3H), 2.47-2.35 (m, 1H), 2.14-2.06 (m, 1H), 1.97-1.81 (m, 2H), 1.81-1.72 (m, 1H), 1.64 (dd, J=15.9, 13.1 Hz, 1H), 1.48-1.39 (m, 2H), 1.37 (dddt, J=13.1, 10.0, 7.0, 3.4 Hz, 1H), 1.25-1.10 (m, 1H), 0.85-0.80 (m, 2H).

Example 69. (1R,2S,5R)-1-amino-5-(2-boronoethyl)-2-((ethyl(methyl)amino)methyl)cyclohexane-1-carboxylic acid

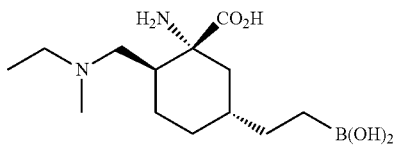 [SMILES: CCN(C)C[C@@H]1CC[C@@H](CCB(O)O)C[C@]1(N)C(=O)O]

Step A. (1R,2S,5R)-1-acetamido-N-(tert-butyl)-2-((ethyl(methyl)amino)methyl)-5-vinylcyclohexane-1-carboxamide

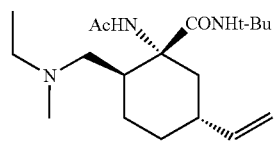

The title compound was obtained in the same manner like in Example 26, step A, using ethyl (1R,2R,4R)-2-acetamido-2-(tert-butylcarbamoyl)-4-vinylcyclohexane-1-carboxylate (Intermediate 2, 0.47 g, 1.38 mmol, 1 equiv.), DIBAL-H 1M in DCM (4.28 mL, 4.28 mmol, 3.1 equiv.), glacial acetic acid (0.39 mL, 6.90 mmol, 5 equiv.), N-ethylmethylamine (0.24 mL, 2.76 mmol, 2 equiv.), sodium triacetoxyborohydride (1.17 g, 5.52 mmol, 4 equiv.). The reaction mixture was washed with 1M KHSO$_4$ (30 mL). Next the aqueous solution was alkalized to pH 12 with the use of 1M NaOH and product was extracted to DCM (5×30 mL). Combined organic layer was washed with brine, dried over MgSO$_4$, filtered and concentrated in vacuo. The desired product was obtained as a single diastereoisomer (239 mg, 51%, white solid). ESI+MS: m/z=338.1 (M+1)$^+$. [α]$_D$=+42.3 (c 0.250 in CHCl$_3$). $^1$H NMR (700 MHz, Chloroform-d) δ 10.47 (s, 1H), 8.28 (s, 1H), 5.72 (ddd, J=17.1, 10.4, 6.5 Hz, 1H), 4.97 (dt, J=17.3, 1.5 Hz, 1H), 4.91 (d, J=10.4 Hz, 1H), 3.51 (t, J=11.7 Hz, 1H), 3.21 (d, J=13.2 Hz, 1H), 2.58-2.48 (m, 1H), 2.37-2.26 (m, 1H), 2.24 (s, 3H), 2.16 (dq, J=13.2, 3.5 Hz, 1H), 2.11-2.04 (m, 1H), 2.00 (d, J=14.2 Hz, 1H), 1.90 (s, 3H), 1.80 (d, J=13.2 Hz, 1H), 1.58-1.50 (m, 1H), 1.39-1.33 (m, 1H), 1.32 (s, 9H), 1.21-1.12 (m, 2H), 1.10-1.01 (m, 3H).

Step B. ((1R,2S,5R)-1-acetamido-N-(tert-butyl)-2-((ethyl(methyl)amino)methyl)-5-(2-(4,4,5,5-tetramethyl-1,3,2-dioxaborolan-2-yl)ethyl)cyclohexane-1-carboxamide and (2-((1R,3R,4S)-3-acetamido-3-(tert-butylcarbamoyl)-4-((ethyl(methyl)amino)methyl)cyclohexyl)ethyl)boronic acid

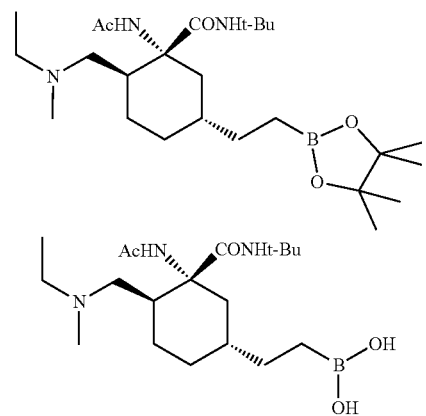

The title compounds were obtained in the same manner like in Example 26, step B, using (1R,2S,5R)-1-acetamido-N-(tert-butyl)-2-((ethyl(methyl)amino)methyl)-5-vinylcyclohexane-1-carboxamide (232 mg, 0.69 mmol, 1 equiv.), dppe (16 mg, 41.0 μmol, 0.06 equiv.), bis(1,5-cyclooctadiene)diiridium(I) dichloride (14 mg, 20.5 μmol, 0.03 equiv.), 4,4,5,5-tetramethyl-1,3,2-dioxaborolane (249 μL, 1.72 mmol, 2.5 equiv.) and DCM (12 mL). The crude product was purified by column chromatography on silica gel (gradient elution, DCM/MeOH 1:0 to 2:1) to give the corresponding products (303 mg, 95%).

((1R,2S,5R)-1-acetamido-N-(tert-butyl)-2-((ethyl (methyl)amino)methyl)-5-(2-(4,4,5,5-tetramethyl-1,3,2-dioxaborolan-2-yl)ethyl)cyclohexane-1-carboxamide: 120 mg, sticky, pale yellow solid. ESI+MS: m/z=466.1 (M+1)$^+$. $^1$H NMR (700 MHz, Chloroform-d) δ 10.51-10.40 (m, 1H), 8.35-8.23 (m, 1H), 3.58-3.47 (m, 1H), 3.24-3.14 (m, 1H), 2.57-2.47 (m, 1H), 2.35-2.25 (m, 1H), 2.25-2.21 (m, 3H), 2.12-2.04 (m, 1H), 2.01-1.95 (m, 1H), 1.91-1.85 (m, 3H), 1.81-1.73 (m, 1H), 1.57-1.48 (m, 1H), 1.36-1.27 (m, 11H), 1.26-1.20 (m, 15H), 1.08-1.03 (m, 3H), 1.00-0.91 (m, 1H), 0.87 (t, J=7.2 Hz, 1H), 0.83-0.69 (m, 1H).

During the purification on silica gel column chromatography pinacolboronate ester was partially deprotected to give a free boronic acid, (2-((1R,3R,4S)-3-acetamido-3-(tert-butylcarbamoyl)-4-((ethyl(methyl)amino)methyl)cyclohexyl)ethyl)boronic acid: 183 mg, sticky, pale yellow solid. ESI+MS: m/z=384.0 (M+1)+.

Step C. (1R,2S,5R)-1-amino-5-(2-boronoethyl)-2-((ethyl(methyl)amino)methyl)cyclohexane-1-carboxylic acid The title compound was obtained in the same manner like in Example 26, step C, using mixture of ((1R,2S,5R)-1-acetamido-N-(tert-butyl)-2-((ethyl(methyl)amino)methyl)-5-(2-(4,4,5,5-tetramethyl-1,3,2-dioxaborolan-2-yl)ethyl)cyclohexane-1-carboxamide and (2-((1R,3R,4S)-3-acetamido-3-(tert-butylcarbamoyl)-4-((ethyl(methyl)amino)methyl)cyclohexyl)ethyl)boronic acid (178 mg), 6 N HCl$_{aq}$ (20 mL). The crude product was purified by preparative HPLC (0.1-1.0% MeCN in water) and next by flash chromatography on DOWEX® 50WX8 ion exchange resin (eluent 0.1 N ammonia in water) to give (after lyophilization) a desired product as a white solid (25 mg, 23%). ESI+MS: m/z=287.1 (M+1)+. $[\alpha]_D$=−41.6 (c=0.125 in H$_2$O). $^1$H NMR (700 MHz, Deuterium Oxide) δ 3.16 (dd, J=13.2, 9.7 Hz, 1H), 3.04-2.98 (m, 1H), 2.92-2.82 (m, 2H), 2.63 (s, 3H), 2.11-2.06 (m, 1H), 1.91-1.83 (m, 2H), 1.74 (dq, J=12.9, 3.7 Hz, 1H), 1.65-1.56 (m, 2H), 1.37-1.26 (m, 2H), 1.22 (t, J=7.2 Hz, 3H), 1.09 (t, J=12.7, 3.9 Hz, 1H), 0.98 (dq, J=12.7, 3.9 Hz, 1H), 0.79 (t, J=8.3 Hz, 2H).

Example 70. (1R,2S,5R)-1-amino-5-(2-boronoethyl)-2-(piperidin-1-ylmethyl)cyclohexane-1-carboxylic acid

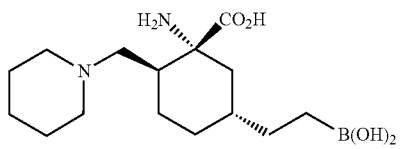 [SMILES: N[C@]1(C(=O)O)C[C@H](CCB(O)O)CC[C@H]1CN1CCCCC1]

Step A. (1R,2S,5R)-1-acetamido-N-(tert-butyl)-2-(piperidin-1-ylmethyl)-5-vinylcyclohexane-1-carboxamide

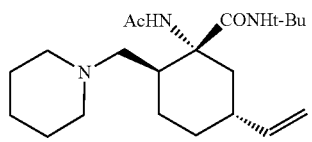

The title compound was obtained in the same manner like in Example 26, step A, using ethyl (1R,2R,4R)-2-acetamido-2-(tert-butylcarbamoyl)-4-vinylcyclohexane-1-carboxylate (Intermediate 2, 0.2 g, 0.59 mmol, 1 equiv.), DIBAL-H 1M in DCM (1.83 mL, 1.83 mmol, 3.1 equiv.), glacial acetic acid (0.17 mL, 2.95 mmol, 5 equiv.), piperidine (0.117 mL, 1.18 mmol, 2 equiv.), sodium triacetoxyborohydride (0.5 g, 2.36 mmol, 4 equiv.). The crude product was purified by silica gel flash chromatography (DCM/MeOH, 70:1 to 25:1) to give corresponding product as a single diastereoisomer (0.123 g, 57%, colorless oil). ESI+MS: m/z=364.20 (M+1)+. $[\alpha]_D$=+32.1 (c=0.250 in CHCl$_3$). $^1$H NMR (700 MHz, Chloroform-d) δ 10.45 (s, 1H), 8.26 (s, 1H), 5.74 (ddd, J=17.1, 10.4, 6.5 Hz, 1H), 5.07-4.85 (m, 2H), 3.46-3.19 (m, 2H), 2.69-2.55 (m, 1H), 2.39-2.24 (m, 1H), 2.26-2.06 (m, 2H), 1.99 (s, 3H), 1.82 (dt, J=13.0, 2.0 Hz, 1H), 1.69-1.45 (m, 7H), 1.38 (dt, J=6.7, 2.1 Hz, 2H), 1.35 (s, 9H), 1.32-1.22 (m, 2H), 1.22-1.10 (m, 2H).

Step B. (1R,2S,5R)-1-acetamido-N-(tert-butyl)-2-(piperidin-1-ylmethyl)-5-(2-(4,4,5,5-tetramethyl-1,3,2-dioxaborolan-2-yl)ethyl)cyclohexane-1-carboxamide

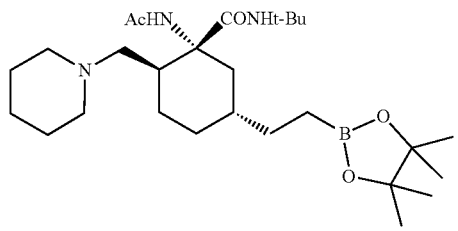

The title compound was obtained in the same manner like in Example 26, step B, using (1R,2S,5R)-1-acetamido-N-(tert-butyl)-2-(piperidin-1-ylmethyl)-5-vinylcyclohexane-1-carboxamide (0.12 g, 0.33 mmol, 1 equiv.), dppe (8 mg, 0.02 mmol, 0.06 equiv.), bis(1,5-cyclooctadiene)diiridium(I) dichloride (6.7 mg, 0.01 mmol, 0.03 equiv.), 4,4,5,5-tetramethyl-1,3,2-dioxaborolane (77 μL, 0.5 mmol, 1.5 equiv.) and DCM (4 mL). The crude product was purified by column chromatography on silica gel (gradient elution, DCM/MeOH 30:1 to 10:1) to give corresponding products as colorless oil (116 mg, 71%). ESI+MS: m/z=492.05 (M+1)+. $^1$H NMR (700 MHz, Chloroform-d) δ 10.43 (s, 1H), 8.32 (s, 1H), 3.38 (dd, J=13.7, 10.6 Hz, 1H), 3.26-3.16 (m, 1H), 2.83-2.45 (m, 2H), 2.35-2.21 (m, 1H), 2.13-2.05 (m, 2H), 1.99 (d, J=1.5 Hz, 1H), 1.98 (s, 3H), 1.79 (d, J=12.8 Hz, 2H), 1.62-1.46 (m, 7H), 1.33 (s, 9H), 1.28 (d, J=9.9 Hz, 2H), 1.25 (s, 12H), 1.01-0.86 (m, 3H), 0.86-0.70 (m, 2H).

Step C. (1R,2S,5R)-1-amino-5-(2-boronoethyl)-2-(piperidin-1-ylmethyl)cyclohexane-1-carboxylic acid The title compound was obtained in the same manner like in Example 26, step C, using (1R,2S,5R)-1-acetamido-N-(tert-butyl)-2-(piperidin-1-ylmethyl)-5-(2-(4,4,5,5-tetramethyl-1,3,2-dioxaborolan-2-yl)ethyl)cyclohexane-1-carboxamide (110 mg, 0.22 mmol, 1 equiv.), 6 N HCl$_{aq}$(10 mL). The crude product was purified by preparative HPLC (0.1-1% MeCN in water) and next flash chromatography on DOWEX® 50WX8 ion exchange resin (eluent 0.1 N ammonia in water) to give (after lyophilization) a desired product as a white solid (14 mg, 20%). ESI+MS: m/z=313.05 (M+1)+. $[\alpha]_D$=+39.1 (c=0.125 in H$_2$O). $^1$H NMR (700 MHz, Deuterium Oxide) δ 3.17-2.60 (m, 6H), 2.00 (ddd, J=13.0, 3.5, 1.9 Hz, 1H), 1.85-1.70 (m, 2H), 1.71-1.34 (m, 9H), 1.25-1.15 (m, 2H), 0.98 (t, J=12.6 Hz, 1H), 0.90-0.78 (m, 1H), 0.70-0.61 (m, 2H).

Example 71. (1R,2S,5R)-1-amino-5-(2-borono-ethyl)-2-(pyrrolidin-1-ylmethyl)cyclohexane-1-carboxylic acid

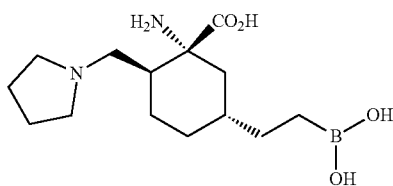 [SMILES: N[C@]1(C(=O)O)C[C@H](CCB(O)O)CC[C@H]1CN1CCCC1]

The title compound was obtained in the same manner like in Example 23 (Step A to C) but starting from enantiomerically pure Intermediate 2 (>99% e.e.). The crude product after hydrolysis was purified by preparative HPLC (0.1-1% MeCN in water) and next flash chromatography on DOWEX® 50WX8 ion exchange resin (eluent 0.1 N ammonia in water) to give (after lyophilization) a desired product as a white solid (0.46 g, 53%, after step C). ESI+MS: m/z=298.80 (M+1)$^+$. $[\alpha]_D$=−49.3 (c=0.125 in H$_2$O). $^1$H NMR (700 MHz, Deuterium Oxide) δ 3.18 (dd, J=13.2, 7.5 Hz, 1H), 3.10 (d, J=6.6 Hz, 4H), 3.00 (dd, J=13.2, 5.6 Hz, 1H), 1.99 (ddd, J=12.9, 3.4, 1.9 Hz, 1H), 1.93-1.87 (m, 4H), 1.81-1.73 (m, 1H), 1.70 (qd, J=7.7, 5.8 Hz, 1H), 1.61 (ddt, J=10.9, 8.1, 3.6 Hz, 2H), 1.48 (ddh, J=12.3, 9.6, 3.2 Hz, 1H), 1.30-1.15 (m, 2H), 0.95 (t, J=12.6 Hz, 1H), 0.92-0.81 (m, 1H), 0.74-0.59 (m, 2H).

Human Arginase Activity Assay

An enzymatic assay with recombinant human arginases 1 (Biolegend, Cat. No. 552502) and 2 (homemade in eukaryotic expression system of CHO, purified by FPLC) was used in order to assess inhibitory activity of the compounds. The assay was run in the 96-well plate format, each reaction in the total volume of 100 uL. The assay is based on urea measurement, which is a product of L-arginine enzymatic degradation. (Baggio et al. *J Pharmacol. Exp. Ther.* 1999, 290, 1409-1416). The color product is developed by adding a mixture of reagent A (4 mM oPA in 50 mM boric acid in 1M sulfuric acid, 0.03% Brij-35) and reagent B (4 mM NED in 50 mM boric acid in 1M sulfuric acid, 0.03% Brij-35) in equal proportions. The absorbance for each well was measured at 530 nm.

Briefly, to each well of a 96-well microtiter plate 40 μL of enzyme in the reaction assay buffer (pH 7.4, 100 mM sodium phosphate buffer, 130 mM NaCl, 1 mg/mL albumin), 50 μL of the test compound solution and 10 μL of enzyme substrate solution (L-arginine hydrochloride, natural pH 5.6, final concentration 20 mM and a cofactor—manganese chloride, final concentration 150 μM) was added. For positive control, only the enzyme and substrate were used, the negative controls contained substrate solution with assay buffer. After incubating the microtiter plate at 37° C. for 60 min 150 μL of mixed reagents A and B was added to each well to stop the reaction. Absorbance was measured (λ=530 nm) 20 minutes later, after color development. The urea production in the absence of any compound was considered the maximum arginase activity. The absorbance in the absence of arginase (background) was subtracted from all the values. The normalized OD was used to generate a concentration-response curve by plotting the percent of inhibition against log[concentration] of the compound and using regression analysis (GraphPad Prism 7.0) to compute the IC$_{50}$ values.

The IC$_{50}$ values were calculated using GraphPad Prism and divided into the following classes: A=1-100 nM; B=100-1000 nM; C=1-10 μM; D=10-100 μM; and E>100 μM.

The inhibitory activity of the exemplary compounds according to the invention was presented in Table 1.

To illustrate the superior cellular activity of the compounds according to the invention over known arginase inhibitors the selected compounds and comparative examples 1-3 were tested also in cell-based assay using murine primary macrophages.

Cell-Based Assay

Efficacy of Selected Examples Towards Intracellular Arginase in Macrophages Isolated from Murine Bone Marrow—Bone Marrow Derived Macrophages (BMDM)

Background: Macrophages are the most specialized phagocytic cells, and acquire specific phenotype and function in response to a variety of external triggers as a consequence of adaptation to local tissue environmental cues. Th1 pro-inflammatory cytokines such as IL-2, IL-12, IFNγ, TNFα and β, lead to the activation of macrophages towards the so-called classical inflammatory phenotype (CAMs or M1 macrophages). On the other hand, Th2 cytokines such as IL-4 and IL-13 as well as anti-inflammatory molecules like IL-10 and TGFβ activate macrophages towards an alternative phenotype (AAMs or M2 macrophages) (Murray and Wynn 2011, Nat Rev Immunol 11(11): 723-737. Hoeksema, Stoger et al. 2012, Curr Atheroscler Rep 14(3): 254-263). The M1/M2 macrophages use different metabolic pathways for arginine degradation. The preference of macrophages to metabolize arginine via nitric oxide synthase (NOS) to NO and citrulline or via arginase to omithine and urea defines them as M1 (NOS) or M2 (arginase) respectively (Mills 2012, *Crit Rev Immunol* 32(6): 463-488).

Macrophages are a dominant leukocyte population infiltrating the tumor and play critical role in modulating the tumor microenvironment. It has been shown that tumor-associated macrophages (TAMs) exhibit similar phenotype to M2 macrophages and their accumulation in tumor correlates with a poor clinical outcome (Chanmee, Ontong et al. 2014, Cancers (Basel) 6(3): 1670-1690).

Murine bone-marrow derived or peritoneal macrophages comprise convenient in vitro model that enables differentiation of these cells towards M1 or M2 macrophages and further use for the study.

Materials & Methods: The assay was performed according to modified literature protocol modification (Pineda-Torra I et al., Methods Mol Biol. 2015; 1339:101-9. Mia S et al. Scand J Immunol. 2014 May; 79(5):305-14). The femurs and tibias were isolated from Balb/c mice. Bones were cleaned from all attached tissues by using sterile swab without affecting the bone structure. Bones were sterilized by immersion in 70% ethanol for 5 min and then rinsed in PBS. The sides of the bones were cut off and flush with cold sterile PBS by using 26-G needle S into a 50 mL sterile tube with a cell strainer (Falcon™, Cat. No. U00149), until bone cavity appeared white. Then the cells were centrifuged (5 min at 500×G, 4° C.), washed twice with PBS and counted. Cells were plated in Petri dish in density of 1×10$^6$/mL and cultured in DMEM (Gibco, Cat. No. 31331-029) with 10% FBS, 1% pen-strep and 50 ng/mL M-CSF (PeproTech, Cat. No. 315-02), (37° C., 5% CO$_2$). After five days cells were subcultured into P96 plate (BD, Cat. No. 353072) in density of 64 000 cells/well in medium supplemented with 50 ng/mL M-CSF and 20 ng/mL IL-4 (Biomibo Cat. No. 214-1). One day later exemplary compounds (dissolved in PBS) were added in several different concentrations and 24 hours later the level of urea was measured in each well (Jung D et al., Clin Chem. 1975, 21(8):1136-40). The concentration of urea in the absence of any compound was considered as the maximum. The absorbance of cell culture media (background) was subtracted from all the values.

The IC$_{50}$ values were calculated using GraphPad Prism 7.0 and divided into the following classes: A=1-100 nM; B=100-1000 nM; C=1-10 μM; D=10-100 μM; and E>100 μM. For selected examples the activity class for ARG2 was estimated based on % of inhibition for 1 μM and 100 μM concentration of tested compounds.

The inhibitory activity of the exemplary compounds according to the invention was presented in Table 1.

TABLE 1

| Ex. No. | Structure | Activity Class (ARG I) | Activity Class (ARG II) | Activity Class (BMDM) |
|---|---|---|---|---|
| Comparative example 1 (WO1999019295) | [structure] x HCl | B | C | C |
| Comparative example 2 (US20140371175) | [structure] x 2HCl | A | B | C |
| Comparative example 3 (US20140371175) | [structure] x 2HCl | A | B | C |
| 1 | [structure] x HCl | C* | C* | NT |
| 2 | [structure] x HCl | E* | E* | NT |
| 3 | [structure] x HCl | E* | E* | NT |

TABLE 1-continued
| Ex. No. | Structure | Activity Class (ARG I) | Activity Class (ARG II) | Activity Class (BMDM) |
|---|---|---|---|---|
| 4 | 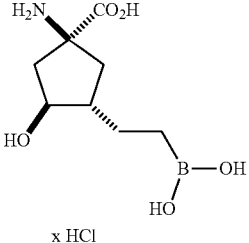 [SMILES: N[C@@]1(C(=O)O)C[C@H](CCB(O)O)[C@@H](O)C1] x HCl | D | D | NT |
| 5 | 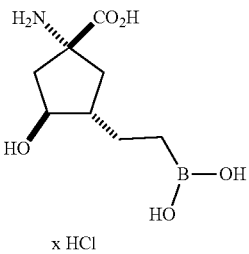 [SMILES: N[C@]1(C(=O)O)C[C@H](CCB(O)O)[C@@H](O)C1] x HCl | E | E | NT |
| 6 | 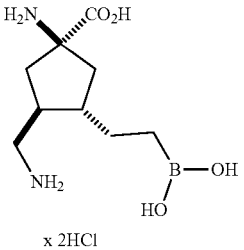 [SMILES: NC[C@H]1C[C@](N)(C(=O)O)C[C@@H]1CCB(O)O] x 2HCl | C | C | NT |
| 7 | 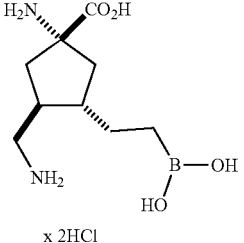 [SMILES: NC[C@H]1C[C@@](N)(C(=O)O)C[C@@H]1CCB(O)O] x 2HCl | C | NT | NT |
| 8 | 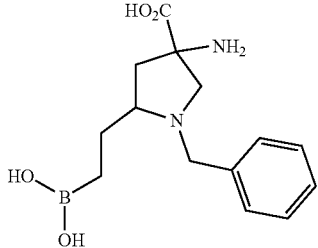 x2 HCl | E | NT | NT |

TABLE 1-continued
| Ex. No. | Structure | Activity Class (ARG I) | Activity Class (ARG II) | Activity Class (BMDM) |
|---|---|---|---|---|
| 9 | 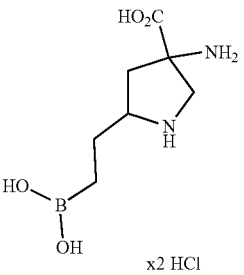 [SMILES: NC1(C(=O)O)CNC(CCB(O)O)C1] x2 HCl | E | E | NT |
| 10 | 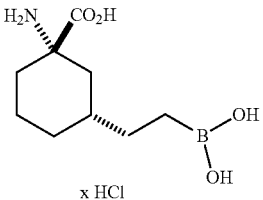 x HCl | C | C | D |
| 11 | 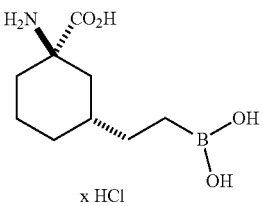 x HCl | D | NT | NT |
| 12 | 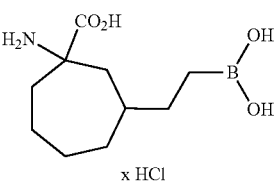 [SMILES: NC1(C(=O)O)CCCCC(CCB(O)O)C1] x HCl | E* | E* | NT |
| 13 | 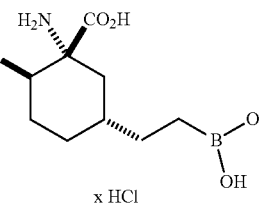 x HCl | B | D | NT |
| 14 | 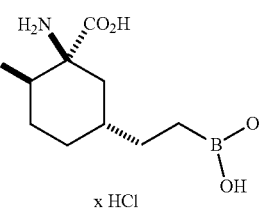 x HCl | D | NT | NT |
| 15 | 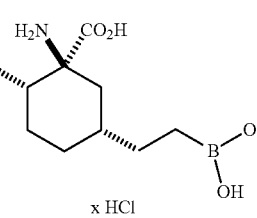 x HCl | E | E | NT |

TABLE 1-continued
| Ex. No. | Structure | Activity Class (ARG I) | Activity Class (ARG II) | Activity Class (BMDM) |
|---|---|---|---|---|
| 16 | 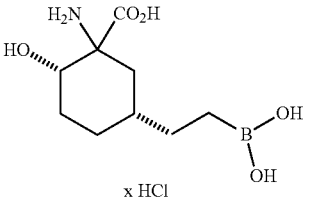 [SMILES: NC1(C(=O)O)C[C@H](CCB(O)O)CC[C@@H]1O] x HCl | D | D | NT |
| 17 | 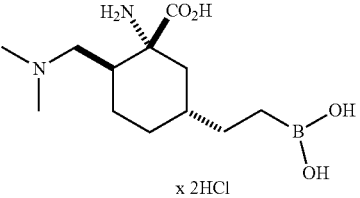 x 2HCl | A | NT | NT |
| 18 | 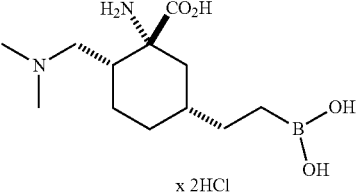 x 2HCl | B | C | B |
| 19 | 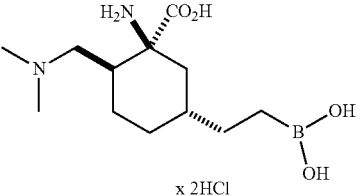 x 2HCl | C | C | NT |
| 20 | 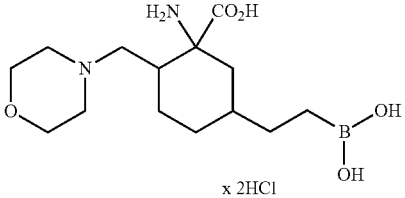 [SMILES: NC1(C(=O)O)CC(CCB(O)O)CCC1CN1CCOCC1] x 2HCl | C | NT | NT |
| 21 | 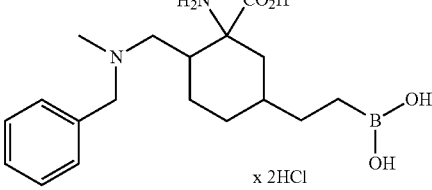 x 2HCl | B | C | NT |
| 22 | 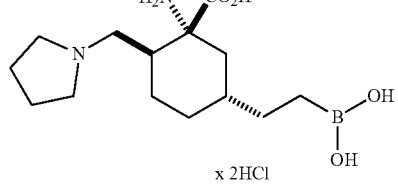 x 2HCl | A | B | B |

TABLE 1-continued

| Ex. No. | Structure | Activity Class (ARG I) | Activity Class (ARG II) | Activity Class (BMDM) |
|---|---|---|---|---|
| 23 | [structure] x 2HCl | A | NT | NT |
| 24 | [structure] x 2HCl | A | B | D |
| 25 | [structure] x 2HCl | A* | NT | NT |
| 26 | [structure] x 2HCl | B | B | C |
| 27 | [structure] x 2HCl | B | NT | NT |
| 28 | [structure] x 2HCl | B | B | D |
| 29 | [structure] x 2HCl | B | NT | NT |

TABLE 1-continued

| Ex. No. | Structure | Activity Class (ARG I) | Activity Class (ARG II) | Activity Class (BMDM) |
|---|---|---|---|---|
| 30 | [structure with diethylaminomethyl group] × 2HCl | B | B | B |
| 31 | [structure with piperidinylmethyl group] × 2HCl | A | B | A |
| 32 | [structure with N-isopropyl-N-methylaminomethyl group] | B | NT | B |
| 33 | [structure with tert-butylaminomethyl group] × 2HCl | A | NT | B |
| 34 | [structure with azabicyclic aminomethyl group] × 2HCl | A | NT | B |
| 35 | [structure with tetrahydroisoquinolinylmethyl group] × 2HCl | B | C | D |
| 36 | [structure with 2,2,2-trifluoroethylaminomethyl group] × 2HCl | E | B | NT |

TABLE 1-continued

| Ex. No. | Structure | Activity Class (ARG I) | Activity Class (ARG II) | Activity Class (BMDM) |
|---|---|---|---|---|
| 37 | [Structure: cyclohexane with H2N, CO2H, CH2-N(Me)(4-methoxyphenyl), and CH2CH2-B(OH)2 groups; x 2HCl] | C | C | NT |
| 38 | [Structure: cyclohexane with H2N, CO2H, CH2-NMe2, and CH2CH2-B(OH)2 groups] | A | A | A |
| 39 | [Structure: cyclohexane with H2N, CO2H, CH2-NHMe, and CH2CH2-B(OH)2 groups; x 2HCl] | A | A | B |
| 40 | [Structure: cyclohexane with H2N, CO2H, CH2-N(Me)(phenyl), and CH2CH2-B(OH)2 groups; x 2HCl] | C | C | NT |
| 41 | [Structure: cyclohexane with H2N, CO2H, CH2-NMe2, and CH2CH2-B(OH)2 groups; x 2HCl] | D | NT | NT |
| 42 | [Structure: cyclohexane with H2N, CO2H, CH(wavy)-NMe2, and CH2CH2-B(OH)2 groups; x 2HCl] | D | NT | NT |
| 43 | [Structure: cyclohexane with H2N, CO2Me, CH2-NMe2, and CH2CH2-B(OH)2 groups; x2HCl] | D | NT | NT |

TABLE 1-continued

| Ex. No. | Structure | Activity Class (ARG I) | Activity Class (ARG II) | Activity Class (BMDM) |
| --- | --- | --- | --- | --- |
| 44 | (structure) x2HCl | A | A | A |
| 45 | (structure) x 2HCl | A | B | A |
| 46 | (structure) x 2HCl | A* | A* | B |
| 47 | (structure) x 2HCl | B* | A* | NT |
| 48 | (structure) x2HCl | B* | B* | D* |
| 49 | (structure) x HCl | C | NT | NT |
| 50 | (structure) x HCl | B | B | D |

TABLE 1-continued
| Ex. No. | Structure | Activity Class (ARG I) | Activity Class (ARG II) | Activity Class (BMDM) |
|---|---|---|---|---|
| 51 | 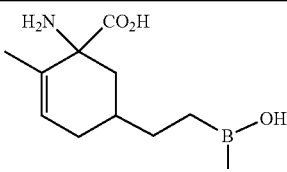 x HCl | B | C | NT |
| 52 | 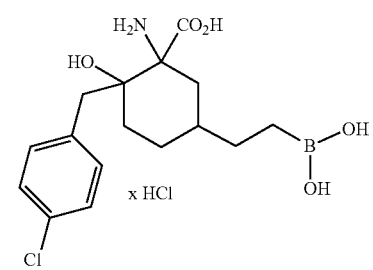 [SMILES: NC1(C(=O)O)CC(CCB(O)O)CCC1(O)Cc1ccc(Cl)cc1] x HCl | D* | D* | NT |
| 53 | 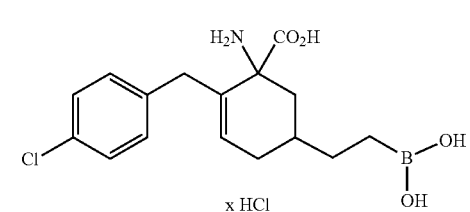 [SMILES: NC1(C(=O)O)CC(CCB(O)O)CC=C1Cc1ccc(Cl)cc1] x HCl | B | C | C |
| 54 | 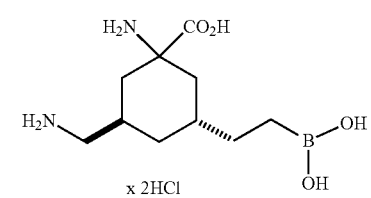 [SMILES: NC[C@@H]1C[C@@H](CCB(O)O)CC(N)(C(=O)O)C1] x 2HCl | B* | C* | D* |
| 55 | 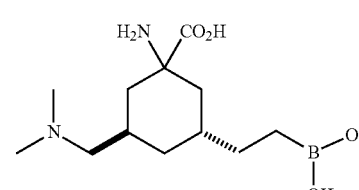 x 2HCl | C | NT | NT |
| 56 | 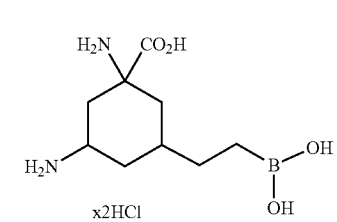 [SMILES: NC1CC(CCB(O)O)CC(N)(C(=O)O)C1] x2HCl | C* | B* | E* |
| 57 | 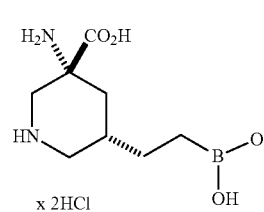 x 2HCl | C | NT | D |

TABLE 1-continued

| Ex. No. | Structure | Activity Class (ARG I) | Activity Class (ARG II) | Activity Class (BMDM) |
|---|---|---|---|---|
| 58 | (structure) | D | NT | NT |
| 59 | (structure) | C | C | NT |
| 60 | (structure) x HCl | D | NT | NT |
| 61 | (structure) x HCl | B | C | C |
| 62 | (structure) x 2HCl | C* | B* | D* |
| 63 | (structure) x HCl | C* | D* | NT |
| 64 | (structure) x 2HCl | D* | NT | NT |

TABLE 1-continued
| Ex. No. | Structure | Activity Class (ARG I) | Activity Class (ARG II) | Activity Class (BMDM) |
|---|---|---|---|---|
| 65 | 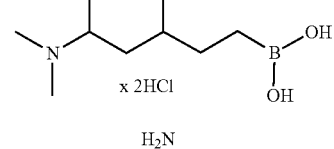 x 2HCl | D* | D* | E* |
| 66 | 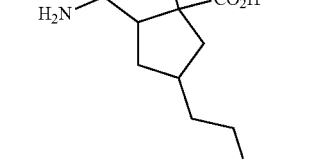 x 2HCl | B* | NT | NT |
| 67 | 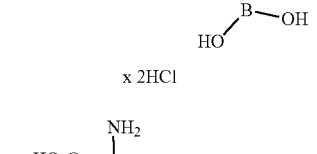 | D | NT | NT |
| 68 | 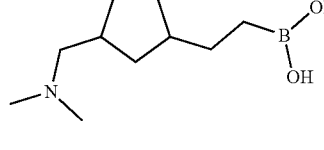 x 2HCl | D* | D* | D* |
| 69 | 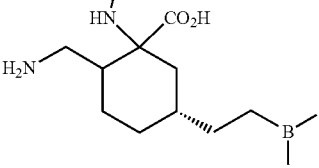 | A | A | B |
| 70 | 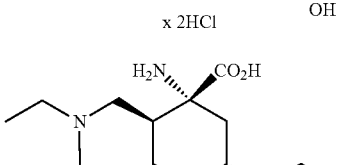 | A | B | A |
| 71 | 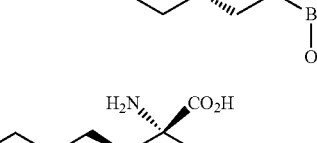 | A | A | A |
*The value for the most potent diastereoisomer or the mixture of diastereoisomers.

It should be noted that selected compound from the compounds of the invention showed promising in vivo efficacy in tumor xenografts models in mice and rats (CT26 colon carcinoma, B16F10 melanoma, LLC Lewis lung carcinoma, C6 brain glioma). Compound was administered orally or intraperitoneally in dosage 10-50 mg/kg (body weight), twice daily. Tumor growth inhibition ranged from 31% to 53%.

INCORPORATION BY REFERENCE

All U.S. patents, U.S. published patent applications, and PCT published patent application designating the U.S. mentioned herein are hereby incorporated by reference in their entirety as if each individual publication or patent was specifically and individually indicated to be incorporated by reference. In case of conflict, the present application, including any definitions herein, will control.

EQUIVALENTS

The foregoing written specification is sufficient to enable one skilled in the art to practice the invention. The present invention is not to be limited in scope by the examples provided, since each of the examples is intended as a single illustration of one aspect of the invention—other functionally equivalent embodiments are within the scope of the invention. Various modifications of the invention in addition to those shown and described herein will become apparent to those skilled in the art from the foregoing description and fall within the scope of the appended claims. All of the many advantages and objects of the invention are not necessarily encompassed by each embodiment of the invention.

What is claimed is:

1. A compound of the formula:

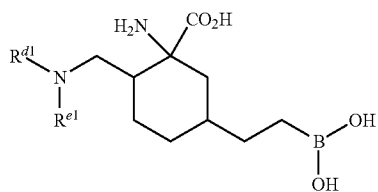

or a pharmaceutically acceptable salt thereof
wherein
$R^{d1}$ and $R^{e1}$ are each independently selected from hydrogen, methyl, or ethyl,
or $R^{d1}$ and $R^{e1}$ combine with the nitrogen atom to which they are attached to form an azetidinyl, pyrrolidinyl, piperidinyl, (7-azabicyclo[2.2.1]heptyl), morpholinyl, (4,4-dimethylpiperidinyl), isoindolinyl, (4-chlorophenyl-piperidinyl) or tetrahydroisoquinolinyl.

2. A compound according to claim 1, of the formula:

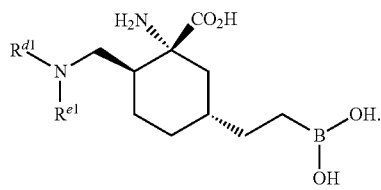

3. A compound according to claim 1 of the formula:

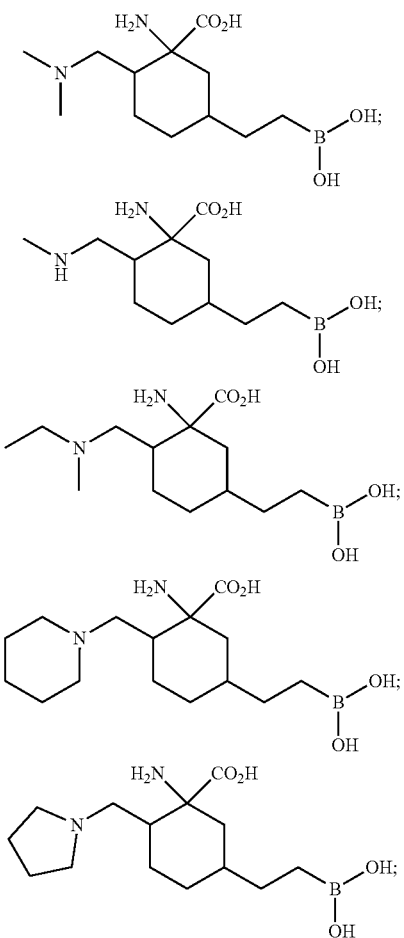

or a pharmaceutically acceptable salt thereof.

4. A compound according to claim 1 of the formula:

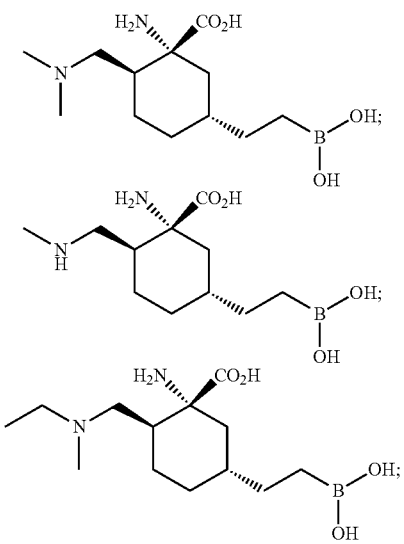

-continued

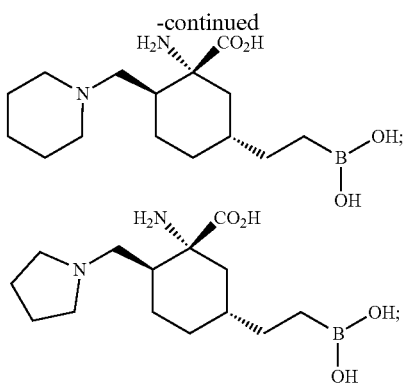

or
a pharmaceutically acceptable salt thereof.

5. A compound according to claim 1, which is
(1R,2S,5R)-1-amino-5-(2-boronoethyl)-2-((dimethylamino)methyl) cyclohexane-1-carboxylic acid;
(1R,2S,5R)-1-amino-5-(2-boronoethyl)-2-((methylamino)methyl) cyclohexane-1-carboxylic acid;
(1R,2S,5R)-1-amino-5-(2-boronoethyl)-2-((ethyl(methyl)amino) methyl)cyclohexane-1-carboxylic acid;
(1R,2S,5R)-1-amino-5-(2-boronoethyl)-2-(piperidin-1-ylmethyl) cyclohexane-1-carboxylic acid;
(1R,2S,5R)-1-amino-5-(2-boronoethyl)-2-(pyrrolidin-1-ylmethyl) cyclohexane-1-carboxylic acid;
rac-(1R,2S,5R)-1-amino-5-(2-boronoethyl)-2-((dimethylamino)methyl) cyclohexane-1-carboxylic acid;
rac-(1R,2S,5R)-1-amino-5-(2-boronoethyl)-2-(piperidin-1-ylmethyl) cyclohexane-1-carboxylic acid;
rac-(1R,2S,5R)-1-amino-5-(2-boronoethyl)-2-(pyrrolidin-1-ylmethyl) cyclohexane-1-carboxylic acid; or
a pharmaceutically acceptable salt thereof.

6. A pharmaceutical composition comprising a compound or salt according claim 1 together with a pharmaceutically acceptable carrier.

7. A pharmaceutical composition comprising a compound or salt according to claim 4 together with a pharmaceutically acceptable carrier.

8. A pharmaceutical composition comprising a compound or salt according to claim 5 together with a pharmaceutically acceptable carrier.

9. A method for treatment or prevention of a disease or condition associated with overexpression or overactivity of arginase I, arginase II, or a combination thereof in a subject in need of such treatment or prevention, comprising administering to the subject a therapeutically effective amount of at least one compound according to claim 1.

10. A method for therapeutic treatment of a disease or condition associated with overexpression or overactivity of arginase I, arginase II, or a combination thereof in a patient in need of such treatment, comprising administering to the subject a therapeutically effective amount of at least one compound according to claim 1.

11. A compound of Formula (Ib-1):

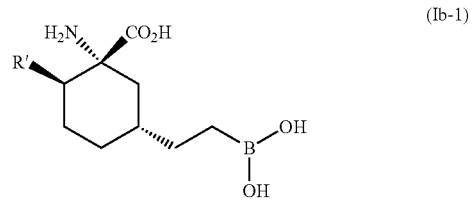

(Ib-1)

or a pharmaceutically acceptable salt thereof, wherein
R' is —OH, —$CH_2NH_2$, —$CH_2NHCH_3$, —$CH_2NHC(CH_3)_3$, —$CH_2N(CH_3)_2$, —$CH_2N(CH_3)(CH_2CH_3)$, —$CH_2N(CH_2CH_3)_2$, —$CH_2N(CH_3)(CH(CH_3)_2)$, —$CH_2$-pyrrolidinyl, —$CH_2$-piperidinyl, —$CH_2$-(7-azabicyclo[2.2.1]heptyl), —$CH_2$-morpholinyl, —$CH_2NCH_3Bn$, —$CH_2$-(4,4-dimethylpiperidinyl), —$CH_2$-isoindolinyl, —$CH_2$-(4-chlorophenyl-piperidinyl), —$CH_2$-tetrahydroisoquinolinyl, —$CH_2N(CH_3)$Ph, —$CH_2N(CH_3)(4-CH_3OC_6H_4)$ or —$CH_2N(CH_3)$(dichlorobenzyl).

12. A compound of the formula:

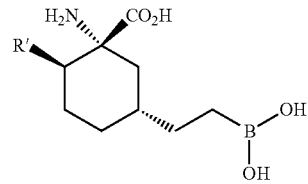

or a pharmaceutically acceptable salt thereof, wherein
R' is ($C_1$-$C_4$)alkyl substituted with —$NR^dR^e$ or a heterocyclyl having from 5 to 6 ring member atoms;
wherein $R^d$ and $R^e$ are each independently H or straight or branched ($C_1$-$C_6$)alkyl.

* * * * *